US009582035B2

(12) United States Patent
Connor

(10) Patent No.: US 9,582,035 B2
(45) Date of Patent: Feb. 28, 2017

(54) WEARABLE COMPUTING DEVICES AND METHODS FOR THE WRIST AND/OR FOREARM

(71) Applicant: Robert A. Connor, Forest Lake, MN (US)

(72) Inventor: Robert A. Connor, Forest Lake, MN (US)

(73) Assignee: Medibotics LLC, St. Paul, MN (US)

( * ) Notice: Subject to any disclaimer, the term of this patent is extended or adjusted under 35 U.S.C. 154(b) by 0 days.

(21) Appl. No.: 14/623,337

(22) Filed: Feb. 16, 2015

(65) Prior Publication Data

US 2015/0309535 A1    Oct. 29, 2015

Related U.S. Application Data

(60) Provisional application No. 61/944,090, filed on Feb. 25, 2014, provisional application No. 61/948,124, filed on Mar. 5, 2014, provisional application No. 62/100,217, filed on Jan. 6, 2015, provisional application No. 62/106,856, filed on Jan. 23, 2015, provisional application No. 62/111,163, filed on Feb. 3, 2015, provisional application No. 62/113,423, filed on Feb. 7, 2015, provisional application No. 62/115,691, filed on Feb. 13, 2015.

(51) Int. Cl.
*G06F 1/16* (2006.01)
*G06F 3/01* (2006.01)

(52) U.S. Cl.
CPC ............ *G06F 1/163* (2013.01); *G06F 1/1637* (2013.01); *G06F 1/1694* (2013.01); *G06F 3/014* (2013.01); *G06F 3/017* (2013.01)

(58) Field of Classification Search
CPC ...... G06F 1/163; G06F 1/1637; G06F 1/1694; G06F 3/017; G06F 3/014
See application file for complete search history.

(56) References Cited

U.S. PATENT DOCUMENTS

| 4,627,739 A * | 12/1986 | Shingo ................. G04B 37/225 368/281 |
| 5,514,861 A | 5/1996 | Swartz et al. |
| 5,610,528 A | 3/1997 | Neely et al. |
| 6,050,962 A | 4/2000 | Kramer et al. |
| 6,216,490 B1 * | 4/2001 | Radley-Smith ...... A44C 5/0015 345/56 |
| 6,428,490 B1 | 8/2002 | Kramer et al. |
| 6,487,906 B1 | 12/2002 | Hock |
| 6,513,532 B2 | 2/2003 | Mault et al. |
| 6,525,997 B1 | 2/2003 | Narayanaswami |

(Continued)

FOREIGN PATENT DOCUMENTS

WO    WO2012170584    12/2012

*Primary Examiner* — Zachary M Pape
*Assistant Examiner* — Douglas Burtner

(57) ABSTRACT

This invention comprises wearable computing devices and methods for the wrist and/or forearm including a bifurcating attachment member and/or proximal and distal display members. These wearable devices can provide relatively-large display areas without looking too clunky or being uncomfortable to wear. This invention also comprises methods for conserving energy and for modifying the communication interface between a human and a computer based on data from environmental sensors and/or body sensors.

9 Claims, 90 Drawing Sheets

(56) References Cited

U.S. PATENT DOCUMENTS

| | | | |
|---|---|---|---|
| 6,556,222 B1 | 4/2003 | Narayanaswami | |
| 6,697,048 B2 | 2/2004 | Rosenberg et al. | |
| 6,857,775 B1* | 2/2005 | Wilson | G04B 37/1486 224/164 |
| 6,930,608 B2 | 8/2005 | Grajales et al. | |
| 6,984,208 B2 | 1/2006 | Zheng | |
| 7,020,508 B2 | 3/2006 | Stivoric et al. | |
| 7,070,571 B2 | 7/2006 | Kramer et al. | |
| 7,073,129 B1 | 7/2006 | Robarts et al. | |
| D548,113 S * | 8/2007 | Burton | D10/32 |
| 7,261,690 B2 | 8/2007 | Teller et al. | |
| 7,285,090 B2* | 10/2007 | Stivoric | A61B 5/01 128/905 |
| 7,395,507 B2 | 7/2008 | Robarts et al. | |
| 7,450,107 B2* | 11/2008 | Radley-Smith | A44C 5/0007 345/1.3 |
| 7,451,056 B2 | 11/2008 | Flentov et al. | |
| 7,460,085 B2* | 12/2008 | Ishii | G06F 3/1423 345/1.1 |
| 7,506,269 B2* | 3/2009 | Lang | G06F 1/163 715/786 |
| 7,512,515 B2 | 3/2009 | Vock et al. | |
| 7,558,057 B1 | 7/2009 | Naksen et al. | |
| 7,654,732 B2* | 2/2010 | Burton | A44C 5/12 224/173 |
| 7,658,612 B2 | 2/2010 | Lee et al. | |
| 7,785,001 B2 | 8/2010 | Tao et al. | |
| 7,821,496 B2 | 10/2010 | Rosenberg et al. | |
| 8,036,851 B2 | 10/2011 | Vock et al. | |
| 8,111,165 B2 | 2/2012 | Ortega et al. | |
| 8,146,171 B2 | 4/2012 | Chung et al. | |
| 8,149,212 B2 | 4/2012 | Radley-Smith | |
| 8,161,826 B1 | 4/2012 | Taylor | |
| 8,180,440 B2 | 5/2012 | McCombie et al. | |
| 8,184,070 B1 | 5/2012 | Taubman | |
| 8,228,315 B1 | 7/2012 | Starner et al. | |
| 8,279,716 B1 | 10/2012 | Gossweiler et al. | |
| 8,352,211 B2 | 1/2013 | Vock et al. | |
| 8,362,882 B2 | 1/2013 | Heubel et al. | |
| 8,379,488 B1 | 2/2013 | Gossweiler et al. | |
| 8,396,530 B1 | 3/2013 | Wilder-Smith et al. | |
| 8,412,317 B2 | 4/2013 | Mazar | |
| 8,416,088 B2 | 4/2013 | Ortega et al. | |
| 8,446,275 B2 | 5/2013 | Utter | |
| 8,457,719 B2 | 6/2013 | Moctezuma et al. | |
| 8,464,036 B2 | 6/2013 | Rubin et al. | |
| 8,475,370 B2 | 7/2013 | McCombie et al. | |
| 8,527,217 B2 | 9/2013 | Moodie | |
| 8,538,376 B2 | 9/2013 | Lee et al. | |
| 8,576,199 B1 | 11/2013 | Pryor | |
| 8,594,776 B2 | 11/2013 | McCombie et al. | |
| 8,595,645 B2 | 11/2013 | Boettcher et al. | |
| 8,624,836 B1 | 1/2014 | Miller et al. | |
| 8,634,873 B2 | 1/2014 | Jones et al. | |
| 8,648,799 B1 | 2/2014 | Lloyd | |
| 8,659,553 B1 | 2/2014 | Chan et al. | |
| D701,504 S | 3/2014 | Christopher et al. | |
| 8,662,362 B1 | 3/2014 | Bastian et al. | |
| 8,662,742 B2 | 3/2014 | Damasko | |
| 8,665,223 B2 | 3/2014 | Harada et al. | |
| 8,665,236 B2 | 3/2014 | Myers | |
| 8,666,115 B2 | 3/2014 | Perski et al. | |
| 8,666,447 B2 | 3/2014 | Cathey | |
| 8,670,222 B2 | 3/2014 | Rothkopf | |
| 8,676,238 B2 | 3/2014 | Marcellino et al. | |
| 8,686,947 B2 | 4/2014 | Wine | |
| 8,698,744 B2 | 4/2014 | Wehrenberg et al. | |
| 8,717,852 B2 | 5/2014 | Cohen et al. | |
| 8,744,418 B2 | 6/2014 | Novet | |
| 8,754,831 B2 | 6/2014 | Kollin et al. | |
| D709,874 S | 7/2014 | Aumiller et al. | |
| D709,875 S | 7/2014 | Aumiller et al. | |
| 8,764,653 B2 | 7/2014 | Kaminska et al. | |
| 8,784,271 B2 | 7/2014 | Brumback et al. | |
| 8,795,138 B1 | 8/2014 | Yeh et al. | |
| 8,795,174 B2 | 8/2014 | Manicka et al. | |
| 8,797,748 B2 | 8/2014 | Dabov | |
| 8,851,372 B2* | 10/2014 | Zhou | G06F 1/163 235/380 |
| 8,888,701 B2 | 11/2014 | LeBoeuf et al. | |
| 8,947,441 B2 | 2/2015 | Hodgins et al. | |
| 8,947,864 B2 | 2/2015 | Whitt et al. | |
| 8,956,293 B2 | 2/2015 | McCombie et al. | |
| 8,956,294 B2 | 2/2015 | McCombie et al. | |
| 8,957,858 B2 | 2/2015 | Osborn et al. | |
| 8,961,413 B2 | 2/2015 | Teller et al. | |
| 8,961,414 B2 | 2/2015 | Teller et al. | |
| 8,961,415 B2 | 2/2015 | LeBoeuf et al. | |
| 2001/0020937 A1 | 9/2001 | Rosenberg et al. | |
| 2001/0049470 A1 | 12/2001 | Mault et al. | |
| 2001/0056225 A1 | 12/2001 | DeVito | |
| 2002/0109600 A1 | 8/2002 | Mault et al. | |
| 2003/0065257 A1 | 4/2003 | Mault et al. | |
| 2003/0083596 A1 | 5/2003 | Kramer et al. | |
| 2003/0214408 A1 | 11/2003 | Grajales et al. | |
| 2004/0152957 A1 | 8/2004 | Stivoric et al. | |
| 2004/0164959 A1 | 8/2004 | Rosenberg et al. | |
| 2004/0203414 A1* | 10/2004 | Satou | H04M 1/03 455/66.1 |
| 2005/0131288 A1 | 6/2005 | Turner et al. | |
| 2006/0007059 A1* | 1/2006 | Bell | A41D 27/085 345/55 |
| 2006/0122474 A1 | 6/2006 | Teller et al. | |
| 2006/0264730 A1 | 11/2006 | Stivoric et al. | |
| 2006/0284979 A1 | 12/2006 | Clarkson | |
| 2007/0100666 A1 | 5/2007 | Stivoric et al. | |
| 2007/0106145 A1 | 5/2007 | Kim et al. | |
| 2007/0173705 A1 | 7/2007 | Teller et al. | |
| 2008/0167535 A1 | 7/2008 | Andre et al. | |
| 2008/0223890 A1 | 9/2008 | Tecchiolli et al. | |
| 2008/0262557 A1 | 10/2008 | Brown | |
| 2008/0287751 A1 | 11/2008 | Stivoric et al. | |
| 2008/0287817 A1 | 11/2008 | Stivoric et al. | |
| 2009/0163241 A1 | 6/2009 | Vossoughi et al. | |
| 2009/0171180 A1 | 7/2009 | Pering et al. | |
| 2010/0049004 A1* | 2/2010 | Edman | A61B 5/1118 600/300 |
| 2010/0049010 A1 | 2/2010 | Goldreich | |
| 2010/0176166 A1 | 7/2010 | Siagri et al. | |
| 2010/0227642 A1* | 9/2010 | Kim | H04M 1/0256 455/556.1 |
| 2010/0284135 A1 | 11/2010 | Tecchiolli et al. | |
| 2011/0187681 A1* | 8/2011 | Kim | G06F 1/1652 345/204 |
| 2011/0205851 A1 | 8/2011 | Harris | |
| 2011/0288379 A1 | 11/2011 | Wu | |
| 2012/0004883 A1 | 1/2012 | Vock et al. | |
| 2012/0016210 A1 | 1/2012 | Kim et al. | |
| 2012/0056509 A1 | 3/2012 | Anderson et al. | |
| 2012/0082013 A1 | 4/2012 | Yeung et al. | |
| 2012/0086366 A1 | 4/2012 | Anderson et al. | |
| 2012/0242626 A1 | 9/2012 | Hu | |
| 2012/0264446 A1 | 10/2012 | Xie et al. | |
| 2012/0271121 A1 | 10/2012 | Della Torre et al. | |
| 2012/0274508 A1 | 11/2012 | Brown et al. | |
| 2012/0274554 A1 | 11/2012 | Kinoshita et al. | |
| 2012/0310971 A1 | 12/2012 | Tran | |
| 2012/0313746 A1 | 12/2012 | Rahman et al. | |
| 2012/0313776 A1 | 12/2012 | Utter | |
| 2012/0326873 A1 | 12/2012 | Utter | |
| 2013/0016070 A1 | 1/2013 | Starner et al. | |
| 2013/0044215 A1 | 2/2013 | Rothkopf | |
| 2013/0107674 A1 | 5/2013 | Gossweiler et al. | |
| 2013/0110011 A1 | 5/2013 | McGregor et al. | |
| 2013/0120106 A1 | 5/2013 | Cauwels et al. | |
| 2013/0120459 A1* | 5/2013 | Dickinson | G06F 1/163 345/650 |
| 2013/0154838 A1 | 6/2013 | Alameh et al. | |
| 2013/0169560 A1 | 7/2013 | Cederlund et al. | |
| 2013/0173171 A1 | 7/2013 | Drysdale et al. | |
| 2013/0190903 A1 | 7/2013 | Balakrishnan et al. | |
| 2013/0191741 A1 | 7/2013 | Dickinson et al. | |
| 2013/0198694 A1 | 8/2013 | Rahman et al. | |

(56) References Cited

U.S. PATENT DOCUMENTS

| | | |
|---|---|---|
| 2013/0201098 A1 | 8/2013 | Schilit et al. |
| 2013/0217978 A1 | 8/2013 | Ma |
| 2013/0222137 A1 | 8/2013 | Alameh et al. |
| 2013/0222271 A1* | 8/2013 | Alberth ............... G06F 1/163 345/173 |
| 2013/0234924 A1 | 9/2013 | Janefalkar et al. |
| 2013/0241823 A1 | 9/2013 | Pryor |
| 2013/0275058 A1 | 10/2013 | Awad |
| 2013/0285577 A1 | 10/2013 | O'Brien et al. |
| 2013/0328842 A1 | 12/2013 | Barnhoefer et al. |
| 2013/0347102 A1 | 12/2013 | Shi |
| 2014/0002402 A1 | 1/2014 | Kang et al. |
| 2014/0006994 A1 | 1/2014 | Koch et al. |
| 2014/0007010 A1 | 1/2014 | Blom |
| 2014/0012154 A1 | 1/2014 | Mazar |
| 2014/0025973 A1 | 1/2014 | Schillings et al. |
| 2014/0028688 A1 | 1/2014 | Houjou et al. |
| 2014/0031081 A1 | 1/2014 | Vossoughi et al. |
| 2014/0031698 A1 | 1/2014 | Moon et al. |
| 2014/0035794 A1 | 2/2014 | Chen |
| 2014/0035875 A2 | 2/2014 | Theimer et al. |
| 2014/0036643 A1 | 2/2014 | Messenger et al. |
| 2014/0042406 A1 | 2/2014 | Degner et al. |
| 2014/0047864 A1 | 2/2014 | Lo et al. |
| 2014/0051948 A1 | 2/2014 | LeBoeuf et al. |
| 2014/0055338 A1 | 2/2014 | Ryan |
| 2014/0055483 A1 | 2/2014 | Pance et al. |
| 2014/0056452 A1 | 2/2014 | Moss et al. |
| 2014/0058220 A1 | 2/2014 | LeBoeuf et al. |
| 2014/0062469 A1 | 3/2014 | Yang et al. |
| 2014/0062510 A1 | 3/2014 | Cok et al. |
| 2014/0062511 A1 | 3/2014 | Cok et al. |
| 2014/0066124 A1 | 3/2014 | Novet |
| 2014/0087685 A1 | 3/2014 | Kellond et al. |
| 2014/0094675 A1 | 4/2014 | Luna et al. |
| 2014/0097765 A1 | 4/2014 | Hussain et al. |
| 2014/0098067 A1 | 4/2014 | Yang et al. |
| 2014/0104197 A1 | 4/2014 | Khosravy et al. |
| 2014/0104241 A1 | 4/2014 | Huppi et al. |
| 2014/0105086 A1 | 4/2014 | Chhabra et al. |
| 2014/0112371 A1 | 4/2014 | Yang et al. |
| 2014/0112510 A1 | 4/2014 | Yang et al. |
| 2014/0112556 A1 | 4/2014 | Kalinli-Akbacak |
| 2014/0113592 A1 | 4/2014 | Wu et al. |
| 2014/0116085 A1 | 5/2014 | Lam |
| 2014/0120839 A1 | 5/2014 | Lam |
| 2014/0120983 A1 | 5/2014 | Lam |
| 2014/0121982 A1 | 5/2014 | Rauhala |
| 2014/0122102 A1 | 5/2014 | Utter |
| 2014/0125480 A1 | 5/2014 | Utter |
| 2014/0125481 A1 | 5/2014 | Utter |
| 2014/0125493 A1 | 5/2014 | Utter |
| 2014/0127649 A1 | 5/2014 | Utter |
| 2014/0128754 A1 | 5/2014 | Luna et al. |
| 2014/0129007 A1 | 5/2014 | Utter |
| 2014/0129008 A1 | 5/2014 | Utter |
| 2014/0129239 A1 | 5/2014 | Utter |
| 2014/0129242 A1 | 5/2014 | Utter |
| 2014/0129243 A1 | 5/2014 | Utter |
| 2014/0132481 A1* | 5/2014 | Bell ..................... H05K 5/0017 345/1.3 |
| 2014/0138637 A1 | 5/2014 | Yang et al. |
| 2014/0139340 A1 | 5/2014 | Yang et al. |
| 2014/0139422 A1 | 5/2014 | Mistry et al. |
| 2014/0139454 A1 | 5/2014 | Mistry et al. |
| 2014/0139486 A1 | 5/2014 | Mistry et al. |
| 2014/0139637 A1 | 5/2014 | Mistry et al. |
| 2014/0143678 A1 | 5/2014 | Mistry et al. |
| 2014/0145150 A1 | 5/2014 | De Jong et al. |
| 2014/0146987 A1 | 5/2014 | Pontoppidan et al. |
| 2014/0156084 A1 | 6/2014 | Rahman et al. |
| 2014/0159903 A1 | 6/2014 | Tropper et al. |
| 2014/0160078 A1* | 6/2014 | Seo ..................... G06F 3/017 345/175 |
| 2014/0164541 A1 | 6/2014 | Marcellino |
| 2014/0166850 A1 | 6/2014 | Zheng |
| 2014/0166867 A1 | 6/2014 | Shiu et al. |
| 2014/0167619 A1 | 6/2014 | Land et al. |
| 2014/0167973 A1 | 6/2014 | Letchner et al. |
| 2014/0171132 A1 | 6/2014 | Ziemianska et al. |
| 2014/0171146 A1 | 6/2014 | Ma et al. |
| 2014/0171759 A1 | 6/2014 | White et al. |
| 2014/0171809 A1 | 6/2014 | Bonutti et al. |
| 2014/0176335 A1 | 6/2014 | Brumback et al. |
| 2014/0176346 A1 | 6/2014 | Brumback et al. |
| 2014/0176422 A1 | 6/2014 | Brumback et al. |
| 2014/0176439 A1 | 6/2014 | Keller et al. |
| 2014/0176475 A1 | 6/2014 | Myers et al. |
| 2014/0180020 A1 | 6/2014 | Stivoric et al. |
| 2014/0180021 A1 | 6/2014 | Stivoric et al. |
| 2014/0180022 A1 | 6/2014 | Stivoric et al. |
| 2014/0180023 A1 | 6/2014 | Stivoric et al. |
| 2014/0180137 A1 | 6/2014 | Stivoric et al. |
| 2014/0180582 A1 | 6/2014 | Pontarelli et al. |
| 2014/0180595 A1 | 6/2014 | Brumback et al. |
| 2014/0181715 A1 | 6/2014 | Axelrod et al. |
| 2014/0181741 A1 | 6/2014 | Apacible et al. |
| 2014/0183342 A1 | 7/2014 | Shedletsky et al. |
| 2014/0191926 A1 | 7/2014 | Mathew et al. |
| 2014/0192002 A1 | 7/2014 | Herz et al. |
| 2014/0195166 A1 | 7/2014 | Rahman et al. |
| 2014/0197317 A1 | 7/2014 | Yang et al. |
| 2014/0206289 A1 | 7/2014 | Rahman et al. |
| 2014/0206323 A1 | 7/2014 | Scorcioni |
| 2014/0206327 A1 | 7/2014 | Ziemianska et al. |
| 2014/0206328 A1 | 7/2014 | Varoglu et al. |
| 2014/0206954 A1 | 7/2014 | Yuen et al. |
| 2014/0210640 A1 | 7/2014 | Rahman et al. |
| 2014/0210708 A1 | 7/2014 | Simmons et al. |
| 2014/0218856 A1 | 8/2014 | Raff et al. |
| 2014/0221020 A1 | 8/2014 | Xie et al. |
| 2014/0222734 A1 | 8/2014 | Stivoric et al. |
| 2014/0223165 A1 | 8/2014 | Rahman et al. |
| 2014/0228649 A1 | 8/2014 | Rayner et al. |
| 2014/0232516 A1 | 8/2014 | Stivoric et al. |
| 2014/0240103 A1 | 8/2014 | Lake et al. |
| 2014/0240122 A1 | 8/2014 | Roberts et al. |
| 2014/0240144 A1 | 8/2014 | Rahman et al. |
| 2014/0240223 A1 | 8/2014 | Lake et al. |
| 2014/0244505 A1 | 8/2014 | Kim |
| 2014/0245161 A1 | 8/2014 | Yuen et al. |
| 2014/0245213 A1 | 8/2014 | Gardenfors et al. |
| 2014/0253412 A1 | 9/2014 | Blaich et al. |
| 2014/0267024 A1 | 9/2014 | Keller et al. |
| 2014/0267543 A1 | 9/2014 | Kerger et al. |
| 2014/0269224 A1 | 9/2014 | Huh et al. |
| 2014/0273848 A1 | 9/2014 | Rahman et al. |
| 2014/0275812 A1 | 9/2014 | Stivoric et al. |
| 2014/0275813 A1 | 9/2014 | Stivoric et al. |
| 2014/0278139 A1 | 9/2014 | Hong et al. |
| 2014/0281956 A1 | 9/2014 | Anderson et al. |
| 2014/0288878 A1 | 9/2014 | Donaldson |
| 2014/0295811 A1 | 10/2014 | Uusitalo et al. |
| 2014/0303523 A1 | 10/2014 | Hong et al. |
| 2014/0310643 A1 | 10/2014 | Karmanenko et al. |
| 2014/0313154 A1 | 10/2014 | Bengtsson et al. |
| 2014/0318699 A1 | 10/2014 | Longinotti-Buitoni et al. |
| 2014/0320381 A1 | 10/2014 | Enzmann et al. |
| 2014/0320435 A1 | 10/2014 | Modarres et al. |
| 2014/0321245 A1 | 10/2014 | Sharpe |
| 2014/0323826 A1 | 10/2014 | Wilder-Smith et al. |
| 2014/0325448 A1 | 10/2014 | Han et al. |
| 2014/0328041 A1 | 11/2014 | Rothkopf et al. |
| 2014/0329561 A1* | 11/2014 | Kim ..................... H04M 1/72577 455/557 |
| 2014/0342782 A1 | 11/2014 | Karmanenko et al. |
| 2014/0347963 A1 | 11/2014 | El Alej et al. |
| 2014/0351770 A1 | 11/2014 | Abercrombie |
| 2014/0362020 A1 | 12/2014 | Rothkopf et al. |
| 2014/0368336 A1 | 12/2014 | Felix |
| 2014/0372940 A1 | 12/2014 | Cauwels et al. |
| 2014/0373338 A1 | 12/2014 | O'Connor et al. |
| 2014/0375465 A1 | 12/2014 | Fenuccio et al. |
| 2014/0378786 A1 | 12/2014 | Hong et al. |

(56) References Cited

U.S. PATENT DOCUMENTS

| | | |
|---|---|---|
| 2014/0378872 A1 | 12/2014 | Hong et al. |
| 2015/0006290 A1 | 1/2015 | Tomkins et al. |
| 2015/0026647 A1 | 1/2015 | Park et al. |
| 2015/0029227 A1 | 1/2015 | Park et al. |
| 2015/0031964 A1 | 1/2015 | Bly et al. |
| 2015/0031967 A1 | 1/2015 | LeBoeuf et al. |
| 2015/0040282 A1 | 2/2015 | Longinotti-Buitoni et al. |
| 2015/0043770 A1 | 2/2015 | Chen et al. |
| 2015/0045634 A1 | 2/2015 | Goldberg et al. |
| 2015/0057964 A1 | 2/2015 | Albinali |
| 2015/0065893 A1 | 3/2015 | Ye |
| 2015/0091781 A1 | 4/2015 | Yu et al. |
| 2015/0105671 A1 | 4/2015 | Shibuya et al. |
| 2015/0105678 A1 | 4/2015 | Takei et al. |
| 2015/0113473 A1 | 4/2015 | Otsuka et al. |
| 2015/0123647 A1 | 5/2015 | Gisby et al. |
| 2015/0126169 A1 | 5/2015 | Kerger et al. |
| 2016/0070410 A1* | 3/2016 | Lin .................. G06F 3/0421 345/173 |
| 2016/0091980 A1* | 3/2016 | Baranski ............ A61B 5/7475 345/156 |
| 2016/0116940 A1* | 4/2016 | Jones .................. G06F 1/1698 361/679.03 |
| 2016/0192428 A1* | 6/2016 | Friedman ........... H04W 76/023 455/41.2 |
| 2016/0192526 A1* | 6/2016 | Gao .................... G06F 1/163 361/679.01 |
| 2016/0192716 A1* | 7/2016 | Lee ..................... A41D 1/002 2/422 |
| 2016/0239083 A1* | 8/2016 | Cheng ................ G06F 3/014 |
| 2016/0239190 A1* | 8/2016 | Forutanpour ....... G06F 1/163 |
| 2016/0240154 A1* | 8/2016 | Forutanpour ....... G06F 3/0412 |
| 2016/0259367 A1* | 9/2016 | Huang ................ G06F 1/163 |
| 2016/0267310 A1* | 9/2016 | AlNasser ........... G06K 7/10009 |
| 2016/0299570 A1* | 10/2016 | Davydov ............ G06F 1/163 |
| 2016/0349790 A1* | 12/2016 | Connor .............. G06F 1/1694 |

\* cited by examiner

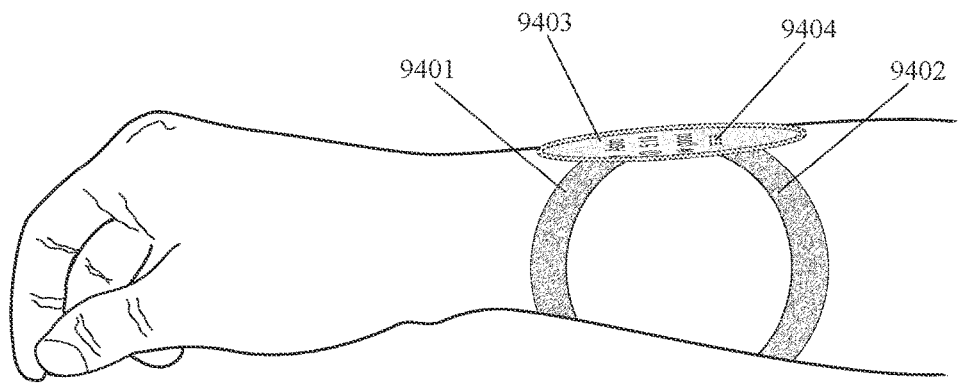
Fig. 94
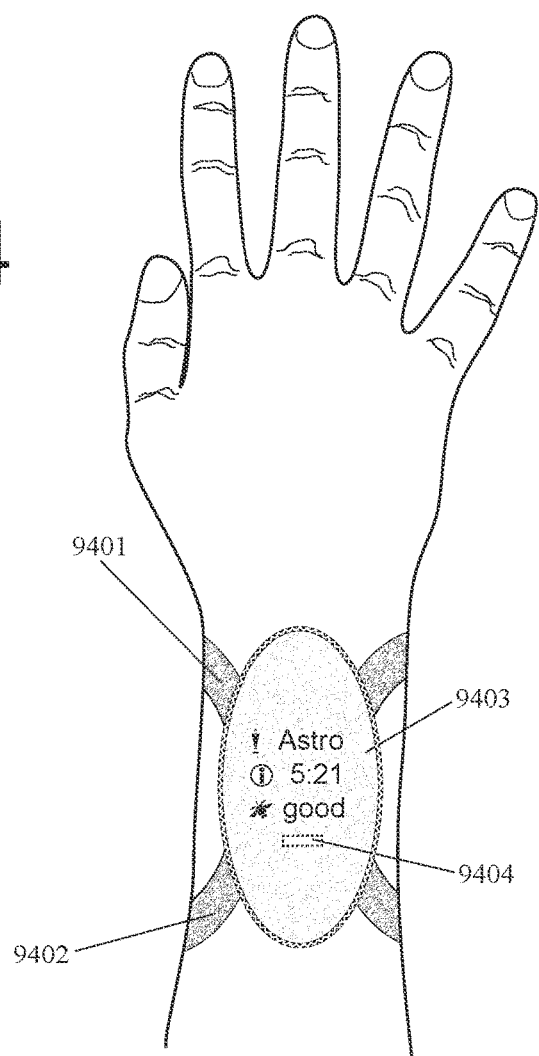

WEARABLE COMPUTING DEVICES AND METHODS FOR THE WRIST AND/OR FOREARM

CROSS-REFERENCE TO RELATED APPLICATIONS

This patent application claims the priority benefit of: U.S. Provisional Patent Application No. 61/944,090 entitled "Wearable Computing Device for the Wrist and/or Arm" by Robert A. Connor with a filing date of Feb. 25, 2014; U.S. Provisional Patent Application No. 61/948,124 entitled "Wearable Computing Device for the Wrist and/or Arm" by Robert A. Connor with a filing date of Mar. 5, 2014; U.S. Provisional Patent Application No. 62/100,217 entitled "Forearm Wearable Device with Distal-to-Proximal Flexibly-Connected Display Modules" by Robert A. Connor with a filing date of Jan. 6, 2015; U.S. Provisional Patent Application No. 62/106,856 entitled "Forearm Wearable Computing Device with Proximal and Distal Arcuate Bands" by Robert A. Connor with a filing date of Jan. 23, 2015; U.S. Provisional Patent Application No. 62/111,163 entitled "Forearm-Wearable Computing Device with Large Display Area" by Robert A. Connor with a filing date of Feb. 3, 2015; U.S. Provisional Patent Application No. 62/113,423 entitled "Sensor-Informed Modification of the Interface Modality Between a Human and a Wearable Computing Device" by Robert A. Connor with a filing date of Feb. 7, 2015; and U.S. Provisional Patent Application No. 62/115,691 entitled "Adjustment of Wearable Computer-to-Human Interface Based on Environmental and/or Physiological Sensors" by Robert A. Connor with a filing date of Feb. 13, 2015.

FEDERALLY SPONSORED RESEARCH

Not Applicable

SEQUENCE LISTING OR PROGRAM

Not Applicable

BACKGROUND

Field of Invention

This invention relates to wearable computing devices and methods for the wrist and/or arm.

INTRODUCTION

During the past decade handheld computing devices have become ubiquitous, but there is now growing interest in the development of wearable computing devices and methods for the wrist and/or arm which may supplement or even replace handheld computing devices to some extent. There are specific challenges and new opportunities which are more relevant to wearable computing devices for the wrist and/or arm than they were for handheld computing devices. The goals of this invention are to create innovative devices and methods which: (a) overcome some of the specific challenges associated with such wearable devices; and (b) take advantage of specific new opportunities provided by such wearable devices.

One of the challenges associated with such wearable devices is that the human wrist and/or arm provides a relatively small space for a visual computer-to-human interface, but non-visual modes of communication (such as those based on sound or vibration) can be obscured by environmental noise or vibration and may not be very private. How can one create a visual computer-to-human interface with a relatively large display area that does not look too clunky and/or become uncomfortable to wear? The wearable devices disclosed herein address this challenge with arcuate and/or flexibly-connected displays and display arrays that cumulatively provide relatively-large display areas without looking too clunky or becoming uncomfortable to wear.

Another challenge for such wearable devices is that the human wrist and/or arm provides a relatively small space for a battery. This invention address this challenge with wearable devices and methods which modify device functions based on data from environmental and/or automatic body sensors in order to use energy more efficiently. Another challenge is that the human wrist and/or arm can have different levels of movement and move into different positions relative to the eyes of the person wearing the device and the eyes of other nearby people (from whom information on the device should be kept private). This invention addresses this challenge with wearable devices which selectively enable the wearer to see information on their device from various angles while selectively preventing other people from seeing this information.

One of the new opportunities provided by such wearable devices is the creative use of sensors worn on the body. Sensors worn on the body open up new opportunities for human-to-computer interfaces to expand the usefulness of such devices and even to overcome some of the limitations of handheld computing devices. For example, computing devices which are worn on the body can sense and respond to electromagnetic signals from muscles and nerves in ways that are difficult, or even impossible, with handheld devices. As another example, a computing device which is worn on the body can be easier to see and less likely to be forgotten than a handheld device. Further, systems of wearable devices can measure configurations of body movement based on multiple points of motion, not just a single point of motion as with a handheld device. This invention discloses novel device designs and methods to take better advantage of the unique new opportunities created by wearable devices with various sensors worn on the body.

The inventor apologies to the reader for the length of this disclosure, but it incorporates multiple provisional patents over the span of a very prolific year. Hopefully, the section with a brief introduction to the figures will provide the reader with a relatively-concise guide to help the reader navigate to specific device designs and methods at different locations in this disclosure.

Review and Limitations of the Prior Art

There is a growing body of innovative prior art for wearable computing devices and methods for the wrist and/or arm. Several hundred examples of the most relevant prior art are included in the Information Disclosure Statement which accompanies this disclosure. Since motion sensors (such as accelerometers, gyroscopes, and inclinometers) have become relatively small and inexpensive, much of the recent art concerning wearable computing devices for the wrist and/or arm includes motion sensors. The prior art includes the use of motion sensors for a growing variety of functions including: single-point estimation of energy expenditure; single-point estimation of sleeping activity;

single-point recognition of gestures; single-point estimation of body position and health status; and filtering message notifications.

Since touch screens and speech recognition have become common forms of human-to-computer communication, much of the prior art for wearable devices for the wrist and/or arm also includes touch screens and speech recognition. One of the challenges for touch screens is that the human wrist and/or arm provides a relatively small space for a touch screen. The challenge of how to create a relatively large display area on a wearable device without looking too clunky or becoming uncomfortable has not yet been fully solved by the prior art. One of the challenges for speech recognition is that speech can be obscured when the environment is noisy and may not be very private if the environment is quiet. The challenges of speech-based human-to-computer interaction in different environments have not yet been fully solved by the prior art.

With the trend toward larger visual displays and multiple functions for wearable devices, energy use has become a significant challenge in the field because there is limited space on the wrist and/or forearm for a battery. The prior art is beginning to include more mechanisms for conserving energy and for harvesting energy from human motion or thermal energy. Also, there is continued progress toward more efficient batteries. Nonetheless, energy use remains a challenge which has not yet been fully solved by the prior art.

Since the orientation of a wearer's wrist and/or arm relative to their eyes changes as the arm moves, it can be challenging to make information on a wrist and/or arm device consistently visible to the wearer, but not visible to other nearby people (in order to keep this information private). There is increasing awareness of this problem in the prior art, but it does not appear to have been fully solved yet.

The incorporation of sensors worn on the body opens up a variety of new opportunities for device functionality beyond those which were possible with handheld devices. The prior art is beginning to provide devices and methods to take advantage of these new possibilities, especially with respect to motion sensors and blood pressure sensors. However, the new functional possibilities which can be created from the incorporation of wearable electromagnetic energy sensors, ultrasonic sensors, and spectroscopic sensors into devices worn on the wrist and/or forearm have not yet been fully developed in the prior art.

These are exciting times for the development of new devices and methods for wearable technology and there has been a good deal of innovation in the prior art to date. However, there are still many challenges which have not yet been fully addressed by the prior art and many opportunities which have not yet been fully realized by the prior art. The devices and methods disclosed herein are intended to solve some of these challenges and to realize some of these opportunities.

SUMMARY OF THE INVENTION

This invention comprises wearable computing devices and methods for the wrist and/or forearm which overcome some of the challenges associated with such wearable devices and take advantage of new opportunities provided by such devices. This invention can be embodied in a wearable computing device for the wrist and/or forearm including: (a) a bifurcating attachment member which is configured to be worn on a person's wrist and/or forearm; (b) one or more display members which are attached to and/or part of the branches of the bifurcating attachment member; (c) a data control unit; and (d) one or more sensors.

This invention can also be embodied in a wearable computing device for the wrist and/or forearm including: (a) an attachment member which is configured to be worn on a person's wrist and/or forearm; (b) a first display member, wherein this first display member is attached to and/or part of the attachment member at a first location, and wherein this first location is a first distance from the outer circumference of the person's arm at the elbow when the arm is fully extended; (c) a second display member, wherein this second display member is attached to and/or part of the attachment member at a second location, wherein this second location is a second distance from the outer circumference of the person's arm at the elbow when the arm is fully extended, and wherein the second distance is less than the first distance; (d) a data control unit; and (e) one or more sensors.

One of the challenges associated with such wearable devices is that the human wrist and/or arm provides a relatively small space for a visual computer-to-human interface, but non-visual modes of communication (such as those based on sound or vibration) can be obscured by environmental noise or vibration and may not be very private. The wearable devices disclosed herein address this challenge with arcuate and/or flexibly-connected displays and display arrays that cumulatively provide relatively-large display areas without looking too clunky or becoming uncomfortable to wear.

Another challenge for such wearable devices is that the human wrist and/or arm provides a relatively small space for a battery. This invention address this challenge with wearable devices and methods which modify device functions based on data from environmental and/or automatic body sensors in order to use energy more efficiently. Another challenge is that the human wrist and/or arm can have different levels of movement and move into different positions relative to the eyes of the person wearing the device and the eyes of other nearby people (from whom information on the device should be kept private). This invention addresses this challenge with wearable devices which selectively enable the wearer to see information on their device from various angles while selectively preventing other people from seeing this information.

One of the new opportunities provided by such wearable devices is the creative use of sensors worn on the body. Sensors worn on the body open up new opportunities for human-to-computer interfaces to expand the usefulness of such devices and even to overcome some of the limitations of handheld computing devices. For example, computing devices which are worn on the body can sense and respond to electromagnetic signals from muscles and nerves in ways that are difficult, or even impossible, with handheld devices. As another example, a computing device which is worn on the body can be easier to see and less likely to be forgotten than a handheld device. Further, systems of wearable devices can measure configurations of body movement based on multiple points of motion, not just a single point of motion as with a handheld device. This invention discloses novel device designs and methods to better take advantage of the unique new opportunities created by wearable devices with various sensors worn on the body.

BRIEF INTRODUCTION TO THE FIGURES

Figure 83:
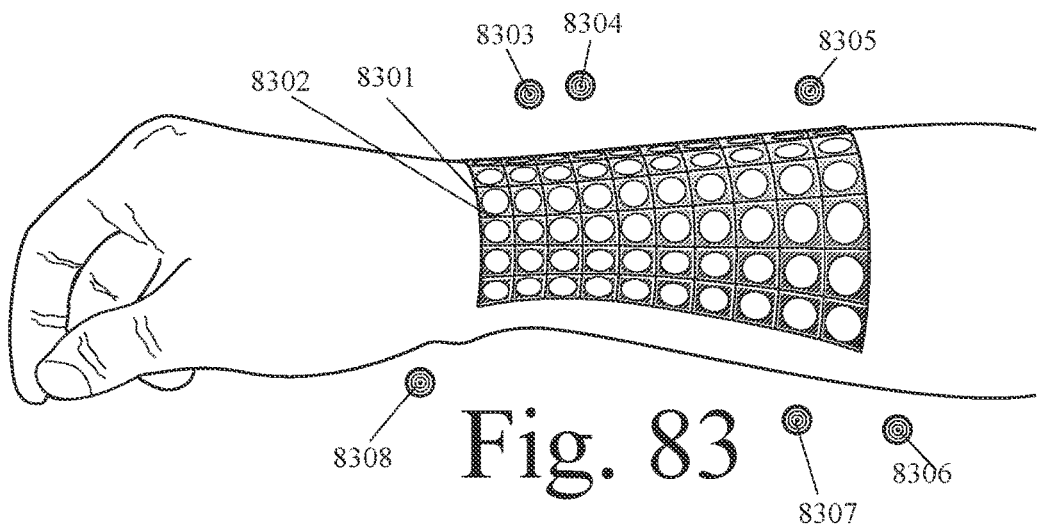
Figure 84:
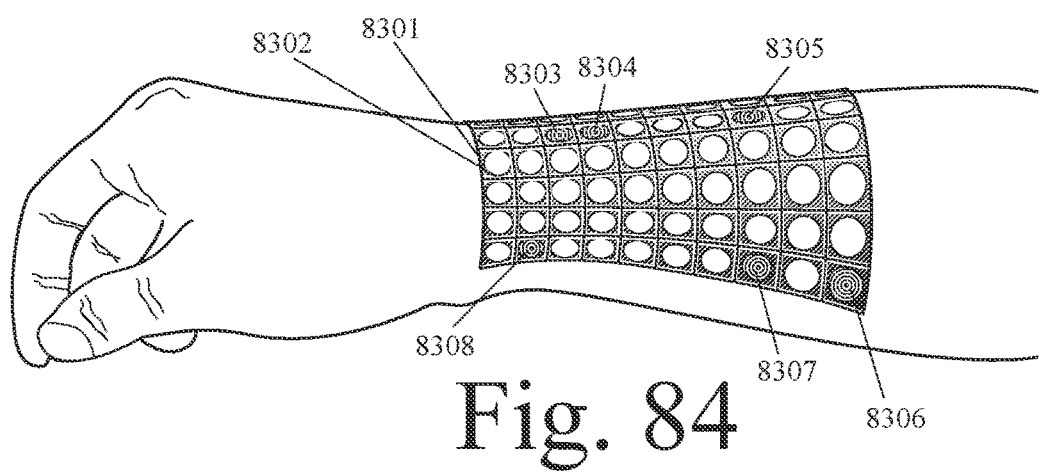
Figure 85:
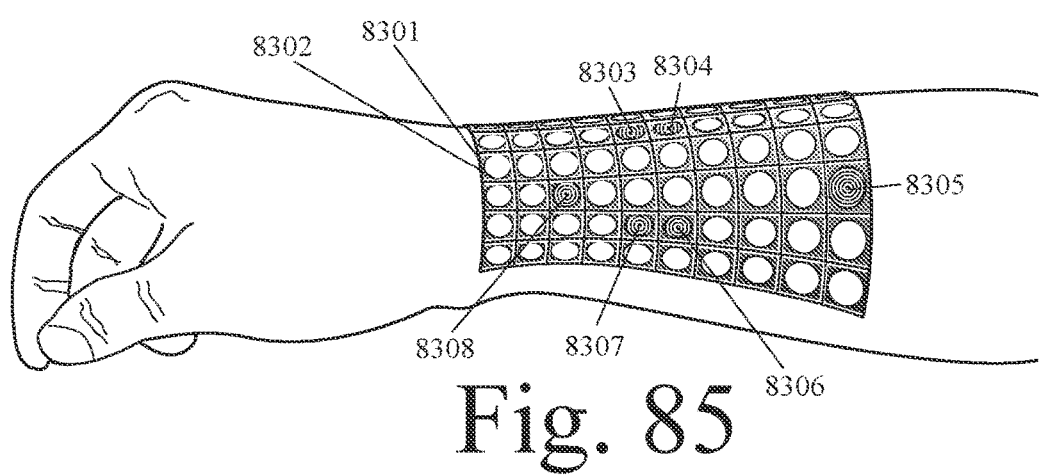

FIGS. 83, 84, and 85 show a wearable device with a distal-to-proximal array of removably-attachable and reconfigurable displays, sensors, and other modules.

Figure 86:
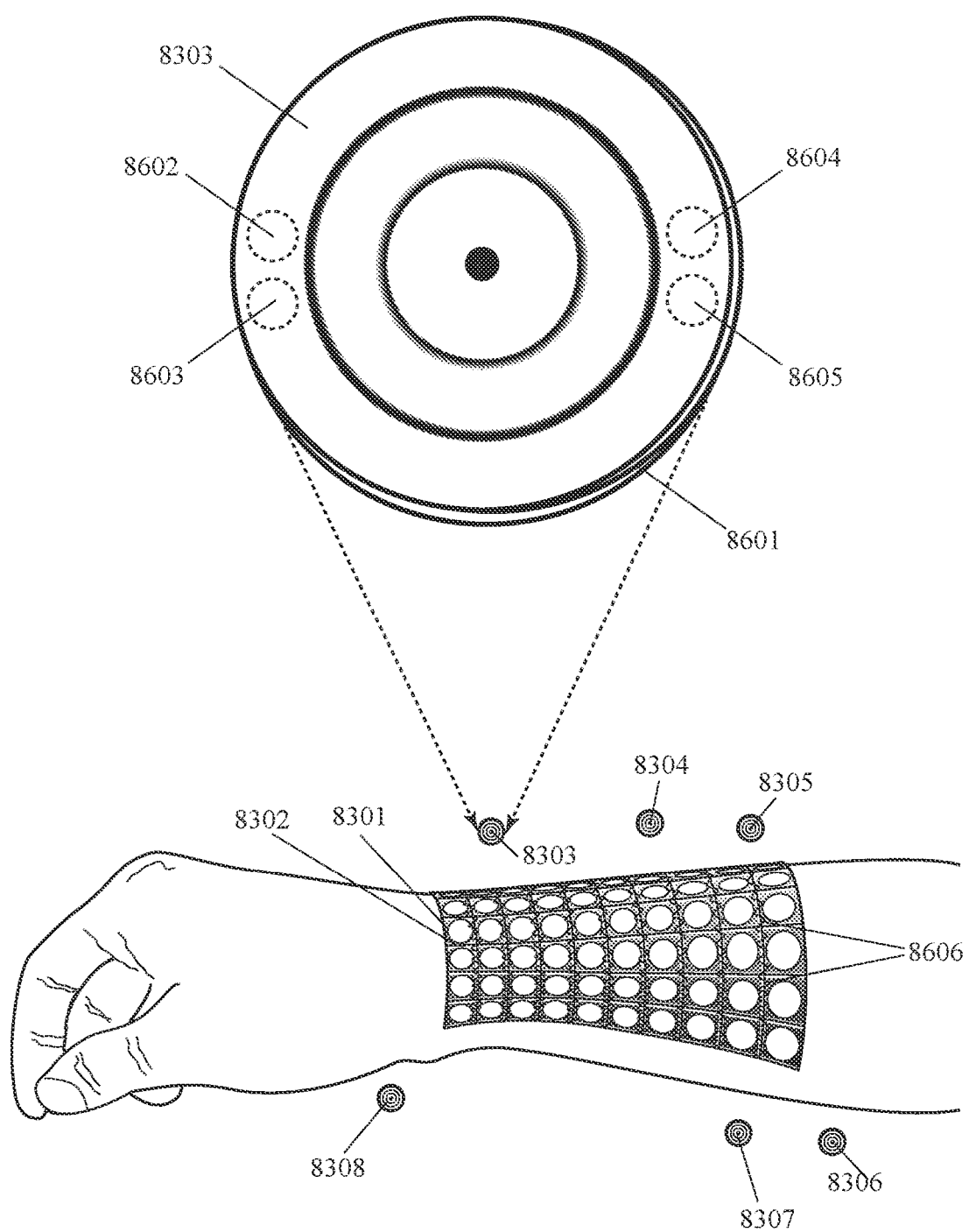

FIG. 86 shows a wearable device with a distal-to-proximal array of circular displays and other modules which are rotationally inserted into openings in an attachment member.

Figure 87:
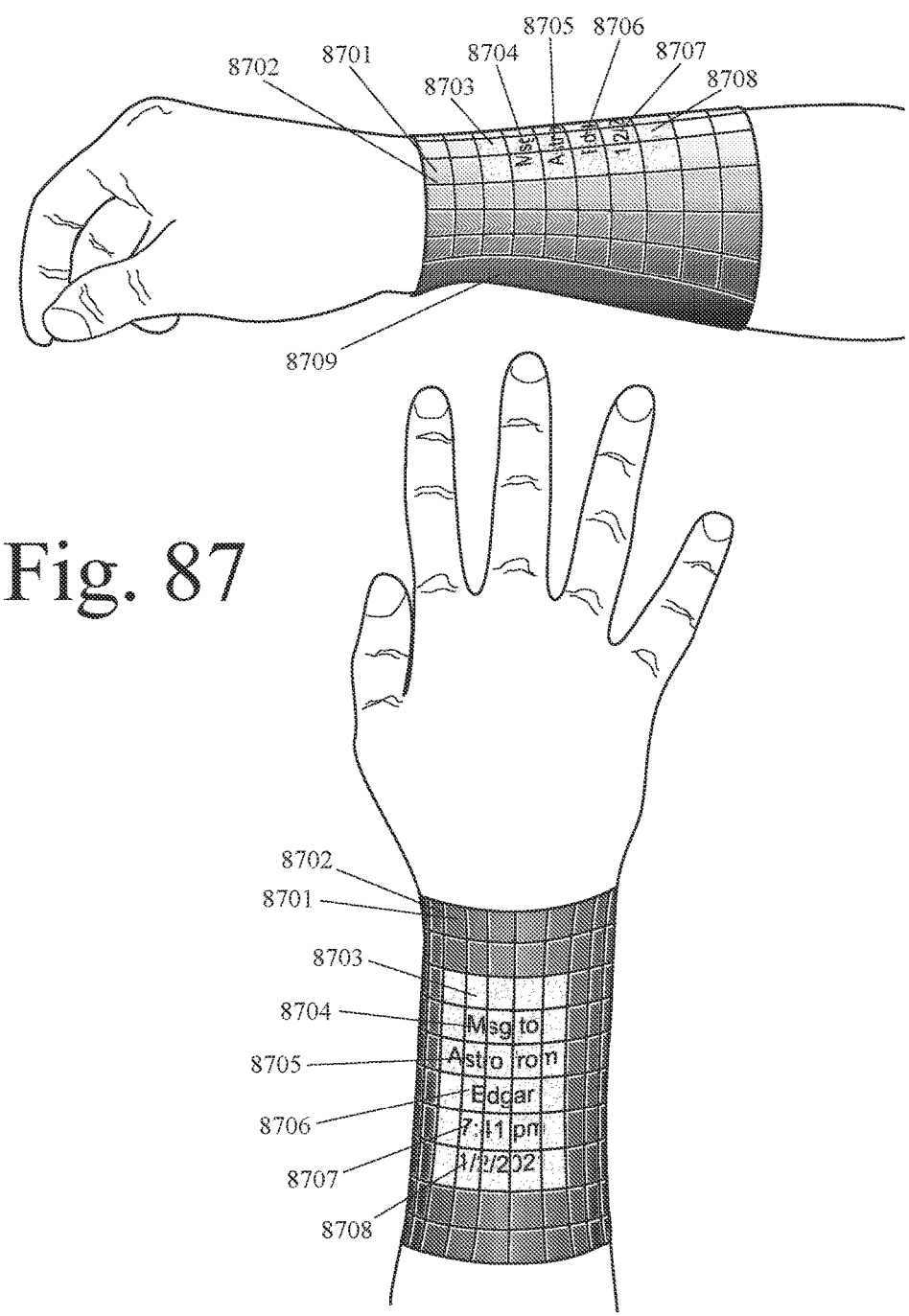

FIG. 87 shows a wearable device with a distal-to-proximal array of flexibly-connected displays, wherein a portion of the device is elastic and/or stretchable.

Figure 88:
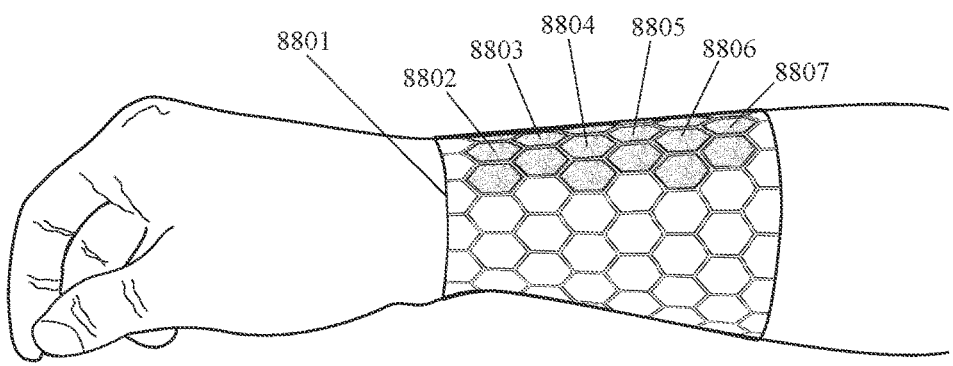
Figure 88:
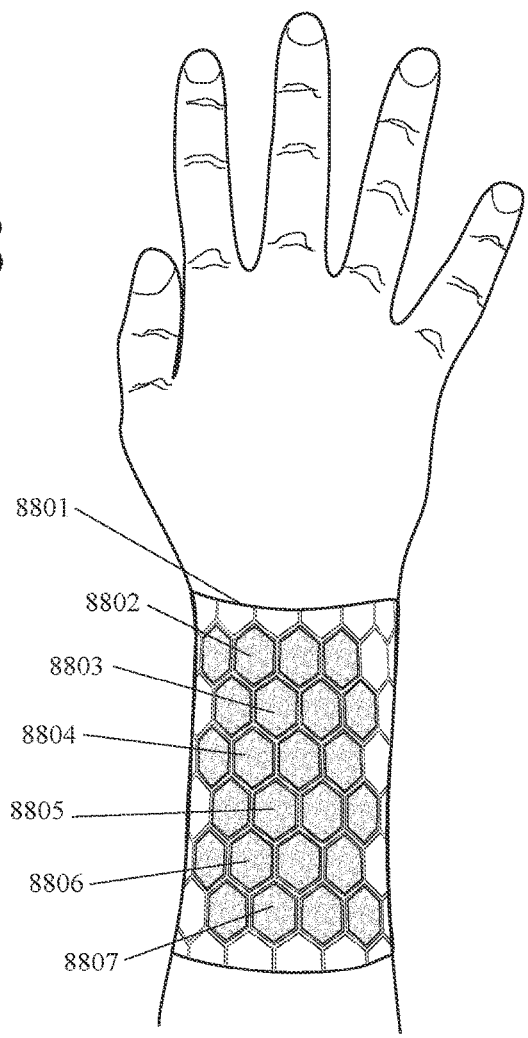

FIG. 88 shows a wearable device with a distal-to-proximal array of flexibly-connected hexagonal displays.

Figure 89:
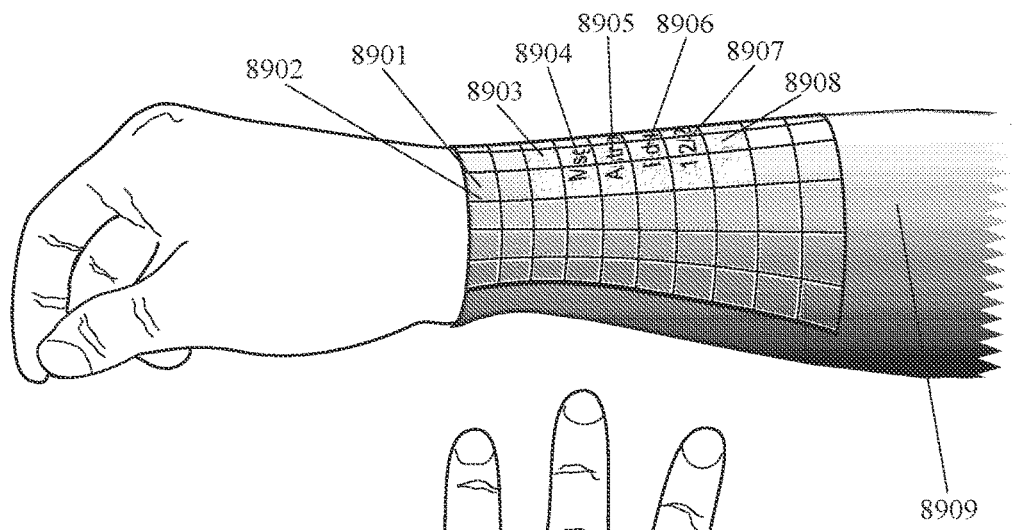
Figure 89:
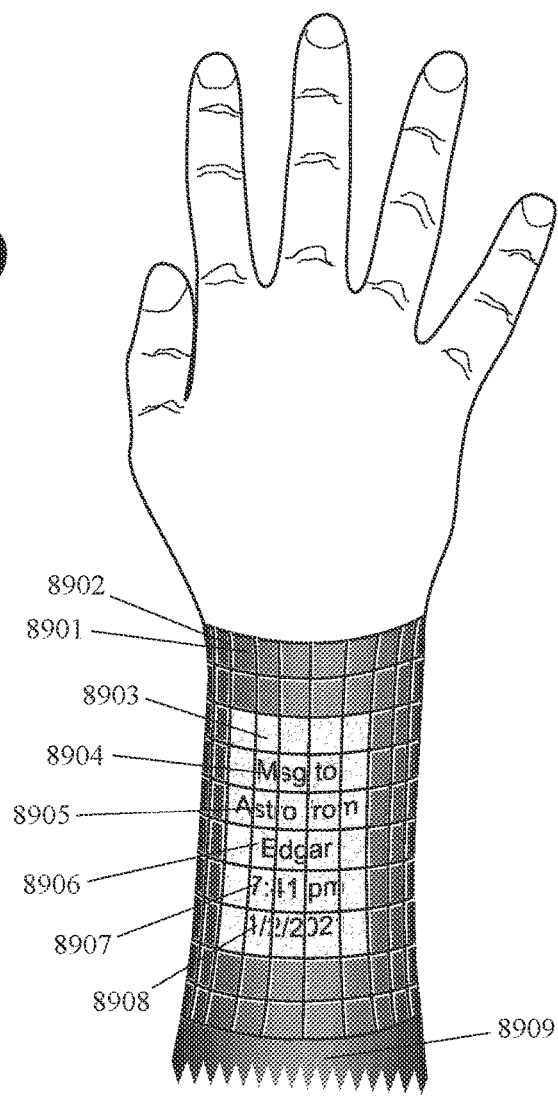

FIG. 89 shows a wearable system including a distal-to-proximal array of flexibly-connected displays and an upper body garment.

Figure 90:
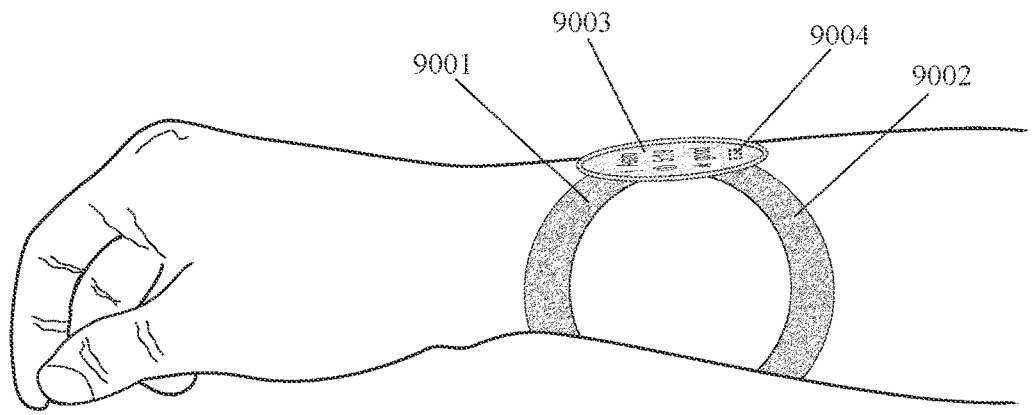
Figure 90:
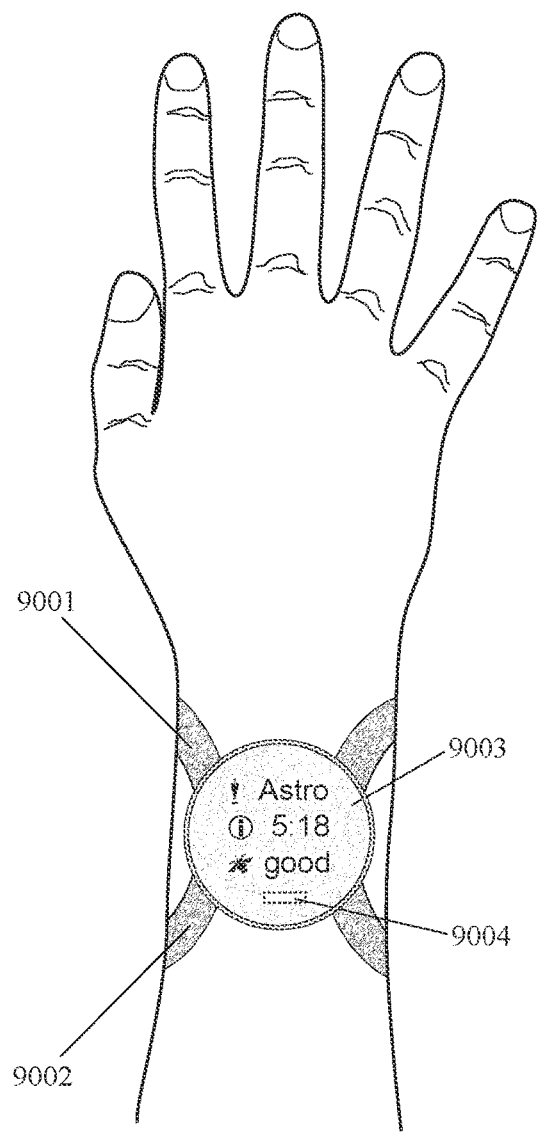

FIG. 90 shows a wearable device with an arcuate display, a proximal arcuate band, and a distal arcuate band.

Figure 91:
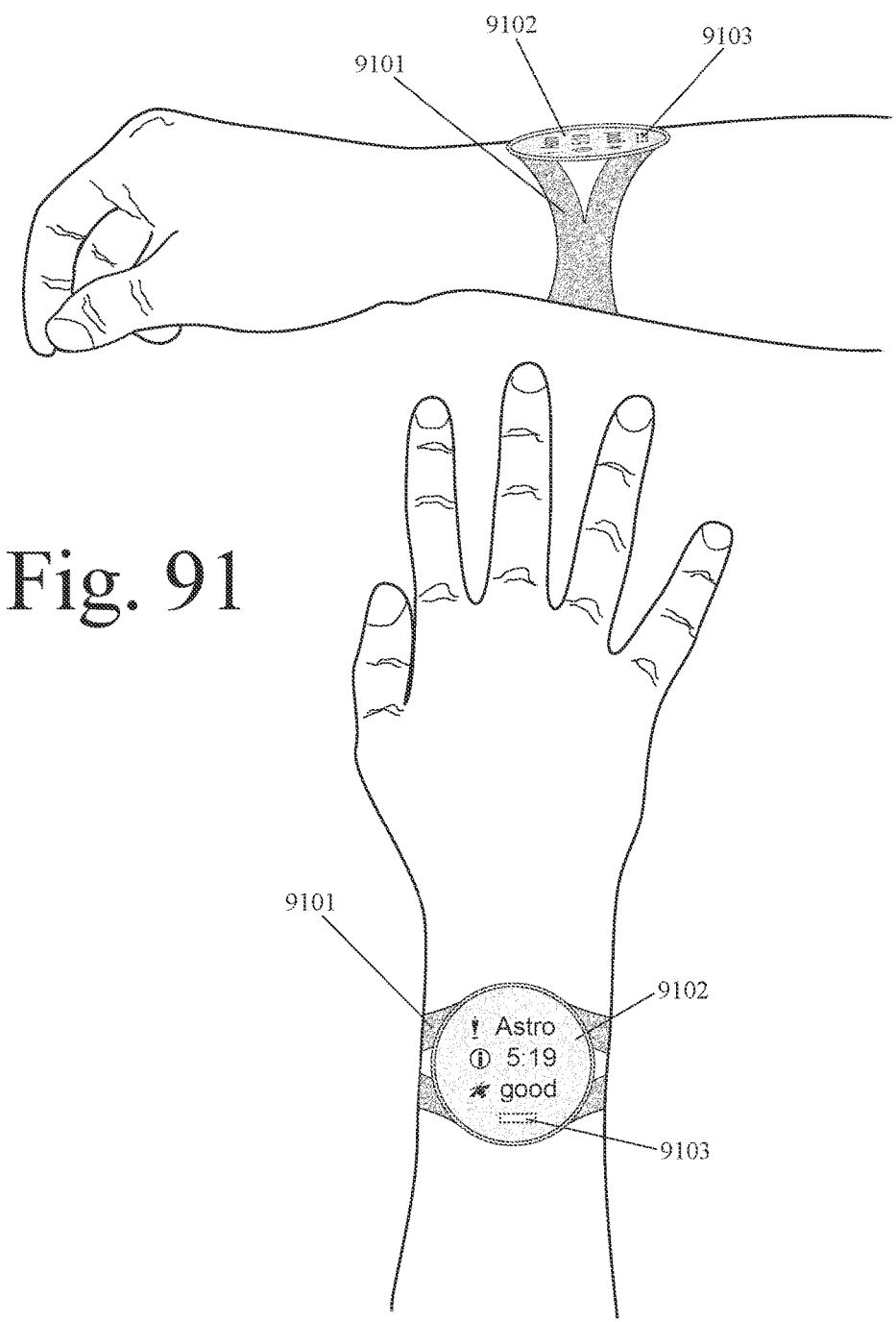

FIG. 91 shows a wearable device with an arcuate display and a circumferentially-converging band with two branches connected to the display.

Figure 92:
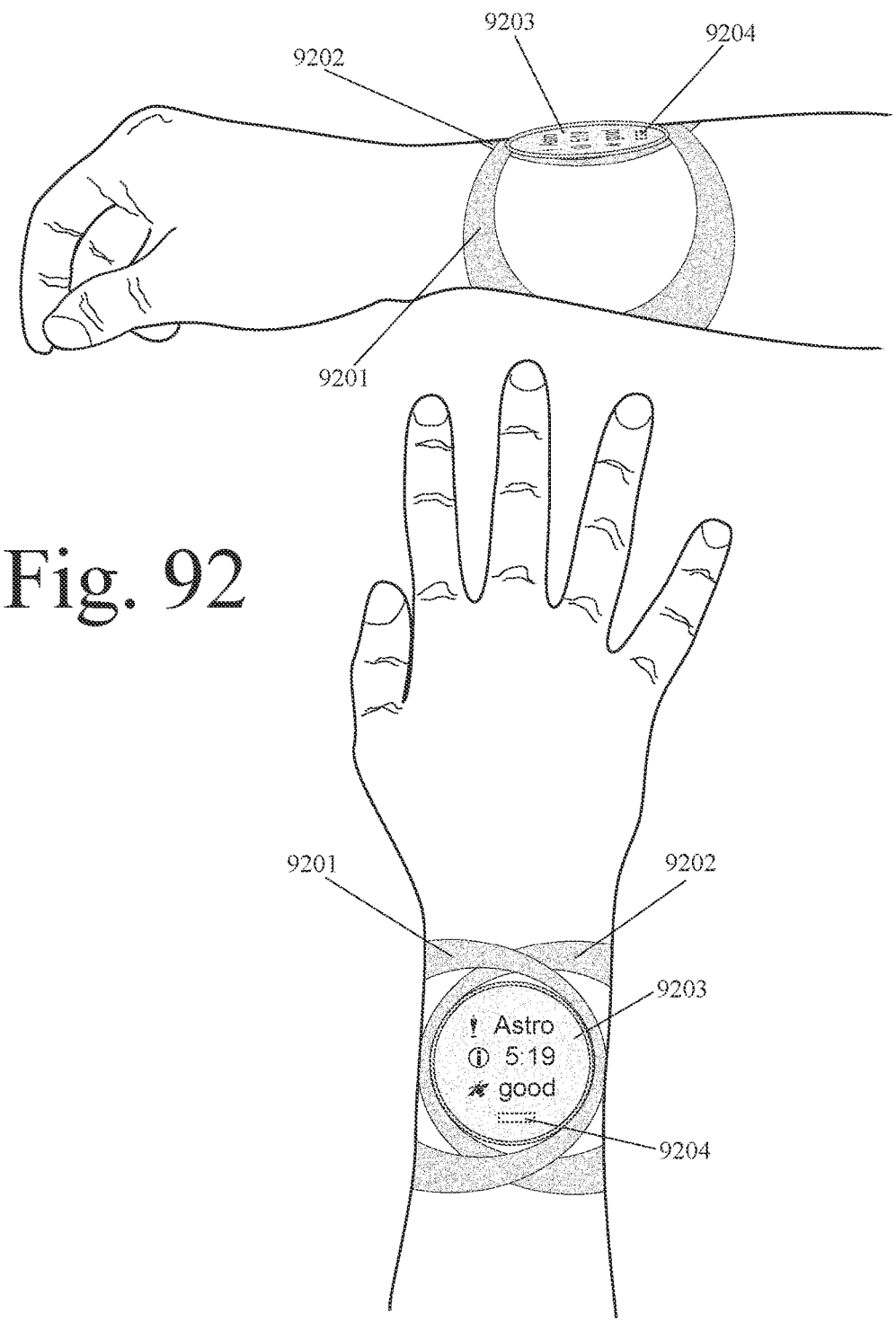

FIG. 92 shows a wearable device with a left loop around the right side of a display and a right loop around the left side of the display.

Figure 93:
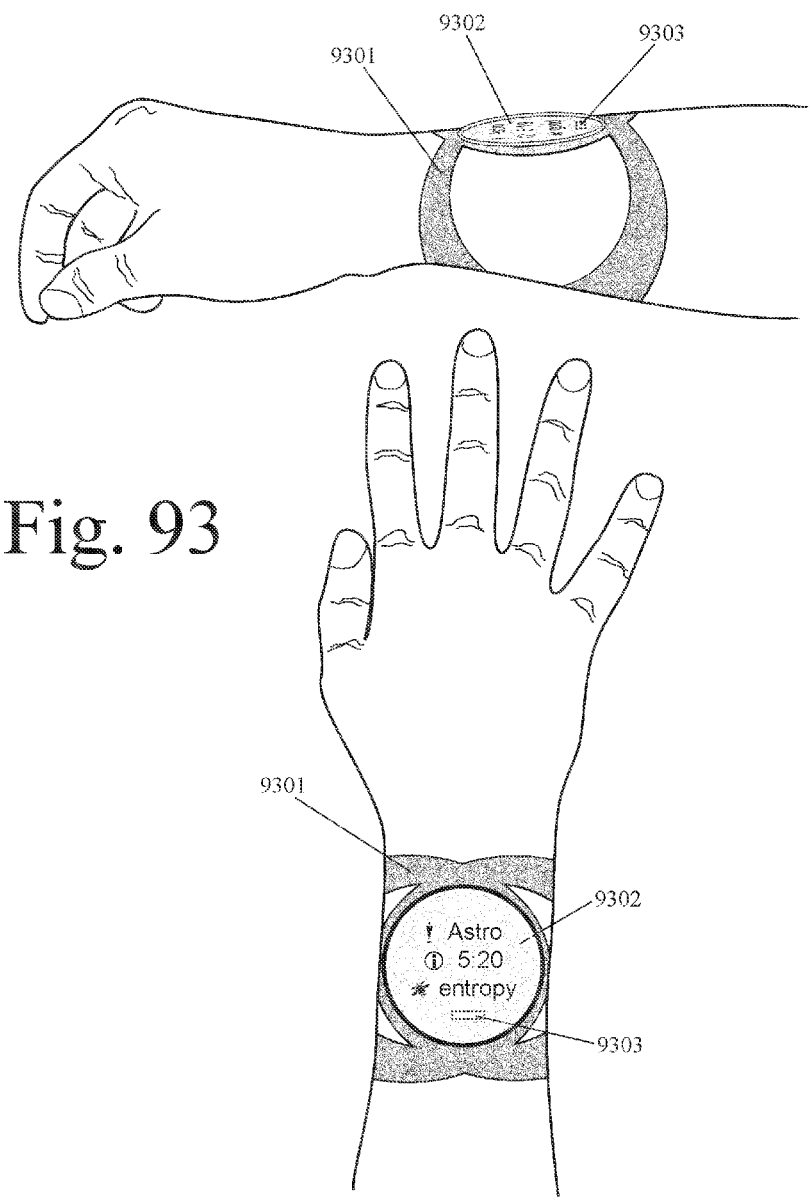

FIG. 93 shows a wearable device like the one in FIG. 92 except that the loops are merged.

FIG. 94 shows a wearable device with an elliptical display, a proximal band, and a distal band.

Figure 95:
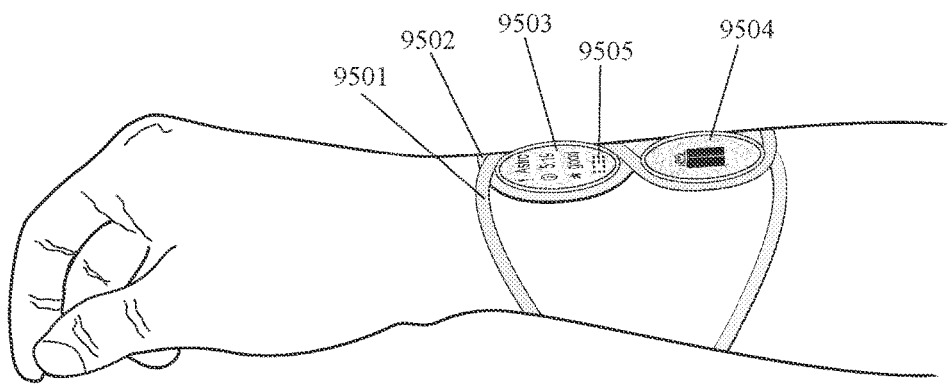
Figure 95:
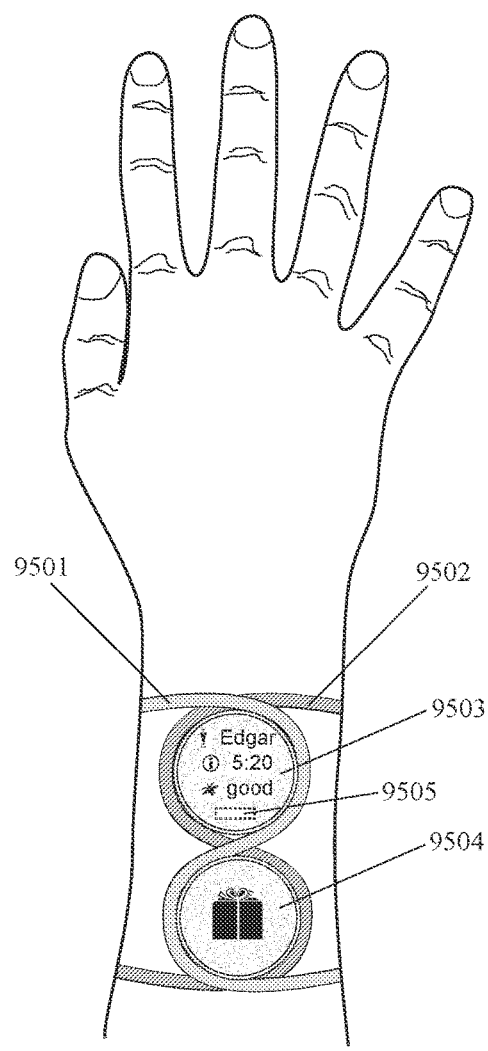

FIG. 95 shows a wearable device with a proximal arcuate display, a distal arcuate display, a first loop around the right side of the distal display and the left side of the proximal display, and a second loop around the left side of the distal display and the right side of the proximal display.

Figure 96:
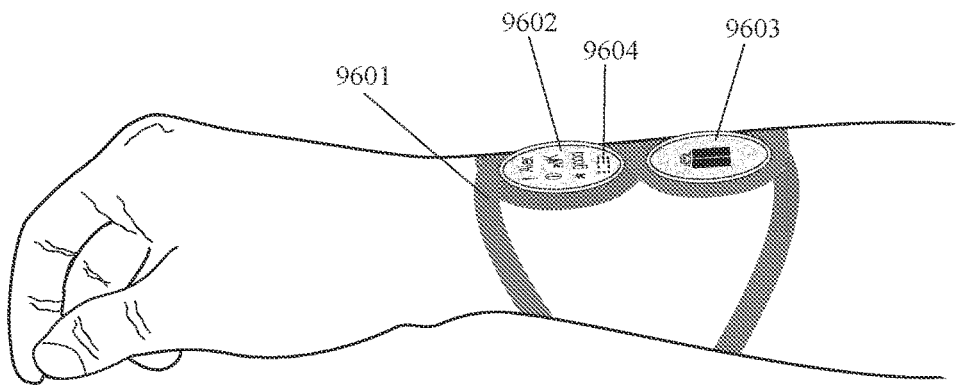
Figure 96:
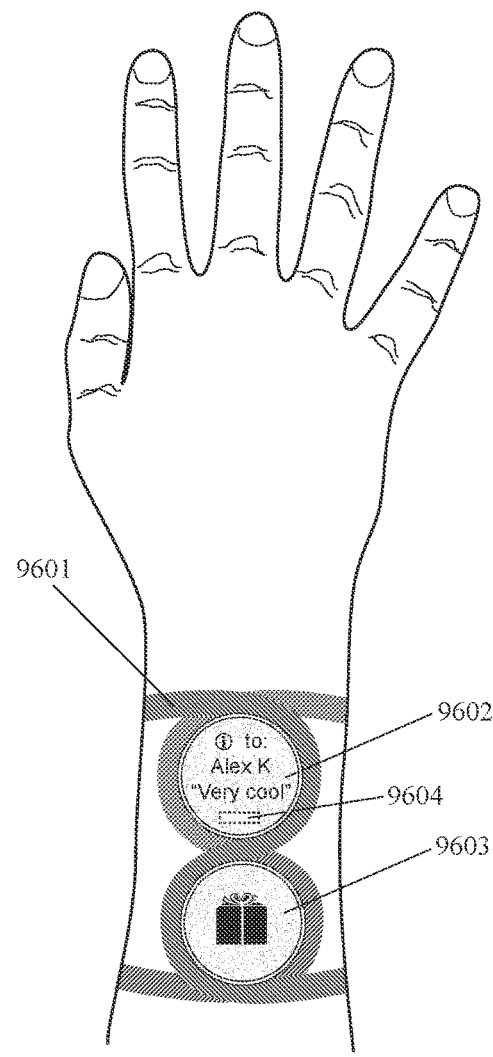

FIG. 96 shows a wearable device like the one in FIG. 95 except that the loops are merged to form a figure eight.

Figure 97:
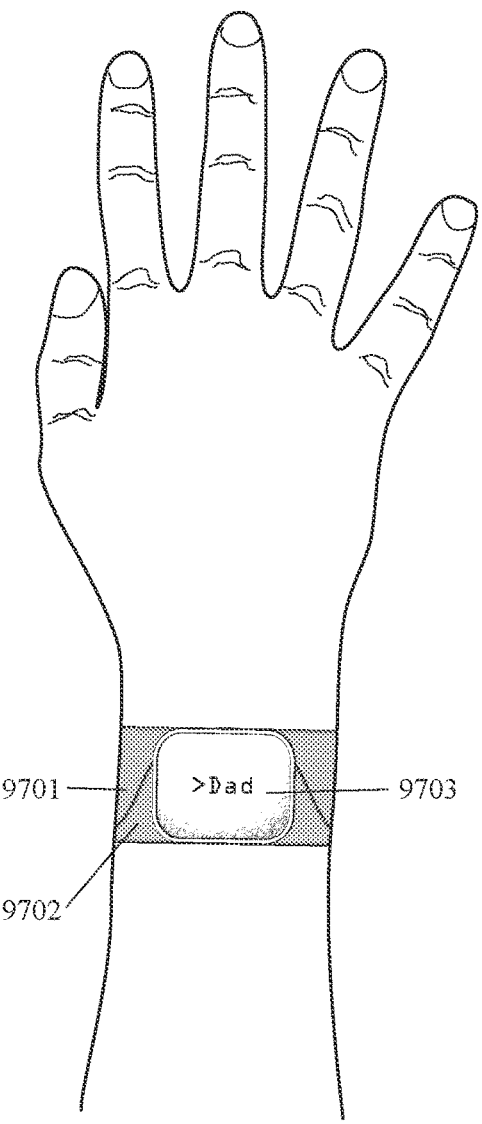
Figure 98:
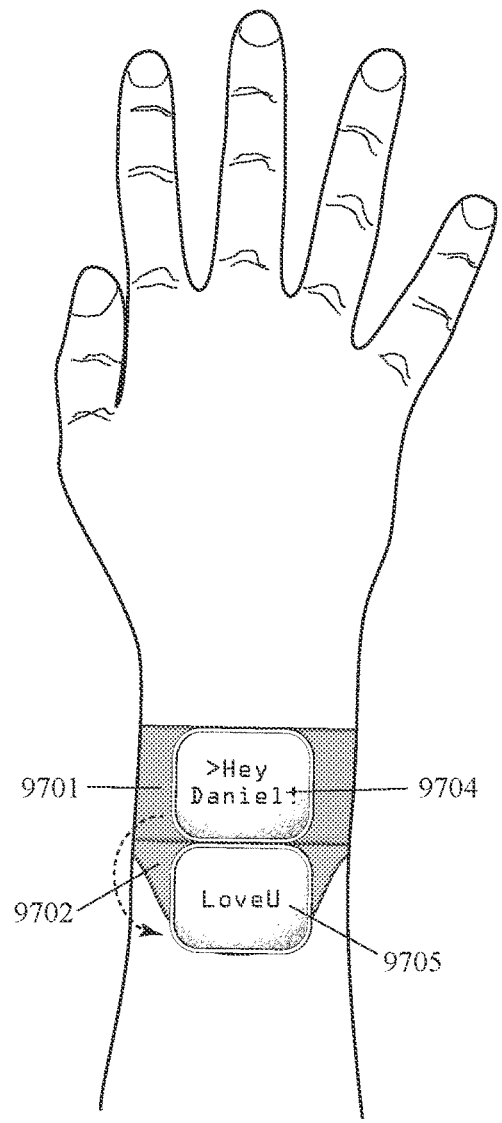

FIGS. 97 and 98 show a wearable device with a folding display and band.

Figure 99:
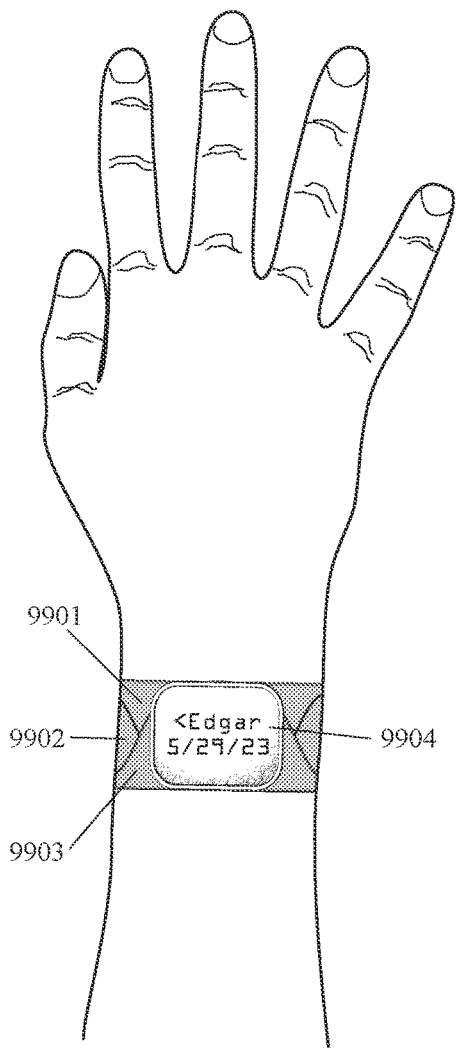
Figure 100:
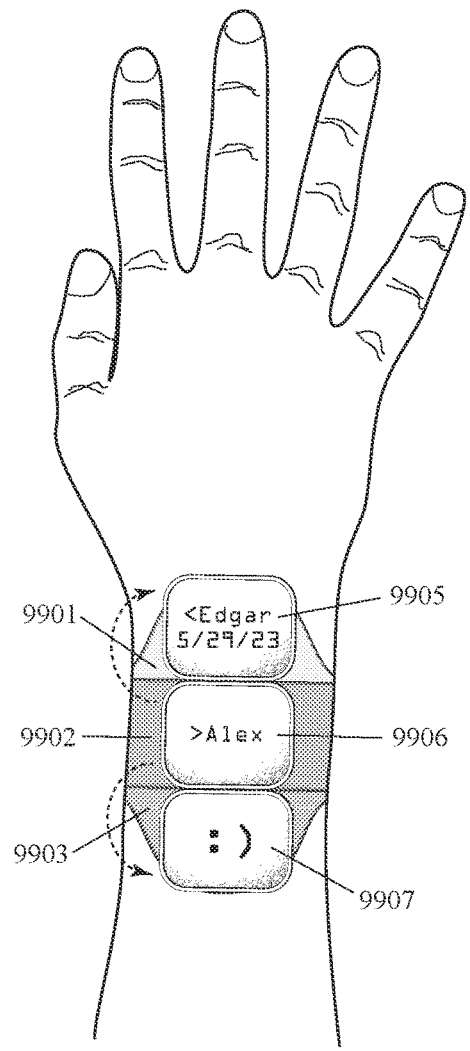

FIGS. 99 and 100 show a wearable device with multiple folding displays and bands.

Figure 101:
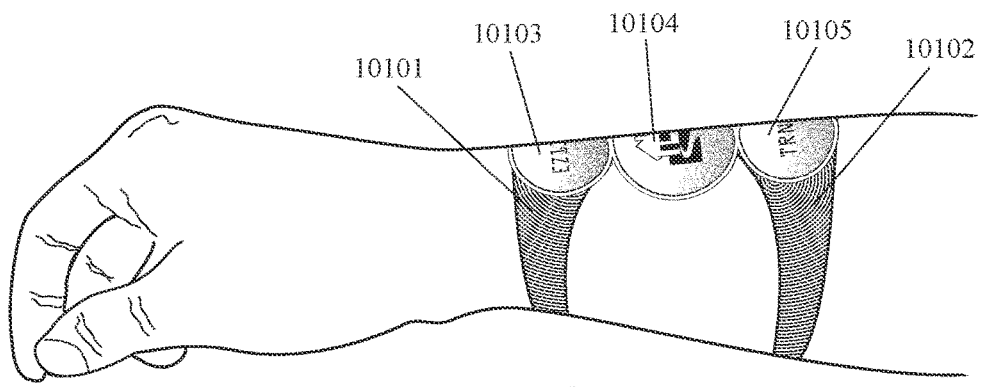
Figure 101:
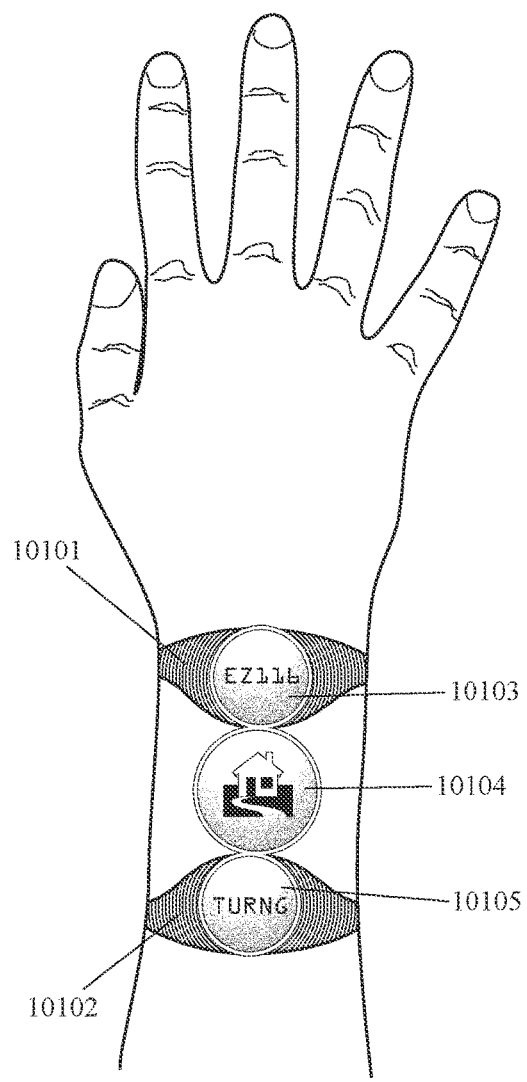

FIG. 101 shows a wearable device with three arcuate displays in a distal-to-proximal configuration.

Figure 102:
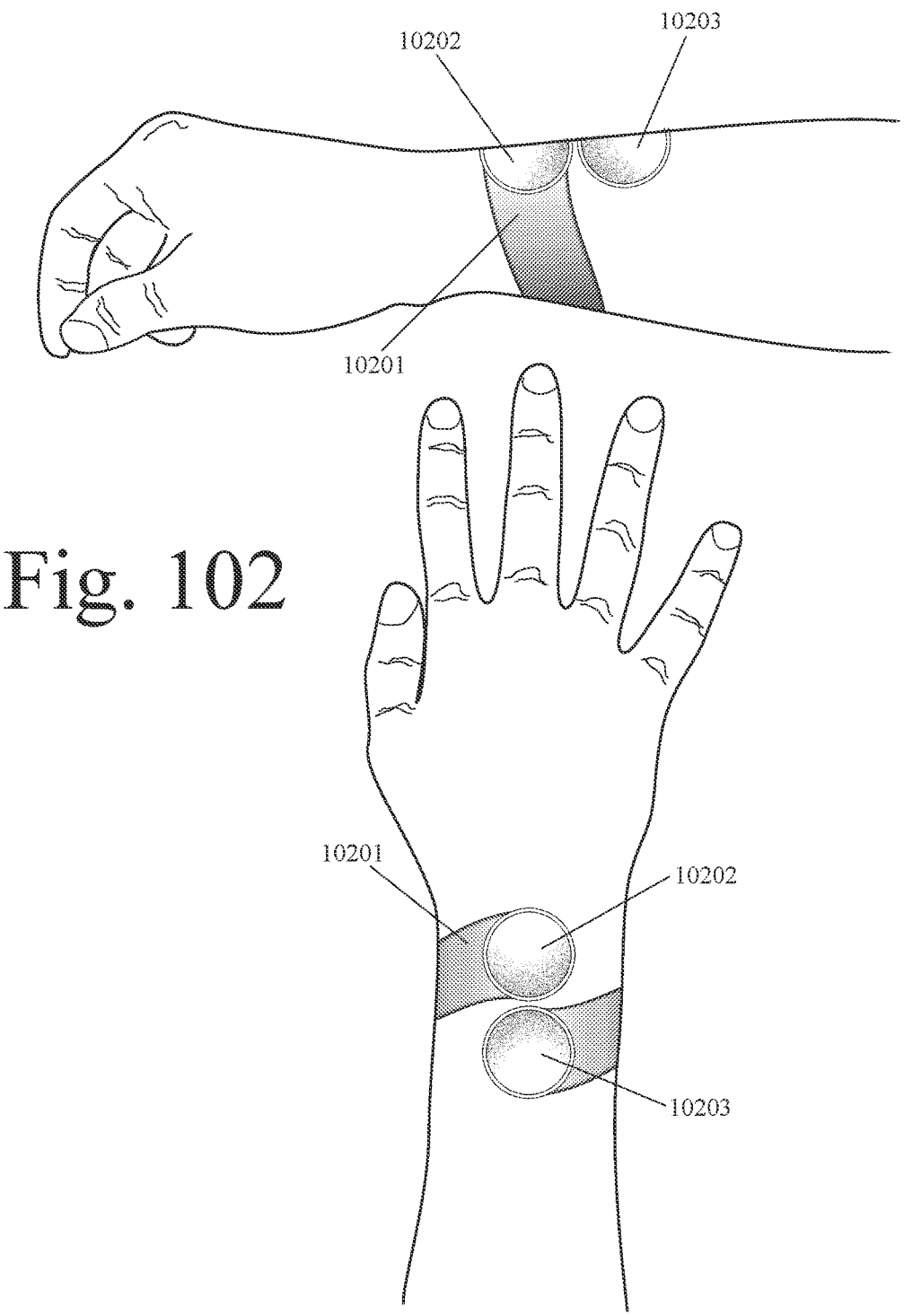

FIG. 102 shows a wearable device with two displays on the ends of a spiral bracelet.

Figure 103:
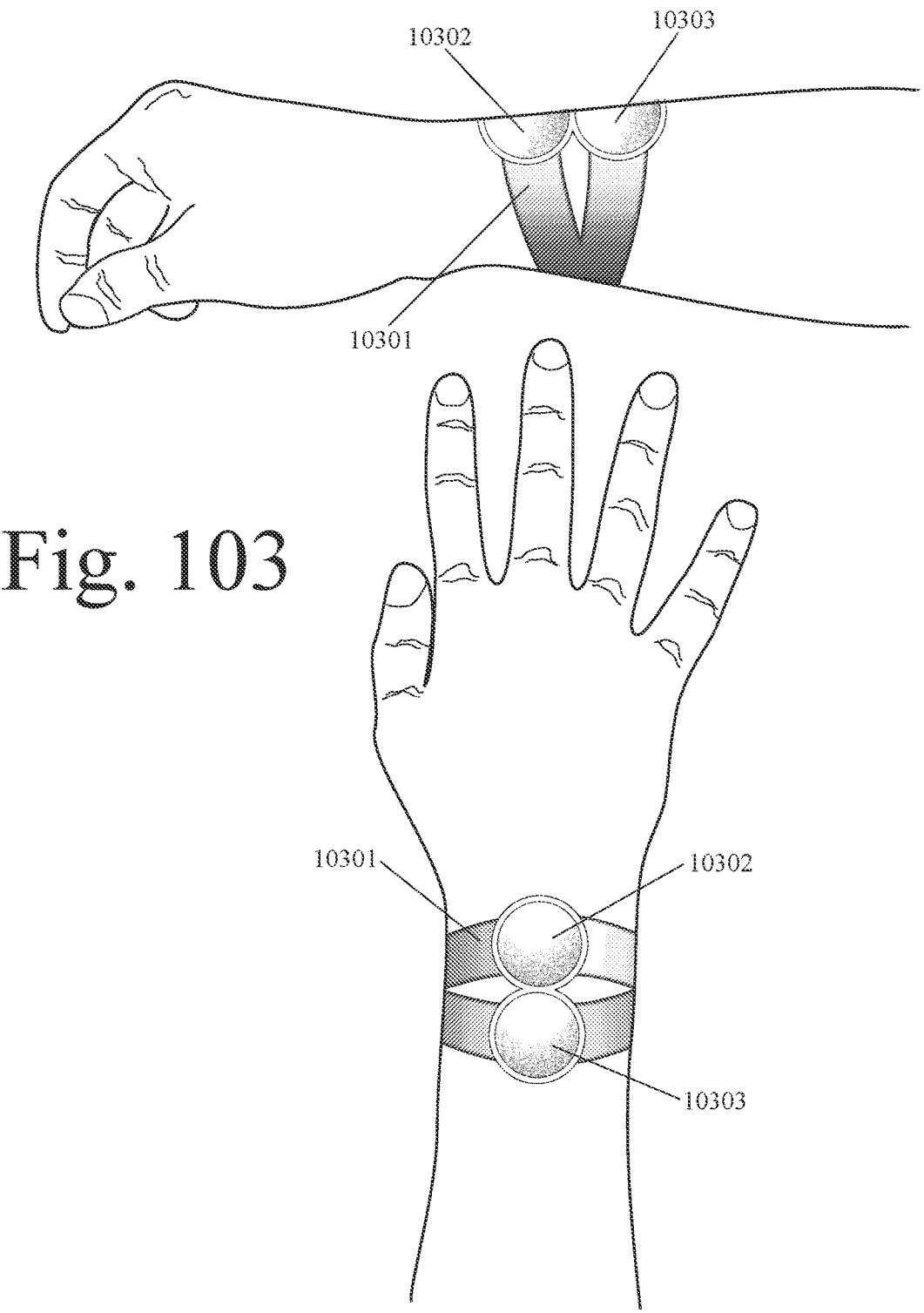

FIG. 103 shows a wearable device with two displays on the branches a bifurcated bracelet.

Figure 104:
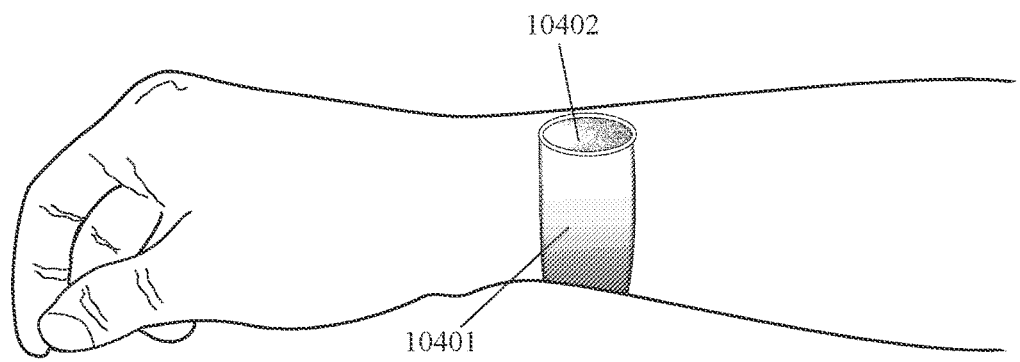
Figure 104:
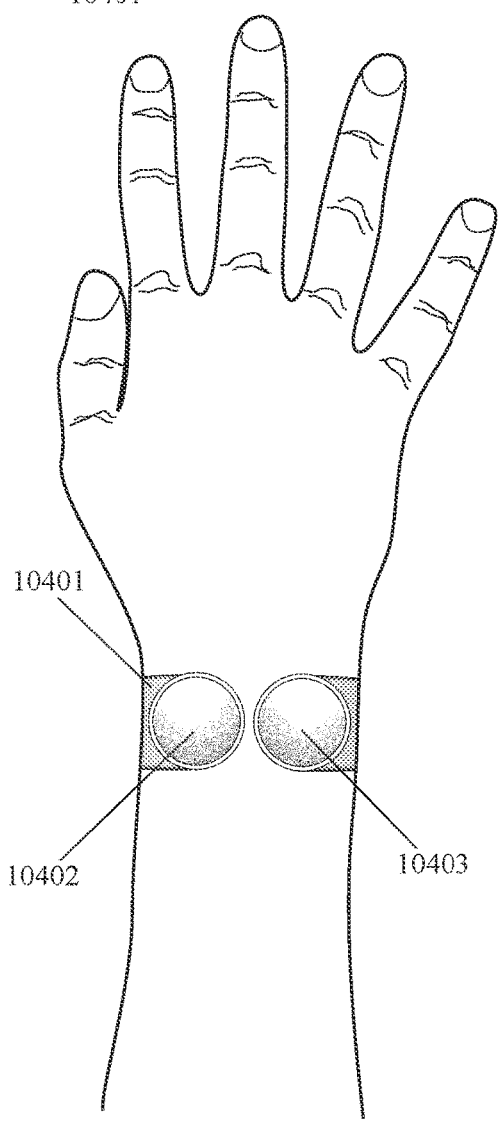

FIG. 104 shows a wearable device with two displays on the ends of a partial-circle bracelet.

FIGS. 105, 106, 107, and 108 show a wearable device with two displays which can be independently rotated around the wrist and/or forearm conference.

Figures 109, 110:
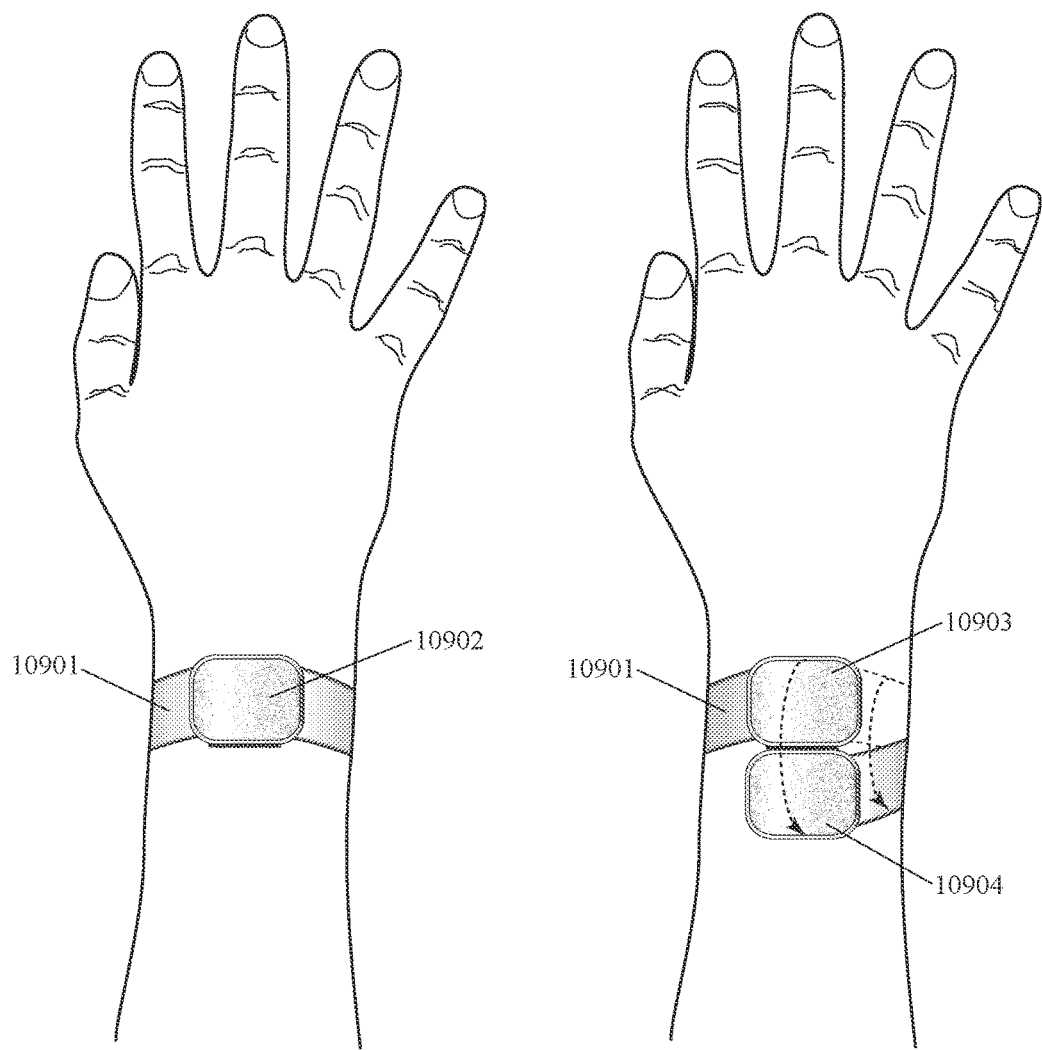

FIGS. 109 and 110 show a wearable device with a single folding display attached to a band.

Figure 111:
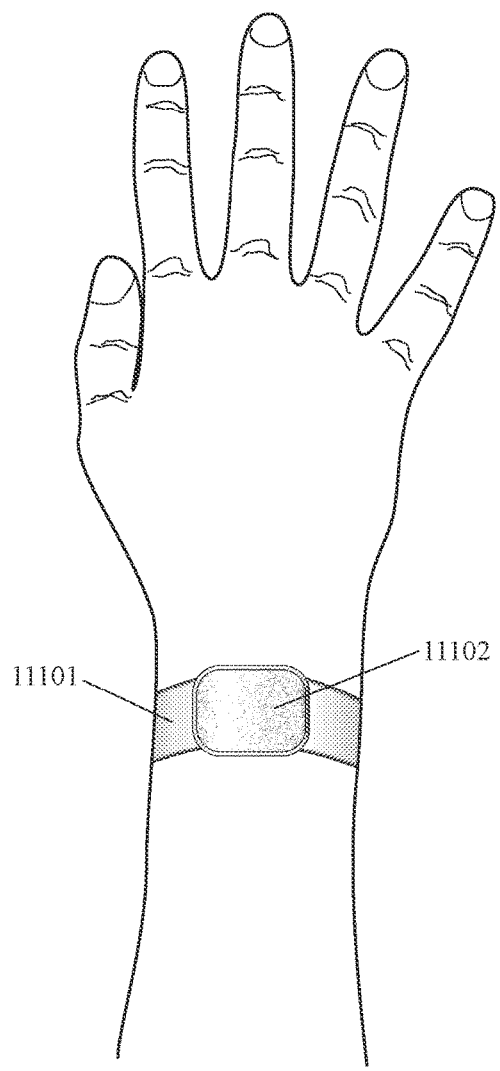
Figure 112:
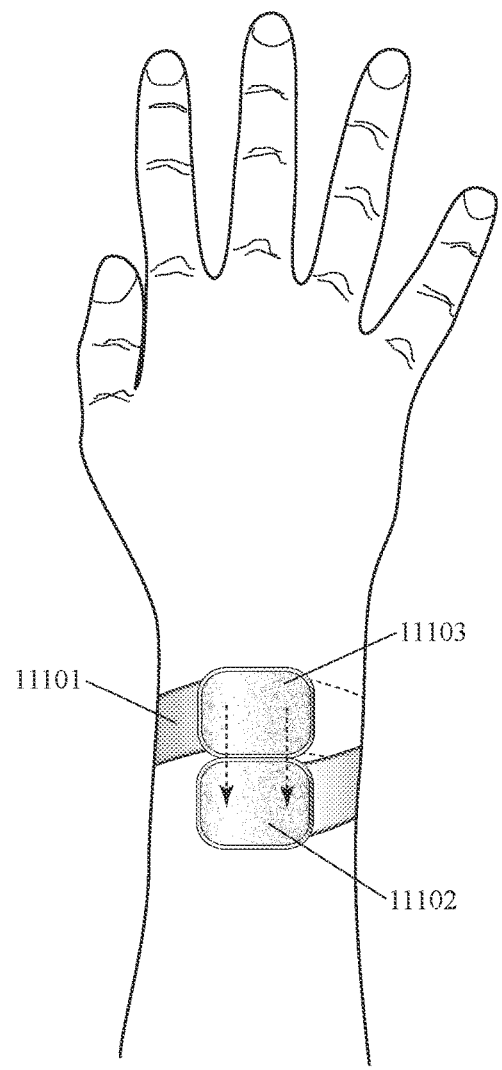

FIGS. 111 and 112 show a wearable device with a single sliding display attached to a band.

Figure 113:
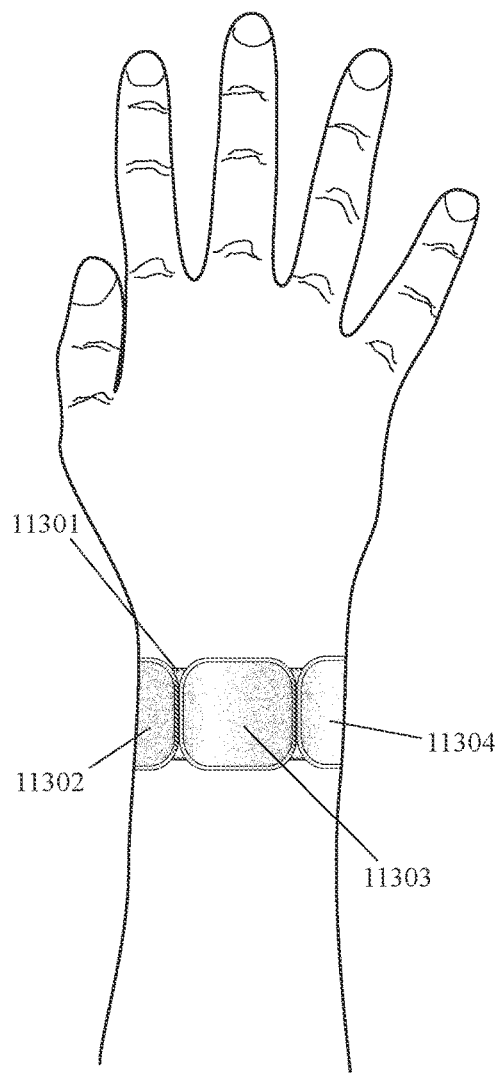
Figure 114:
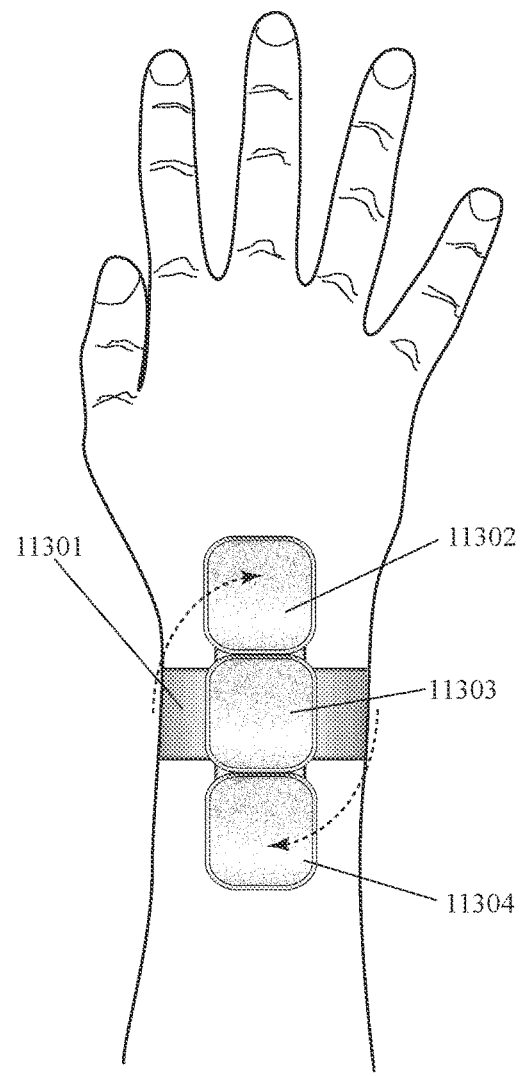

FIGS. 113 and 114 show a wearable device with a rotating sequence of three displays.

Figure 115:
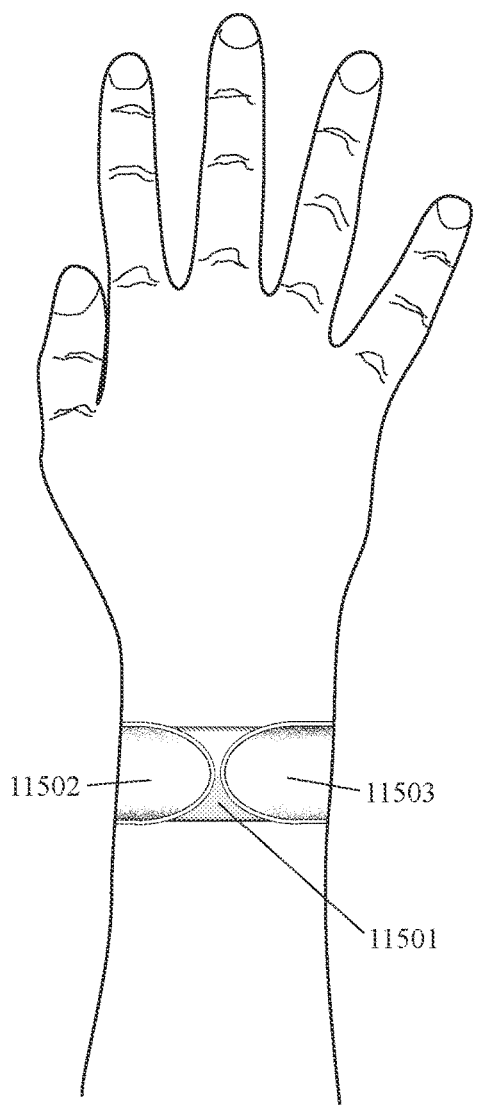
Figure 116:
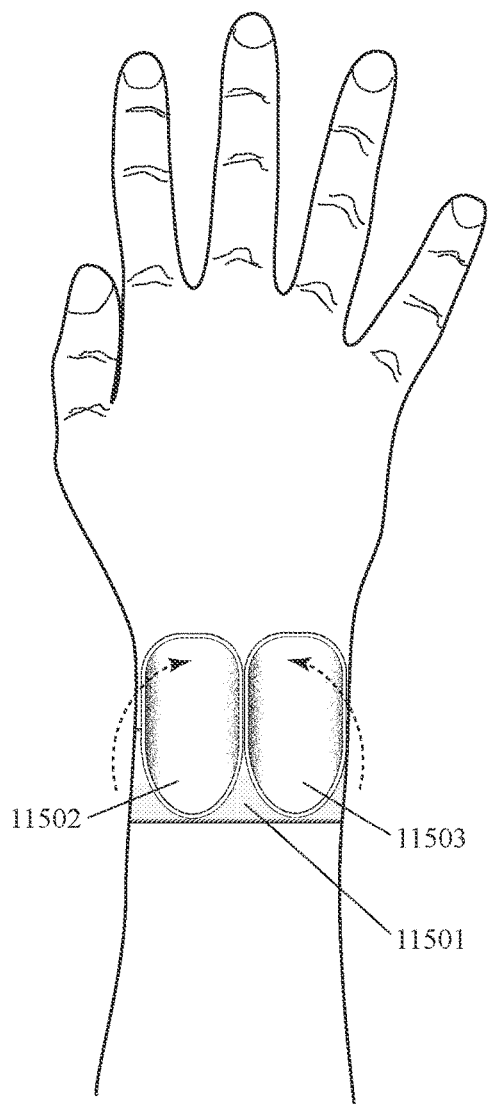

FIGS. 115 and 116 show a wearable device with two rotating displays.

Figures 117, 118:
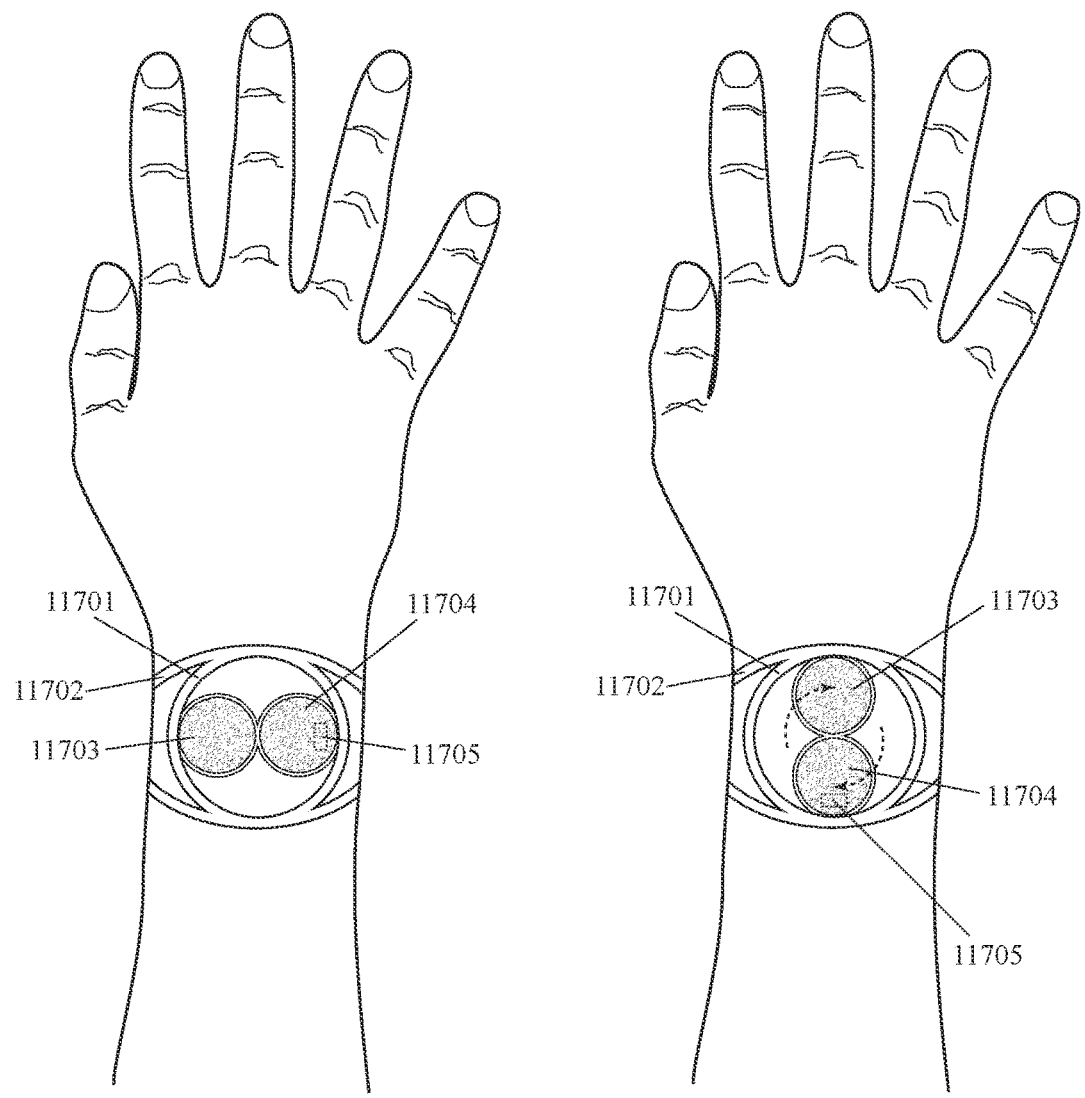

FIGS. 117 and 118 show a wearable device with two displays which are rotatable within an attachment member with an inner circular portion and an outer arcuate portion.

Figure 119:
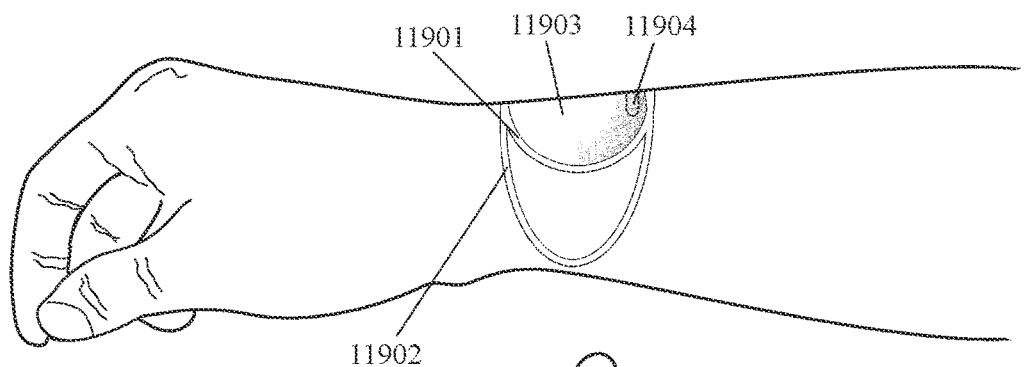
Figure 119:
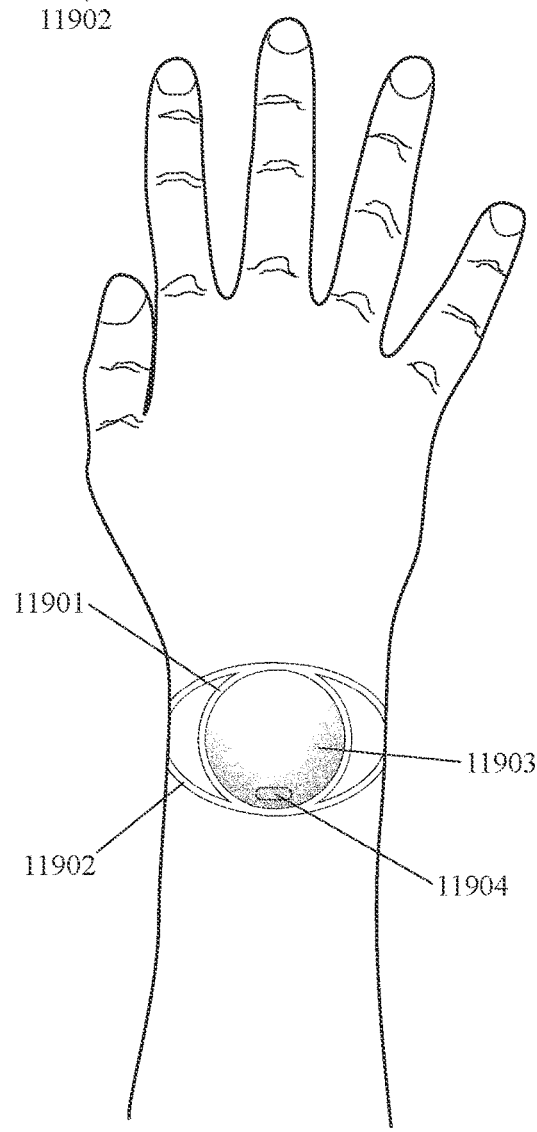

FIG. 119 shows a wearable device with a display inside an attachment member with an inner circular portion and an outer convex portion.

Figure 120:
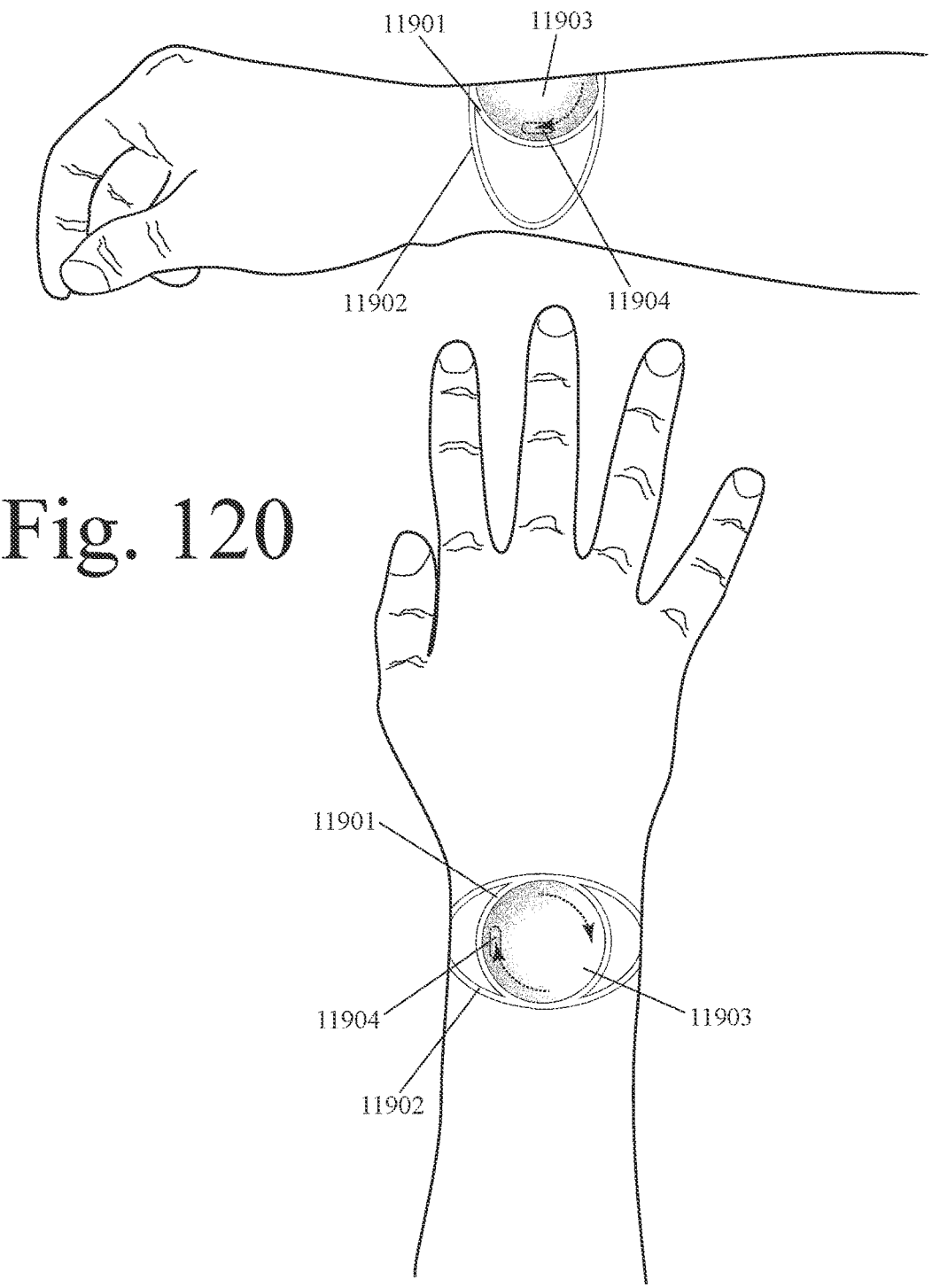

FIG. 120 shows a wearable device with a display which is rotatable within an attachment member with an inner circular portion and an outer convex portion.

Figure 121:
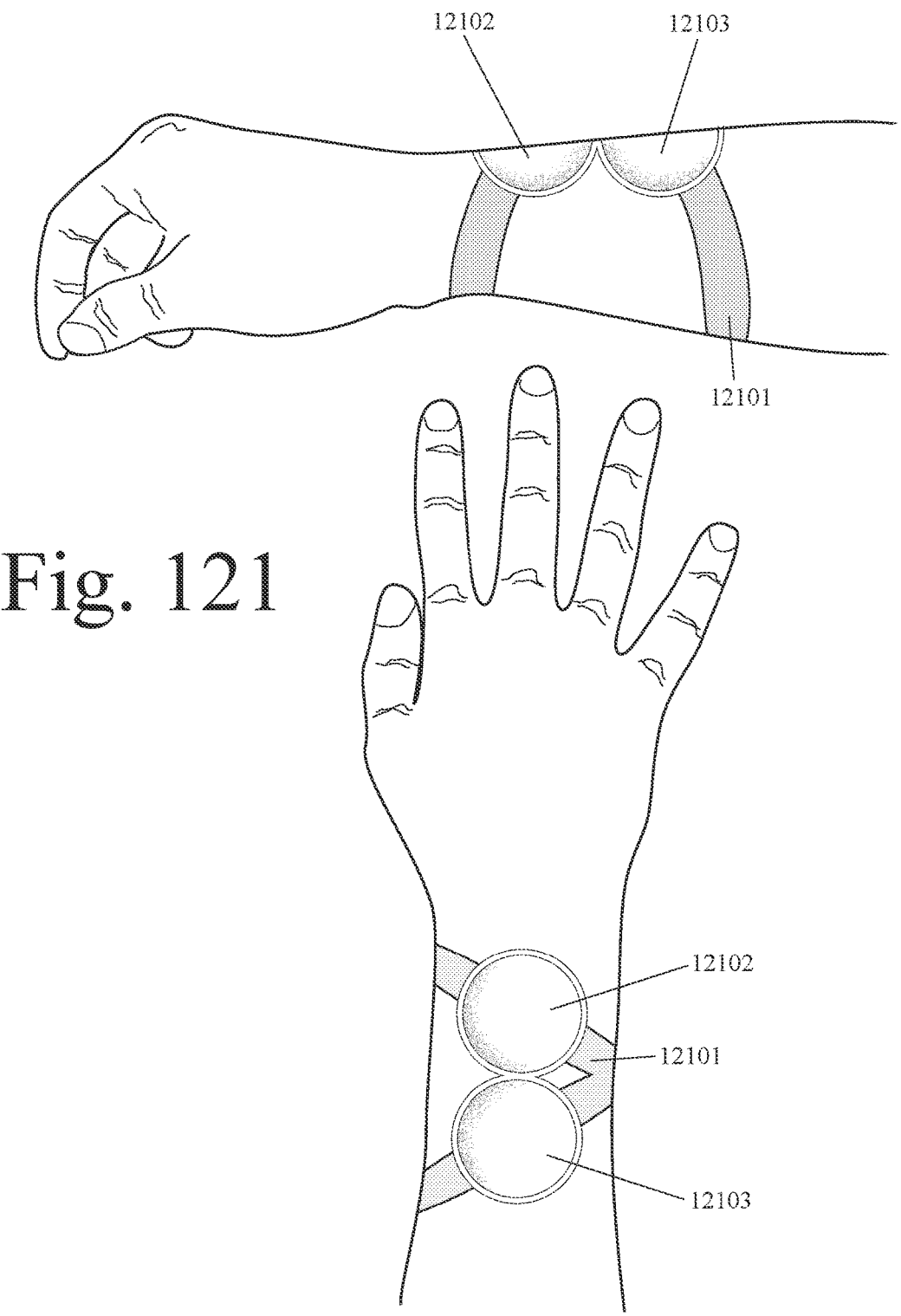

FIG. 121 shows a wearable device with two displays and a longitudinally-asymmetric bifurcated attachment member.

Figure 122:
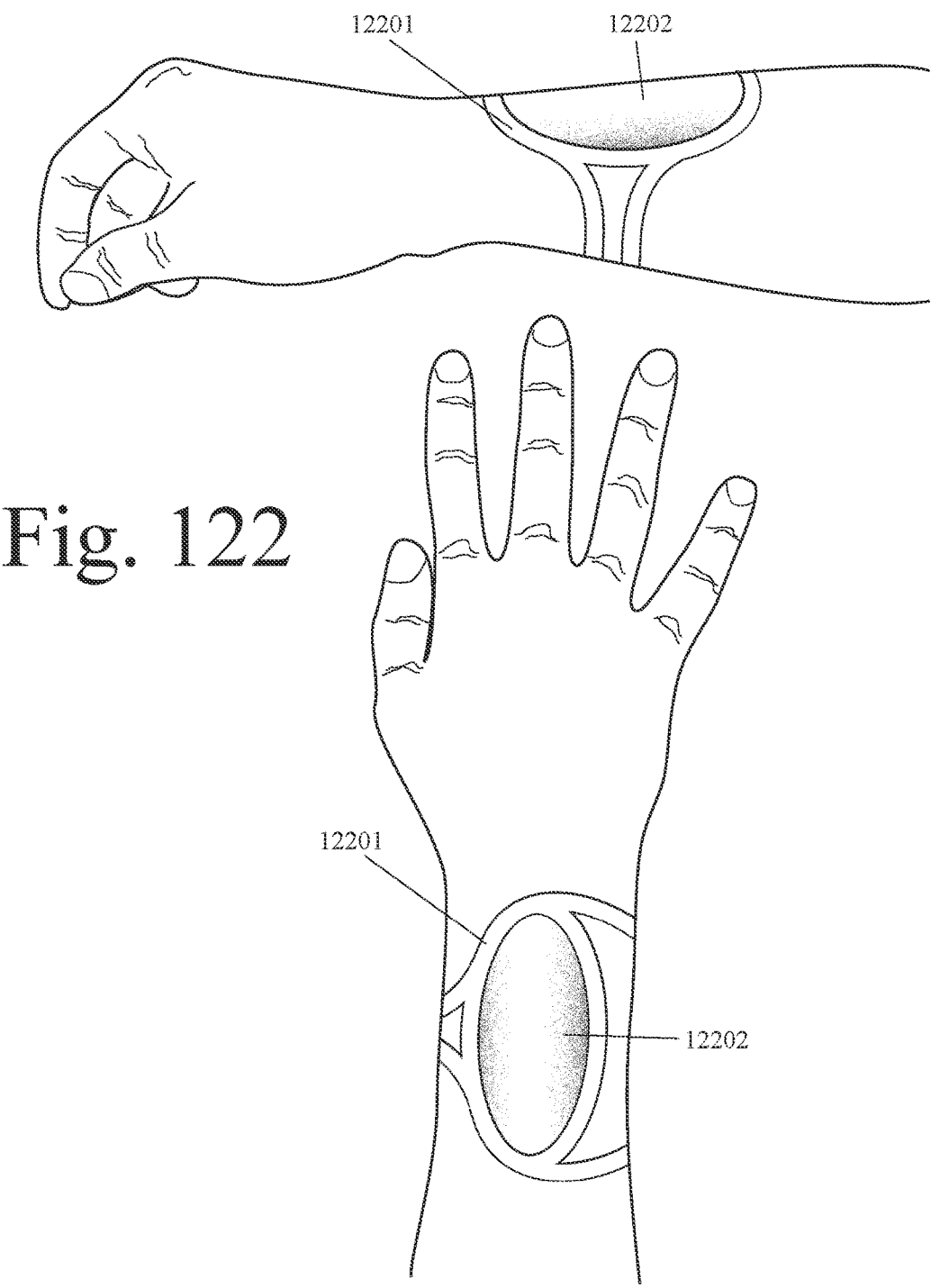
Figure 123:
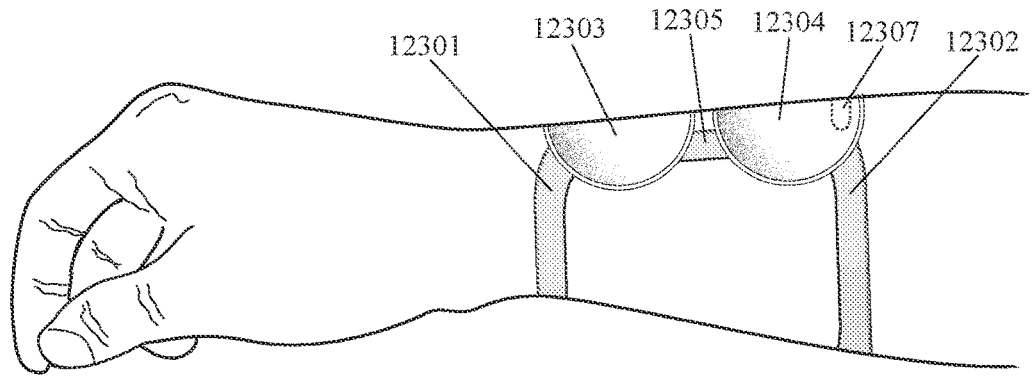
Figure 123:
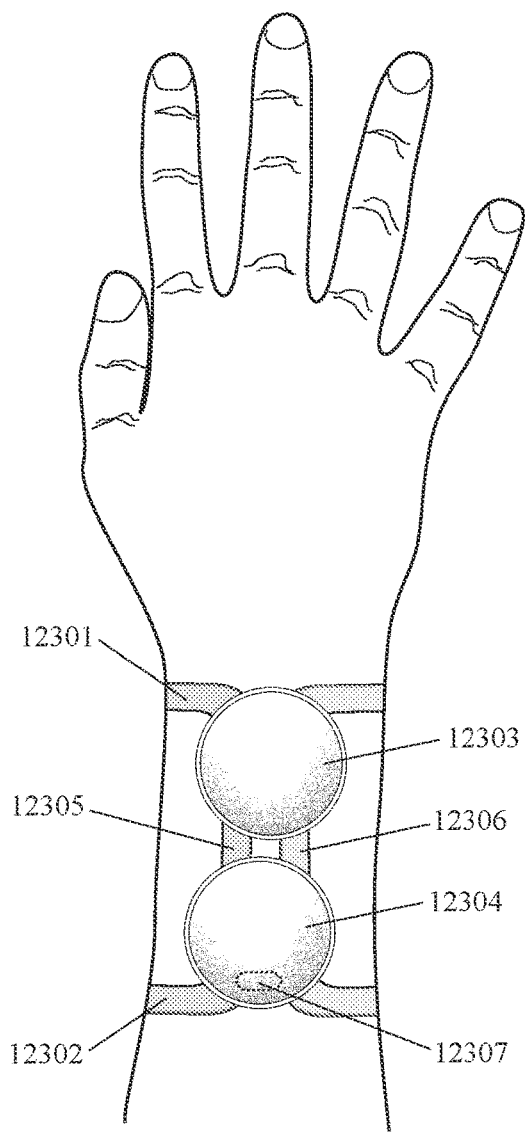

FIG. 122 shows a wearable device with a display and a longitudinally-asymmetric attachment member comprising an elliptical member, a distal arcuate member, and a proximal arcuate member FIG. 123 shows a wearable device with two displays, a distal attachment member, a proximal attachment member, and two connectors between the displays.

Figure 124:
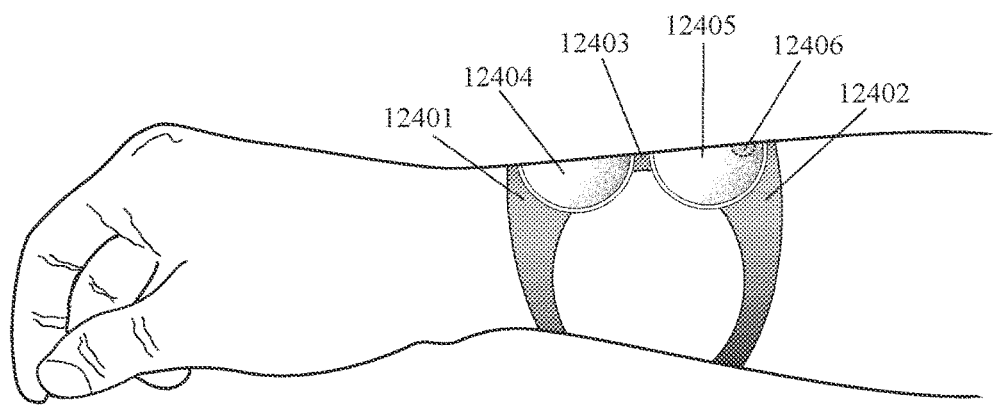
Figure 124:
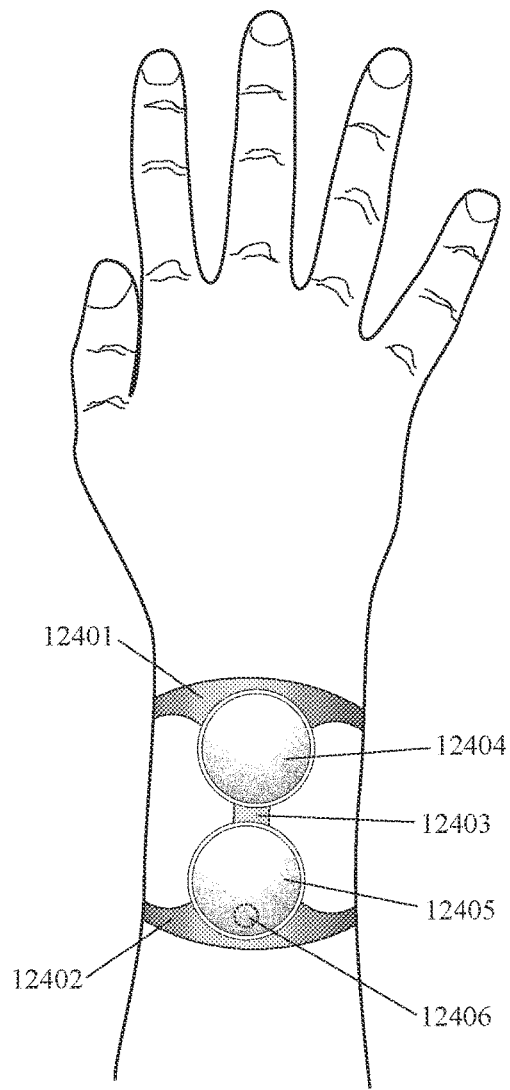

FIG. 124 shows a wearable device with two displays, a distal attachment member, a proximal attachment member, and a central connector between the displays.

Figure 125:
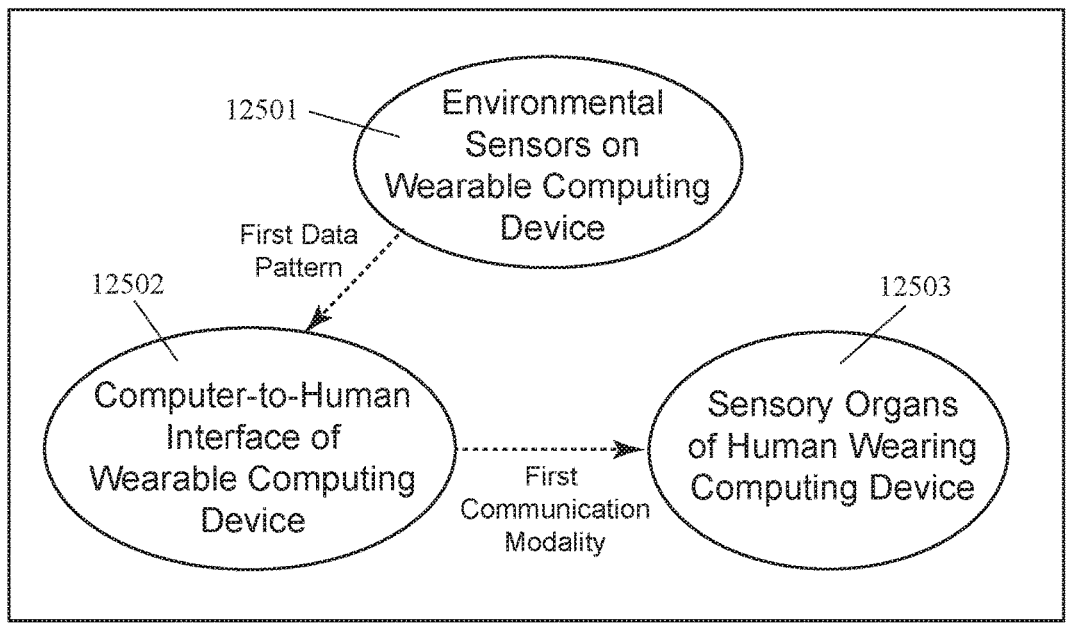
Figure 126:
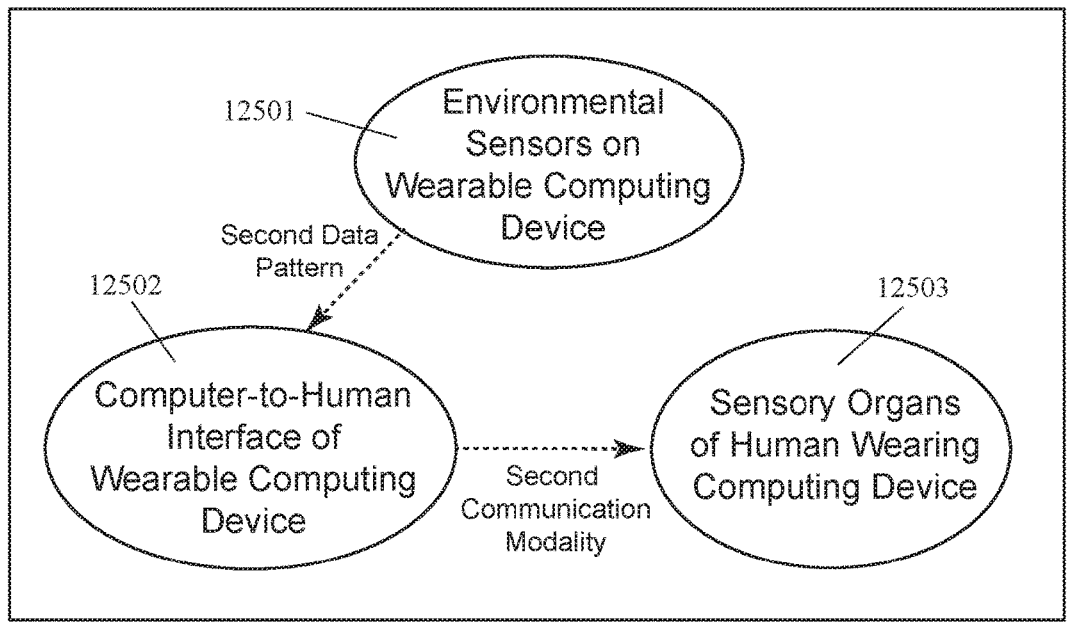

FIGS. 125 and 126 show a method for modifying the communication mode from a wearable device to a human based on environmental sensors.

Figure 127:
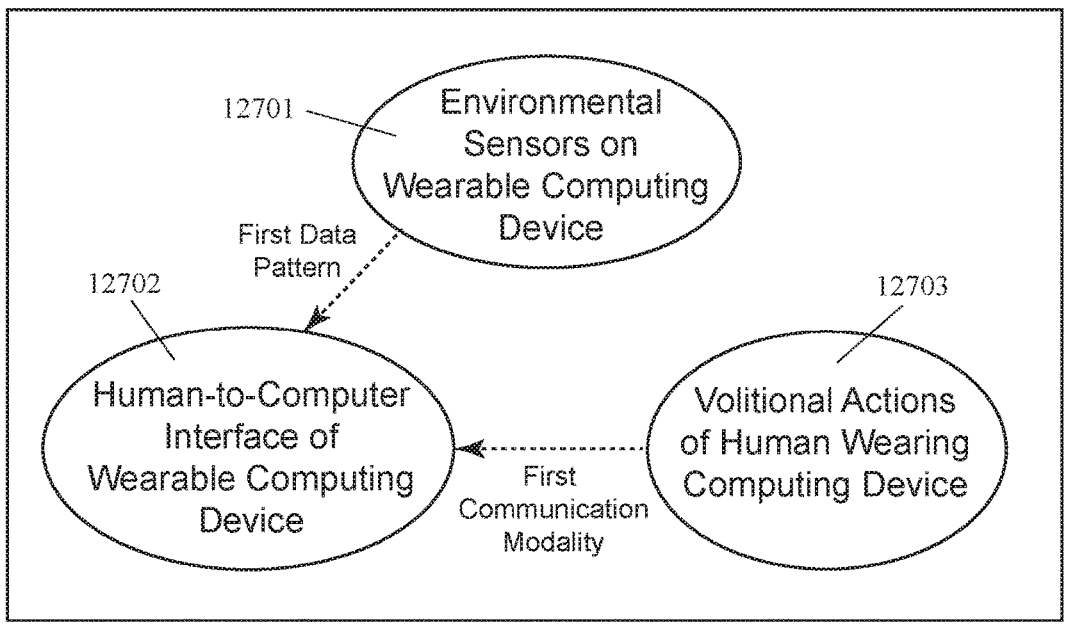
Figure 128:
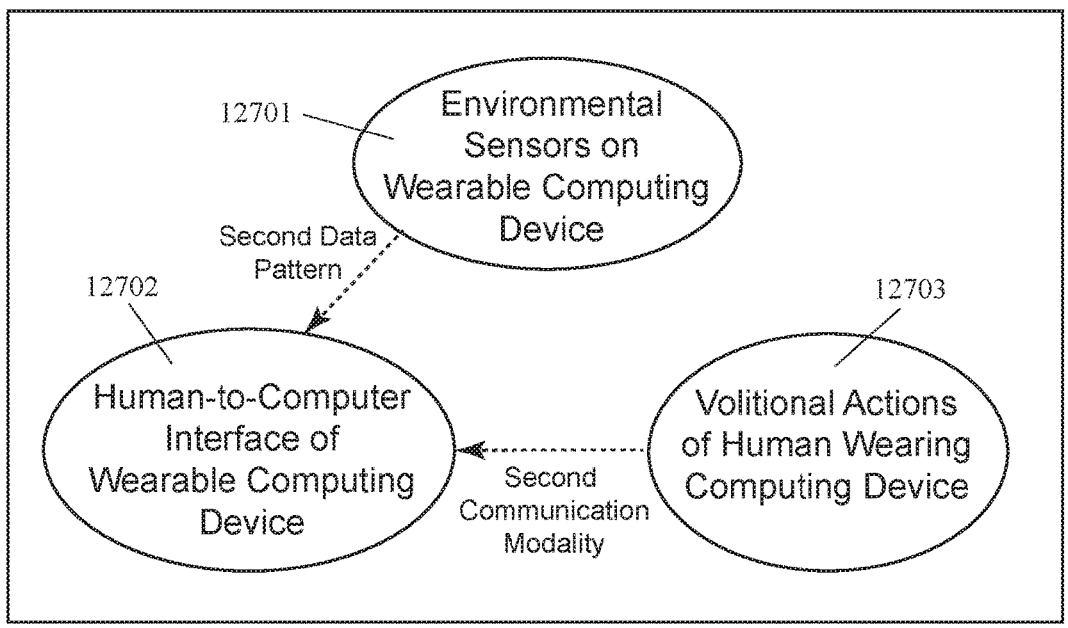

FIGS. 127 and 128 show a method for modifying the communication mode from a human to a wearable device based on environmental sensors.

Figure 129:
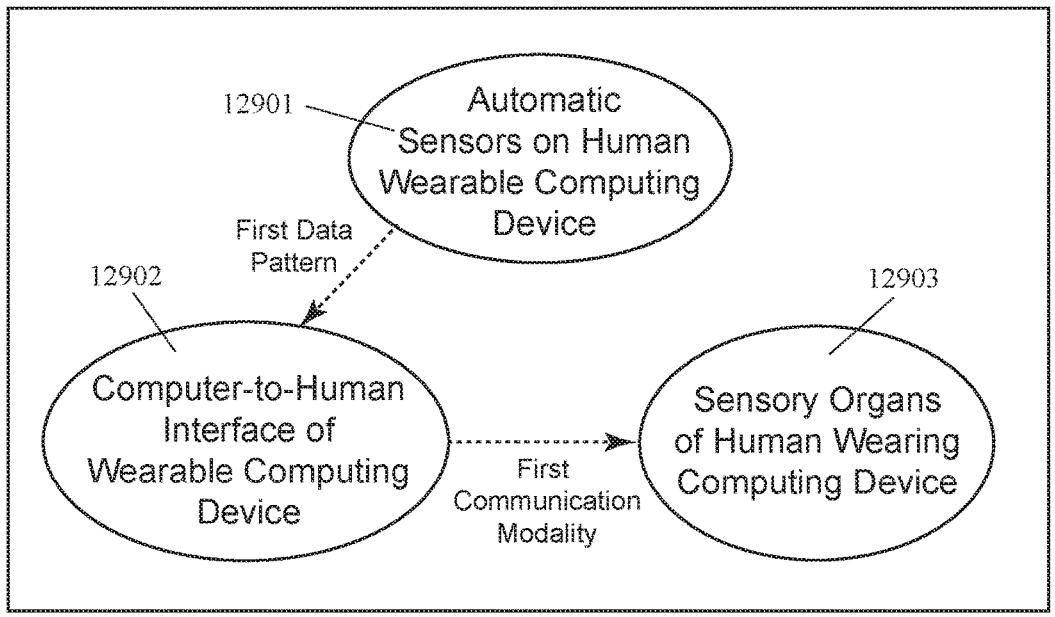
Figure 130:
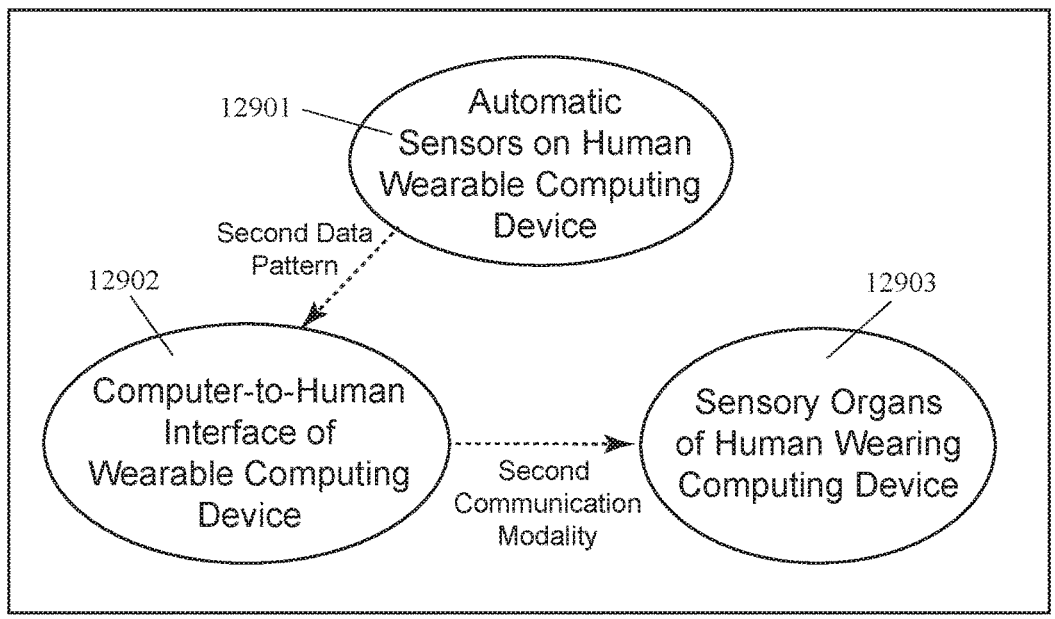

FIGS. 129 and 130 show a method for modifying the communication mode from a wearable device to a human based on automatic body sensors.

Figure 131:
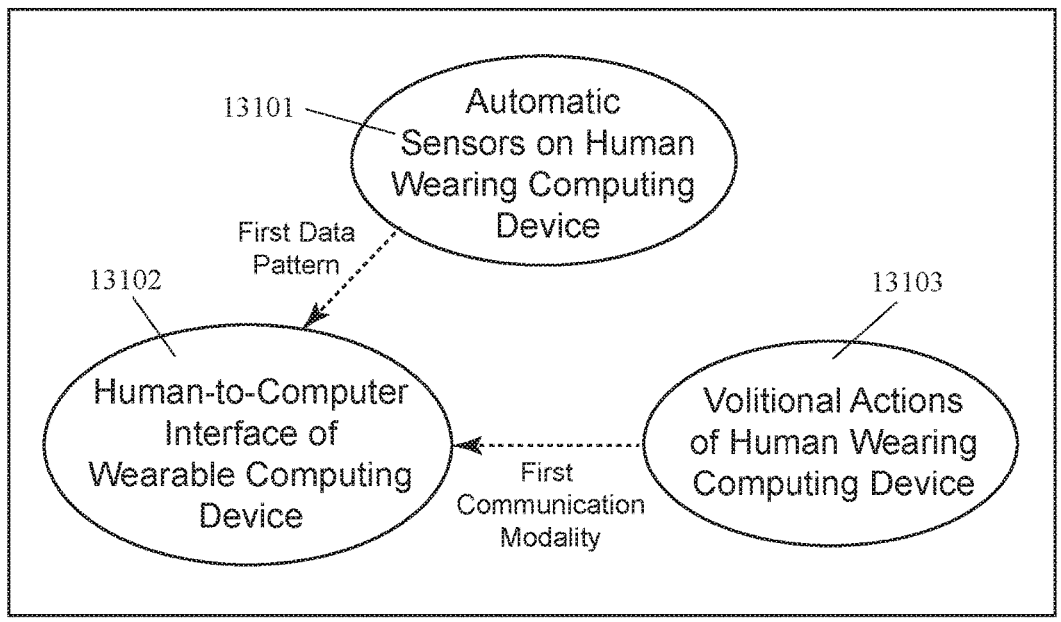
Figure 132:
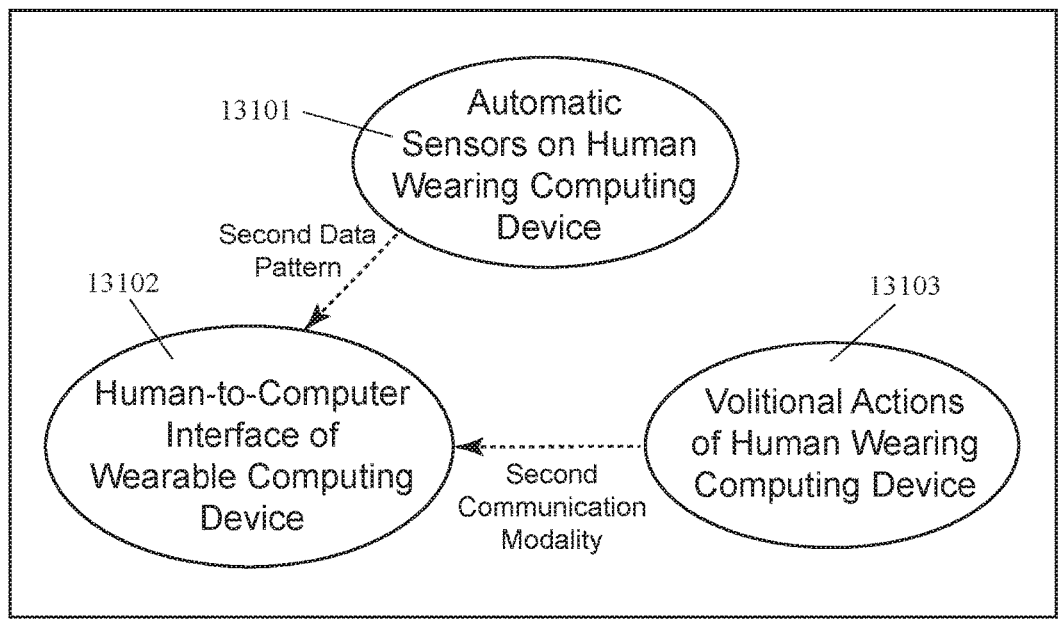

FIGS. 131 and 132 show a method for modifying the communication mode from a human to a wearable device based on automatic body sensors.

Figure 133:
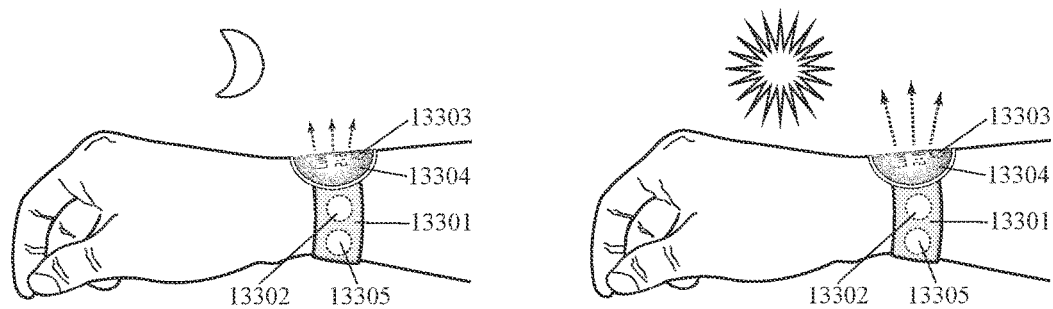

FIG. 133 shows a wearable band with a display whose brightness is automatically adjusted based on the light level in the environment.

Figure 134:
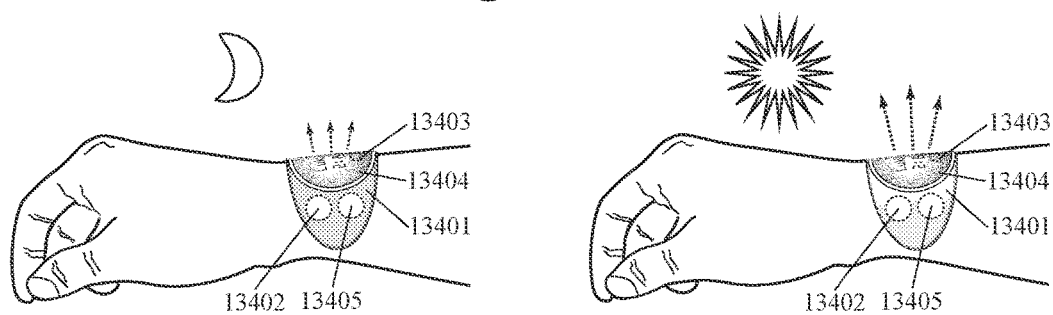

FIG. 134 shows a bracelet with a display whose brightness is automatically adjusted based on the light level in the environment.

Figure 135:
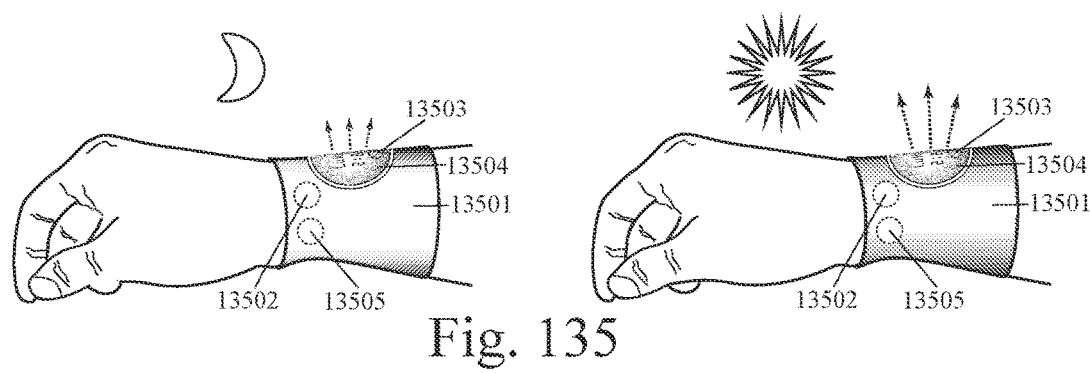

FIG. 135 shows a cuff with a display whose brightness is automatically adjusted based on the light level in the environment.

Figure 136:
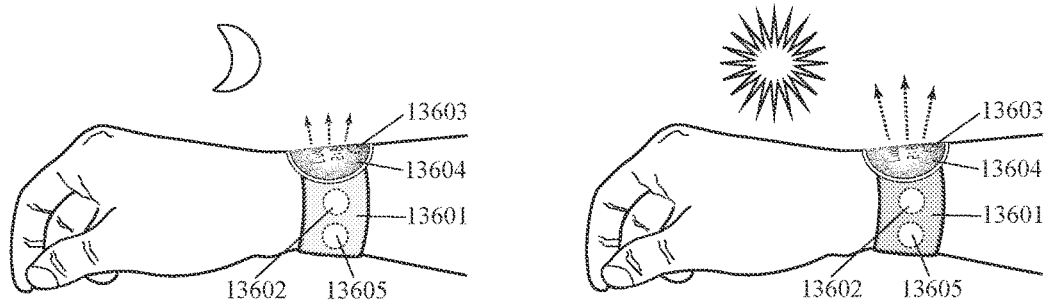

FIG. 136 shows a wearable device with a display whose brightness is automatically adjusted based on the light level in the environment.

Figure 137:
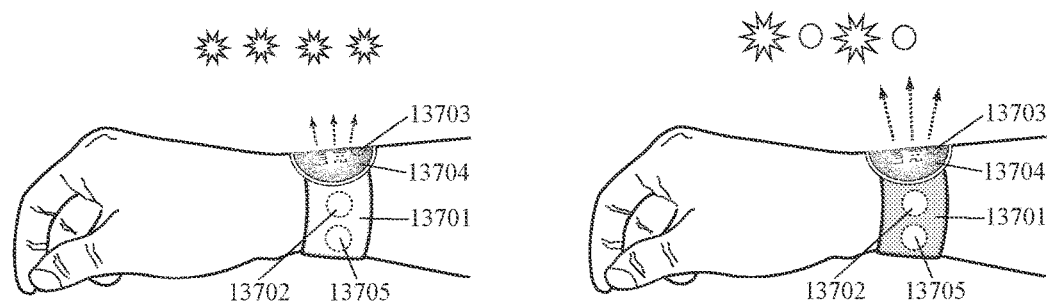

FIG. 137 shows a wearable device with a display whose brightness is automatically adjusted based on the variability of light in the environment.

Figure 138:
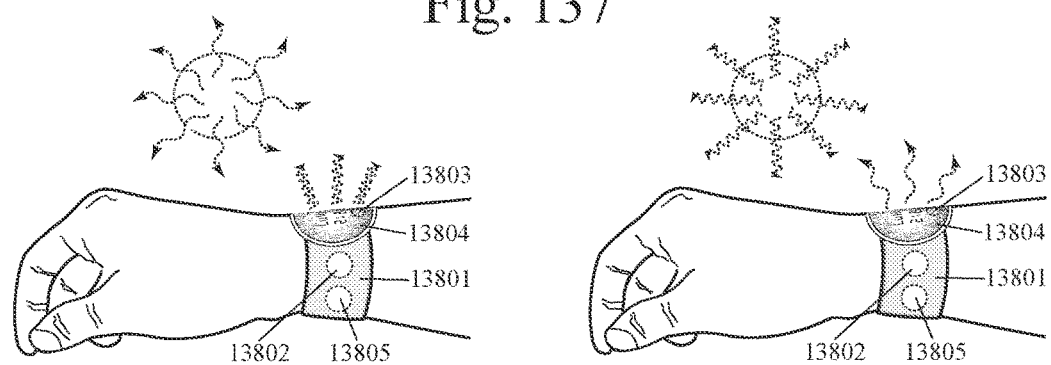

FIG. 138 shows a wearable device with a display whose light emission spectrum is automatically adjusted based on the light spectrum in the environment.

Figure 139:
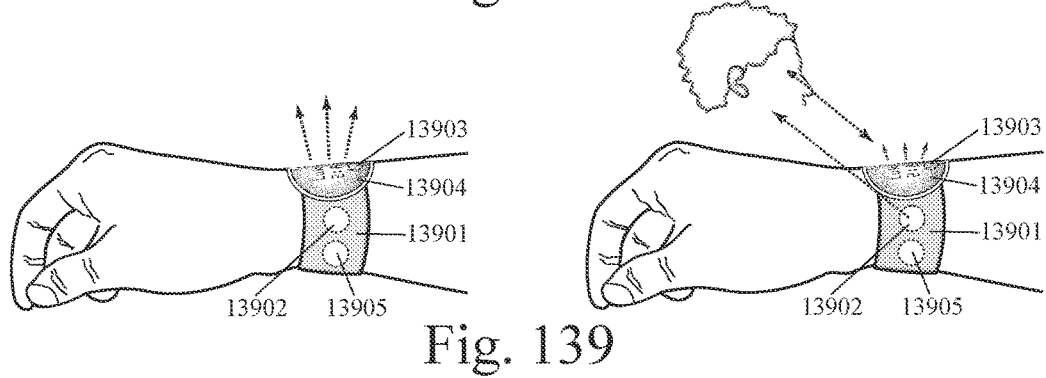

FIG. 139 shows a wearable device with a display whose brightness is automatically adjusted based on recognition of a selected object or person.

Figure 140:
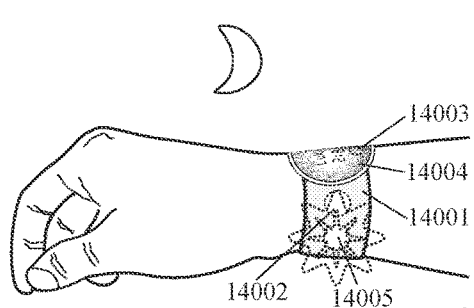
Figure 140:
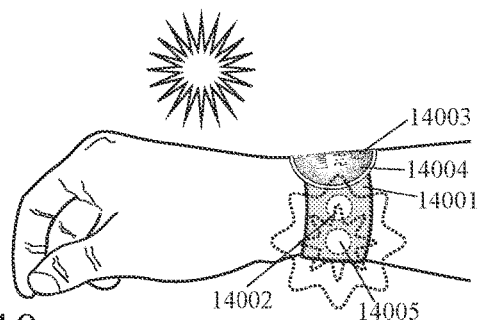

FIG. 140 shows a wearable device with a speaker whose sound level is automatically adjusted based on the light level in the environment.

Figure 141:
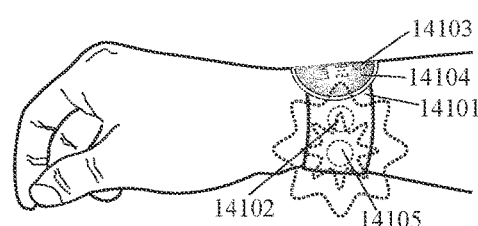
Figure 141:
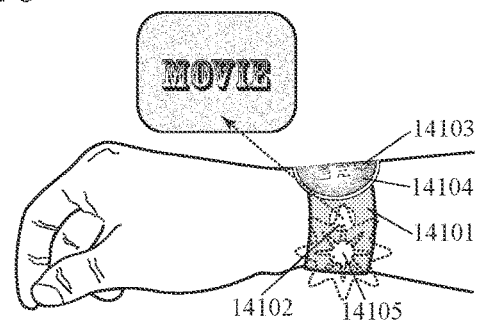

FIG. 141 shows a wearable device with a speaker whose sound level is automatically adjusted based on recognition of a selected object or person.

Figure 142:
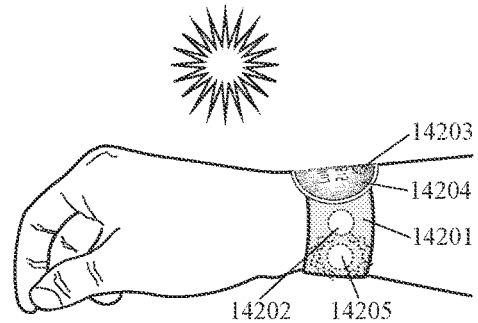
Figure 142:
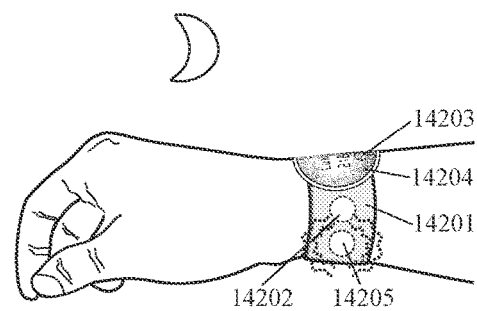

FIG. 142 shows a wearable device with a vibrating member whose vibration level is automatically adjusted based on the light level in the environment.

Figure 143:
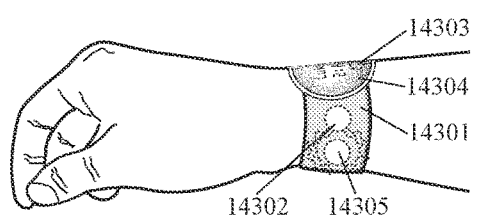
Figure 143:
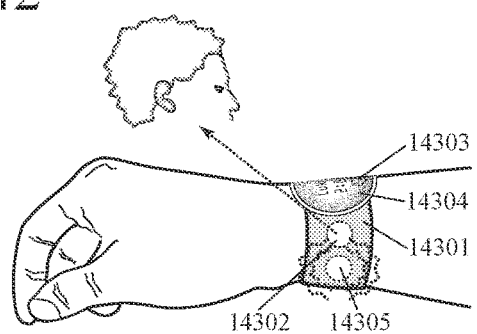

FIG. 143 shows a wearable device with a vibrating member whose vibration level is automatically based on recognition of a selected object or person.

Figure 144:
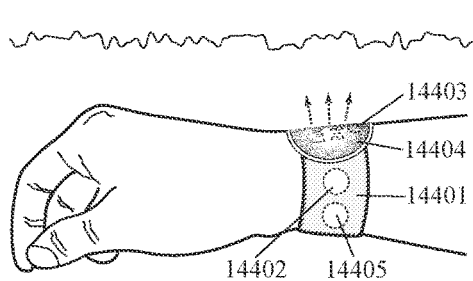
Figure 144:
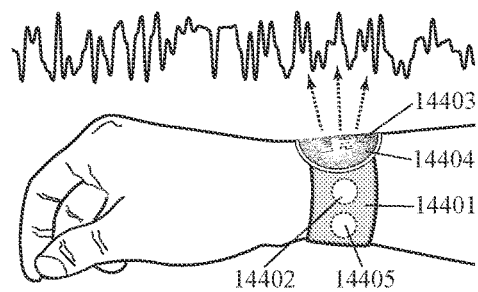

FIG. 144 shows a wearable device with a display whose brightness is automatically adjusted based on the sound level in the environment.

Figure 145:
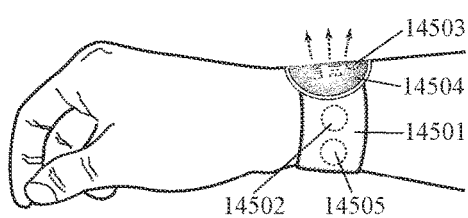
Figure 145:
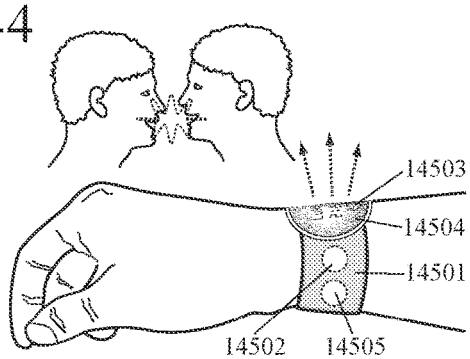

FIG. 145 shows a wearable device with a display whose brightness is automatically adjusted based on the amount of speech in the environment.

Figure 146:
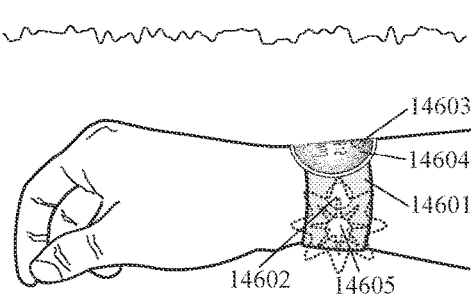
Figure 146:
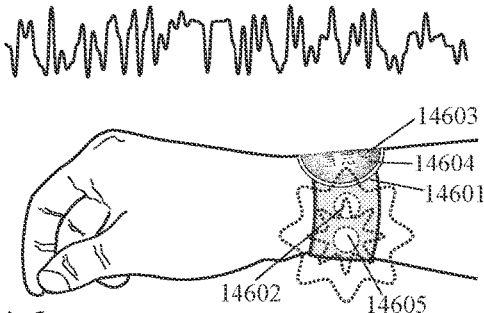

FIG. 146 shows a wearable device with a speaker whose sound level is automatically adjusted based on the sound level in the environment.

Figure 147:
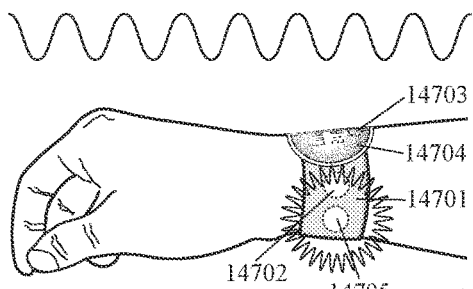
Figure 147:
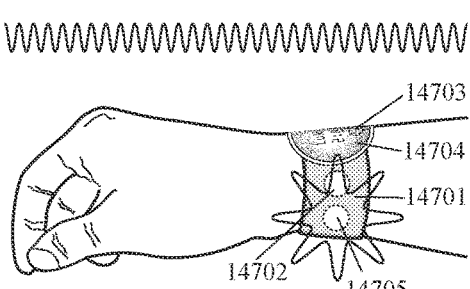

FIG. 147 shows a wearable device with a speaker whose sound emission frequency is automatically adjusted based on the sound frequency spectrum in the environment.

Figure 148:
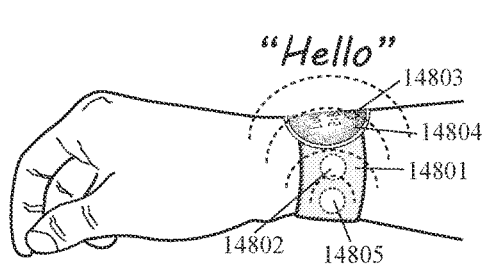
Figure 148:
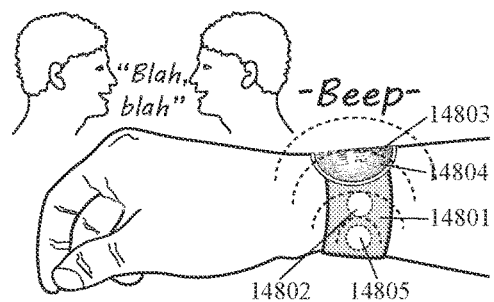

FIG. 148 shows a wearable device with a speaker wherein the amount of speech from the device is automatically adjusted based on the amount of speech in the environment.

Figure 149:
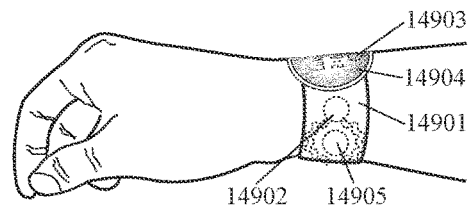
Figure 149:
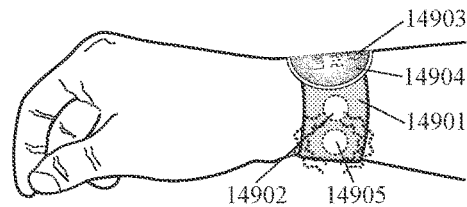

FIG. 149 shows a wearable device with a vibrating member whose vibration level is automatically adjusted based on the sound level in the environment.

Figure 150:
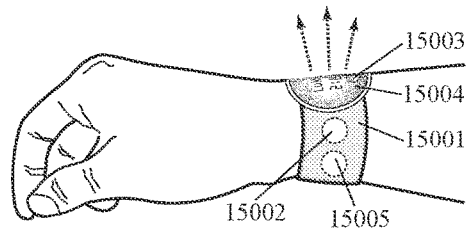
Figure 150:
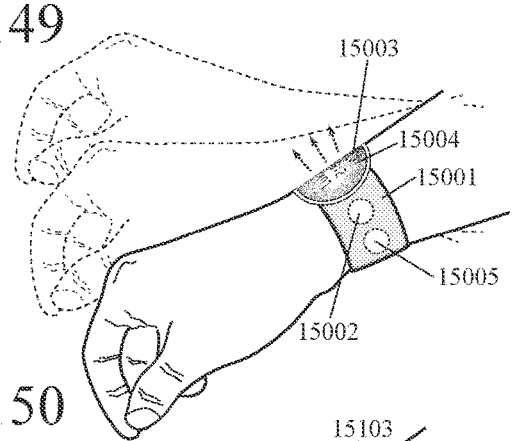

FIG. 150 shows a wearable device with a display whose brightness is automatically adjusted based on the amount of device motion.

Figure 151:
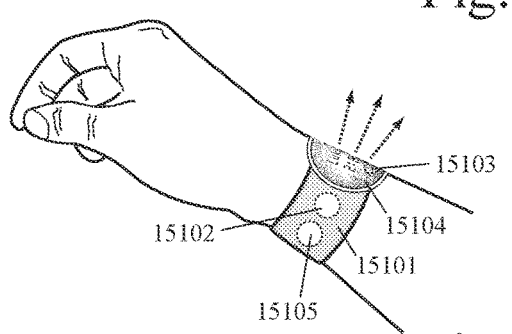
Figure 151:
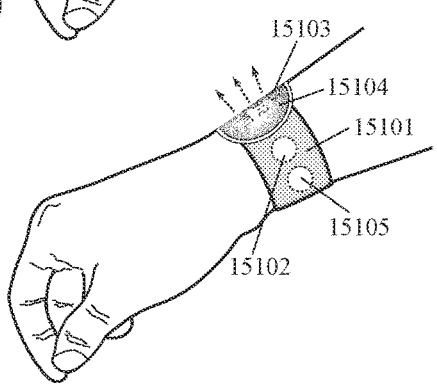

FIG. 151 shows a wearable device with a display whose brightness is automatically adjusted based on the position and/or orientation of the device.

Figure 152:
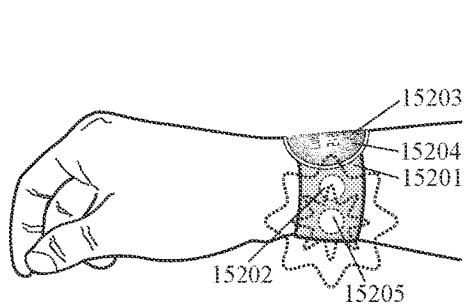
Figure 152:
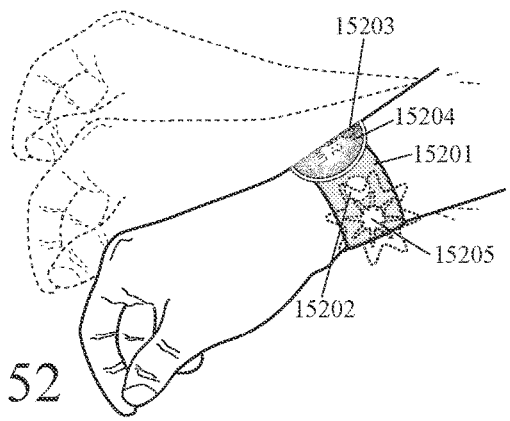

FIG. 152 shows a wearable device with a speaker whose sound level is automatically adjusted based on the amount of device motion.

Figure 153:
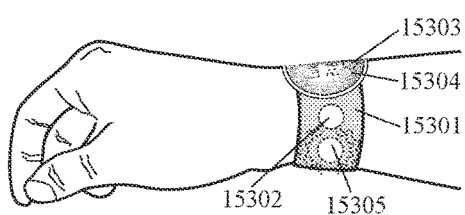
Figure 153:
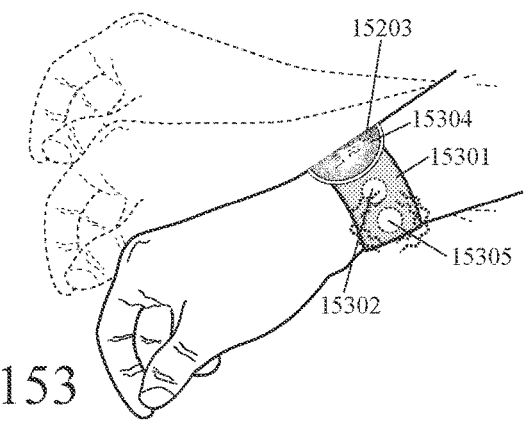

FIG. 153 shows a wearable device with a vibrating member whose vibration level is automatically adjusted based on the amount of device motion.

Figure 154:
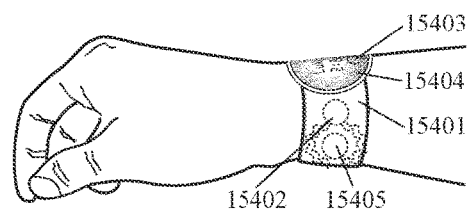
Figure 154:
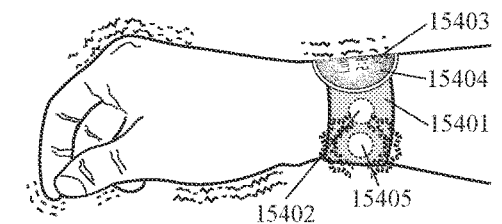

FIG. 154 shows a wearable device with a vibrating member whose frequency of vibration is automatically adjusted based on the frequency of environmental vibration.

Figure 155:
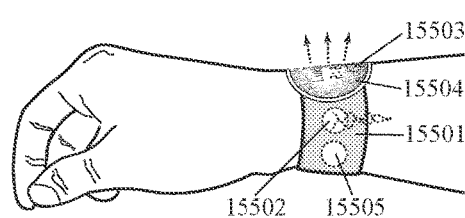
Figure 155:
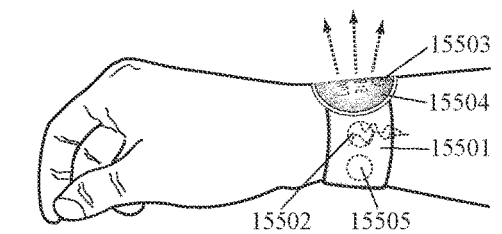

FIG. 155 shows a wearable device with a display whose brightness is automatically adjusted based on the spectrum of light reflected from (or passing through) tissue.

Figure 156:
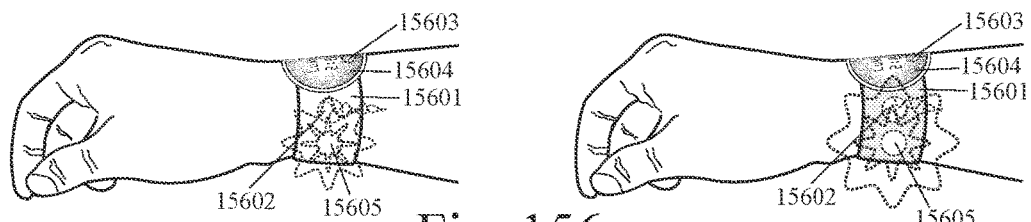

FIG. 156 shows a wearable device with a speaker whose sound level is automatically adjusted based on the spectrum of light reflected from (or passing through) tissue.

Figure 157:
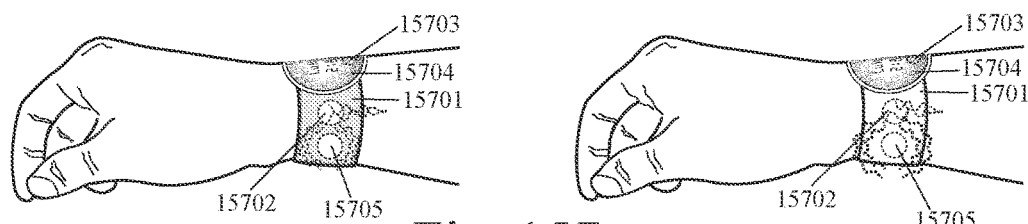

FIG. 157 shows a wearable device with a vibrating member whose vibration level is automatically adjusted based on the spectrum of light reflected from (or passing through) tissue.

Figure 158:
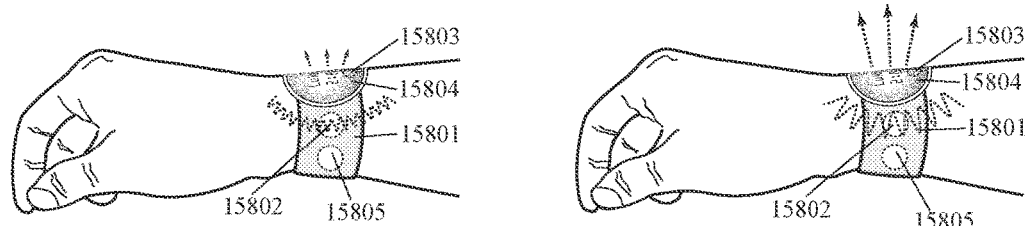

FIG. 158 shows a wearable device with a display whose brightness is automatically adjusted based on the pattern of ultrasonic energy reflected from (or passing through) tissue.

Figure 159:
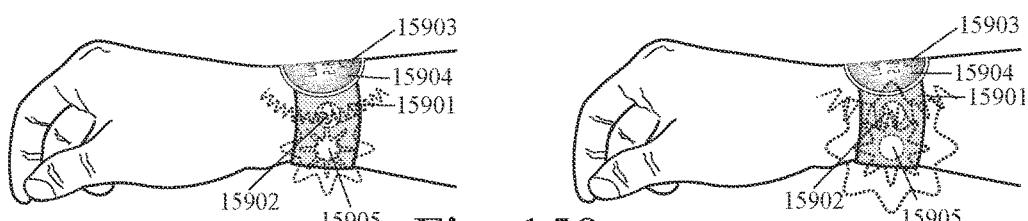

FIG. 159 shows a wearable device with a speaker whose sound level is automatically adjusted based on the pattern of ultrasonic energy reflected from (or passing through) tissue.

Figure 160:
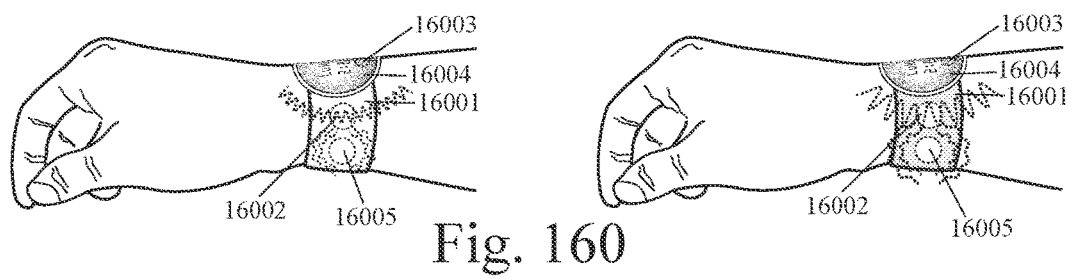

FIG. 160 shows a wearable device with a vibrating member whose vibration level is automatically adjusted based on the pattern of ultrasonic energy reflected from (or passing through) tissue.

Figure 161:
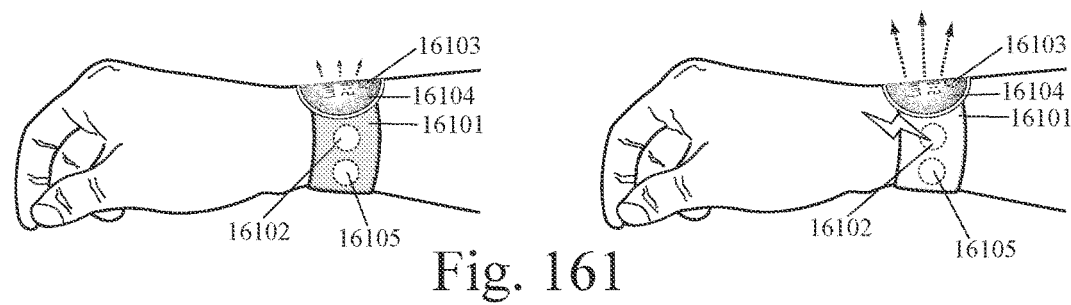

FIG. 161 shows a wearable device with a display whose brightness is automatically adjusted based on the pattern of electromagnetic energy emitted by (or transmitted through) tissue.

Figure 162:
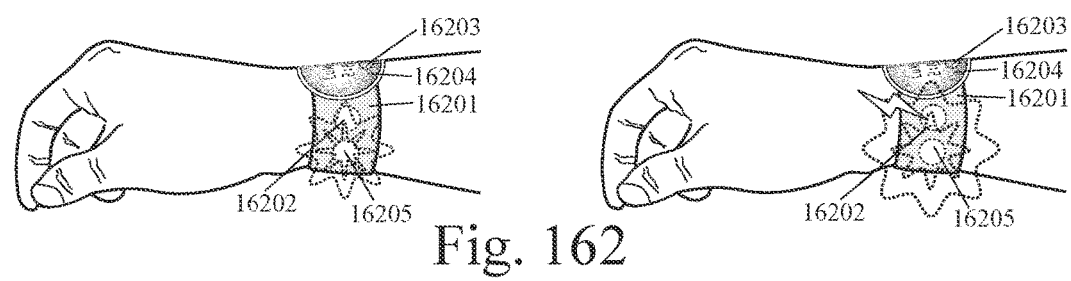

FIG. 162 shows a wearable device with a speaker whose sound level is automatically adjusted based on the pattern of electromagnetic energy emitted by (or transmitted through) tissue.

Figure 163:
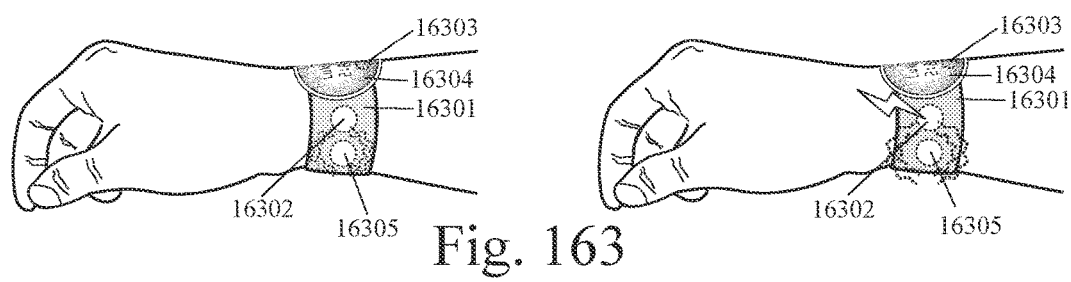

FIG. 163 shows a wearable device with a vibrating member whose vibration level is automatically adjusted based on the pattern of electromagnetic energy emitted by (or transmitted through) tissue.

Figure 164:
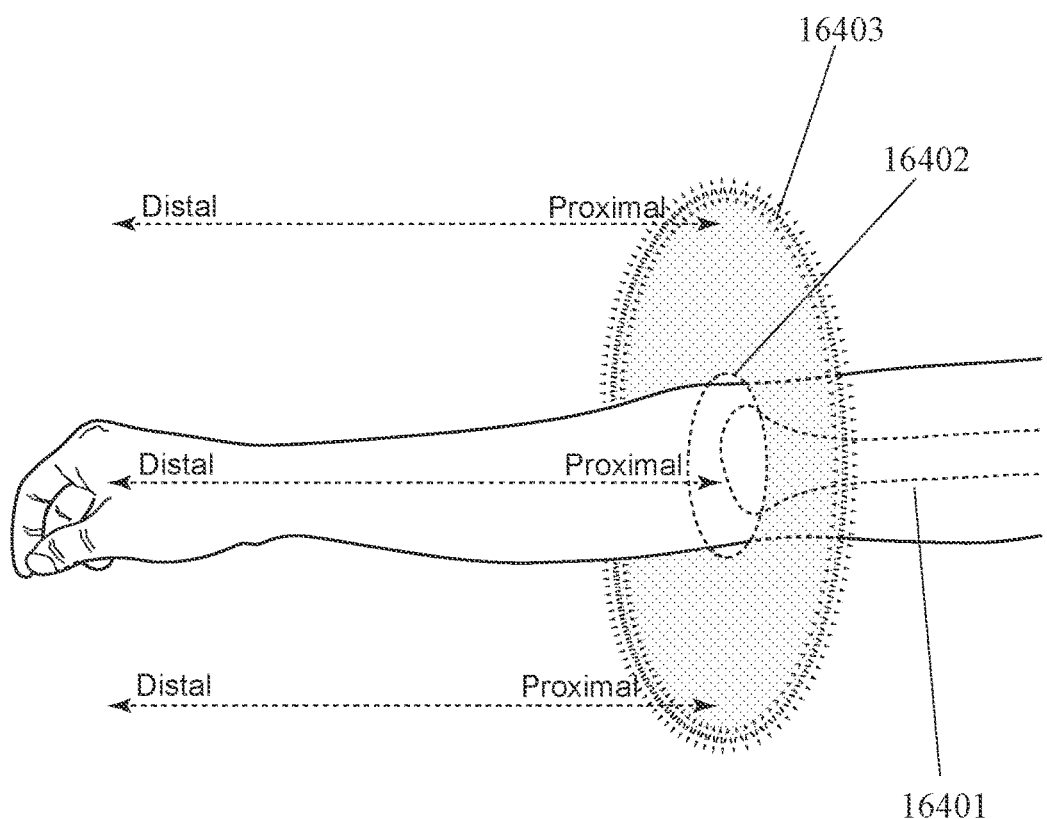

FIG. 164 provides visual illustration and clarification of the definitions of distal and proximal for the purpose of this disclosure.

DETAILED DESCRIPTION OF THE FIGURES

Figure 1:
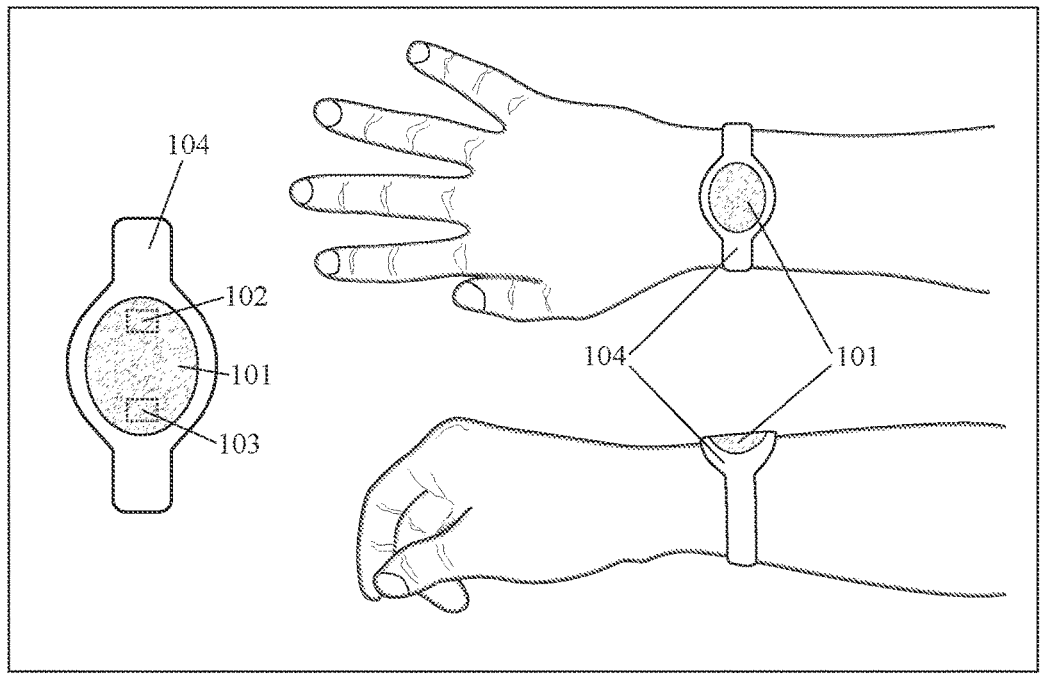
FIG. 1 shows a wearable device with an arcuate display and centrally-flared attachment member.

FIGS. 1 through 163 show different examples of how this invention can be embodied in wearable computing devices and methods for the wrist and/or arm, but they do not limit the full generalizability of the claims. FIG. 1 shows an example of a wearable computing device for the wrist and/or arm comprising: arcuate display member 101; data control unit 102; sensor 103; and centrally-flared attachment member 104. The left portion of FIG. 1 shows a detailed top-down view of the device by itself. The upper-right portion of FIG. 1 shows a top-down view of this device as worn on a person's wrist. The lower-right portion of FIG. 1 shows a side view of this device worn on a person's wrist. A person's wrist, hand, finger, forearm, or upper arm is herein defined to be part of their arm.

In this example, arcuate display member 101 has a cross-sectional shape in a plane which is substantially parallel to (or tangentially parallel to) the proximate surface of a person's wrist and/or arm. In FIG. 1, this shape is seen in the top-down views. In this example, this shape is an oval. In an example, this shape can be selected from the group consisting of: circle, ellipse, or other conic section. In an example, this shape can be selected from the group consisting of: circle, ellipse, oval, egg-shape, figure eight, hourglass, clover leaf, and teardrop. In an example, this shape can be selected from the group consisting of: square with rounded corners, rectangle with rounded corners, hexagon with rounded vertexes, or other polygon with rounded vertexes.

In an example, arcuate display member 101 can have a top surface which faces away from the proximate surface of a person's wrist and/or arm. In an example this top surface can have a side-view or lateral cross-sectional shape (in a plane which is substantially perpendicular to the surface of a person's wrist and/or arm). In an example, this side-view or lateral cross-sectional shape can be flat or curved. In FIG. 1, arcuate display member 101 is worn on the dorsal surface of a person's wrist and/or arm. In an example, arcuate display member 101 can be worn on the ventral surface or on a side surface of a person's wrist and/or arm. In an example, arcuate display member 101 can comprise a computer display screen—such as a touch-responsive interactive screen, infrared-emitting interactive screen, and/or gesture-recognizing interactive screen.

In this example, centrally-flared attachment member 104 holds arcuate display member 101, data control unit 102, and sensor 103 within three inches from the surface of a person's body. In this example, centrally-flared attachment member 104 spans the entire circumference of a person's wrist. In an example, centrally-flared attachment member 104 can span between 50% and 100% of the circumference of the person's wrist. In this example, centrally-flared attachment member 104 is worn on a person's wrist. In other examples, centrally-flared attachment member 104 can be worn on a person's forearm, upper arm, or hand.

In the example shown in FIG. 1, centrally-flared attachment member 104 further comprises a central flared portion which surrounds two outer perimeter portions of arcuate display member 101. In this example, this flared portion is centrally located on the dorsal surface of the person's wrist. In this example, the shape of the flared portion follows the shape of the outer perimeter portions of arcuate display member 101. In this example, centrally-flared attachment member 104 further comprises a substantially-cylindrical strap or band portion which encircles the person's wrist. In this example, the central flared portion and the cylindrical strap or band are physically combined as a single component of the device. In another example, a central flared portion and a cylindrical strap can be separate components of the device.

In an example, centrally-flared attachment member 104 can comprise a flexible strap or band which spans the circumference of the person's wrist and/or arm. In an example, the ends of the strap or band can connect with each other so as to fasten around the circumference of the person's wrist and/or arm. In an example, centrally-flared attachment member 104 can include one or more clips, clasps, snaps, buckles, or hook-and-eye mechanisms which connect in order to hold the device onto the person's wrist and/or arm.

In an example, centrally-flared attachment member 104 can be sufficiently resilient or rigid that it can fasten securely around a person's wrist and/or arm even though it spans less than 100% of the circumference of the person's wrist and/or arm. In an example, centrally-flared attachment member 104 can fasten securely around a person's wrist and/or arm even thought it spans between 50% and 95% of the circumference of the person's wrist and/or arm. In an example, centrally-flared attachment member 104 can be made with flexible metal or a resilient polymer.

In an example, centrally-flared attachment member 104 can be stretchable, elastic, or expandable. In an example, centrally-flared attachment member 104 can be made with a stretchable or elastic fabric or polymer. In an example, centrally-flared attachment member 104 can be made with a series of expandable and/or interlocking links. In an example, centrally-flared attachment member 104 can be stretched or expanded to a sufficiently-large circumference that it can be slipped over a person's hand and onto the person's wrist and/or arm.

Data control unit 102 can further comprise one or more components selected from the group consisting of: data processing member, data transmitting member, data receiving member, power source, and energy transducer. In various examples, data control unit 102 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy. In an example, data control unit 102 can be co-located with arcuate display member 101. In an example, data control unit 102 can be located elsewhere in the device.

In various examples, sensor 103 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 2:
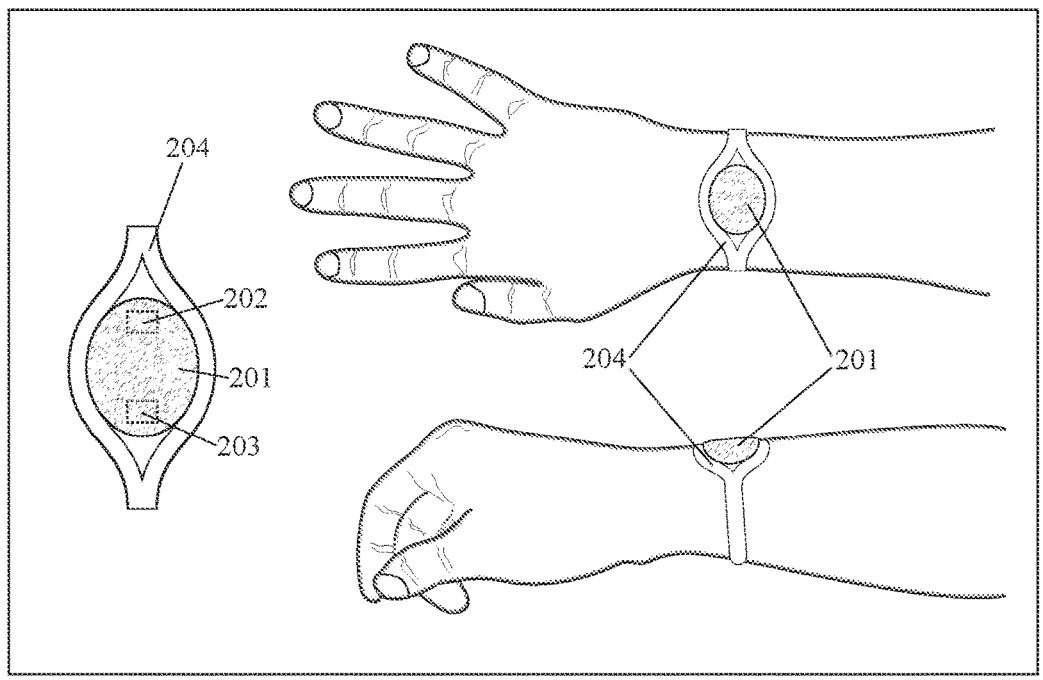
FIG. 2 shows a wearable device with an arcuate display and a bifurcating attachment member.

FIG. 2 shows an example of a wearable computing device for the wrist and/or arm comprising: arcuate display member 201; data control unit 202; sensor 203; and bifurcating attachment member 204. The left portion of FIG. 2 shows a detailed top-down view of the device by itself. The upper-right portion of FIG. 2 shows a top-down view of this device on a person's wrist. The lower-right portion of FIG. 2 shows a side view of this device on a person's wrist. A person's wrist or hand is considered to be part of their arm.

In this example, arcuate display member 201 has an arcuate cross-sectional shape in a plane which is substantially parallel to (or tangentially parallel to) the proximate surface of a person's wrist and/or arm. In this example, this shape is an oval. In an example, this shape can be a circle, ellipse, or other conic section. In an example, this shape can be selected from the group consisting of: circle, ellipse, oval, egg shape, figure eight, clover leaf shape, teardrop shape, hourglass shape, square with rounded corners, rectangle with rounded corners, hexagon with rounded vertexes, or other polygon with rounded vertexes.

In an example, arcuate display member 201 can have a top surface which faces away from the proximate surface of a person's wrist and/or arm. In an example this top surface can have a lateral cross-sectional shape in a plane which is substantially perpendicular to the proximate surface of a person's wrist and/or arm. This shape can be flat or curved. In an example, arcuate display member 201 can be worn on the dorsal surface, ventral, or side surface of a person's wrist and/or arm. In an example, arcuate display member 201 can comprise a computer display screen such as a touch-responsive interactive screen, infrared-emitting interactive screen, or gesture-recognizing interactive screen.

In this example, bifurcating attachment member 204 is configured to position arcuate display member 201, data control unit 202, and sensor 203 within three inches of the surface of a person's body. In this example, bifurcating attachment member 204 spans the entire circumference of a person's wrist and/or arm. In an example, bifurcating attachment member 204 can span between 50% and 100% of the circumference of the person's wrist and/or arm In the example shown in FIG. 2, bifurcating attachment member 204 splits into two segments on a first side of the arcuate display member. These two segments then traverse along opposite sides of the perimeter of the arcuate display member 201 and thereby hold arcuate display member 201 in place. These two segments then reconverge on the other side of arcuate display member 201, the side that is opposite to the first side. In this example, the bifurcated portion of bifurcating attachment member 204 is substantially located on the side of the person's wrist on which arcuate display member 201 is located. In this example, the bifurcated portion of bifurcating attachment member 204 is substantially located on the dorsal surface of the person's wrist.

In an example, bifurcating attachment member 204 can be a flexible strap or band. In an example, portions of a strap or band can connect with each other (such as with a clip, buckle, snap, or hook-and-eye mechanism) to fasten bifurcating attachment member 204 around a person's wrist and/or arm. In another example, bifurcating attachment member 204 can be sufficiently resilient or rigid that it fastens securely around a person's wrist and/or arm even though it spans less than 100% of the circumference of the person's wrist and/or arm. In an example, bifurcating attachment member 204 can be made with flexible metal or a resilient polymer. In an example, bifurcating attachment member 204 can be stretchable, elastic, or expandable. In an example, bifurcating attachment member 204 can be made with a stretchable or elastic material, such as stretchable or elastic fabric. In an example, bifurcating attachment member 204 can comprise a series or chain of expandable, interconnected links. In an example, bifurcating attachment member 204 can be stretched or expanded to a sufficiently-large circumference that it can be slipped over a person's hand onto a person's wrist and/or arm.

Data control unit 202 can further comprise one or more components selected from the group consisting of: data processing member, data transmitting member, data receiving member, power source, and energy transducer. In various examples, data control unit 202 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 203 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 3:
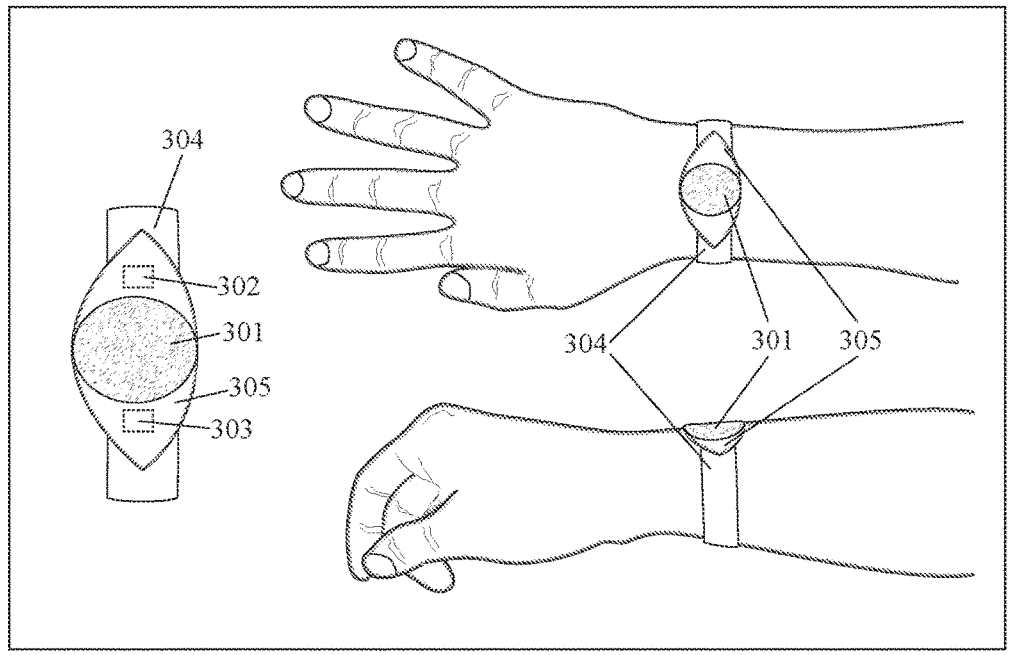
FIG. 3 shows a wearable device with an eye-shaped display.

FIG. 3 shows an example of a wearable computing device for the wrist and/or arm comprising: eye-shaped display member 305; data control unit 302; sensor 303; and attachment member 304. Eye-shaped display member 305 further comprises an inner circular member 301. The left portion of FIG. 3 shows a detailed top-down view of the device alone, the upper-right portion of this figure shows a top-down view of this device on a person's wrist, and the lower-right portion of this figure shows a side view of this device on the person's wrist.

In this example, the image display member looks like a human eye for dramatic effect. It may also be a continual source of technology-related puns. In the example shown in FIG. 3, eye-shaped display member 305 further comprises: an eye-shaped exterior portion; and a pupil-like inner circular member 301. The shape of the exterior portion is formed by the intersection of two concave arc lines. Inner circular member 301 looks like the pupil of an eye within the eye-shaped exterior portion. In this example, only the inner circular member 301 of eye-shaped display member 305 is a computer display screen—such as a touch-responsive interactive screen, infrared-emitting interactive screen, and/ or gesture-recognizing interactive screen. Alternatively, all of eye-shaped display member 305 can comprise a computer display screen.

In this example, eye-shaped display member 305 has a top surface which faces away from the proximate surface of a person's wrist and/or arm. In an example, this top surface can have a lateral cross-sectional shape in a plane which is substantially perpendicular to the proximate surface of a person's wrist and/or arm. This shape can be substantially flat or curved. In an example, eye-shaped display member 305 can be worn on the dorsal surface, the ventral surface, or a side surface of a person's wrist and/or arm. In this example, eye-shaped display member 305 has a longitudinal axis which is perpendicular to the longitudinal axis of the person's forearm. In another example, eye-shaped display member 305 can have a longitudinal axis which is parallel to the longitudinal axis of the person's forearm.

In this example, attachment member 304 holds eye-shaped display member 305, data control unit 302, and sensor 303 within three inches from the surface of a person's body. In this example, attachment member 304 spans the entire circumference of a person's wrist and/or arm. In an example, attachment member 304 can span between 50%-100% of the circumference of the person's wrist and/or arm. In an example, attachment member 304 can be a flexible strap or band. In an example, portions of a strap or band can connect with each other (such as with one or more clips, clasps, snaps, buckles, or hook-and-eye mechanisms) to fasten attachment member 304 around a person's wrist and/or arm. In an example, attachment member 304 can be sufficiently resilient or rigid such that it can fasten securely around a person's wrist and/or arm even though it spans less than 100% of the circumference of the person's wrist and/or arm.

In an example, attachment member 304 can be stretchable, elastic, or expandable. In an example, attachment member 304 can comprise stretchable or elastic fabric. In an example, attachment member 304 can comprise a chain or series of expandable or interlocking links. In an example, attachment member 304 can be stretched or expanded to a sufficiently-large circumference that it can be slipped over a person's hand onto the person's wrist and/or arm, spanning the full circumference of a person's wrist and/or arm.

Data control unit 302 can further comprise one or more components selected from the group consisting of: data processing member, data transmitting member, data receiving member, power source, and energy transducer. In various examples, data control unit 302 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 303 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 4:
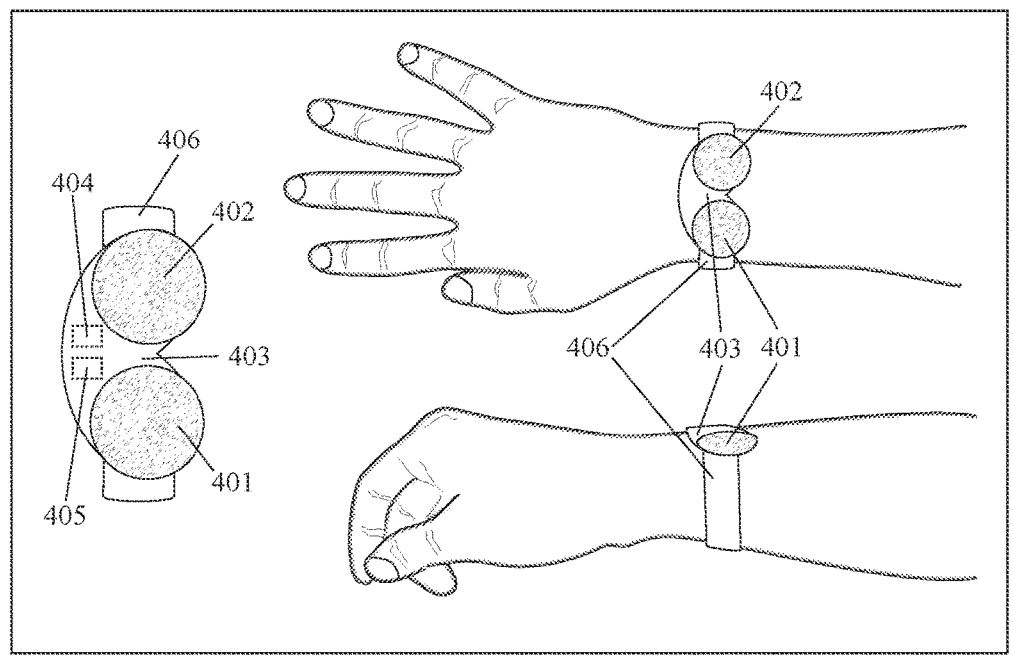
FIG. 4 shows a wearable device with two arcuate displays in a kidney-shaped housing.

FIG. 4 shows an example of a wearable computing device for the wrist and/or arm comprising: arcuate display members 401 and 402; kidney-shaped housing 403; data control unit 404; sensor 405; and attachment member 406. The left portion of FIG. 4 shows a detailed top-down view of the device alone. The upper-right portion of FIG. 4 shows a top-down view of this device worn on a person's wrist and the lower-right portion of this figure shows a side view of this device worn on a person's wrist.

In this example, kidney-shaped housing 403 holds arcuate display members 401 and 402, data control unit 404, and sensor 405. In this example, kidney-shaped housing 403 has a cross-sectional shape in a plane which is substantially parallel to, or tangentially parallel to, the proximate surface of a person's wrist and/or arm. In this example, this shape is like that of a kidney or a compressed heart shape with a rounded central vertex. In an example, one or both of arcuate display members 401 and 402 can be touch-responsive interactive screens, infrared-emitting interactive screens, or gesture-recognizing interactive screens.

In an example, kidney-shaped housing 403 can have a top surface which faces away from the proximate surface of a person's wrist and/or arm. This top surface is visible in the top-down views in FIG. 4. In an example, this top surface has a lateral cross-sectional shape in a plane which is substantially perpendicular to the proximate surface of a person's wrist and/or arm. In various examples, this shape can be substantially flat or arcuate. In an example, kidney-shaped housing 403 can be configured to be worn on the dorsal surface of a person's wrist and/or arm, on the ventral surface of a person's wrist and/or arm, or on the side of a person's wrist and/or arm.

In this example, attachment member 406 is configured to hold arcuate display members 401 and 402, kidney-shaped housing 403, data control unit 404, and sensor 405 within three inches from the surface of a person's body. In this example, attachment member 406 spans the entire circumference of a person's wrist and/or arm. In other examples, attachment member 406 can span between 50%-100% of the circumference of the person's wrist and/or arm.

In an example, attachment member 406 can be a flexible strap or band with portions which connect to each other (as with a clip, snap, buckle, or hook-and-eye mechanism) so as to fasten the device around the person's wrist and/or arm. In another example, attachment member 406 can be sufficiently resilient or rigid such that it fastens securely even though it spans less than 100% of the circumference of the person's wrist and/or arm. In an example, attachment member 406 can be stretchable, elastic, or expandable. In an example, attachment member 406 can comprise stretchable or elastic fabric or a series of expandable links. In an example, attachment member 406 can be stretched or expanded to a sufficiently-large circumference that it can be slipped over a person's hand onto the person's wrist and/or arm.

Data control unit 404 can further comprise one or more components selected from the group consisting of: data processing member, data transmitting member, data receiving member, power source, and energy transducer. In various examples, data control unit 404 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 405 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 5:
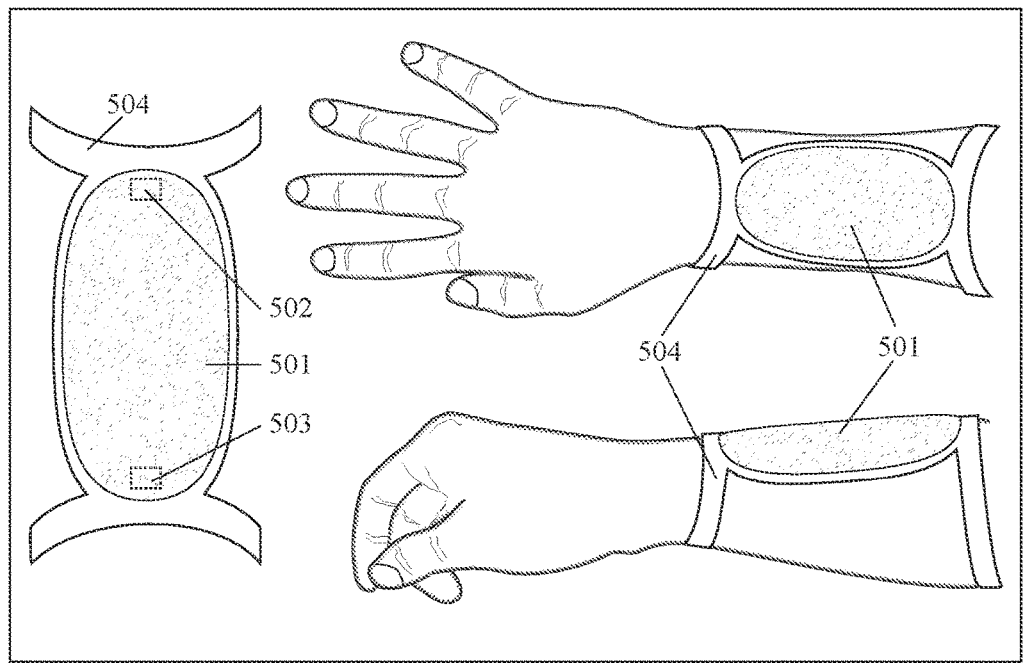
FIG. 5 shows a wearable device with a longitudinal arcuate display and a longitudinal flared-two-strap attachment member.

FIG. 5 shows an example of a wearable computing device for the wrist and/or arm comprising: longitudinal arcuate display member 501; data control unit 502; sensor 503; and longitudinal flared-two-strap attachment member 504. The left portion of FIG. 5 shows a detailed top-down view of the device by itself. The upper-right portion of FIG. 5 shows a top-down view of this device on a person's forearm. The lower-right portion of FIG. 5 shows a side view of this device on a person's forearm.

Longitudinal arcuate display member 501 has a longitudinal axis which is substantially parallel to the longitudinal axis of the person's forearm. The length of longitudinal arcuate display member 501 is more than 50% greater than its width. In this example, longitudinal arcuate display member 501 has a substantially-oval shape. In various examples, a longitudinal arcuate display member can have a shape which is selected from the group consisting of: oval, ellipse, other conic section, rectangle with rounded corners, egg shape, figure eight, tear drop, kidney shape, heart shape, or hourglass.

In this example, longitudinal arcuate display member 501 is configured to be worn on the dorsal surface of a person's wrist and/or arm. In other examples, a longitudinal arcuate display member 501 can be worn on the ventral surface or a side surface of a person's wrist and/or arm. In an example, longitudinal arcuate display member 501 can comprise a computer display screen—such as a touch-responsive interactive screen, infrared-emitting interactive screen, or gesture-recognizing interactive screen.

In this example, longitudinal flared-two-strap attachment member 504 is configured to hold longitudinal arcuate display member 501, data control unit 502, and sensor 503 within three inches of the surface of a person's body. In this example, longitudinal flared-two-strap attachment member 504 further comprises two straps or bands which each span the circumference of the person's wrist and/or arm. This holds the device onto a person's arm at two different locations along the longitudinal axis of the person's forearm.

In an example, these straps or bands can be flexible. In an example, these straps or bands can each have portions which interconnect so as to fasten longitudinal flared-two-strap attachment member 504 around the person's wrist and/or arm in two different longitudinal locations. In an example, these straps or bands can further comprise clips, clasps, snaps, buckles, or hook-and-eye connectors. In another example, these straps or bands can be stretched or expanded to a sufficiently-large circumference so that they can be slipped over a person's hand onto the person's wrist and/or arm.

In this example, longitudinal flared-two-strap attachment member 504 also comprises a central longitudinal portion between the two straps or bands. This central longitudinal flared portion follows the outer perimeter of longitudinal arcuate display member 501 and holds this display member on the person's wrist and/or arm. In this example, the two straps or bands flare outwards from the central longitudinal portion towards the person's hand at one end and toward the person's elbow at the other end. Accordingly, the distance between the two straps or bands is shorter on the side of the arm with longitudinal arcuate display member 501 and longer on the opposite side.

Data control unit 502 can further comprise one or more components selected from the group consisting of: data processing member, data transmitting member, data receiving member, power source, and energy transducer. In various examples, data control unit 502 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 503 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 6:
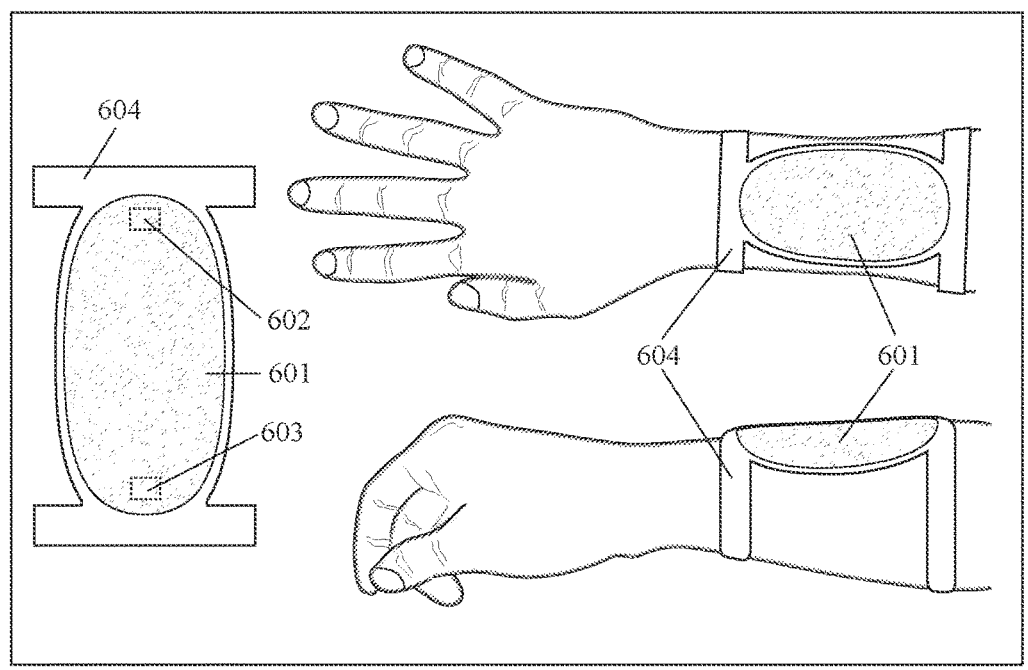
FIG. 6 shows a wearable device with a longitudinal arcuate display and a longitudinal two-strap attachment member.

FIG. 6 shows an example of a wearable computing device for the wrist and/or arm comprising: longitudinal arcuate display member 601; data control unit 602; sensor 603; and longitudinal two-strap attachment member 604. The left portion of FIG. 6 shows a detailed top-down view of the device by itself. The upper-right portion of FIG. 6 shows a top-down view of this device worn on a person's forearm. The lower-right portion of FIG. 6 shows a side view of this device worn on a person's forearm. This example is like the example shown in FIG. 5 except that the two straps or bands of the longitudinal two-strap attachment member do not flare outwards. Accordingly, the distance between the two straps or bands is substantially the same on both opposing sides of the arm.

Figure 7:
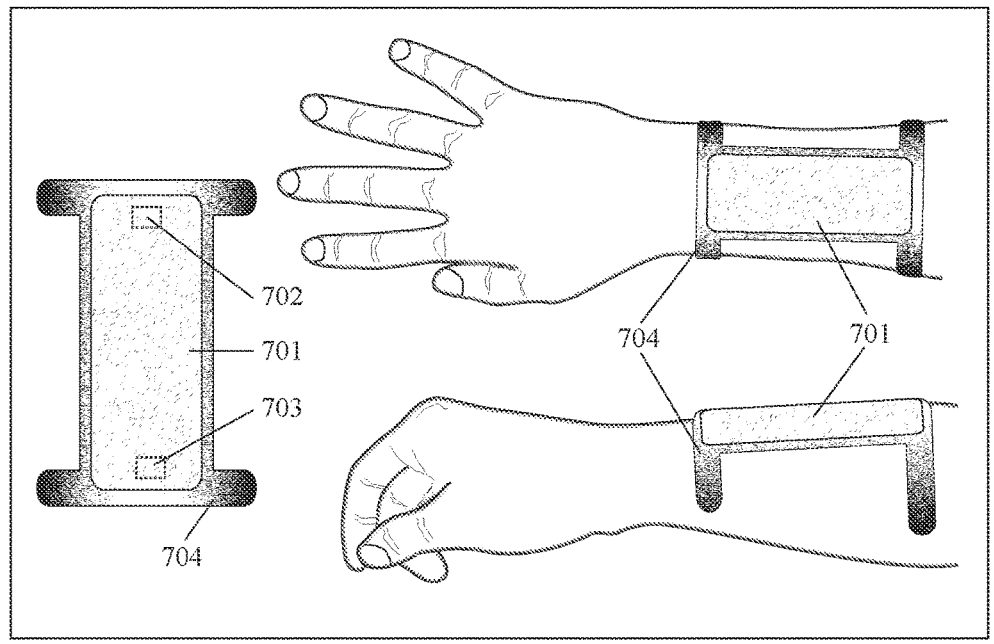
FIG. 7 shows a wearable device with a rounded-rectangle display and a two-bangle attachment member.

FIG. 7 shows an example of a wearable computing device for the wrist and/or arm comprising: rounded-rectangle display member 701; data control unit 702; sensor 703; and two-bangle attachment member 704. In this example, two bangle-like elements each span between 50% and 95% of the perimeter of the person's arm. The left portion of FIG. 7 shows a detailed top-down view of the device alone, the upper-right portion of this figure shows a top-down view of this device on a person's forearm, and the lower-right portion of this figure shows a side view of this device on a person's forearm.

Rounded-rectangle display member 701 has a longitudinal axis which is substantially parallel to the longitudinal axis of the person's forearm. In this example, rounded-rectangle display member 701 is configured to be worn on the dorsal surface of a person's wrist and/or arm. In other examples, it can be worn on the ventral surface or a side surface of a person's wrist and/or arm. In an example, rounded-rectangle display member 701 can comprise a computer display screen such as a touch-responsive interactive screen, infrared-emitting interactive screen, or gesture-recognizing interactive screen. In different examples, rounded-rectangle display member 701 can be flat or can curve around a portion of the circumference of the person's forearm.

Two-bangle attachment member 704 is configured to hold rounded-rectangle display member 701, data control unit 702, and sensor 703 within three inches of the surface of a person's body. In this example, two-bangle attachment member 704 further comprises: (a) two bangle-like elements; and (b) a central longitudinal portion between the two bangle-like elements. In this example, each of the two bangle-like elements spans between 50% and 95% of the circumference of the person's arm. The bangle-like elements are sufficiently flexible to allow them to be fitted around a portion of the circumference of the person's arm, but also sufficiently resilient to hold the device onto the person's arm once they have placed around the person's arm. In this example, the bangle-like elements hold the device onto the person's arm at two different locations along the longitudinal axis of the person's forearm. In this example, the central longitudinal portion encompasses opposite sides of the outer perimeter of rounded-rectangle display member 701. In this example, the central longitudinal portion has a shape which substantially follows the shape of rounded-rectangle display member 701.

Data control unit 702 can further comprise one or more components selected from the group consisting of: data processing member, data transmitting member, data receiving member, power source, and energy transducer. In various examples, data control unit 702 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 703 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 8:
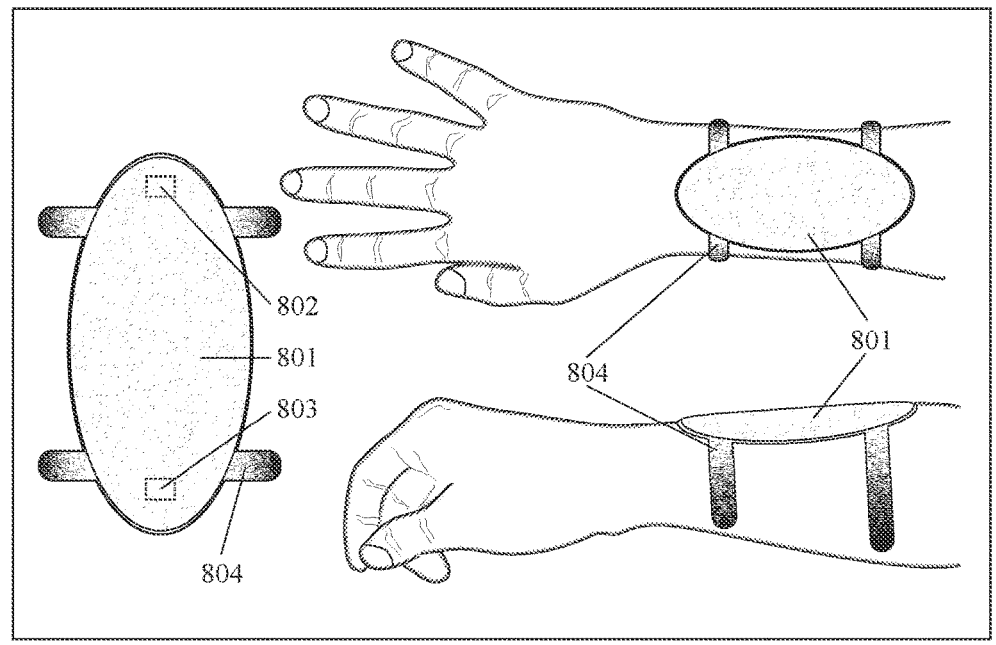
FIG. 8 shows a wearable device with a longitudinal arcuate display and a two-bangle attachment member.

FIG. 8 shows an example of a wearable computing device for the wrist and/or arm comprising: longitudinal arcuate display member 801; data control unit 802; sensor 803; and two-bangle attachment member 804. In this example, two bangle-like elements each span between 50% and 95% of the perimeter of the person's arm. The left portion of FIG. 8 shows a detailed top-down view of the device alone, the upper-right portion of this figure shows a top-down view of this device on a person's forearm, and the lower-right portion of this figure shows a side view of this device on a person's forearm.

This example is like the one shown in FIG. 7 except that the shape of display member 801 is more arcuate. In this example, this shape is an oval. In an example, this shape can be selected from the group consisting of: oval, circle, ellipse, or other conic section. In an example, this shape can be selected from the group consisting of: oval, circle, ellipse, egg-shape, figure eight, hourglass, clover leaf, and teardrop. The shape of the two-bangle attachment 804 also differs from that in FIG. 7 in order to conform to the oval shape of longitudinal arcuate display member 801.

Figure 9:
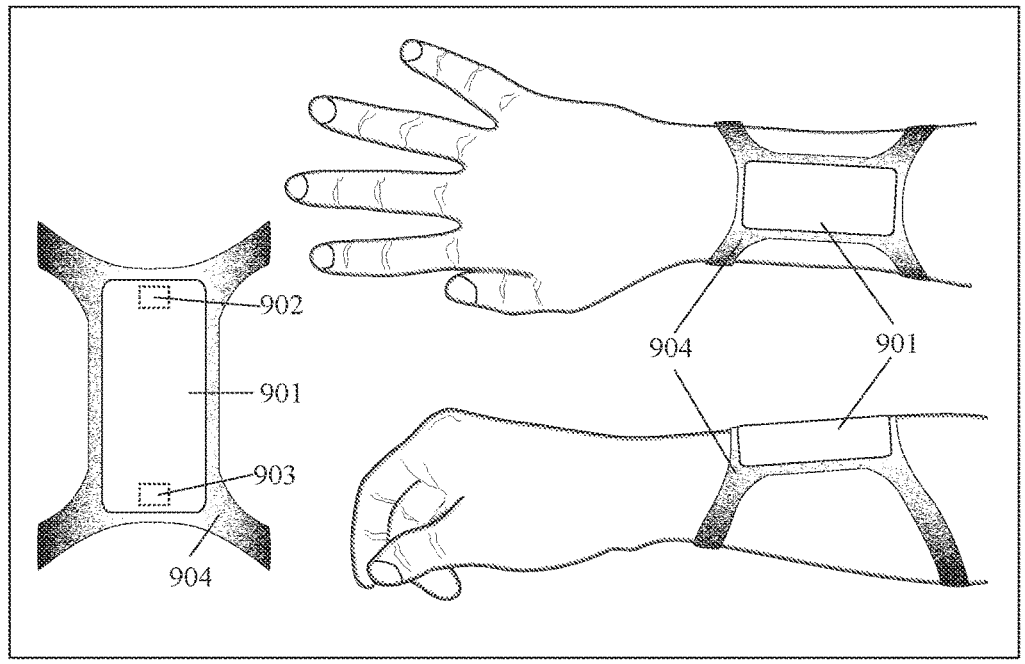
FIG. 9 shows a wearable device with a rounded-rectangle display and a longitudinal flared two-strap attachment member.

FIG. 9 shows an example of a wearable computing device for the wrist and/or arm comprising: rounded-rectangle display member 901; data control unit 902; sensor 903; and longitudinal flared-two-strap attachment member 904. The left portion of FIG. 9 shows a detailed top-down view of the device by itself. The upper-right portion of FIG. 9 shows a top-down view of this device on a person's forearm and the lower-right portion of FIG. 9 shows a side view of this device on a person's forearm.

Rounded-rectangle display member 901 has a longitudinal axis which is substantially parallel to the longitudinal axis of a person's forearm. In this example, rounded-rectangle display member 901 is worn on the dorsal surface of the person's wrist and/or arm. In other examples, it can be worn on the ventral surface or a side surface. In an example, rounded-rectangle display member 901 can comprise a computer display screen such as a touch-responsive interactive screen, infrared-emitting interactive screen, or gesture-recognizing interactive screen. Rounded-rectangle display member 901 can be flat or, alternatively, it can curve around a portion of the circumference of the person's forearm.

In this example, longitudinal flared-two-strap attachment member 904 holds rounded-rectangle display member 901, data control unit 902, and sensor 903 within three inches of the surface of a person's body. Longitudinal flared-two-strap attachment member 904 further comprises two straps or bands which each span the circumference of the person's wrist and/or arm. This holds the device onto the person's arm at two different locations along the longitudinal axis of the person's forearm. In an example, these straps or bands can be flexible. In an example, these straps or bands can each have portions which interconnect (such as with clips, clasps, snaps, buckles, or hook-and-eye) to fasten the device to the person's wrist and/or arm at two different places. In another example, these straps or bands can be stretched or expanded so that they can slip over a person's hand onto their wrist.

In this example, longitudinal flared-two-strap attachment member 904 also comprises a central longitudinal portion between the two straps or bands. This central longitudinal flared portion follows the outer perimeter of rounded-rectangle display member 901. In this example, the two straps or bands flare outwards from the central longitudinal portion—one towards the person's hand and one toward the person's elbow. As a result, the distance between the two straps or bands is shorter on the side of the arm with rounded-rectangle display member 901 and longer on the opposite side.

Data control unit 902 can further comprise one or more components selected from the group consisting of: data processing member, data transmitting member, data receiving member, power source, and energy transducer. In various examples, data control unit 902 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 903 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 10:
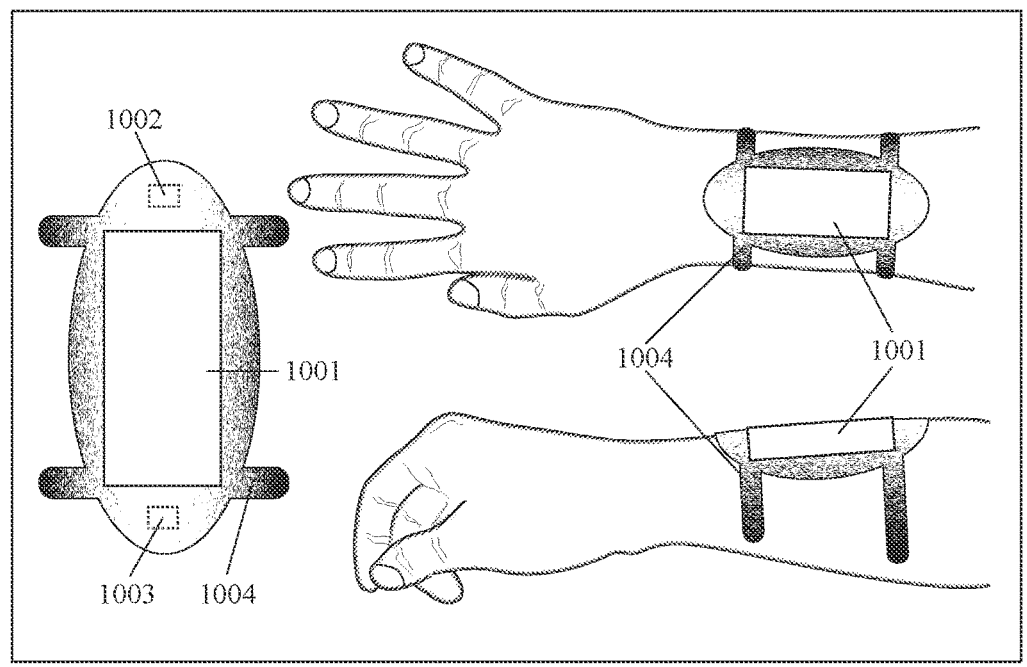
FIG. 10 shows a wearable device with a rectangular display and a two-bangle arcuate attachment member.

FIG. 10 shows an example of a wearable computing device for the wrist and/or arm comprising: rectangular display member 1001; data control unit 1002; sensor 1003; and two-bangle arcuate attachment member 1004. In this example, two bangle-like elements each span between 50% and 95% of the perimeter of the person's arm. In FIG. 10, the left portion shows a detailed top-down view of the device alone, the upper-right portion shows a top-down view of this device on a person's forearm, and the lower-right portion shows a side view of this device on a person's forearm.

In this example, rectangular display member 1001 has a longitudinal axis which is substantially parallel to the longitudinal axis of the person's forearm and is worn on the dorsal surface of their wrist and/or arm. Alternatively, it can be worn on the ventral surface or a side surface of their wrist and/or arm. In an example, rectangular display member 1001 can comprise a computer display screen such as a touch-responsive interactive screen, infrared-emitting interactive screen, or gesture-recognizing interactive screen. In different examples, rectangular display member 1001 can be flat or can curve around a portion of the circumference of the person's forearm.

Two-bangle arcuate attachment member 1004 is configured to hold rectangular display member 1001, data control unit 1002, and sensor 1003 within three inches of the surface of a person's body. In this example, two-bangle arcuate attachment member 1004 further comprises: (a) two bangle-like elements; and (b) a central longitudinal arcuate portion between the two bangle-like elements. In this example, each of the two bangle-like elements spans between 50% and 95% of the circumference of the person's arm. The bangle-like elements are flexible enough to be fitted around the person's arm, but resilient enough to hold the device in place once placed on the arm. The bangle-like elements hold the device onto the person's arm at two different locations along the longitudinal axis of the person's forearm.

In this example, the perimeter of the central longitudinal portion of two-bangle arcuate attachment member 1004 surrounds and exceeds the perimeter of rectangular display member 1001. In this example, the shape of the central longitudinal portion of two-bangle arcuate attachment member 1004 is an oval. In an example, the shape of this portion can be selected from the group consisting of: oval, circle, ellipse, or (other) conic section. In an example, the shape of this portion can be selected from the group consisting of: oval, circle, ellipse, egg-shape, figure eight, hourglass, clover leaf, and teardrop.

Data control unit 1002 can further comprise one or more components selected from the group consisting of: data processing member, data transmitting member, data receiving member, power source, and energy transducer. In various examples, data control unit 1002 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 1003 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 11:
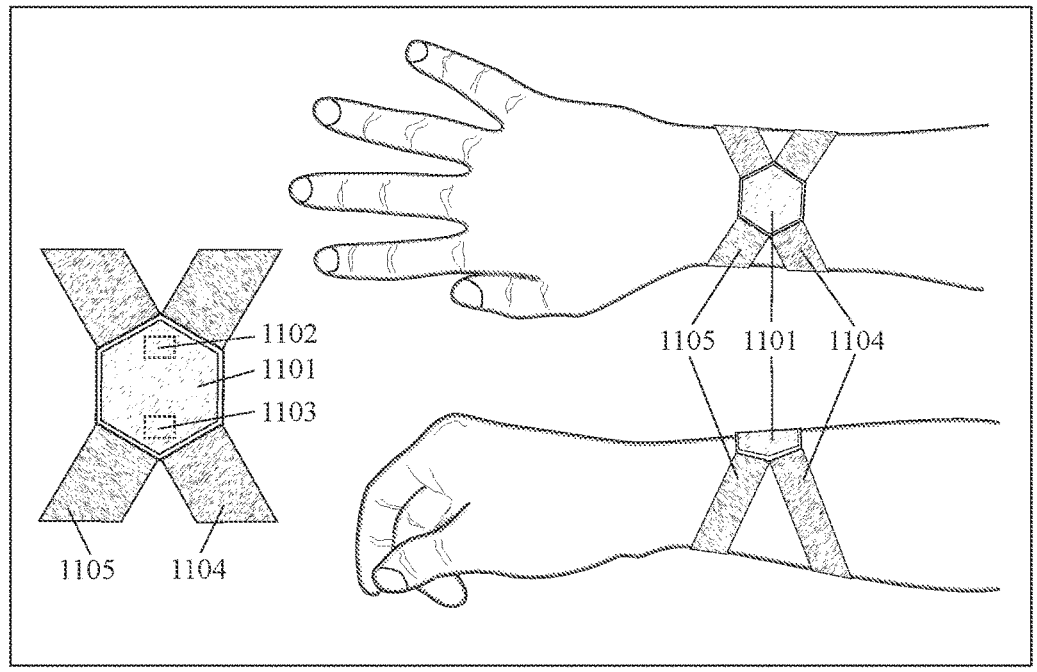
FIG. 11 shows a wearable device with a hexagonal display and straps.

FIG. 11 shows an example of a wearable computing device for the wrist and/or arm comprising: hexagonal display member 1101; data control unit 1102; sensor 1103; and straps 1104 and 1105. The left portion of FIG. 11 shows a detailed top-down view of the device by itself. The upper-right portion of FIG. 11 shows a top-down view of this device on a person's wrist. The lower-right portion of FIG. 11 shows a side view of this device on a person's wrist. A person's wrist or hand is considered to be part of their arm.

In this example, the shape of hexagonal display member 1101 is a hexagon. In an example, the vertexes of the hexagon can be rounded. In an example, hexagonal display member 1101 can be worn on the dorsal surface, ventral surface, or side surface of a person's wrist and/or arm. In an example, hexagonal display member 1101 can comprise a computer display screen, such as a touch-responsive interactive screen, infrared-emitting interactive screen, or gesture-recognizing interactive screen.

In this example, hexagonal display member 1101 is attached to a person's arm by straps 1104 and 1105. In this example, straps 1104 and 1105 each span the entire circumference of the person's wrist and/or arm. In this example, straps 1104 and 1105 flare outwards from adjacent sides of hexagonal display member 1101, forming an acute angle (in the range of 40-75 degrees) where they connect to hexagonal display member 1101. One strap flares out towards the person's hand and the other one toward the person's elbow. The distance between straps 1104 and 1105 is shorter on the (dorsal) side of the arm with hexagonal display member 1101 and longer on the opposite (ventral) side.

In an example, straps 1104 and 1105 can be flexible straps or bands. In an example, portions of a strap can connect with each other (such as with a clip, buckle, snap, or hook-and-eye mechanism) to fasten it around a person's wrist and/or arm. In another example, straps 1104 and 1105 can be sufficiently resilient or rigid that they fasten securely around a person's wrist and/or arm even though they span less than 100% of the circumference of the person's wrist and/or arm. In an example, straps 1104 and 1105 can be made with flexible metal or a resilient polymer. In an example, straps 1104 and 1105 can be stretchable, elastic, or expandable. In an example, straps 1104 and 1105 can be made with a stretchable or elastic material, such as stretchable or elastic fabric. In an example, straps 1104 and 1105 can comprise a series or chain of expandable, interconnected links. In an example, straps 1104 and 1105 can be stretched or expanded to slip over a person's hand onto a person's wrist.

Data control unit 1102 can further comprise one or more components selected from the group consisting of: data processing member, data transmitting member, data receiving member, power source, and energy transducer. In various examples, data control unit 1102 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 1103 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member.

Figure 12:
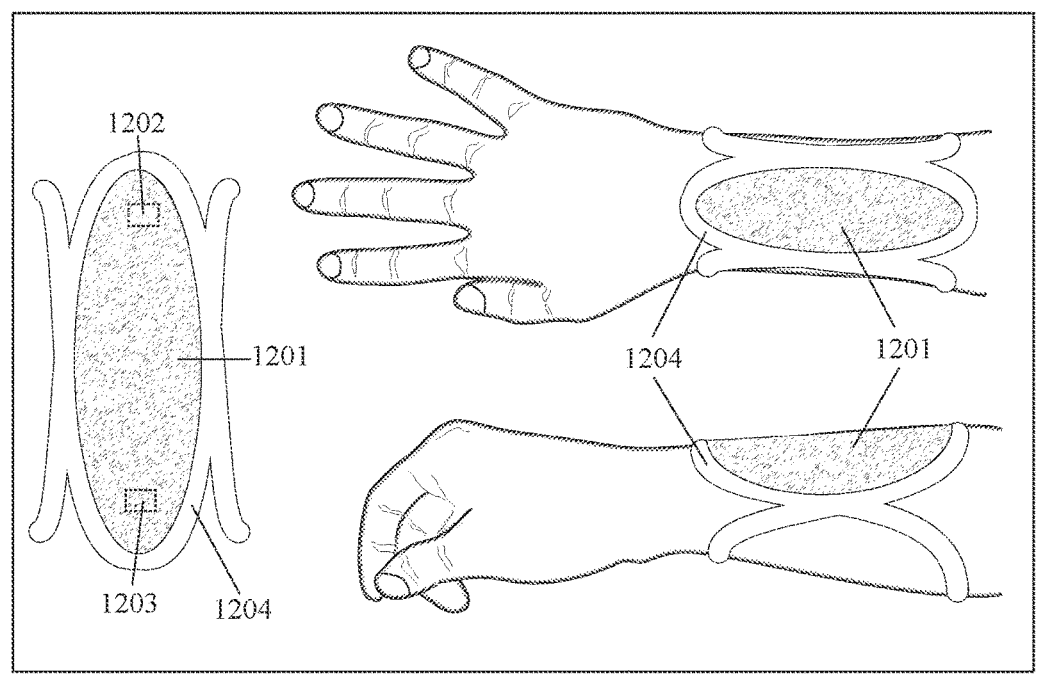
FIG. 12 shows a wearable device with a longitudinal arcuate display and a 3D figure-eight attachment member.

FIG. 12 shows an example of a wearable computing device for the wrist and/or arm comprising: longitudinal arcuate display member 1201; data control unit 1202; sensor 1203; and 3D figure-eight attachment member 1204. Within FIG. 12, the left portion shows a detailed top-down view of the device alone, the upper-right portion shows a top-down view of this device on a person's forearm, and the lower-right portion shows a side view of this device on a person's forearm. A person's wrist, fingers, hand, forearm, and upper arm are considered to be parts of their arm.

Longitudinal arcuate display member 1201 has a longitudinal axis which is substantially parallel to the longitudinal axis of the person's forearm. The length of longitudinal arcuate display member 1201 is greater than its width. In this example, longitudinal arcuate display member 1201 has an elliptical shape. A longitudinal arcuate display member can have a shape which is selected from the group consisting of: ellipse, other conic section, oval, oblong, egg shape, tear drop, kidney shape, yin-yang element, and hourglass. In various examples, longitudinal arcuate display member 1201 can be substantially on the dorsal surface, ventral surface, or a side surface of a person's wrist and/or arm. In various examples, longitudinal arcuate display member 1201 can be a non-interactive computer display screen, a touch-responsive interactive screen, an infrared-emitting interactive screen, and/or a gesture-recognizing interactive screen.

3D figure-eight attachment member 1204 holds longitudinal arcuate display member 1201, data control unit 1202, and sensor 1203 within three inches of the surface of a person's body. In this example, 3D figure-eight attachment member 1204 is shaped like a figure eight which has been curved in three-dimensions around the circumference of the person's forearm. On the dorsal surface of the person's wrist and/or forearm, the dorsal loop of 3D figure-eight attachment member 1204 encompasses longitudinal arcuate display member 1201. On the lateral surfaces of the person's wrist and/or forearm, two arcuate lines of 3D figure-eight attachment member 1204 intersect or overlap. In an example, portions of 3D figure-eight attachment member 1204 can be flexible and/or expandable so that it can be stretched over the person's hand in order to be slipped onto the person's wrist and/or forearm. In another example, the lateral or ventral portions of 3D figure-eight attachment member 1204 can be connected or disconnected by one or more clips, clasps, snaps, buckles, or hook-and-eye mechanisms so that it can be fastened around the person's wrist and/or forearm.

Data control unit 1202 can further comprise one or more components selected from the group consisting of: data processing member, data transmitting member, data receiving member, power source, and energy transducer. In various examples, data control unit 1202 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

Sensor 1203 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software.

Figure 13:
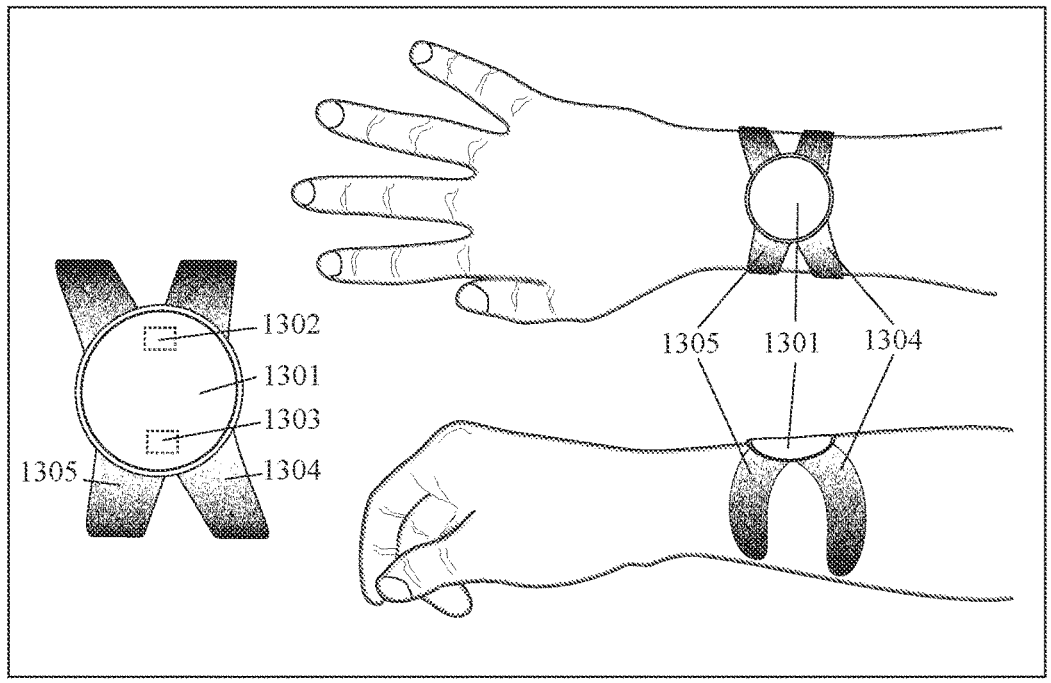
FIG. 13 shows a wearable device with an arcuate display and two flared circumferential attachment members.

FIG. 13 shows an example of a wearable computing device for the wrist and/or arm comprising: arcuate display member 1301; data control unit 1302; sensor 1303; and flared circumferential attachment members 1304 and 1305. Within FIG. 13, the left portion shows a detailed top-down view of the device by itself, the upper-right portion shows a top-down view of this device on a person's wrist, and the lower-right portion shows a side view of this device on a person's wrist. A person's wrist, hand, finger, forearm, and upper arm are considered to be parts of their arm.

Arcuate display member 1301 has a circular shape in this example. In various examples, the shape of arcuate display member 1301 can be selected from the group consisting of: circle, ellipse, other conic section, oval, oblong, egg, teardrop, and clover leaf. Arcuate display member 1301 can be worn on the dorsal, ventral, or side surface of a person's wrist and/or arm. Arcuate display member 1301 can comprise a touch-responsive interactive screen, infrared-emitting interactive screen, or gesture-recognizing interactive screen, or other type of electronic display screen. Arcuate display member 1301 can have a flat or curved lateral cross-sectional shape.

In this example, arcuate display member 1301 is attached to a person's arm by flared circumferential attachment members 1304 and 1305. In this example, flared circumferential attachment members 1304 and 1305 flare outwards from adjacent sides of arcuate display member 1301, forming an acute angle where they connect to arcuate display member 1301. Attachment member 1304 flares out towards the person's elbow and attachment member 1305 flares out toward the person's hand.

In this example, flared circumferential attachment members 1304 and 1305 each span between 50% and 95% of the circumference of the person's wrist and/or arm. In this example, flared circumferential attachment members 1304 and 1305 are sufficiently flexible that they can be flexed to fit around a person's arm, but are also sufficiently resilient to hold the device securely on the arm once they are fitted around the arm. In an example, flared circumferential attachment members 1304 and 1305 can be made with flexible metal or a resilient polymer. In another example, flared circumferential attachment members 1304 and 1305 can each span the entire circumference of the person's wrist and/or arm. In such an example, portions of a flared circumferential attachment member can connect with each other (such as with a clip, buckle, snap, or hook-and-eye mechanism) to fasten it around a person's wrist and/or arm.

Alternatively, flared circumferential attachment members 1304 and 1305 can be stretched or expanded in order to slip over a person's hand onto a person's wrist.

Data control unit 1302 can further comprise one or more components selected from the group consisting of: data processing member, data transmitting member, data receiving member, power source, and energy transducer. In various examples, data control unit 1302 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 1303 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 14:
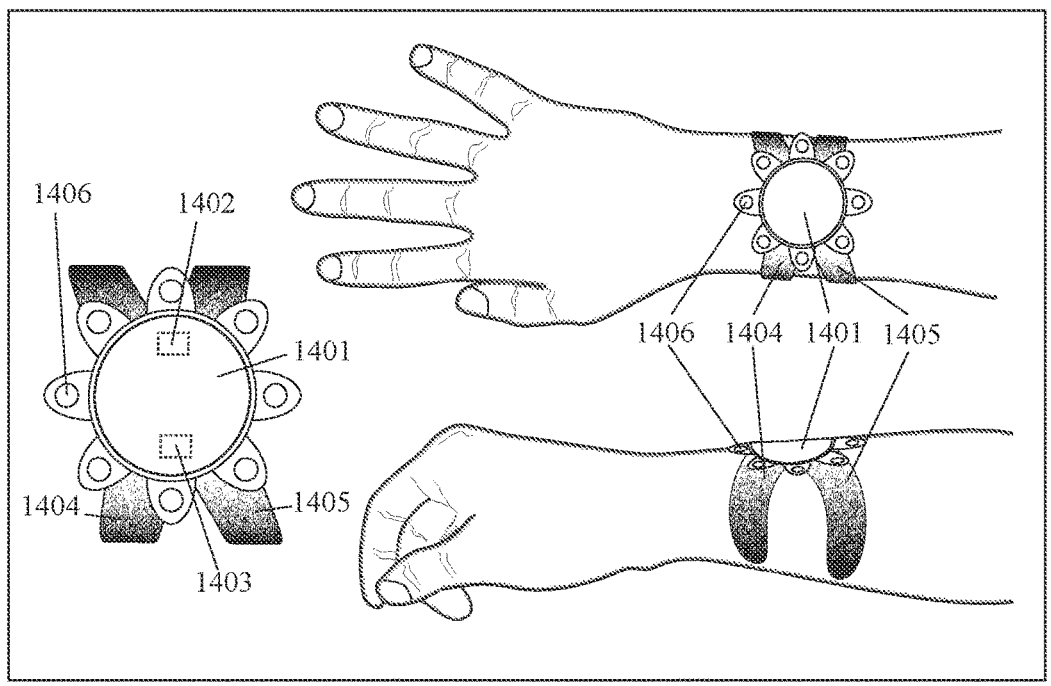
FIG. 14 shows a wearable device with a flower-shaped display and two flared circumferential attachment members.

FIG. 14 shows an example of a wearable computing device for the wrist and/or arm comprising: flower-shaped display member 1401; light-emitting members (including 1406); data control unit 1402; sensor 1403; and flared circumferential attachment members 1404 and 1405. The left portion of this figure shows a detailed top-down view of the device by itself, the upper-right portion shows a top-down view of this device on a person's wrist, and the lower-right portion shows a side view of this device on a person's wrist. A person's wrist, hand, finger, forearm, and upper arm are considered to be parts of their arm.

In this example, flower-shaped display member 1401 comprises a central circular portion and an array of petal portions extending radially outwards from the central circular portion. In this example, there are eight petal portions which are evenly spaced around the circumference of the central circular portion. In other examples, there can be fewer petals. In other examples, there can be more petals. In other examples, the petals can be unevenly spaced and/or overlap. Flower-shaped display member 1401 can be worn on the dorsal, ventral, or side surface of a person's wrist and/or arm. In an example, the central circular portion of flower-shaped display member 1401 can comprise a touch-responsive interactive screen, infrared-emitting interactive screen, or gesture-recognizing interactive screen, or other type of electronic display screen. Flower-shaped display member 1401 can have a flat or curved lateral cross-sectional shape.

In this example, there are light-emitting members (including 1406) on each of the petal portions of flower-shaped display member 1401. In an example, these light-emitting members (including 1406) can be LEDs. In an example, these light-emitting members (including 1406) can comprise a computer-to-human interface. In an example, different patterns of light emission from the light-emitting members can convey different messages. In various examples, different parameters of light emission can be selected from the group consisting of: which lights are on or off; brightness or intensity level; color and/or spectral frequency; and emission duration.

In this example, flower-shaped display member 1401 is attached to a person's arm by flared circumferential attachment members 1404 and 1405. In this example, flared circumferential attachment members 1404 and 1405 flare outwards from adjacent sides of flower-shaped display member 1401, forming an acute angle where they connect to flower-shaped display member 1401. Attachment member 1404 flares out towards the person's elbow and attachment member 1405 flares out toward the person's hand.

In this example, flared circumferential attachment members 1404 and 1405 each span between 50% and 95% of the circumference of the person's wrist and/or arm. In this example, flared circumferential attachment members 1404 and 1405 are sufficiently flexible that they can be flexed to fit around the person's arm, but are also sufficiently resilient to hold the device securely on their arm once they are fitted around the arm. In an example, flared circumferential attachment members 1404 and 1405 can be made with flexible metal or a resilient polymer. In another example, flared circumferential attachment members 1404 and 1405 can each span the entire circumference of the person's wrist and/or arm. In such an example, portions of a flared circumferential attachment member can connect with each other (such as with a clip, buckle, snap, or hook-and-eye mechanism) to fasten it around a person's wrist and/or arm. Alternatively, flared circumferential attachment members 1404 and 1405 can be stretched or expanded in order to slip over a person's hand onto a person's wrist.

Data control unit 1402 can further comprise one or more components selected from the group consisting of: data processing member, data transmitting member, data receiving member, power source, and energy transducer. In various examples, data control unit 1402 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 1403 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 15:
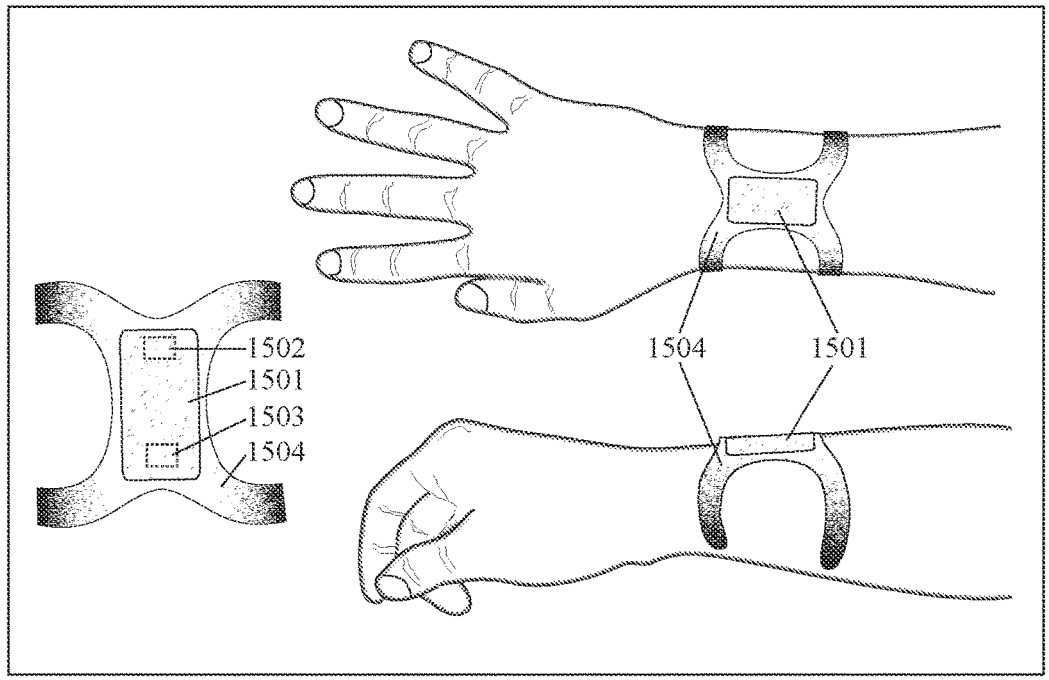
FIG. 15 shows a wearable device with a rectangular display and a truncated figure-eight attachment member.

FIG. 15 shows an example of a wearable computing device for the wrist and/or arm comprising: rectangular display member 1501; data control unit 1502; sensor 1503; and truncated figure-eight attachment member 1504. Within FIG. 15, the left portion shows a detailed top-down view of the device alone, the upper-right portion shows a top-down view of this device on a person's forearm, and the lower-right portion shows a side view of this device on a person's forearm. A person's wrist, hand, finger, forearm, and upper arm are considered to be parts of their arm.

Rectangular display member 1501 has a longitudinal axis which is substantially parallel to the longitudinal axis of a person's forearm. Rectangular display member 1501 can be worn on the dorsal, ventral, or side surface of the person's wrist and/or arm. Rectangular display member 1501 can comprise a touch-responsive interactive screen, infrared-emitting interactive screen, gesture-recognizing interactive screen, or other type of computer display screen. Rectangular display member 1501 can have a flat or curved cross-sectional shape.

Truncated figure-eight attachment member 1504 holds rectangular display member 1501, data control unit 1502, and sensor 1503 within three inches of the surface of a person's body. Truncated figure-eight attachment member 1504 has a shape like a figure eight wherein: (a) the central portion of the figure eight is thicker than the other portions; (b) an upper arc of the upper loop has been removed; (c) a lower arc of the lower loop has been removed, and (d) the remaining truncated figure eight has been curved around a portion of the circumference of the person's arm. Expressing this geometry in a different manner, truncated figure-eight attachment member 1504 can have a shape like a capital letter "H" in which the two upper lines bow outwards from the center to the top and in which the two lower lines bow outwards from the center to the bottom.

In an example, truncated figure-eight attachment member 1504 can span between 50% and 95% of the circumference of the person's wrist and/or arm. In an example, truncated figure-eight attachment member 1504 can be sufficiently flexible to fit around the person's arm, but also sufficiently resilient to hold the device on the arm once it is fitted around the arm. In an example, truncated figure-eight attachment member 1504 can comprise a flexible metal or resilient polymer. In this example, truncated figure-eight attachment member 1504 further comprises a central portion (e.g. the "thick" center of the figure eight) which encompasses the perimeter of rectangular display member 1501.

Data control unit 1502 can further comprise one or more components selected from the group consisting of: data processing member, data transmitting member, data receiving member, power source, and energy transducer. In various examples, data control unit 1502 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 1503 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 16:
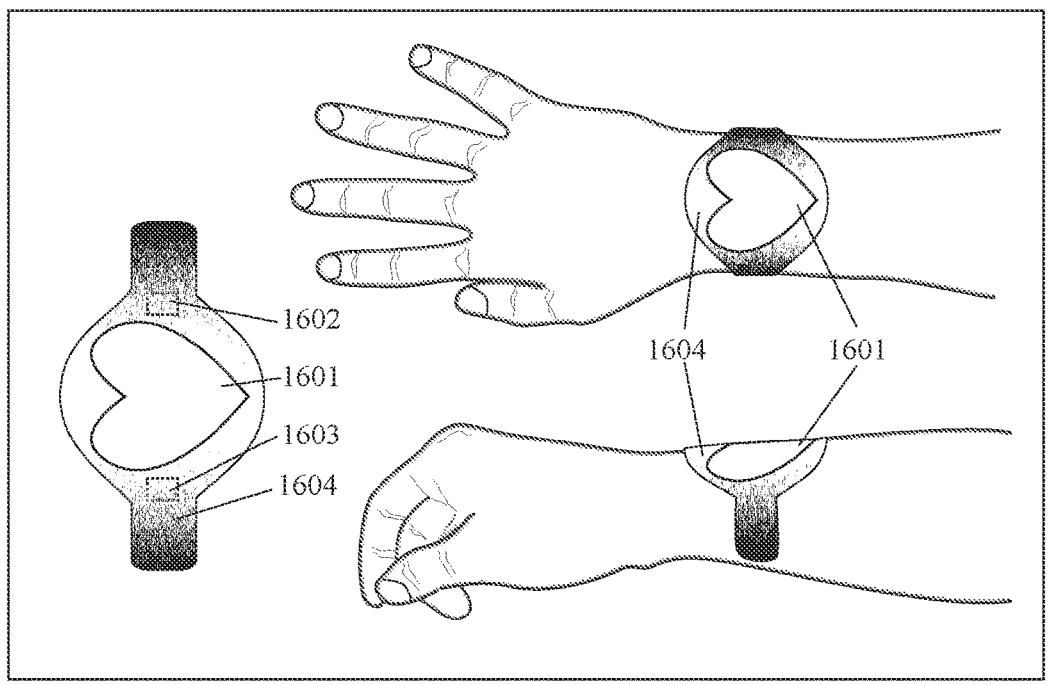
FIG. 16 shows a wearable device with a heart-shaped display and a circumferential attachment member.

FIG. 16 shows an example of a wearable computing device for the wrist and/or arm comprising: heart-shaped display member 1601; data control unit 1602; sensor 1603; and circumferential attachment member 1604. Within FIG. 16, the left portion shows a detailed top-down view of the device alone, the upper-right portion shows a top-down view of this device on a person's forearm, and the lower-right portion shows a side view of this device on a person's forearm. A person's wrist, hand, finger, forearm, and upper arm are considered to be parts of their arm.

In this example, heart-shaped display member 1601 is oriented with its longitudinal axis being substantially parallel to the longitudinal axis of a person's forearm. Alternatively, heart-shaped display member 1601 can have its longitudinal axis be substantially perpendicular to the forearm longitudinal axis. Heart-shaped display member 1601 can be worn on the dorsal, ventral, or side surfaces of a person's arm. In an example, the entirety of heart-shaped display member 1601 can comprise a touch-responsive interactive screen, infrared-emitting interactive screen, gesture-recognizing interactive screen, or other type of computer display screen. In an example, a subset or inner member of heart-shaped display member 1601 can comprise a touch-responsive interactive screen, infrared-emitting interactive screen, gesture-recognizing interactive screen, or other type of computer display screen.

Circumferential attachment member 1604 holds heart-shaped display member 1601, data control unit 1602, and sensor 1603 within three inches of the surface of a person's body. In an example, circumferential attachment member 1604 can span between 50% and 95% of the circumference of the person's arm. In an example, circumferential attachment member 1604 can be flexible enough to fit onto the person's arm, but also resilient enough to hold the device on the arm once it is fitted on the arm. In an example, circumferential attachment member 1604 can comprise a flexible metal or resilient polymer. In this example, circumferential attachment member 1604 can have a flared portion which encompasses the perimeter of heart-shaped display member 1601.

In an alternative example, circumferential attachment member 1604 can span the entire circumference of the person's arm. In an example, portions of circumferential attachment member 1604 can connect with each other (such as with one or more clips, clasps, snaps, buckles, or hook-and-eye mechanisms) in order to fasten it around a person's arm. Alternatively, circumferential attachment member 1604 can stretch or expand around a person's hand in order to slip the device over the hand and onto the arm.

Data control unit 1602 can further comprise one or more components selected from the group consisting of: data processing member, data transmitting member, data receiving member, power source, and energy transducer. In various examples, data control unit 1602 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 1603 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software.

Figure 17:
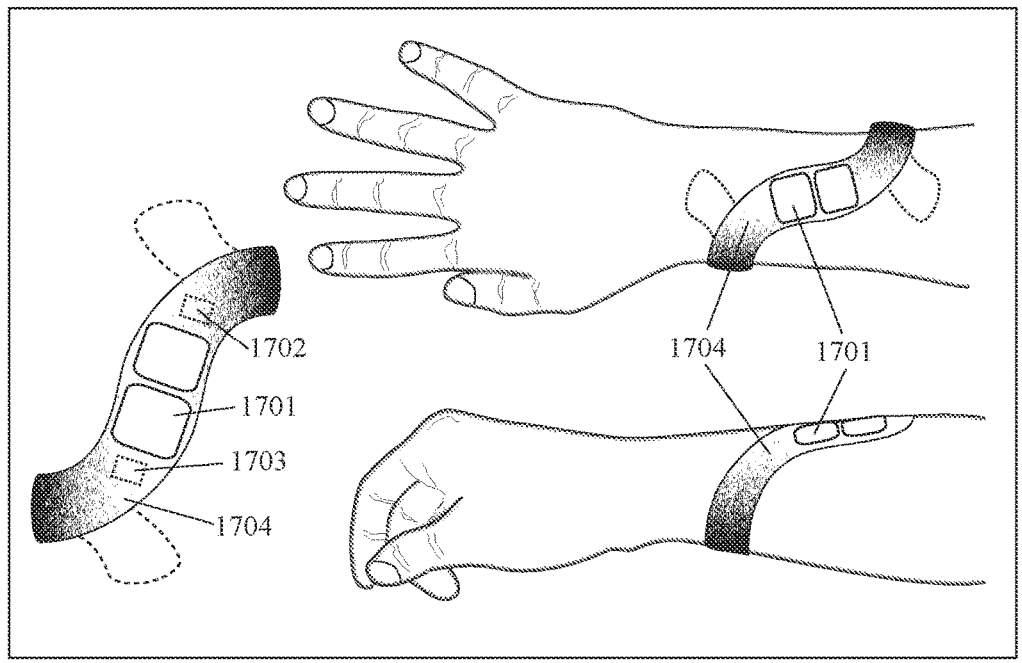
FIG. 17 shows a wearable device with at least one display and a spiral attachment member.

FIG. 17 shows an example of a wearable computing device for the wrist and/or arm comprising: at least one display member 1701; data control unit 1702; sensor 1703; and spiral attachment member 1704. Within FIG. 17, the left portion shows a detailed top-down view of the device alone, the upper-right portion shows a top-down view of this device on a person's forearm, and the lower-right portion shows a side view of this device on a person's forearm. A person's wrist, hand, finger, forearm, and upper arm are considered to be parts of their arm.

In this example, at least one display member 1701 is encompassed by spiral attachment member 1704. In this example, there are two display members, of which 1701 is one. In alternative example, there can be just one display member. In other examples, there can three or more display members. The at least one display member 1701 can be worn on the dorsal, ventral, and/or side surfaces of a person's arm. In various examples, at least one display member 1701 can comprise a touch-responsive interactive screen, infrared-emitting interactive screen, gesture-recognizing interactive screen, or other type of computer display screen.

Spiral attachment member 1704 holds the at least one display member 1701, data control unit 1702, and sensor 1703 within three inches of the surface of a person's body. As shown in FIG. 17, spiral attachment member 1704 can spiral around the full circumference of the person's arm. This does not have to be within the same circumferential plane. In an example, a spiral attachment member can spiral around 50%-100% of the circumference of a person's arm. This does not have to be within the same circumferential plane. In an example, a spiral attachment member can spiral around more than 100% of the circumference of a person's arm. This does not have to be within the same circumferential plane. In an example, a spiral attachment can spiral multiple times around the circumference of a person's arm. This does not have to be within the same circumferential plane.

In an example, spiral attachment member 1704 can be flexible enough to fit around a person's arm without a clip, buckle, snap, or hook-and-eye mechanism, but can also be resilient enough to hold the device on the arm once it is fitted on the arm. In an example, spiral attachment member 1704 can comprise a flexible metal or resilient polymer. In an example, spiral attachment member 1704 can further comprise one or more clips, clasps, snaps, buckles, or hook-and-eye mechanisms in order to fasten it around a person's arm. In an example, spiral attachment member 1704 can stretch or expand around a person's hand in order to slip the device over the hand and onto the arm.

Data control unit 1702 can further comprise one or more components selected from the group consisting of: data processing member, data transmitting member, data receiving member, power source, and energy transducer. In various examples, data control unit 1702 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 1703 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software.

Figure 18:
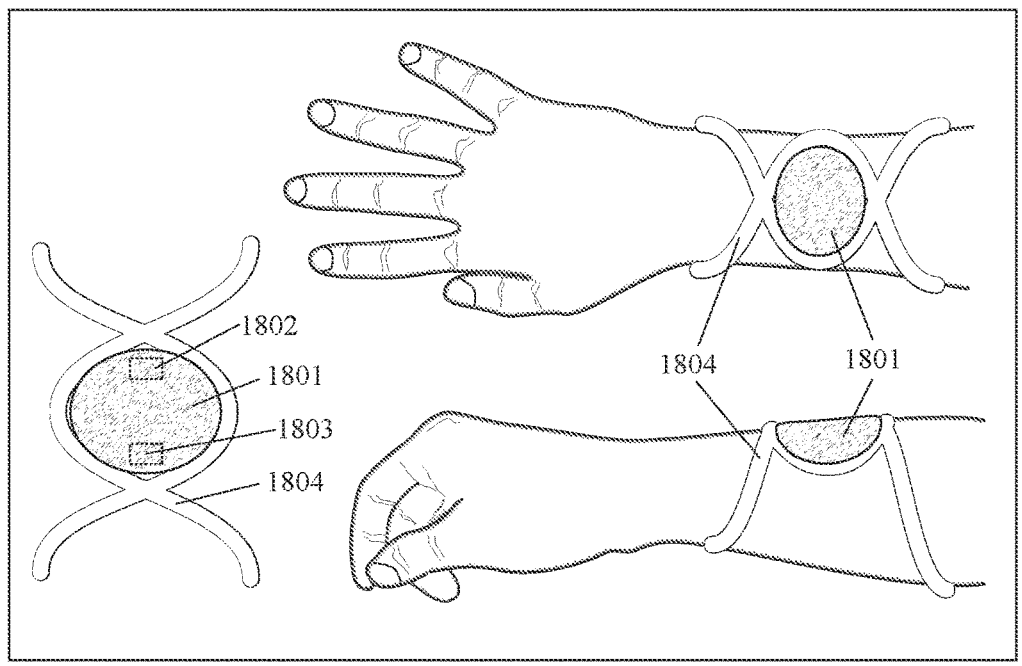
FIG. 18 shows a wearable device with an arcuate display and a symmetrically-sinusoidal attachment member.

FIG. 18 shows an example of a wearable computing device for the wrist and/or arm comprising: arcuate display member 1801; data control unit 1802; sensor 1803; and symmetrically-sinusoidal attachment member 1804. Within FIG. 18, the left portion shows a detailed top-down view of the device alone, the upper-right portion shows a top-down view of this device on a person's forearm, and the lower-right portion shows a side view of this device on a person's forearm. A person's wrist, hand, finger, forearm, and upper arm are considered to be parts of their arm.

In this example, arcuate display member 1801 is encompassed by symmetrically-sinusoidal attachment member 1804. Arcuate display member 1801 can be worn on the dorsal, ventral, or side surfaces of a person's arm. In various examples, arcuate display member 1801 can comprise a touch-responsive interactive screen, infrared-emitting interactive screen, gesture-recognizing interactive screen, or other type of computer display screen. Arcuate display member 1801 can have a flat or curved cross-sectional shape.

Symmetrically-sinusoidal attachment member 1804 holds arcuate display member 1801, data control unit 1802, and sensor 1803 within three inches of the surface of a person's body. Symmetrically-sinusoidal attachment member 1804 has a shape that is the merger of first and second sinusoidal elements, wherein the second element comprises a reflection of the first element around the longitudinal axis of the first element. In this example, the first and second elements are positioned so that they share substantially the same longitudinal axis, around which the second element is reflected.

In an example, when a first sinusoidal element has 1-2 wavelengths, then combination of first and reflected second sinusoidal elements can create a shape with a middle loop. In an example, arcuate display member 1801 can be encompassed by this middle loop. In an example, symmetrically-sinusoidal attachment member 1804 can have two outer loops, one on each side of the middle loop, which each span the full circumference of the person's arm and hold the device onto the arm. In an example, symmetrically-sinusoidal attachment member 1804 can have two outer arcing members, one on each side of the middle loop, which each span between 50%-95% of the circumference of the person's arm. Viewed from the top down, symmetrically-sinusoidal attachment member 1804 can look similar to a (two-wave half-phase) portion of a double helix, but with a different structure in 3D space. Also viewed from the top down, symmetrically-sinusoidal attachment member 1804 can look similar to the "Green Lantern" ™ superhero symbol, but with curved side portions rather than straight side portions.

In an example, symmetrically-sinusoidal attachment member 1804 can be sufficiently flexible that it can be fitted around a person's arm, but also sufficiently resilient that is holds the device on the arm once it is fitted around the arm. In an example, symmetrically-sinusoidal attachment member 1804 can be stretched or expanded so that it can be slipped over a person's hand to fit on their arm. In an example, symmetrically-sinusoidal attachment member 1804 can include one or more clips, buckles, snaps, or hook-and-eye mechanisms which enable it to be disconnected and then reconnected in order to fasten it around a person's wrist and/or arm.

Data control unit 1802 can further comprise one or more components selected from the group consisting of: data processing member, data transmitting member, data receiving member, power source, and energy transducer. In various examples, data control unit 1802 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 1803 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software. In an example, one or more sensors can be co-located with display member or located elsewhere.

Figure 19:
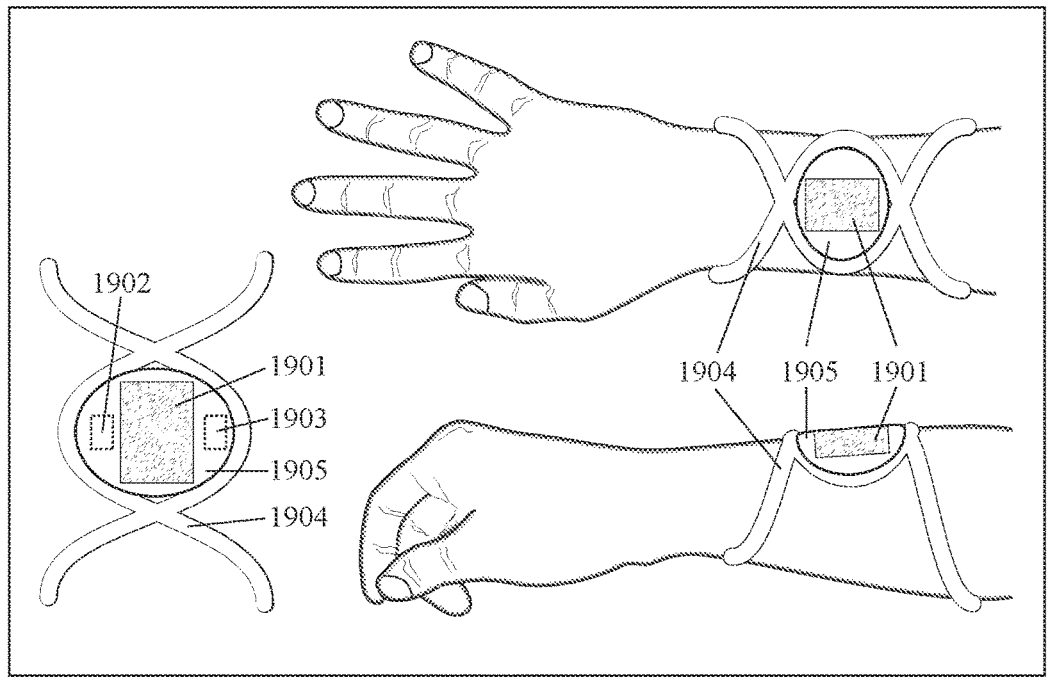
FIG. 19 shows a wearable device with a display and a symmetrically-sinusoidal attachment member.

FIG. 19 shows an example of a wearable computing device for the wrist and/or arm comprising: display member 1901; housing 1905; data control unit 1902; sensor 1903; and symmetrically-sinusoidal attachment member 1904. Within FIG. 19, the left portion shows a detailed top-down view of the device alone, the upper-right portion shows a top-down view of this device on a person's forearm, and the lower-right portion shows a side view of this device on a person's forearm. A person's wrist, hand, finger, forearm, and upper arm are considered to be parts of their arm. The example shown in FIG. 19 is similar to the example shown in FIG. 18 except that the display member (1901) is contained within a housing (1905) which, in turn, is encompassed by the middle loop of symmetrically-sinusoidal attachment member 1904. In the example in FIG. 19, housing 1905 can be arcuate and display member 1901 need not be arcuate.

Figure 20:
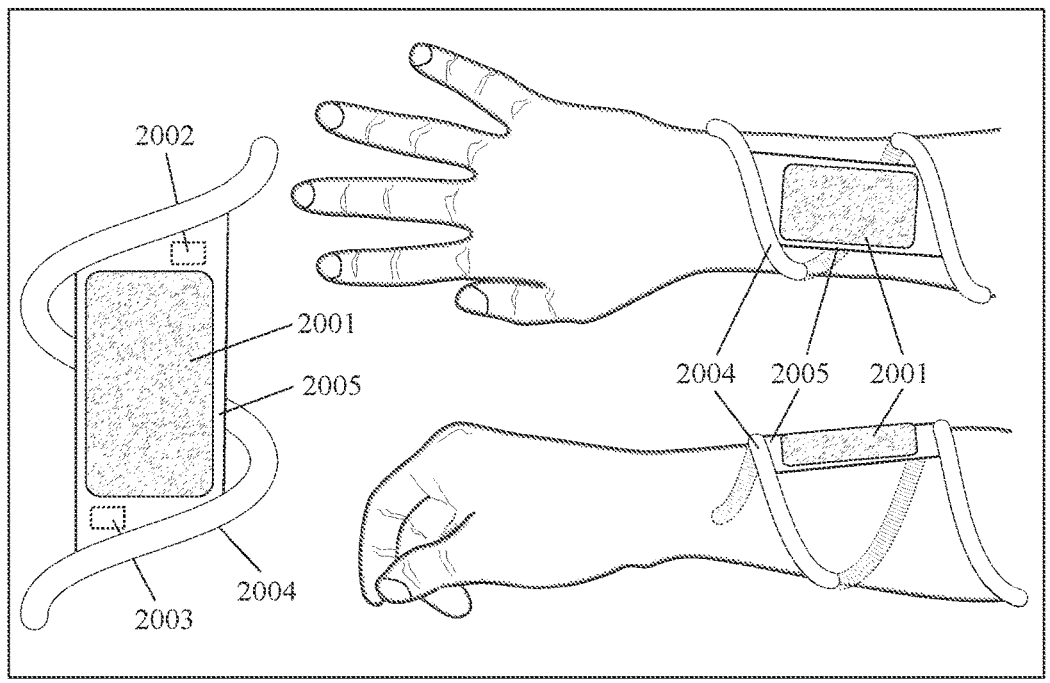
FIG. 20 shows a wearable device with a display, an inter-spiral housing, and a spiral attachment member.

FIG. 20 shows an example of a wearable computing device for the wrist and/or arm comprising: display member 2001; inter-spiral housing 2005; data control unit 2002; sensor 2003; and spiral attachment member 2004. Within FIG. 20, the left portion shows a detailed top-down view of the device alone, the upper-right portion shows a top-down view of this device on a person's forearm, and the lower-right portion shows a side view of this device on a person's forearm. A person's wrist, hand, finger, forearm, and upper arm are considered to be parts of their arm.

In this example, inter-spiral housing 2005 houses display member 2001. In this example, inter-spiral housing 2005 spans from a first arc (or arm) to a second arc (or arm) of spiral attachment member 2004 along a single side of the person's forearm. In this example, this side is the dorsal side. In this example, inter-spiral housing 2005 has a substantially parallelogram shape. In an alternative example, inter-spiral housing 2005 can be arcuate. In various examples, inter-spiral housing can be flat or it can curve around a portion of the circumference of the person's arm. In various examples, inter-spiral housing 2005 and display member 2001 can be on the dorsal, ventral, or side surface of a person's arm. In various examples, display member 2001 can comprise a touch-responsive interactive screen, infrared-emitting interactive screen, gesture-recognizing interactive screen, or other type of computer display screen.

Spiral attachment member 2004 holds inter-spiral housing 2005, display member 2001, data control unit 2002, and sensor 2003 within three inches of the surface of a person's body. As shown in FIG. 20, spiral attachment member 2004 can spiral multiple times around the circumference of the person's arm. This does not have to be within the same circumferential plane. In an example, spiral attachment member 2004 can be flexible enough to fit around a person's arm without a clip, buckle, snap, or hook-and-eye mechanism, but can also be resilient enough to hold the device on the arm once it is fitted on the arm. In an example, spiral attachment member 2004 can comprise a flexible metal or resilient polymer. In an example, spiral attachment member 2004 can further comprise one or more clips, clasps, snaps, buckles, or hook-and-eye mechanisms in order to fasten it around a person's arm. In an example, spiral attachment member 2004 can stretch or expand around a person's hand in order to slip the device over the hand and onto the arm.

Data control unit 2002 can further comprise one or more components selected from the group consisting of: data processing member, data transmitting member, data receiving member, power source, and energy transducer. In various examples, data control unit 2002 can be in wireless communication with a handheld electronic device, a different wearable technology device, an array of wearable sensors, a communication network tower, a satellite, a home control system, and/or an implantable medical device. In an example, a power source can be a battery. In various examples, an energy transducer can harvest energy from kinetic energy, thermal energy, biochemical energy, ambient light energy, and/or ambient electromagnetic energy.

In various examples, sensor 2003 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, other motion sensor, piezoelectric sensor, pressure sensor, oximetry sensor, spectroscopic sensor or other light-spectrum-analyzing sensor, strain gauge, ultrasonic sensor, MEMS sensor, GPS sensor, compass, humidity sensor, and temperature sensor.

In various examples, one or more sensors can be in kinetic, electromagnetic, optical, fluid, and/or chemical communication with the person's body. In various examples, this device can further comprise: one or more LEDs, lasers, or other light-emitting members; one or more infrared light emitters; a coherent light projector; an image projector; one or more speakers or other sound-emitting members; one or more vibrating or other tactile-sensation-creating members; one or more neurostimulators, myostimulators, or other electromagnetic energy emitters; one or more buttons, knobs, or keys; gesture recognition hardware and software; and speech recognition hardware and software.

Figure 21:
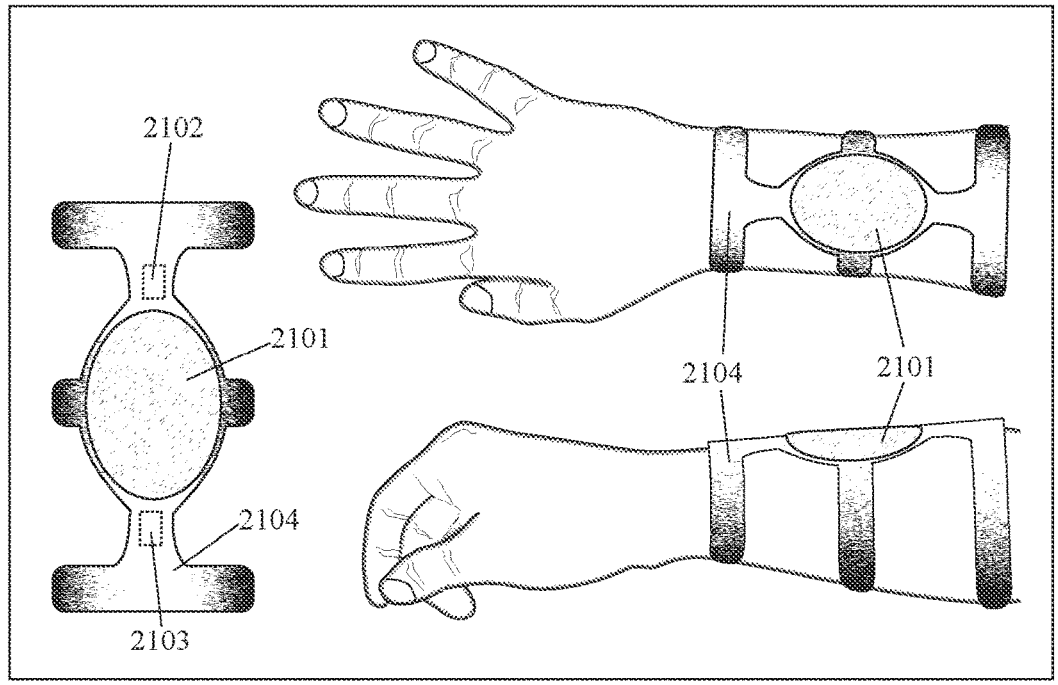
FIG. 21 shows a wearable device with an arcuate display and a three-band attachment member.

FIG. 21 shows an example of a wearable computing device for the wrist and/or arm comprising: arcuate display member 2101; data control unit 2102; sensor 2103; and three-band attachment member 2104. Within FIG. 21, the left portion shows a top-down view of the device alone, the upper-right portion shows a top-down view of the device on a person's forearm, and the lower-right portion shows a lateral view of the device on a person's forearm. The wrist, hand, finger, forearm, and upper arm are considered to be parts of the arm.

Three-band attachment member 2104 holds arcuate display member 2101, data control unit 2102, and sensor 2103 within three inches of the surface of a person's body. Three-band attachment member 2104 further comprises three bands, straps, or loops which each span a portion, or all, of the circumference of the person's forearm. In an example, these bands, straps, or loops: can each span 100% of the circumference of the person's forearm; and can have buckles, snaps, adhesive, hook-and-eye mechanisms or other connecting elements which enable them to be connected around the circumference of the person's forearm. In an example, these bands, straps, or loops: can each span 100% of the circumference of the person's forearm; and can be stretched or expanded around the person's hand to slip onto the person's forearm. In an example, these bands, straps, or loops: can each span between 50% and 95% of the circumference of the person's forearm; and are sufficiently flexible to fit around the forearm, but sufficiently rigid to hold on to the forearm once fitted.

In this example, arcuate display member 2101: (a) has a longitudinal axis which is substantially parallel to the longitudinal axis of a person's forearm; (b) can be worn on the dorsal, ventral, and/or lateral surface of the person's forearm; and (c) can comprise a flat or curved computer display screen. In this example, arcuate display member 2101 has a top-down shape selected from the group consisting of: ellipse, conic section, oval, oblong, and rectangle with rounded vertexes. In this example, arcuate display member 2101 is centrally located along the longitudinal axis of three-band attachment member 2104.

Data control unit 2102 can further comprise one or more components selected from the group consisting of: data processing member, data transmitting member, data receiving member, power source, and energy transducer. In various examples, data control unit 2102 can communicate with a handheld electronic device, a different wearable technology device, an array of wearable sensors, a communication network tower, a satellite, a home control system, and/or an implantable medical device. In various examples, an energy transducer can harvest energy from kinetic energy, thermal energy, biochemical energy, ambient light energy, and/or ambient electromagnetic energy.

Sensor 2103 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

One or more sensors which are part of this device can be in kinetic, electromagnetic, optical, fluid, and/or chemical communication with the person's body. This device can further comprise: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 22:
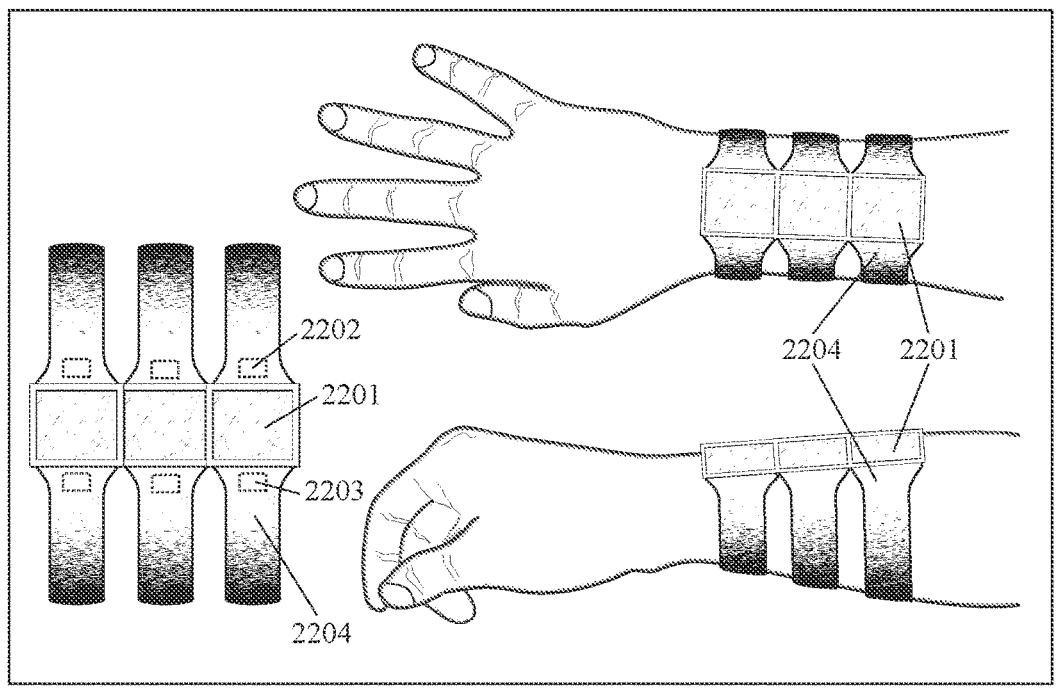
FIG. 22 shows a wearable system with a plurality of connectible modules, wherein each module comprises a display and a band attachment member.

FIG. 22 shows an example of a wearable computing system for the wrist and/or arm comprising: a plurality of connectible modules; wherein each connecting module further comprises a display member (such as 2201), a data control unit (such as 2202), a sensor (such as 2203), and a band attachment member (such as 2204); wherein the majority of the connecting modules connect to each other on a single surface of the forearm; and wherein this surface is selected from the group consisting of: dorsal, ventral, and lateral. In the example shown in FIG. 22, there are three connectible modules. Within FIG. 22, the left portion shows a top-down view of the device alone, the upper-right portion shows a top-down view of the device on a person's forearm, and the lower-right portion shows a lateral view of the device on a person's forearm. The wrist, hand, finger, forearm, and upper arm are considered to be parts of the arm.

In this example, each of the connectible modules has its own display member (such as 2001), its own data control unit (such as 2202), its own sensor (such as 2203), and its own band attachment member (such as 2204). In other examples, one or more connectible modules may not have its own data control unit, its own sensor, or its own band attachment member. In an example, each connectible module can perform a different function. In an alternative example, different connectible models can collectively perform a single function, but they can collectively provide a larger display area for that function. This gives the user the option of expanding total system display area by adding additional connectible modules.

In this example, one or more band attachment members (such as 2204) hold the connectible modules within three inches of the surface of a person's body. In an example, a band attachment member (such as 2204) can span 100% of the circumference of the person's forearm and have buckles, snaps, adhesive, hook-and-eye mechanisms or other connecting elements. In an example, a band attachment member (such as 2204) can be stretched or expanded around the hand to slip onto the forearm. In an example, a band attachment member (such as 2204) can span between 50% and 95% of the circumference of the forearm and can be flexible enough to bend around the forearm.

In an example, arcuate display members (such as 2201) can each comprise a flat or curved computer display screen and can each have shape selected from the group consisting of square, rectangle, rhombus, trapezoid, hexagon, octagon, conic section, oval, oblong, and hemisphere.

In an example, data control units (such as 2202) can further comprise one or more components selected from the group consisting of: data processing member, data transmitting member, data receiving member, power source, and energy transducer. In various examples, data control units can communicate with a handheld electronic device, a different wearable technology device, an array of wearable sensors, a communication network tower, a satellite, a home control system, and/or an implantable medical device. In various examples, an energy transducer can harvest energy from kinetic energy, thermal energy, biochemical energy, ambient light energy, and/or ambient electromagnetic energy.

Sensor 2203 and/or other sensors which are part of this system can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

Sensor 2203 and/or other sensors which are part of this system can be in kinetic, electromagnetic, optical, fluid, and/or chemical communication with the person's body. This device can further comprise: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 23:
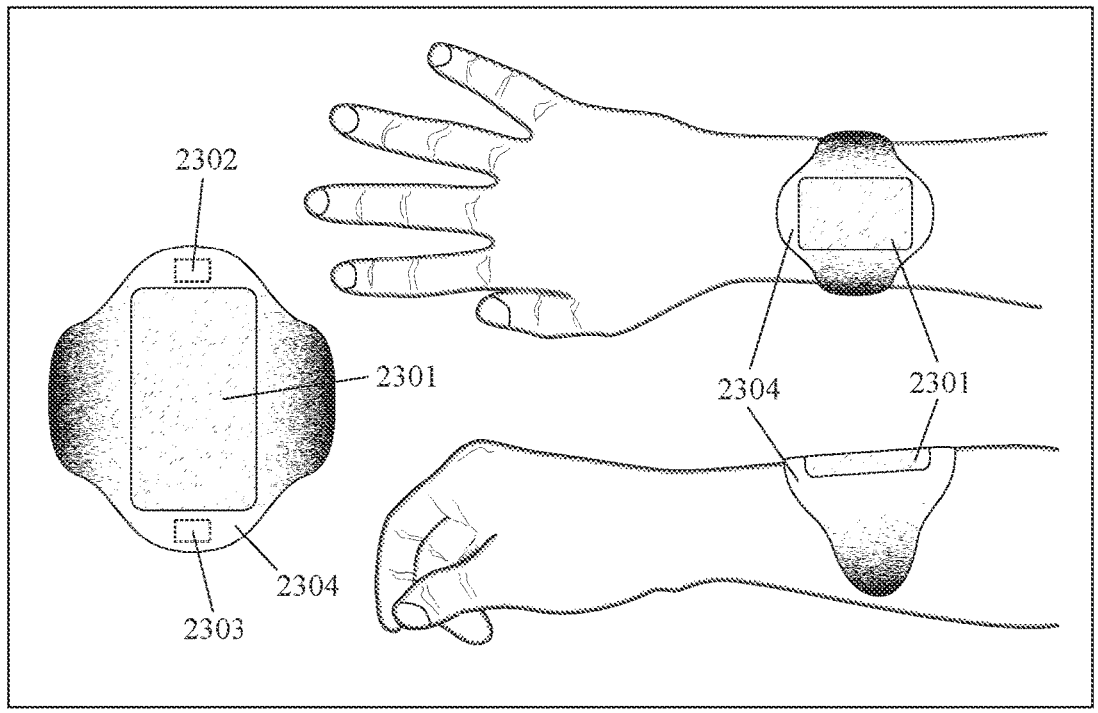
FIG. 23 shows a wearable device with an arcuate display and a flared-bangle attachment member.

FIG. 23 shows an example of a wearable computing device for the wrist and/or arm comprising: arcuate display member 2301; data control unit 2302; sensor 2303; and flared-bangle attachment member 2304. Within FIG. 23, the left portion shows a top-down view of the device alone, the upper-right portion shows a top-down view of the device on a person's forearm, and the lower-right portion shows a lateral view of the device on a person's forearm. The wrist, hand, finger, forearm, and upper arm are considered to be parts of the arm.

In an example, flared-bangle attachment member 2304: (a) holds arcuate display member 2301, data control unit 2302, and sensor 2303 within three inches of the surface of a person's body; (b) spans between 50% and 95% of the circumference of the person's forearm; (c) is sufficiently flexible to fit around the forearm, but also sufficiently rigid to hold on to the forearm once fitted; and (d) is flared on the surface of the person's forearm wherein the arcuate display member located. In various examples, arcuate display member 2301: can comprise a flat or curved computer display screen; can be worn on the dorsal, ventral, and/or lateral surface of the person's forearm; and can have a shape selected from the group consisting of: rectangle with rounded vertexes; square with rounded vertexes; conic section; oval; and oblong.

In an example, data control unit 2302 can further comprise one or more components selected from the group consisting of: data processing member, data transmitting member, data receiving member, power source, and energy transducer. In various examples, data control unit 2302 can communicate with a handheld electronic device, a different wearable technology device, an array of wearable sensors, a communication network tower, a satellite, a home control system, and/or an implantable medical device.

Sensor 2303 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor. One or more sensors which are part of this device can be in kinetic, electromagnetic, optical, fluid, and/or chemical communication with the person's body.

This device can further comprise: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 24:
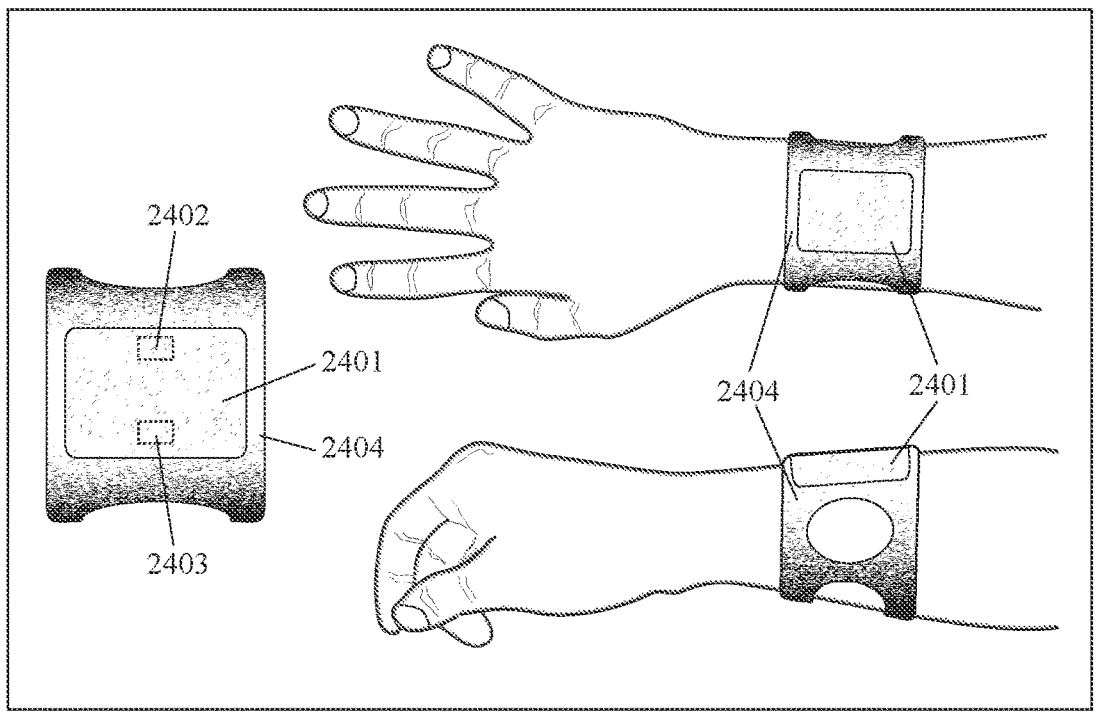
FIG. 24 shows a wearable device with an arcuate display and a holey attachment member.

FIG. 24 shows an example of a wearable computing device for the wrist and/or arm comprising: arcuate display member 2401; data control unit 2402; sensor 2403; and holey attachment member 2404. Within FIG. 24, the left portion shows a top-down view of the device alone, the upper-right portion shows a top-down view of the device on a forearm, and the lower-right portion shows a lateral view of the device on a forearm.

In this example, holey attachment member 2404 further comprises at least one hole which spans at least 50% of the width of holey attachment member 2404, wherein this width is a distance along the longitudinal axis of the forearm. In this example, holey attachment member 2404 holds arcuate display member 2401, data control unit 2402, and sensor 2403 within three inches of the surface of a person's body. In various examples, holey attachment member 2404: (a) can have buckles, snaps, adhesive, hook-and-eye mechanisms or other connecting elements so as to be fastened around the circumference of the forearm; (b) can be stretched or expanded around the hand to slip onto the forearm; (c) or can span between 50% and 95% of the circumference of the forearm and be flexible enough to bend around the forearm.

In an example, arcuate display member 2401: can comprise a flat or curved computer display screen; can be worn on the dorsal, ventral, and/or lateral surface of the person's forearm; and can have a shape selected from the group consisting of: rectangle with rounded vertexes; square with rounded vertexes; conic section; oval; and oblong.

In an example, data control unit 2402 can further comprise one or more components selected from the group consisting of: data processing member, data transmitting member, data receiving member, power source, and energy transducer. In various examples, data control unit 2402 can communicate with a handheld electronic device, a different wearable technology device, an array of wearable sensors, a communication network tower, a satellite, a home control system, and/or an implantable medical device.

Sensor 2403 and/or other sensors which are part of the device can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor. One or more sensors which are part of this device can be in kinetic, electromagnetic, optical, fluid, and/or chemical communication with the person's body.

This device can further comprise: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 25:
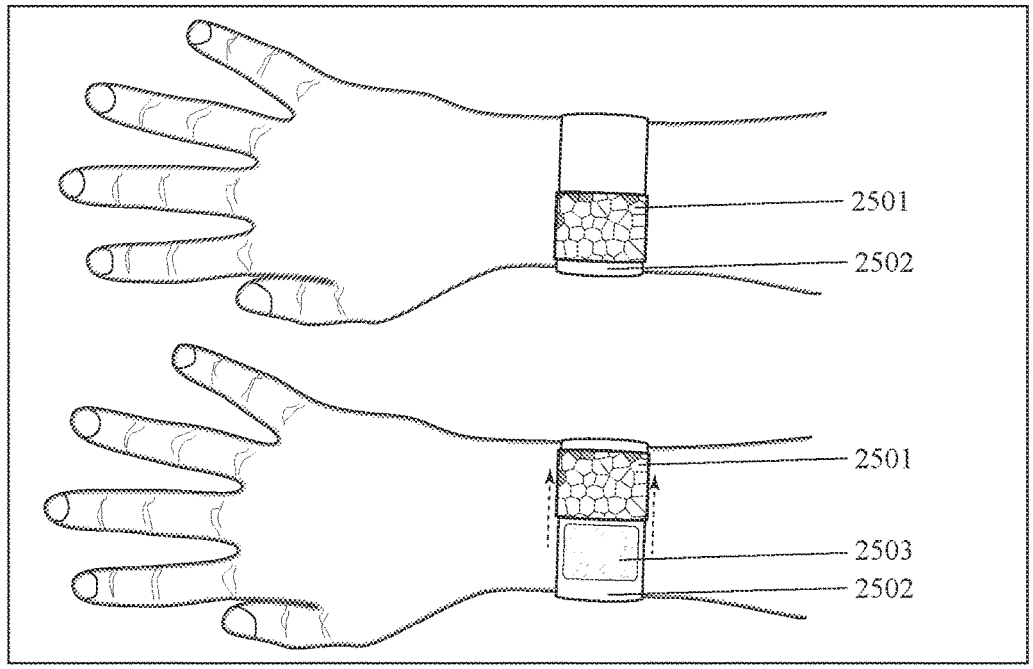
FIG. 25 shows a wearable device with a movable ornamental cover over a display.

FIG. 25 shows an example of a wearable computing device for the wrist and/or arm comprising: ornamental cover 2501; attachment member 2502; and display member 2503. In an example, this device has a first configuration in which ornamental cover 2501 substantially covers display member 2503 and a second configuration in which ornamental cover does not substantially cover display member 2503. The upper portion of FIG. 25 shows this device in the first configuration and the lower portion of FIG. 25 shows this device in the second configuration. In an example, this device transitions from the first configuration to the second configuration by movement of ornamental cover 2501. In an example, ornamental cover 2501 is moved manually by the person wearing the device. In an example, ornamental cover 2501 is moved automatically by an actuator in the device. In various examples, automatic movement can be triggered by one or more events selected from the group consisting of: body motion detected by a sensor in the device; an incoming communication; a touch detected by a sensor in the device; and a voice command.

In an example, ornamental cover 2501 can move by sliding in a direction which is substantially perpendicular to the longitudinal axis of the person's forearm and/or along a segment of the circumference of attachment member 2502. In an example, the surface of ornamental cover 2501 can be substantially parallel to the surface of display member 2503.

In an example, display member 2503: (a) can comprise a flat or curved computer display screen; (b) can be worn on the dorsal, ventral, and/or lateral surface of the person's forearm; and (c) can have a shape selected from the group consisting of square, rectangle, conic section, hexagon, polygon with rounded vertexes, oval, and oblong.

In an example, attachment member 2502 can be worn on a person's body or attached to clothing. In various examples, attachment member 2502: (a) can have buckles, snaps, adhesive, hook-and-eye mechanisms or other connecting elements so as to be fastened around the circumference of the forearm; (b) can be stretched or expanded around the hand to slip onto the forearm; (c) or can span between 50% and 95% of the circumference of the forearm and be flexible enough to bend around the forearm.

In an example, this device can further comprise a data control unit. In various examples, this device can further comprise one or more components selected from the group consisting of: data processing member, data transmitting member, data receiving member, power source, and energy harvester. In various examples, a data control unit can communicate with a handheld electronic device, a different wearable technology device, an array of wearable sensors, a communication network tower, a satellite, a home control system, and/or an implantable medical device.

In an example, this device can further comprise one or more sensors which are selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can further comprise: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 26:
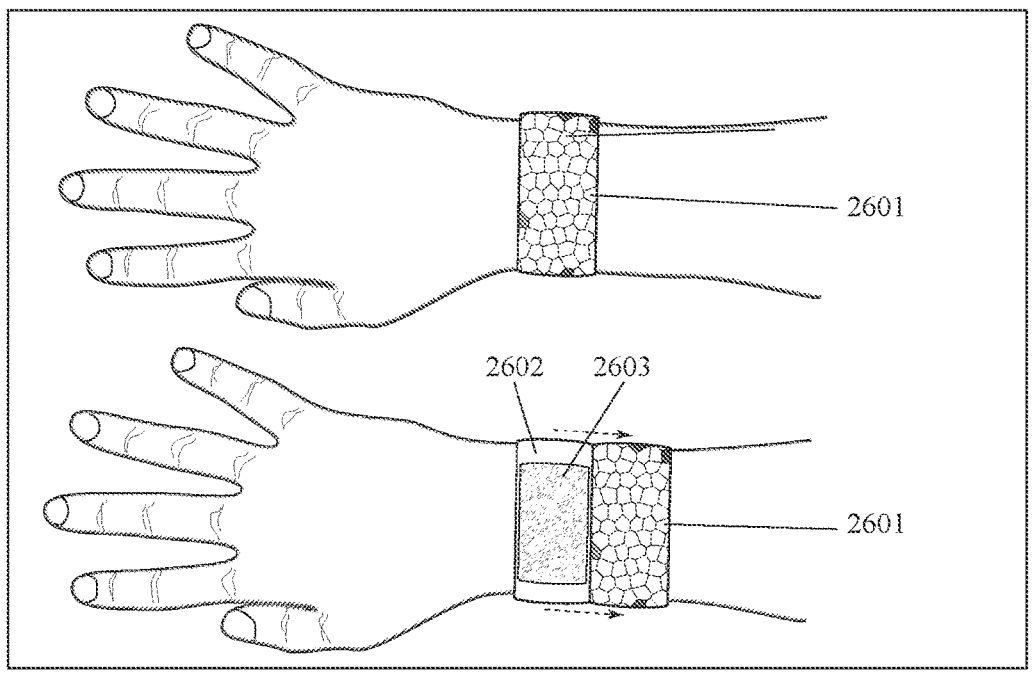
FIG. 26 shows a wearable device with a sliding ornamental cover over a display.

FIG. 26 shows an example of a wearable computing device for the wrist and/or arm comprising: ornamental cover 2601; attachment member 2602; and display member 2603. This device has a first configuration in which ornamental cover 2601 substantially covers display member 2603 and a second configuration in which ornamental cover does not substantially cover display member 2603. The upper portion of FIG. 26 shows this device in the first configuration and the lower portion of FIG. 26 shows this device in the second configuration. In an example, this device transitions from the first configuration to the second configuration by movement of ornamental cover 2601. In an example, ornamental cover 2601 is moved manually by the person wearing the device. In an example, ornamental cover 2601 is moved automatically by an actuator in the device. In various examples, automatic movement can be triggered by one or more events selected from the group consisting of: body motion detected by a sensor in the device; an incoming communication; a touch detected by a sensor in the device; and a voice command.

In an example, ornamental cover 2601 can move by sliding in a direction which is substantially parallel to the longitudinal axis of the person's forearm and/or perpendicular to the circumference of attachment member 2602. In an example, the surface of ornamental cover 2601 can be substantially parallel to the surface of display member 2603.

In an example, display member 2603: (a) can comprise a flat or curved computer display screen; (b) can be worn on the dorsal, ventral, and/or lateral surface of the person's forearm; and (c) can have a shape selected from the group consisting of square, rectangle, conic section, hexagon, polygon with rounded vertexes, oval, and oblong.

In an example, attachment member 2602 can be worn on a person's body or attached to clothing. In various examples, attachment member 2602: (a) can have buckles, snaps, adhesive, hook-and-eye mechanisms or other connecting elements so as to be fastened around the circumference of the forearm; (b) can be stretched or expanded around the hand to slip onto the forearm; (c) or can span between 50% and 95% of the circumference of the forearm and be flexible enough to bend around the forearm.

In various examples, this device can further comprise one or more components selected from the group consisting of: data processing member, data transmitting member, data receiving member, power source, and energy harvester. In various examples, this device can communicate with a handheld electronic device, a different wearable technology device, an array of wearable sensors, a communication network tower, a satellite, a home control system, and/or an implantable medical device.

In an example, this device can further comprise one or more sensors which are selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can further comprise one or more components selected from the group consisting of: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 27:
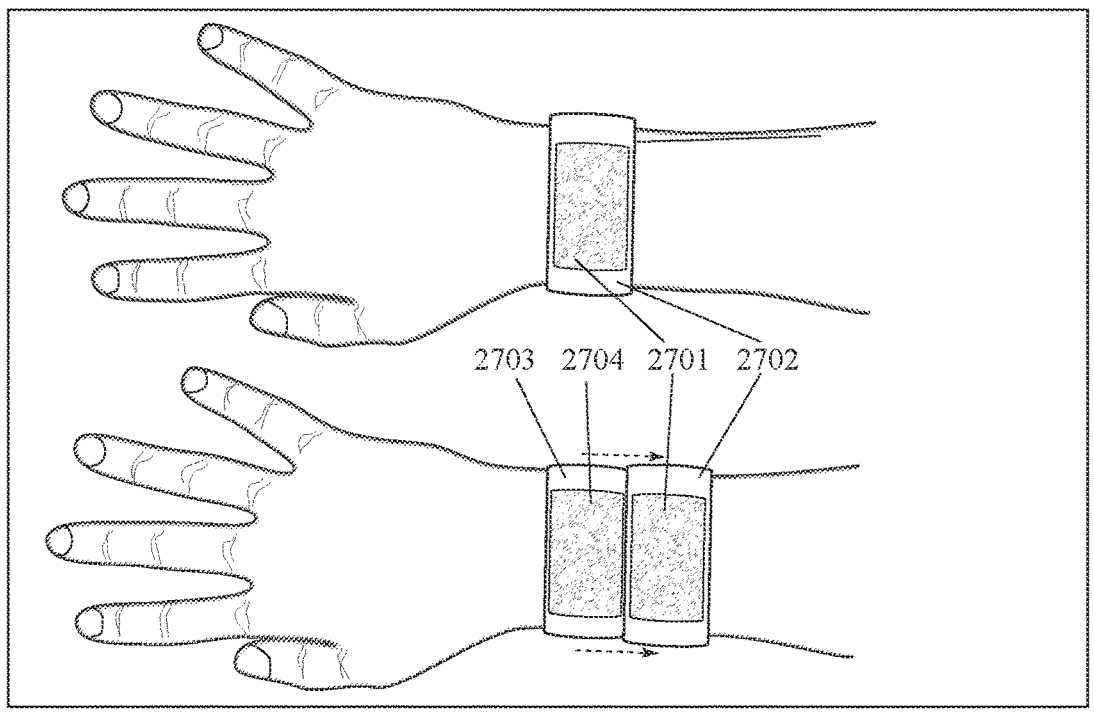
FIG. 27 shows a wearable device with a first display which slides over a second display.

FIG. 27 shows an example of a wearable computing device for the wrist and/or arm comprising: first display member 2701, second display member 2704, first attachment member 2703, and second attachment member 2702. This device has a first configuration in which only first display member 2701 is substantially visible to the user and a second configuration in which both first display member 2701 and second display member 2704 are substantially visible to the user. The upper portion of FIG. 27 shows this device in the first configuration and the lower portion of FIG. 27 shows this device in the second configuration.

In an example, this device transitions from the first configuration to the second configuration by: movement of first display member 2701; movement of second display member 2704; or movement of both display members. In an example, movement of one or both display members is done manually by the person wearing the device. In an example, movement of one or both display members is done automatically by an actuator in the device. In various examples, automatic movement can be triggered by one or more events selected from the group consisting of: body motion detected by a sensor in the device; an incoming communication; a touch detected by a sensor in the device; and a voice command.

In an example, one or both display members (2701 and 2704) can move by sliding in a direction which is substantially parallel to the longitudinal axis of the person's forearm and/or perpendicular to the circumference of attachment member 2702. In an example, one or both display members (2701 and 2704) can move by sliding in a direction which is substantially perpendicular to the longitudinal axis of the person's forearm and/or along a segment of the circumference of attachment member 2702. In an example, one or both display members (2701 and 2704) can move by rotating around an axis. In an example, one or both display members (2701 and 2704) can move by flipping them open around a rotational axis.

In an example, first display member 2701, second display member 2704, or both display members (2701 and 2704) can: comprise a flat or curved computer display screen; be worn on the dorsal, ventral, and/or lateral surface of the person's forearm; and have a shape selected from the group consisting of square, rectangle, conic section, hexagon, polygon with rounded vertexes, oval, and oblong. In an example, first display member 2701 and second display member 2704 can display different content. In an example, first display member 2701 and second display member 2704 can display different portions of the same content, together comprising a larger display area that either display member by itself. In an example, this allows a user to transition the device from a first configuration with a smaller display area to a second configuration with a larger display area.

In an example, first attachment member 2703, second attachment member 2702, or both attachment members can be worn on a person's body or attached to clothing. In an example, both first attachment member 2703 and second attachment member 2702 can be worn around the person's forearm. In an example, first attachment member 2703, second attachment member 2702, or both attachment members: can have buckles, snaps, adhesive, hook-and-eye mechanisms or other connecting elements so as to be fastened around the circumference of the forearm; can be stretched or expanded around the hand to slip onto the forearm; or can span between 50% and 95% of the circumference of the forearm and be flexible enough to bend around the forearm. In an example, only first attachment member 2703 is worn around the person's forearm and second attachment member 2702 slides out from first attachment member 2703.

In various examples, this device can further comprise one or more components selected from the group consisting of: data processing member, data transmitting member, data receiving member, power source, and energy harvester. In various examples, this device can communicate with a handheld electronic device, a different wearable technology device, an array of wearable sensors, a communication network tower, a satellite, a home control system, and/or an implantable medical device.

In an example, this device can further comprise one or more sensors which are selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can further comprise one or more components selected from the group consisting of: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 28:
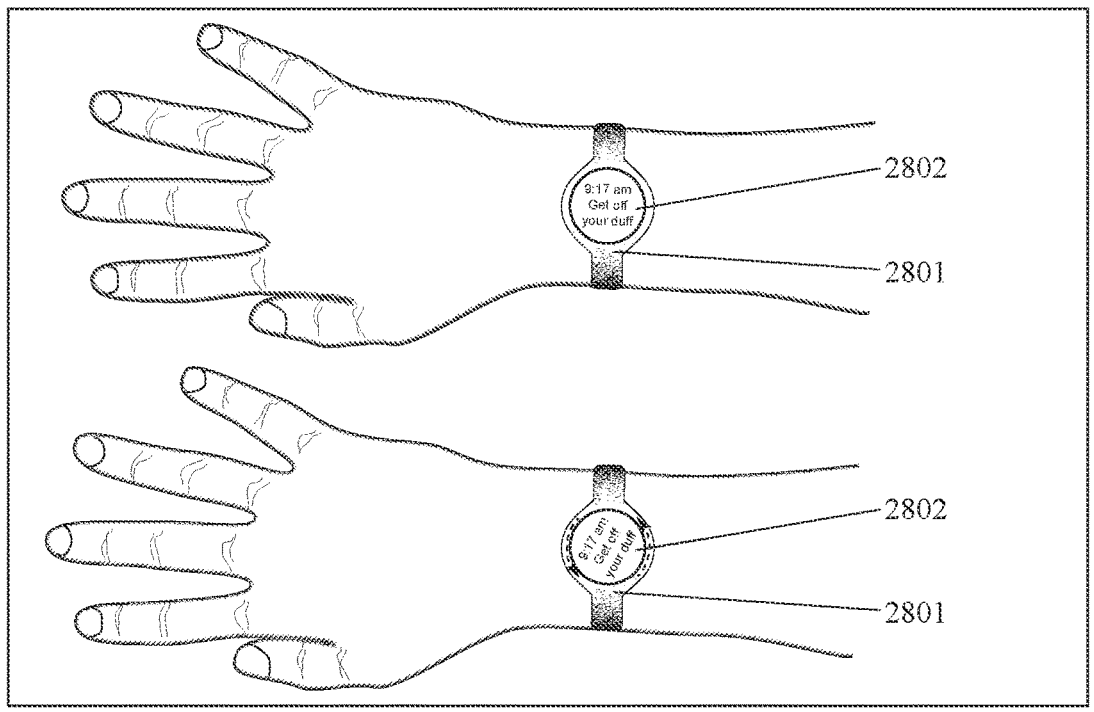
FIG. 28 shows a wearable device with a rotating display.

FIG. 28 shows an example of a wearable computing device for the wrist and/or arm comprising: rotating display member 2802; and attachment member 2801. This device has a first configuration in which rotating display member 2802 (or the image displayed therein) has a first display angle and a second configuration in which rotating display member 2802 (or the image displayed therein) has a second display angle. In FIG. 28, the upper portion shows this device in the first configuration and the lower portion shows this device in the second configuration. This device transitions from the first configuration to the second configuration by the rotation of rotating display member 2802 or the image displayed therein. In an example, rotating display member 2802 can be physically rotated from a first polar angle to a second polar angle. In an example, the image displayed by rotating display member 2802 can be virtually rotated from a first polar angle to a second polar angle. In an example, rotation of rotating display member 2802 can be done manually by the person wearing the device.

In an example, rotation of rotating display member 2802 or the image displayed therein can be done automatically by the device. In an example, automatic rotation of rotating display member 2802 or the image displayed therein can be triggered by movement of the person's arm. In an example, the angle of rotating display member 2802 or the image displayed therein can be automatically adjusted to maintain the proper angle for viewing by the person wearing the device, wherein this automatic adjustment is based on movement of the person's forearm as sensed by a sensor, such as an accelerometer or gyroscope. In an example, the angle of rotating display member 2802 or the image displayed therein can be automatically adjusted to maintain the proper angle for viewing by the person wearing the device, wherein this automatic adjustment is based on the relative location of the person's head and/or eyes as sensed by a sensor, such as by using facial recognition. In an example, rotating display member 2802: can comprise a flat or curved computer display screen; can be worn on the dorsal, ventral, and/or lateral surface of a person's forearm; and can have a shape selected from the group consisting of square, rectangle, conic section, hexagon, polygon with rounded vertexes, oval, and oblong.

In an example, attachment member 2801 can be worn on a person's body or attached to clothing. In an example, attachment member 2801: can have buckles, snaps, adhesive, hook-and-eye mechanisms or other connecting elements so as to be fastened around the circumference of the forearm; can be stretched or expanded around the hand to slip onto the forearm; or can span between 50% and 95% of the circumference of the forearm and be flexible enough to bend around the forearm.

In an example, this device can further comprise one or more sensors which are selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can further comprise one or more components selected from the group consisting of: data processing member, data transmitting member, data receiving member, power source, and energy harvester. In various examples, this device can communicate with a handheld electronic device, a different wearable technology device, an array of wearable sensors, a communication network tower, a satellite, a home control system, and/or an implantable medical device. In various examples, this device can further comprise one or more components selected from the group consisting of: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 29:
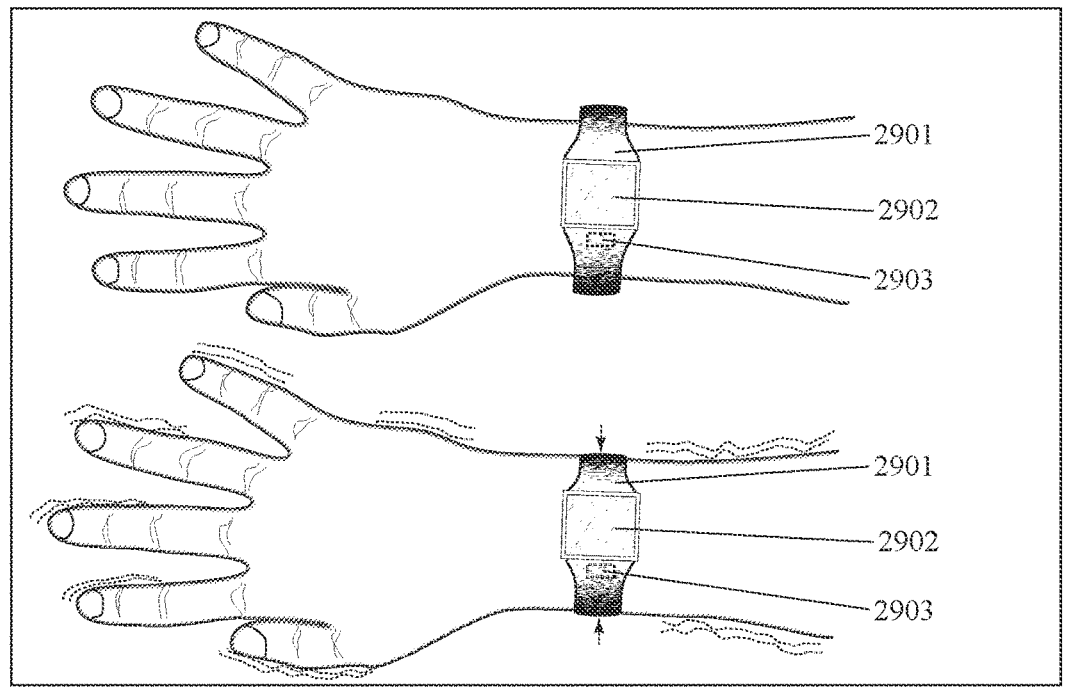
FIG. 29 shows a wearable device with a display and a contracting attachment member.

FIG. 29 shows an example of a wearable computing device for the wrist and/or arm comprising: display member 2902; sensor 2903; and contracting attachment member 2901. This device has a first configuration in which contracting attachment member 2901 has a first degree of contraction and a second configuration in which contracting attachment member 2901 has a second degree of contraction. In FIG. 29, the upper portion shows this device in the first configuration and the lower portion shows this device in the second configuration. The device transitions from the first configuration to the second configuration based on information from sensor 2903. In this example, sensor 2903 is a motion sensor and the contracting attachment member contracts when sensor 2903 detects a high level of movement. This can enable the device to fit in a relatively loose manner when the person is relatively stationary and to fit in a relatively snug manner when the person is relatively active. This can help to make the device fit comfortably when the person is resting, but not slip off when the person is very active.

In various examples, sensor 2903 can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In an example, expanding and contracting attachment member 2901 can be worn on a person's body or attached to clothing. In an example, contracting attachment member 2901 can comprise material which contracts when exposed to electrical current. In an example, contracting attachment member 2901 can comprise one or more actuators which respond to data from sensor 2903. In an example, expanding and contracting attachment member 2901: can have buckles, snaps, adhesive, hook-and-eye mechanisms or other connecting elements so as to be fastened around the circumference of the forearm; can be stretched or expanded around the hand to slip onto the forearm; or can span between 50% and 95% of the circumference of the forearm and be flexible enough to bend around the forearm.

In various examples, this device can further comprise one or more components selected from the group consisting of: data processing member, data transmitting member, data receiving member, power source, and energy harvester. In various examples, this device can communicate with a handheld electronic device, a different wearable technology device, an array of wearable sensors, a communication network tower, a satellite, a home control system, and/or an implantable medical device. In various examples, this device can further comprise one or more components selected from the group consisting of: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 30:
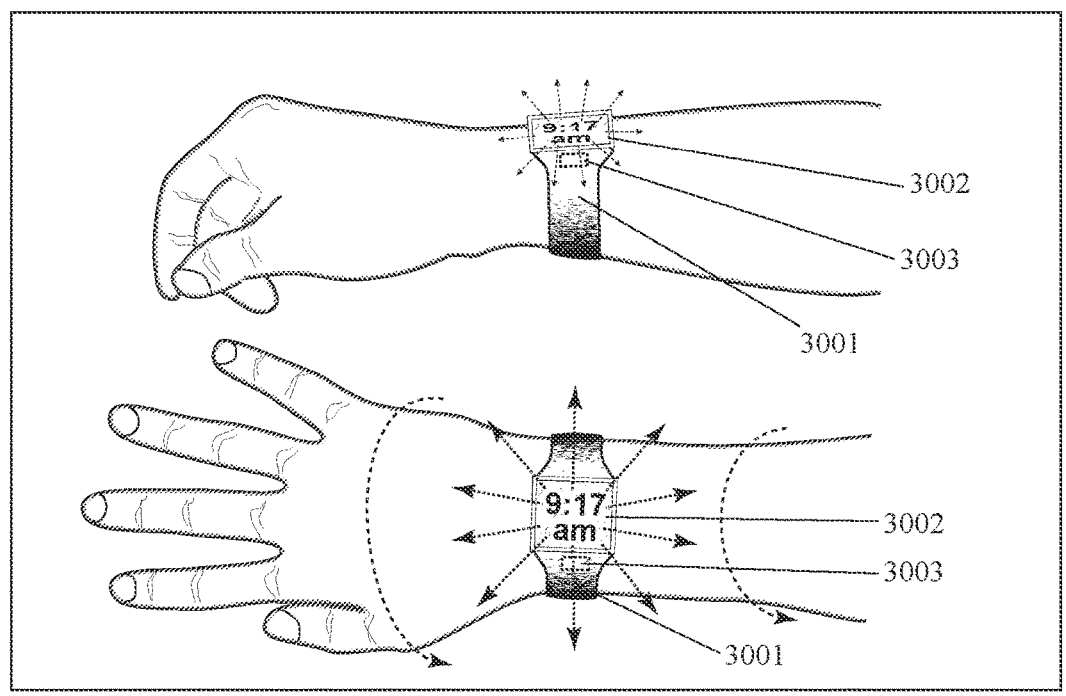
FIG. 30 shows a wearable device with a display whose brightness changes based on movement or orientation.

FIG. 30 shows an example of a wearable computing device for the wrist and/or arm comprising: variable-brightness display member 3002; sensor 3003; and attachment member 3001. This device has a first configuration in which variable-brightness display member 3002 has a first brightness level and a second configuration in which variable-brightness display member 3002 has a second brightness level. This can help to conserve power. This can also help to maintain the privacy of information displayed on the device. In FIG. 30, the upper portion shows this device in the first configuration and the lower portion shows this device in the second configuration. The device transitions from the first configuration to the second configuration based on information from sensor 3003.

In this example, the brightness of variable-brightness display member 3002 is changed based on the movement or orientation of the person's arm. In an example, when the person moves their wrist and/or forearm to look at the device, the variable-brightness display member 3002 transitions from a lower (power saving) first brightness level to a higher (easier-to-see) second brightness level. This can help to provide a bright display when needed, but conserve power when not needed. In an example, sensor 3003 can be selected from the group consisting of: accelerometer; inclinometer, and gyroscope. In an example, sensor 3003 can be an imaging sensor and the brightness of variable-brightness display member 3002 can be increased when the device detects that the user is looking at it, such as by using facial recognition methods.

More generally, sensor 3003 can be selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, expanding and attachment member 3001: can have buckles, snaps, adhesive, hook-and-eye mechanisms or other connecting elements so as to be fastened around the circumference of the forearm; can be stretched or expanded around the hand to slip onto the forearm; or can span between 50% and 95% of the circumference of the forearm and be flexible enough to bend around the forearm.

In various examples, this device can further comprise one or more components selected from the group consisting of: data processing member, data transmitting member, data receiving member, power source, and energy harvester. In various examples, this device can communicate with a handheld electronic device, a different wearable technology device, an array of wearable sensors, a communication network tower, a satellite, a home control system, and/or an implantable medical device. In various examples, this device can further comprise one or more components selected from the group consisting of: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface; and an eye-gaze-tracking interface.

Figure 31:
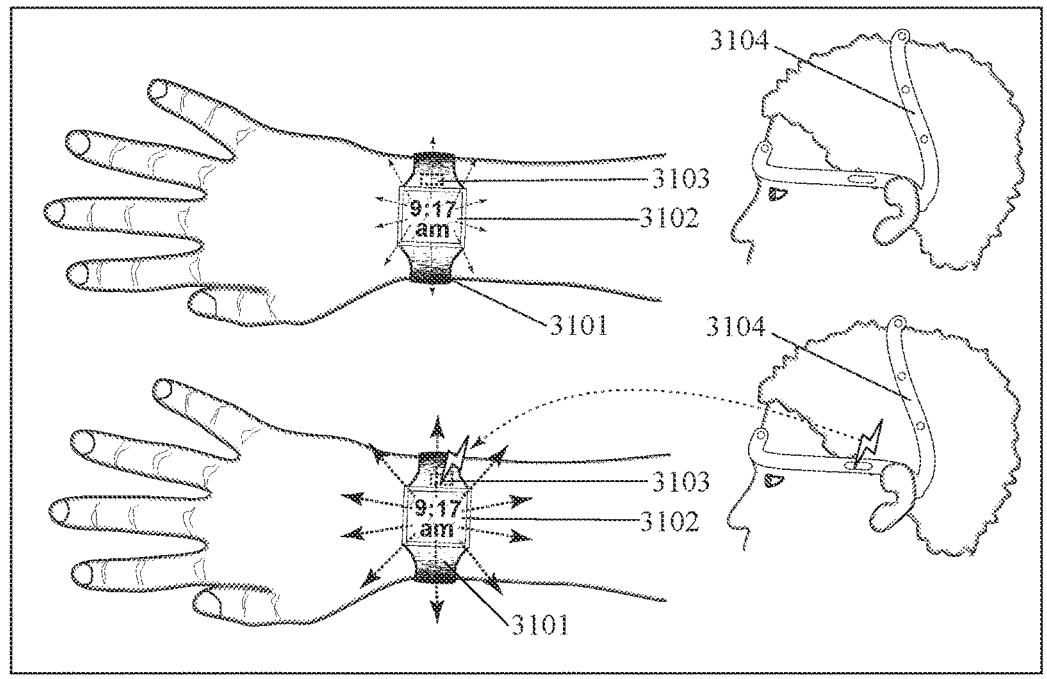
FIG. 31 shows a wearable system with a display whose brightness changes based on electromagnetic brain activity.

FIG. 31 shows an example of a wearable computing system for the wrist and/or arm comprising: variable-brightness display member 3102; wireless data receiver 3103; attachment member 3101; and electromagnetic brain activity monitor 3104. This system has a first configuration in which variable-brightness display member 3102 has a first brightness level and a second configuration in which variable-brightness display member 3102 has a second brightness level. This can help to conserve power. This can also help to maintain the privacy of information displayed on the device. In FIG. 31, the upper portion shows this system in the first configuration and the lower portion shows this system in the second configuration. The system transitions from the first configuration to the second configuration based on information from electromagnetic brain activity monitor 3104 via wireless data receiver 3103.

In this example, the brightness of variable-brightness display member 3102 is changed based on a pattern and/or change in a person's electromagnetic brain activity that is detected by electromagnetic brain activity monitor 3104. In an example, when a particular pattern and/or change in electromagnetic brain activity is detected, variable-brightness display member 3102 transitions from a lower (power saving) first brightness level to a higher (easier-to-see) second brightness level. In an example, a pattern and/or change in electromagnetic brain activity can be a one-time pattern. In another example, a pattern of electromagnetic brain activity can repeat over time in a rhythmic manner. In an example, a pattern of electromagnetic brain activity can comprise frequency of repetition, frequency band or range of repetition, recurring amplitude, wave phase, and/or waveform. In an example repeating patterns and/or waveforms can be analyzed using Fourier Transform methods.

In various examples, this system can further comprise one or more components selected from the group consisting of: data processing member, data transmitting member, data receiving member, power source, energy harvester, one or more LEDs, coherent light emitter or projector, infrared light emitter or projector, sound-emitting member, tactile-sensation-creating members, neurostimulator, other electromagnetic energy emitters, hardware buttons, knobs, or keys, virtual projected keypad, gesture-recognition interface, speech-recognition interface, and eye-gaze-tracking interface. In various examples, this system can communicate with a handheld electronic device, a different wearable technology device, an array of wearable sensors, a communication network tower, a satellite, a home control system, and/or an implantable medical device.

Figure 32:
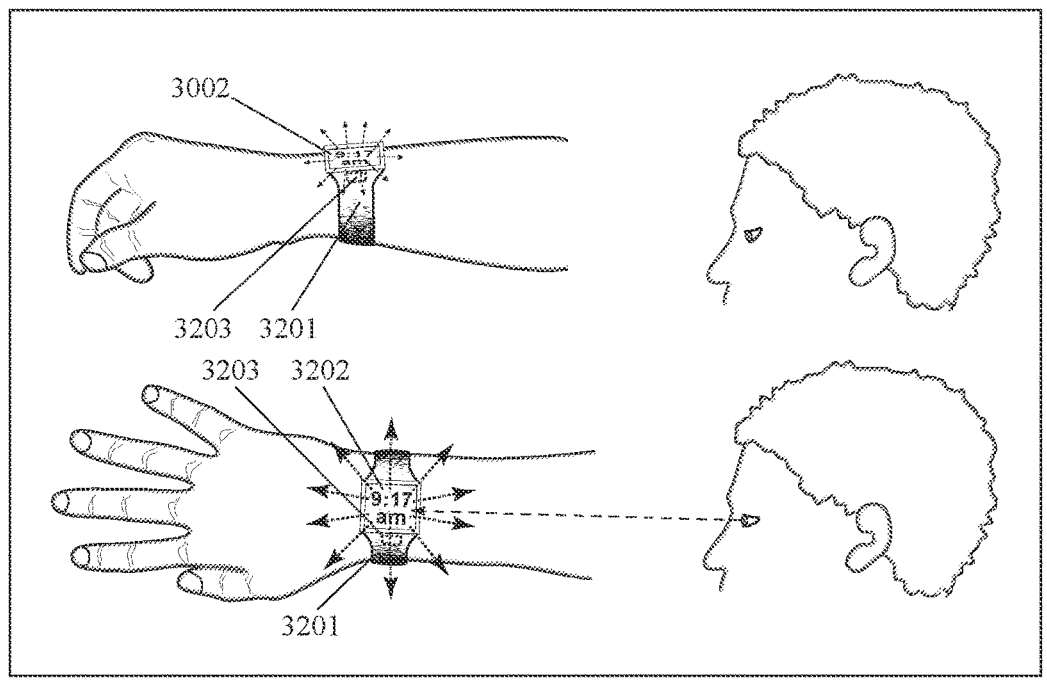
FIG. 32 shows a wearable device with a display whose brightness changes based on eye gaze.

FIG. 32 shows an example of a wearable computing device for the wrist and/or arm comprising: variable-brightness display member 3202; camera 3203; and attachment member 3201. This device has a first configuration in which variable-brightness display member 3202 has a first brightness level and a second configuration in which variable-brightness display member 3202 has a second brightness level. Having different brightness levels can help to conserve power. It can also help to maintain the privacy of information displayed on the device. In FIG. 32, the upper portion shows this device in the first configuration and the lower portion shows this device in the second configuration.

In this example, the device transitions from the first configuration to the second configuration due to eye gaze detection based on images from camera 3203. In this example, the variable-brightness display member 3202 is brighter when the person looks at the device and is dimmer when the person does not look at the device. In an example, images from camera 3203 are analyzed using facial recognition methods in order to detect when the person wearing the device looks at the device.

In various examples, this device can further comprise one or more components selected from the group consisting of: data processing member, data transmitting member, data receiving member, power source, energy harvester, one or more LEDs, coherent light emitter or projector, infrared light emitter or projector, sound-emitting member, tactile-sensation-creating members, neurostimulator, other electromagnetic energy emitters, hardware buttons, knobs, or keys, virtual projected keypad, gesture-recognition interface, speech-recognition interface, and eye-gaze-tracking interface. In various examples, this device can communicate with a handheld electronic device, a different wearable technology device, an array of wearable sensors, a communication network tower, a satellite, a home control device, and/or an implantable medical device.

Figure 33:
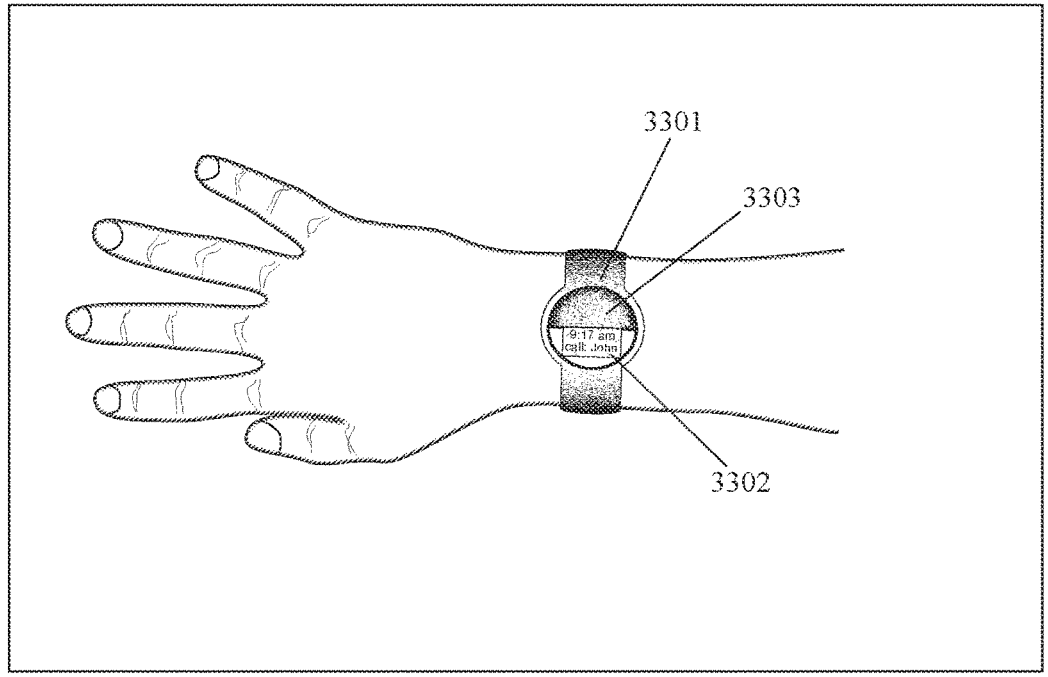
FIG. 33 shows a wearable device with a display and a partial-dome privacy shield.

FIG. 33 shows an example of a wearable computing device for the wrist and/or arm comprising: display member 3302; privacy shield 3303; and attachment member 3301. In an example, display member 3302 is a computer display screen. In an example, attachment member 3301 is a strap or band. In an example, privacy shield 3303 is a three-dimensional structure that allows the content on display member 3302 to be seen from a first set of view angles and prevents this content from being seen from a second set of view angles. In an example, privacy shield 3303 can allow this content to be seen from a first set of polar angles ranging from 90 degrees to 270 degrees (wherein 0 or 360 degrees corresponds to the 12 o'clock position on display member 3302). In an example, privacy shield 3303 can prevent content on display member 3303 from being seen from a second set of polar angles ranging from 270 degrees to 90 degrees (wherein 0 or 360 degrees corresponds to the 12 o'clock position on display member 3302).

In an example, privacy shield 3303 can have a fixed shape. In an example, privacy shield 3303 can have a quarter-spherical shape. In an example, privacy shield 3303 can have an adjustable shape, wherein adjustment of this shape adjusts the range of the first set of view angles, the second set of view angles, or both. In an example, privacy shield 3303 can be manually rotated to change the direction of the first set of view angles, the second set of view angles, or both. In an example, privacy shield 3303 can rotate automatically based on information from one or more sensors.

In various examples, the device can further comprise one or more sensors selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can further comprise one or more components selected from the group consisting of: data processing member, data transmitting member, data receiving member, power source, energy harvester, one or more LEDs, coherent light emitter or projector, infrared light emitter or projector, sound-emitting member, tactile-sensation-creating members, neurostimulator, other electromagnetic energy emitters, hardware buttons, knobs, or keys, virtual projected keypad, gesture-recognition interface, speech-recognition interface, and eye-gaze-tracking interface. In various examples, this device can communicate with a handheld electronic device, a different wearable technology device, an array of wearable sensors, a communication network tower, a satellite, a home control device, and/or an implantable medical device.

Figure 34:
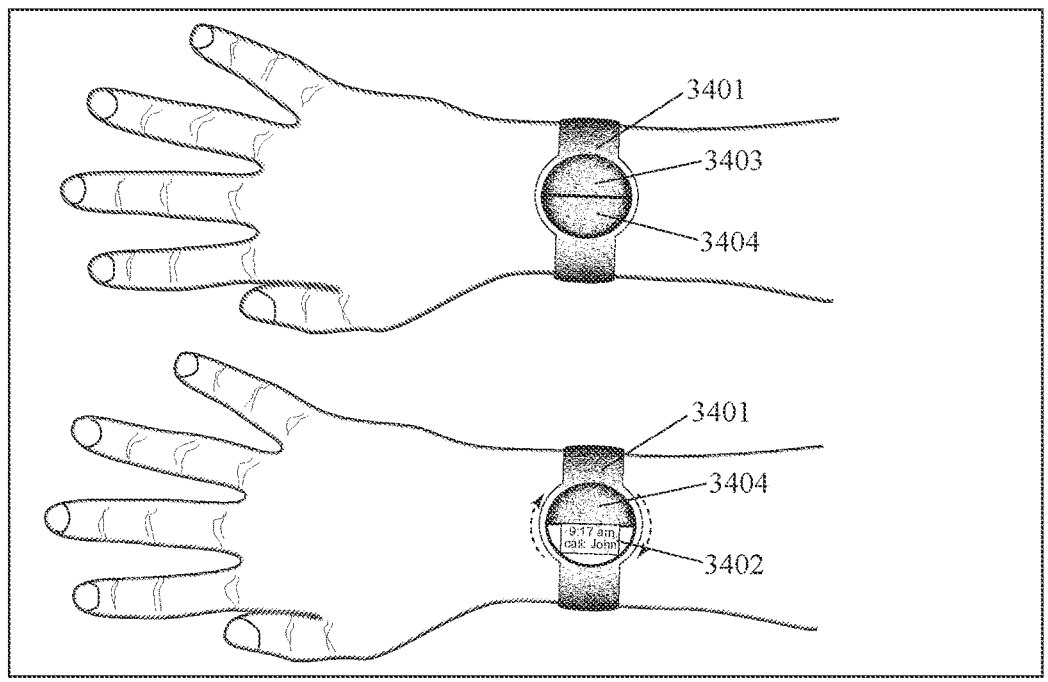
FIG. 34 shows a wearable device with a display and a rotating privacy shield.

FIG. 34 shows an example of a wearable computing device for the wrist and/or arm comprising: display member 3402; first privacy shield 3403; second privacy shield 3404, and attachment member 3401. In an example, display member 3402 is a computer display screen. In an example, attachment member 3401 is a strap or band. In an example, privacy shield 3403 is a three-dimensional structure that blocks viewing of display member 3402 from a first set of view angles. In an example, privacy shield 3404 is a three-dimensional structure that blocks viewing of display member 3402 from a second set of view angles.

In this example, the device has a first configuration in which privacy shield 3403 and privacy shield 3404 collectively block viewing of display member 3402 from all angles. This device also has a second configuration in which privacy shield 3403 and privacy shield 3404 block viewing of display member 3402 from only the first or second set of angles. The upper portion of FIG. 34 shows this device in the first configuration. The lower portion of FIG. 34 shows this device in the second configuration. In an example, the device can switch from the first to the second configuration by moving and/or rotating privacy shield 3403 and/or privacy shield 3404. In an example, this movement and/or rotation can be done manually.

In an example, this movement and/or rotation can occur automatically. In an example, this movement and/or rotation can be based on information from one or more sensors selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can further comprise one or more components selected from the group consisting of: data processing member, data transmitting member, data receiving member, power source, energy harvester, one or more LEDs, coherent light emitter or projector, infrared light emitter or projector, sound-emitting member, tactile-sensation-creating members, neurostimulator, other electromagnetic energy emitters, hardware buttons, knobs, or keys, virtual projected keypad, gesture-recognition interface, speech-recognition interface, and eye-gaze-tracking interface. In various examples, this device can communicate with a handheld electronic device, a different wearable technology device, an array of wearable sensors, a communication network tower, a satellite, a home control device, and/or an implantable medical device.

Figure 35:
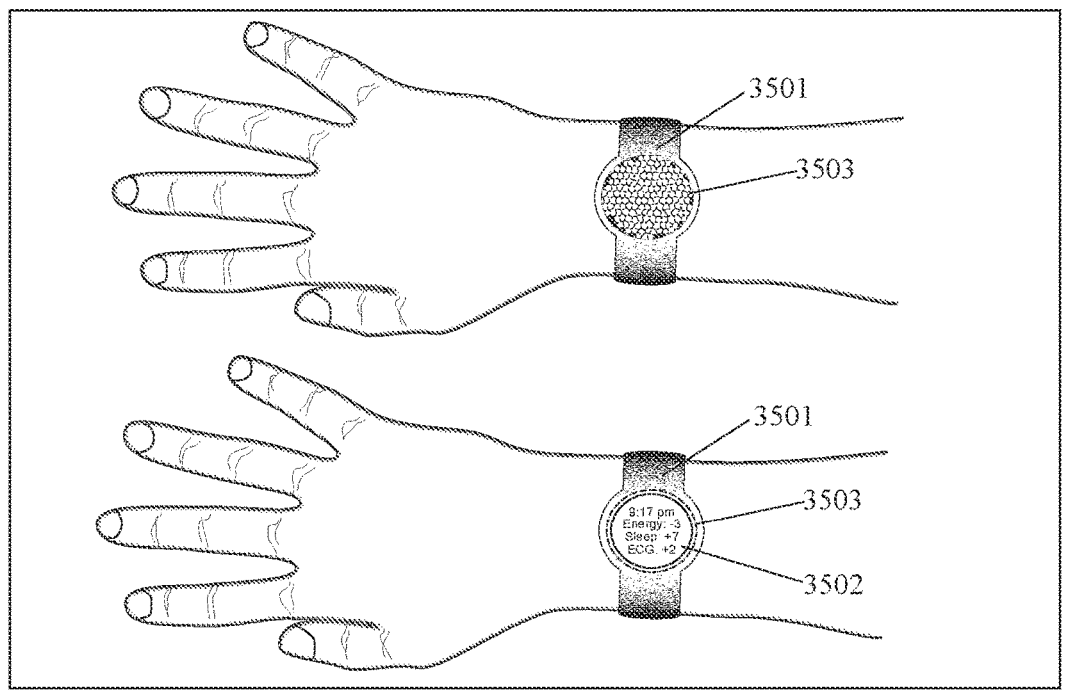
FIG. 35 shows a wearable device with a display and a variable-opacity ornamental cover.

FIG. 35 shows an example of a wearable computing device for the wrist and/or arm comprising: display member 3502; variable-opacity ornamental member 3503; and attachment member 3501. In an example, display member 3502 is a computer display screen. In an example, attachment member 3501 is a strap or band. In an example, variable-opacity ornamental member 3503 substantially covers display member 3502. In this example, the device has a first configuration in which variable-opacity ornamental member 3503 is substantially opaque and does not allow viewing of display member 3502. In this example, the device has a second configuration in which variable-opacity ornamental member 3503 is substantially transparent and allows viewing of display member 3502. In an example, the user can activate the transition from the first configuration to the second configuration. In an example, the transition from the first configuration to the second configuration can occur automatically when the device receives incoming communication.

In an example, the device can transition from the first configuration to the second configuration based on information from one or more sensors selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can further comprise one or more components selected from the group consisting of: data processing member, data transmitting member, data receiving member, power source, energy harvester, one or more LEDs, coherent light emitter or projector, infrared light emitter or projector, sound-emitting member, tactile-sensation-creating members, neurostimulator, other electromagnetic energy emitters, hardware buttons, knobs, or keys, virtual projected keypad, gesture-recognition interface, speech-recognition interface, and eye-gaze-tracking interface. In various examples, this device can communicate with a handheld electronic device, a different wearable technology device, an array of wearable sensors, a communication network tower, a satellite, a home control device, and/or an implantable medical device.

Figure 36:
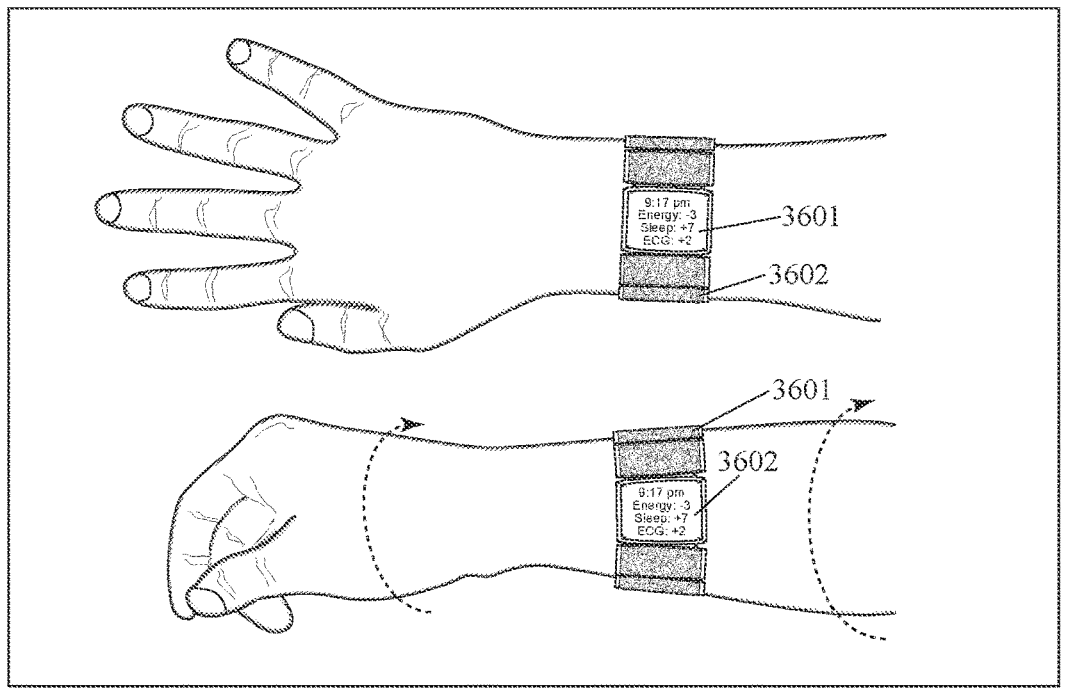
FIG. 36 shows a wearable device with a plurality of displays around the arm wherein the subset of displays which show content changes as the arm rotates.

FIG. 36 shows an example of a wearable computing device for the wrist and/or arm comprising: a plurality of display members (including 3601 and 3602) around all or part of the circumference of a person's forearm. This device has a first configuration in which a first subset of these display members display content and a second configuration in which a second subset of these display members display content. The device transitions from the first configuration to the second configuration based on the movement and/or changes in orientation of the device. In an example, the display member are computer display screens and the attachment member is a strap or band.

In an example, the subset of display members which display content changes as the person's arm rotates so that the display members that display content are those which the person is viewing, based on the movement and/or orientation of the device. In an example, when the dorsal side of the person's forearm faces upwards, then display members on the dorsal side display content. The upper portion of FIG. 36 shows this device in a first configuration. The lower portion of FIG. 36 shows this device in a second configuration. In an example, the device can automatically transition from the first configuration to the second configuration based on information from one or more sensors selected from the group consisting of accelerometer, gyroscope, inclinometer, and compass.

In various examples, this device can further comprise one or more components selected from the group consisting of: data processing member, data transmitting member, data receiving member, power source, energy harvester, one or more LEDs, coherent light emitter or projector, infrared light emitter or projector, sound-emitting member, tactile-sensation-creating members, neurostimulator, other electromagnetic energy emitters, hardware buttons, knobs, or keys, virtual projected keypad, gesture-recognition interface, speech-recognition interface, and eye-gaze-tracking interface. In various examples, this device can communicate with a handheld electronic device, a different wearable technology device, an array of wearable sensors, a communication network tower, a satellite, a home control device, and/or an implantable medical device.

Figure 37:
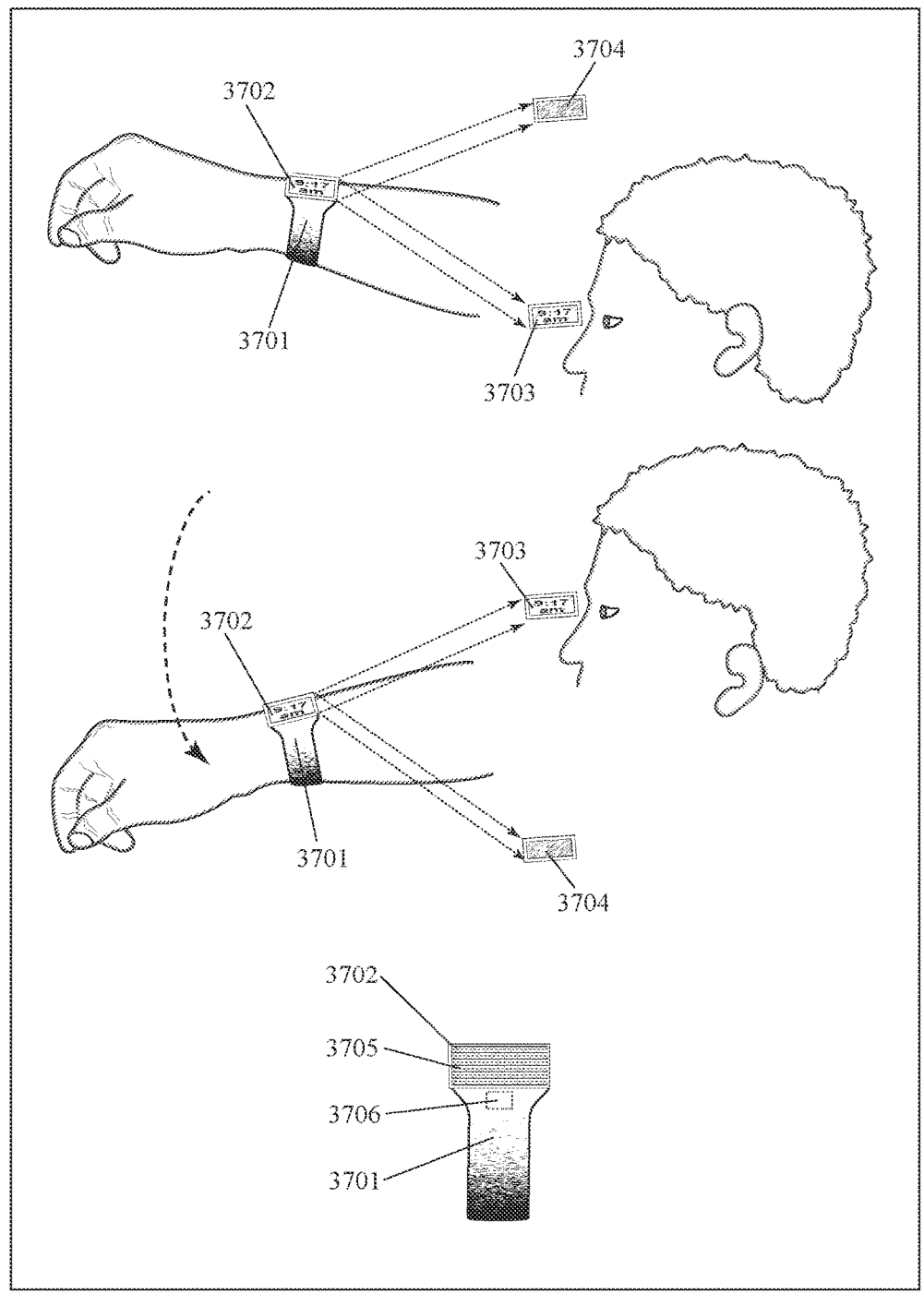
FIG. 37 shows a wearable device with a display with an adjustable parallax filter.

FIG. 37 shows an example of a wearable computing device for the wrist and/or arm comprising: variable-angle display member 3702; adjustable parallax filter 3705; sensor 3706; and attachment member 3701. This device has a first configuration in which the content of variable-angle display member 3702 can only be seen from a first viewing angle (or location) and a second configuration in which the content of variable-angle display member 3702 can only be seen from a second viewing angle (or location).

In FIG. 37, the upper portion shows this device in the first configuration and the lower portion shows this device in the second configuration. In the first configuration, a wearer viewing variable-angle display member 3702 from a first angle sees the appropriate content (represented in the diagram as image 3703 in the diagram), but a person viewing variable-angle display member from another perspective only sees a blocked image (represented in the diagram as image 3704). In the second configuration, a wearer viewing variable-angle display member 3702 from a second angle still sees the appropriate content (represented in the diagram as image 3703 in the diagram), but a person viewing variable-angle display member from another perspective only sees a blocked image (represented in the diagram as image 3704).

In this example, the transition from the first configuration to the second configuration is achieved by adjusting parallax members 3705 in response to motion information from sensor 3706. In an example, parallax members 3705 are adjusted in real time so that the person wearing the device always sees the content displayed by variable-angle display member 3702, but people viewing the device from other view angles cannot see this content. This helps to maintain the privacy of information displayed by the device. In an example, variable-angle display member 3702 can be a computer display screen. In an example, adjustable parallax filter 3705 can be physically or virtually shifted as the device moves in three-dimensional space. In an example, sensor 3706 can be an accelerometer, gyroscope, inclinometer, or compass. In an example, attachment member 3701 can be a strap or band.

In various examples, this device can further comprise one or more components selected from the group consisting of: data processing member, data transmitting member, data receiving member, power source, and energy harvester. In various examples, this device can communicate with a handheld electronic device, a different wearable technology device, an array of wearable sensors, a communication network tower, a satellite, a home control system, and/or an implantable medical device. In various examples, this device can further comprise one or more components selected from the group consisting of: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 38:
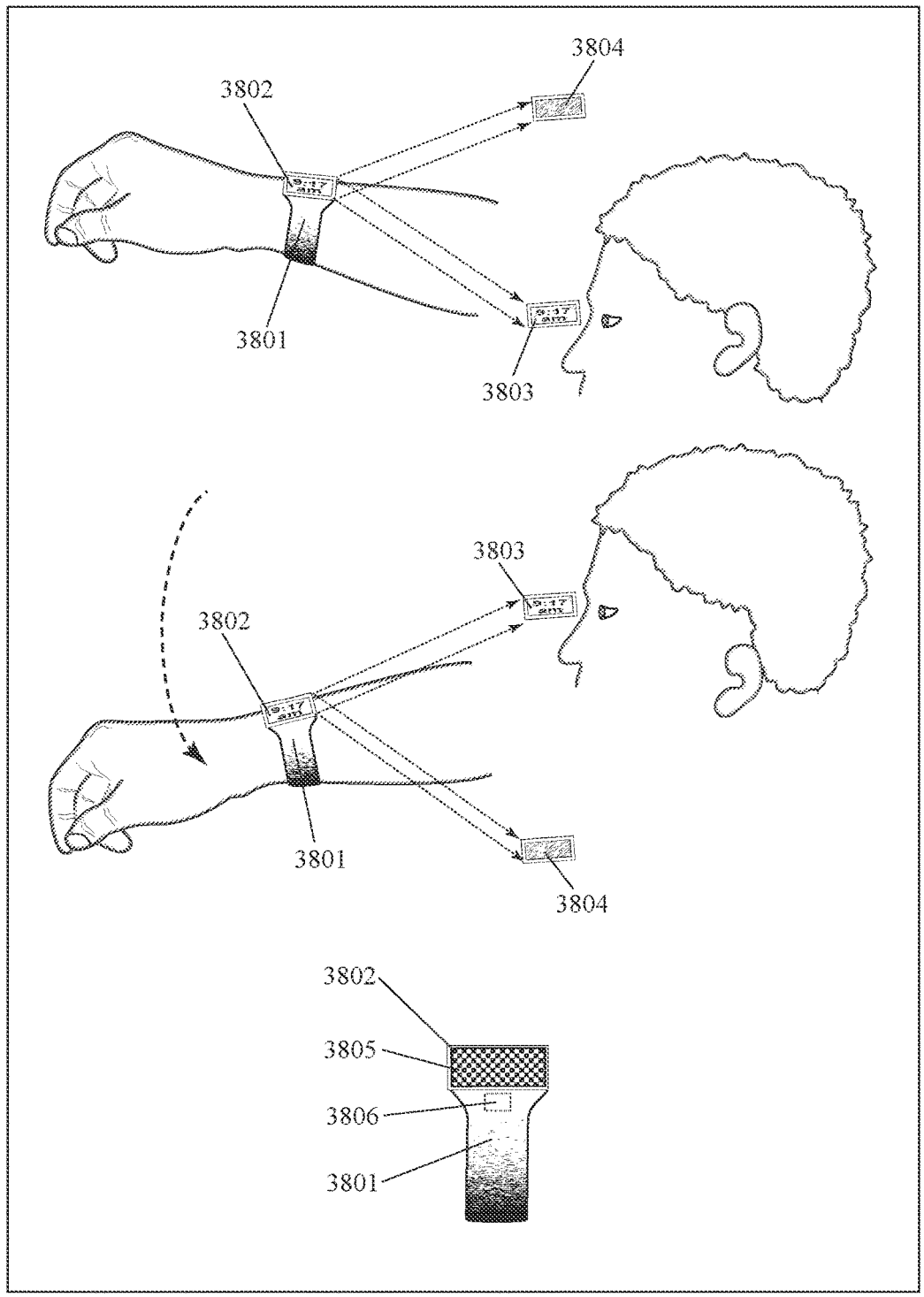
FIG. 38 shows a wearable device with a display with an adjustable prism or lens array.

FIG. 38 shows an example of a wearable computing device for the wrist and/or arm comprising: variable-angle display member 3802; adjustable prism or lens array 3805; sensor 3806; and attachment member 3801. This device has a first configuration in which the content of variable-angle display member 3802 can only be seen from a first viewing angle (or location) and a second configuration in which the content of variable-angle display member 3802 can only be seen from a second viewing angle (or location).

In FIG. 38, the upper portion shows this device in the first configuration and the lower portion shows this device in the second configuration. In the first configuration, a wearer viewing variable-angle display member 3802 from a first angle sees the appropriate content, but a person viewing variable-angle display member from another perspective only sees a blocked image. In the second configuration, a wearer viewing variable-angle display member 3802 from a second angle still sees the appropriate content, but a person viewing variable-angle display member from another perspective only sees a blocked image.

In this example, the transition from the first configuration to the second configuration is achieved by adjusting parallax members 3805 in response to motion information from sensor 3806. In an example, parallax members 3805 are adjusted in real time so that the person wearing the device always sees the content displayed by variable-angle display member 3802, but people viewing the device from other view angles cannot see this content. This helps to maintain the privacy of information displayed by the device. In an example, variable-angle display member 3802 can be a computer display screen. In an example, adjustable prism or lens array 3805 can be physically adjusted as the device moves. In an example, sensor 3806 can be an accelerometer, gyroscope, inclinometer, or compass. In an example, attachment member 3801 can be a strap or band.

In various examples, this device can further comprise one or more components selected from the group consisting of: data processing member, data transmitting member, data receiving member, power source, and energy harvester. In various examples, this device can communicate with a handheld electronic device, a different wearable technology device, an array of wearable sensors, a communication network tower, a satellite, a home control system, and/or an implantable medical device. In various examples, this device can further comprise one or more components selected from the group consisting of: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 39:
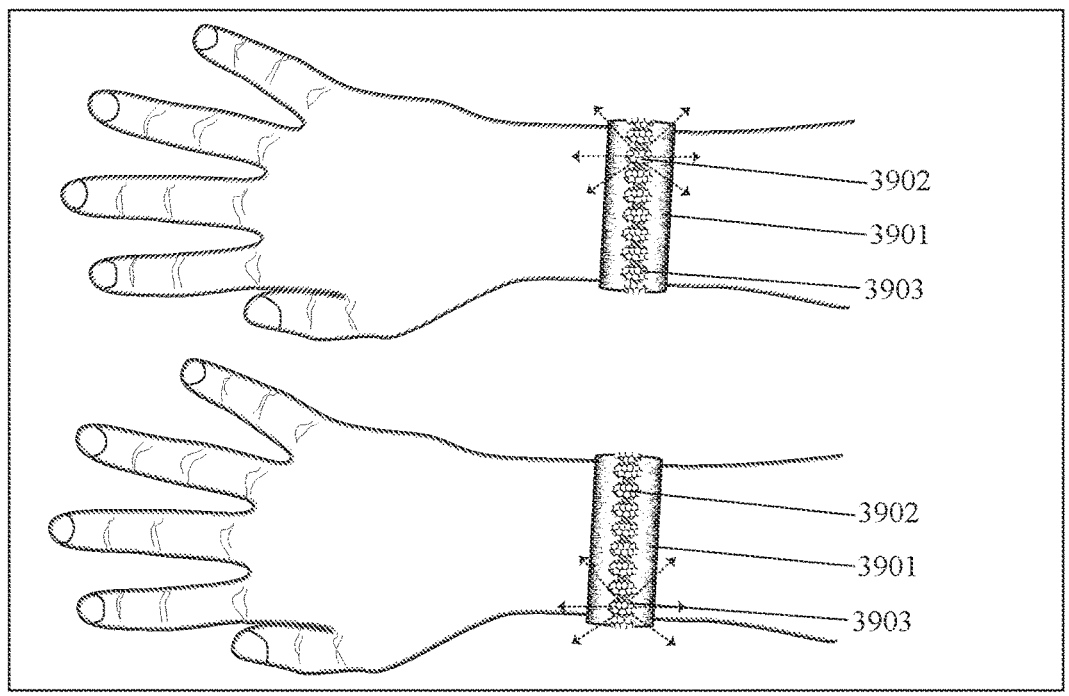
FIG. 39 shows a wearable device with light-emitting members with varying color, spectral range, intensity, emission sequence, and/or emission frequency.

FIG. 39 shows an example of a wearable computing device for the wrist and/or arm comprising: a plurality of light-emitting members including 3902 and 3903; and attachment member 3901. This device has a first configuration with a first pattern of light emission from one or more light-emitting members and a second configuration with a second pattern of light emission from one or more light-emitting members. The upper portion of FIG. 39 shows this device in a first configuration and the lower portion shows this device in a second configuration. Light-emitting member 3902 is turned on in the first configuration and light-emitting member 3903 is turned on in the second configuration.

In an example, a first configuration can comprise no light emission at all. In an example, a device configuration or light pattern can comprise emission of a selected set of one or more light colors. In an example, a device configuration or light pattern can comprise emission of a selected level of light intensity or brightness. In an example, a device configuration or light pattern can comprise having of a selected subset of light-emitting members being on. In various examples, a first device configuration can differ from a second device configuration in one or more parameters selected from the group consisting of: light color; light spectral range; light intensity; which light-emitting members are turned on or off; light emission sequence; and light emission frequency.

In various examples, this device can transition from a first configuration to a second configuration based on an incoming communication from a specific person and/or source. In an example, the pattern of light emission that is associated with a device configuration can be based on one or more factors selected from the group consisting of: person and/or source of an incoming communication; data from sensors worn by the person sending a communication or by the person wearing the device; location of the person sending a communication or of the person wearing the device; categorization or rating of an incoming communication by the person sending it; and content of an incoming communication. In an example, light emitted by light-emitting members can be in a spectral range that is only visible via selected eyewear which is worn by the person wearing the device.

In an example, light-emitting members can be Light Emitting Diodes (LEDs). In an example, light-emitting members can encircle the circumference of attachment member 3901. In an example, attachment member 3901 can be a strap or band. In an example, attachment member 3901 can span the full circumference the forearm. In an example, attachment member 3901 can span 50% to 95% of the circumference the forearm and be flexed to fit around the forearm. In an example, attachment member 3901 can be fastened around the forearm with a buckle, clip, adhesive, or hook-and-eye mechanism. In an example, attachment member 3901 can be stretched or expanded around the hand in order to slip it onto the forearm.

In various examples, this device can further comprise one or more components selected from the group consisting of: data processing member, data transmitting member, data receiving member, power source, and energy harvester. In various examples, this device can communicate with a handheld electronic device, a different wearable technology device, an array of wearable sensors, a communication network tower, a satellite, a home control system, and/or an implantable medical device. In various examples, this device can further comprise one or more components selected from the group consisting of: one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface.

Figure 40:
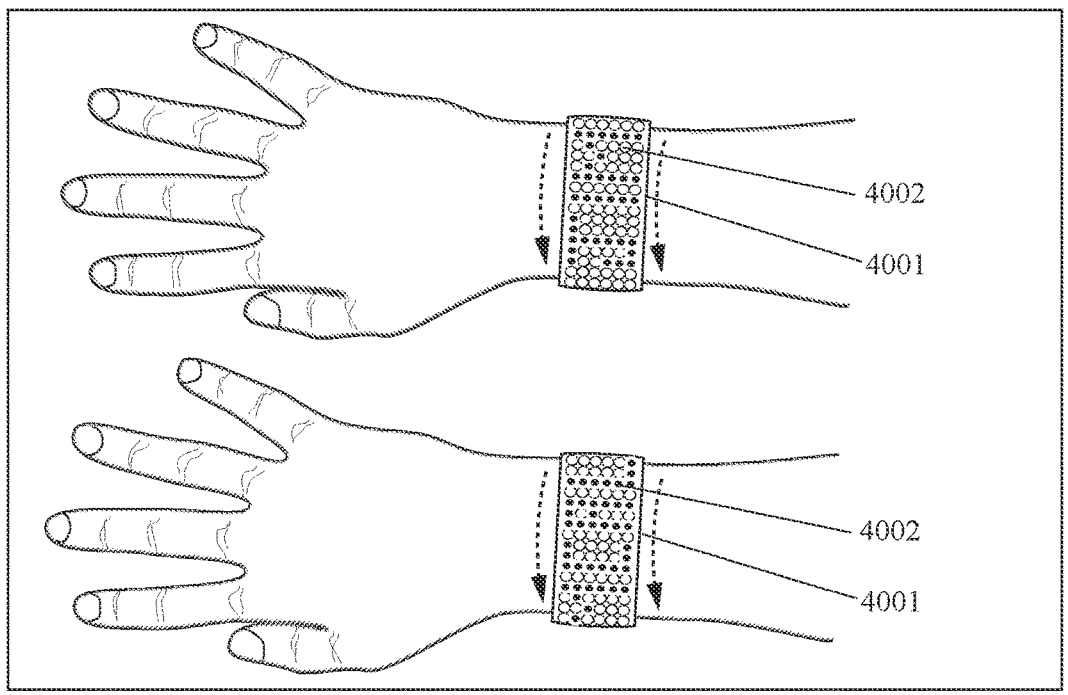
FIG. 40 shows a wearable device which displays circumferentially-scrolling messages.

FIG. 40 shows an example of a wearable computing device for the wrist and/or arm comprising: attachment member 4001, wherein this member spans at least 50% of the circumference of a person's wrist and/or arm; and array of light-emitting members 4002, wherein this array spans at least 30% of the circumference of the person's wrist and/or arm. In an example, array of light-emitting members 4002 has a longitudinal axis which is substantially parallel to the circumference of attachment member 4001 and a lateral axis which is substantially perpendicular to the longitudinal axis. In an example, array of light-emitting members 4002 comprises a longitudinal sequence of lateral lines of light-emitting members which span the surface of attachment member 4001. In an example, there can be at least five light-emitting members in a lateral line of light-emitting members. In an example, there can be at least ten lateral lines of light-emitting members in the longitudinal sequence.

This device has a first configuration comprising a first pattern of light from the array of light-emitting members 4002 and a second configuration comprising a second pattern of light from the array of light-emitting members 4002. The upper portion of FIG. 40 shows the first configuration and the lower portion of FIG. 40 shows the second configuration. The first pattern of light comprises a first segment of a message. The second pattern of light comprises a second segment of the same message. In an example, the second segment is shifted one (or more) lateral lines of light-emitting members to the right of the first segment. In this manner, the device displays the message in a circumferentially-scrolling manner which can be read from multiple angles. In the example shown in FIG. 40, the circumferentially-scrolling message is "JIM CALLED".

In an example, array of light-emitting members 4002 can comprise an arcuate array of Light Emitting Diodes (LEDs). In an example, array of light-emitting members 4002 can comprise an array of pixels in a single arcuate computer display screen. In an example, this arcuate computer display screen can be substantially cylindrical or a portion of a cylinder. In an example, array of light-emitting members 4002 can comprise an array of pixels in a connected sequence of flat computer display screens.

In an example, attachment member 4001 can be a strap or band. In an example, attachment member 4001 can span the full circumference the forearm. In an example, attachment member 4001 can span 50% to 95% of the circumference the forearm and be flexed to fit around the forearm. In an example, attachment member 4001 can be fastened around the forearm with a buckle, clip, adhesive, or hook-and-eye mechanism. In an example, attachment member 4001 can be stretched or expanded around the hand in order to slip it onto the forearm. In various examples, this device can further comprise one or more components selected from the group consisting of: data processing member, data transmitting member, data receiving member, power source, and energy harvester.

Figure 41:
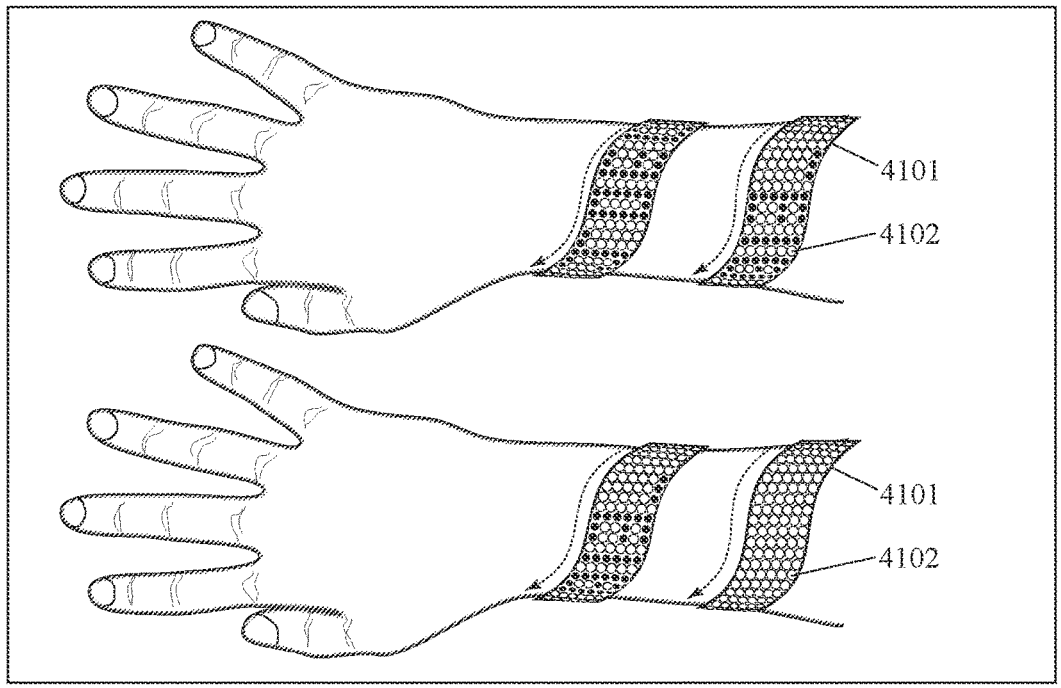
FIG. 41 shows a wearable device which displays spiral-scrolling messages.

FIG. 41 shows an example of a wearable computing device for the wrist and/or arm comprising: spiraling attachment member 4101 which spans the circumference of a person's wrist and/or arm; and array of light-emitting members 4102 which spans at least 30% of the circumference of the person's wrist and/or arm. In an example, array of light-emitting members 4102 has a longitudinal axis which is substantially parallel to the spiraling longitudinal axis of spiraling attachment member 4101 and a lateral axis which is substantially perpendicular to the longitudinal axis. In an example, array of light-emitting members 4102 comprises a longitudinal sequence of lateral lines of light-emitting members which span the surface of attachment member 4101. In an example, there can be at least five light-emitting members in a lateral line of light-emitting members. In an example, there can be at least ten lateral lines of light-emitting members in the longitudinal sequence.

This device has a first configuration comprising a first pattern of light from the array of light-emitting members 4102 and a second configuration comprising a second pattern of light from the array of light-emitting members 4102. The upper portion of FIG. 41 shows the first configuration and the lower portion of FIG. 41 shows the second configuration. The first pattern of light comprises a first segment of a message. The second pattern of light comprises a second segment of the same message. In an example, the second segment is shifted one (or more) lateral lines of light-emitting members to the right of the first segment. In this manner, the device displays the message in a spiral-scrolling manner which can be read from multiple angles.

In an example, array of light-emitting members 4102 can comprise an arcuate array of Light Emitting Diodes (LEDs). In an example, array of light-emitting members 4102 can comprise an array of pixels in a single arcuate computer display screen. In an example, array of light-emitting members 4102 can comprise an array of pixels in a connected sequence of flat computer display screens. In an example, spiral spiraling attachment member 4101 can be flexed to fit around the forearm or can expand to slip over the hand onto the forearm. In various examples, this device can further comprise one or more components selected from the group consisting of: data processing member, data transmitting member, data receiving member, power source, and energy harvester.

Figure 42:
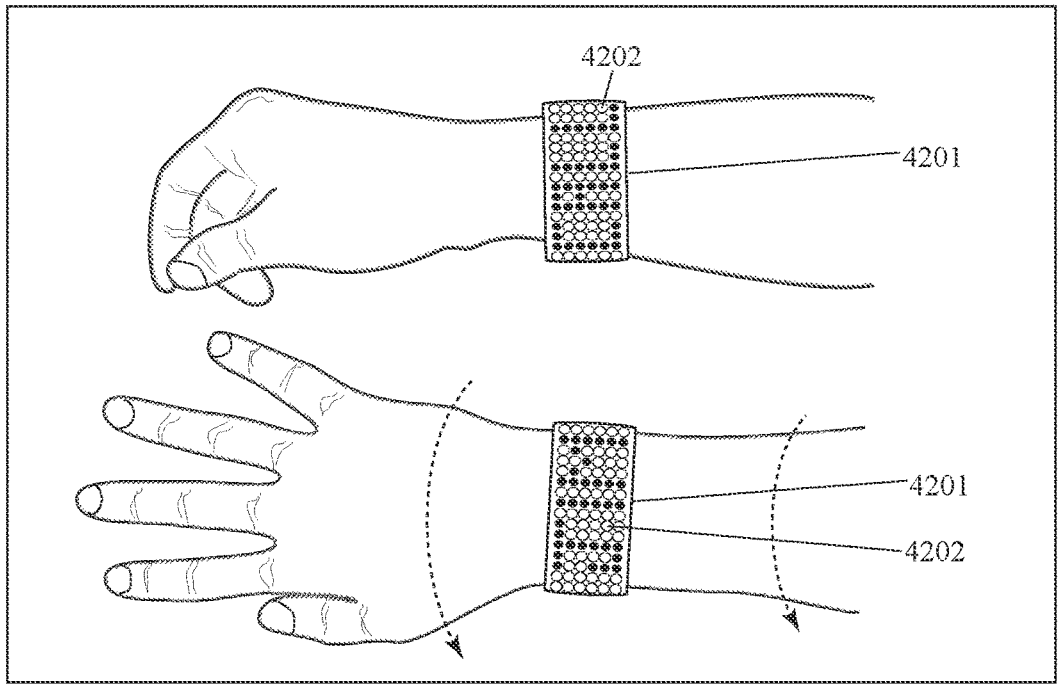
FIG. 42 shows a wearable device with a motion-triggered scrolling display.

FIG. 42 shows an example of a wearable computing device for the wrist and/or arm comprising: attachment member 4201; and array of light-emitting members 4202. In an example, array of light-emitting members 4202 has a longitudinal axis which is substantially parallel to the circumference of attachment member 4201 and a lateral axis which is substantially perpendicular to the longitudinal axis. In an example, array of light-emitting members 4202 comprises a longitudinal sequence of lateral lines of light-emitting members which span the surface of attachment member 4201. In an example, there can be at least five light-emitting members in a lateral line of light-emitting members. In an example, there can be at least ten lateral lines of light-emitting members in the longitudinal sequence.

This device has a first configuration comprising a first pattern of light from the array of light-emitting members 4202 and a second configuration comprising a second pattern of light from the array of light-emitting members 4202. The upper portion of FIG. 42 shows the first configuration and the lower portion of FIG. 42 shows the second configuration. The first pattern of light comprises a first segment of a message. The second pattern of light comprises a second segment of the same message. In an example, the second segment is shifted one (or more) lateral lines of light-emitting members to the right of the first segment. In this manner, the device displays the message in a circumferentially-scrolling manner which can be read from multiple angles. In this example, the device transitions from the first configuration to the second configuration based on movement of the forearm. In an example, the device can further comprise a motion sensor and the scrolling action can be triggered when this motion sensor detects that the person moves their arm. In an example, the message scrolls when the person rotates their forearm.

In an example, array of light-emitting members 4202 can comprise an arcuate array of Light Emitting Diodes (LEDs). In an example, array of light-emitting members 4202 can comprise an array of pixels in a single arcuate computer display screen. In an example, this arcuate computer display screen can be substantially cylindrical or a portion of a cylinder. In an example, array of light-emitting members 4202 can comprise an array of pixels in a connected sequence of flat computer display screens.

In an example, attachment member 4201 can be a strap or band. In an example, attachment member 4201 can span the full circumference the forearm. In an example, attachment member 4201 can span 50% to 95% of the circumference the forearm and be flexed to fit around the forearm. In an example, attachment member 4201 can be fastened around the forearm with a buckle, clip, adhesive, or hook-and-eye mechanism. In an example, attachment member 4201 can be stretched or expanded around the hand in order to slip it onto the forearm. In various examples, this device can further comprise one or more components selected from the group consisting of: data processing member, data transmitting member, data receiving member, power source, and energy harvester.

Figure 43:
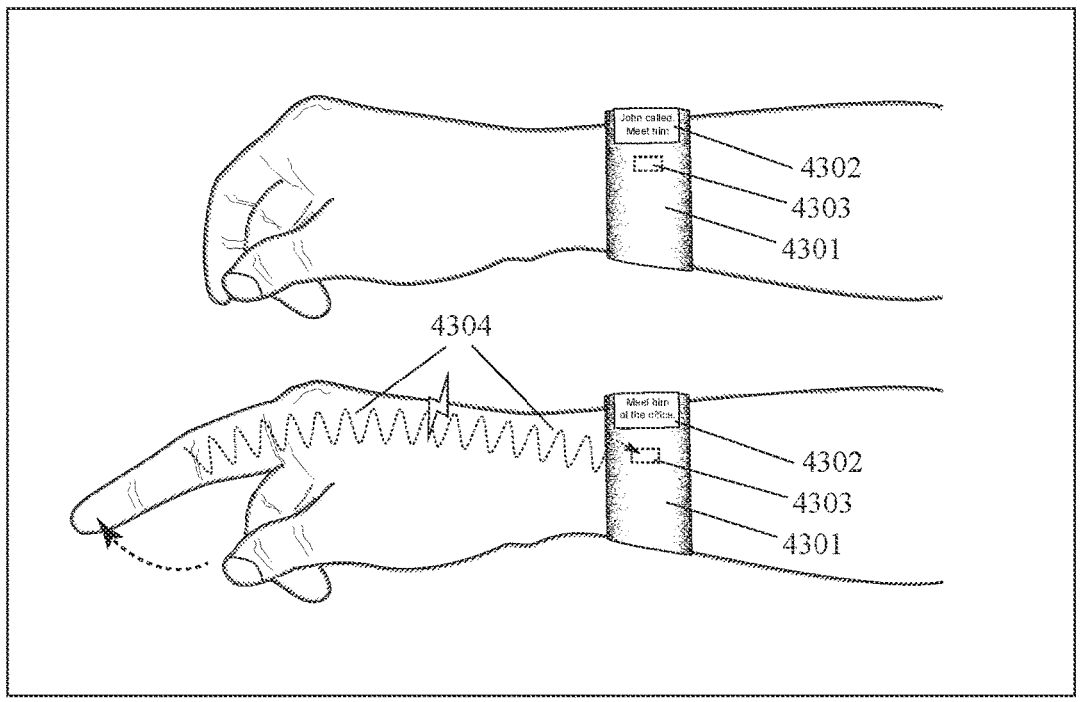
FIG. 43 shows a wearable device with a display and an EMG sensor.

FIG. 43 shows an example of a wearable computing device for the wrist and/or arm comprising: attachment member 4301 which is configured to be worn on a person's wrist and/or arm; display member 4302; and electromagnetic sensor 4303. This device has a first configuration wherein display member 4302 displays a first set of content and a second configuration wherein display member 4302 displays a second set of content. In FIG. 43, the upper portion shows the first configuration and the lower portion shows the second configuration. In this example, the device transitions from the first configuration to the second configuration based on electromagnetic energy measured by electromagnetic sensor 4303. In this example, movement of the person's finger causes electromagnetic signals from the person's muscles and/or nerves which are detected by electromagnetic sensor 4303 which, in turn, trigger the transition from the first configuration to the second configuration. In this manner, the person can change the content which is displayed on display member 4302 by moving their fingers, hand, and/or arm. In this manner, the device has a gesture-recognizing user interface.

In an example, attachment member 4301 can be a strap or band. In various examples, attachment member 4301: can be fastened around the forearm with a buckle, clip, adhesive, or hook-and-eye mechanism; can be stretched or expanded around the hand in order to slip it onto the forearm; or can span 50% to 95% of the circumference the forearm and be flexed to fit around the forearm. In an example, display member 4302 can be a computer display screen. In an example, electromagnetic sensor 4303 can be an electromyography (EMG) sensor.

In various examples, this device can further comprise one or more sensors selected from the group consisting of: accelerometer, blood pressure sensor, camera or other imaging sensor, electrochemical sensor, electrogoniometer, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can communicate with a handheld electronic device, a different wearable technology device, an array of wearable sensors, a communication network tower, a satellite, a home control system, and/or an implantable medical device. In various examples, this device can further comprise one or more components selected from the group consisting of: data processing member; data transmitting member; data receiving member; power source; energy harvester; one or more LEDs; one or more image projectors; one or more coherent light emitters; one or more infrared light emitters; one or more sound-emitting members; one or more tactile-sensation-creating members; one or more neurostimulators, myostimulators, or other electromagnetic energy emitters; one or more hardware buttons, knobs, or keys, virtually-projected keypad; speech-recognition interface, and eye-gaze-tracking interface.

Figure 44:
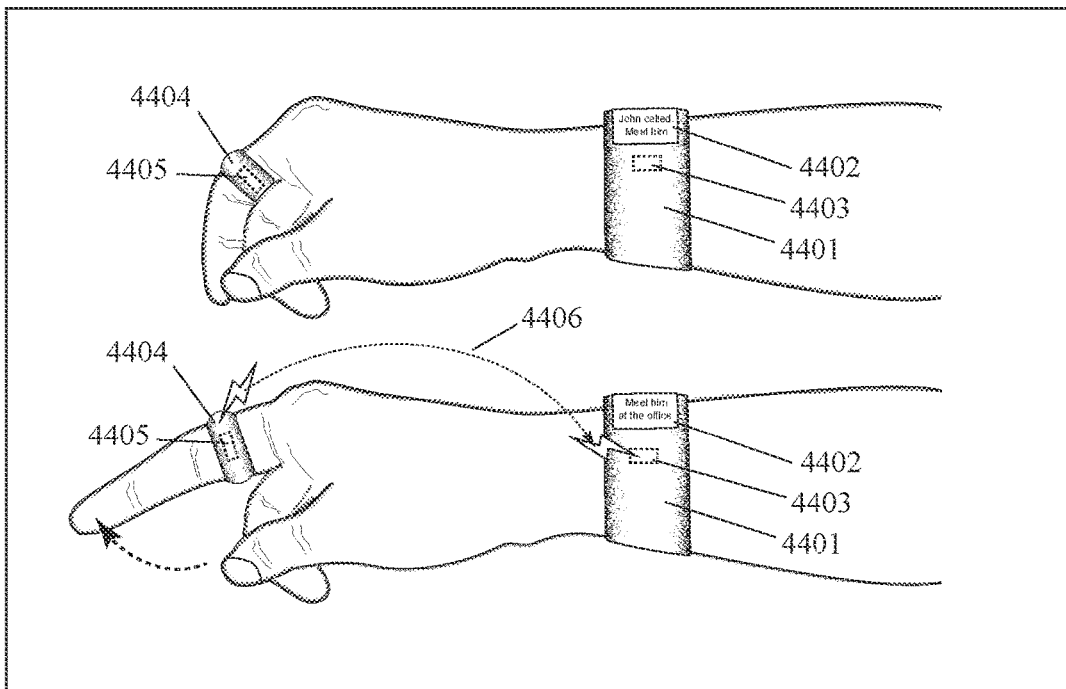
FIG. 44 shows a wearable system with a display, an arm attachment member, and a finger ring.

FIG. 44 shows an example of a wearable computing system for the wrist and/or arm comprising: attachment member 4401 which is configured to be worn on a person's wrist and/or arm; display member 4402; data control unit 4403; finger ring 4404; and motion sensor 4405. This system has a first configuration wherein display member 4402 displays a first set of content and a second configuration wherein display member 4402 displays a second set of content. In FIG. 44, the upper portion shows the first configuration and the lower portion shows the second configuration.

In this example, the system transitions from the first configuration to the second configuration based on finger motion measured by motion sensor 4405. In this example, movement of the person's finger is detected by motion sensor 4405, which transmits motion data to data control unit 4403, which triggers the transition from the first configuration to the second configuration. In this example, there is only one finger ring and motion sensor. In other examples, there can be finger rings and motion sensors on multiple fingers. Using this device, a person can change the content which is displayed on display member 4402 by moving their fingers (and/or their hand and arm). In this manner, this system has a gesture-recognizing user interface.

In an example, attachment member 4401 can be a strap or band. In various examples, attachment member 4401: can be fastened around the forearm with a buckle, clip, adhesive, or hook-and-eye mechanism; can be stretched or expanded around the hand in order to slip it onto the forearm; or can span 50% to 95% of the circumference the forearm and be flexed to fit around the forearm. In an example, display member 4402 can be a computer display screen. In an example, motion sensor 4405 can be an accelerometer, gyroscope, or inclinometer.

In various examples, this system can further comprise one or more sensors selected from the group consisting of: blood pressure sensor, camera or other imaging sensor, electrochemical sensor, electrogoniometer, electromyography (EMG) sensor or other electromagnetic sensor, optoelectronic sensor, galvanic skin response (GSR) sensor, glucose sensor, heart rate sensor, infrared light sensor, ultraviolet light sensor, microphone or other sound sensor, neurosensor, motion sensor, piezoelectric sensor, pressure sensor, pun detector, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this system can communicate with a handheld electronic system, a different wearable technology device, an array of wearable sensors, a communication network tower, a satellite, a home control system, and/or an implantable medical device. In various examples, this system can further comprise one or more components selected from the group consisting of: data processing member; data transmitting member; data receiving member; power source; energy harvester; one or more LEDs; one or more image projectors; one or more coherent light emitters; one or more infrared light emitters; one or more sound-emitting members; one or more tactile-sensation-creating members; one or more neurostimulators, myostimulators, or other electromagnetic energy emitters; one or more hardware buttons, knobs, or keys, virtually-projected keypad; gesture-recognition interface; speech-recognition interface, and eye-gaze-tracking interface.

Figure 45:
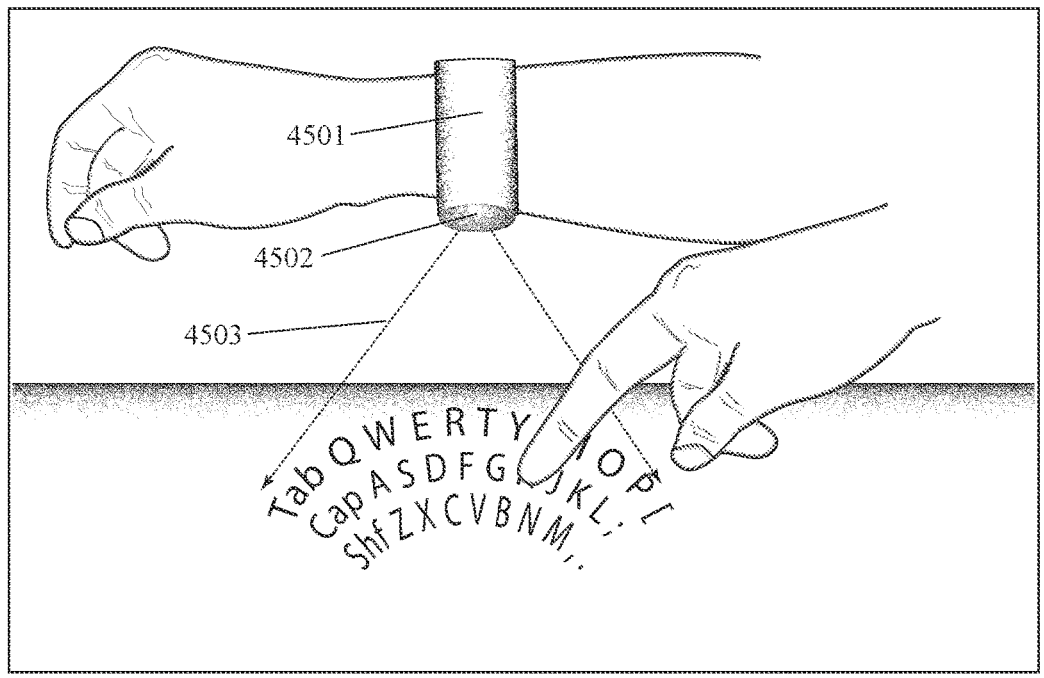
FIG. 45 shows a wearable device with an interactive image projector.

FIG. 45 shows an example of a wearable computing device for the wrist and/or arm comprising: attachment member 4501; and interactive image projector 4502. In an example, attachment member 4501 can be a strap or band. In various examples, attachment member 4501: can be fastened around the forearm with a buckle, clip, adhesive, or hook-and-eye mechanism; can be stretched or expanded around the hand in order to slip it onto the forearm; or can span 50% to 95% of the circumference the forearm and be flexed to fit around the forearm. In an example, this device can further comprise a display screen.

In an example, interactive image projector 4502 can project a virtual keypad or other virtual image onto an external surface. In an example, interactive image projector 4502 can project a virtual keypad or other virtual image onto a body member of the person wearing the device. In an example, interactive image projector 4502 can further comprise an image-projecting mechanism and a gesture-detecting mechanism. In an example, an image-projecting mechanism can project coherent light 4503. In an example, a gesture-detecting mechanism can comprise an infrared light emitter and reflection detector. In an example, a gesture-detecting mechanism can comprise a camera and pattern recognition software. In an example, this device projects a virtual user interface and detects virtual contact between the wearer and this virtual interface. In an example, the operation of this device is controlled by this virtual contact. In an example, this device can serve as a human-to-computer user interface for other devices or purposes.

In various examples, this device can further comprise one or more sensors selected from the group consisting of: accelerometer, blood pressure sensor, camera or other imaging sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can communicate with a handheld electronic device, a different wearable technology device, an array of wearable sensors, a communication network tower, a satellite, a home control system, and/or an implantable medical device. In various examples, this device can further comprise one or more components selected from the group consisting of: data processing member; data transmitting member; data receiving member; power source; energy harvester; one or more LEDs; one or more sound-emitting members; one or more tactile-sensation-creating members; one or more neurostimulators, myostimulators, or other electromagnetic energy emitters; one or more hardware buttons, knobs, or keys; speech-recognition interface, and eye-gaze-tracking interface.

Figure 46:
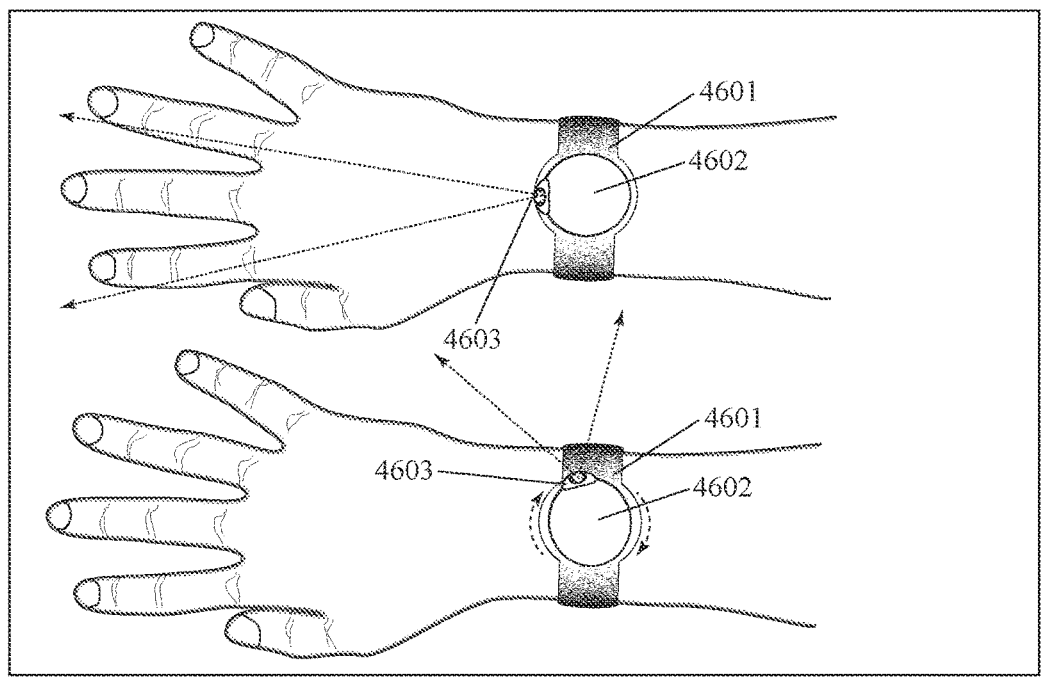
FIG. 46 shows a wearable device with a rotating camera.

FIG. 46 shows an example of a wearable computing device for the wrist and/or arm comprising: attachment member 4601; display member 4602; and moving imaging member 4603. In an example, this device has a first configuration in which moving imaging member 4603 has a first focal direction and a second configuration in which moving imaging member 4603 has a second focal direction. In FIG. 46, the upper portion shows the device in a first configuration and the lower portion shows the device in a second configuration.

In an example, moving imaging member 4603 can be a camera. In an example, the focal direction of moving imaging member 4603 can be changed by rotation. In an example, moving imaging member 4603 can be rotated or otherwise moved manually. In an example, moving imaging member 4603 can rotated or otherwise moved automatically. In various examples, moving imaging member 4603 can rotate or otherwise move automatically in response to movement of the device and/or movement of an object on which moving imaging member 4603 is focused. In an example, moving imaging member 4603 can be rotated or otherwise moved automatically in order to maintain focal direction toward a selected object.

In various examples attachment member 4601: can be a strap or band; can be fastened around the arm with a buckle, clip, adhesive, or hook-and-eye mechanism; can be expanded around the hand in order to slip onto the arm; and/or can span 50% to 95% of the circumference the arm and be flexed so that it can fit around the forearm. In an example, display member 4602 can comprise a computer display screen.

In various examples, automatic movement of imaging member 4603 can be based on information from one or more sensors within the device which are selected from the group consisting of: accelerometer, blood pressure sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can communicate with a handheld electronic device, a different wearable technology device, an array of wearable sensors, a communication network tower, a satellite, a home control device, and/or an implantable medical device. In various examples, this device can further comprise one or more components selected from the group consisting of: data processing member; data transmitting member; data receiving member; power source; energy harvester; one or more LEDs; one or more image projectors; one or more coherent light emitters; one or more infrared light emitters; one or more sound-emitting members; one or more tactile-sensation-creating members; one or more neurostimulators, myostimulators, or other electromagnetic energy emitters; one or more hardware buttons, knobs, or keys, virtually-projected keypad; gesture-recognition interface; speech-recognition interface, and eye-gaze-tracking interface.

Figure 47:
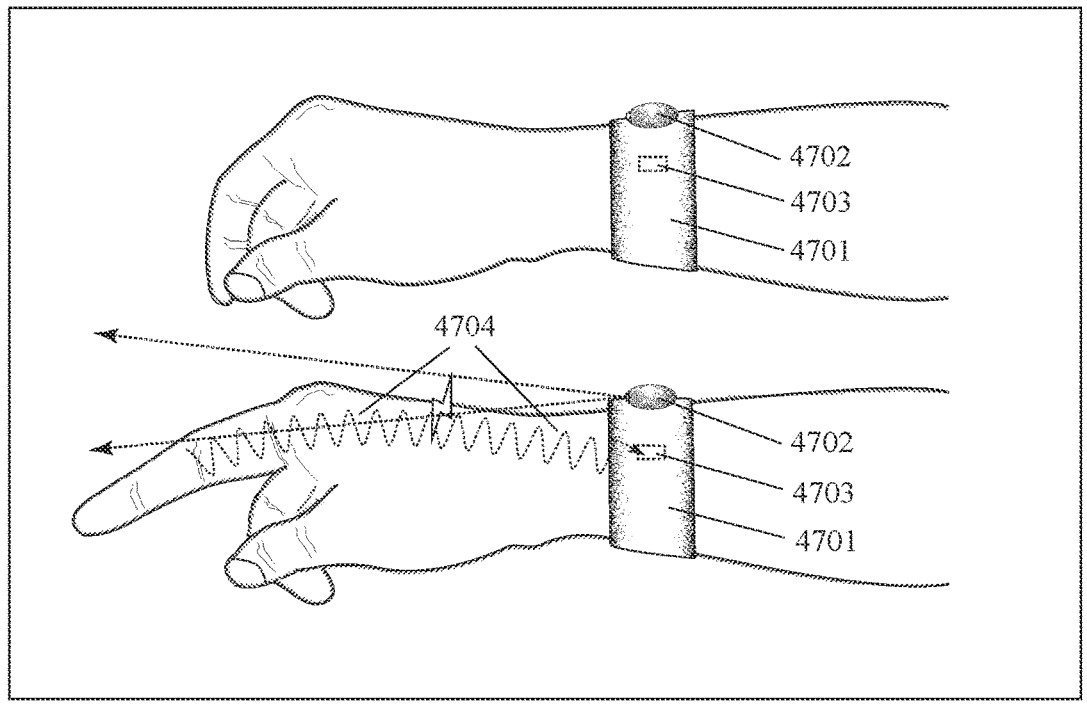
FIG. 47 shows a wearable device with a camera triggered by an electromagnetic sensor.

FIG. 47 shows an example of a wearable computing device for the wrist and/or arm comprising: attachment member 4701; imaging member 4702; and electromagnetic energy sensor 4703. In FIG. 47, the upper portion shows the device when imaging member 4702 is not taking pictures and the lower portion shows the device when imaging member 4702 is taking pictures. In this example, the device takes pictures in response to movement of the person's fingers, hand, and/or arm, wherein this movement is detected by electromagnetic energy sensor 4703.

In various examples, attachment member 4701: can be a strap or band; can be fastened around the arm with a buckle, clip, adhesive, or hook-and-eye mechanism; can be expanded around the hand in order to slip onto the arm; and/or can span 50% to 95% of the circumference the arm and be flexed so that it can fit around the forearm. In an example, imaging member 4702 can be a camera.

In an example, electromagnetic energy sensor 4703 can be an electromyography sensor or neurological sensor. In an example, activation of the muscles moving the person's fingers, hand, and/or arm causes electromagnetic signals 4704 which are detected by electromagnetic energy sensor 4703 which, in turn, triggers imaging member 4702 to take pictures. In an example, transmission of impulses through the nerves which innervate the person's fingers, hand, and/or arm causes electromagnetic signals which are detected by electromagnetic energy sensor 4703 which, in turn, triggers imaging member 4702 to take pictures. In an example, the focal direction of imaging member 4702 can be controlled by selected movements of the person's fingers, hand, and/or arm. In an example, this device comprises a gesture-controlled imaging device.

Figure 48:
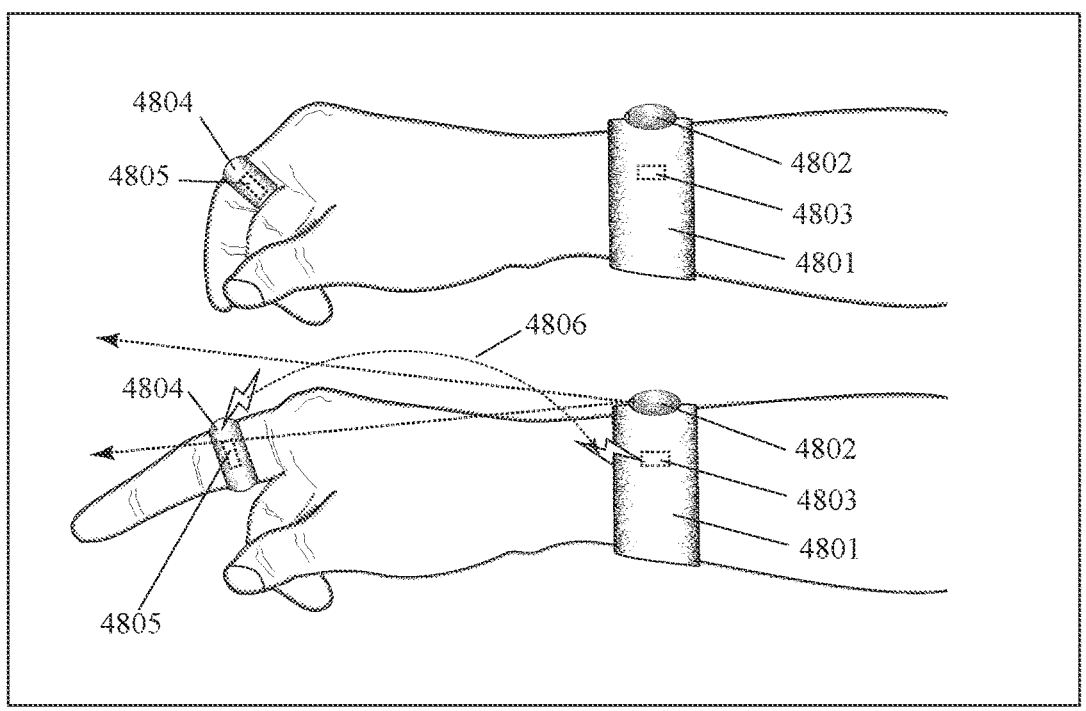
FIG. 48 shows a wearable system with a camera triggered by movement of a finger ring.

FIG. 48 shows an example of a wearable computing system for the wrist and/or arm comprising: attachment member 4801; imaging member 4802; data control unit 4803; finger ring 4804; and motion sensor 4805. In an example, imaging member 4802 can be a camera. In FIG. 48, the upper portion shows the system when imaging member 4802 is not taking pictures and the lower portion shows the system when imaging member 4802 is taking pictures. In this example, the system takes pictures in response to movement of the person's finger. This movement is detected by motion sensor 4805, this information is then wirelessly transmitted 4806 to data control unit 4803, and this then triggers imaging member 4802 to take pictures. In an example, the focal direction of imaging member 4802 can be controlled by selected movements of the person's finger, hand, and/or arm. In an example, there can be multiple finger rings and motion sensors. In an example, this system can comprise a gesture-controlled imaging device.

In various examples, attachment member 4801: can be a strap or band; can be fastened around the arm with a buckle, clip, adhesive, or hook-and-eye mechanism; can be expanded around the hand in order to slip onto the arm; and/or can span 50% to 95% of the circumference the arm and be flexed so that it can fit around the forearm.

Figure 49:
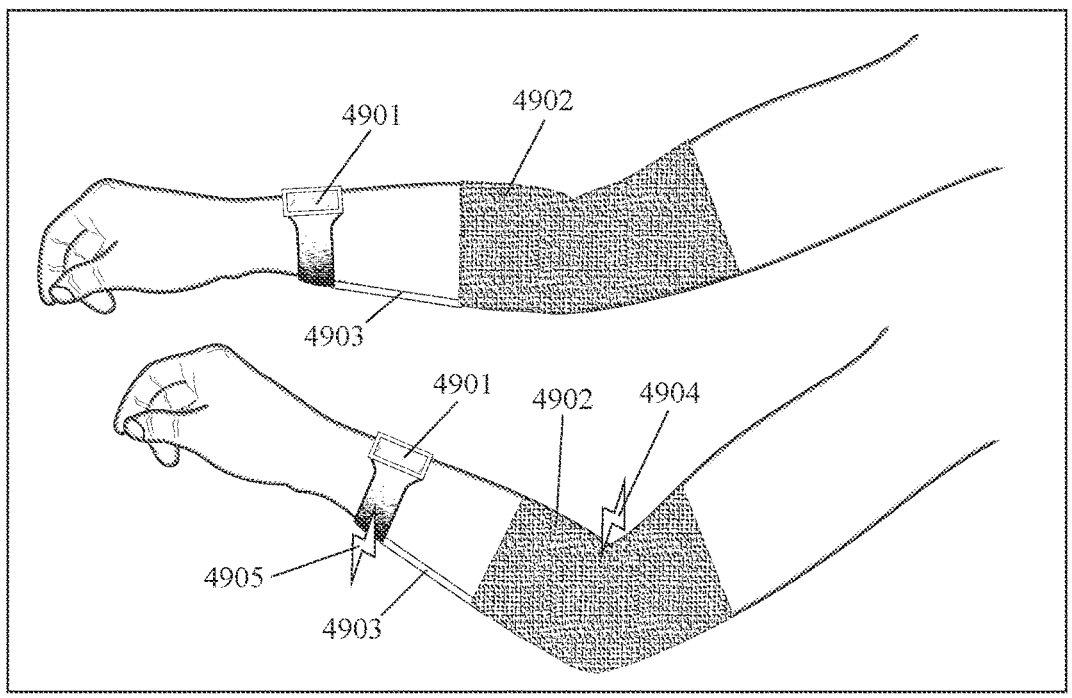
FIG. 49 shows a wearable system which harvests energy from elbow movement.

FIG. 49 shows an example of a wearable computing system for the wrist and/or arm comprising: wearable computing device 4901; and wearable energy transducer 4902. This system has a first configuration in which wearable energy transducer 4902 has a first shape and a second configuration in which wearable energy transducer 4902 has a second shape. The upper portion of FIG. 49 shows this device in the first configuration and the lower portion of FIG. 49 shows this device in the second configuration.

In an example, wearable energy transducer 4902 generates and/or harvests electricity 4904 from kinetic, thermal, or electromagnetic energy. In an example, wearable energy transducer 4902 is worn over the person's elbow and harvests energy from movement of the elbow joint. In an example, energy transducer 4903 can be piezoelectric. In an example, energy transducer 4903 can transduce energy from the flow of a flowable substance. In an example, electricity that is generated and/or harvested by energy transducer 4903 is conducted to wearable computing device 4901 via energy conduit 4903 in order to help power 4905 wearable computing device 4901.

Figure 50:
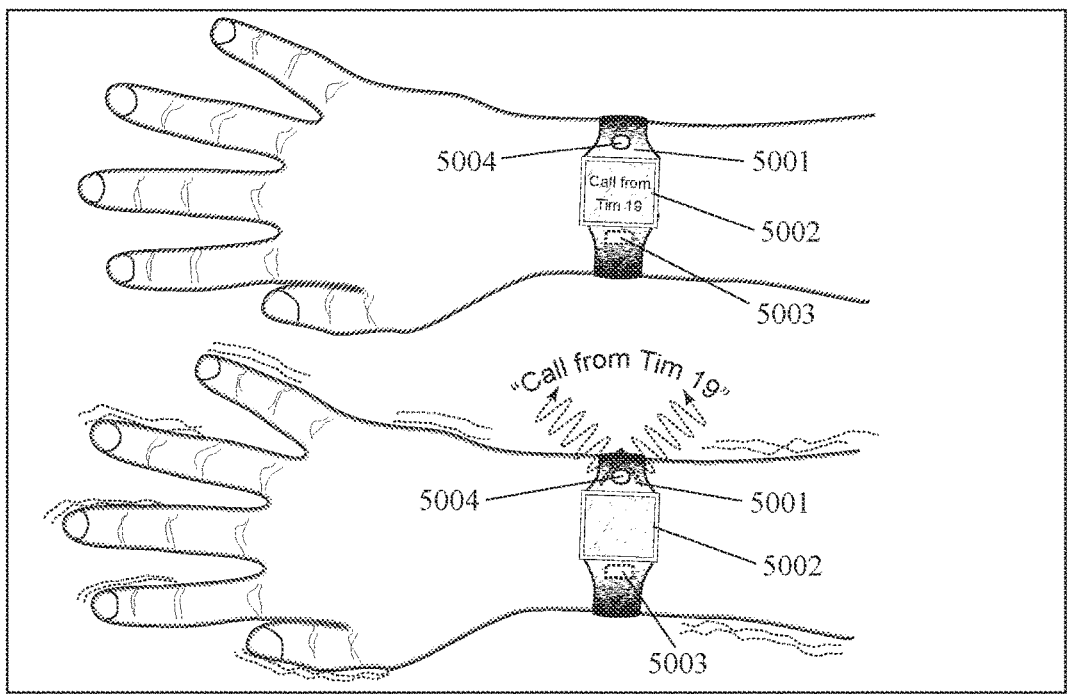
FIG. 50 shows a wearable device wherein the mode (e.g. visual vs. audio) for incoming message notifications depends on the wearer's movement.

FIG. 50 shows an example of a wearable computing system for the wrist and/or arm comprising: attachment member 5001; display member 5002; motion sensor 5003; and speaker 5004. The upper portion of FIG. 50 shows the device receiving an incoming message at a time when a person's arm is stationary. The lower portion of FIG. 50 shows the device receiving an incoming message at a time when the person's arm is actively moving. In this example, the mode by which a message is communicated to a person depends on the amount and/or type of movement by that person.

In this example, when the person's arm is stationary (as detected by motion sensor 5003), then an incoming message is communicated to the wearer by a visual mode; the message is visually displayed via display member 5002. In this example, when the person's arm is actively moving (as detected by motion sensor 5003), then an incoming message is communicated to the wearer by an audio mode; the message is played from speaker 5004. A device which changes its mode of communication based on the amount and/or type of body motion can be very useful. For example, a person who is running or otherwise actively moving may not easily notice a visual display and a person who is sitting quietly in a meeting may not wish to be disturbed by an audio signal. For example, a person need never be embarrassed by having an audio signal occur during a meeting or during a performance because they forgot to silence their communication device.

In various examples, the mode of communication to a user can be based on one or more sensors within the device which are selected from the group consisting of: accelerometer, blood pressure sensor, camera or other imaging sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In various examples, this device can communicate with a handheld electronic device, a different wearable technology device, an array of wearable sensors, a communication network tower, a satellite, a home control device, and/or an implantable medical device. In various examples, this device can further comprise one or more components selected from the group consisting of: data processing member; data transmitting member; data receiving member; power source; energy harvester; one or more LEDs; one or more image projectors; one or more coherent light emitters; one or more infrared light emitters; one or more tactile-sensation-creating members; one or more neurostimulators, myostimulators, or other electromagnetic energy emitters; one or more hardware buttons, knobs, or keys, virtually-projected keypad; gesture-recognition interface; speech-recognition interface, and eye-gaze-tracking interface.

Figure 51:
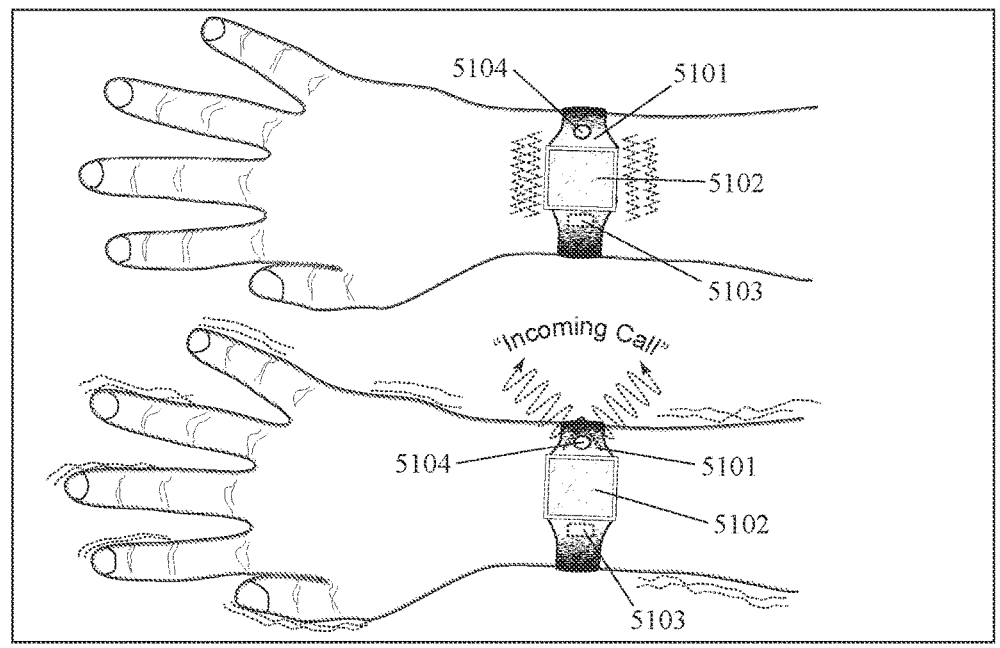
FIG. 51 shows a wearable device wherein the mode (e.g. tactile vs. audio) for incoming message notifications depends on the wearer's movement.

FIG. 51 shows an example of a wearable computing device for the wrist and/or arm comprising: attachment member 5101; display member 5102; motion sensor 5103; and speaker 5104. In an example, this device can further comprise a vibrating member. In FIG. 51, the upper portion shows how the device responds to an incoming message at a time when the arm is stationary and the lower portion shows how the device responds to an incoming message at a time when the arm is actively moving. In this example, the mode by which an incoming message is communicated to the person wearing the device depends on the amount and/or type of their movement. In this example, when the person's arm is stationary (as detected by motion sensor 5103) then an incoming message is communicated to the wearer by vibration and when the person's arm is actively moving (as detected by motion sensor 5103) then an incoming message is communicated to the wearer by an audio signal from speaker 5104. A device which changes its mode of communication based on the amount and/or type of the wearer's body motion can be useful.

In various examples, this mode by which the device communicates an incoming message can be based on information from one or more sensors selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

In various examples, this device can communicate with one or more other devices selected from the group consisting of: handheld electronic device; laptop or desktop computer; other wearable device; array of wearable sensors; communication tower; satellite; home appliance or control system; internet server; and implantable medical device. In various examples, this device can further comprise one or more components selected from the group consisting of: button, knob, dial, or keys; coherent light image projector; data processing member; data receiving member; data transmitting member; EEG-recognition interface; electromagnetic energy emitter; energy transducing and/or harvesting member; eye-gaze-tracking interface; gesture-recognition interface; infrared light projector; laser; LED or other light-emitting member; MEMS actuator; MEMS sensor; myostimulator; neurostimulator; power source; speaker or other sound-emitting member; speech-recognition interface; tactile-sensation-creating member; and virtually-projected user interface.

Figure 52:
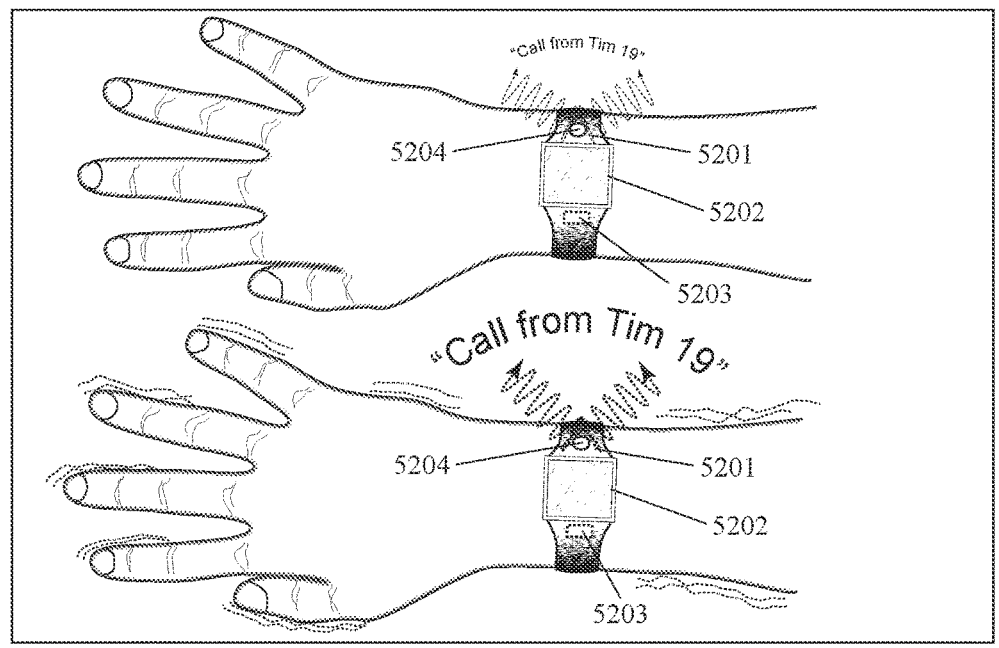
FIG. 52 shows a wearable device wherein the energy level of incoming message notifications depends on the wearer's movement.

FIG. 52 shows an example of a wearable computing device for the wrist and/or arm comprising: attachment member 5201; display member 5202; motion sensor 5203; and speaker 5204. In FIG. 52, the upper portion shows how the device responds to an incoming message at a time when the arm is stationary and the lower portion shows how the device responds to an incoming message at a time when the arm is actively moving.

In this example, the energy level, magnitude, and/or intensity of communication of an incoming message to the person wearing the device depends on the amount and/or type of the wearer's movement. In an example, when the person's arm is stationary (as detected by motion sensor 5203) then an incoming message is communicated to the wearer in a low energy level, low magnitude, and/or low intensity manner. In this example, this is a quiet audio signal. In an example, when the person's arm is actively moving (as detected by motion sensor 5203) then an incoming message is communicated to the wearer in a high energy level, high magnitude, and/or high intensity manner. In this example, this is a loud audio signal. A device which changes its energy level of communication based on the amount and/or type of the wearer's body motion can be useful.

In various examples, this energy level with which a device communicates an incoming message can be based on information from one or more sensors selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

Figure 53:
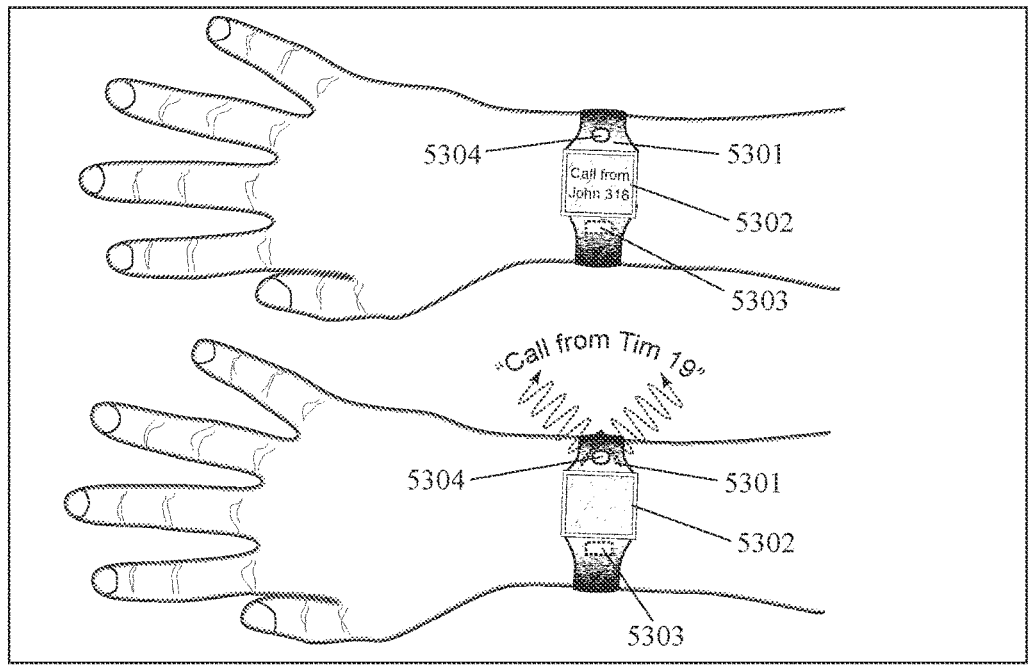
FIG. 53 shows a wearable device wherein the mode for incoming message notifications depends on message source.

FIG. 53 shows an example of a wearable computing device for the wrist and/or arm comprising: attachment member 5301; display member 5302; data control unit 5303; and speaker 5304. The upper portion of FIG. 53 shows the device receiving a message from a first source and the lower portion of FIG. 53 shows the device receiving a message from a second source. In this example, the mode by which a message is communicated to the person wearing the device depends on the source of the message. When a message is received from the first source, then this message is communicated to the wearer by a visual mode; the message is visually displayed via display member 5302. When a message is received from the second source, then this message is communicated to the wearer by an audio mode; the message is played from speaker 5304. A device which changes its mode of communication based on the source of a message can be very useful. In an example, the person wearing the device can select different communication modes for different sources.

In various examples, this device can further comprises one or more sensors selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

In various examples, this device can communicate with one or more other devices selected from the group consisting of: handheld electronic device; laptop or desktop computer; other wearable device; array of wearable sensors; communication tower; satellite; home appliance or control system; internet server; and implantable medical device. In various examples, this device can further comprise one or more components selected from the group consisting of: button, knob, dial, or keys; coherent light image projector; data processing member; data receiving member; data transmitting member; EEG-recognition interface; electromagnetic energy emitter; energy transducing and/or harvesting member; eye-gaze-tracking interface; gesture-recognition interface; infrared light projector; laser; LED or other light-emitting member; MEMS actuator; MEMS sensor; myostimulator; neurostimulator; power source; speech-recognition interface; tactile-sensation-creating member; and virtually-projected user interface.

Figure 54:
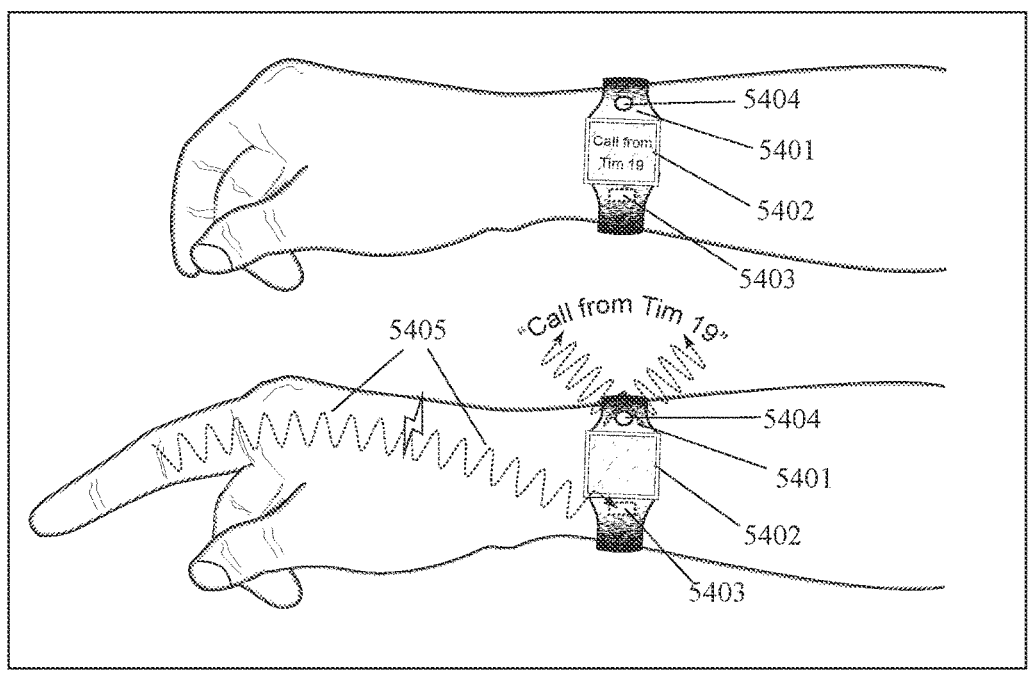
FIG. 54 shows a wearable device wherein the mode for incoming message notifications depends on the configuration of the wearer's fingers, hand, and/or arm.

FIG. 54 shows an example of a wearable computing device for the wrist and/or arm comprising: attachment member 5401; display member 5402; electromagnetic energy sensor 5403; and speaker 5404. The upper portion of FIG. 54 shows the device receiving a message when the person's hand is in a first configuration and the lower portion of FIG. 54 shows the device receiving a message when the person's hand is in a second configuration. In this example, the mode by which a message is communicated to the person wearing the device depends on the configuration and/or gesture of the wearer's fingers, hand, and/or arm.

In this example, when the person's finger is retracted, then messages are communicated to the wearer by a visual mode; the message is visually displayed via display member 5402. When the person's finger is extended, then messages are communicated to the wearer by an audio mode; the message is played from speaker 5404. This enables the wearer to subtly change the mode of message communication by making finger, hand, and/or arm gestures. In an example, the configuration and/or movement of a person's fingers, hand, and/or arm causes electromagnetic signals from the person's muscles which are detected by electromagnetic energy sensor 5403. In an example, electromagnetic energy sensor 5403 can be an EMG sensor. In an example, the configuration and/or movement of a person's fingers, hand, and/or arm causes electromagnetic signals from the person's nerves which are detected by electromagnetic energy sensor 5403. In an example, electromagnetic energy sensor 5403 can be a neurosensor.

In various examples, the mode by which the device communicates with the person wearing the device can be based on information from one or more sensors selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

In various examples, this device can communicate with one or more other devices selected from the group consisting of: handheld electronic device; laptop or desktop computer; other wearable device; array of wearable sensors; communication tower; satellite; home appliance or control system; internet server; and implantable medical device. In various examples, this device can further comprise one or more components selected from the group consisting of: button, knob, dial, or keys; coherent light image projector; data processing member; data receiving member; data transmitting member; EEG-recognition interface; electromagnetic energy emitter; energy transducing and/or harvesting member; eye-gaze-tracking interface; gesture-recognition interface; infrared light projector; laser; LED or other light-emitting member; MEMS actuator; MEMS sensor; myostimulator; neurostimulator; power source; speech-recognition interface; tactile-sensation-creating member; and virtually-projected user interface.

Figure 55:
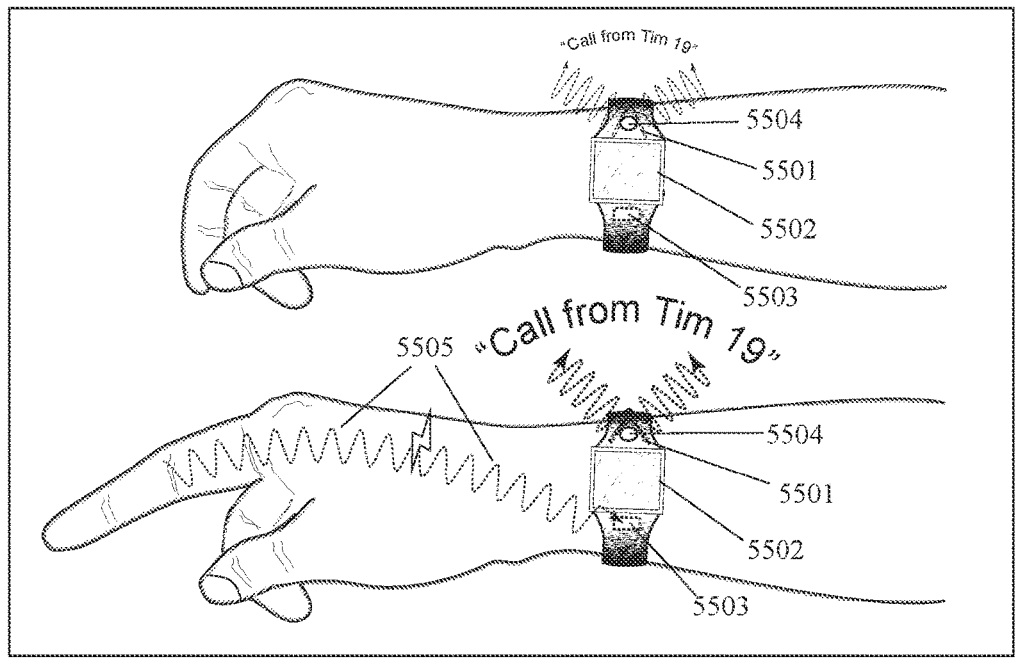
FIG. 55 shows a wearable device wherein the energy level of incoming message notifications depends on the configuration of the wearer's fingers, hand, and/or arm.

FIG. 55 shows an example of a wearable computing device for the wrist and/or arm comprising: attachment member 5501; display member 5502; electromagnetic energy sensor 5503; and speaker 5504. The upper portion of FIG. 55 shows the device receiving a message when a person's hand is in a first configuration and the lower portion of FIG. 55 shows the device receiving a message when the person's hand is in a second configuration. In this example, the energy level, magnitude, and/or intensity with which a message is communicated to the person wearing the device depends on the configuration, movement, and/or gesturing of the person's fingers, hand, and/or arm.

In this example, when the person's finger is retracted, then messages are communicated to the wearer with a low energy level, such as with a quiet audio signal from speaker 5504. When the person's finger is extended, then messages are communicated to the wearer with a high energy level, such as with a loud audio signal from speaker 5504. This enables the wearer to subtly change the energy level of message communication by making finger, hand, and/or arm gestures. In an example, the configuration, movement, and/or gesturing of a person's fingers, hand, and/or arm causes electromagnetic signals from the person's muscles which are detected by electromagnetic energy sensor 5503. In an example, electromagnetic energy sensor 5503 can be an EMG sensor. In an example, the configuration, movement, and/or gesturing of a person's fingers, hand, and/or arm causes electromagnetic signals from the person's nerves which are detected by electromagnetic energy sensor 5503. In an example, electromagnetic energy sensor 5503 can be a neurosensor.

Figure 56:
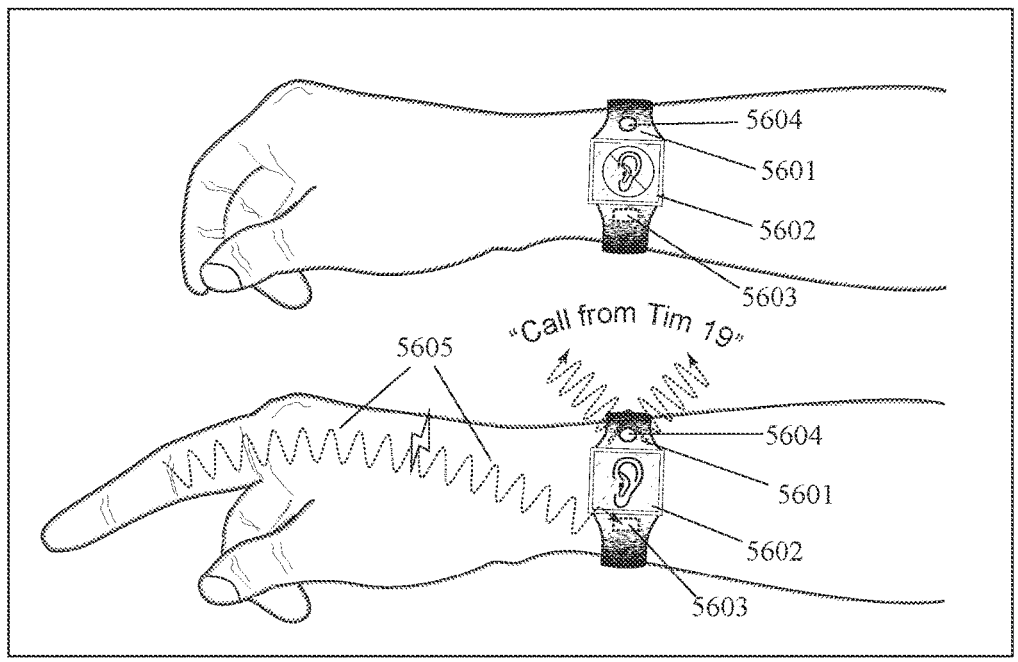
FIG. 56 shows a wearable device wherein silencing of incoming message notifications depends on the configuration of the wearer's fingers, hand, and/or arm.

FIG. 56 shows an example of a wearable computing device for the wrist and/or arm comprising: attachment member 5601; display member 5602; electromagnetic energy sensor 5603; and speaker 5604. The upper portion of FIG. 56 shows the device receiving a message when a person's hand is in a first configuration and the lower portion of FIG. 56 shows the device receiving a message when the person's hand is in a second configuration. In this example, whether or not a message is communicated in real time to the person wearing the device depends on the configuration, movement, and/or gesturing of the person's fingers, hand, and/or arm.

In this example, when the person's finger is retracted, then the device is silenced and messages are not communicated in real time to the wearer. When the person's finger is extended, then messages are communicated in real time to the wearer via an audio signal from speaker 5604. This enables the wearer to subtly change whether they are interrupted by messages or not by making casual finger, hand, and/or arm gestures. It would be wise to exclude potentially-inflammatory hand gestures from the set of valid inputs because people nearby might get the wrong idea. In an example, the configuration, movement, and/or gesturing of a person's fingers, hand, and/or arm causes electromagnetic signals from the person's muscles which are detected by electromagnetic energy sensor 5603. In an example, electromagnetic energy sensor 5603 can be an EMG sensor. In an example, the configuration, movement, and/or gesturing of a person's fingers, hand, and/or arm causes electromagnetic signals from the person's nerves which are detected by electromagnetic energy sensor 5603. In an example, electromagnetic energy sensor 5603 can be a neurosensor.

Figure 57:
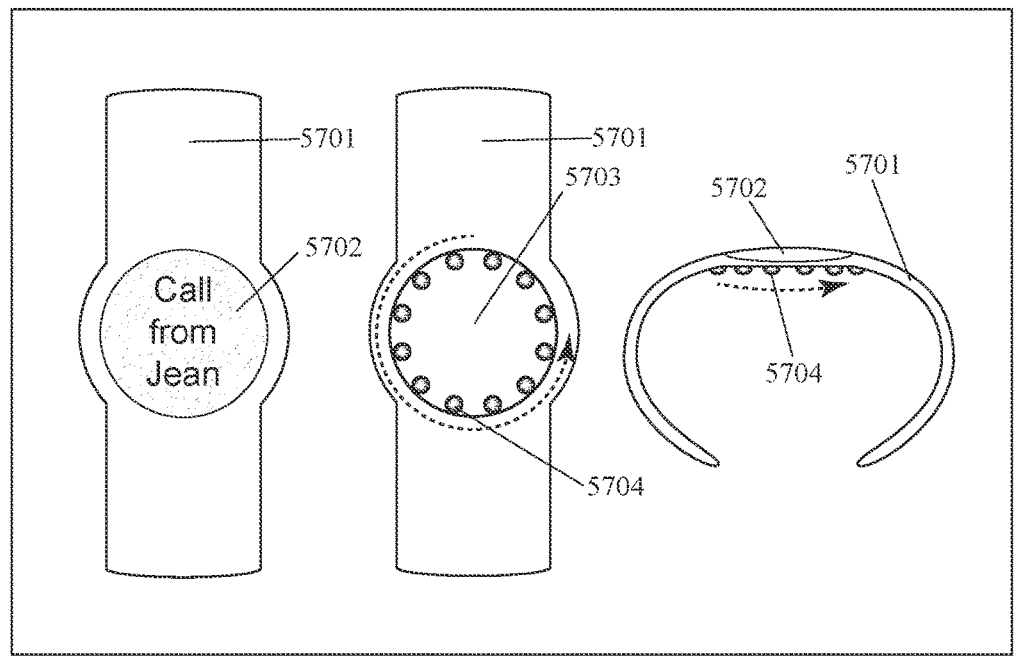
FIG. 57 shows a wearable device with a rotating tactile computer-to-human interface.

FIG. 57 shows an example of a wearable computing device for the wrist and/or arm comprising attachment member 5701, display member 5702, rotating member 5703, and protrusion 5704. The left portion of FIG. 57 shows a top view of this device. The middle portion of FIG. 57 shows a bottom view of this device. The right portion of FIG. 57 shows a side view of this device. In this example, rotating member 5703 is on the bottom of the device which contacts the surface of the person's arm when the device is worn. In this example, there are a plurality of protrusions (including protrusion 5704) on rotating member 5703. These protrusions move in a circular manner when rotating member 5703 is rotated. In this example, circular movement of these protrusions along the skin of the person's arm creates a tactile sensation. In an example, this tactile sensation comprises a computer-to-human interface through which the device can communicate with the person wearing the device.

In an example, a device which creates a tactile sensation by moving rotating member 5703 can be quieter and more subtle than a device which creates a tactile sensation by vibration. In an example, this device can rotate rotating member 5703 when there is an incoming message in order to quietly notify the person wearing the device. In an example, this device can automatically rotate rotating member 5703 in order to prompt the person to do something. In an example, rotation of rotating member 5703 can serve as a quiet alarm.

In this example, there are twelve protrusions, including 5704, on rotating member 5703. In another example, there can be a lesser number of protrusions or even just one protrusion on rotating member 5703. In this example, the protrusions have a fixed depth and positions on rotating member 5703. In an example, the depth or position of one or more protrusions on rotating member 5703 can be changed in order to change the magnitude of the tactile sensation. In an example, the speed at which rotating member 5703 is rotated can be changed in order to change the magnitude of the tactile sensation. In various examples, one or more parameters of the rotation of rotating member 5703 and/or the position of protrusions including 5704 can be modified based on one or more factors selected from the group consisting of: source of an incoming message; urgency an incoming message; content of an incoming message; amount of movement by the person wearing the device; classification of activity of the person wearing the device; geographic location; time of day; pressure of the device on the person's skin; and duration of rotation before the person wearing the device responds.

In various examples, parameters of the tactile sensation which is created by this device can be adjusted based on information from one or more wearable sensors selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

Figure 58:
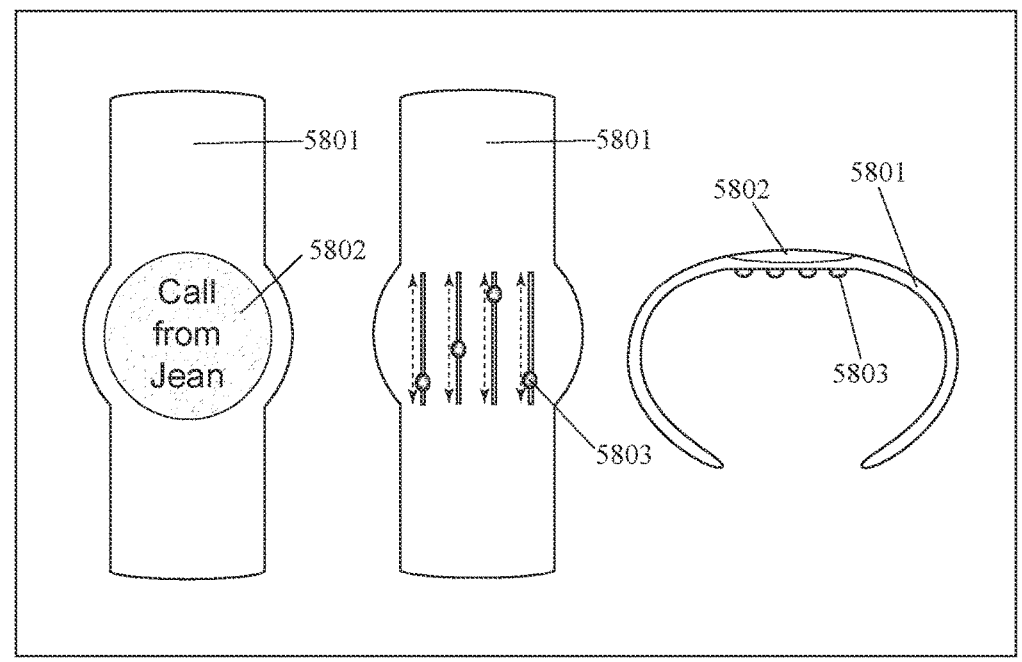
FIG. 58 shows a wearable device with a linearly-moving tactile computer-to-human interface.

FIG. 58 shows an example of a wearable computing device for the wrist and/or arm comprising attachment member 5801, display member 5802, and a plurality of linearly-moving protrusions (including 5803). The left portion of FIG. 58 shows a top view of this device. The middle portion of FIG. 58 shows a bottom view of this device. The right portion of FIG. 58 shows a side view of this device. In this example, the plurality of linearly-moving protrusions (including 5803) are on the bottom of the device which contacts the surface of the person's arm when the device is worn. In this example, back-and-forth linear movement of the plurality of linearly-moving protrusions (including 5803) along the skin of the person's arm creates a tactile sensation. In an example, this tactile sensation comprises a computer-to-human interface through which the device can communicate with the person wearing the device.

In an example, a device which creates a tactile sensation by linearly-moving protrusions can be quieter and more subtle than a device which creates a tactile sensation by vibration. In an example, this device can move linearly-moving protrusions (including 5803) when there is an incoming message. In an example, this device can automatically move linearly-moving protrusions (including 5803) in order to prompt the person to do something. In an example, movement of linearly-moving protrusions can serve as a quiet alarm.

In this example, there are four linearly-moving protrusions (including 5803). In another example, there can be a lesser number of protrusions or even just one. In this example, these protrusions have a fixed depth. In an example, the depth, speed, number, and/or configuration of linearly-moving protrusions being moved can be changed in order to change the magnitude of the tactile sensation and/or convey information about the source and/or content of an incoming message. In various examples, the depth, speed, number, and/or configuration of linearly-moving protrusions being moved can be based on one or more factors selected from the group consisting of: source of an incoming message; urgency an incoming message; content of an incoming message; amount of movement by the person wearing the device; classification of activity of the person wearing the device; geographic location; time of day; pressure of the device on the person's skin; and duration of protrusion movement before the person wearing the device responds.

In various examples, the parameters of the tactile sensation which is created by this device can be adjusted based on information from one or more wearable sensors selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

Figure 59:
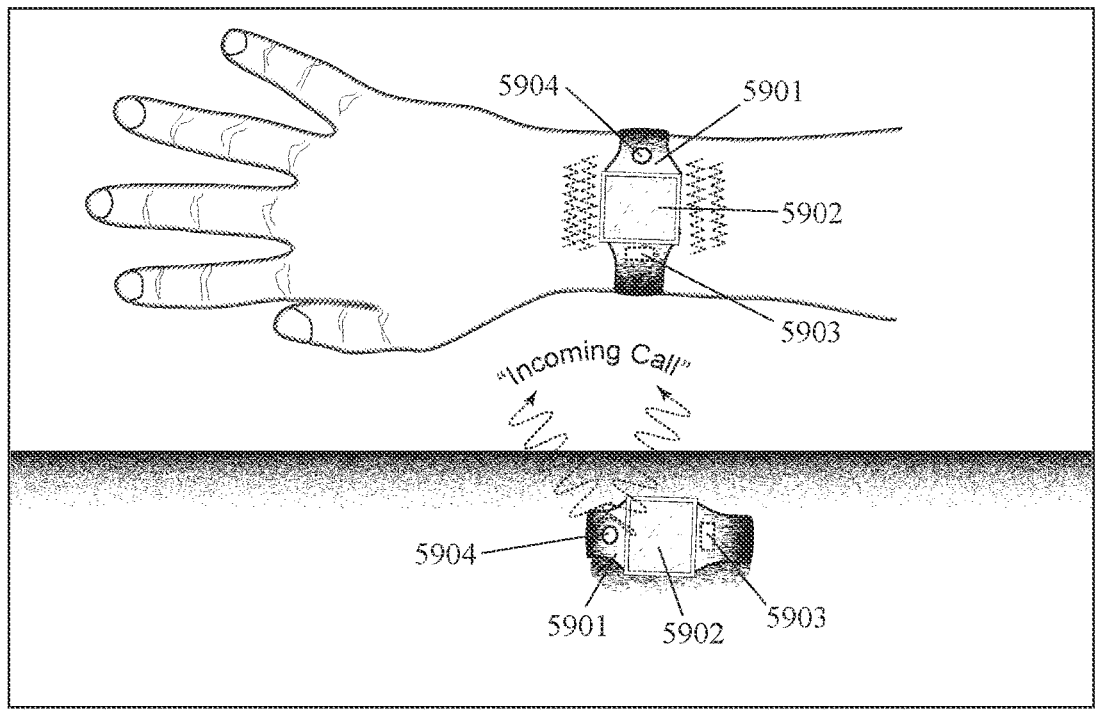
FIG. 59 shows a wearable device wherein the mode for incoming message notifications depends on whether the device is being worn.

FIG. 59 shows an example of a wearable computing device for the wrist and/or arm comprising attachment member 5901, display member 5902, sensor 5903, and speaker 5904. In an example, this device can further comprise a vibrating member. The upper portion of FIG. 59 shows this device functioning when it is worn by a person. The lower portion of FIG. 59 shows this device functioning when it is not worn by a person. In an example, sensor 5903 detects whether the device is being worn by a person or not.

In various examples, sensor 5903 can be selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

In this example, the notification mode for incoming messages depends on whether the device is worn by a person or not. In this example, as shown in the upper portion of FIG. 59, when there is an incoming message and the device is worn by a person, then the device provides notification of the incoming message by vibrating. Since the device is worn, the vibration is felt. However, as shown in the lower portion of FIG. 59, when there is an incoming message and the device is not worn by a person, then the device provides notification of the incoming message by an audio signal via speaker 5904. Since the device is not being worn, a vibration notification might have been missed, but the audio signal is more likely to be heard if the person is nearby. In an alternative example, notification when the device is worn can be visual notification.

Figure 60:
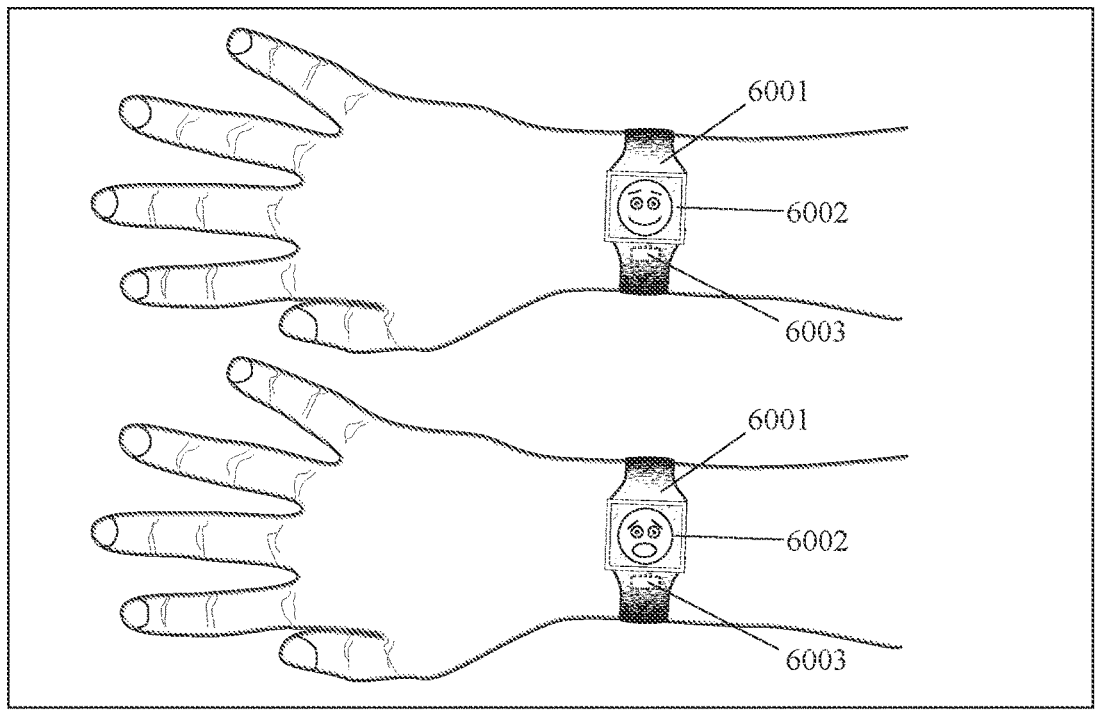
FIG. 60 shows a wearable device with a face-expression display for message notifications.

FIG. 60 shows an example of a wearable computing device for the wrist and/or arm comprising: attachment member 6001; face-configuration display member 6002; and data control unit 6003. The upper portion of FIG. 60 shows the device with a first configuration of face-configuration display member 6002. In this example, this first configuration is a smiling face with centrally-uptilted eye-brows. The lower portion of FIG. 60 shows the device with a second configuration of face-configuration display member 6002. In this example, this second configuration is an open-mouthed face with centrally-uptilted eye-brows. In various examples, the configuration of face-configuration display member 6002 can depend on one or more factors selected from the group consisting of: identity of the source of an incoming message; status or mood of a person sending an incoming message; urgency of an incoming message; content of an incoming message; and tone or style of an incoming message.

In various examples, the status or mood of a person sending an incoming message can be based on one or more sensors worn by that person which are selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electroencephalogram (EEG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

Figure 61:
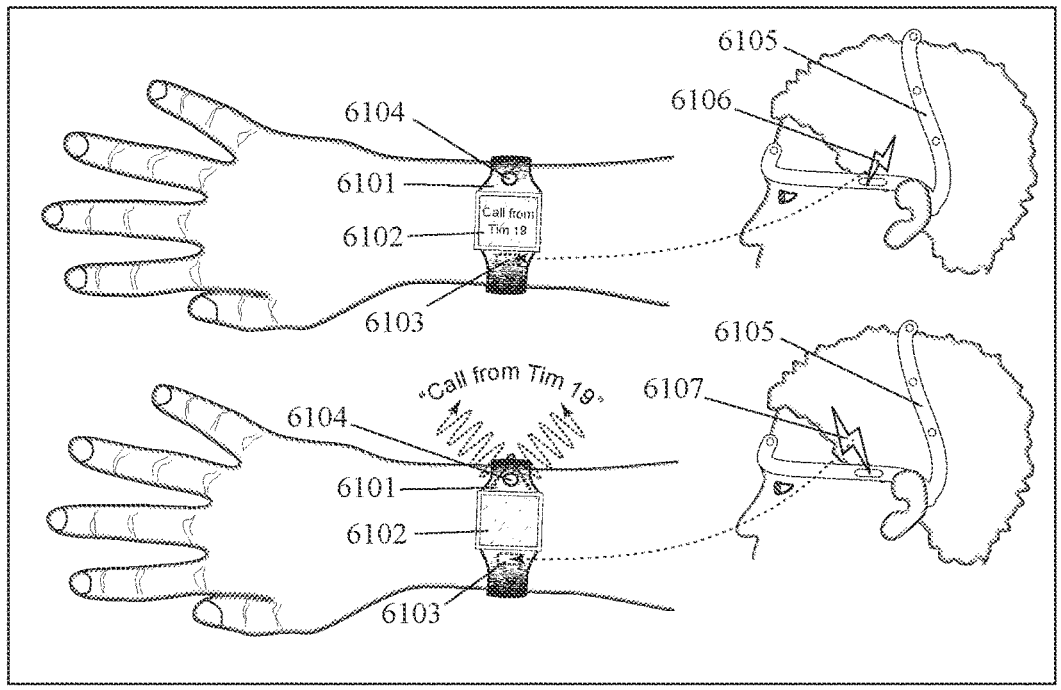
FIG. 61 shows a wearable device wherein the mode for incoming message notifications depends on electromagnetic brain activity.

FIG. 61 shows an example of a wearable computing system comprising: attachment member 6101; display member 6102; data control unit 6103; speaker 6104; and wearable electromagnetic brain activity monitor 6105. The upper portion of FIG. 61 shows how the system responds when it receives an incoming message at a time when wearable electromagnetic brain activity monitor 6105 is detecting a first pattern of electromagnetic brain activity. In this first situation, the system provides notification of the incoming message in a first mode. In this example, this first mode is visual notification via display member 6102. The lower portion of FIG. 61 shows how the system responds when it receives an incoming message at a time when wearable electromagnetic brain activity monitor 6105 is detecting a second pattern of electromagnetic brain activity. In this second situation, the system provides notification of the incoming message in a second mode. In this example, this second mode is audio notification via speaker 6104. A system which changes its notification mode based on a person's electromagnetic brain activity can be useful.

In an example, the notification mode of this device can depend on detection of a specific pattern and/or change in electromagnetic brain activity. In an example, a pattern and/or change in electromagnetic brain activity can be a one-time pattern. In another example, a pattern of electromagnetic brain activity can repeat over time in a rhythmic manner. In an example, a pattern of electromagnetic brain activity can comprise frequency of repetition, frequency band or range of repetition, recurring amplitude, wave phase, and/or waveform. In an example repeating patterns and/or waveforms can be analyzed using Fourier Transform methods.

In various examples, this system can communicate with one or more other devices selected from the group consisting of: handheld electronic device; laptop or desktop computer; other wearable device; array of wearable sensors; communication tower; satellite; home appliance or control system; internet server; and implantable medical device. In various examples, this system can further comprise one or more components selected from the group consisting of: button, knob, dial, or keys; coherent light image projector; data processing member; data receiving member; data transmitting member; electromagnetic energy emitter; energy transducing and/or harvesting member; eye-gaze-tracking interface; gesture-recognition interface; infrared light projector; laser; LED or other light-emitting member; MEMS actuator; MEMS sensor; myostimulator; neurostimulator; power source; speech-recognition interface; tactile-sensation-creating member; and virtually-projected user interface.

Figure 62:
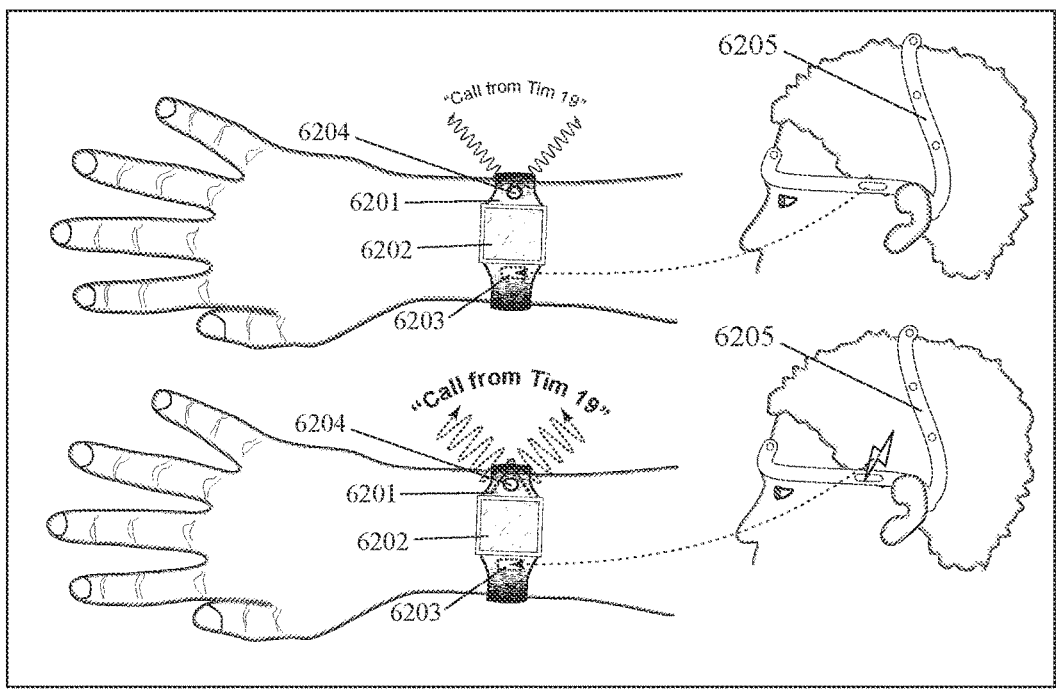
FIG. 62 shows a wearable device wherein the energy level of incoming message notifications depends on electromagnetic brain activity.

FIG. 62 shows an example of a wearable computing system comprising: attachment member 6201; display member 6202; data control unit 6203; speaker 6204; and wearable electromagnetic brain activity monitor 6205. The upper portion of FIG. 62 shows how the system responds when it receives an incoming message at a time when wearable electromagnetic brain activity monitor 6205 is detecting a first pattern of electromagnetic brain activity. In this first situation, the system provides notification of the incoming message at a lower energy level, magnitude, or intensity. In this example, this comprises a quiet audio notification via speaker 6204. The lower portion of FIG. 62 shows how the system responds when it receives an incoming message at a time when wearable electromagnetic brain activity monitor 6205 is detecting a second pattern of electromagnetic brain activity. In this second situation, the system provides notification of the incoming message at a higher energy level, magnitude, or intensity. In this example, this comprises a loud audio notification via speaker 6204. A system which changes its notification magnitude based on a person's electromagnetic brain activity can be useful.

In an example, notification magnitude can depend on detection of a specific pattern and/or change in electromagnetic brain activity. In an example, a pattern and/or change in electromagnetic brain activity can be a one-time pattern. In another example, a pattern of electromagnetic brain activity can repeat over time in a rhythmic manner. In an example, a pattern of electromagnetic brain activity can comprise frequency of repetition, frequency band or range of repetition, recurring amplitude, wave phase, and/or waveform. In an example repeating patterns and/or waveforms can be analyzed using Fourier Transform methods.

In various examples, this system can communicate with one or more other devices selected from the group consisting of: handheld electronic device; laptop or desktop computer; other wearable device; array of wearable sensors; communication tower; satellite; home appliance or control system; internet server; and implantable medical device. In various examples, this system can further comprise one or more components selected from the group consisting of: button, knob, dial, or keys; coherent light image projector; data processing member; data receiving member; data transmitting member; electromagnetic energy emitter; energy transducing and/or harvesting member; eye-gaze-tracking interface; gesture-recognition interface; infrared light projector; laser; LED or other light-emitting member; MEMS actuator; MEMS sensor; myostimulator; neurostimulator; power source; speech-recognition interface; tactile-sensation-creating member; and virtually-projected user interface.

Figure 63:
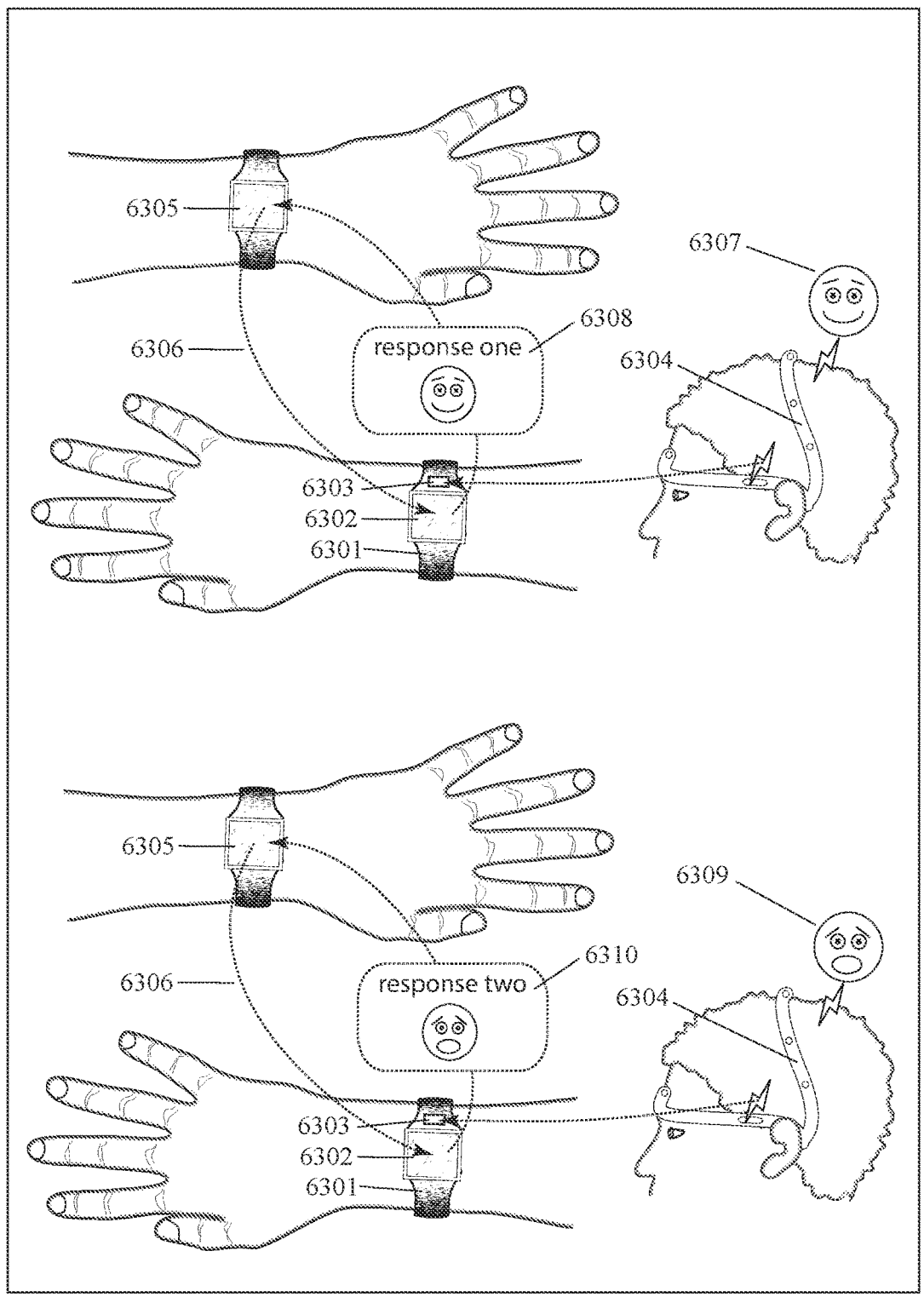
FIG. 63 shows a wearable system wherein an automatic response to incoming messages depends on electromagnetic brain activity.

FIG. 63 shows an example of a wearable computing system comprising: attachment member 6301; display member 6302; data control unit 6303; and wearable electromagnetic brain activity monitor 6304. In this example, this system sends different automatic face-configuration responses and/or messages to other people, depending on the pattern of electromagnetic brain activity which is detected by wearable electromagnetic brain activity monitor 6304.

The upper portion of FIG. 63 shows a first situation in which a message 6306 being sent from device 6305 worn by another person triggers response one ("smiling face") 6308 based on the pattern 6307 of electromagnetic brain activity which is detected by wearable electromagnetic brain activity monitor 6304. Information concerning this first pattern 6307 of electromagnetic brain activity is wirelessly transmitted from wearable electromagnetic brain activity monitor 6304 to data control unit 6303, which triggers "smiling face" 6308 response to incoming message 6306.

The lower portion of FIG. 63 shows a second situation in which a message 6306 being sent from device 6305 worn by another person triggers response two ("anxious face") 6310 based on the pattern 6309 of electromagnetic brain activity which is detected by wearable electromagnetic brain activity monitor 6304. Information concerning this first pattern 6307 of electromagnetic brain activity is wirelessly transmitted from wearable electromagnetic brain activity monitor 6304 to data control unit 6303, which triggers "anxious face" 6310 response to incoming message 6306.

In an example, a face-configuration response such as 6308 or 6310 can be an automatic response when the person wearing the device does not manually respond to the incoming message in real time. In an example, a face-configuration response such as 6308 or 6310 can be incorporated into a manual response by the person wearing the device. In an example, a specific configuration of facial features and/or expressions in a face-configuration response can reflect a specific pattern of electromagnetic brain activity.

In various examples, a face-configuration response can be based on one or more sensors selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electroencephalogram (EEG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

Figure 64:
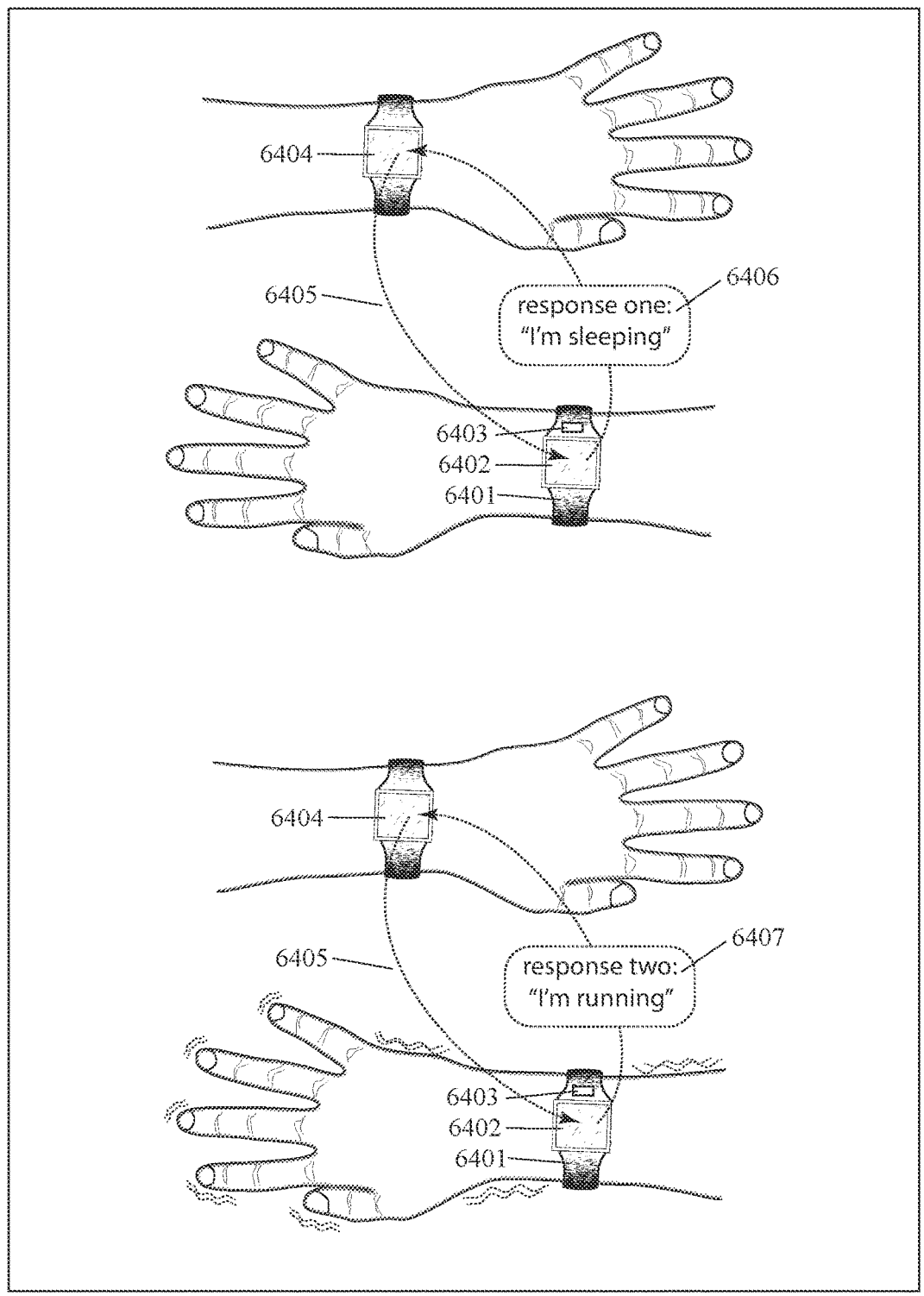
FIG. 64 shows a wearable system wherein an automatic response to incoming messages depends on the wearer's movement.

FIG. 64 shows an example of a wearable computing device for the wrist and/or arm comprising: attachment member 6401; display member 6402; and sensor 6403. In this example, this device sends different responses and/or messages to other people, depending on the pattern of movement which is detected by sensor 6403. The upper portion of FIG. 64 shows a first situation in which a message 6405 being sent from device 6404 worn by another person triggers response one (e.g. "I'm sleeping") 6406. The lower portion of FIG. 64 shows a second situation in which a message 6405 being sent from device 6404 worn by another person triggers response two (e.g. "I'm running") 6407. In an example, a response such as 6406 or 6407 can be an automatic response when the person wearing the device does not manually respond to the incoming message in real time. In an example, a response such as 6408 or 6410 can be incorporated into a manual response by the person wearing the device.

In various examples, a response can be based on one or more sensors selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electroencephalogram (EEG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

Figure 65:
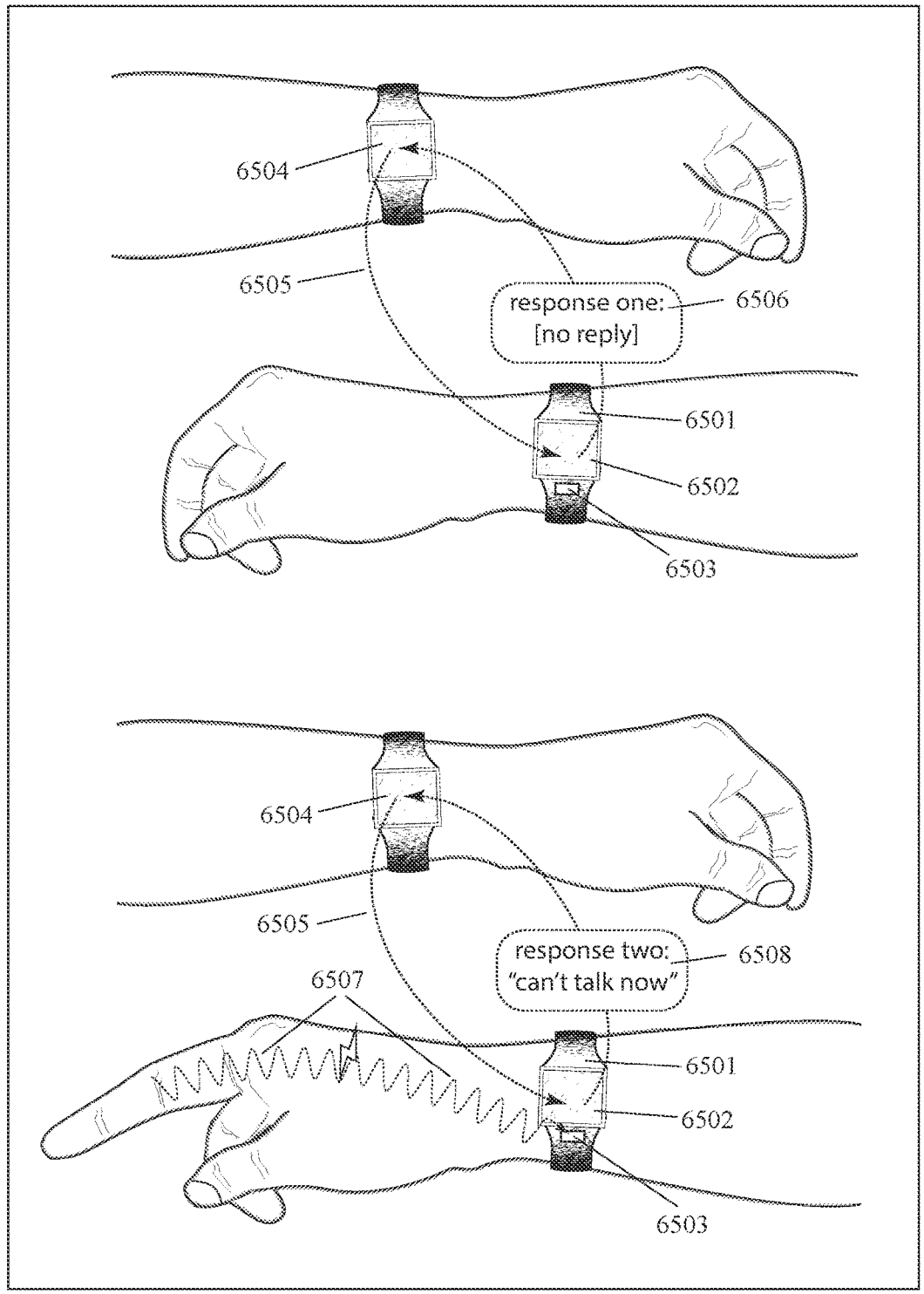
FIG. 65 shows a wearable system wherein a (standard) response to an incoming message depends on the configuration or movement of fingers, hand, and/or arm.

FIG. 65 shows an example of a wearable computing device for the wrist and/or arm comprising: attachment member 6501, display member 6502, and electromagnetic energy sensor 6503. This device sends a different response to a message depending on a gesture, configuration, and/or movement of the fingers, hand, and/or arm of the person wearing the device. A gesture, configuration, and/or movement of the fingers, hand, and/or arm creates a pattern of electromagnetic energy 6507 which is detected by electromagnetic energy sensor 6503. In an example, electromagnetic energy sensor 6503 detects electromagnetic energy 6507 from the person's muscles. In an example, electromagnetic energy sensor 6503 can be an EMG sensor. In an example, electromagnetic energy sensor 6503 detects electromagnetic energy from the person's nerves. In an example, electromagnetic energy sensor 6503 can be a neurosensor.

The upper half of FIG. 65 shows a first case in which the person wearing the device receives message 6505 from a second person wearing a second device 6504. In this example, electromagnetic energy sensor 6503 detects that the person's fingers are retracted and triggers the device to give a first type of response ("no reply") 6506 to message 6505. The lower half of FIG. 65 shows a second case in which the person wearing the device receives message 6505 from a second person wearing a second device 6504. In this example, electromagnetic energy sensor 6503 detects that one of the person's fingers is extended and triggers the device to give a second type of response ("can't talk now") 6506 to message 6505. In various examples, various selected gestures, configurations, and/or movements can trigger various selected types of responses. In an example, this device can comprise a gesture-based human-to-computer interface for multiple purposes.

Figure 66:
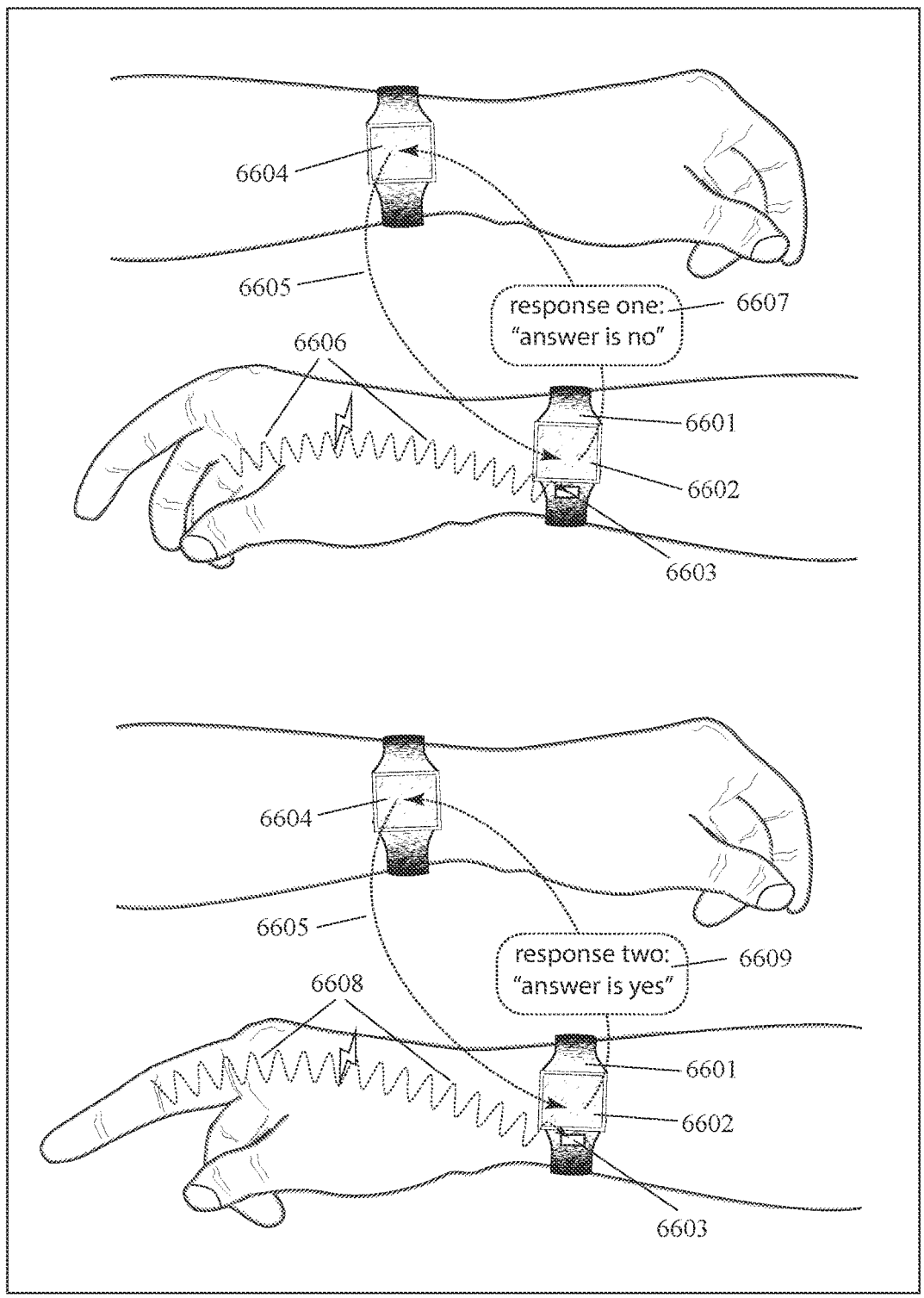
FIG. 66 shows a wearable system wherein a (selected) response to an incoming message depends on the configuration or movement of fingers, hand, and/or arm.

FIG. 66 shows an example of a wearable computing device for the wrist and/or arm comprising: attachment member 6601, display member 6602, and electromagnetic energy sensor 6603. This device sends a different response to a message depending on a gesture, configuration, and/or movement of the fingers, hand, and/or arm of the person wearing the device. A gesture, configuration, and/or movement of the fingers, hand, and/or arm creates a pattern of electromagnetic energy 6607 which is detected by electromagnetic energy sensor 6603. In an example, electromagnetic energy sensor 6603 detects electromagnetic energy 6607 from the person's muscles. In an example, electromagnetic energy sensor 6603 can be an EMG sensor. In an example, electromagnetic energy sensor 6603 detects electromagnetic energy from the person's nerves. In an example, electromagnetic energy sensor 6603 can be a neurosensor.

The upper half of FIG. 66 shows a first case in which the person wearing the device receives message 6605 from a second person wearing a second device 6604. In this example, electromagnetic energy sensor 6603 detects that the person's fingers are in a first configuration and triggers the device to give a first type of response ("answer is no") 6606 to message 6605. The lower half of FIG. 66 shows a second case in which the person wearing the device receives message 6605 from a second person wearing a second device 6604. In this example, electromagnetic energy sensor 6603 detects that the person's fingers are in a second configuration and triggers the device to give a second type of response ("answer is yes") 6606 to message 6605. In various examples, various selected gestures, configurations, and/or movements can trigger various selected types of responses. In an example, this device can comprise a gesture-based human-to-computer interface for multiple purposes.

Figure 67:
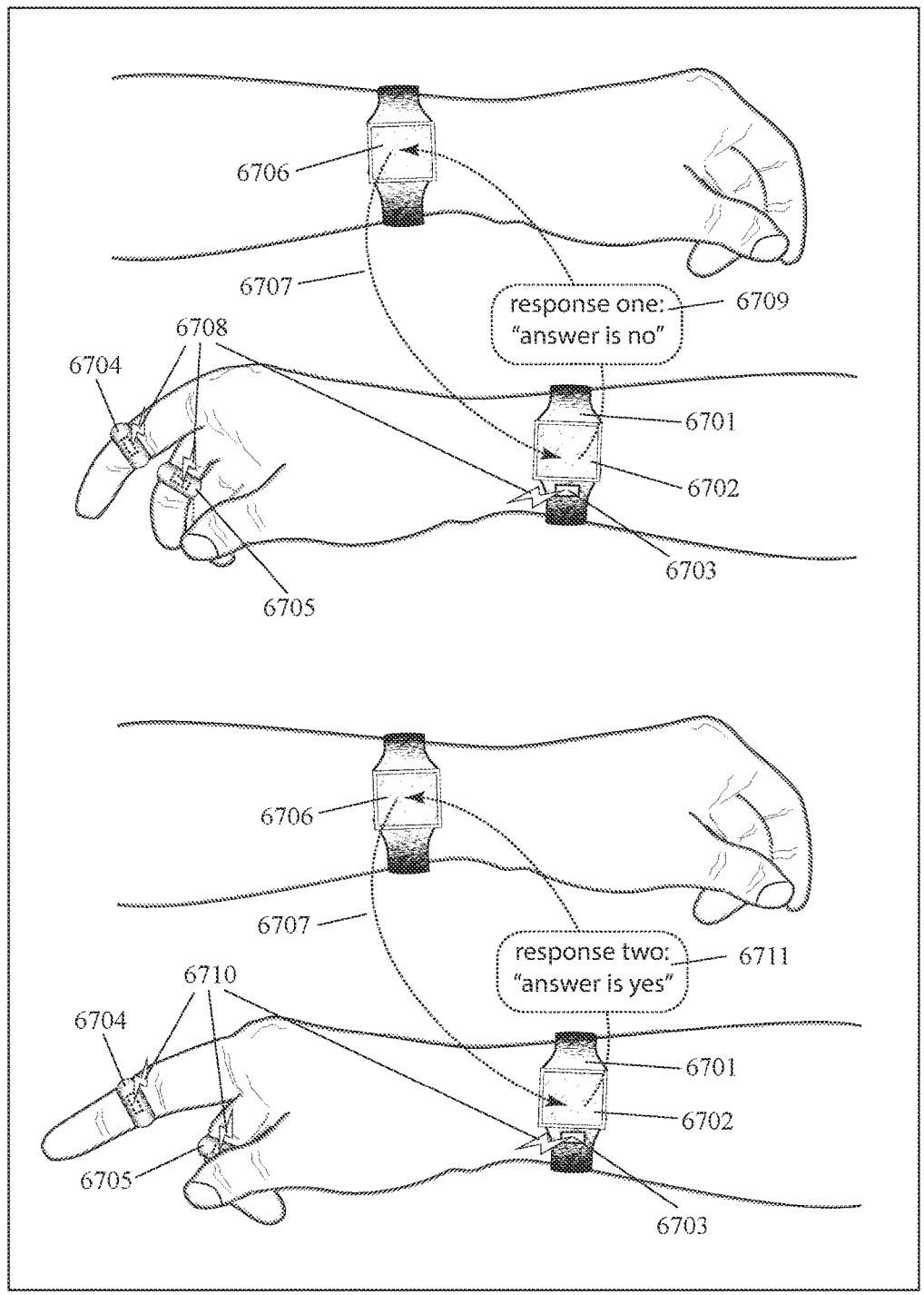
FIG. 67 shows a wearable system wherein a (selected) response to an incoming message depends on the configuration or movement of finger rings.

FIG. 67 shows an example of a wearable computing system comprising: attachment member 6701, display member 6702, data control unit 6703; and plurality of finger rings 6704 and 6705. In an example, finger rings 6704 and 6705 further comprise motion sensors and data transmitters. This device sends a different response to a message depending on a gesture, configuration, and/or movement of the fingers, hand, and/or arm of the person wearing the system. In this example, a gesture, configuration, and/or movement of the fingers, hand, and/or arm is detected by finger rings 6704 and 6705. In this example, a gesture, configuration, and/or movement of the fingers, hand, and/or arm is detected by motion sensors within finger rings 6704 and 6705 and transmitted 6708 to data control unit 6703.

The upper half of FIG. 67 shows a first case in which the person wearing the system receives message 6705 from a second person wearing device 6704. In this example, motion sensors in finger rings 6704 and 6705 detect that the person's fingers are in a first configuration and triggers the system to give a first type of response ("answer is no") 6706 to message 6705. The lower half of FIG. 67 shows a second case in which the person wearing the system receives message 6705 from a second person wearing device 6704. In this example, motion sensors in finger rings 6704 and 6705 detect that the person's fingers are in a second configuration and triggers the system to give a second type of response ("answer is yes") 6706 to message 6705. In various examples, various selected gestures, configurations, and/or movements can trigger various selected types of responses. In an example, this system can comprise a gesture-based human-to-computer interface for multiple purposes.

Figure 68:
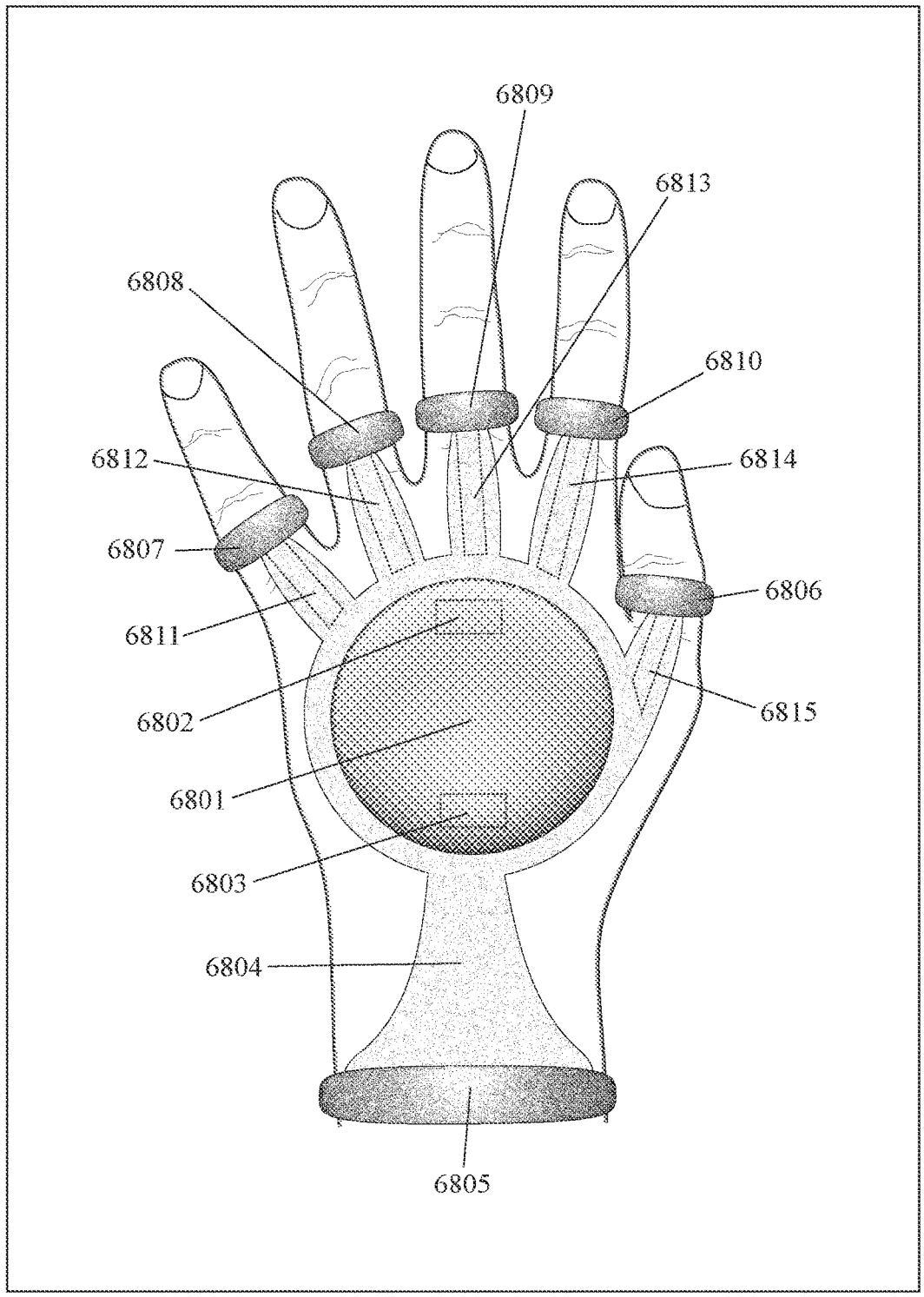
FIG. 68 shows a first wearable device with a central hand display and multiple finger bending sensors.

FIG. 68 shows an example of a wearable computing device for the hand comprising: display member 6801; sensor 6802; data control unit 6803; housing 6804; wrist attachment member 6805; finger and/or thumb attachment members 6806, 6807, 6808, 6809, and 6810; and bend sensors 6811, 6812, 6813, 6814, and 6815. In an example, display member 6801 can comprise a computer display screen. In an example, this can be an interactive touch screen. In various examples, wrist attachment member 6805 can comprise a strap, band, bangle, loop, buckle, ring, or bracelet. In various examples, finger and/or thumb attachment members 6806, 6807, 6808, 6809, and 6810 can comprise rings, straps, bands, or loops.

In an example, information collected by bend sensors 6811, 6812, 6813, 6814, and 6815 can be used to detect gestures, configurations, and/or patterns of movement of the person's fingers and/or hand. In an example, the device can further comprise a plurality of motion sensors whose outputs are used to detect gestures, configurations, and/or patterns of movement of the person's fingers and/or hand. In an example, information from a combination of bend sensors (6811, 6812, 6813, 6814, and 6815) and motion sensors can be collectively used to detect gestures, configurations, and/or patterns of movement of the person's fingers and/or hand. In an example, the device can further comprise a plurality of electromagnetic energy sensors whose outputs are used to detect gestures, configurations, and/or patterns of movement of the person's fingers and/or hand. In an example, information from a combination of bend sensors (6811, 6812, 6813, 6814, and 6815) and electromagnetic energy sensors can be collectively used to detect gestures, configurations, and/or patterns of movement of the person's fingers and/or hand.

In various examples, bend sensors 6811, 6812, 6813, 6814, and 6815 can be selected from the group consisting of: electrogoniometer, fiber optic bend sensor, microcantilever sensor, other optical sensor, piezoelectric sensor, piezomechanical sensor, pressure sensor, strain gauge, and stretch sensor. In this example, bend sensors 6811, 6812, 6813, 6814, and 6815 each span one joint of a finger and/or thumb. In another example, bend sensors 6811, 6812, 6813, 6814, and 6815 can each span multiple finger and/or thumb joints. In this example, there are bend sensors on all four fingers and the thumb. In another example, there can be bend sensors on a subset of the four fingers and thumb. In another example, there can be multiple bend sensors per finger or thumb. In this example, bend sensors are on the dorsal surfaces of the fingers and thumb. In an example, bend sensors can be located on other surfaces of the fingers and/or thumb. In an example, bend sensors can span the circumferences of the fingers and/or thumb.

In various examples, one or more sensors which comprise the device, including sensor 6802, can be selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

In an example, data control unit 6803 can further comprise one or more components selected from the group consisting of: data processing member, data transmitting member, data receiving member, power source, and energy harvesting member. In various examples, an energy harvesting member can harvest, transduce, or generate electrical energy from kinetic energy, thermal energy, biochemical energy, ambient light energy, and/or ambient electromagnetic energy. In various examples, this device can communicate with one or more other devices selected from the group consisting of: handheld electronic device; laptop or desktop computer; other wearable device; array of wearable sensors; communication tower; satellite; home appliance or control system; internet server; and implantable medical device. In various examples, this device can further comprise one or more components selected from the group consisting of: button, knob, dial, or keys; coherent light image projector; EEG-recognition interface; electromagnetic energy emitter; eye-gaze-tracking interface; infrared light projector; laser; LED or other light-emitting member; MEMS actuator; MEMS sensor; myostimulator; neurostimulator; speaker or other sound-emitting member; speech-recognition interface; tactile-sensation-creating member; and virtually-projected user interface.

Figure 69:
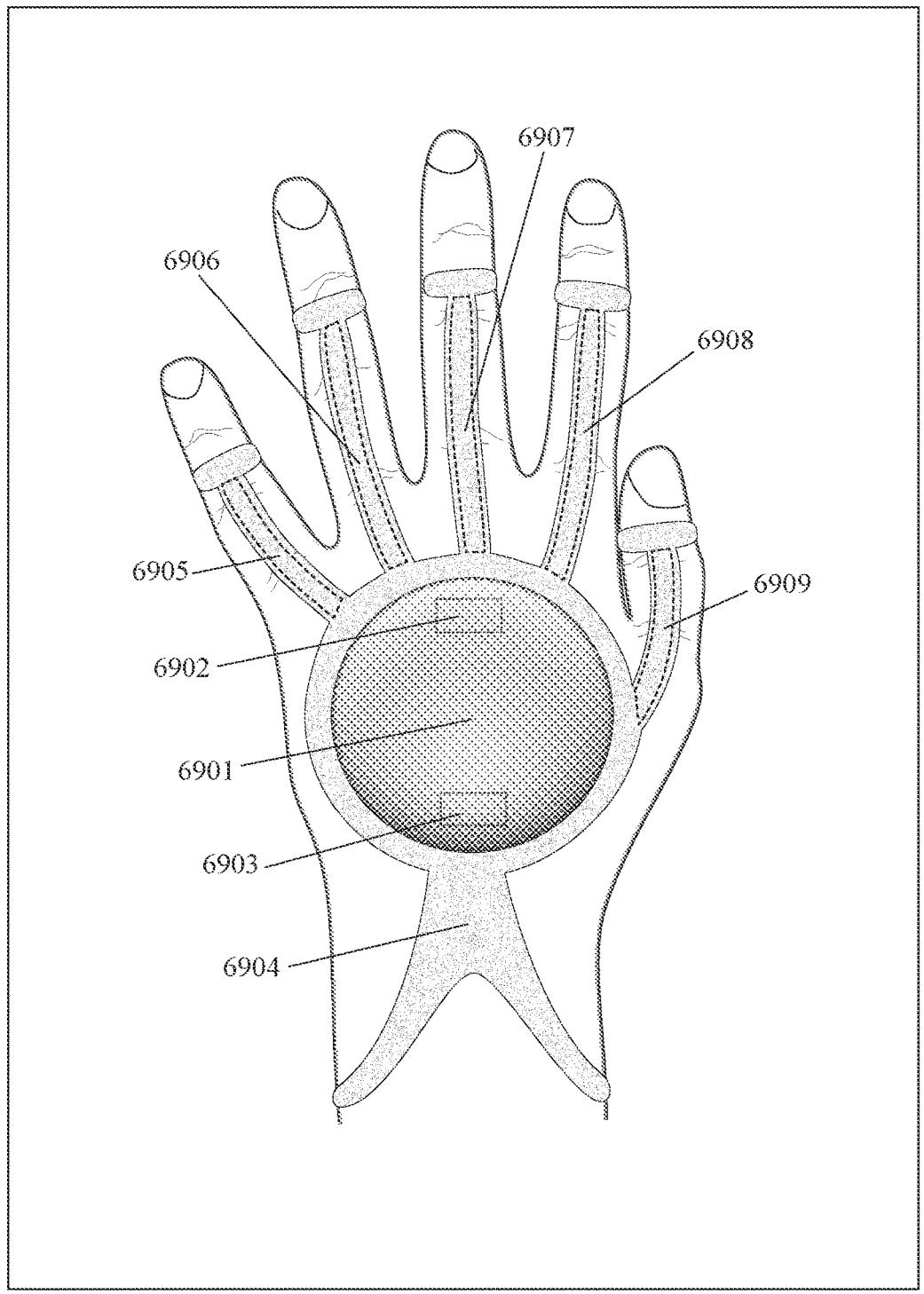
FIG. 69 shows a second wearable device with a central hand display and multiple finger bending sensors.

FIG. 69 shows an example of a wearable computing device for the hand comprising: display member 6901; sensor 6902; data control unit 6903; attachment member 6904; and bend sensors 6905, 6906, 6907, 6908, and 6909. In this example, display member 6901 comprises a computer display screen. In an example, this can be an interactive touch screen.

In this example, attachment member 6904 spans the dorsal surface of a person's hand from sections of one or more of their fingers to their wrist and/or forearm. In this example, the distal portions of attachment member 6904 encircle the circumference of one or more fingers and/or thumb and the proximal portion of attachment member 6904 holds on to the wrist and/or forearm. In an example, the portion of attachment member 6904 which holds on to the wrist and/or forearm can further comprise one or more clasps, clips, buckles, or hook-and-eye mechanisms by which it is held on the wrist and/or forearm. In an example, the portion of attachment member 6904 which holds on to the wrist and/or forearm can stretch or expand around the hand in order to be slipped onto the wrist and/or forearm.

In an example, information collected by bend sensors 6905, 6906, 6907, 6908, and 6909 can be used to detect gestures, configurations, and/or patterns of movement of the person's fingers and/or hand. In an example, the device can further comprise a plurality of motion sensors whose outputs are used to detect gestures, configurations, and/or patterns of movement of the person's fingers and/or hand. In an example, information from a combination of bend sensors (6905, 6906, 6907, 6908, and 6909) and motion sensors can be collectively used to detect gestures, configurations, and/or patterns of movement of the person's fingers and/or hand. In an example, the device can further comprise a plurality of electromagnetic energy sensors whose outputs are used to detect gestures, configurations, and/or patterns of movement of the person's fingers and/or hand. In an example, information from a combination of bend sensors (6905, 6906, 6907, 6908, and 6909) and electromagnetic energy sensors can be collectively used to detect gestures, configurations, and/or patterns of movement of the person's fingers and/or hand.

In various examples, bend sensors 6905, 6906, 6907, 6908, and 6909 can be selected from the group consisting of: electrogoniometer, fiber optic bend sensor, microcantilever sensor, other optical sensor, piezoelectric sensor, piezomechanical sensor, pressure sensor, strain gauge, and stretch sensor. In this example, bend sensors 6905, 6906, 6907, 6908, and 6909 each span one joint of a finger and/or thumb. In another example, bend sensors 6905, 6906, 6907, 6908, and 6909 can each span multiple finger and/or thumb joints. In this example, there are bend sensors on all four fingers and the thumb. In another example, there can be bend sensors on a subset of the four fingers and thumb. In another example, there can be multiple bend sensors per finger or thumb. In this example, bend sensors are on the dorsal surfaces of the fingers and thumb. In an example, bend sensors can be located on other surfaces of the fingers and/or thumb. In an example, bend sensors can span the circumferences of the fingers and/or thumb.

In various examples, one or more sensors which comprise the device, including sensor 6902, can be selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

In an example, data control unit 6903 can further comprise one or more components selected from the group consisting of: data processing member, data transmitting member, data receiving member, power source, and energy harvesting member. In various examples, an energy harvesting member can harvest, transduce, or generate electrical energy from kinetic energy, thermal energy, biochemical energy, ambient light energy, and/or ambient electromagnetic energy. In various examples, this device can communicate with one or more other devices selected from the group consisting of: handheld electronic device; laptop or desktop computer; other wearable device; array of wearable sensors; communication tower; satellite; home appliance or control system; internet server; and implantable medical device. In various examples, this device can further comprise one or more components selected from the group consisting of: button, knob, dial, or keys; coherent light image projector; EEG-recognition interface; electromagnetic energy emitter; eye-gaze-tracking interface; infrared light projector; laser; LED or other light-emitting member; MEMS actuator; MEMS sensor; myostimulator; neurostimulator; speaker or other sound-emitting member; speech-recognition interface; tactile-sensation-creating member; and virtually-projected user interface.

Figure 70:
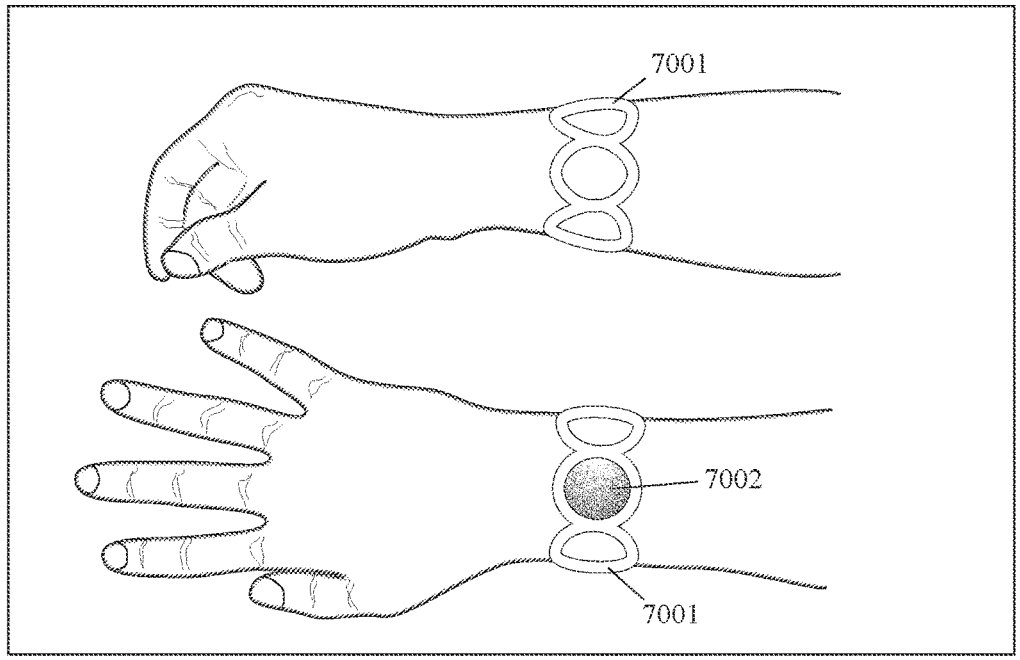
FIG. 70 shows a wearable device with a display and at least four arcuate members which span the circumference of the wrist and/or arm.

FIG. 70 shows an example of a wearable computing device for the wrist and/or arm comprising attachment member 7001 and display member 7002. The upper portion of FIG. 70 shows this device from a side (lateral arm surface) perspective as the device is worn on a person's wrist and/or arm. The lower portion of FIG. 70 shows this device from a top-down (dorsal arm surface) perspective as the device is worn on a person's wrist and/or arm. A person's wrist, hand, finger, forearm, and upper arm are each considered to be part of their arm.

In this example, attachment member 7001 further comprises four or more connected arcuate members. In an example, attachment member 7001 further comprises six connected arcuate members or eight connected arcuate members. In an example, attachment member 7001 further comprises four or more connected arcuate members which are configured to collectively span the circumference of a person's wrist and/or arm. In an example, the four or more arcuate members are tangentially connected. In an example, attachment member 7001 further comprises a chain or series of four or more tangentially-connected arcuate members which are configured to collectively span the circumference of a person's wrist and/or arm.

In an example, each of the four or more arcuate members has an arcuate cross-sectional shape in a plane which is substantially parallel to (or tangentially parallel to) the proximate surface of a person's wrist and/or arm. In an example, this arcuate cross-sectional shape can be substantially circular. In an example, this arcuate cross-sectional shape can be selected from the group consisting of circular, elliptical, other conic section, oval, oblong, teardrop shape, egg shape, heart shape, kidney shape, hexagon with rounded vertexes, and octagon with rounded vertexes. In an example, this arcuate cross-sectional shape can be—the shape formed by the intersection of first and second sinusoidal curves, wherein these curves share a common central longitudinal axis and wherein the second sinusoidal curve is the first sinusoidal curve as reflected around this common axis. In an example, arcuate members can each have the same shape and size. In an example, arcuate members can have different shapes or sizes.

In an example, one of these arcuate members encompasses display member 7002. In an example, one of these arcuate members holds display member 7002. In an example, display member 7002 can be encompassed by an arcuate member that is substantially on the dorsal surface, ventral surface, or a lateral surface of the person's arm. In an example, display member 7002 comprises a flat computer display screen. In an example, display member 7002 comprises a curved computer display screen.

In an example, attachment member 7001 further comprises one or more clasps, clips, snaps, buckles, hook-and-eye mechanisms, or other attachment mechanisms which enable it to be fastened around the person's wrist and/or arm. In an example, two of the four or more arcuate members can be connected together or disconnected by a clasp, clip, snap, buckle, hook-and-eye mechanism, or other attachment mechanism. In an example, attachment member 7001 can further comprise an expandable or stretchable member which enables attachment member 7001 to slide around the hand and fit onto the wrist and/or arm.

In various examples, this device can further comprise one or more sensors selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

In various examples, this device can communicate with one or more other devices selected from the group consisting of: handheld electronic device; laptop or desktop computer; other wearable device; array of wearable sensors; communication tower; satellite; home appliance or control system; internet server; and implantable medical device. In various examples, this device can further comprise one or more components selected from the group consisting of: button, knob, dial, or keys; coherent light image projector; data processing member; data receiving member; data transmitting member; EEG-recognition interface; electromagnetic energy emitter; energy transducing and/or harvesting member; eye-gaze-tracking interface; gesture-recognition interface; infrared light projector; laser; LED or other light-emitting member; MEMS actuator; MEMS sensor; myostimulator; neurostimulator; power source; speaker or other sound-emitting member; speech-recognition interface; tactile-sensation-creating member; and virtually-projected user interface. In various examples, an energy transducing and/or harvesting member can harvest energy from kinetic energy, thermal energy, biochemical energy, ambient light energy, and/or ambient electromagnetic energy.

Figure 71:
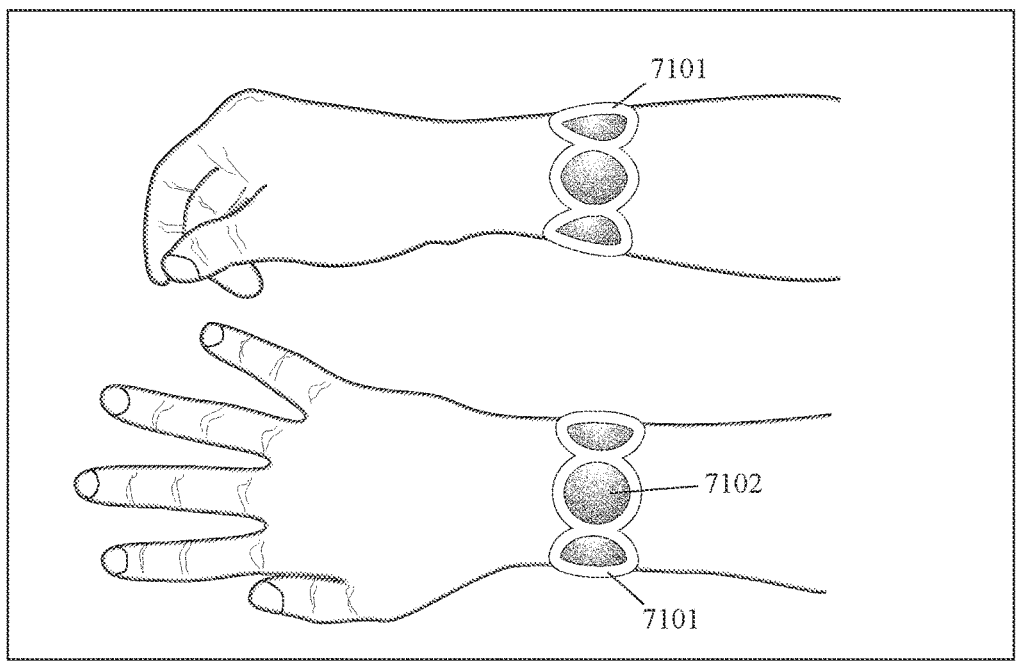
FIG. 71 shows a wearable device with a plurality of displays within at least four arcuate members which span the circumference of the wrist and/or arm.

FIG. 71 shows an example of a wearable computing device for the wrist and/or arm comprising attachment member 7101 and a plurality of display members including 7102. The upper portion of FIG. 71 shows this device from a side (lateral arm surface) perspective as the device is worn on a person's wrist and/or arm. The lower portion of FIG. 71 shows this device from a top-down (dorsal arm surface) perspective as the device is worn on a person's wrist and/or arm. A person's wrist, hand, finger, forearm, and upper arm are each considered to be part of their arm.

In this example, attachment member 7101 further comprises four or more connected arcuate members. In an example, attachment member 7101 further comprises six connected arcuate members or eight connected arcuate members. In an example, attachment member 7101 further comprises four or more connected arcuate members which are configured to collectively span the circumference of a person's wrist and/or arm. In an example, the four or more arcuate members are tangentially connected. In an example, attachment member 7101 further comprises a chain or series of four or more tangentially-connected arcuate members which are configured to collectively span the circumference of a person's wrist and/or arm.

In an example, each of the four or more arcuate members has an arcuate cross-sectional shape in a plane which is substantially parallel to (or tangentially parallel to) the proximate surface of a person's wrist and/or arm. In an example, this arcuate cross-sectional shape can be substantially circular. In an example, this arcuate cross-sectional shape can be selected from the group consisting of: circular, elliptical, other conic section, oval, oblong, teardrop shape, egg shape, heart shape, kidney shape, hexagon with rounded vertexes, and octagon with rounded vertexes. In an example, this arcuate cross-sectional shape can be—the shape formed by the intersection of first and second sinusoidal curves, wherein these curves share a common central longitudinal axis and wherein the second sinusoidal curve is the first sinusoidal curve as reflected around this common axis. In an example, arcuate members can each have the same shape and size. In an example, arcuate members can have different shapes or sizes.

In an example, there can be the same number of display members as arcuate members. In an example, the arcuate members can each encompass and/or hold one of the display members (such as display member 7102). In an example, there can be more arcuate members than display members. In an example, a subset of the arcuate members can each encompass and/or hold one of the display members. In an example, one of the plurality of display members can comprise a flat computer display screen. In an example, one of the plurality of display members can comprise a curved computer display screen. In an example, each of the plurality of display members can display different images and/or virtual content.

In an example, attachment member 7101 further comprises one or more clasps, clips, snaps, buckles, hook-and-eye mechanisms, or other attachment mechanisms which enable it to be fastened around the person's wrist and/or arm. In an example, two of the four or more arcuate members can be connected together or disconnected by a clasp, clip, snap, buckle, hook-and-eye mechanism, or other attachment mechanism. In an example, attachment member 7101 can further comprise an expandable or stretchable member which enables attachment member 7101 to slide around the hand and fit onto the wrist and/or arm.

In various examples, this device can further comprise one or more sensors selected from the group consisting of: accelerometer, biochemical sensor, blood oximetry sensor, blood pressure sensor, camera, chemiresistor, chemoreceptor sensor, chromatography sensor, compass, dual-axial accelerometer, electrocardiogram (ECG) sensor, electrochemical sensor, electrogoniometer, electromagnetic sensor, electromyography (EMG) sensor, electroporation sensor, fluorescence sensor, galvanic skin response (GSR) sensor, glucose sensor, GPS sensor, gyroscope, heart rate sensor, humidity sensor, imaging sensor, inclinometer, inertial sensor, infrared light sensor, light-spectrum-analyzing sensor, magnetometer, MEMS sensor, microcantilever sensor, microphone, motion sensor, multi-axis accelerometer, near-infrared spectroscopy sensor, neurosensor, optoelectronic sensor, pH level sensor, photochemical sensor, piezoelectric sensor, piezomechanical sensor, pressure sensor, single-axis accelerometer, sound sensor, spectral analysis sensor, spectrometry sensor, spectrophotometer sensor, spectroscopic sensor, spectroscopy sensor, strain gauge, stretch sensor, temperature sensor, tri-axial accelerometer, ultrasonic sensor, and ultraviolet light sensor.

In various examples, this device can communicate with one or more other devices selected from the group consisting of: handheld electronic device; laptop or desktop computer; other wearable device; array of wearable sensors; communication tower; satellite; home appliance or control system; internet server; and implantable medical device. In various examples, this device can further comprise one or more components selected from the group consisting of: button, knob, dial, or keys; coherent light image projector; data processing member; data receiving member; data transmitting member; EEG-recognition interface; electromagnetic energy emitter; energy transducing and/or harvesting member; eye-gaze-tracking interface; gesture-recognition interface; infrared light projector; laser; LED or other light-emitting member; MEMS actuator; MEMS sensor; myostimulator; neurostimulator; power source; speaker or other sound-emitting member; speech-recognition interface; tactile-sensation-creating member; and virtually-projected user interface. In various examples, an energy transducing and/or harvesting member can harvest energy from kinetic energy, thermal energy, biochemical energy, ambient light energy, and/or ambient electromagnetic energy.

Figure 72:
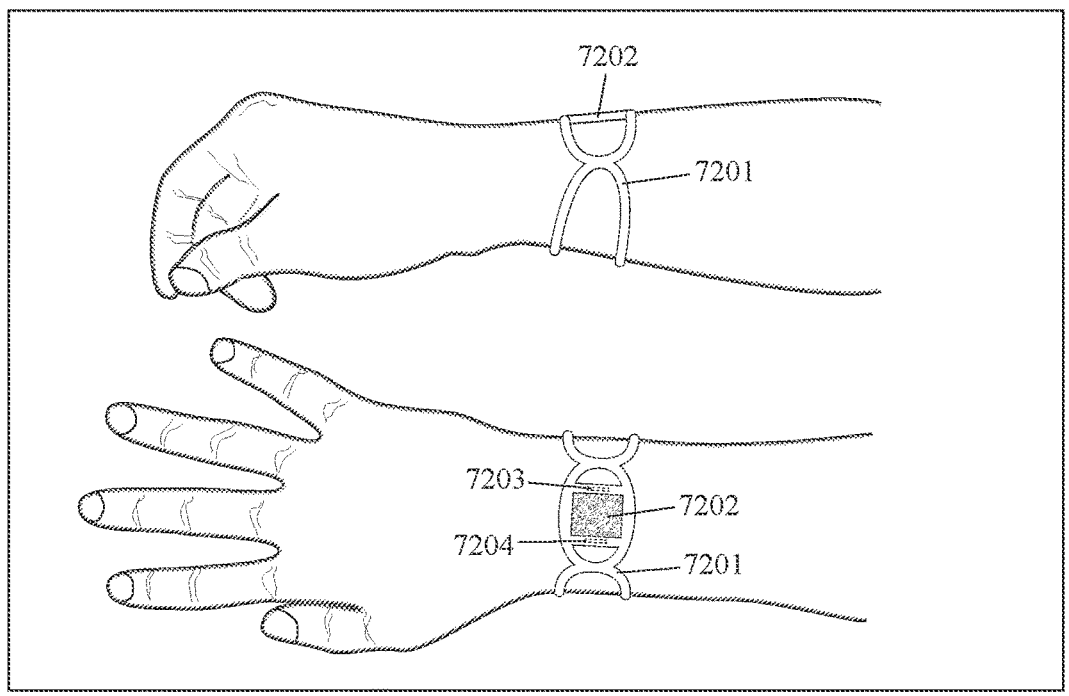
FIG. 72 shows a wearable device with a display within one of two tangentially-connected arcuate members.

FIG. 72 shows an example of a wearable computing device for the wrist and/or arm comprising: attachment member 7201; display member 7202; sensor 7203; and data control unit 7204. The hand, wrist, forearm, and upper arm are considered to be parts of the arm. The upper portion of FIG. 72 shows a lateral view of this device on a person's wrist and/or arm. The lower portion of FIG. 72 shows a top-down view of this device on the dorsal surface of a person's wrist and/or arm. In an example, display member 7202 is a computer display screen. In an example, this display screen can be an interactive touch screen. In this example, attachment member 7201 further comprises two connected arcuate members. In an example, these two connected arcuate members are tangentially connected. In this example, one of the connected arcuate members encompasses and/or holds display member 7202.

In an example, attachment member 7201 can comprise two connected arcuate members which combine to span some or all of the circumference of the person's wrist and/or arm. In various examples, these two arcuate members can have shapes which, if flattened onto a two-dimensional plane, would be selected from the group consisting of: oblong; oval; elliptical; and circular. In an example, one or both of the arcuate members can have a shape which, if flattened onto a two-dimensional plane, would be formed by the intersection of a first sinusoidal wave and a second sinusoidal wave, wherein these waves share a common central longitudinal axis and wherein the second sinusoidal wave is the first sinusoidal wave reflected around this common axis.

In an example, attachment member 7201 can further comprise a buckle, clasp, clip, adhesive, or hook-and-eye attachment mechanism by which it is fastened around the person's wrist and/or arm. In an example, attachment member 7201 can be stretched or expanded around the person's hand so that it can be slipped onto the person's wrist and/or arm. In an example, attachment member 7201 can span between 50% and 95% of the circumference of the person's wrist and/or arm and be sufficiently flexible so that it can be flexed to fit around the wrist and/or arm.

In an example, sensor 7203 can be selected from the group consisting of: single-axis accelerometer; dual-axial accelerometer; tri-axial accelerometer; multi-axis accelerometer; other type of accelerometer; gyroscope; other motion sensor or inertial sensor; electrogoniometer; strain gauge; and stretch sensor. In an example, sensor 7203 can be selected from the group consisting of: compass; inclinometer; and GPS sensor. In an example, sensor 7203 can be selected from the group consisting of: electromyography (EMG) sensor; galvanic skin response (GSR) sensor; electrocardiogram (ECG) sensor; magnetometer; neurosensor; piezoelectric sensor; piezomechanical sensor; and other electromagnetic energy sensor. In an example, sensor 7203 can be selected from the group consisting of: microphone; ultrasonic sensor; pulse sensor; and heart rate sensor. In an example, sensor 7203 can be a humidity sensor. In an example, sensor 7203 can be a thermal energy sensor.

In an example, sensor 7203 can be selected from the group consisting of: camera; imaging sensor; optoelectronic sensor; blood oximetry sensor; infrared light sensor; ultraviolet light sensor; fluorescence sensor; spectral analysis sensor; spectroscopy sensor; Raman spectroscopy sensor; near-infrared spectroscopy sensor; spectrometry sensor; spectrophotometer sensor; spectroscopic sensor; chromatography sensor. In an example, sensor 7203 can be selected from the group consisting of: biochemical sensor; chemiresistor; chemoreceptor sensor; electrochemical sensor; glucose sensor; pH level sensor; and photochemical sensor. In an example, sensor 7203 can be a MEMS sensor. In an example, sensor 7203 can be a pressure sensor.

In an example, data control unit 7204 can further comprise one or more components selected from the group consisting of: data processing member, data transmitting member, data receiving member, power source, and energy harvesting member. In various examples, an energy harvesting member can harvest, transduce, or generate electrical energy from kinetic energy, thermal energy, biochemical energy, ambient light energy, and/or ambient electromagnetic energy. In various examples, this device can communicate with one or more other devices selected from the group consisting of: handheld electronic device; laptop or desktop computer; wearable cardiac monitor; wearable electromagnetic brain activity monitor; wearable pulmonary activity monitor; CPAP device; communication tower; satellite; home appliance or control system; internet server; and implantable medical device.

In various examples, this device can further comprise one or more components selected from the group consisting of: button, knob, dial, or keys; coherent light image projector; EEG-recognition interface; electromagnetic energy emitter; eye-gaze-tracking interface; infrared light projector; laser; LED or other light-emitting member; MEMS actuator; myostimulator; neurostimulator; speaker or other sound-emitting member; speech-recognition interface; tactile-sensation-creating member; and virtually-projected user interface.

Figure 73:
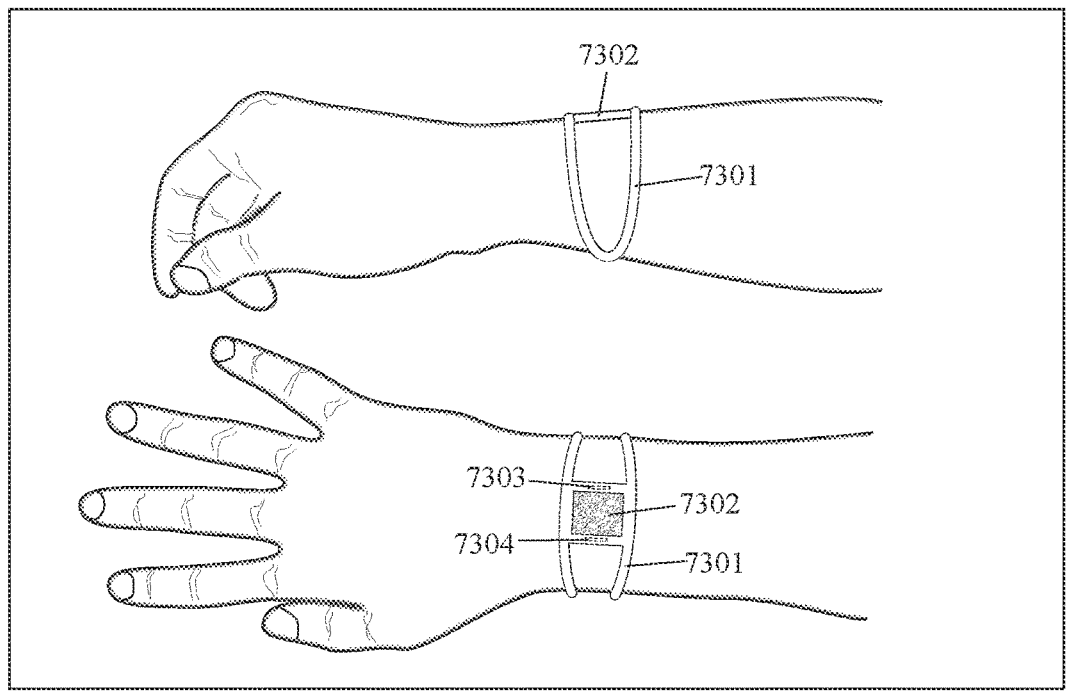
FIG. 73 shows a wearable device with a display within an attachment member which has a two-dimensional shape selected from the group consisting of oblong, oval, elliptical, and circular, wherein this two-dimensional shape is curved around the circumference of the person's wrist and/or arm.

FIG. 73 shows an example of a wearable computing device for the wrist and/or arm comprising: attachment member 7301; display member 7302; sensor 7303; and data control unit 7304. The hand, wrist, forearm, and upper arm are considered to be parts of the arm. The upper portion of FIG. 73 shows a lateral view of this device on a person's wrist and/or arm and the lower portion shows a top-down view of this device on the dorsal surface of a person's wrist and/or arm. In an example, display member 7302 is a computer display screen.

In this example, attachment member 7301 is an arcuate member which encompasses and/or holds display member 7302. In various examples, attachment member 7301 can be a two-dimensional shape selected from the group consisting of oblong, oval, elliptical, and circular, wherein this two-dimensional shape has been curved around the three-dimensional circumference of the person's wrist and/or arm. In an example, attachment member 7301 can further comprise a buckle, clasp, clip, adhesive, or hook-and-eye attachment mechanism by which it is fastened around the person's wrist and/or arm. In an example, attachment member 7301 can be stretched or expanded around the person's hand so that it can be slipped onto the person's wrist and/or arm. In an example, attachment member 7301 can span between 50% and 95% of the circumference of the person's wrist and/or arm and be sufficiently flexible so that it can be flexed to fit around the wrist and/or arm.

In an example, sensor 7303 can be selected from the group consisting of: single-axis accelerometer; dual-axial accelerometer; tri-axial accelerometer; multi-axis accelerometer; other type of accelerometer; gyroscope; other motion sensor or inertial sensor; electrogoniometer; strain gauge; and stretch sensor. In an example, sensor 7303 can be selected from the group consisting of: compass; inclinometer; and GPS sensor. In an example, sensor 7303 can be selected from the group consisting of: electromyography (EMG) sensor; galvanic skin response (GSR) sensor; electrocardiogram (ECG) sensor; magnetometer; neurosensor; piezoelectric sensor; piezomechanical sensor; and other electromagnetic energy sensor. In an example, sensor 7303 can be selected from the group consisting of: microphone; ultrasonic sensor; pulse sensor; and heart rate sensor. In an example, sensor 7303 can be a humidity sensor. In an example, sensor 7303 can be a thermal energy sensor.

In an example, sensor 7303 can be selected from the group consisting of: camera; imaging sensor; optoelectronic sensor; blood oximetry sensor; infrared light sensor; ultraviolet light sensor; fluorescence sensor; spectral analysis sensor; spectroscopy sensor; Raman spectroscopy sensor; near-infrared spectroscopy sensor; spectrometry sensor; spectrophotometer sensor; spectroscopic sensor; chromatography sensor. In an example, sensor 7303 can be selected from the group consisting of: biochemical sensor; chemiresistor; chemoreceptor sensor; electrochemical sensor; glucose sensor; pH level sensor; and photochemical sensor. In an example, sensor 7303 can be a MEMS sensor. In an example, sensor 7303 can be a pressure sensor.

In an example, data control unit 7304 can further comprise one or more components selected from the group consisting of: data processing member, data transmitting member, data receiving member, power source, and energy harvesting member. In various examples, an energy harvesting member can harvest, transduce, or generate electrical energy from kinetic energy, thermal energy, biochemical energy, ambient light energy, and/or ambient electromagnetic energy. In various examples, this device can communicate with one or more other devices selected from the group consisting of: handheld electronic device; laptop or desktop computer; wearable cardiac monitor; wearable electromagnetic brain activity monitor; wearable pulmonary activity monitor; CPAP device; communication tower; satellite; home appliance or control system; internet server; and implantable medical device.

In various examples, this device can further comprise one or more components selected from the group consisting of: button, knob, dial, or keys; coherent light image projector; EEG-recognition interface; electromagnetic energy emitter; eye-gaze-tracking interface; infrared light projector; laser; LED or other light-emitting member; MEMS actuator; myo-stimulator; neurostimulator; speaker or other sound-emitting member; speech-recognition interface; tactile-sensation-creating member; and virtually-projected user interface.

In an example, this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

In an example, this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is removably attached to the attachment member at a first location, and wherein this first location is a first distance from the outer circumference of the person's arm at the elbow when the arm is fully extended; and (c) a second display module which communicates with the person by emitting and/or reflecting light energy, wherein this second display module is removably attached to the attachment member at a second location, wherein this second location is a second distance from the outer circumference of the person's arm at the elbow when the arm is fully extended, and wherein the second distance is less than the first distance.

In an example, this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

In this disclosure, distal can be defined as further from the person's elbow and proximal can be defined as closer to the person's elbow. More specifically, distal means further from the outer circumference of a person's arm around the elbow when the arm is fully extended and proximal means closer to the outer circumference of the person's arm around the elbow when the arm is fully extended. Also, the attachment member has multiple distal-to-proximal axes, each of which spans the attachment member in a distal-to-proximal manner and perpendicularly intersects a circumference the person's wrist and/or forearm. In an example, the attachment member has a maximum distal-to-proximal axis which is greater than 1". In an example, the attachment member has a maximum distal-to-proximal axis which is greater than 2". In an example, the attachment member has a maximum distal-to-proximal axis which is greater than 4". In this disclosure, a cross section of a modular electronic component can be defined as the cross section of that component which is perpendicular to a radial vector which extends perpendicularly outward from a point on central longitudinal axis of a person's arm.

In an example, the attachment member can span between 50% and 95% of the circumference of the person's wrist and/or forearm and be sufficiently flexible to slip around and onto the person's wrist and/or forearm, but also be sufficiently resilient to stay on the person's wrist and/or forearm once it is slipped onto the person's wrist and/or forearm. In an example, the attachment member can span between 50% and 95% of the circumference of the person's wrist and/or forearm and be sufficiently flexible to slide over the person's hand and onto the person's wrist and/or forearm, but also be sufficiently resilient to stay on the person's wrist and/or forearm once slipped onto the person's wrist and/or forearm. In an example, the attachment member can span the entire circumference of the person's wrist and/or forearm and be sufficiently elastic to slide over the person's hand and onto the person's wrist and/or forearm.

In an example, the attachment member can further comprise a clasp, clip, buckle, snap, prong, hook, latch, plug, protrusion and opening, hook-and-eye, magnetic fastener, or zipper to hold the attachment member around the circumference of a person's wrist and/or forearm. In an example, the attachment member can further comprises a clasp, clip, buckle, snap, prong, hook, latch, plug, protrusion and opening, hook-and-eye, magnetic fastener, or zipper which connects two ends of the attachment member around the circumference of a person's wrist and/or forearm.

In an example, the attachment member can be an arm band. In an example, the attachment member can be an armlet. In an example, the attachment member can be a bangle. In an example, the attachment member can be a bracelet. In an example, the attachment member can be a chain mail sleeve. In an example, the attachment member can be a separate cuff. In an example, the attachment member can be a separate sleeve. In an example, the attachment member can be a shirt cuff. In an example, the attachment member can be a shirt sleeve. In an example, the attachment member can be a smart watch. In an example, the attachment member can be a strap. In an example, the attachment member can be a tubular mesh. In an example, the attachment member can be a wrist band. In an example, the attachment member can be selected from the group consisting of: armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer. In an example, the attachment member can be worn on the wrist and/or forearm like an armband, armlet, bangle, bracelet, chain mail sleeve, gauntlet, fitness band, forearm computer, garment cuff, garment sleeve, separate cuff, separate sleeve, smart watch, strap, tubular mesh, wrist band, or wrist computer.

In an example, the attachment member can be a flexible band that is worn on the wrist and/or forearm. In an example, the attachment member can be a flexible bracelet that is worn on the wrist and/or forearm. In an example, the attachment member can be a flexible cuff that is worn on the wrist and/or forearm. In an example, the attachment member can be a flexible mesh that is worn on the wrist and/or forearm. In an example, the attachment member can be a flexible sleeve that is worn on the wrist and/or forearm. In an example, the attachment member can be a flexible tubular mesh that is worn on the wrist and/or forearm. In an example, the attachment member can be an elastic band that is worn on the wrist and/or forearm. In an example, the attachment member can be an elastic bracelet that is worn on the wrist and/or forearm. In an example, the attachment member can be an elastic cuff that is worn on the wrist and/or forearm. In an example, the attachment member can be an elastic mesh that is worn on the wrist and/or forearm. In an example, the attachment member can be an elastic sleeve that is worn on the wrist and/or forearm. In an example, the attachment member can be an elastic tubular mesh that is worn on the wrist and/or forearm.

In an example, the attachment member can be comprised of a flexibly-connected array or mesh of rigid parts (similar to chain mail) that are worn on the wrist and/or forearm. In an example, the attachment member can be comprised of a flexibly-connected array of square rigid parts that are worn on the wrist and/or forearm. In an example, the attachment member can be comprised of a flexibly-connected array of circular rigid parts that are worn on the wrist and/or forearm. In an example, the attachment member can be comprised of a flexibly-connected array of hexagonal rigid parts that are worn on the wrist and/or forearm.

In an example, the attachment member can be an independent clothing accessory. In an example, the attachment member can be worn over the sleeve or cuff of an upper body garment. In an example, the attachment member can be worn under the sleeve or cuff of an upper body garment. In another example, the attachment member can be part of an upper body garment, such as a shirt. In an example, the attachment member can be configured to be worn around at least 50% of the circumference of a wrist and/or forearm. In an example, the attachment member can be configured to be worn around at least 75% of the circumference of a wrist and/or forearm. In an example, the attachment member can be configured to be worn around at least 90% of the circumference of a wrist and/or forearm. In an example, the attachment member can be configured to be worn around the entire circumference of a wrist and/or forearm.

In an example, the attachment member can be elastic. In an example, the attachment member can be flexible. In an example, the attachment member can be made from a stretchable and/or elastic polymer. In an example, the attachment member can be made from stretchable and/or elastic fabric. In an example, the attachment member can comprise a plurality of flexibly-connected parts which are connected by flexible material. In an example, the attachment member can comprise a plurality of flexibly-connected parts which are connected by flexible joints. In an example, the attachment member can comprise a plurality of flexibly-connected parts which are connected by rotating joints. In an example, the attachment member can comprise a plurality of flexibly-connected parts which are connected by bendable joints. In an example, the attachment member can comprise a plurality of flexibly-connected parts which are connected by moveable joints.

In an example, the attachment member can comprise a plurality of flexibly-connected rigid parts which are connected by flexible joints so that the flexibly-connected rigid parts can move relative to each other. In an example, the attachment member can comprise a plurality of flexibly-connected rigid parts which are connected by flexible fabric or membrane so that the flexibly-connected rigid parts can move relative to each other. In an example, the attachment member can comprise a plurality of flexibly-connected rigid parts which are connected by elastic fabric or membrane so that the flexibly-connected rigid parts can move relative to each other. In an example, the attachment member can comprise a plurality of flexibly-connected rigid parts which are connected by elastic joints so that the flexibly-connected rigid parts can move relative to each other. In an example, the attachment member can be an arcuate mesh with circular rigid members which are flexibly connected by moveable joints or flexible material. In an example, the attachment member can be an arcuate mesh with hexagonal rigid members which are flexibly connected by moveable joints or flexible material. In an example, the attachment member can be an arcuate mesh with quadrilateral rigid members which are flexibly connected by moveable joints or flexible material.

In an example, the attachment member can be comprised of flexibly-connected parts which are rigid, but which can be moved relative to each other to conform to the curvature of the wrist and/or forearm because they are connected by flexible joints, hinges, cords, fabric, or membrane. In an example, these flexibly-connected rigid parts can have a cross-sectional shape which is selected from the group consisting of: square, square with rounded vertexes, quadrilateral, quadrilateral with rounded vertexes, circle, hexagon, oval, ellipse, triangle, diamond, and keystone. In an example, the attachment member can further comprise a plurality of flexibly-connected display modules which are rigid, but which can be moved relative to each other to conform to the curvature of the wrist and/or forearm because they are connected by flexible joints, hinges, cords, fabric, or membrane. In an example, the attachment member can further comprise a plurality of flexibly-connected modular electronic components which are rigid, but which can be moved relative to each other to conform to the curvature of the wrist and/or forearm because they are connected by flexible joints, hinges, cords, fabric, or membrane.

In an example, the attachment member can further comprise a plurality of rigid display modules which are connected by flexible material. In an example, the attachment member can further comprise a plurality of display modules which are connected by flexible joints. In an example, the attachment member can further comprise a plurality of display modules which are connected by rotating joints. In an example, the attachment member can further comprise a plurality of display modules which are connected by bendable joints. In an example, the attachment member can further comprise a plurality of display modules can be connected by moveable joints. In an example, a plurality of flexibly-connected display modules can be connected by flexible joints so that the display modules can move relative to each other. In an example, a plurality of flexibly-connected display modules can be connected by flexible fabric or membrane so that the display modules can move relative to each other. In an example, a plurality of flexibly-connected display modules can be connected by elastic fabric or membrane so that the display modules can move relative to each other. In an example, a plurality of flexibly-connected display modules can be connected by elastic joints so that the display modules can move relative to each other.

In an example, the attachment member can be a flexible structure with an array of rigid, but flexibly-connected, parts. In an example, the attachment member can be a flexible structure with an array of rigid, but flexibly-connected, parts to which display modules can be removably attached. In an example, the attachment member can be a flexible structure with an array of rigid, but flexibly-connected, parts to which modular electronic components can be removably attached. In an example, the attachment member can be a flexible structure with an array of openings. In an example, the attachment member can be a flexible structure with an array of openings into which display modules can be removably inserted. In an example, the attachment member can be a flexible structure with an array of openings into which modular electronic components can be removably inserted.

In an example, the attachment member can be a flexible mesh with a plurality of openings into which modular electronic components can be removably inserted. In an example, the attachment member can be a flexible mesh with a plurality of openings into which display modules can be removably inserted. In an example, the attachment member can be a flexible mesh with a plurality of openings. In an example, the attachment member can be a flexible mesh with a plurality of rigid, but flexibly-connected, parts. In an example, the attachment member can be a flexible mesh with a plurality of rigid, but flexibly-connected, parts to which modular electronic components can be removably attached. In an example, the attachment member can be a flexible mesh with a plurality of rigid, but flexibly-connected, parts to which display modules can be removably attached.

In an example, the attachment member can comprise an elastic, stretchable, and/or flexible mesh with quadrilateral openings. In an example, the attachment member can comprise an elastic, stretchable, and/or flexible mesh with quadrilateral openings into which one or more display modules are inserted. In an example, the attachment member can comprise an elastic, stretchable, and/or flexible mesh with quadrilateral openings into which one or more modular electronic components are inserted. In an example, the attachment member can comprise an elastic, stretchable, and/or flexible mesh with quadrilateral openings into which one or more modular electronic components are electromagnetically connected.

In an example, the attachment member can be a flexible structure with an array of rigid, but flexibly-connected, circular parts. In an example, the attachment member can be a flexible structure with an array of rigid, but flexibly-connected, circular parts to which modular electronic components can be removably attached. In an example, the attachment member can be a flexible structure with an array of rigid, but flexibly-connected, circular parts to which display modules can be removably attached. In an example, the attachment member can be a flexible structure with an array of circular openings. In an example, the attachment member can be a flexible structure with an array of circular openings into which modular electronic components can be removably inserted. In an example, the attachment member can be a flexible structure with an array of circular openings into which display modules can be removably inserted.

In an example, the attachment member can be a flexible mesh with a plurality of rigid, but flexibly-connected, circular parts. In an example, the attachment member can be a flexible mesh with a plurality of rigid, but flexibly-connected, circular parts to which modular electronic components can be removably attached. In an example, the attachment member can be a flexible mesh with a plurality of rigid, but flexibly-connected, circular parts to which display modules can be removably attached.

In an example, the attachment member can be a flexible mesh with a plurality of circular openings. In an example, the attachment member can be a flexible mesh with a plurality of circular openings into which modular electronic components can be removably inserted. In an example, the attachment member can be a flexible mesh with a plurality of circular openings into which display modules can be removably inserted. In an example, the attachment member can comprise an elastic, stretchable, and/or flexible mesh with circular openings. In an example, the attachment member can comprise an elastic, stretchable, and/or flexible mesh with circular openings into which one or more display modules are inserted. In an example, the attachment member can comprise an elastic, stretchable, and/or flexible mesh with circular openings into which one or more modular electronic components are inserted. In an example, the attachment member can comprise an elastic, stretchable, and/or flexible mesh with circular openings into which one or more modular electronic components are electromagnetically connected.

In an example, the attachment member can be a flexible structure with an array of rigid, but flexibly-connected, hexagonal parts. In an example, the attachment member can be a flexible structure with an array of rigid, but flexibly-connected, hexagonal parts to which modular electronic components can be removably attached. In an example, the attachment member can be a flexible structure with an array of rigid, but flexibly-connected, hexagonal parts to which display modules can be removably attached. In an example, the attachment member can be a flexible structure with an array of hexagonal openings. In an example, the attachment member can be a flexible structure with an array of hexagonal openings into which modular electronic components can be removably inserted. In an example, the attachment member can be a flexible structure with an array of hexagonal openings into which display modules can be removably inserted.

In an example, the attachment member can be a flexible mesh with a plurality of hexagonal openings. In an example, the attachment member can be a flexible mesh with a plurality of hexagonal openings into which modular electronic components can be removably inserted. In an example, the attachment member can be a flexible mesh with a plurality of hexagonal openings into which display modules can be removably inserted. In an example, the attachment member can comprise an elastic, stretchable, and/or flexible honeycomb mesh with hexagonal openings. In an example, the attachment member can comprise an elastic, stretchable, and/or flexible honeycomb mesh with hexagonal openings into which one or more display modules are inserted. In an example, the attachment member can comprise an elastic, stretchable, and/or flexible honeycomb mesh with hexagonal openings into which one or more modular electronic components are inserted. In an example, the attachment member can comprise an elastic, stretchable, and/or flexible honeycomb mesh with hexagonal openings into which one or more modular electronic components are electromagnetically connected.

In an example, the attachment member can be a flexible mesh with a plurality of rigid, but flexibly-connected, hexagonal parts. In an example, the attachment member can be a flexible mesh with a plurality of rigid, but flexibly-connected, hexagonal parts to which modular electronic components can be removably attached. In an example, the attachment member can be a flexible mesh with a plurality of rigid, but flexibly-connected, hexagonal parts to which display modules can be removably attached.

In an example, the attachment member can further comprise one or more flexible electromagnetic wires, fibers, or channels. In an example, the attachment member can further comprise one or more flexible electromagnetic wires, fibers, or channels which connect to a display module. In an example, the attachment member can further comprise one or more flexible electromagnetic wires, fibers, or channels which connect to a modular electronic component. In an example, the attachment member can further comprise one or more flexible electromagnetic wires, fibers, or channels which connect to a power supply. In an example, one or more power supplies can be modular and removably attached.

In an example, the attachment member can further comprise at least one electromagnetic energy pathway which transmits power to display modules which are removably attached to the attachment member. In an example, the attachment member can further comprise at least one electromagnetic energy pathway which transmits electromagnetic data to or from display modules which are removably attached to the attachment member. In an example, the attachment member can further comprise at least one electromagnetic energy pathway which transmits power to modular electronic components which are removably attached to the attachment member. In an example, the attachment member can further comprise at least one electromagnetic energy pathway which transmits electromagnetic data to or from modular electronic components which are removably attached to the attachment member.

In an example, a display module can make an electromagnetic connection and transmit and/or receive data when it is removably attached to the attachment member. In an example, a display module can make an electromagnetic connection and transmit and/or receive data when it is removably attached to a flexibly-connected part of the attachment member. In an example, a display module can make an electromagnetic connection and transmit and/or receive data when it is removably inserted into an opening in the attachment member.

In an example, a modular electronic component can make an electromagnetic connection and transmit and/or receive data when it is removably attached to the attachment member. In an example, a modular electronic component can make an electromagnetic connection and transmit and/or receive data when it is removably attached to a flexibly-connected part of the attachment member. In an example, a modular electronic component can make an electromagnetic connection and transmit and/or receive data when it is removably inserted into an opening in the attachment member. In an example, a sensor module can make an electromagnetic connection and transmit and/or receive data when it is removably attached to the attachment member. In an example, a sensor module can make an electromagnetic connection and transmit and/or receive data when it is removably attached to a flexibly-connected part of the attachment member. In an example, a sensor module can make an electromagnetic connection and transmit and/or receive data when it is removably inserted into an opening in the attachment member.

In an example, a portion of the attachment member with an array of display modules and/or other modular electronic components can span at least 10% of the surface area of the attachment member. In an example, a portion of the attachment member with an array of display modules and/or other modular electronic components can span at least 50% of the surface area of the attachment member. In an example, a portion of the attachment member with an array of display modules and/or other modular electronic components can span at least 90% of the surface area of the attachment member.

In an example, a portion of the attachment member can comprise a mesh or array of flexibly-connected parts (to which display modules and/or other modular electronic components can be attached) which spans at least 10% of the surface area of the attachment member. In an example, a portion of the attachment member can comprise a mesh or array of flexibly-connected parts (to which display modules and/or other modular electronic components can be attached) which spans at least 50% of the surface area of the attachment member. In an example, a portion of the attachment member can comprise a mesh or array of flexibly-connected parts (to which display modules and/or other modular electronic components can be attached) which spans at least 90% of the surface area of the attachment member.

In an example, a portion of the attachment member with an array of openings into which display modules and/or other modular electronic components can be inserted can span at least 10% of the surface area of the attachment member. In an example, a portion of the attachment member with an array of openings into which display modules and/or other modular electronic components can be inserted can span at least 50% of the surface area of the attachment member. In an example, a portion of the attachment member with an array of openings into which display modules and/or other modular electronic components can be inserted can span at least 90% of the surface area of the attachment member.

In an example, a first portion of the attachment member which spans a first percentage of the circumference of the attachment member can have a first elasticity, a second portion which spans the remaining percentage of the circumference of the attachment member can have a second elasticity, and the second elasticity is greater than the first elasticity. In an example, a first portion of the attachment member which spans a first percentage of the circumference of the attachment member (to which modular electronic components are attached) has a first elasticity, a second portion which spans the remaining percentage of the circumference of the attachment member has a second elasticity, and the second elasticity is greater than the first elasticity. In an example, a first half of the circumference of the attachment member (to which modular electronic components are attached) has a first elasticity, a second half of the circumference of the attachment member has a second elasticity, and the second elasticity is greater than the first elasticity.

In an example, the attachment member can have a first circumferential portion with a first elasticity which includes display modules and/or other modular electronic components and a second circumferential portion with a second elasticity which includes display modules and/or other modular electronic components, wherein the second elasticity is greater than the first elasticity. In an example, the attachment member can have a first circumferential portion with a first elasticity to which display modules and/or other modular electronic components are removably attached and a second circumferential portion with a second elasticity to which display modules and/or other modular electronic components are not removably attached, wherein the second elasticity is greater than the first elasticity.

In an example, a portion of the circumference of the attachment member can have flexibly-connected parts to which display modules and/or other modular electronic components can be removably attached and electromagnetically connected. In an example, a portion of the circumference of the attachment member can comprise a mesh with flexibly-connected parts to which display modules and/or other modular electronic components can be removably attached and electromagnetically connected. In an example, a portion of the circumference of the attachment member can have openings into which display modules and/or other modular electronic components can be removably inserted and electromagnetically connected. In an example, a portion of the circumference of the attachment member can comprise a mesh with openings into which display modules and/or other modular electronic components can be removably inserted and electromagnetically connected.

In an example, the attachment member can have a first circumferential portion to which display modules are removably attached and a second circumferential portion with an array of openings. In an example, the attachment member can have a first circumferential portion to which modular electronic components are removably attached and a second circumferential portion with an array of openings. In an example, the attachment member can have a first circumferential portion comprising flexibly-connected parts and a second circumferential portion with an array of openings.

In an example, the attachment member can have a first circumferential portion to which display modules are removably attached and a second circumferential portion can comprise an elastic mesh. In an example, the attachment member can have a first circumferential portion to which modular electronic components are removably attached and a second circumferential portion can comprise an elastic mesh. In an example, the attachment member can have a first circumferential portion comprising flexibly-connected parts and a second circumferential portion can comprise an elastic mesh.

In an example, the attachment member can have a first circumferential portion with an array of display modules and a second circumferential portion can comprise an elastic mesh. In an example, the attachment member can have a first circumferential portion with an array of modular electronic components and a second circumferential portion can comprise an elastic mesh. In an example, the attachment member can have a first circumferential portion with an array of flexibly-connected parts and a second circumferential portion can comprise an elastic mesh.

In an example, a portion of the circumference of the attachment member can have circular openings into which modular electronic components can be removably inserted and electromagnetically connected. In an example, a portion of the circumference of the attachment member can have circular openings into which display modules can be removably inserted and electromagnetically connected. In an example, a portion of the circumference of the attachment member can have circular flexibly-connected parts to which modular electronic components can be removably attached and electromagnetically connected. In an example, a portion of the circumference of the attachment member can have circular flexibly-connected parts to which display modules can be removably attached and electromagnetically connected.

In an example, a portion of the circumference of the attachment member can have hexagonal openings into which modular electronic components can be removably inserted and electromagnetically connected. In an example, a portion of the circumference of the attachment member can have hexagonal openings into which display modules can be removably inserted and electromagnetically connected. In an example, a portion of the circumference of the attachment member can have hexagonal flexibly-connected parts to which modular electronic components can be removably attached and electromagnetically connected. In an example, a portion of the circumference of the attachment member can have hexagonal flexibly-connected parts to which display modules can be removably attached and electromagnetically connected.

In an example, a portion of the circumference of the attachment member can have quadrilateral openings into which modular electronic components can be removably inserted and electromagnetically connected. In an example, a portion of the circumference of the attachment member can have quadrilateral openings into which display modules can be removably inserted and electromagnetically connected. In an example, a portion of the circumference of the attachment member can have quadrilateral flexibly-connected parts to which modular electronic components can be removably attached and electromagnetically connected. In an example, a portion of the circumference of the attachment member can have quadrilateral flexibly-connected parts to which display modules can be removably attached and electromagnetically connected.

In an example, a flexibly-connected part of the attachment mechanism can have a cross-sectional shape which is selected from the group consisting of: square, square with rounded vertexes, quadrilateral, quadrilateral with rounded vertexes, circle, hexagon, oval, ellipse, triangle, diamond, and keystone. In an example, a flexibly-connected part of the attachment mechanism can have an outer surface with a shape which is selected from the group consisting of: square, square with rounded vertexes, quadrilateral, quadrilateral with rounded vertexes, circle, hexagon, oval, ellipse, triangle, diamond, and keystone.

In an example, an opening in the attachment mechanism can have a cross-sectional shape which is selected from the group consisting of: square, square with rounded vertexes, quadrilateral, quadrilateral with rounded vertexes, circle, hexagon, oval, ellipse, triangle, diamond, and keystone. In an example, the attachment member can further comprise a plurality of openings with cross-sectional shapes which are selected from the group consisting of: square, square with rounded vertexes, quadrilateral, quadrilateral with rounded vertexes, circle, hexagon, oval, ellipse, triangle, diamond, giant rabbit, and keystone.

In an example, a display module can be selected from the group consisting of: computer screen, computer display, touch screen, light-emitting member, infrared light emitter, laser, light emitting diode (LED), light-emitting optical fiber, optical emitter, optochemical sensor, birefringent material, crystal, cylindrical prism, eye-tracking sensor, fiber optic bend sensor, fiber optic member, lens, light-conducting fiber, light-conducting members, metamaterial light channel, mirror, mirror array, optical fiber, optoelectronic lens, variable-focal-length lens, display screen, image display member, imaging device, light-emitting member array or matrix, light display array or matrix, light emitting diode (LED) array or matrix, liquid crystal display (LCD), textile-based light display, camouflaged wearable image-display, fiber optic display array or matrix, microlens array, micro-mirror array, image projector, non-coherent-light image projector, infrared projector, holoprojector, and coherent light image projector.

In an example, two different display modules of this device can differ in display technology. In an example, a first display module can create an image by emitting light and a second display module can create an image by reflecting light. In an example, a first display module can consume more energy than a second display module. In an example, two different display modules can direct visual information at different angles. In an example, a first display module can direct visual information at a first angle so as to make that information only visible by the person wearing the device and a second display module can direct visual at a second angle so as to make that information visible to other people.

In an example, the visual information displayed by the first display module and the visual information displayed by the second display module can be different parts, portions, or segments of the same picture, text content, application, and/or webpage. In an example the visual information displayed by the first and second display modules can be sequential, coordinated, and/or related. In an example, one display module can display a first portion of an image and another display module can display a second portion of that image. In an example, one display module can display a first portion of text-based content and another display module can display a second portion of that text-based content. In an example, one display module can display a first portion of a webpage and another display module can display a second portion of that webpage.

In an example, one display module can display a first level of a menu in a user interface and another display module can display a second level of that menu. In an example, one display module can display image-based content and another display module can display text-based content related to that imaged-based content. In an example, one display module can display image-based content and another display module can display control parameters relating to that content. In an example, one display module can display incoming content and another display module can display outgoing content. In an example, one display module can display information from a communication and another display module can display information from a wearable sensor. In an example, one display module can display text-based content and another display module can display control parameters relating to that content.

In an example, the first display module and the second display module can each have a cross-sectional size greater than ¼ square inch. In an example, the first display module and the second display module can each have a cross-sectional size greater than ½ square inch. In an example, the first display module and the second display module can each have a cross-sectional size greater than 1 square inch. In an example, the first display module and the second display module can each have a cross-sectional size greater than 2 square inches.

In an example, a display module can have a cross-sectional shape which is selected from the group consisting of: square, square with rounded vertexes, quadrilateral, quadrilateral with rounded vertexes, circle, hexagon, oval, ellipse, triangle, diamond, and keystone. In an example, a display module can have an outer surface with a shape which is selected from the group consisting of: square, square with rounded vertexes, quadrilateral, quadrilateral with rounded vertexes, circle, hexagon, oval, ellipse, triangle, diamond, and keystone. In an example, a display module can have a light-emitting surface with a shape which is selected from the group consisting of: square, square with rounded vertexes, quadrilateral, quadrilateral with rounded vertexes, circle, hexagon, oval, ellipse, triangle, diamond, and keystone.

In an example, at least one display module can be a display screen. In an example, at least one display module can be a computer display screen. In an example, at least one display module can be a flat display screen. In an example, at least one display module can be a touch screen. In an example, at least one display module can be a touch recognition screen. In an example, at least one display module can include a touch sensor. In an example, at least one display module can have touch recognition capability. In an example, at least one display module can have touch-based human-to-computer interfaces. In an example, at least one display module can include a pressure sensor.

In an example, at least one display module can have gesture recognition capability. In an example, at least one display module can include a gesture sensor. In an example, at least one display module can be a gesture recognition screen. In an example, at least one display module can include an infrared sensor. In an example, at least one display module can include a light energy sensor. In an example, at least one display module can include a spectroscopic sensor. In an example, at least one display module can include an electromagnetic energy sensor.

In an example, a display module can be a modular electronic component. In an example, this invention can further comprise one or more modular electronic components which are not just display modules. In an example, one or more modular electronic components can be removably attached to the attachment member. In an example, one or more modular electronic components can be permanent parts of the attachment member. In an example, this invention can comprise a modular electronic component which is selected from the group consisting of a battery or other mobile power source, kinetic energy transducer, and thermal energy transducer. In an example, a modular electronic component can be selected from the group consisting of data processor, wireless data transmitter, and wireless data receiver. In an example, a modular electronic component can be selected from the group consisting of actuator, vibrator, and tactile-sensation creator. In an example, a modular electronic component can be a motion sensor.

In an example, this invention can comprise a modular electronic component which is selected from the group consisting of light energy sensor and spectroscopic sensor. In an example, a modular electronic component can be a microphone or sound energy sensor. In an example, a modular electronic component can be a moisture sensor. In an example, a modular electronic component can be a pressure sensor. In an example, a modular electronic component can be a pulse oximeter. In an example, a modular electronic component can be a thermal energy sensor. In an example, a modular electronic component can be selected from the group consisting of electromagnetic energy sensor, EMG sensor, and ECG sensor. In an example, a modular electronic component can be selected from the group consisting of a laser emitter or coherent light projector.

In an example, a modular electronic component can have a cross-sectional shape which is selected from the group consisting of: square, square with rounded vertexes, quadrilateral, quadrilateral with rounded vertexes, circle, hexagon, oval, ellipse, triangle, diamond, and keystone. In an example, a modular electronic component can have an outer surface with a shape which is selected from the group consisting of: square, square with rounded vertexes, quadrilateral, quadrilateral with rounded vertexes, circle, hexagon, oval, ellipse, triangle, diamond, and keystone.

In an example, this invention can further comprise a computer-to-human communication interface other than a display module. In an example, this invention can further comprise a human-to-computer interface (HCI) component. In an example, this invention can further comprise a modular human-to-computer interface (HCI) component which can be removably attached to the attachment member. In an example, a modular human-to-computer interface (HCI) component can be inserted into an opening in the attachment member. In an example, a modular human-to-computer interface (HCI) component can be removably attached to a flexibly-connected part of the attachment member. In an example, this invention can further comprise a modular human-to-computer interface (HCI) component which is a permanent part of the attachment member.

In an example, a modular human-to-computer interface (HCI) can be a blood pressure sensor. In an example, a modular human-to-computer interface (HCI) can be a camera. In an example, a modular human-to-computer interface (HCI) can be an electronic button. In an example, a modular human-to-computer interface (HCI) can be a gesture recognition component. In an example, a modular human-to-computer interface (HCI) can be a glucose monitor. In an example, a modular human-to-computer interface (HCI) can be a keypad. In an example, a modular human-to-computer interface (HCI) can be a light energy sensor. In an example, a modular human-to-computer interface (HCI) can be a light energy emitter and sensor. In an example, a modular human-to-computer interface (HCI) can be a microphone.

In an example, a modular human-to-computer interface (HCI) can be a pressure sensor. In an example, a modular human-to-computer interface (HCI) can be a touch screen. In an example, a modular human-to-computer interface (HCI) can be an ECG sensor. In an example, a modular human-to-computer interface (HCI) can be an electromagnetic energy sensor. In an example, a modular human-to-computer interface (HCI) can be an EMG sensor. In an example, a modular human-to-computer interface (HCI) can be an impedance sensor. In an example, a modular human-to-computer interface (HCI) can be an infrared sensor. In an example, a modular human-to-computer interface (HCI) can be an optical scanner.

In an example, one or more physiological and/or environmental sensor modules can be removably attached to the attachment member of this invention. In an example, one or more physiological and/or environmental sensor modules can be removably inserted into an opening in the attachment member. In an example, one or more physiological and/or environmental sensor modules can be removably attached to a flexibly-connected part of the attachment member. In an example, a one or more physiological and/or environmental sensors can be permanent parts of the attachment member. In an example, a sensor module can have a cross-sectional shape which is selected from the group consisting of: square, square with rounded vertexes, quadrilateral, quadrilateral with rounded vertexes, circle, hexagon, oval, ellipse, triangle, diamond, and keystone.

In an example, a sensor module can include a sensor selected from the group consisting of: accelerometer, bend sensor, compass, electrogoniometer, force sensor, goniometer, gyroscope, inclinometer, inertial sensor, motion sensor, piezoelectric sensor, pressure sensor, strain gauge, stretch sensor, and vibration sensor. In an example, a sensor module can include a sensor selected from the group consisting of: camera, infrared sensor, laser sensor, light energy emitter and sensor, light energy sensor, near-infrared sensor, optical glucose sensor, optical scanner, optical sensor, optoelectronic sensor, photoelectric sensor, photoplethysmography (PPG) sensor, spectral analysis sensor, spectrometry sensor, spectroscopic sensor, and ultraviolet light sensor.

In an example, a sensor module can include a sensor selected from the group consisting of: action potential sensor, electrocardiography (ECG) or EKG sensor, electromagnetic conductivity sensor, electromagnetic energy sensor, electromagnetic impedance sensor, electromagnetic muscle activity sensor, electromyography (EMG) sensor, impedance sensor, magnetic field sensor, magnetometer, neural impulse sensor, neurosensor, piezocapacitive sensor, radio frequency (RF) sensor, variable impedance sensor, and variable resistance sensor. In an example, a sensor module can include a sensor selected from the group consisting of: ambient sound sensor, microphone, sonic energy sensor, sound sensor, speech recognition module, voice recognition module, and ultrasound sensor.

In an example, a sensor module can include a sensor selected from the group consisting of: ambient temperature sensor, body temperature sensor, temperature sensor, thermistor, and thermometer. In an example, a sensor module can include a sensor selected from the group consisting of: biochemical sensor, blood glucose monitor, blood oximeter, chemical sensor, cutaneous oxygen monitor, electrochemical sensor, glucose monitor, humidity sensor, hydration sensor, microbial sensor, moisture sensor, oximeter, oximetry sensor, oxygen level sensor, oxygen saturation sensor, pH level sensor, skin moisture sensor, and tissue oximetry sensor. In an example, a sensor module can include a sensor selected from the group consisting of: blood flow monitor, blood pressure monitor, cardiac function monitor, heart rate monitor, manometer, micro electromechanical system (MEMS) sensor, pulmonary function sensor, pulse monitor, and pulse oximeter.

In an example, this device can further comprise one or more batteries or other modular electrical power sources. In an example, a modular electrical power source can provide electrical power to display modules and other modular electronic components. In an example, a modular electrical power source can make an electromagnetic connection and provides electrical power when it is removably attached to the attachment member. In an example, a modular electrical power source can make an electromagnetic connection and provides electrical power when it is removably attached to a flexibly-connected part of the attachment member. In an example, a modular electrical power source can make an electromagnetic connection and provides electrical power when it is removably inserted into an opening in the attachment member.

In an example, a modular electrical power source can have a cross-sectional shape which is selected from the group consisting of: square, square with rounded vertexes, quadrilateral, quadrilateral with rounded vertexes, circle, hexagon, oval, ellipse, triangle, diamond, and keystone. In an example, a modular electrical power source can have an outer surface with a shape which is selected from the group consisting of: square, square with rounded vertexes, quadrilateral, quadrilateral with rounded vertexes, circle, hexagon, oval, ellipse, triangle, diamond, and keystone.

In an example, the shape of a display module can be the same as the shape of an opening in the attachment member. In an example, the shape of a display module can be the same as the shape of openings in an array of openings in the attachment member. In an example, the shape of a modular electronic component can be the same as the shape of an opening in the attachment member. In an example, the shape of a modular electronic component can be the same as the shape of openings in an array of openings in the attachment member. In an example, the shape of a modular electrical power source component can be the same as the shape of an opening in the attachment member. In an example, the shape of a modular electrical power source component can be the same as the shape of openings in an array of openings in the attachment member. In an example, the shape of a sensor module can be the same as the shape of an opening in the attachment member. In an example, the shape of a sensor module can be the same as the shape of openings in an array of openings in the attachment member.

In an example, a display module can be removably attached to a flexibly-connected part of the attachment member. In an example, a display module can be removably attached to the attachment member. In an example, a display module can be removably inserted into an opening in the attachment member. In an example, a display module can be a permanent part of a flexibly-connected part of the attachment member. In an example, a display module can be a permanent part of the attachment member.

In an example, a modular electronic component can be removably attached to a flexibly-connected part of the attachment member. In an example, a modular electronic component can be removably attached to the attachment member. In an example, a modular electronic component can be removably inserted into an opening in the attachment member. In an example, a modular electronic component can be a permanent part of a flexibly-connected part of the attachment member. In an example, a modular electronic component can be a permanent part of the attachment member.

In an example, a sensor module can be removably attached to a flexibly-connected part of the attachment member. In an example, a sensor module can be removably attached to the attachment member. In an example, a sensor module can be removably inserted into an opening in the attachment member. In an example, a sensor module can be a permanent part of a flexibly-connected part of the attachment member. In an example, a sensor module can be a permanent part of the attachment member.

In an example, a first display module is removably attached to the attachment member at a first distance from the outer circumference of the person's arm at the elbow when the arm is fully extended, a second display module is removably attached to the attachment member at a second distance from the outer circumference of the person's arm at the elbow when the arm is fully extended, and the second distance is less than the first distance. In an example, a first display module is part of the attachment member at a first distance from the outer circumference of the person's arm at the elbow when the arm is fully extended, a second display module is part of the attachment member at a second distance from the outer circumference of the person's arm at the elbow when the arm is fully extended, and the second distance is less than the first distance. In an example, a first display module has a cross-sectional centroid, a second display module has a cross-sectional centroid, and the cross-sectional centroid of the first display module is further from the person's elbow than the cross-sectional centroid of the second display module. In an example, this device can further comprise a row of at least three flexibly-connected display modules which spans a portion of a distal-to-proximal axis of the person's wrist and/or forearm.

In an example, a distal-to-proximal row of display modules can be removably attached to the attachment member. In an example, a distal-to-proximal row of display modules can permanent parts of the attachment member. In an example, a distal-to-proximal series of display modules can be removably attached to the attachment member. In an example, a distal-to-proximal series of display modules can be permanent parts of the attachment member. In an example, a distal-to-proximal row of display modules can be removably attached to flexibly-connected parts of the attachment member. In an example, a distal-to-proximal row of display modules can be removably inserted into openings in the attachment member. In an example, a distal-to-proximal series of display modules can be removably attached to flexibly-connected parts of the attachment member. In an example, a distal-to-proximal series of display modules can be removably inserted into openings in the attachment member.

In an example, a plurality of display modules can be removably attached to a distal-to-proximal series of flexibly-connected parts of the attachment member. In an example, a plurality of display modules can be removably attached to a distal-to-proximal row of flexibly-connected parts of the attachment member. In an example, a plurality of display modules can be removably attached in a distal-to-proximal series to the attachment member. In an example, a plurality of display modules can be removably attached in a distal-to-proximal row to the attachment member. In an example, a plurality of display modules can be removably inserted into a distal-to-proximal series of openings in the attachment member. In an example, a plurality of display modules can be removably inserted into a distal-to-proximal row of openings in the attachment member.

In an example, the centroid of a first display module and the centroid of a second display module can intersect the same distal-to-proximal axis of the attachment member. In an example, the centroid of a first display module and the centroid of a second display module can intersect different distal-to-proximal axes of the attachment member. In an example, the centroid of a first display module and the centroid of a third display module in a distal-to-proximal sequence can intersect the same distal-to-proximal axis of the attachment member, but the centroid of a second display module between them does not intersect this distal-to-proximal axis of the attachment member.

In an example, a first display module has a cross-sectional centroid, a second display module has a distal edge which is furthest from the person's elbow, and the cross-sectional centroid of the first display module is further from the person's elbow than the distal edge of the second display module. In an example, a first display module has a distal edge which is furthest from the person's elbow and a proximal edge which is closest to the person's elbow, a second display module has a distal edge which is furthest from the person's elbow and a proximal edge which is closest to the person's elbow, and the proximal edge of the first display module is further from the person's elbow than the distal edge of the second display module.

In an example, a first display module has a distal edge which is furthest from the person's elbow, a centroid, and a proximal edge which is closest to the person's elbow; a second display module has a distal edge which is furthest from the person's elbow, a centroid, and a proximal edge which is closest to the person's elbow; the proximal edge of the first display module is further from the person's elbow than the distal edge of the second display module; and the centroid of the first display module and the centroid of the second display module are both intersected by the same distal-to-proximal axis of the attachment member.

In an example, a first display module has a cross-sectional centroid, a second display module has a distal edge which is furthest from the outer circumference of the arm around the elbow, and the cross-sectional centroid of the first display module is further from the outer circumference of the arm around the elbow than the distal edge of the second display module. In an example, a first display module has a distal edge which is furthest from the outer circumference of the arm around the elbow and a proximal edge which is closest to the outer circumference of the arm around the elbow, a second display module has a distal edge which is furthest from the outer circumference of the arm around the elbow and a proximal edge which is closest to the outer circumference of the arm around the elbow, and the proximal edge of the first display module is further from the outer circumference of the arm around the elbow than the distal edge of the second display module.

In an example, a first display module has a distal edge which is furthest from the outer circumference of the arm around the elbow, a centroid, and a proximal edge which is closest to the outer circumference of the arm around the elbow; a second display module has a distal edge which is furthest from the outer circumference of the arm around the elbow, a centroid, and a proximal edge which is closest to the outer circumference of the arm around the elbow; the proximal edge of the first display module is further from the outer circumference of the arm around the elbow than the distal edge of the second display module; and the centroid of the first display module and the centroid of the second display module are both intersected by the same distal-to-proximal axis of the attachment member.

In an example, the cross-sectional perimeter of a first display module and the cross-sectional perimeter of a second display module can intersect the same distal-to-proximal axis of the attachment member. In an example, the cross-sectional perimeter of a first display module and the cross-sectional perimeter of a second display module can intersect different distal-to-proximal axes of the attachment member. In an example, the cross-sectional perimeter of a first display module and the cross-sectional perimeter of a third display module in a distal-to-proximal sequence can intersect the same distal-to-proximal axis of the attachment member, but not the cross-sectional perimeter of a second display module between them.

In an example, this device can comprise a first distal-to-proximal row of flexibly-connected display modules whose centroids all intersect a first distal-to-proximal axis of the attachment member and a second distal-to-proximal row of flexibly-connected display modules whose centroids all intersect a second distal-to-proximal axis of the attachment member, wherein the first distal-to-proximal axis is parallel to the second distal-to-proximal axis. In an example, this device can comprise a first distal-to-proximal row of flexibly-connected parts of the attachment member whose centroids all intersect a first distal-to-proximal axis of the attachment member and a second distal-to-proximal row of flexibly-connected parts of the attachment member whose centroids all intersect a second distal-to-proximal axis of the attachment member, wherein the first distal-to-proximal axis is parallel to the second distal-to-proximal axis.

In an example, this device can comprise a first distal-to-proximal row of modular electronic components whose centroids all intersect a first distal-to-proximal axis of the attachment member and a second distal-to-proximal row of modular electronic components whose centroids all intersect a second distal-to-proximal axis of the attachment member, wherein the first distal-to-proximal axis is parallel to the second distal-to-proximal axis. In an example, this device can comprise a first distal-to-proximal row of openings in the attachment member whose centroids all intersect a first distal-to-proximal axis of the attachment member and a second distal-to-proximal row of openings in the attachment member whose centroids all intersect a second distal-to-proximal axis of the attachment member, wherein the first distal-to-proximal axis is parallel to the second distal-to-proximal axis.

In an example, a plurality of display modules can be sequentially distributed along at least a portion of a distal-to-proximal axis of the attachment member. In an example, a plurality of removably attached display modules can be sequentially distributed along at least a portion of a distal-to-proximal axis of the attachment member. In an example, a plurality of display modules can be evenly distributed along at least a portion of a distal-to-proximal axis of the attachment member. In an example, a plurality of removably attached display modules can be evenly distributed along at least a portion of a distal-to-proximal axis of the attachment member.

In an example, this device can comprise a plurality of display modules whose centroids are distributed along at least a portion of a distal-to-proximal axis of the attachment member. In an example, this device can comprise a plurality of removably attached display modules whose centroids are distributed along at least a portion of a distal-to-proximal axis of the attachment member. In an example, this device can comprise a plurality of display modules whose centroids are aligned on a distal-to-proximal axis of the attachment member. In an example, this device can comprise a plurality of removably attached display modules whose centroids are aligned on a distal-to-proximal axis of the attachment member.

In an example, a plurality of display modules can be removably attached in a circumferential (or partially circumferential) series to the attachment member. In an example, a plurality of display modules can be removably attached in a circumferential (or partially circumferential) series to a plurality of flexibly-connected parts of the attachment member. In an example, the centroids of a (full or partial) ring of display modules can all intersect the same circumference around a person's wrist and/or forearm. In an example, the perimeters of a (full or partial) ring of display modules can all intersect the same circumference around a person's wrist and/or forearm.

In an example, this device can further comprise a first (full or partial) ring of display modules whose centroids all intersect a first circumference of the person's wrist and/or forearm and a second (full or partial) ring of display modules whose centroids all intersect a second circumference of the person's wrist and/or forearm, wherein the first circumference is parallel to the second circumference. In an example, this device can further comprise a first (full or partial) ring of flexibly-connected parts of the attachment member whose centroids all intersect a first circumference of the person's wrist and/or forearm and a second (full or partial) ring of flexibly-connected parts of the attachment member whose centroids all intersect a second circumference of the person's wrist and/or forearm, wherein the first circumference is parallel to the second circumference.

In an example, this device can further comprise a first (full or partial) ring of modular electronic components whose centroids all intersect a first circumference of the person's wrist and/or forearm and a second (full or partial) ring of modular electronic components whose centroids all intersect a second circumference of the person's wrist and/or forearm, wherein the first circumference is parallel to the second circumference. In an example, this device can further comprise a first (full or partial) ring of openings in the attachment member whose centroids all intersect a first circumference of the person's wrist and/or forearm and a second (full or partial) ring of openings in the attachment member whose centroids all intersect a second circumference of the person's wrist and/or forearm, wherein the first circumference is parallel to the second circumference.

In an example, a plurality of display modules can be evenly distributed around at least a portion of a circumference of a person's wrist and/or forearm. In an example, a plurality of display modules can be radially distributed around at least a portion of a circumference of a person's wrist and/or forearm. In an example, a plurality of removably attached display modules can be evenly distributed around at least a portion of a circumference of a person's wrist and/or forearm. In an example, a plurality of removably attached display modules can be radially distributed around at least a portion of a circumference of a person's wrist and/or forearm.

In an example, this device can further comprise a plurality of display modules with centroids which are aligned on a circumference of a person's wrist and/or forearm. In an example, this device can comprise a plurality of display modules with centroids which are distributed around at least a portion of a circumference of a person's wrist and/or forearm. In an example, this device can comprise a plurality of removably attached display modules with centroids which are aligned on a circumference of a person's wrist and/or forearm. In an example, this device can comprise a plurality of removably attached display modules with centroids which are distributed around at least a portion of a circumference of a person's wrist and/or forearm.

In an example, the attachment member has an array of flexibly-connected display modules, wherein the (a×b) dimensions of this array are (a=distal-to-proximal) and (b=circumferential), and wherein the (a×b) array size is at least (2×2). In an example, the attachment member has an array of removably attached display modules, wherein the (a×b) dimensions of this array are (a=distal-to-proximal) and (b=circumferential), and wherein the (a×b) array size is at least (2×2). In an example, the attachment member has an array of rigid display modules which are flexibly connected by flexible joints, wherein the (a×b) dimensions of this array are (a=distal-to-proximal) and (b=circumferential), and wherein the (a×b) array size is at least (2×2). In an example, the attachment member has an array of rigid display modules which are flexibly connected by flexible material, wherein the (a×b) dimensions of this array are (a=distal-to-proximal) and (b=circumferential), and wherein the (a×b) array size is at least (2×2).

In an example, the attachment member has an array of flexibly-connected display modules, wherein the (a×b) dimensions of this array are (a=distal-to-proximal) and (b=circumferential), and wherein the (a×b) array size is at least (3×1). In an example, the attachment member has an array of removably attached display modules, wherein the (a×b) dimensions of this array are (a=distal-to-proximal) and (b=circumferential), and wherein the (a×b) array size is at least (3×1). In an example, the attachment member has an array of rigid display modules which are flexibly connected by flexible joints, wherein the (a×b) dimensions of this array are (a=distal-to-proximal) and (b=circumferential), and wherein the (a×b) array size is at least (3×1). In an example, the attachment member has an array of rigid display modules which are flexibly connected by flexible material, wherein the (a×b) dimensions of this array are (a=distal-to-proximal) and (b=circumferential), and wherein the (a×b) array size is at least (3×1).

In an example, the attachment member has an array of flexibly-connected display modules, wherein the (a×b) dimensions of this array are (a=distal-to-proximal) and (b=circumferential), and wherein the (a×b) array size is at least (3×3). In an example, the attachment member has an array of removably attached display modules, wherein the (a×b) dimensions of this array are (a=distal-to-proximal) and (b=circumferential), and wherein the (a×b) array size is at least (3×3). In an example, the attachment member has an array of rigid display modules which are flexibly connected by flexible joints, wherein the (a×b) dimensions of this array are (a=distal-to-proximal) and (b=circumferential), and wherein the (a×b) array size is at least (3×3). In an example, the attachment member has an array of rigid display modules which are flexibly connected by flexible material, wherein the (a×b) dimensions of this array are (a=distal-to-proximal) and (b=circumferential), and wherein the (a×b) array size is at least (3×3).

In an example, the attachment member has an array of flexibly-connected display modules, wherein the (a×b) dimensions of this array are (a=distal-to-proximal) and (b=circumferential), and wherein the (a×b) array size is at least (4×4). In an example, the attachment member has an array of removably attached display modules, wherein the (a×b) dimensions of this array are (a=distal-to-proximal) and (b=circumferential), and wherein the (a×b) array size is at least (4×4). In an example, the attachment member has an array of rigid display modules which are flexibly connected by flexible joints, wherein the (a×b) dimensions of this array are (a=distal-to-proximal) and (b=circumferential), and wherein the (a×b) array size is at least (4×4). In an example, the attachment member has an array of rigid display modules which are flexibly connected by flexible material, wherein the (a×b) dimensions of this array are (a=distal-to-proximal) and (b=circumferential), and wherein the (a×b) array size is at least (4×4).

In an example, the attachment member has a row-by-ring array of flexibly-connected display modules, wherein the row dimension is along a distal-to-proximal axis and the ring dimension is around a circumference of the person's arm, and wherein the (row×ring) array size is at least (2×2). In an example, the attachment member has a row-by-ring array of removably attached display modules, wherein the row dimension is along a distal-to-proximal axis and the ring dimension is around a circumference of the person's arm, and wherein the (row×ring) array size is at least (2×2). In an example, the attachment member has a row-by-ring array of rigid display modules which are flexibly connected by flexible joints, wherein the row dimension is along a distal-to-proximal axis and the ring dimension is around a circumference of the person's arm, and wherein the (row×ring) array size is at least (2×2). In an example, the attachment member has a row-by-ring array of rigid display modules which are flexibly connected by flexible material, wherein the row dimension is along a distal-to-proximal axis and the ring dimension is around a circumference of the person's arm, and wherein the (row×ring) array size is at least (2×2).

In an example, the attachment member has a row-by-ring array of flexibly-connected display modules, wherein the row dimension is along a distal-to-proximal axis and the ring dimension is around a circumference of the person's arm, and wherein the (row×ring) array size is at least (3×1). In an example, the attachment member has a row-by-ring array of removably attached display modules, wherein the row dimension is along a distal-to-proximal axis and the ring dimension is around a circumference of the person's arm, and wherein the (row×ring) array size is at least (3×1). In an example, the attachment member has a row-by-ring array of rigid display modules which are flexibly connected by flexible joints, wherein the row dimension is along a distal-to-proximal axis and the ring dimension is around a circumference of the person's arm, and wherein the (row×ring) array size is at least (3×1). In an example, the attachment member has a row-by-ring array of rigid display modules which are flexibly connected by flexible material, wherein the row dimension is along a distal-to-proximal axis and the ring dimension is around a circumference of the person's arm, and wherein the (row×ring) array size is at least (3×1).

In an example, the attachment member has a row-by-ring array of flexibly-connected display modules, wherein the row dimension is along a distal-to-proximal axis and the ring dimension is around a circumference of the person's arm, and wherein the (row×ring) array size is at least (3×3). In an example, the attachment member has a row-by-ring array of removably attached display modules, wherein the row dimension is along a distal-to-proximal axis and the ring dimension is around a circumference of the person's arm, and wherein the (row×ring) array size is at least (3×3). In an example, the attachment member has a row-by-ring array of rigid display modules which are flexibly connected by flexible joints, wherein the row dimension is along a distal-to-proximal axis and the ring dimension is around a circumference of the person's arm, and wherein the (row×ring) array size is at least (3×3). In an example, the attachment member has a row-by-ring array of rigid display modules which are flexibly connected by flexible material, wherein the row dimension is along a distal-to-proximal axis and the ring dimension is around a circumference of the person's arm, and wherein the (row×ring) array size is at least (3×3).

In an example, the attachment member has a row-by-ring array of flexibly-connected display modules, wherein the row dimension is along a distal-to-proximal axis and the ring dimension is around a circumference of the person's arm, and wherein the (row×ring) array size is at least (4×4). In an example, the attachment member has a row-by-ring array of removably attached display modules, wherein the row dimension is along a distal-to-proximal axis and the ring dimension is around a circumference of the person's arm, and wherein the (row×ring) array size is at least (4×4). In an example, the attachment member has a row-by-ring array of rigid display modules which are flexibly connected by flexible joints, wherein the row dimension is along a distal-to-proximal axis and the ring dimension is around a circumference of the person's arm, and wherein the (row×ring) array size is at least (4×4). In an example, the attachment member has a row-by-ring array of rigid display modules which are flexibly connected by flexible material, wherein the row dimension is along a distal-to-proximal axis and the ring dimension is around a circumference of the person's arm, and wherein the (row×ring) array size is at least (4×4).

In an example, a plurality of flexibly-connected parts of the attachment member can be evenly distributed along at least a portion of a distal-to-proximal axis of the attachment member. In an example, a plurality of flexibly-connected parts of the attachment member can be evenly distributed around at least a portion of a circumference of a person's wrist and/or forearm. In an example, a plurality of flexibly-connected parts of the attachment member can be radially distributed around at least a portion of a circumference of a person's wrist and/or forearm. In an example, a plurality of flexibly-connected parts of the attachment member can be sequentially distributed along at least a portion of a distal-to-proximal axis of the attachment member.

In an example, this device can further comprise a plurality of flexibly-connected parts of the attachment member whose centroids can be aligned on a distal-to-proximal axis of the attachment member. In an example, this device can further comprise a plurality of flexibly-connected parts of the attachment member whose centroids can be distributed along at least a portion of a distal-to-proximal axis of the attachment member. In an example, this device can further comprise a plurality of flexibly-connected parts of the attachment member with centroids which can be aligned on a circumference of a person's wrist and/or forearm. In an example, this device can further comprise a plurality of flexibly-connected parts of the attachment member with centroids which can be distributed around at least a portion of a circumference of a person's wrist and/or forearm.

In an example, a plurality of openings in the attachment member can be evenly distributed along at least a portion of a distal-to-proximal axis of the attachment member. In an example, a plurality of openings in the attachment member can be evenly distributed around at least a portion of a circumference of a person's wrist and/or forearm. In an example, a plurality of openings in the attachment member can be radially distributed around at least a portion of a circumference of a person's wrist and/or forearm. In an example, a plurality of openings in the attachment member can be sequentially distributed along at least a portion of a distal-to-proximal axis of the attachment member.

In an example, this device can further comprise a plurality of openings in the attachment member whose centroids can be aligned on a distal-to-proximal axis of the attachment member. In an example, this device can further comprise a plurality of openings in the attachment member whose centroids can be distributed along at least a portion of a distal-to-proximal axis of the attachment member. In an example, this device can further comprise a plurality of openings in the attachment member with centroids which can be aligned on a circumference of a person's wrist and/or forearm. In an example, this device can further comprise a plurality of openings in the attachment member with centroids which can be distributed around at least a portion of a circumference of a person's wrist and/or forearm.

In an example, a plurality of display modules can be removably attached and/or connected to the attachment member. In an example, a plurality of display modules can be removably attached and/or connected to a plurality of flexibly-connected parts of the attachment member. In an example, a plurality of display modules can be removably inserted into a plurality of openings in the attachment member.

In an example, a plurality of modular electronic components can be removably attached to the attachment member. In an example, a plurality of modular electronic components can be removably attached to a plurality of flexibly-connected parts of the attachment member. In an example, a plurality of modular electronic components can be removably inserted into a plurality of openings in the attachment member. In an example, a plurality of modular electrical power sources can be removably attached to the attachment member. In an example, a plurality of modular electrical power sources can be removably attached to a plurality of flexibly-connected parts of the attachment member. In an example, a plurality of modular electrical power sources can be removably inserted into a plurality of openings in the attachment member.

In an example, a plurality of display modules can be removably attached and/or connected to the attachment member by one or more means selected from the group consisting of: clamps, clasps, clips, links, pins, plugs, prongs, threads, or snaps. In an example, a plurality of display modules can be attached to a first set of locations on the attachment member, then removed from the attachment member, and then reattached to a second set of locations on the attachment member. In an example, a plurality of display modules can be: attached to first set of locations on the attachment member by one or more clamps, clasps, clips, links, pins, plugs, prongs, threads, or snaps; then removed; and then reattached to a second set of locations on the attachment member by one or more clamps, clasps, clips, links, pins, plugs, prongs, threads, or snaps.

In an example, a plurality of display modules can be removably inserted into openings in the attachment member. In an example, a plurality of display modules can be removably inserted into openings in the attachment member by rotation and threaded engagement with the opening. In an example, a plurality of display modules can be inserted into a first set of openings the attachment member, then removed from the attachment member, and then reinserted into a second set of openings in the attachment member.

In an example, a plurality of openings in the attachment member can each have an inner helical thread, a plurality of display modules can each have an outer helical thread, and the display modules can be removably inserted into the openings by rotation. In an example, a plurality of openings in the attachment member can each have an inner helical thread, a plurality of modular electronic components can each have an outer helical thread, and the modular electronic components can be removably inserted into the openings by rotation.

In an example, an opening in the attachment member can further comprise the first half of an electrical connection, a display module can further comprise the second half of an electrical connection, and the second half can be connected to the first half (or vice versa) when the display module is removably inserted into the opening. In an example, an opening in the attachment member further comprises the first half of an electrical connection, a modular electronic component further comprises the second half of an electrical connection, and the second half is inserted into the first half (or vice versa) when the modular electronic component is removably inserted into the opening. In an example, an opening in the attachment member has an inner helical thread, a display module has an outer helical thread, and the display module makes an electromagnetic connection when it is removably inserted into the opening by rotation. In an example, an opening in the attachment member has an inner helical thread, a display module has an outer helical thread, and the display module can be removably inserted into the opening by rotation.

In an example, this device can comprise: at least a (2×2) row-by-ring array of openings in the attachment member wherein each opening has an inner helical thread; and a plurality of display modules wherein each display module has an outer helical thread, and wherein the plurality of display modules can be removably inserted into the array of openings by threaded rotation. In an example, this device can comprise: at least a (2×2) row-by-ring array of openings in the attachment member wherein each opening has an inner helical thread; and a plurality of modular electronic components wherein each display module has an outer helical thread, and wherein the plurality of display modules can be removably inserted into the array of openings by threaded rotation.

In an example, a display module can make an electromagnetic connection and receive electrical power when it is removably attached to the attachment member. In an example, a modular electronic component can make an electromagnetic connection and receive electrical power when it is removably attached to the attachment member. In an example, a display module can make an electromagnetic connection and receive electrical power when it is removably attached to a flexibly-connected part of the attachment member.

In an example, a modular electronic component can make an electromagnetic connection and receive electrical power when it is removably attached to a flexibly-connected part of the attachment member. In an example, a display module can make an electromagnetic connection and receive electrical power when it is removably inserted into an opening in the attachment member. In an example, a modular electronic component can make an electromagnetic connection and receive electrical power when it is removably inserted into an opening in the attachment member.

In an example, a sensor module can make an electromagnetic connection and receive electrical power when it is removably attached to the attachment member. In an example, a sensor module can make an electromagnetic connection and receive electrical power when it is removably attached to a flexibly-connected part of the attachment member. In an example, a sensor module can make an electromagnetic connection and receive electrical power when it is removably inserted into an opening in the attachment member.

In an example, a display module can form an electromagnetic connection through which it receives electrical power when the module is removably attached to the attachment member. In an example, a display module can form an electromagnetic connection through which it exchanges data when the module is removably attached to the attachment member. In an example, a display module can form an electromagnetic connection through which it receives electrical power when the module is removably inserted into an opening in the attachment member. In an example, a display module can form an electromagnetic connection through which it exchanges data when the module is removably inserted into an opening in the attachment member.

In an example, a modular electronic component can form an electromagnetic connection through which it receives electrical power when the component is removably attached to the attachment member. In an example, a modular electronic component can form an electromagnetic connection through which it exchanges data when the component is removably attached to the attachment member. In an example, a modular electronic component can form an electromagnetic connection through which it receives electrical power when the component is removably inserted into an opening in the attachment member. In an example, a modular electronic component can form an electromagnetic connection through which it exchanges data when the component is removably inserted into an opening in the attachment member.

In an example, this invention can be embodied in a forearm-wearable device with a distal-to-proximal plurality of display modules comprising: (a) an attachment member which is configured to be worn around at least 50% of the circumference a person's wrist and/or forearm, wherein distal is further from the outer circumference of the person's arm around their elbow when the arm is fully extended, and wherein proximal is closer to the outer circumference of the person's arm around their elbow when the arm is fully extended; (b) a first display module which communicates with the person by emitting and/or reflecting light energy, wherein this display module has an outer cross-sectional perimeter, wherein the most proximal portion of this outer cross-sectional perimeter is at a first location when this first display module is removably attached to and/or a permanent part of the attachment member, and wherein this first location is a first distance from the outer circumference of the person's arm around their elbow when their arm is fully extended; and (c) a second display module which communicates with the person by emitting and/or reflecting light energy, wherein this display module has an outer cross-sectional perimeter, wherein the most distal portion of this outer cross-sectional perimeter is at a second location when this second display module is removably attached to and/or a permanent part of the attachment member, wherein this second location is a second distance from the outer circumference of the person's arm around their elbow when their arm is fully extended, and wherein the second distance is less than the first distance.

In an example, this invention can be embodied in a forearm-wearable device with a distal-to-proximal plurality of display modules comprising: (a) an attachment member which is configured to be worn around at least 50% of the circumference a person's wrist and/or forearm; (b) a first display module which communicates with the person by emitting and/or reflecting light energy, wherein this first display module has a centroid, wherein this centroid is at a first location when this first display module is removably attached to and/or a permanent part of the attachment member, and wherein this first location is a first distance from the outer circumference of the person's arm around the elbow when the arm is fully extended; and (c) a second display module which communicates with the person by emitting and/or reflecting light energy, wherein this second display module has a centroid, wherein this centroid is at a second location when this second display module is removably attached to and/or a permanent part of the attachment member, and wherein this second location is a second distance from the outer circumference of the person's arm around the elbow when the arm is fully extended; and wherein the second distance is less than the first distance.

In an example, this invention can be embodied in a forearm-wearable device with a distal-to-proximal plurality of display modules comprising: (a) a band, strap, sleeve, or cuff which is configured to be worn around at least 50% of a circumference of a person's wrist and/or forearm; wherein the band, strap, sleeve, or cuff has multiple distal-to-proximal axes, each of which spans the band, strap, sleeve, or cuff in a distal-to-proximal manner and perpendicularly intersects the circumference the person's wrist and/or forearm; wherein distal means further from the circumference of the person's arm around the elbow when the arm is fully extended; and wherein proximal means closer to the circumference of the person's arm around the elbow when the arm is fully extended; (b) a first display module; wherein this first display module is removably attached to and/or a permanent part of the band, strap, sleeve, or cuff; wherein this first display module communicates with the person by emitting and/or reflecting light energy; wherein the light-emitting surface of this first display module has a first centroid; and (c) a second display module; wherein this second display module is removably attached to and/or a permanent part of the band, strap, sleeve, or cuff; wherein this display module communicates with the person by emitting and/or reflecting light energy; wherein the light-emitting surface of this second display module has a second centroid; and wherein the second centroid is closer to the circumference of the person's arm around the elbow when the arm is fully extended than the first centroid.

In an example, this invention can be embodied in a forearm-wearable device with a distal-to-proximal plurality of display modules comprising: (a) a band, strap, sleeve, or cuff which is configured to be worn around at least 50% of a circumference of a person's wrist and/or forearm; wherein the band, strap, sleeve, or cuff has multiple distal-to-proximal axes, each of which spans the band, strap, sleeve, or cuff in a distal-to-proximal manner and perpendicularly intersects the circumference the person's wrist and/or forearm; wherein distal means further from the circumference of the person's arm around the elbow when the arm is fully extended; and wherein proximal means closer to the circumference of the person's arm around the elbow when the arm is fully extended; (b) a first display module; wherein this first display module is removably attached to and/or a permanent part of the band, strap, sleeve, or cuff; wherein this first display module communicates with the person by emitting and/or reflecting light energy; wherein the light-emitting surface of this first display module has a first distal edge which is furthest from the person's elbow; wherein the light-emitting surface of this first display module has a first proximal edge which is closest to the person's elbow; and (c) a second display module; wherein this second display module is removably attached to and/or a permanent part of the band, strap, sleeve, or cuff; wherein this display module communicates with the person by emitting and/or reflecting light energy; wherein the light-emitting surface of this second display module has a second distal edge which is furthest from the person's elbow; wherein the light-emitting surface of this second display module has a second proximal edge which is closest to the person's elbow; and wherein the second distal edge is closer to the circumference of the person's arm around the elbow when the arm is fully extended than the first proximal edge.

In an example, this invention can be embodied in a forearm-wearable device with a distal-to-proximal plurality of display modules comprising: (a) a band, strap, sleeve, or cuff which is configured to be worn around at least 50% of a circumference of a person's wrist and/or forearm; wherein the band, strap, sleeve, or cuff has multiple distal-to-proximal axes, each of which spans the band, strap, sleeve, or cuff in a distal-to-proximal manner and perpendicularly intersects the circumference the person's wrist and/or forearm; wherein distal means further from the circumference of the person's arm around the elbow when the arm is fully extended; and wherein proximal means closer to the circumference of the person's arm around the elbow when the arm is fully extended; (b) a first display module; wherein this first display module is removably attached to and/or a permanent part of the band, strap, sleeve, or cuff; wherein this first display module communicates with the person by emitting and/or reflecting light energy; wherein the light-emitting surface of this first display module has a first centroid; and (c) a second display module; wherein this second display module is removably attached to and/or a permanent part of the band, strap, sleeve, or cuff; wherein this display module communicates with the person by emitting and/or reflecting light energy; wherein the light-emitting surface of this second display module has a second centroid; wherein the second centroid is closer to the circumference of the person's arm around the elbow when the arm is fully extended than the first centroid; and wherein the first and second centroids are both intersected by the same distal-to-proximal axis of the band, strap, sleeve, or cuff.

In an example, this invention can be embodied in a forearm-wearable device with a distal-to-proximal plurality of display modules comprising: (a) an attachment member, wherein this attachment member is configured to be worn around at least 50% of a circumference of the person's wrist and/or forearm, wherein inner is defined as closer to the person's skin and outer is defined as further from the person's skin, and wherein distal is defined as further from the circumference of the person's arm around the elbow when the arm is fully extended and proximal is defined as closer to the circumference of the person's arm around the elbow when the arm is fully extended; (b) a first display module which is removably attached to the attachment member, wherein this first display module has an outer surface with a first centroid; and (c) a second display module which is removably attached to the attachment member, wherein this second display module has an outer surface with a second centroid, and wherein the second centroid is more proximal than the first centroid.

In an example, this invention can be embodied in a forearm-wearable device with a distal-to-proximal plurality of display modules comprising: (a) an attachment member, wherein this attachment member is configured to be worn around at least 50% of a circumference of the person's wrist and/or forearm, wherein inner is defined as closer to the person's skin and outer is defined as further from the person's skin, and wherein distal is defined as further from the circumference of the person's arm around the elbow when the arm is fully extended and proximal is defined as closer to the circumference of the person's arm around the elbow when the arm is fully extended; (b) a first display module which is removably attached to the attachment member, wherein this first display module has an outer surface with a first distal edge and a first proximal edge; and (c) a second display module which is removably attached to the attachment member, wherein this second display module has an outer surface with a second distal edge and a second proximal edge, and wherein the second distal edge is more proximal than the first proximal edge.

In an example, this invention can be embodied in a forearm-wearable device with a distal-to-proximal plurality of display modules comprising: (a) an attachment member, wherein this attachment member is configured to be worn around at least 50% of a circumference of the person's wrist and/or forearm, wherein inner is defined as closer to the person's skin and outer is defined as further from the person's skin, wherein distal is defined as further from the circumference of the person's arm around the elbow when the arm is fully extended and proximal is defined as closer to the circumference of the person's arm around the elbow when the arm is fully extended, and wherein there is a selected distal-to-proximal axis which spans the surface of the attachment member at a selected radial position on the circumference of the person's wrist and/or forearm; (b) a first display module which is removably attached to the attachment member, wherein this first display module has an outer surface with a first distal edge along the selected distal-to-proximal axis and a first proximal edge along the selected distal-to-proximal axis; and; (c) a second display module which is removably attached to the attachment member, wherein this second display module has an outer surface with a second distal edge along the selected distal-to-proximal axis and a second proximal edge on the selected distal-to-proximal axis, and wherein the second distal edge is more proximal than the first proximal edge.

In an example, this invention can be embodied in a forearm sleeve, cuff, strap, or band device with a distal-to-proximal plurality of display modules comprising: (a) a sleeve, cuff, strap, or band, wherein this sleeve, cuff, strap, or band is configured to be worn around at least 50% of a circumference of the person's wrist and/or forearm, wherein inner is defined as closer to the person's skin and outer is defined as further from the person's skin, and wherein distal is defined as further from the circumference of the person's arm around the elbow when the arm is fully extended and proximal is defined as closer to the circumference of the person's arm around the elbow when the arm is fully extended; (b) a first display module which is removably attached to the sleeve, cuff, strap, or band, wherein this first display module has an outer surface with a first centroid; and (c) a second display module which is removably attached to the sleeve, cuff, strap, or band, wherein this second display module has an outer surface with a second centroid, and wherein the second centroid is more proximal than the first centroid.

In an example, this invention can be embodied in a forearm sleeve, cuff, strap, or band device with a distal-to-proximal plurality of display modules comprising: (a) a sleeve, cuff, strap, or band, wherein this sleeve, cuff, strap, or band is configured to be worn around at least 50% of a circumference of the person's wrist and/or forearm, wherein inner is defined as closer to the person's skin and outer is defined as further from the person's skin, and wherein distal is defined as further from the circumference of the person's arm around the elbow when the arm is fully extended and proximal is defined as closer to the circumference of the person's arm around the elbow when the arm is fully extended; (b) a first display module which is removably attached to the sleeve, cuff, strap, or band, wherein this first display module has an outer surface with a first distal edge and a first proximal edge; and (c) a second display module which is removably attached to the sleeve, cuff, strap, or band, wherein this second display module has an outer surface with a second distal edge and a second proximal edge, and wherein the second distal edge is more proximal than the first proximal edge.

In an example, this invention can be embodied in a forearm sleeve, cuff, strap, or band device with a distal-to-proximal plurality of display modules comprising: (a) a sleeve, cuff, strap, or band, wherein this sleeve, cuff, strap, or band is configured to be worn around at least 50% of a circumference of the person's wrist and/or forearm, wherein inner is defined as closer to the person's skin and outer is defined as further from the person's skin, wherein distal is defined as further from the circumference of the person's arm around the elbow when the arm is fully extended and proximal is defined as closer to the circumference of the person's arm around the elbow when the arm is fully extended, and wherein there is a selected distal-to-proximal axis which spans the surface of the sleeve, cuff, strap, or band at a selected radial position on the circumference of the person's wrist and/or forearm; (b) a first display module which is removably attached to the sleeve, cuff, strap, or band, wherein this first display module has an outer surface with a first distal edge along the selected distal-to-proximal axis and a first proximal edge along the selected distal-to-proximal axis; and; (c) a second display module which is removably attached to the sleeve, cuff, strap, or band, wherein this second display module has an outer surface with a second distal edge along the selected distal-to-proximal axis and a second proximal edge on the selected distal-to-proximal axis, and wherein the second distal edge is more proximal than the first proximal edge.

In an example, this invention can be embodied in a forearm-wearable device with a distal-to-proximal plurality of display modules comprising: (a) an attachment member, wherein this attachment member is configured to be worn around at least 50% of a circumference of the person's wrist and/or forearm, wherein inner is defined as closer to the person's skin and outer is defined as further from the person's skin, and wherein distal is defined as further from the circumference of the person's arm around the elbow when the arm is fully extended and proximal is defined as closer to the circumference of the person's arm around the elbow when the arm is fully extended; (b) a first display module which is an integral part of the attachment member, wherein this first display module has an outer surface with a first centroid; and (c) a second display module which is an integral part of the attachment member, wherein this second display module has an outer surface with a second centroid, and wherein the second centroid is more proximal than the first centroid.

In an example, this invention can be embodied in a forearm-wearable device with a distal-to-proximal plurality of display modules comprising: (a) an attachment member, wherein this attachment member is configured to be worn around at least 50% of a circumference of the person's wrist and/or forearm, wherein inner is defined as closer to the person's skin and outer is defined as further from the person's skin, and wherein distal is defined as further from the circumference of the person's arm around the elbow when the arm is fully extended and proximal is defined as closer to the circumference of the person's arm around the elbow when the arm is fully extended; (b) a first display module which is an integral part of the attachment member, wherein this first display module has an outer surface with a first distal edge and a first proximal edge; and (c) a second display module which is an integral part of the attachment member, wherein this second display module has an outer surface with a second distal edge and a second proximal edge, and wherein the second distal edge is more proximal than the first proximal edge.

In an example, this invention can be embodied in a forearm-wearable device with a distal-to-proximal plurality of display modules comprising: (a) an attachment member, wherein this attachment member is configured to be worn around at least 50% of a circumference of the person's wrist and/or forearm, wherein inner is defined as closer to the person's skin and outer is defined as further from the person's skin, wherein distal is defined as further from the circumference of the person's arm around the elbow when the arm is fully extended and proximal is defined as closer to the circumference of the person's arm around the elbow when the arm is fully extended, and wherein there is a selected distal-to-proximal axis which spans the surface of the attachment member at a selected radial position on the circumference of the person's wrist and/or forearm; (b) a first display module which is an integral part of the attachment member, wherein this first display module has an outer surface with a first distal edge along the selected distal-to-proximal axis and a first proximal edge along the selected distal-to-proximal axis; and; (c) a second display module which is an integral part of the attachment member, wherein this second display module has an outer surface with a second distal edge along the selected distal-to-proximal axis and a second proximal edge on the selected distal-to-proximal axis, and wherein the second distal edge is more proximal than the first proximal edge.

In an example, this invention can be embodied in a forearm-wearable device with a distal-to-proximal plurality of display modules comprising: (a) an attachment member, wherein this attachment member is configured to be worn around at least 50% of a circumference of the person's wrist and/or forearm, wherein inner is defined as closer to the person's skin and outer is defined as further from the person's skin, and wherein distal is defined as further from the circumference of the person's arm around the elbow when the arm is fully extended and proximal is defined as closer to the circumference of the person's arm around the elbow when the arm is fully extended; (b) a first human-computer-interface (HCI) component which is removably attached to the attachment member, wherein this first HCl component has an outer surface with a first centroid; and (c) a second human-computer-interface (HCI) component which is removably attached to the attachment member, wherein this second HCl component has an outer surface with a second centroid, and wherein the second centroid is more proximal than the first centroid.

In an example, this invention can be embodied in a forearm-wearable device with a distal-to-proximal plurality of display modules comprising: (a) an attachment member, wherein this attachment member is configured to be worn around at least 50% of a circumference of the person's wrist and/or forearm, wherein inner is defined as closer to the person's skin and outer is defined as further from the person's skin, and wherein distal is defined as further from the circumference of the person's arm around the elbow when the arm is fully extended and proximal is defined as closer to the circumference of the person's arm around the elbow when the arm is fully extended; (b) a first human-computer-interface (HCI) component which is removably attached to the attachment member, wherein this first HCl component has an outer surface with a first distal edge and a first proximal edge; and (c) a second human-computer-interface (HCI) component which is removably attached to the attachment member, wherein this second HCl component has an outer surface with a second distal edge and a second proximal edge, and wherein the second distal edge is more proximal than the first proximal edge.

In an example, this invention can be embodied in a forearm-wearable device with a distal-to-proximal plurality of display modules comprising: (a) an attachment member, wherein this attachment member is configured to be worn around at least 50% of a circumference of the person's wrist and/or forearm, wherein inner is defined as closer to the person's skin and outer is defined as further from the person's skin, wherein distal is defined as further from the circumference of the person's arm around the elbow when the arm is fully extended and proximal is defined as closer to the circumference of the person's arm around the elbow when the arm is fully extended, and wherein there is a selected distal-to-proximal axis which spans the surface of the attachment member at a selected radial position on the circumference of the person's wrist and/or forearm; (b) a first human-computer-interface (HCI) component which is removably attached to the attachment member, wherein this first HCl component has an outer surface with a first distal edge along the selected distal-to-proximal axis and a first proximal edge along the selected distal-to-proximal axis; and; (c) a second human-computer-interface (HCI) component which is removably attached to the attachment member, wherein this second HCl component has an outer surface with a second distal edge along the selected distal-to-proximal axis and a second proximal edge on the selected distal-to-proximal axis, and wherein the second distal edge is more proximal than the first proximal edge.

In an example, this invention can be embodied in a forearm-wearable device with a distal-to-proximal plurality of modular electronic components comprising: (a) an attachment member, wherein this attachment member is configured to be worn around at least 50% of a circumference of the person's wrist and/or forearm, wherein inner is defined as closer to the person's skin and outer is defined as further from the person's skin, and wherein distal is defined as further from the circumference of the person's arm around the elbow when the arm is fully extended and proximal is defined as closer to the circumference of the person's arm around the elbow when the arm is fully extended; (b) a first modular electronic component which is removably attached to the attachment member, wherein this first modular electronic component has an outer surface with a first centroid; and (c) a second modular electronic component which is removably attached to the attachment member, wherein this second modular electronic component has an outer surface with a second centroid, and wherein the second centroid is more proximal than the first centroid.

In an example, this invention can be embodied in a forearm-wearable device with a distal-to-proximal plurality of modular electronic components comprising: (a) an attachment member, wherein this attachment member is configured to be worn around at least 50% of a circumference of the person's wrist and/or forearm, wherein inner is defined as closer to the person's skin and outer is defined as further from the person's skin, and wherein distal is defined as further from the circumference of the person's arm around the elbow when the arm is fully extended and proximal is defined as closer to the circumference of the person's arm around the elbow when the arm is fully extended; (b) a first modular electronic component which is removably attached to the attachment member, wherein this first modular electronic component has an outer surface with a first distal edge and a first proximal edge; and (c) a second modular electronic component which is removably attached to the attachment member, wherein this second modular electronic component has an outer surface with a second distal edge and a second proximal edge, and wherein the second distal edge is more proximal than the first proximal edge.

In an example, this invention can be embodied in a forearm-wearable device with a distal-to-proximal plurality of modular electronic components comprising: (a) an attachment member, wherein this attachment member is configured to be worn around at least 50% of a circumference of the person's wrist and/or forearm, wherein inner is defined as closer to the person's skin and outer is defined as further from the person's skin, wherein distal is defined as further from the circumference of the person's arm around the elbow when the arm is fully extended and proximal is defined as closer to the circumference of the person's arm around the elbow when the arm is fully extended, and wherein there is a selected distal-to-proximal axis which spans the surface of the attachment member at a selected radial position on the circumference of the person's wrist and/or forearm; (b) a first modular electronic component which is removably attached to the attachment member, wherein this first modular electronic component has an outer surface with a first distal edge along the selected distal-toproximal axis and a first proximal edge along the selected distal-to-proximal axis; and; (c) a second modular electronic component which is removably attached to the attachment member, wherein this second modular electronic component has an outer surface with a second distal edge along the selected distal-to-proximal axis and a second proximal edge on the selected distal-to-proximal axis, and wherein the second distal edge is more proximal than the first proximal edge.

Figure 74:
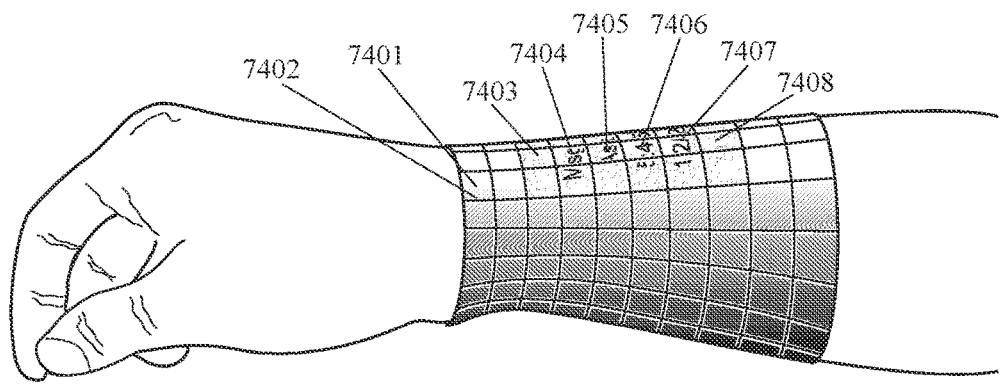
FIG. 74 shows a wearable device with a distal-to-proximal array of flexibly-connected displays, wherein this device spans the entire wrist and/or forearm circumference.
Figure 74:
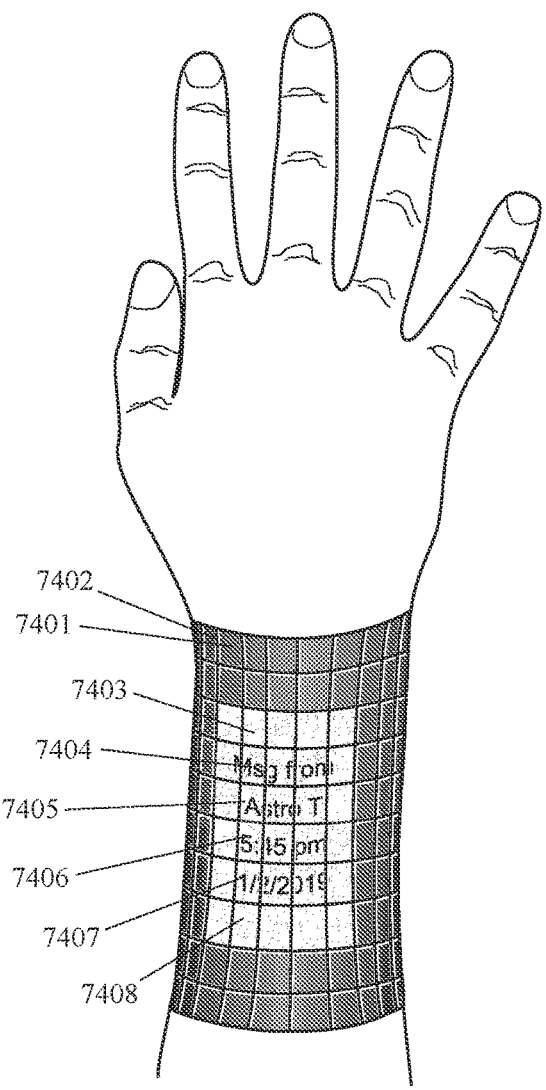

We now discuss the examples shown in FIGS. 74 through 89 in detail. The component, parameter, and other example variations which have just been discussed can be applied (where relevant) to the examples shown in FIG. 74 through 89. FIG. 74 shows an example of how this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

FIG. 74 also shows an example of how this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

The upper section of FIG. 74 shows a side view of this device being worn on a person's forearm. The lower section of FIG. 74 shows a top-down view of this same device. The component, parameter, and other example variations which were discussed in previous sections can also be applied where relevant to the example shown here in FIG. 74. The example shown in FIG. 74 comprises: attachment member 7401 with multiple flexibly-connected parts which are connected by flexible and/or stretchable joints (including 7402); and a distal-to-proximal row of display modules (including 7403, 7404, 7405, 7406, 7407, and 7408) which are connected by flexible and/or stretchable joints. In an example, the joints which connect the display modules can stretch less than the joints elsewhere in attachment member 7401; this enables the display modules to move and collectively conform to the curve of the forearm without having large gaps between them.

In the example that is shown in FIG. 74, attachment member 7401 is configured to be worn around the entire circumference of the person's wrist and/or forearm. In this example, first display module 7403 and second display module 7404 communicate with the person by emitting and/or reflecting light energy. In this example, these display modules are small computer touch screens, each of which displays a portion of a text message. The flexible connections between these display modules enable these display modules to move and collectively conform to the curved shape of the person's wrist and/or forearm. In this example, first display module 7403 is a first distance from the outer circumference of the person's arm at the elbow (when the arm is fully extended) and second display module 7404 is a second distance from the outer circumference of the person's arm at the elbow (when the arm is fully extended). In this example, the second distance is less than the first distance.

In this example, one can draw multiple distal-to-proximal axes across the width of attachment member 7401. Each of these distal-to-proximal axes is perpendicular to the circumference of the attachment member at a particular point on that circumference. In this example, these distal-to-proximal axes are approximately-equal in size because the width of attachment member 7401 is approximately constant. In this example, a distal-to-proximal axis (the width of the attachment member) spans more than 4". In this example, attachment member 7401 encircles the entire circumference of the person's wrist and/or forearm. In this example, attachment member 7401 is sufficiently flexible and stretchable to be slid over the person's hand onto the person's wrist and/or forearm.

In this example, attachment member 7401 is worn in a manner similar to an elastic and/or stretchable armband, armlet, bangle, bracelet, chain mail sleeve, gauntlet, fitness band, forearm computer, garment cuff, garment sleeve, separate cuff, separate sleeve, smart watch, strap, tubular mesh, wrist band, or wrist computer. In this example, attachment member 7401 has been selected from the group consisting of: armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer.

In this example, a distal-to-proximal row of display modules (including 7403, 7404, 7405, 7406, 7407, and 7408) is a permanent part of attachment member 7401. In another example, a distal-to-proximal row of display modules can be removably attached to different locations an attachment member. In this example, there is a 5×6 (row× column) array of display modules with 5 rows and 6 columns (or rings). In this example, the portion of attachment member 7401 that includes this array of display modules spans at least 10% of the surface area of the attachment member.

In this example, display modules (including 7403, 7404, 7405, 7406, 7407, and 7408) are selected from the group consisting of: computer screen, computer display, touch screen, light-emitting member, infrared light emitter, laser, light emitting diode (LED), light-emitting optical fiber, optical emitter, optochemical sensor, birefringent material, crystal, cylindrical prism, eye-tracking sensor, fiber optic bend sensor, fiber optic member, lens, light-conducting fiber, light-conducting members, metamaterial light channel, mirror, mirror array, optical fiber, optoelectronic lens, variable-focal-length lens, display screen, image display member, imaging device, light-emitting member array or matrix, light display array or matrix, light emitting diode (LED) array or matrix, liquid crystal display (LCD), textile-based light display, camouflaged wearable image-display, fiber optic display array or matrix, microlens array, micro-mirror array, image projector, non-coherent-light image projector, infra-red projector, holoprojector, selected-angle projector, and coherent light image projector.

In this example, the visual information which is displayed by first display module 7403 and the visual information which is displayed by second display module 7404 are two different parts of the same text message. In this example, the entire message is conveyed by the entire 5×6 array of display modules. In an example, visual information displayed by these two display modules can be different parts of the same image, document, map, menu, webpage, or application. In an alternative example, visual information displayed by two display modules can be different contents. In this example, display modules (including 7403, 7404, 7405, 7406, 7407, and 7408) have the same display technology. In an example, two display modules can have different display technologies. In an example, one display module can create an image by emitting light and the other display can create an image by reflecting light.

In this example, first display module 7403 and second display module 7404 each have a cross-sectional size that is greater than ¼ square inch. In an example, they can be even larger. In an example, two display modules can differ in size. In this example, a display module has a cross-sectional shape which is selected from the group consisting of: square, square with rounded vertexes, quadrilateral, quadrilateral with rounded vertexes, circle, hexagon, oval, ellipse, triangle, diamond, and keystone. In an example, two display modules can differ in shape.

In this example, the centroid of first display module 7403 and the centroid of second display module 7404 are laterally aligned in a row; the centroid of first display module 7403 and the centroid of second display module 7404 both intersect the same virtual distal-to-proximal axis of the attachment member. Also, first display module 7403 has a cross-sectional centroid, second display module 7404 has a distal edge which is furthest from the person's elbow, and the cross-sectional centroid of the first display module is further from the person's elbow than the distal edge of the second display module. Also, first display module 7403 has a distal edge which is furthest from the person's elbow and a proximal edge which is closest to the person's elbow, second display module 7404 has a distal edge which is furthest from the person's elbow and a proximal edge which is closest to the person's elbow, and the proximal edge of the first display module is further from the person's elbow than the distal edge of the second display module.

In this example, first display module 7403 has a distal edge which is furthest from the person's elbow, a centroid, and a proximal edge which is closest to the person's elbow; second display module 7404 has a distal edge which is furthest from the person's elbow, a centroid, and a proximal edge which is closest to the person's elbow; the proximal edge of the first display module is further from the person's elbow than the distal edge of the second display module; and the centroid of the first display module and the centroid of the second display module are both intersected by the same distal-to-proximal axis of the attachment member.

In this example, first display module 7403 has a cross-sectional centroid, second display module 7404 has a distal edge which is furthest from the outer circumference of the arm around the elbow, and the cross-sectional centroid of the first display module is further from the outer circumference of the arm around the elbow than the distal edge of the second display module. In this example, first display module 7403 has a distal edge which is furthest from the outer circumference of the arm around the elbow and a proximal edge which is closest to the outer circumference of the arm around the elbow, second display module 7404 has a distal edge which is furthest from the outer circumference of the arm around the elbow and a proximal edge which is closest to the outer circumference of the arm around the elbow, and the proximal edge of the first display module is further from the outer circumference of the arm around the elbow than the distal edge of the second display module.

In this example, first display module 7403 has a distal edge which is furthest from the outer circumference of the arm around the elbow, a centroid, and a proximal edge which is closest to the outer circumference of the arm around the elbow; a second display module 7404 has a distal edge which is furthest from the outer circumference of the arm around the elbow, a centroid, and proximal edge which is closest to the outer circumference of the arm around the elbow; the proximal edge of the first display module is further from the outer circumference of the arm around the elbow than the distal edge of the second display module; and the centroid of the first display module and the centroid of the second display module are both intersected by the same distal-to-proximal axis of the attachment member.

In this example, the cross-sectional perimeter of first display module 7403 and the cross-sectional perimeter of second display module 7404 both intersect the same distal-to-proximal axis of the attachment member. In this example, this device comprises a first distal-to-proximal row of flexibly-connected display modules whose centroids all intersect a first distal-to-proximal axis of the attachment member and a second distal-to-proximal row of flexibly-connected display modules whose centroids all intersect a second distal-to-proximal axis of the attachment member, wherein the first distal-to-proximal axis is parallel to the second distal-to-proximal axis. In this example, this device comprises a first distal-to-proximal row of flexibly-connected parts of the attachment member whose centroids all intersect a first distal-to-proximal axis of the attachment member and a second distal-to-proximal row of flexibly-connected parts of the attachment member whose centroids all intersect a second distal-to-proximal axis of the attachment member, wherein the first distal-to-proximal axis is parallel to the second distal-to-proximal axis.

In this example, the display modules are configured to form (partial) rings as well as rows. In this example, there are six (partial) rings of display modules in a display module array on the attachment member. In this example, a plurality of display modules form a circumferential (or partially circumferential) ring with respect to the attachment member. In this example, the centroids of a (full or partial) ring of display modules all intersect the same circumference around a person's wrist and/or forearm. In this example, this device further comprises a first (full or partial) ring of display modules whose centroids all intersect a first circumference of the person's wrist and/or forearm and a second (full or partial) ring of display modules whose centroids all intersect a second circumference of the person's wrist and/or forearm, wherein the first circumference is parallel to the second circumference. In total, this example includes six (partial) rings of display modules.

In this example, attachment member 7401 has a 5×6 row-by-ring array of flexibly-connected display modules, wherein the row dimension is along a distal-to-proximal axis and the ring dimension is around a circumference of the person's arm. In this example, the (row×ring) array size is at greater than (4×4). In this example, the attachment member has a row-by-ring array of rigid display modules which are flexibly connected by flexible and/or stretchable joints, wherein the row dimension is along a distal-to-proximal axis and the ring dimension is around a circumference of the person's arm, and wherein the (row×ring) array size is at least (4×4). In this example, the attachment member has a row-by-ring array of rigid display modules which are flexibly connected by flexible and/or stretchable material, wherein the row dimension is along a distal-to-proximal axis and the ring dimension is around a circumference of the person's arm, and wherein the (row×ring) array size is at least (4×4). In an example, an attachment member can have a row-by-ring array of removably attached display modules, wherein the row dimension is along a distal-to-proximal axis and the ring dimension is around a circumference of the person's arm, and wherein the (row×ring) array size is at least (4×4).

In this example, attachment member 7401 has a 5×6 array of flexibly-connected display modules, wherein the (a×b) dimensions of this array are (a=distal-to-proximal) and (b=circumferential). In this example, the (a×b) array size is greater than (4×4). In this example, the attachment member has an array of rigid display modules which are flexibly connected by flexible and/or stretchable joints, wherein the (a×b) dimensions of this array are (a=distal-to-proximal) and (b=circumferential), and wherein the (a×b) array size is at least (4×4). In this example, the attachment member has an array of rigid display modules which are flexibly connected by flexible and/or stretchable material, wherein the (a×b) dimensions of this array are (a=distal-to-proximal) and (b=circumferential), and wherein the (a×b) array size is at least (4×4). In an example, an attachment member can have an array of removably attached display modules, wherein the (a×b) dimensions of this array are (a=distal-to-proximal) and (b=circumferential), and wherein the (a×b) array size is at least (4×4).

In this example, attachment member 7401 includes a flexibly-connected array (or mesh) of rigid quadrilateral parts. In this example, these flexibly-connected rigid parts are connected by flexible and/or stretchable material, flexible and/or stretchable joints, rotating joints, bendable joints, and/or moveable joints (including 7402). In an example, this device can also comprise modular electronic components other than display modules. In an example, attachment member 7401 can further comprise other modular electronic components which can be permanent parts of the attachment member or removably attached to the attachment member. In an example, these modular electronic components can have cross-sectional shapes which are selected from the group consisting of: square, square with rounded vertexes, quadrilateral, quadrilateral with rounded vertexes, circle, hexagon, oval, ellipse, triangle, diamond, and keystone.

Figure 75:
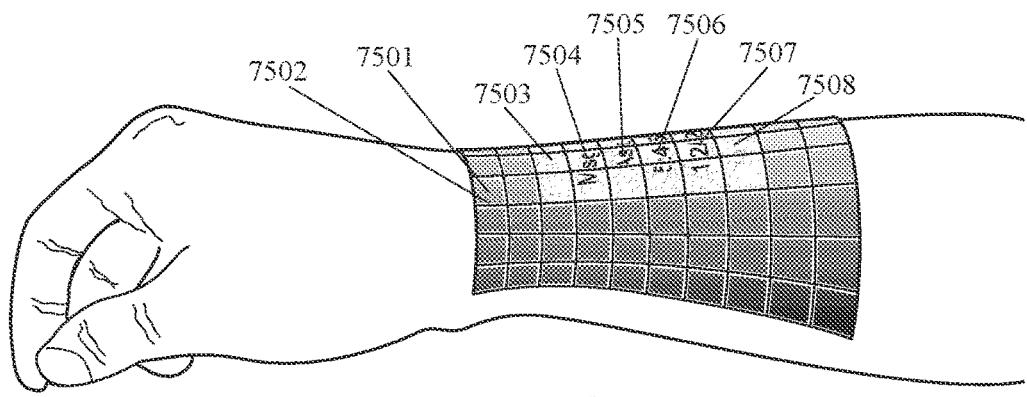
FIG. 75 shows a first wearable device with a distal-to-proximal array of flexibly-connected displays, wherein this device spans at least 50% of the wrist and/or forearm circumference.
Figure 75:
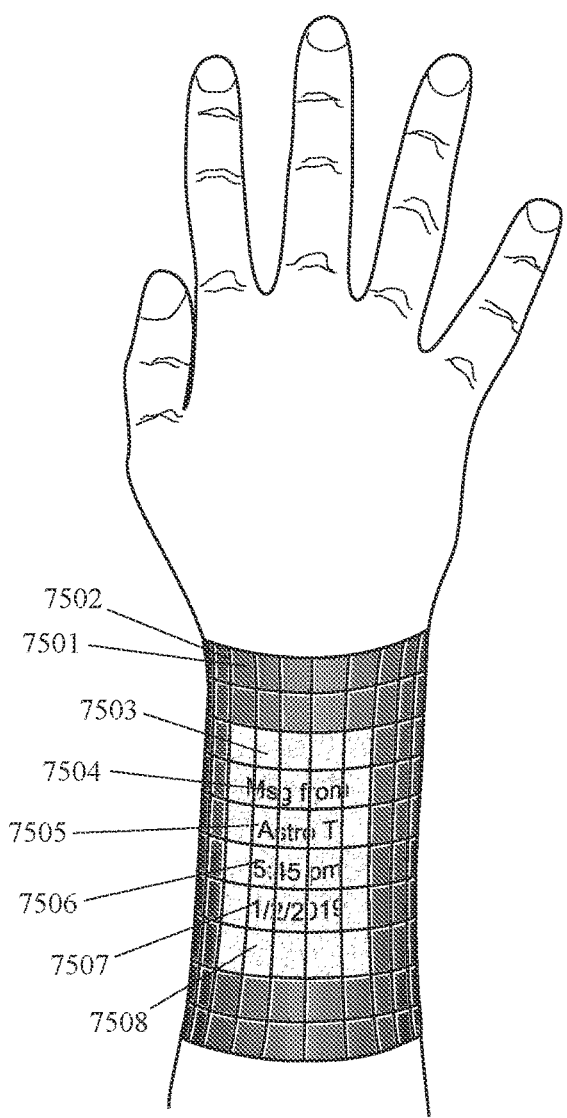

FIG. 75 shows another example of how this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

FIG. 75 also shows another example of how this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

The example device that is shown in FIG. 75 is similar to the one that was shown in FIG. 74, except that now the attachment member does not span the entire circumference of the person's forearm. In this example, the attachment member spans approximately 70% of the circumference of the person's forearm. In order to hold the attachment member in FIG. 75 on the forearm, the attachment member in FIG. 75 must be less elastic than the attachment member in FIG. 74. The attachment member must be sufficiently flexible to slip laterally onto the person's forearm, but also be sufficiently resilient to hug the forearm once it is placed there. This can be done by making the attachment member resiliently flexible. In an example, flexible joints (including 7502) in FIG. 75 can include tensile members which enable the attachment member to be expanded over the forearm, but also cause the attachment member to hug the forearm once it is placed there. In another example, ends of an attachment member can be connected around the forearm by a clasp, buckle, or other closure mechanism in order to hold the attachment member on the forearm.

The upper section of FIG. 75 shows a side view of this device being worn on a person's forearm. The lower section of FIG. 75 shows a top-down view of this same device. The example in FIG. 75 comprises: attachment member 7501 with multiple flexibly-connected parts which are connected by resiliently-flexible joints (including 7502); and a distal-to-proximal row of flexibly-connected display modules (including 7503, 7504, 7505, 7506, 7507, and 7508) which are also connected by resiliently-flexible joints. The component, parameter, and other example variations which have been discussed in previous sections can also be applied where relevant to the example shown here in FIG. 75.

In this example, first display module 7503 and second display module 7504 communicate with the person by emitting and/or reflecting light energy. In this example, these display modules are small computer touch screens, each of which displays a portion of a text message. The flexible connections between these display modules enable them to move and collectively conform to the curved shape of the person's wrist and/or forearm. In this example, first display module 7503 is a first distance from the outer circumference of the person's arm at the elbow (when the arm is fully extended) and second display module 7504 is a second distance from the outer circumference of the person's arm at the elbow (when the arm is fully extended). In this example, the second distance is less than the first distance.

Figure 76:
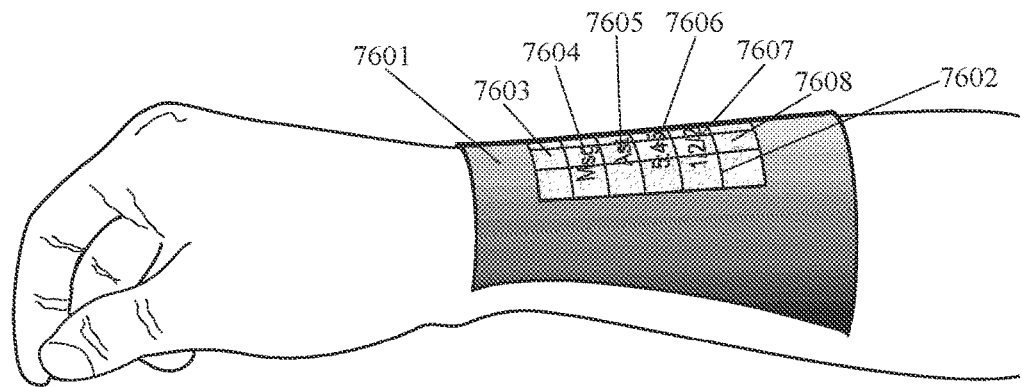
FIG. 76 shows a second wearable device with a distal-to-proximal array of flexibly-connected displays, wherein this device spans at least 50% of the wrist and/or forearm circumference.
Figure 76:
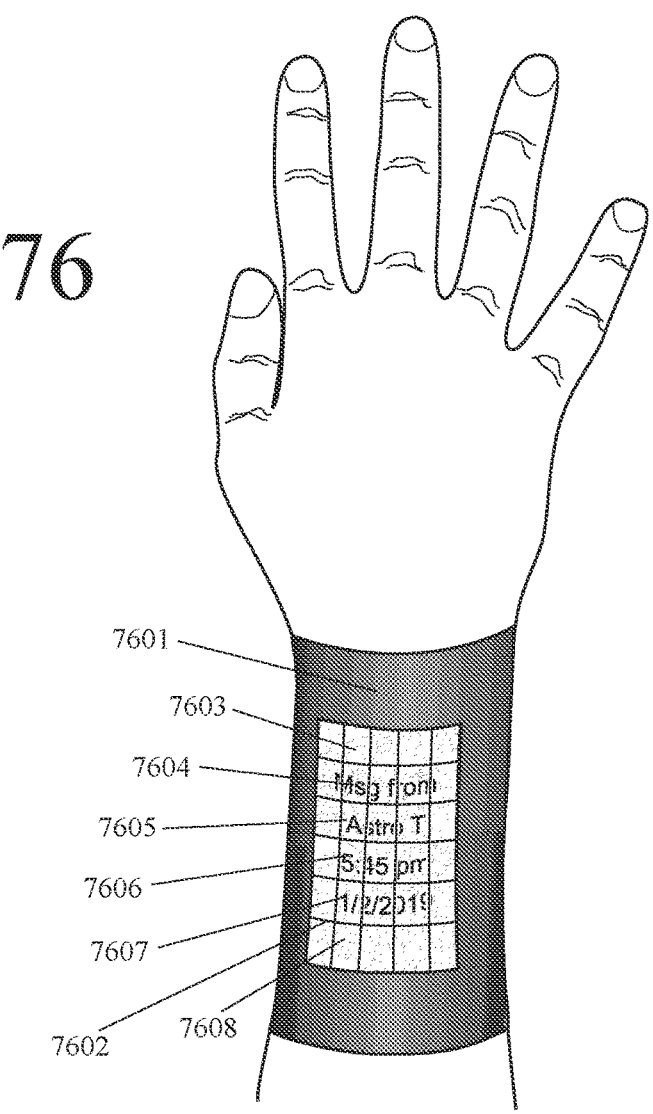

FIG. 76 shows another example of how this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

FIG. 76 also shows another example of how this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

The example of this invention that is shown in FIG. 76 is similar to the one shown in FIG. 75, except that only the portion of the attachment member containing display modules comprises an array of flexibly-connected members. The rest of the attachment member is a single resiliently-flexible piece. The upper section of FIG. 76 shows a side view of this device being worn on a person's forearm. The lower section of FIG. 76 shows a top-down view of this same device. The example in FIG. 76 comprises: attachment member 7601; and a distal-to-proximal row of flexibly-connected display modules (including 7603, 7604, 7605, 7606, 7607, and 7608) which are connected by flexible joints. The component, parameter, and other example variations which have been discussed in previous sections can also be applied where relevant to the example shown here in FIG. 76.

In this example, first display module 7603 and second display module 7604 communicate with the person by emitting and/or reflecting light energy. In this example, these display modules are small computer touch screens which each display a portion of a text message. The flexible connections between these display modules enable them to move and collectively conform to the curved shape of the person's wrist and/or forearm. In this example, first display module 7603 is a first distance from the outer circumference of the person's arm at the elbow (when the arm is fully extended) and second display module 7604 is a second distance from the outer circumference of the person's arm at the elbow (when the arm is fully extended). In this example, the second distance is less than the first distance.

Figure 77:
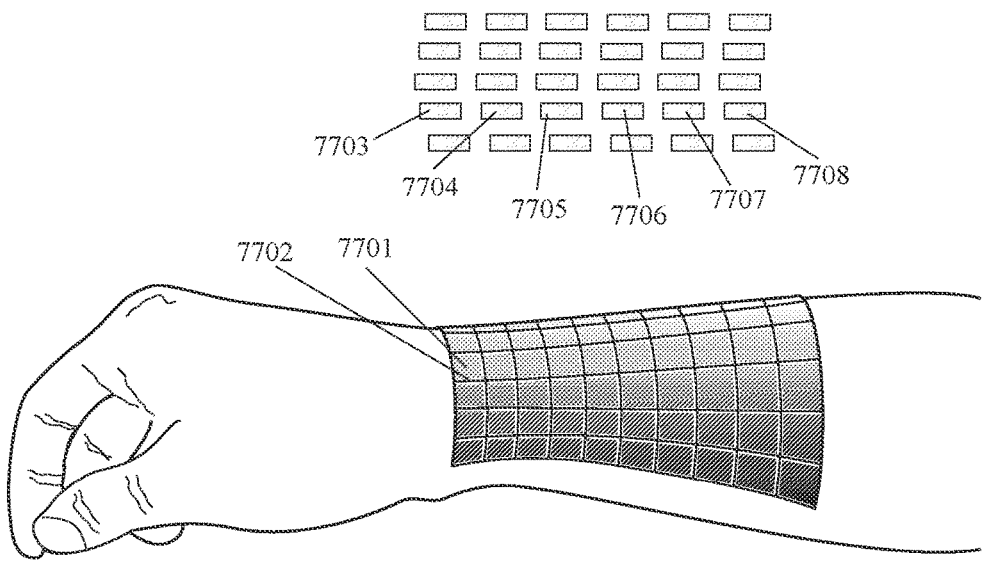
FIGS. 77 and 78 show a wearable device with a distal-to-proximal array of removably-attachable and flexibly-connected displays.
Figure 78:
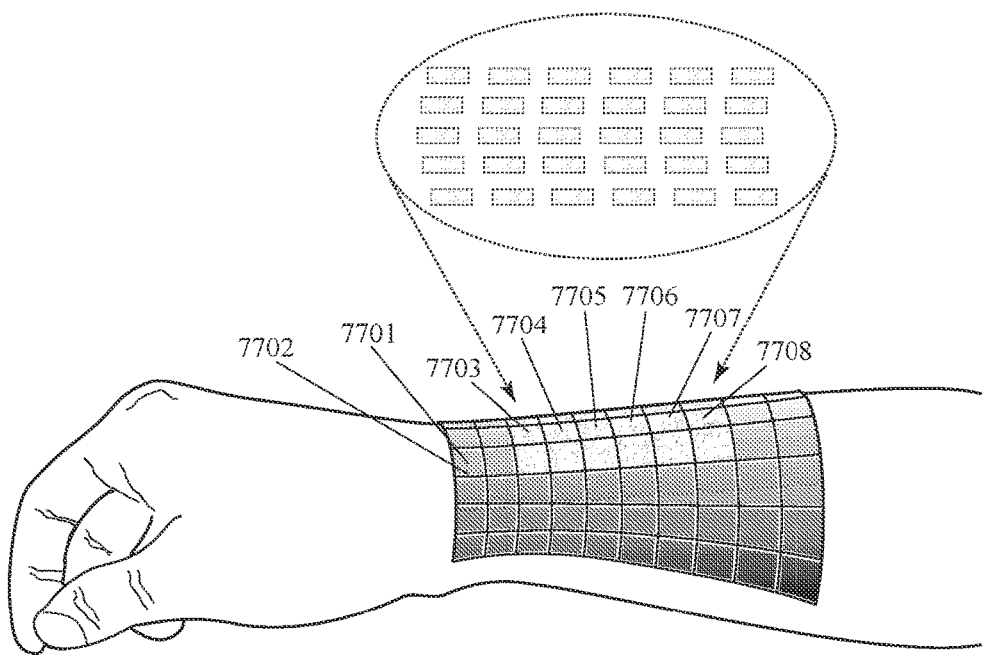

FIGS. 77 and 78 show another example of how this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

FIGS. 77 and 78 also show another example of how this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

The example of this invention that is shown in FIGS. 77 and 78 is similar to the one that was shown in FIG. 75, except that the display modules are removably attachable to attachment member 7701. In order to stay on the forearm, attachment member 7701 in FIGS. 77 and 78 is less elastic than the attachment member in FIG. 74. In an example, flexible joints (such as 7702) in FIGS. 77 and 78 can have tensile members which enable attachment member 7701 to be expanded over the forearm and then fit snugly on the forearm. In another example, the ends of attachment member 7701 can be connected around the forearm by a clasp, buckle, or other closure mechanism.

In an example, display modules (including 7703, 7704, 7705, 7706, 7707, and 7708) can be removably attached to attachment member 7701 by one or more means selected from the group consisting of: clamps, clasps, clips, links, pins, plugs, prongs, threads, or snaps. In an example, a plurality of display modules (including 7703, 7704, 7705, 7706, 7707, and 7708) can be attached to a first set of locations on the attachment member, removed, and then reattached to a second set of locations on the attachment member.

FIG. 77 shows a side view of this device being worn on a person's forearm at a first point in time, before display modules (including 7703, 7704, 7705, 7706, 7707, and 7708) are attached to attachment member 7701. FIG. 78 shows a side view of this same device at a second point in time, after display modules (including 7703, 7704, 7705, 7706, 7707, and 7708) have been attached to attachment member 7701. The example shown in FIGS. 77 and 78 comprises: attachment member 7701 with multiple flexibly-connected parts which are connected by resiliently-flexible joints (including 7702); and a distal-to-proximal row of removably attached flexibly-connected display modules (including 7703, 7704, 7705, 7706, 7707, and 7708) which are connected by resiliently-flexible joints. The component, parameter, and other example variations which have been discussed in previous sections can also be applied where relevant to the example shown here in FIGS. 77 and 78.

In this example, first display module 7703 and second display module 7704 communicate with the person by emitting and/or reflecting light energy. In this example, these display modules are small computer touch screens which each display a portion of a text message. The flexible connections between these display modules enable them to move and collectively conform to the curved shape of the person's wrist and/or forearm. In this example, first display module 7703 is a first distance from the outer circumference of the person's arm at the elbow (when the arm is fully extended) and second display module 7704 is a second distance from the outer circumference of the person's arm at the elbow (when the arm is fully extended). In this example, the second distance is less than the first distance.

In this example, attachment member 7702 is a flexibly-resilient structure with an array of flexibly-connected, parts. In an example, the display modules (including 7703, 7704, 7705, 7706, 7707, and 7708) can be removably attached to these flexibly-connected parts. In an example, attachment member 7701 can further comprise one or more electromagnetic wires, fibers, or channels which connect to display modules (to provide power and/or transfer data) when display modules are attached to the attachment member. In an example, attachment member 7701 can further comprise electromagnetic energy pathways which provide power and/or transmit electromagnetic data to or from display modules (including 7703, 7704, 7705, 7706, 7707, and 7708), power sources, or other modular electronic components which are removably attached to attachment member 7701.

Figure 79:
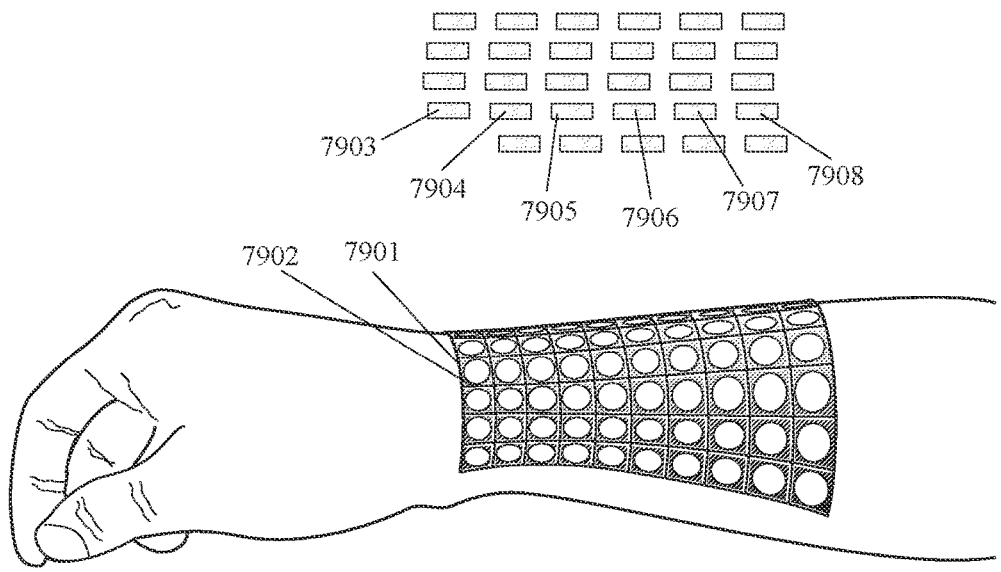
FIGS. 79 and 80 show a wearable device with a distal-to-proximal array of quadrilateral removably-attachable and flexibly-connected displays which are removably inserted into openings in an attachment member.
Figure 80:
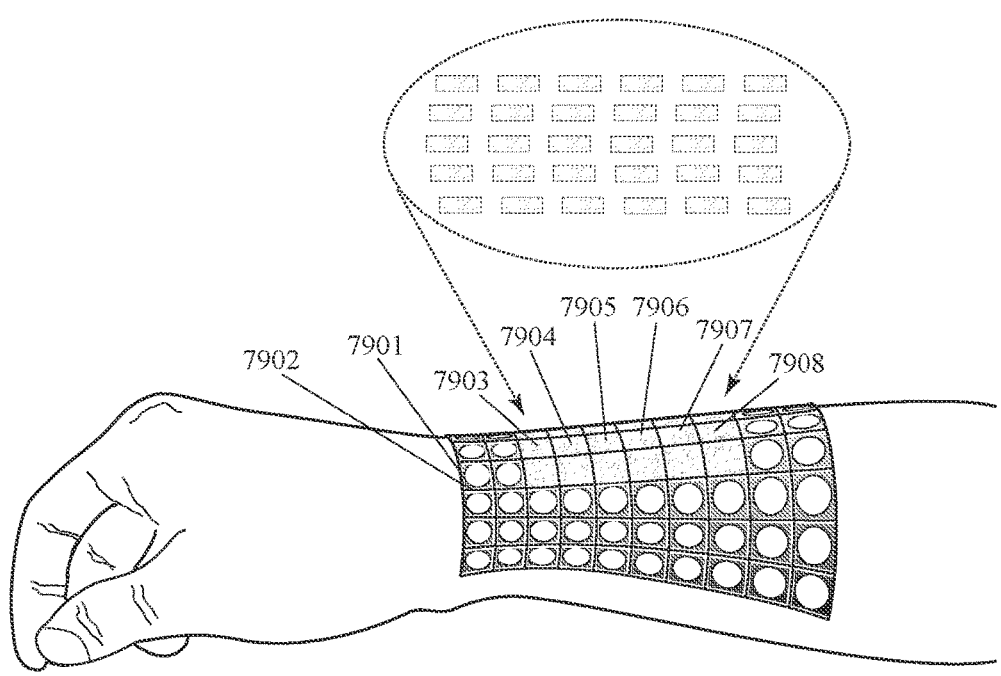

FIGS. 79 and 80 show another example of how this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

FIGS. 79 and 80 also show another example of how this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

The example of this invention that is shown in FIGS. 79 and 80 is similar to the one that was shown in FIGS. 77 and 78 except that the display modules are removably inserted into openings in attachment member 7901. In an example, display modules can be removably inserted into openings by being pushed into the openings. In an example, a display module can form an electromagnetic connection with the attachment member (for providing power or transmitting data) when the display module is inserted into an opening in the attachment member. In an example, display modules can be inserted, removed, and reinserted into different openings in order to form different display configurations and patterns.

FIG. 79 shows a side view of this device being worn on a person's forearm at a first point in time, before display modules (including 7903, 7904, 7905, 7906, 7907, and 7908) are inserted into openings in attachment member 7901. FIG. 80 shows a side view of this same device at a second point in time, after display modules (including 7903, 7904, 7905, 7906, 7907, and 7908) have been inserted into openings in attachment member 7901. The example in FIGS. 79 and 80 comprises: attachment member 7901 with an array (or mesh) of openings which are connected by flexible joints (including 7902); and a distal-to-proximal row of removably attached flexibly-connected display modules (including 7903, 7904, 7905, 7906, 7907, and 7908) which are connected by flexible joints. The component, parameter, and other example variations which have been discussed in previous sections can also be applied (where relevant) to the example shown here in FIGS. 79 and 80.

In this example, first display module 7903 and second display module 7904 communicate with the person by emitting and/or reflecting light energy. In this example, these display modules are small computer touch screens which each display a portion of a text message. The flexible connections between these display modules enable them to move and collectively conform to the curved shape of the person's wrist and/or forearm. In this example, first display module 7903 is a first distance from the outer circumference of the person's arm at the elbow (when the arm is fully extended) and second display module 7904 is a second distance from the outer circumference of the person's arm at the elbow (when the arm is fully extended). In this example, the second distance is less than the first distance.

In this example, attachment member 7902 has a flexible array (or mesh) of openings. In this example, these openings are circular. In other examples, openings can be quadrilateral, hexagonal, or other shapes. As shown by this example, a device can comprise at least a (2×2) row-by-ring array of openings. In an example, display modules can be removably inserted into different sets of openings to create different display configurations and patterns. In an example, attachment member 7901 further comprises one or more flexible electromagnetic wires, fibers, or channels which connect to display modules (to provide power and/or transfer data) when the display modules are inserted into openings. In this example, a distal-to-proximal row of display modules is removably inserted into openings in the attachment member. In an example, other modular electronic components can also be inserted into openings.

In this example, a plurality of openings in the attachment member are evenly distributed along at least a portion of a distal-to-proximal axis of the attachment member. In this example, a plurality of openings in the attachment member are evenly distributed around at least a portion of a circumference of a person's wrist and/or forearm. In this example, a plurality of openings in the attachment member are radially distributed around at least a portion of a circumference of a person's wrist and/or forearm. In this example, a plurality of openings in the attachment member are sequentially distributed along at least a portion of a distal-to-proximal axis of the attachment member.

In this example, this device comprises a plurality of openings in the attachment member whose centroids are aligned on a distal-to-proximal axis of the attachment member. This device furthers comprise a plurality of openings with centroids which are aligned on a circumference of a person's wrist and/or forearm. In this example, this device can further comprise a plurality of openings in the attachment member with centroids which are distributed around at least a portion of a circumference of a person's wrist and/or forearm.

Figure 81:
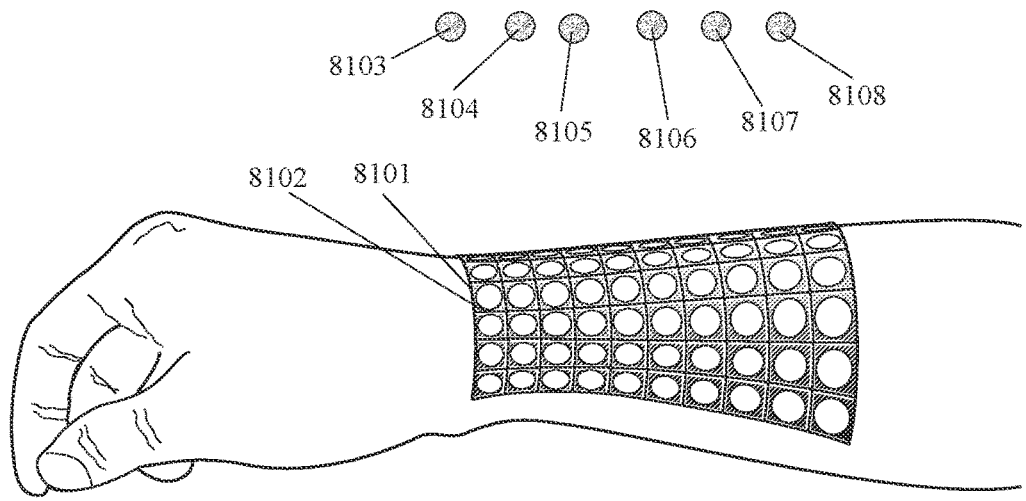
FIGS. 81 and 82 show a wearable device with a distal-to-proximal array of circular removably-attachable and flexibly-connected displays which are removably inserted into openings in an attachment member.
Figure 82:
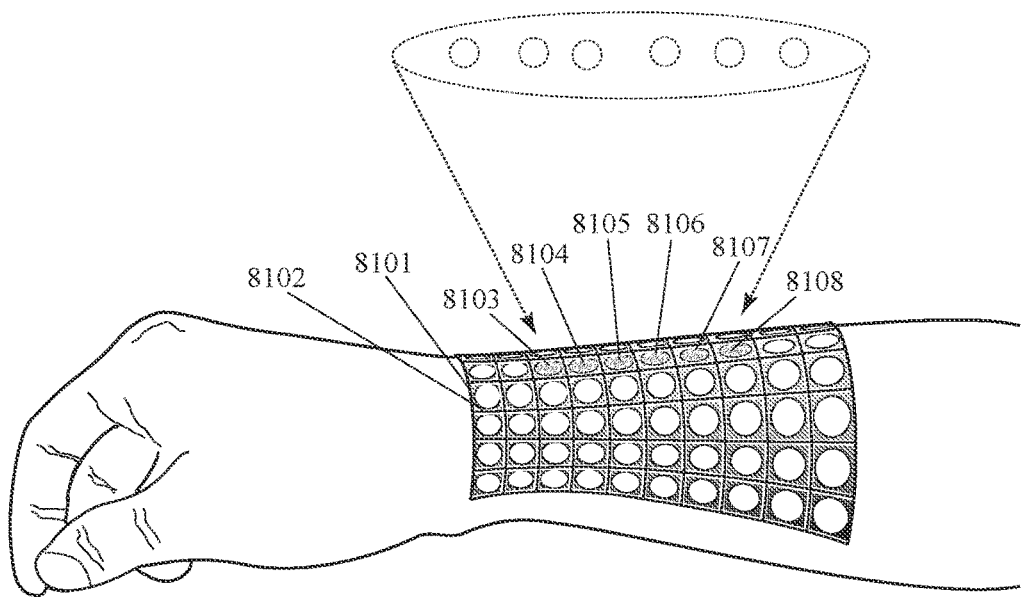

FIGS. 81 and 82 show another example of how this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

FIGS. 81 and 82 also show another example of how this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

The example of this invention that is shown in FIGS. 81 and 82 is similar to the one that was shown in FIGS. 79 and 80 except that the display modules are circular. In this example, the display modules are the same shape as the openings in the attachment member. In an example, display modules can be removably inserted into openings by rotation in a first direction and threaded engagement. In an example, display modules can be also be removed from openings by rotation in a second direction. In an example, a display module can form an electromagnetic connection with the attachment member (for providing power or transmitting data) when the display module is inserted into an opening in the attachment member. In an example, display modules can be inserted, removed, and reinserted into different openings in order to form different display configurations and patterns.

FIG. 81 shows a side view of this device being worn on a person's forearm at a first point in time, before display modules (including 8103, 8104, 8105, 8106, 8107, and 8108) are inserted into openings in attachment member 8101. FIG. 82 shows a side view of this same device at a second point in time, after display modules (including 8103, 8104, 8105, 8106, 8107, and 8108) have been inserted into openings in attachment member 8101. The example in FIGS. 81 and 82 comprises: attachment member 8101 with an array (or mesh) of openings which are connected by flexible joints (including 8102); and a distal-to-proximal row of removably attached flexibly-connected display modules (including 8103, 8104, 8105, 8106, 8107, and 8108) which are connected by flexible joints. The component, parameter, and other example variations which have been discussed in previous sections can also be applied (where relevant) to the example shown here in FIGS. 81 and 82.

In this example, first display module 8103 and second display module 8104 communicate with the person by emitting and/or reflecting light energy. In this example, these display modules are small computer touch screens which each display a portion of a text message. The flexible connections between these display modules enable them to move and collectively conform to the curved shape of the person's wrist and/or forearm. In this example, first display module 8103 is a first distance from the outer circumference of the person's arm at the elbow (when the arm is fully extended) and second display module 8104 is a second distance from the outer circumference of the person's arm at the elbow (when the arm is fully extended). In this example, the second distance is less than the first distance.

In this example, attachment member 8102 has a flexible array (or mesh) of openings. In this example, these openings are circular. In an example, a display module can be removably inserted into a circular opening in the attachment member by rotation and threaded engagement with the opening. In an example, openings in the attachment member can each have an inner helical thread, display modules can each have an outer helical thread, and display modules can be removably inserted into openings by rotation. As shown by this example, a device can comprise at least a (2×2) row-by-ring array of openings.

In an example, display modules can be removably inserted into different sets of openings to create different display configurations and patterns. In an example, attachment member 8101 further comprises one or more flexible electromagnetic wires, fibers, or channels which connect to display modules (to provide power and/or transfer data) when the display modules are inserted into openings. In this example, a distal-to-proximal row of display modules is removably inserted into openings in the attachment member. In an example, other modular electronic components can also be inserted into openings.

In this example, a plurality of openings in the attachment member are evenly distributed along at least a portion of a distal-to-proximal axis of the attachment member. In this example, a plurality of openings in the attachment member are evenly distributed around at least a portion of a circumference of a person's wrist and/or forearm. In this example, a plurality of openings in the attachment member are radially distributed around at least a portion of a circumference of a person's wrist and/or forearm. In this example, a plurality of openings in the attachment member are sequentially distributed along at least a portion of a distal-to-proximal axis of the attachment member.

In this example, this device comprises a plurality of openings in the attachment member whose centroids are aligned on a distal-to-proximal axis of the attachment member. This device furthers comprise a plurality of openings with centroids which are aligned on a circumference of a person's wrist and/or forearm. In this example, this device can further comprise a plurality of openings in the attachment member with centroids which are distributed around at least a portion of a circumference of a person's wrist and/or forearm.

FIGS. 83 through 85 show another example of how this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

FIGS. 83 through 85 also show another example of how this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

The example of this invention that is shown in FIGS. 83 through 85 is similar to the one that was shown in FIGS. 81 and 82 except that: (a) this present example explicitly shows other types of modular electronic components in addition to display modules; and (b) this present example explicitly shows how display modules and other modular electronic components can be attached, removed, and reattached to different locations. This present example includes the follow modular electronic components: a first display module 8303, a second display module 8304, a modular electrical power source 8305, a data processing and transmission module 8306, a sensor module 8307, and a modular human-to-computer interface (HCI) component 8308. Since this device gives the person the ability removably attach different modular electronic components to create different device configurations, it enables the person to create a customized wearable device which best matches their specific needs and budget.

The example shown in FIGS. 83 through 85 comprises: attachment member 8301 with an array (or mesh) of openings which are connected by flexible joints (including 8302); a two-module distal-to-proximal row of removably attached flexibly-connected display modules (8303 and 8304) which are connected by flexible joints; a modular electrical power source 8305; a data processing and transmission module 8306; a sensor module 8307; and modular human-to-computer interface (HCI) component 8308. The component, parameter, and other example variations which have been discussed in previous sections can also be applied where relevant to the example shown here in FIGS. 83 through 85.

FIG. 83 shows a side view of this device being worn on a person's forearm at a first point in time, before display modules (8303 and 8304) and other modular electronic components (8305, 8306, 8307, and 8308) are inserted into openings in attachment member 8301. FIG. 84 shows a side view of this device being worn on a person's forearm at a second point in time, after display modules (8303 and 8304) and other modular electronic components (8305, 8306, 8307, and 8308) have been inserted into openings in attachment member 8301 in a first configuration or pattern. FIG. 85 shows a side view of this device being worn on a person's forearm at a third point in time, after display modules (8303 and 8304) and other modular electronic components (8305, 8306, 8307, and 8308) have been removed and then reinserted into openings in attachment member 8301 in a second configuration or pattern.

In an example, display modules and other modular electronic components can be removably inserted into openings by threaded engagement with rotation in a first direction (e.g. clockwise). In an example, display modules and other modular electronic components can be removed from openings by rotation in a second direction (e.g. counter-clockwise). In an example, a display module or other modular electronic component can form an electromagnetic connection with the attachment member (for providing power and/or transmitting data) when the display module or other electronic component is inserted into an opening in the attachment member. In an example, attachment member 8301 further comprises one or more flexible electromagnetic wires, fibers, or channels which connect to display modules or other modular electronic components (to provide power and/or transfer data) when the modules are inserted into openings. In an example, display modules and other modular electronic components can be inserted, removed, and reinserted into different openings in order to form different modular configurations and patterns.

In this example, first display module 8303 and second display module 8304 communicate with the person by emitting and/or reflecting light energy. In this example, these display modules are small computer touch screens which each display a portion of a text message. The flexible connections between these display modules enable them to move and collectively conform to the curved shape of the person's wrist and/or forearm. In this example, first display module 8303 is a first distance from the outer circumference of the person's arm at the elbow (when the arm is fully extended) and second display module 8304 is a second distance from the outer circumference of the person's arm at the elbow (when the arm is fully extended). In this example, the second distance is less than the first distance.

In this example, the device further comprises modular electrical power source 8305. In this example, modular electrical power source 8305 is a battery. In an example, a modular electrical power source can be selected from the group consisting of a battery, other mobile power source, kinetic energy transducer, and thermal energy transducer. In an example, modular electrical power source 8305 can provide electrical power to display modules and other modular electronic components. In an example, modular electrical power source 8305 can make an electromagnetic connection and provide electrical power when it is removably inserted into an opening in the attachment member. In this example, the shape of modular electrical power source 8305 component is the same as the shape of openings in the attachment member.

In an example, the attachment member can further comprise one or more flexible electromagnetic wires, fibers, or channels which connect to modular electrical power source 8305. In an example, other modular electronic components can form electromagnetic connections through which they receive electrical power when they are removably attached to the attachment member. In an example, a modular electronic component can form an electromagnetic connection through which it receives electrical power when the component is removably inserted into an opening in the attachment member.

In this example, the device further comprises data processing and transmission module 8306. In an example, data processing and transmission module 8306 can be a small-scale computing component, computer chip, and/or microprocessor. In this example, a modular electronic component is selected from the group consisting of data processor, wireless data transmitter, and wireless data receiver. In an example, data processing and transmission module 8306 can process data from the display modules and other modular electronic components of this device. In an example, data processing and transmission module 8306 can send data to the display modules and other modular electronic components of this device. In an example, data processing and transmission module 8306 can receive data that is transmitted from an external and/or remote device (e.g. a server of the internet). In an example, data processing and transmission module 8306 can send data to an external and/or remote device (e.g. a server of the internet).

In an example, a display module, sensor module, or other modular electronic component can make an electromagnetic connection and transmit and/or receive data when it is removably attached to the attachment member. In this example, a display module, sensor module, or other modular electronic component can make an electromagnetic connection and transmit and/or receive data when it is removably inserted into an opening in the attachment member. In an example, data processing and transmission module 8306 can locally process data from a display module, sensor module, or other modular electronic component. In an example, data processing and transmission module 8306 can wirelessly transmit data from a display module, sensor module, or other modular electronic component to an external or remote computing device which, in turn, processes that data.

The device shown in FIGS. 83 through 85 also comprises sensor module 8307. In an example, sensor module 8307 can be a physiological sensor which measures processes, activities, conditions, levels, or other parameters concerning the person's body. In an example, sensor module 8307 can be an environmental sensor which measures processes, conditions, locations, levels, or other parameters concerning the person's local environment and/or objects in that local environment. In an example, a physiological and/or environmental sensor module can be removably attached to the attachment member. In an example, one or more physiological and/or environmental sensor modules can be removably inserted into openings in the attachment member. In an example, a one or more physiological and/or environmental sensors can be permanent parts of the attachment member. In an example, a sensor module can have a cross-sectional shape which is selected from the group consisting of: square, square with rounded vertexes, quadrilateral, quadrilateral with rounded vertexes, circle, hexagon, oval, ellipse, triangle, diamond, and keystone.

In an example, sensor module 8307 can include a sensor selected from the group consisting of: accelerometer, bend sensor, compass, electrogoniometer, force sensor, goniometer, gyroscope, inclinometer, inertial sensor, motion sensor, piezoelectric sensor, pressure sensor, strain gauge, stretch sensor, and vibration sensor. In an example, sensor module 8307 can include a sensor selected from the group consisting of: camera, infrared sensor, laser sensor, light energy emitter and sensor, light energy sensor, near-infrared sensor, optical glucose sensor, optical scanner, optical sensor, optoelectronic sensor, photoelectric sensor, photoplethysmography (PPG) sensor, spectral analysis sensor, spectrometry sensor, spectroscopic sensor, and ultraviolet light sensor.

In an example, sensor module 8307 can include a sensor selected from the group consisting of: action potential sensor, electrocardiography (ECG) or EKG sensor, electromagnetic conductivity sensor, electromagnetic energy sensor, electromagnetic impedance sensor, electromagnetic muscle activity sensor, electromyography (EMG) sensor, impedance sensor, magnetic field sensor, magnetometer, neural impulse sensor, neurosensor, piezocapacitive sensor, radio frequency (RF) sensor, variable impedance sensor, and variable resistance sensor. In an example, sensor module 8307 can include a sensor selected from the group consisting of: ambient sound sensor, microphone, sonic energy sensor, sound sensor, speech recognition module, voice recognition module, and ultrasound sensor.

In an example, sensor module 8307 can include a sensor selected from the group consisting of: ambient temperature sensor, body temperature sensor, temperature sensor, thermistor, and thermometer. In an example, sensor module 8307 can include a sensor selected from the group consisting of: biochemical sensor, blood glucose monitor, blood oximeter, chemical sensor, cutaneous oxygen monitor, electrochemical sensor, glucose monitor, humidity sensor, hydration sensor, microbial sensor, moisture sensor, oximeter, oximetry sensor, oxygen level sensor, oxygen saturation sensor, pH level sensor, skin moisture sensor, and tissue oximetry sensor. In an example, sensor module 8307 can include a sensor selected from the group consisting of: blood flow monitor, blood pressure monitor, cardiac function monitor, heart rate monitor, manometer, micro electromechanical system (MEMS) sensor, pulmonary function sensor, pulse monitor, and pulse oximeter.

In this example, the device further comprises a human-to-computer interface (HCI) component 8308 in addition to a sensor module. In this example, modular human-to-computer interface (HCI) component 8308 is inserted into an opening in the attachment member. In another example, this invention can further comprise a modular human-to-computer interface (HCI) component which is a permanent part of the attachment member. In an example, modular human-to-computer interface (HCI) 8308 can be a microphone. In an example, modular human-to-computer interface (HCI) 8308 can be an electronic button. In an example, modular human-to-computer interface (HCI) 8308 can be a gesture recognition component.

FIG. 86 shows more detail concerning the example which was introduced in FIGS. 83 through 85. The bottom portion of FIG. 86 repeats a side view of the device which was shown in FIG. 83. The upper portion of FIG. 86 shows an enlarged semi-transparent cross-sectional view of display module 8303. Specifically, the upper portion of FIG. 86 shows that display module 8303 further comprises: helical thread 8601 around the circumference of display module 8303; electrical power connections 8602 and 8603; and data transmission connections 8604 and 8605.

Helical thread 8601 engages the inside of an opening in attachment member 8301 when display module 8303 is rotationally inserted into an opening in attachment member 8301. Electrical power connections 8602 and 8602 connect with electrical power pathways in attachment member 8301 to provide power to display module 8303 when display module 8303 is inserted into an opening in attachment member 8301. Data transmission connections 8604 and 8605 connect with data transmission pathways in attachment member 8301 to send or receive data when display module 8303 is inserted into an opening in attachment member 8301. Other display modules and other modular electronic components can also have the same features and sub-components.

In this example, display modules and other modular electronic components can be removably inserted into openings by threaded engagement with rotation in a first direction (e.g. clockwise). In this example, display modules and other modular electronic components can be removed from openings by rotation in a second direction (e.g. counter-clockwise). In this example, a display module or other modular electronic component can form an electromagnetic connection with the attachment member (for providing power and/or transmitting data) when the display module or other electronic component is inserted into an opening in the attachment member.

In this example, attachment member 8301 further comprises one or more flexible electromagnetic wires, fibers, or channels which connect to display modules or other modular electronic components (to provide power and/or transfer data) when the modules are inserted into openings. In an example, display modules and other modular electronic components can be inserted, removed, and reinserted into different openings in order to form different modular configurations and patterns.

FIG. 87 shows another example of how this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

FIG. 87 also shows another example of how this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

The example of this invention that is shown in FIG. 87 is similar to the one that was shown in FIG. 74 except that a portion of the circumference of the attachment member is an arcuate elastic and/or stretchable portion instead of an continuation of the array (or mesh) of flexibly-connected parts. In this example, the portion of the attachment member which comprises an array of display modules is less elastic than the rest of the attachment member. This design can enable greater circumferential stretching so that the device can be easily slid over the person's hand onto the forearm, without having large gaps between the flexibly-connected display modules.

The upper section of FIG. 87 shows a side view of this device being worn on a person's forearm. The lower section of FIG. 87 shows a top-down view of this same device. The component, parameter, and other example variations which were discussed in previous sections can also be applied where relevant to the example shown here in FIG. 87. The example shown in FIG. 87 comprises: a first portion 8701 of an attachment member which comprises an array (or mesh) of flexibly-connected parts which are connected by flexible joints (including 8702), wherein this first portion spans a first portion of the circumference of the attachment member; a second portion 8709 of the attachment member comprising an elastic and/or stretchable material, wherein this second portion spans a second portion of the circumference of the attachment member; and a distal-to-proximal row of removably attached flexibly-connected display modules (including 8703, 8704, 8705, 8706, 8707, and 8708) which are connected by flexible joints.

In this example, first display module 8703 and second display module 8704 communicate with the person by emitting and/or reflecting light energy. In this example, these display modules are small computer touch screens which each display a portion of a text message. The flexible connections between these display modules enable them to move and collectively conform to the curved shape of the person's wrist and/or forearm. In this example, first display module 8703 is a first distance from the outer circumference of the person's arm at the elbow (when the arm is fully extended) and second display module 8704 is a second distance from the outer circumference of the person's arm at the elbow (when the arm is fully extended). In this example, the second distance is less than the first distance.

In this example, a first portion of the attachment member which spans a first percentage of the circumference of the attachment member has a first elasticity, a second portion which spans the remaining percentage of the circumference of the attachment member has a second elasticity, and the second elasticity is greater than the first elasticity. In this example, a first portion of the attachment member which spans a first percentage of the circumference of the attachment member (to which modular electronic components are attached) has a first elasticity, a second portion which spans the remaining percentage of the circumference of the attachment member has a second elasticity, and the second elasticity is greater than the first elasticity. In an example, a first half of the circumference of the attachment member (to which modular electronic components are attached) can have a first elasticity, a second half of the circumference of the attachment member can have a second elasticity, and the second elasticity can be greater than the first elasticity.

In this example, the attachment member has a first circumferential portion with a first elasticity to which display modules and/or other modular electronic components are removably attached and a second circumferential portion with a second elasticity to which display modules and/or other modular electronic components are not removably attached, wherein the second elasticity is greater than the first elasticity. In this example, the attachment member has a first circumferential portion to which display modules are removably attached and a second circumferential portion comprises an elastic mesh. In this example, the attachment member has a first circumferential portion to which modular electronic components are removably attached and a second circumferential portion comprises an elastic mesh. In this example, the attachment member has a first circumferential portion comprising flexibly-connected parts and a second circumferential portion comprising an elastic mesh.

FIG. 88 shows another example of how this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

FIG. 88 also shows another example of how this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

The example of this invention that is shown in FIG. 88 is similar to the one that was shown in FIG. 74 except that the display modules and flexibly-connected parts are hexagonal in shape. In this example, the attachment member is a honeycomb array (or mesh) of hexagonal flexibly-connected parts. The component, parameter, and other example variations which were discussed in previous sections can also be applied where relevant to the example shown here in FIG. 88.

The upper section of FIG. 88 shows a side view of this device being worn on a person's forearm. The lower section of FIG. 88 shows a top-down view of this same device. The example shown in FIG. 88 comprises: attachment member 8801 with multiple hexagonal flexibly-connected parts which are connected by flexible and/or stretchable joints; and a distal-to-proximal (zigzag centroid) row of hexagonal display modules (including 8802, 8803, 8804, 8805, 8806, and 8807) which are connected by flexible and/or stretchable joints.

In this example, first display module 8802 and second display module 8803 communicate with the person by emitting and/or reflecting light energy. In this example, these display modules are small computer touch screens. The flexible connections between these display modules enable them to move and collectively conform to the curved shape of the person's wrist and/or forearm. In this example, first display module 8802 is a first distance from the outer circumference of the person's arm at the elbow (when the arm is fully extended) and second display module 8803 is a second distance from the outer circumference of the person's arm at the elbow (when the arm is fully extended). In this example, the second distance is less than the first distance.

In this example, the attachment member is a flexible structure with an array of rigid, but flexibly-connected, hexagonal parts. In this example, the attachment member is a flexible structure with an array of rigid, but flexibly-connected, hexagonal parts which include display modules or other modular electronic components. In an example, an attachment member can be a flexible structure with an array of rigid, but flexibly-connected, hexagonal parts to which display modules or other modular electronic components can be removably attached. In an example, an attachment member can be a flexible structure with an array of hexagonal openings into which display modules or other modular electronic components can be removably inserted. In an example, an attachment member can comprise an elastic, stretchable, and/or flexible honeycomb mesh with hexagonal openings. In an example, an attachment member can comprise an elastic, stretchable, and/or flexible honeycomb mesh with hexagonal openings into which one or more display modules or other modular electronic components can be inserted.

FIG. 89 shows another example of how this invention can be embodied in a forearm-wearable device with a distal-to-proximal plurality of flexibly-connected display modules comprising: (a) an attachment member which is configured to be worn around at least 50% of the circumference a person's wrist and/or forearm; (b) a first display module which communicates with the person by emitting and/or reflecting light energy, wherein this first display module is part of the attachment member at a first location, and wherein this first location is a first distance from the outer circumference of the person's arm at the elbow when the arm is fully extended; and (c) a second display module which communicates with the person by emitting and/or reflecting light energy, wherein this second display module is part of the attachment member at a second location, wherein this second location is a second distance from the outer circumference of the person's arm at the elbow when the arm is fully extended, and wherein the second distance is less than the first distance.

FIG. 89 also shows another example of how this invention can be embodied in a forearm-wearable device with a distal-to-proximal plurality of flexibly-connected display modules comprising: (a) an attachment member which is configured to be worn around at least 50% of the circumference of a person's wrist and/or forearm; wherein this attachment member is selected from the group consisting of a armband, armlet, bangle, bracelet, chain mail sleeve, gauntlet, fitness band, forearm computer, garment cuff, garment sleeve, separate cuff, separate sleeve, smart watch, strap, tubular mesh, wrist band, and wrist computer; wherein this attachment member further comprises: (b) a first display module which communicates with the person by emitting and/or reflecting light energy, wherein this first display module is located at a first distance from the outer circumference of the person's arm at the elbow when the arm is fully extended; (c) a second display module which communicates with the person by emitting and/or reflecting light energy, wherein this second display module is located at a second distance from the outer circumference of the person's arm at the elbow when the arm is fully extended, wherein the second distance is less than the first distance; and (d) a flexible connection between the first display module and the second display module which allows the first display module to move relative to the second display module.

The example of this invention that is shown in FIG. 89 is similar to the one that was shown in FIG. 87 except that it is part of an upper body garment. In an example, this device can be integrated into the sleeve or cuff of an upper body garment, such as a shirt, blouse, jacket, or coat. The upper section of FIG. 89 shows a side view of this device being worn on a person's forearm. The lower section of FIG. 89 shows a top-down view of this same device. The component, parameter, and other example variations which were discussed in previous sections can also be applied where relevant to the example shown here in FIG. 89.

The example shown in FIG. 89 comprises: a first portion 8901 of an attachment member which comprises an array (or mesh) of flexibly-connected parts which are connected by flexible joints (including 8902); a second portion 8909 of the attachment member which is integrated with an upper body garment; and a distal-to-proximal row of removably attached flexibly-connected display modules (including 8903, 8904, 8905, 8906, 8907, and 8908) which are connected by flexible joints.

In this example, first display module 8903 and second display module 8904 communicate with the person by emitting and/or reflecting light energy. In this example, these display modules are small computer touch screens which each display a portion of a text message. The flexible connections between these display modules enable them to move and collectively conform to the curved shape of the person's wrist and/or forearm. In this example, first display module 8903 is a first distance from the outer circumference of the person's arm at the elbow (when the arm is fully extended) and second display module 8904 is a second distance from the outer circumference of the person's arm at the elbow (when the arm is fully extended). In this example, the second distance is less than the first distance.

FIGS. 90 through 96 show examples of a forearm wearable computing device comprising: one or two arcuate computer display screens which are configured to be worn a person's wrist and/or forearm; a sensor; and one or two arcuate bands which attach the arcuate computer display screen to the person's wrist and/or forearm by spanning at least 50% of the perimeter of the person's wrist and/or forearm.

FIG. 90 shows an example of a forearm wearable computing device comprising: an arcuate computer display screen (9003) which is configured to be worn a person's wrist and/or forearm, wherein this display screen has a display area which is greater than 1 square inch; a sensor (9004); proximal band (9002) which is configured to attach a proximal portion of the arcuate computer display screen to the person's wrist and/or forearm by spanning at least 50% of the perimeter of the person's wrist and/or forearm, wherein this proximal band is connected to the arcuate computer display screen at a first distance from the person's elbow; and a distal band (9001) which is configured to attach a distal portion of the arcuate computer display screen to the person's wrist and/or forearm by spanning at least 50% of the perimeter of the person's wrist and/or forearm, wherein this distal band is connected to the arcuate computer display screen at a second distance from the person's elbow; and wherein the second distance is greater than the first distance.

In an example, the arcuate computer display screen can have a cross-sectional shape which is selected from the group consisting of: circular, elliptical, oblong, rectangular with rounded vertexes, and hexagonal with rounded vertexes. In an example, the arcuate computer display screen can have a display area in the range of 1 to 10 square inches. In an example, the arcuate computer display screen can have a flat display surface. In an example, the arcuate display screen can have a curved display surface. In an example, the arcuate computer display screen can be rigid. In an example, the arcuate computer display screen can be flexible. In an example, the arcuate computer display screen can be a touch screen which responds to finger movements.

In an example, the sensor can be a motion sensor. In an example, the sensor can be a multi-axial accelerometer. In an example, the sensor can be a gyroscope. In an example, the sensor can be a light energy sensor. In an example, the sensor can be a spectroscopic sensor which collects data concerning the spectrum of light reflected from and/or transmitted through tissue of the person's wrist and/or forearm. In an example, the sensor can be an electromagnetic energy sensor. In an example, the sensor can measure the resistance, impedance, and/or conductivity of tissue of the person's wrist and/or forearm with respect to the transmission of electromagnetic energy. In an example, the sensor can measure electromagnetic energy emitted from muscles and/or nerves in the person's wrist and/or forearm. In an example, the sensor can be a capacitive electromagnetic energy sensor.

In an example, the sensor can be an environmental light energy sensor. In an example, the arcuate computer display screen can have a first display mode which requires less energy and a second display mode which requires more energy. In an example, the arcuate computer display screen can automatically switch from the first display mode to the second display mode when the second display mode is required for the person to be able to see information on the display screen. In an example, the device can switch the display screen from the first mode to the second mode when there is a high level of environmental light energy and the display would not be visible in bright light in the first display mode. In an example, the device can switch the display screen from the first mode to the second mode when there is a low level of environmental light energy and the display would not be visible in dim light (or darkness) in the first display mode.

In an example, the arcuate computer display screen can display information with a proximal-to-distal orientation. In an example, the arcuate computer display screen can display information with a lateral orientation (which is perpendicular to the proximal-to-distal axis of the display screen). In an example, the arcuate computer display screen can be manually rotated to change the radial orientation of information displayed relative to the proximal-to-distal axis of the person's forearm. In an example, the device can automatically change the radial orientation of information displayed by the arcuate computer display screen based on the orientation and/or movement of the computer display screen as detected by a gyroscope and/or motion sensor. In an example, the orientation of information displayed by the arcuate computer display screen can be automatically changed based on the orientation and/or position of the computer display screen relative to the person's eyes. In an example, the orientation and/or position of the computer display screen relative to the person's eyes can be determined based on data from one or more cameras, motion sensors, inertial sensors, and/or bend sensors.

The arcuate display screen has a central longitudinal proximal-to-distal axis. In an example, the proximal and distal bands can be connected to the arcuate computer display screen in a symmetric manner with respect to this central longitudinal axis. The arcuate display screen also has a central lateral axis which is perpendicular to the central longitudinal proximal-to-distal axis. In an example, proximal and distal bands can be connected to the arcuate computer display screen in a symmetric manner with respect to this central lateral axis.

In an example, the proximal band can be arcuate, curving in a proximal direction as it spans from the arcuate computer display screen around at least 50% of the perimeter of the person's wrist and/or forearm. In an example, the distal band can be arcuate, curving in a distal direction as it spans from the arcuate computer display screen around at least 50% of the perimeter of the person's wrist and/or forearm. In an example the proximal band and the distal band can be separated by a maximum distance which is not less than 2 inches as they span at least 50% of the perimeter of the person's wrist and/or forearm. In another example, the proximal band can be arcuate, curving in a distal direction as it spans from the arcuate computer display screen around at least 50% of the perimeter of the person's wrist and/or forearm. In another example, the distal band can be arcuate, curving in a proximal direction as it spans from the arcuate computer display screen around at least 50% of the perimeter of the person's wrist and/or forearm.

In an example, the proximal band can further comprise a buckle, clasp, clip, hook, hook-and-eye material, pin, latch, button, and/or zipper which enables the proximal band to fasten around the complete perimeter of the person's wrist and/or forearm. In an example, the distal band can further comprise a buckle, clasp, clip, hook, hook-and-eye material, pin, latch, button, and/or zipper which enables the proximal band to fasten around the complete perimeter of the person's wrist and/or forearm. In an example, the proximal band can be stretchable, expandable, and/or elastic so that it can be slipped over the hand onto the person's wrist and/or forearm. In an example, the distal band can be stretchable, expandable, and/or elastic so that it can be slipped over the hand onto the person's wrist and/or forearm.

In an example, the proximal and distal bands can be separate from each other apart from their mutual connection to the arcuate computer display screen. In an example, the proximal and distal bands can converge and/or connect. In an example, the proximal and distal bands can converge and/or connect on the surface of the person's wrist and/or forearm which is diametrically opposite to the surface of the person's wrist and/or forearm where the arcuate computer display screen is located. In an example, if the proximal and distal bands converge and/or connect, then they can share a common a buckle, clasp, clip, hook, hook-and-eye material, pin, latch, button, and/or zipper which fastens them around the person's wrist and/or forearm.

FIG. 91 shows an example of a forearm wearable computing device comprising: an arcuate computer display screen (9102) which is configured to be worn a person's wrist and/or forearm, wherein this display screen has a display area which is greater than 1 square inch; a sensor (9103); and a circumferentially-converging band (9101) which is configured to attach the arcuate computer display screen to the person's wrist and/or forearm by spanning at least 50% of the perimeter of the person's wrist and/or forearm, wherein this circumferentially-converging band has a first branch which is connected to the arcuate computer display screen at a first distance from the person's elbow, wherein this circumferentially-converging band has a second branch which connected to the arcuate computer display screen at a second distance from the person's elbow, wherein the second distance is greater than the first distance, and wherein the first and second branches of the circumferentially-converging band converge away from the arcuate computer display screen as the circumferentially-converging band spans at least 50% of the perimeter of the person's wrist and/or forearm.

In an example, the arcuate computer display screen can have a cross-sectional shape which is selected from the group consisting of: circular, elliptical, oblong, rectangular with rounded vertexes, and hexagonal with rounded vertexes. In an example, the arcuate computer display screen can have a display area in the range of 1 to 10 square inches. In an example, the arcuate computer display screen can have a flat display surface. In an example, the arcuate display screen can have a curved display surface. In an example, the arcuate computer display screen can be rigid. In an example, the arcuate computer display screen can be flexible. In an example, the arcuate computer display screen can be a touch screen which responds to finger movements.

In an example, the sensor can be a motion sensor. In an example, the sensor can be a multi-axial accelerometer. In an example, the sensor can be a gyroscope. In an example, the sensor can be a light energy sensor. In an example, the sensor can be a spectroscopic sensor which collects data concerning the spectrum of light reflected from and/or transmitted through tissue of the person's wrist and/or forearm. In an example, the sensor can be an electromagnetic energy sensor. In an example, the sensor can measure the resistance, impedance, and/or conductivity of tissue of the person's wrist and/or forearm with respect to the transmission of electromagnetic energy. In an example, the sensor can measure electromagnetic energy emitted from muscles and/or nerves in the person's wrist and/or forearm. In an example, the sensor can be a capacitive electromagnetic energy sensor.

In an example, the sensor can be an environmental light energy sensor. In an example, the arcuate computer display screen can have a first display mode which requires less energy and a second display mode which requires more energy. In an example, the arcuate computer display screen can automatically switch from the first display mode to the second display mode when the second display mode is required for the person to be able to see information on the display screen. In an example, the device can switch the display screen from the first mode to the second mode when there is a high level of environmental light energy and the display would not be visible in bright light in the first display mode. In an example, the device can switch the display screen from the first mode to the second mode when there is a low level of environmental light energy and the display would not be visible in dim light (or darkness) in the first display mode.

In an example, the arcuate computer display screen can display information with a proximal-to-distal orientation. In an example, the arcuate computer display screen can display information with a lateral orientation (which is perpendicular to the proximal-to-distal axis of the display screen). In an example, the arcuate computer display screen can be manually rotated to change the radial orientation of information displayed relative to the proximal-to-distal axis of the person's forearm. In an example, the device can automatically change the radial orientation of information displayed by the arcuate computer display screen based on the orientation and/or movement of the computer display screen as detected by a gyroscope and/or motion sensor. In an example, the orientation of information displayed by the arcuate computer display screen can be automatically changed based on the orientation and/or position of the computer display screen relative to the person's eyes. In an example, the orientation and/or position of the computer display screen relative to the person's eyes can be determined based on data from one or more cameras, motion sensors, inertial sensors, and/or bend sensors.

In an example, the circumferentially-converging band can further comprise a buckle, clasp, clip, hook, hook-and-eye material, pin, latch, button, and/or zipper which enables the circumferentially-converging band to fasten around the complete perimeter of the person's wrist and/or forearm. In an example, the circumferentially-converging band can be stretchable, expandable, and/or elastic so that it can be slipped over the hand onto the person's wrist and/or forearm.

FIG. 92 shows an example of a forearm wearable computing device comprising: an arcuate computer display screen (9203) which is configured to be worn a person's wrist and/or forearm, wherein this display screen has a display area which is greater than 1 square inch; a sensor (9204); a left loop (9201) which is connected to the arcuate computer display screen, curving around the right side of the perimeter of the display screen; and a right loop (9202) which is connected to the arcuate computer display screen, curving around the left side of the perimeter of the display screen, wherein the left loop and the right loop collectively attach the arcuate computer display screen to the person's wrist and/or forearm by spanning at least 50% of the perimeter of the person's wrist and/or forearm.

In an example, the arcuate computer display screen can have a cross-sectional shape which is selected from the group consisting of: circular, elliptical, oblong, rectangular with rounded vertexes, and hexagonal with rounded vertexes. In an example, the arcuate computer display screen can have a display area in the range of 1 to 10 square inches. In an example, the arcuate computer display screen can have a flat display surface. In an example, the arcuate display screen can have a curved display surface. In an example, the arcuate computer display screen can be rigid. In an example, the arcuate computer display screen can be flexible. In an example, the arcuate computer display screen can be a touch screen which responds to finger movements.

In an example, the sensor can be a motion sensor. In an example, the sensor can be a multi-axial accelerometer. In an example, the sensor can be a gyroscope. In an example, the sensor can be a light energy sensor. In an example, the sensor can be a spectroscopic sensor which collects data concerning the spectrum of light reflected from and/or transmitted through tissue of the person's wrist and/or forearm. In an example, the sensor can be an electromagnetic energy sensor. In an example, the sensor can measure the resistance, impedance, and/or conductivity of tissue of the person's wrist and/or forearm with respect to the transmission of electromagnetic energy. In an example, the sensor can measure electromagnetic energy emitted from muscles and/or nerves in the person's wrist and/or forearm. In an example, the sensor can be a capacitive electromagnetic energy sensor.

In an example, the sensor can be an environmental light energy sensor. In an example, the arcuate computer display screen can have a first display mode which requires less energy and a second display mode which requires more energy. In an example, the arcuate computer display screen can automatically switch from the first display mode to the second display mode when the second display mode is required for the person to be able to see information on the display screen. In an example, the device can switch the display screen from the first mode to the second mode when there is a high level of environmental light energy and the display would not be visible in bright light in the first display mode. In an example, the device can switch the display screen from the first mode to the second mode when there is a low level of environmental light energy and the display would not be visible in dim light (or darkness) in the first display mode.

In an example, the arcuate computer display screen can display information with a proximal-to-distal orientation. In an example, the arcuate computer display screen can display information with a lateral orientation (which is perpendicular to the proximal-to-distal axis of the display screen). In an example, the arcuate computer display screen can be manually rotated to change the radial orientation of information displayed relative to the proximal-to-distal axis of the person's forearm. In an example, the device can automatically change the radial orientation of information displayed by the arcuate computer display screen based on the orientation and/or movement of the computer display screen as detected by a gyroscope and/or motion sensor. In an example, the orientation of information displayed by the arcuate computer display screen can be automatically changed based on the orientation and/or position of the computer display screen relative to the person's eyes. In an example, the orientation and/or position of the computer display screen relative to the person's eyes can be determined based on data from one or more cameras, motion sensors, inertial sensors, and/or bend sensors.

In an example, the left loop can further comprise a buckle, clasp, clip, hook, hook-and-eye material, pin, latch, button, and/or zipper which enables the left loop to fasten around the complete perimeter of the person's wrist and/or forearm. In an example, the right loop can further comprise a buckle, clasp, clip, hook, hook-and-eye material, pin, latch, button, and/or zipper which enables the right loop to fasten around the complete perimeter of the person's wrist and/or forearm. In an example, the left loop can be stretchable, expandable, and/or elastic so that it can be slipped over the hand onto the person's wrist and/or forearm. In an example, the right loop can be stretchable, expandable, and/or elastic so that it can be slipped over the hand onto the person's wrist and/or forearm.

In an example, the left and right loops can be separate from each other apart from their mutual connection to the arcuate computer display screen. In an example, the left and right loops can connect (as a single continuous loop) on the surface of the person's wrist and/or forearm which is diametrically opposite to the surface of the person's wrist and/or forearm where the arcuate computer display screen is located.

The example shown in FIG. 93 is similar to the one shown in FIG. 92 except that the left and right loops are merged into a single attachment band with a central portion which goes around the perimeter of the arcuate computer display screen. FIG. 93 shows an example of a forearm wearable computing device comprising: an arcuate computer display screen (9302) which is configured to be worn a person's wrist and/or forearm, wherein this display screen has a display area which is greater than 1 square inch; a sensor (9303); and an attachment band (9301) which is configured to attach the arcuate computer display screen to the person's wrist and/or forearm by spanning at least 50% of the perimeter of the person's wrist and/or forearm, wherein this attachment band has a central arcuate portion which goes around the perimeter of the arcuate computer display screen, and wherein this attachment band has two circumferential members (one proximal and one distal) which each go around the person's wrist and/or forearm.

In an example, the arcuate computer display screen can have a cross-sectional shape which is selected from the group consisting of: circular, elliptical, oblong, rectangular with rounded vertexes, and hexagonal with rounded vertexes. In an example, the arcuate computer display screen can have a display area in the range of 1 to 10 square inches. In an example, the arcuate computer display screen can have a flat display surface. In an example, the arcuate display screen can have a curved display surface. In an example, the arcuate computer display screen can be rigid. In an example, the arcuate computer display screen can be flexible. In an example, the arcuate computer display screen can be a touch screen which responds to finger movements.

In an example, the sensor can be a motion sensor. In an example, the sensor can be a multi-axial accelerometer. In an example, the sensor can be a gyroscope. In an example, the sensor can be a light energy sensor. In an example, the sensor can be a spectroscopic sensor which collects data concerning the spectrum of light reflected from and/or transmitted through tissue of the person's wrist and/or forearm. In an example, the sensor can be an electromagnetic energy sensor. In an example, the sensor can measure the resistance, impedance, and/or conductivity of tissue of the person's wrist and/or forearm with respect to the transmission of electromagnetic energy. In an example, the sensor can measure electromagnetic energy emitted from muscles and/or nerves in the person's wrist and/or forearm. In an example, the sensor can be a capacitive electromagnetic energy sensor.

In an example, the sensor can be an environmental light energy sensor. In an example, the arcuate computer display screen can have a first display mode which requires less energy and a second display mode which requires more energy. In an example, the arcuate computer display screen can automatically switch from the first display mode to the second display mode when the second display mode is required for the person to be able to see information on the display screen. In an example, the device can switch the display screen from the first mode to the second mode when there is a high level of environmental light energy and the display would not be visible in bright light in the first display mode. In an example, the device can switch the display screen from the first mode to the second mode when there is a low level of environmental light energy and the display would not be visible in dim light (or darkness) in the first display mode.

In an example, the arcuate computer display screen can display information with a proximal-to-distal orientation. In an example, the arcuate computer display screen can display information with a lateral orientation (which is perpendicular to the proximal-to-distal axis of the display screen). In an example, the arcuate computer display screen can be manually rotated to change the radial orientation of information displayed relative to the proximal-to-distal axis of the person's forearm. In an example, the device can automatically change the radial orientation of information displayed by the arcuate computer display screen based on the orientation and/or movement of the computer display screen as detected by a gyroscope and/or motion sensor. In an example, the orientation of information displayed by the arcuate computer display screen can be automatically changed based on the orientation and/or position of the computer display screen relative to the person's eyes. In an example, the orientation and/or position of the computer display screen relative to the person's eyes can be determined based on data from one or more cameras, motion sensors, inertial sensors, and/or bend sensors.

In an example, the attachment band can further comprise one or more buckles, clasps, clips, hooks, hook-and-eye materials, pins, latches, buttons, and/or zippers which enable the attachment band to fasten around the complete perimeter of the person's wrist and/or forearm. In an example, the attachment band can be stretchable, expandable, and/or elastic so that it can be slipped over the hand onto the person's wrist and/or forearm.

The example shown in FIG. 94 is like the one in FIG. 90 except that now the arcuate computer display screen is elliptical. FIG. 94 shows an example of a forearm wearable computing device comprising: an elliptical computer display screen (9403) which is configured to be worn a person's wrist and/or forearm, wherein this display screen has a display area which is greater than 3 square inches; a sensor (9404); and a proximal band (9402) which is configured to attach a proximal portion of the arcuate computer display screen to the person's wrist and/or forearm by spanning at least 50% of the perimeter of the person's wrist and/or forearm, wherein this proximal band is connected to the arcuate computer display screen at a first distance from the person's elbow; and a distal band (9401) which is configured to attach a distal portion of the arcuate computer display screen to the person's wrist and/or forearm by spanning at least 50% of the perimeter of the person's wrist and/or forearm, wherein this distal band connected to the arcuate computer display screen at a second distance from the person's elbow; and wherein the second distance is greater than the first distance.

The example shown in FIG. 95 is similar to the one shown in FIG. 92 except that now there are two arcuate computer display screens which are configured along the proximal-to-distal axis of the person's wrist and/or forearm. Having two smaller display screens rather than a single large one with the same surface area can increase the total display surface area of the device with greater flexibility over the surface of the person's wrist and/or forearm. Also, having two smaller display screens rather than a single large one with the same surface area can enable less clunky-looking designs which people may find more aesthetically pleasing.

FIG. 95 shows an example of a forearm wearable computing device comprising: a proximal arcuate computer display screen (9504) which is configured to be worn a person's wrist and/or forearm; a distal arcuate computer display screen (9503) which is configured to be worn a person's wrist and/or forearm; a sensor (9505); a first attachment loop (9501) which curves around the right side of the distal display screen and the left side of the proximal display screen; and a second attachment loop (9502) which curves around the left side of the distal display screen and the right side of the proximal display screen, wherein the left attachment loop and the right attachment loop collectively attach the proximal and distal display screens to the person's wrist and/or forearm by spanning at least 50% of the perimeter of the person's wrist and/or forearm.

The first attachment loop (9501) and the second attachment loop (9502) can overlap with different configurations within the scope of this invention. In an example, the first attachment loop can always overlap on top of the second attachment loop. In an example, the second attachment loop can always overlap on top of the first attachment loop. In an example, which loop overlaps on top can be varied as part of an intertwining loop design for the device.

In an example, one or both arcuate computer display screens can have a cross-sectional shape which are selected from the group consisting of: circular, elliptical, oblong, rectangular with rounded vertexes, and hexagonal with rounded vertexes. In an example, one or both arcuate computer display screens can have a display area in the range of 1 to 10 square inches. In an example, one or both arcuate computer display screens can have a flat display surface. In an example, one or both arcuate computer display screens can have a curved display surface. In an example, one or both arcuate computer display screens can be rigid. In an example, one or both arcuate computer display screens can be flexible. In an example, one or both arcuate computer display screens can be touch screens which responds to finger movements.

In an example, the sensor can be a motion sensor. In an example, the sensor can be a multi-axial accelerometer. In an example, the sensor can be a gyroscope. In an example, the sensor can be a light energy sensor. In an example, the sensor can be a spectroscopic sensor which collects data concerning the spectrum of light reflected from and/or transmitted through tissue of the person's wrist and/or forearm. In an example, the sensor can be an electromagnetic energy sensor. In an example, the sensor can measure the resistance, impedance, and/or conductivity of tissue of the person's wrist and/or forearm with respect to the transmission of electromagnetic energy. In an example, the sensor can measure electromagnetic energy emitted from muscles and/or nerves in the person's wrist and/or forearm. In an example, the sensor can be a capacitive electromagnetic energy sensor.

In an example, the sensor can be an environmental light energy sensor. In an example, one or both arcuate computer display screens can have a first display mode which requires less energy and a second display mode which requires more energy. In an example, one or both arcuate computer display screens can automatically switch from the first display mode to the second display mode when the second display mode is required for the person to be able to see information on the display screen. In an example, the device can switch one or both arcuate computer display screens from the first mode to the second mode when there is a high level of environmental light energy and the display would not be visible in bright light in the first display mode. In an example, the device can switch one or both arcuate computer display screens from the first mode to the second mode when there is a low level of environmental light energy and the display would not be visible in dim light (or darkness) in the first display mode.

In an example, one or both arcuate computer display screens can display information with a proximal-to-distal orientation. In an example, one or both arcuate computer display screens can display information with a lateral orientation (which is perpendicular to the proximal-to-distal axis of the display screen). In an example, one or both arcuate computer display screens can be manually rotated to change the radial orientation of information displayed relative to the proximal-to-distal axis of the person's forearm. In an example, the device can automatically change the radial orientation of information displayed by one or both arcuate computer display screens based on the orientation and/or movement of the computer display screen as detected by a gyroscope and/or motion sensor. In an example, the orientation of information displayed by one or both arcuate computer display screens can be automatically changed based on the orientation and/or position of the computer display screen relative to the person's eyes. In an example, the orientation and/or position of one or both arcuate computer display screens relative to the person's eyes can be determined based on data from one or more cameras, motion sensors, inertial sensors, and/or bend sensors.

In an example, the first attachment loop can further comprise a buckle, clasp, clip, hook, hook-and-eye material, pin, latch, button, and/or zipper which enables the proximal band to fasten around the complete perimeter of the person's wrist and/or forearm. In an example, the second attachment loop can further comprise a buckle, clasp, clip, hook, hook-and-eye material, pin, latch, button, and/or zipper which enables the proximal band to fasten around the complete perimeter of the person's wrist and/or forearm. In an example, the first and/or second loops can be stretchable, expandable, and/or elastic so that they can be slipped over the hand onto the person's wrist and/or forearm. In an example, the first and second loops can be separate from each other apart from their mutual connection to the arcuate computer display screens. In an example, the first and second loops can connect (as a single continuous loop) on the surface of the person's wrist and/or forearm which is diametrically opposite to the surface of the person's wrist and/or forearm where the arcuate computer display screens are located.

The example shown in FIG. 96 is similar to the one shown in FIG. 95 except that the first and second attachment loops are merged into a single attachment band. FIG. 96 shows an example of a forearm wearable computing device comprising: a proximal arcuate computer display screen (9603) which is configured to be worn a person's wrist and/or forearm; a distal arcuate computer display screen (9602) which is configured to be worn a person's wrist and/or forearm; a sensor (9604); and an attachment band (9601) which is configured to attach both of the arcuate computer display screens to the person's wrist and/or forearm by spanning at least 50% of the perimeter of the person's wrist and/or forearm, wherein this attachment band has a central arcuate portion which goes around the perimeters of both arcuate computer display screens, and wherein this attachment band has two circumferential members which go around the person's wrist and/or forearm.

FIGS. 97 through 124 show different examples of how this invention can be embodied in a forearm-wearable computing device with a large display area. FIGS. 97 and 98 show two sequential views of a forearm-wearable computing device with a large display area comprising: (a) primary attachment member 9701, wherein this primary attachment member is configured to attach the device to a person's wrist and/or forearm by encircling at least 50% of the circumference of the person's wrist and/or forearm; (b) folding attachment member 9702, wherein this folding attachment member has a first configuration in which it overlaps the primary attachment member by a first amount, wherein this folding attachment member has a second configuration in which it overlaps primary attachment member by a second amount, wherein the second amount is less than the first amount, and wherein the folding attachment member is moved from the first configuration to the second configuration by rotation of the folding attachment member relative to the primary attachment member; (c) first display member 9703, wherein this first display member is on the exterior surface of the device and visible to the person when the folding attachment member is in the first configuration; (d) second display member 9704, wherein this second display member is on the exterior surface of the device and visible to the person when the folding attachment member is in the second configuration; and (e) third display member 9705, wherein this third display member is on the exterior surface of the device and visible to the person when the folding attachment member is in the second configuration.

FIG. 97 shows this device when folding attachment member 9702 is in the first configuration. FIG. 98 shows this device when folding attachment member 9702 has been moved into the second configuration. This movement is symbolically represented by a dotted-line arrow in FIG. 98. In FIG. 98, folding attachment member 9702 has been moved from the first configuration to the second configuration by being rotated around a side-to-side axial joint which connects the folding attachment member to the primary attachment member. In this example, the axial joint is along the surface of the person's wrist and/or forearm and the edge of the folding attachment member which is opposite to the axial joint is rotated away from the surface of the wrist and/or forearm during the transition from the first configuration to the second configuration. In FIG. 98, folding attachment member 9702 has been moved manually (e.g. by the person) from the first configuration to the second configuration. In another example, a folding attachment can be automatically moved from the first configuration to the second configuration by an actuator which is part of the device.

In the example shown in FIG. 98, the device can be said to have been "flipped open" when folding attachment member 9702 has been moved from the first configuration to the second configuration. In this example, folding attachment member 9702 completely overlaps primary attachment member 9701 in the first configuration and does not overlap primary attachment member 9701 at all in the second configuration. In this example, the folding attachment member lies flat against the surface of the person's wrist and/or forearm in the second configuration. In this example, folding attachment member 9702 "flips open" in a proximal direction—moving closer to the person's elbow in the transition from the first configuration to the second configuration. In another example, folding attachment member 9702 could "flip open" in a distal direction—moving away from the person's elbow in the transition from the first configuration to the second configuration.

In an example, primary attachment member 9701 can be a band, strap, chain, bracelet, or bangle. In an example, primary attachment member 9701 can be a flexible and/or elastic band, strap, mesh, cuff, or chain which spans the entire circumference of the person's wrist and/or forearm. In an example, primary attachment member 9701 can be sufficiently flexible and/or elastic that it can be slipped over the hand onto the wrist and/or forearm. In an example, primary attachment member 9701 can be a band, strap, or chain which further comprises a buckle, clasp, clip, hook, hook-and-eye material, pin, latch, button, and/or zipper which fastens it around the circumference of the person's wrist and/or forearm. In an example, primary attachment member 9701 can be a bracelet or bangle. In an example, primary attachment member 9701 can be sufficiently rigid and/or resiliently-flexible that it holds the device on the person's wrist and/or forearm even though it does not span the entire circumference of the person's wrist and/or forearm.

In an example, folding attachment member 9702 can be a band, strap, or protrusion. In an example, folding attachment member 9702 can be a flexible and/or elastic band, strap, or protrusion which spans less of the circumference of the person's wrist and/or forearm than is spanned by primary attachment member 9701. In an example, folding attachment member 9702 may span only the upper (or frontal) surface of the person's wrist and/or arm. In an example, a folding attachment member can have arcuate edges which connect to the lateral sides of the second display member. Such arcuate edges can reduce snagging of the second display member in the second configuration.

In an example, at least 75% of folding attachment member 9702 overlaps primary attachment member 9701 in the first configuration. In an example, at least 90% of folding attachment member 9702 overlaps primary attachment member 9701 in the first configuration. In an example, folding attachment member 9702 completely overlaps primary attachment member 9701 in the first configuration. In an example, less than 75% of folding attachment member 9702 overlaps primary attachment member 9701 in the second configuration. In an example, less than 10% of folding attachment member 9702 overlaps primary attachment member 9701 in the second configuration. In an example, folding attachment member 9702 does not overlap primary attachment member 9701 at all in the second configuration.

In an example, a folding attachment member can be connected to a primary attachment member by a side-to-side (lateral) axial joint. In an example, the surface area of a person's wrist or arm which is covered by the device can be increased when the folding attachment member is moved from the first configuration to the second configuration. This enables the outward-facing surface device to be smaller when only the first display member is in use and larger when the second and third display members are in use. In an example the folding attachment member can be parallel to the plane of the primary attachment member in the first configuration. In an example the folding attachment member can be parallel to the plane of the primary attachment member in both the first configuration and second configuration. In an example, the folding attachment member may temporarily not be parallel to the plane of the primary attachment member during the transition from the first configuration to the second configuration.

In an example, a display member can be a computer display screen. In an example, a display member can have a cross-sectional shape which is selected from the group consisting of: rectangular with rounded vertexes, hexagonal with rounded vertexes, square, rectangular, hexagonal, circular, elliptical, and oblong. In an example, the second and third display members can be centrally aligned along the same proximal-to-distal axis of the person's wrist and/or forearm. In an example, a display member can have a flat display surface. In an example, a display member can be a touch screen which responds to finger movements. In an example, a display member can display images which appear three-dimensional without the need for special eyewear using the technology disclosed in U.S. Pat. No. 7,978,407 entitled "Holovision™ 3D Imaging with Rotating Light-Emitting Members." In this example, the first, second, and third display members are separate components. In another example, the first and third display members can be top and bottom views of the same component. In another example, the device may not have a first display member and only have the second and third display members.

In an example, the first display member can display a summary of the information which is displayed in more detail on the second and third display members. In an example, the second and third display members can display two different sections of the same text content. In an example, the second and third display members can display two different sections of the same image content. In an example, the second and third display members can display text and image, respectively, from the same multi-media content.

In an example, a display member can display information with a proximal-to-distal or distal-to-proximal orientation. In an example, a display member can display information with a lateral orientation. In an example, the device can automatically change the radial orientation of information on a display member based on the orientation and/or movement of the device as detected by a gyroscope and/or motion sensor which is incorporated into the device. In an example, the orientation of information on a display member can be automatically changed based on the orientation and/or position of the device relative to the person's eyes. In an example, the orientation and/or position of the device relative to the person's eyes can be determined based on data from one or more cameras, motion sensors, inertial sensors, and/or bend sensors which are incorporated into the device.

In an example, a forearm-wearable device can further comprise one or more sensors. In an example, a sensor can be a multi-axial accelerometer. In an example, a sensor can be a gyroscope. In an example, a sensor can be a light energy sensor. In an example, a sensor can be a spectroscopic sensor which collects data concerning the spectrum of light reflected from and/or transmitted through tissue of the person's wrist and/or forearm. In an example, a sensor can be an electromagnetic energy sensor. In an example, a sensor can measure the resistance, impedance, and/or conductivity of tissue of the person's wrist and/or forearm with respect to the transmission of electromagnetic energy. In an example, a sensor can measure electromagnetic energy emitted from muscles and/or nerves in the person's wrist and/or forearm. In an example, a sensor can be a capacitive electromagnetic energy sensor.

In an example, a sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

In an example, this device can change one or more display members from a first (lower energy) display mode to a second (higher energy) display mode, or vice versa, based on data from one or more motion and/or inertial sensors which are incorporated into the device or with which the device is in wireless communication. In an example, when a motion and/or inertial sensor indicates a first level of movement of the device or a first orientation of the device, then the assumption is that the person is not looking at the device and the device sets the display member to the first (lower energy) display mode. In an example, when a motion and/or inertial sensor indicates a second level of movement of the device or a second orientation of the device, then the assumption is that the person may be looking at the device and the device sets the display member to the second (higher energy) display mode.

In an example, this device can be part of a multi-device system which includes other locations on a person's body, such as the person's head or torso. In an example, this device can be in communication with a motion and/or inertial sensor which is located elsewhere on the person's body so that the relative motion or relative orientation of the device (relative to the rest of the person's body) can be monitored. Measuring the relative motion or orientation of the device (e.g. relative to the rest of the person's body) rather than absolute motion or position of the device (e.g. relative to the earth) can help to factor out changes in motion or orientation which are due to being in a car, elevator, or airplane. Even though the absolute position or orientation of a device might be changing rapidly in a car, elevator, or airplane, the relative position of the device (relative to the rest of the person) may be stable and the person may wish see the display.

The example embodiment of this invention which is shown in FIGS. 99 and 100 is similar to the one shown in FIGS. 97 and 98 except that there are two folding attachment members and four display members. FIGS. 99 and 100 show two sequential views of a forearm-wearable computing device with a large display area comprising: (a) primary attachment member 9902, wherein this primary attachment member is configured to attach the device to a person's wrist and/or forearm by encircling at least 50% of the circumference of the person's wrist and/or forearm; (b) first folding attachment member 9903, wherein this first folding attachment member has a first configuration in which it overlaps the primary attachment member by a first amount, wherein this first folding attachment member has a second configuration in which it overlaps primary attachment member by a second amount, wherein the second amount is less than the first amount, and wherein this first folding attachment member is moved from the first configuration to the second configuration by rotation relative to the primary attachment member; (c) second folding attachment member 9903, wherein this second folding attachment member has a third configuration in which it overlaps the primary attachment member by a third amount, wherein this second folding attachment member has a fourth configuration in which it overlaps the primary attachment member by a fourth amount, wherein the fourth amount is less than the third amount, and wherein this second folding attachment member is moved from the third configuration to the fourth configuration by rotation relative to the primary attachment member; (d) first display member 9904, wherein this first display member is on the exterior surface of the device and visible to the person when the first folding attachment member is in the first configuration; (e) second display member 9907, wherein this second display member is on the exterior surface of the device and visible to the person when the first folding attachment member is in the second configuration; (f) third display member 9905, wherein this third display member is on the exterior surface of the device and visible to the person when the second folding attachment member is in the fourth configuration; and (g) fourth display member 9906, wherein this fourth display member is on the exterior surface of the device and visible to the person when the first folding attachment member is in the second configuration and the second folding attachment member is in the fourth configuration.

FIG. 101 shows another example of a forearm-wearable computing device with a large display area. This example comprises: (a) a distal attachment member 10101, wherein this distal attachment member is configured to attach the device to a person's wrist and/or forearm by encircling at least 50% of the circumference of the person's wrist and/or forearm, and wherein this distal attachment member is a first distance from the person's elbow; (b) a proximal attachment member 10102, wherein this proximal attachment member is configured to attach the device to a person's wrist and/or forearm by encircling at least 50% of the circumference of the person's wrist and/or forearm, wherein this proximal attachment member is a second distance from the person's elbow, and wherein the second distance is less than the first distance; (c) a first display member 10103, wherein this first display member is a first distance from the person's elbow; (d) a second display member 10104, wherein this second display member is a second distance from the person's elbow, and wherein the second distance is less than the first distance; and (e) a third display member 10105, wherein this third display member is a third distance from the person's elbow, and wherein the third distance is less than the second distance. The upper portion of FIG. 101 shows this forearm-wearable computing device from a lateral (or side) perspective. The lower portion of FIG. 101 shows this forearm-wearable device from a top-down (or frontal) perspective.

In an example, the proximal attachment member and/or the distal attachment member can be a band, strap, chain, bracelet, or bangle. In an example, an attachment member can be a flexible and/or elastic band, strap, mesh, cuff, or chain which spans the entire circumference of the person's wrist and/or forearm. In an example, an attachment member can be sufficiently flexible and/or elastic that it can be slipped over the hand onto the wrist and/or forearm. In an example, an attachment member can be a band, strap, or chain which further comprises a buckle, clasp, clip, hook, hook-and-eye material, pin, latch, button, and/or zipper which fastens it around the circumference of the person's wrist and/or forearm. In an example, an attachment member can be a bracelet or bangle. In an example, an attachment member can be sufficiently rigid and/or resiliently-flexible that it holds the device on the person's wrist and/or forearm even though it does not span the entire circumference of the person's wrist and/or forearm.

In an example, a display member can be a computer display screen. In an example, a display member can have a cross-sectional shape which is selected from the group consisting of: circular, elliptical, oblong, rectangular with rounded vertexes, hexagonal with rounded vertexes, square, rectangular, and hexagonal. In an example, a display member can have a flat display surface. In an example, a display member can be a touch screen which responds to finger movements. In an example, a display member can display images which appear three-dimensional without the need for special eyewear using the technology disclosed in U.S. Pat. No. 7,978,407 entitled "Holovision™ 3D Imaging with Rotating Light-Emitting Members." In an example, the three display members can display different sections of the same text content. In an example, the three display members can display two different sections of the same image content. In an example, two different display members can display text and image, respectively, from the same multi-media content.

In an example, display members can display information with a proximal-to-distal or distal-to-proximal orientation. In an example, display members can display information with a lateral orientation. In an example, the device can automatically change the radial orientation of information on display members based on the orientation and/or movement of the device as detected by a gyroscope and/or motion sensor which is incorporated into the device. In an example, the orientation of information on display members can be automatically changed based on the orientation and/or position of the device relative to the person's eyes. In an example, the orientation and/or position of the device relative to the person's eyes can be determined based on data from one or more cameras, motion sensors, inertial sensors, and/or bend sensors which are incorporated into the device.

In an example, this device can change one or more display members from a first (lower energy) display mode to a second (higher energy) display mode, or vice versa, based on data from one or more motion and/or inertial sensors which are incorporated into the device or with which the device is in wireless communication. In an example, when a motion and/or inertial sensor indicates a first level of movement of the device or a first orientation of the device, then the assumption is that the person is not looking at the device and the device sets the display member to the first (lower energy) display mode. In an example, when a motion and/or inertial sensor indicates a second level of movement of the device or a second orientation of the device, then the assumption is that the person may be looking at the device and the device sets the display member to the second (higher energy) display mode.

In an example, this device can be part of a multi-device system which includes other locations on a person's body, such as the person's head or torso. In an example, this device can be in communication with a motion and/or inertial sensor which is located elsewhere on the person's body so that the relative motion or relative orientation of the device (relative to the rest of the person's body) can be monitored. Measuring the relative motion or orientation of the device (e.g. relative to the rest of the person's body) rather than absolute motion or position of the device (e.g. relative to the earth) can help to factor out changes in motion or orientation which are due to being in a car, elevator, or airplane. Even though the absolute position or orientation of a device might be changing rapidly in a car, elevator, or airplane, the relative position of the device (relative to the rest of the person) may be stable and the person may wish see the display.

In an example, the three display members can be longitudinally aligned along the person's wrist and/or forearm. In an example, the centroids of the three display members can be aligned along a common proximal-to-distal longitudinal axis of the person's wrist and/or forearm. In an example, the three display members can all have the same size display surfaces. In an example, the display surface of the second display member can be larger than the display sizes of the first and third display members. In an example, the perimeters of the display members can be connected along a common proximal-to-distal longitudinal axis. In an example, the perimeters of two of the display members can combine to form a figure-eight symbol or an infinity symbol with a longitudinal orientation along the person's wrist and/or forearm.

In an example, the distal attachment member can be connected to the first display member and hold the first display member onto the person's wrist and/or forearm. In an example, the proximal attachment member can be connected to the third display member and hold the third display member onto the person's wrist and/or forearm. In an example, the second display member can be connected to the first and third display members which collectively hold the second display member onto the person's wrist and/or forearm. In an example, the distal attachment member can have a variable width which is greatest where it attaches to the first display member. In an example, the proximal attachment member can have a variable width which is greatest where it attaches to the third display member.

In an example, this forearm-wearable computing device can further comprise one or more sensors. In an example, a sensor can be a multi-axial accelerometer. In an example, a sensor can be a gyroscope. In an example, a sensor can be a light energy sensor. In an example, a sensor can be a spectroscopic sensor which collects data concerning the spectrum of light reflected from and/or transmitted through tissue of the person's wrist and/or forearm. In an example, a sensor can be an electromagnetic energy sensor. In an example, a sensor can measure the resistance, impedance, and/or conductivity of tissue of the person's wrist and/or forearm with respect to the transmission of electromagnetic energy. In an example, a sensor can measure electromagnetic energy emitted from muscles and/or nerves in the person's wrist and/or forearm. In an example, a sensor can be a capacitive electromagnetic energy sensor.

In an example, a sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

FIG. 102 shows another example of a forearm-wearable computing device with a large display area. This example comprises: (a) a helical and/or spiral attachment member 10201, wherein this helical and/or spiral attachment member spans at least 75% of the circumference of a person's wrist and/or forearm, wherein this helical and/or spiral attachment member has a distal end which is a first distance from the person's elbow, wherein this helical and/or spiral attachment member has a proximal end which is a second distance from the person's elbow, and wherein the second distance is less than the first distance; (b) a distal display member 10202, wherein this distal display member is attached to the helical and/or spiral attachment member at a third distance from the person's elbow; and (c) a proximal display member 10203, wherein this proximal display member is attached to the helical and/or spiral attachment member at a fourth distance from the person's elbow, and wherein the fourth distance is less than the third distance. The upper portion of FIG. 102 shows this forearm-wearable computing device from a lateral (or side) perspective. The lower portion of FIG. 102 shows this forearm-wearable device from a top-down (or frontal) perspective.

In an example, helical and/or spiral attachment member 10201 can be a bracelet, armlet, bangle, coil, or band which is sufficiently inflexible or resiliently-flexible that it holds the device onto the person's wrist and/or forearm even if its ends are not connected to each other. In an example, a helical and/or spiral attachment member can be a band, strap, mesh, cuff, or chain which is flexible, stretchable, and/or elastic and which encircles the entire circumference of the person's wrist and/or forearm after being slipped over the person's hand. In an example, a helical and/or spiral attachment member can be a band, strap, mesh, cuff, or chain with ends which are connected to each other by a buckle, clasp, clip, hook, hook-and-eye material, pin, latch, button, and/or zipper in order to hold it onto the person's wrist and/or forearm.

In an example, a helical and/or spiral attachment member can span at least 75% of the circumference of a person's wrist and/or forearm. In an example, a helical and/or spiral attachment member can span at least 75% of the circumference of a person's wrist and/or forearm in a three-quarter spiral. In an example, a helical and/or spiral attachment member can span the entire circumference of a person's wrist and/or forearm once in a single complete spiral loop. In an example, the distal end and the proximal end of a spiral loop can be aligned along a longitudinal axis of a person's wrist and/or forearm. In an example, the distal end and the proximal end of a spiral loop can both be located on the upper (or frontal) surface of the person's wrist and/or forearm. In an example, a helical and/or spiral attachment member can span the entire circumference of a person's wrist and/or forearm multiple times in multiple spiral loops. In an example, a helical and/or spiral attachment member can span the entire circumference of a person's wrist and/or forearm between one and two times, with one complete spiral loop and an additional partial loop.

In an example, a display member can be a computer display screen. In an example, a display member can have a cross-sectional shape which is selected from the group consisting of: circular, elliptical, oblong, rectangular with rounded vertexes, hexagonal with rounded vertexes, square, rectangular, and hexagonal. In an example, a display member can have a flat display surface. In an example, a display member can be a touch screen which responds to finger movements. In an example, a display member can display images which appear three-dimensional without the need for special eyewear using the technology disclosed in U.S. Pat. No. 7,978,407 entitled "Holovision™ 3D Imaging with Rotating Light-Emitting Members." In an example, the distal and proximal display members can display different sections of the same text content. In an example, the distal and proximal display members can display two different sections of the same image content. In an example, the distal and proximal display members can display text and image, respectively, from the same multi-media content.

In an example, display members can display information with a proximal-to-distal or distal-to-proximal orientation. In an example, display members can display information with a lateral orientation. In an example, the device can automatically change the radial orientation of information on display members based on the orientation and/or movement of the device as detected by a gyroscope and/or motion sensor which is incorporated into the device. In an example, the orientation of information on display members can be automatically changed based on the orientation and/or position of the device relative to the person's eyes. In an example, the orientation and/or position of the device relative to the person's eyes can be determined based on data from one or more cameras, motion sensors, inertial sensors, and/or bend sensors which are incorporated into the device.

In an example, this device can change one or more display members from a first (lower energy) display mode to a second (higher energy) display mode, or vice versa, based on data from one or more motion and/or inertial sensors which are incorporated into the device or with which the device is in wireless communication. In an example, when a motion and/or inertial sensor indicates a first level of movement of the device or a first orientation of the device, then the assumption is that the person is not looking at the device and the device sets the display member to the first (lower energy) display mode. In an example, when a motion and/or inertial sensor indicates a second level of movement of the device or a second orientation of the device, then the assumption is that the person may be looking at the device and the device sets the display member to the second (higher energy) display mode.

In an example, this device can be part of a multi-device system which includes other locations on a person's body, such as the person's head or torso. In an example, this device can be in communication with a motion and/or inertial sensor which is located elsewhere on the person's body so that the relative motion or relative orientation of the device (relative to the rest of the person's body) can be monitored. Measuring the relative motion or orientation of the device (e.g. relative to the rest of the person's body) rather than absolute motion or position of the device (e.g. relative to the earth) can help to factor out changes in motion or orientation which are due to being in a car, elevator, or airplane. Even though the absolute position or orientation of a device might be changing rapidly in a car, elevator, or airplane, the relative position of the device (relative to the rest of the person) may be stable and the person may wish see the display.

In an example, the distal display member can be attached to the distal end of the helical and/or spiral attachment member. In an example, the proximal display member can be attached to the proximal end of the helical and/or spiral attachment member. In an example, the distal and proximal display members can be aligned along a longitudinal axis of the person's wrist and/or forearm. In an example, the centroids of the distal and proximal display members can be aligned along a common proximal-to-distal longitudinal axis of the person's wrist and/or forearm. In an example, the distal and proximal display members can have the same size display surfaces. In an example, the helical and/or spiral attachment member can have a variable width which is greatest where it attaches to a display member.

In an example, this forearm-wearable computing device can further comprise one or more sensors. In an example, a sensor can be a multi-axial accelerometer. In an example, a sensor can be a gyroscope. In an example, a sensor can be a light energy sensor. In an example, a sensor can be a spectroscopic sensor which collects data concerning the spectrum of light reflected from and/or transmitted through tissue of the person's wrist and/or forearm. In an example, a sensor can be an electromagnetic energy sensor. In an example, a sensor can measure the resistance, impedance, and/or conductivity of tissue of the person's wrist and/or forearm with respect to the transmission of electromagnetic energy. In an example, a sensor can measure electromagnetic energy emitted from muscles and/or nerves in the person's wrist and/or forearm. In an example, a sensor can be a capacitive electromagnetic energy sensor.

In an example, a sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

FIG. 103 shows another example of a forearm-wearable computing device with a large display area. This example comprises: (a) a bifurcated attachment member 10301 which encircles at least 50% of the circumference of the person's wrist and/or forearm, wherein this bifurcated attachment member has an upper portion which is configured to be worn on the upper and/or frontal surface of a person's wrist and/or forearm, wherein this upper portion further comprises a distal branch which is a first distance from the person's elbow and a proximal branch which is a second distance from the person's elbow, wherein the second distance is less than the first distance, and wherein the distal and proximal branches converge along the side surfaces or the lower and/or dorsal surface of the person's wrist and/or forearm; (b) a distal display member 10302, wherein this distal display member is attached to the distal branch of the bifurcated attachment member; and (c) a proximal display member 10303, wherein this proximal display member is attached to the proximal branch of the bifurcated attachment member. The upper portion of FIG. 103 shows this forearm-wearable computing device from a lateral (or side) perspective. The lower portion of FIG. 103 shows this forearm-wearable device from a top-down (or frontal) perspective.

In an example, bifurcated attachment member 10301 can be a bracelet, armlet, bangle, coil, or band which is sufficiently inflexible or resiliently-flexible that it holds the device onto the person's wrist and/or forearm even if its ends are not connected to each other. In an example, a bifurcated attachment member can be a band, strap, mesh, cuff, or chain which is flexible, stretchable, and/or elastic and which encircles the entire circumference of the person's wrist and/or forearm after being slipped over the person's hand. In an example, a bifurcated attachment member can be a band, strap, mesh, cuff, or chain with ends which are connected to each other by a buckle, clasp, clip, hook, hook-and-eye material, pin, latch, button, and/or zipper to hold it onto the person's wrist and/or forearm.

In an example, bifurcated attachment member 10301 can be a single band, strap, mesh, cuff, or chain on the lower and/or dorsal surface of a person's wrist and/or forearm and can bifurcate to form two bands, straps, meshes, cuffs, or chains on the upper and/or frontal surface of the person's wrist and/or forearm. In an example, bifurcated attachment member 10301 can be a single band, strap, mesh, cuff, or chain on the lower and/or dorsal surface of a person's wrist and/or forearm and can bifurcate to form two branches (a distal branch and a proximal branch) on the upper and/or frontal surface of the person's wrist and/or forearm. In an example, a bifurcated attachment member can bifurcate into two branches on the sides (lateral surfaces) of a person's wrist and/or forearm.

In an example, a display member can be a computer display screen. In an example, a display member can have a cross-sectional shape which is selected from the group consisting of: circular, elliptical, oblong, rectangular with rounded vertexes, hexagonal with rounded vertexes, square, rectangular, and hexagonal. In an example, a display member can have a flat display surface. In an example, a display member can be a touch screen which responds to finger movements. In an example, a display member can display images which appear three-dimensional without the need for special eyewear using the technology disclosed in U.S. Pat. No. 7,978,407 entitled "Holovision™ 3D Imaging with Rotating Light-Emitting Members." In an example, the distal and proximal display members can display different sections of the same text content. In an example, the distal and proximal display members can display two different sections of the same image content. In an example, the distal and proximal display members can display text and image, respectively, from the same multi-media content.

In an example, the distal and proximal display members can be aligned along a longitudinal axis of the person's wrist and/or forearm. In an example, the centroids of the distal and proximal display members can be aligned along a common proximal-to-distal longitudinal axis of the person's wrist and/or forearm. In an example, the distal and proximal display members can have the same size display surfaces. In an example, display members can display information with a proximal-to-distal or distal-to-proximal orientation. In an example, display members can display information with a lateral orientation. In an example, the device can automatically change the radial orientation of information on display members based on the orientation and/or movement of the device as detected by a gyroscope and/or motion sensor which is incorporated into the device. In an example, the orientation of information on display members can be automatically changed based on the orientation and/or position of the device relative to the person's eyes. In an example, the orientation and/or position of the device relative to the person's eyes can be determined based on data from one or more cameras, motion sensors, inertial sensors, and/or bend sensors which are incorporated into the device.

In an example, this device can change one or more display members from a first (lower energy) display mode to a second (higher energy) display mode, or vice versa, based on data from one or more motion and/or inertial sensors which are incorporated into the device or with which the device is in wireless communication. In an example, when a motion and/or inertial sensor indicates a first level of movement of the device or a first orientation of the device, then the assumption is that the person is not looking at the device and the device sets the display member to the first (lower energy) display mode. In an example, when a motion and/or inertial sensor indicates a second level of movement of the device or a second orientation of the device, then the assumption is that the person may be looking at the device and the device sets the display member to the second (higher energy) display mode.

In an example, this device can be part of a multi-device system which includes other locations on a person's body, such as the person's head or torso. In an example, this device can be in communication with a motion and/or inertial sensor which is located elsewhere on the person's body so that the relative motion or relative orientation of the device (relative to the rest of the person's body) can be monitored. Measuring the relative motion or orientation of the device (e.g. relative to the rest of the person's body) rather than absolute motion or position of the device (e.g. relative to the earth) can help to factor out changes in motion or orientation which are due to being in a car, elevator, or airplane. Even though the absolute position or orientation of a device might be changing rapidly in a car, elevator, or airplane, the relative position of the device (relative to the rest of the person) may be stable and the person may wish see the display.

In an example, this forearm-wearable computing device can further comprise one or more sensors. In an example, a sensor can be a multi-axial accelerometer. In an example, a sensor can be a gyroscope. In an example, a sensor can be a light energy sensor. In an example, a sensor can be a spectroscopic sensor which collects data concerning the spectrum of light reflected from and/or transmitted through tissue of the person's wrist and/or forearm. In an example, a sensor can be an electromagnetic energy sensor. In an example, a sensor can measure the resistance, impedance, and/or conductivity of tissue of the person's wrist and/or forearm with respect to the transmission of electromagnetic energy. In an example, a sensor can measure electromagnetic energy emitted from muscles and/or nerves in the person's wrist and/or forearm. In an example, a sensor can be a capacitive electromagnetic energy sensor.

In an example, a sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

FIG. 104 shows another example of a forearm-wearable computing device with a large display area. This example comprises: (a) an arcuate attachment member 10401 which encircles at least 50% of the circumference of the person's wrist and/or forearm; (b) a left-side display member 10402, wherein this left-side display member is attached to a first end of the arcuate attachment member; and (c) a right-side display member 10403, wherein this right-side display member is attached to a second end of the arcuate attachment member. The upper portion of FIG. 104 shows this forearm-wearable computing device from a lateral (or side) perspective. The lower portion of FIG. 104 shows this forearm-wearable device from a top-down (or frontal) perspective.

In an example, arcuate attachment member 10401 can be a bracelet, armlet, bangle, coil, or band which is sufficiently inflexible or resiliently-flexible that it holds the device onto the person's wrist and/or forearm even if its ends are not connected to each other. In an example, an arcuate attachment member can be a band, strap, mesh, cuff, or chain which is flexible, stretchable, and/or elastic and which encircles the entire circumference of the person's wrist and/or forearm after being slipped over the person's hand. In an example, an arcuate attachment member can be a band, strap, mesh, cuff, or chain with ends which are connected to each other by a buckle, clasp, clip, hook, hook-and-eye material, pin, latch, button, and/or zipper to hold it onto the person's wrist and/or forearm.

In an example, a display member can be a computer display screen. In an example, a display member can have a cross-sectional shape which is selected from the group consisting of: circular, elliptical, oblong, rectangular with rounded vertexes, hexagonal with rounded vertexes, square, rectangular, and hexagonal. In an example, a display member can have a flat display surface. In an example, a display member can be a touch screen which responds to finger movements. In an example, a display member can display images which appear three-dimensional without the need for special eyewear using the technology disclosed in U.S. Pat. No. 7,978,407 entitled "Holovision™ 3D Imaging with Rotating Light-Emitting Members." In an example, the left-side and right-side display members can display different sections of the same text content. In an example, the left-side and right-side display members can display two different sections of the same image content. In an example, the left-side and right-side display members can display text and image, respectively, from the same multi-media content.

In an example, the left-side and right-side display members can be aligned along the same circumferential axis of a person's wrist and/or forearm. In an example, the centroids of the left-side and right-side display members can be aligned along a common circumference of the person's wrist and/or forearm. In an example, the left-side and right-side display members can have the same size display surfaces. In an example, the left-side and right-side display members can be separated by a distance which is at least 5% of the circumference of the person's wrist and/or forearm. In an example, the left-side and right-side display members can be connected to each other by a buckle, clasp, clip, hook, hook-and-eye material, pin, latch, button, and/or zipper.

In an example, display members can display information with a proximal-to-distal or distal-to-proximal orientation. In an example, display members can display information with a lateral orientation. In an example, the device can automatically change the radial orientation of information on display members based on the orientation and/or movement of the device as detected by a gyroscope and/or motion sensor which is incorporated into the device. In an example, the orientation of information on display members can be automatically changed based on the orientation and/or position of the device relative to the person's eyes. In an example, the orientation and/or position of the device relative to the person's eyes can be determined based on data from one or more cameras, motion sensors, inertial sensors, and/or bend sensors which are incorporated into the device.

In an example, this device can change one or more display members from a first (lower energy) display mode to a second (higher energy) display mode, or vice versa, based on data from one or more motion and/or inertial sensors which are incorporated into the device or with which the device is in wireless communication. In an example, when a motion and/or inertial sensor indicates a first level of movement of the device or a first orientation of the device, then the assumption is that the person is not looking at the device and the device sets the display member to the first (lower energy) display mode. In an example, when a motion and/or inertial sensor indicates a second level of movement of the device or a second orientation of the device, then the assumption is that the person may be looking at the device and the device sets the display member to the second (higher energy) display mode.

In an example, this device can be part of a multi-device system which includes other locations on a person's body, such as the person's head or torso. In an example, this device can be in communication with a motion and/or inertial sensor which is located elsewhere on the person's body so that the relative motion or relative orientation of the device (relative to the rest of the person's body) can be monitored. Measuring the relative motion or orientation of the device (e.g. relative to the rest of the person's body) rather than absolute motion or position of the device (e.g. relative to the earth) can help to factor out changes in motion or orientation which are due to being in a car, elevator, or airplane. Even though the absolute position or orientation of a device might be changing rapidly in a car, elevator, or airplane, the relative position of the device (relative to the rest of the person) may be stable and the person may wish see the display.

In an example, this forearm-wearable computing device can further comprise one or more sensors. In an example, a sensor can be a multi-axial accelerometer. In an example, a sensor can be a gyroscope. In an example, a sensor can be a light energy sensor. In an example, a sensor can be a spectroscopic sensor which collects data concerning the spectrum of light reflected from and/or transmitted through tissue of the person's wrist and/or forearm. In an example, a sensor can be an electromagnetic energy sensor. In an example, a sensor can measure the resistance, impedance, and/or conductivity of tissue of the person's wrist and/or forearm with respect to the transmission of electromagnetic energy. In an example, a sensor can measure electromagnetic energy emitted from muscles and/or nerves in the person's wrist and/or forearm. In an example, a sensor can be a capacitive electromagnetic energy sensor.

In an example, a sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

FIGS. 105 through 108 show another example of a forearm-wearable computing device with a large display area. This example comprises: (a) a distal attachment member 10501, wherein this distal attachment member is configured to span the circumference of the person's wrist and/or forearm, wherein this distal attachment member has a first portion of its circumference with a first width, wherein this distal attachment member has a second portion of its circumference with a second width, and wherein the second width is narrower than the first width; (b) a proximal attachment member 10502, wherein this proximal attachment member is configured to span the circumference of the person's wrist and/or forearm, wherein this proximal attachment member has a third portion of its circumference with a third width, wherein this proximal attachment member has a fourth portion of its circumference with a fourth width, wherein the fourth width is wider than the third width, wherein the distal attachment member and the proximal attachment member have a first configuration in which the first portion of the distal attachment member is aligned with third portion of the proximal attachment member, wherein the distal attachment member and the proximal attachment member have a second configuration in which the first portion of the distal attachment member is aligned with fourth portion of the proximal attachment member, and wherein the distal attachment member and the proximal attachment member can be moved from the first configuration to the second configuration by the rotation of one attachment member relative to the other attachment member; (c) a distal display member 10503 which is attached to, or part of, the first portion of the distal attachment member; and (d) a proximal display member 10504 which is attached to, or part of, the fourth portion of the proximal attachment member.

Figures 105, 106:
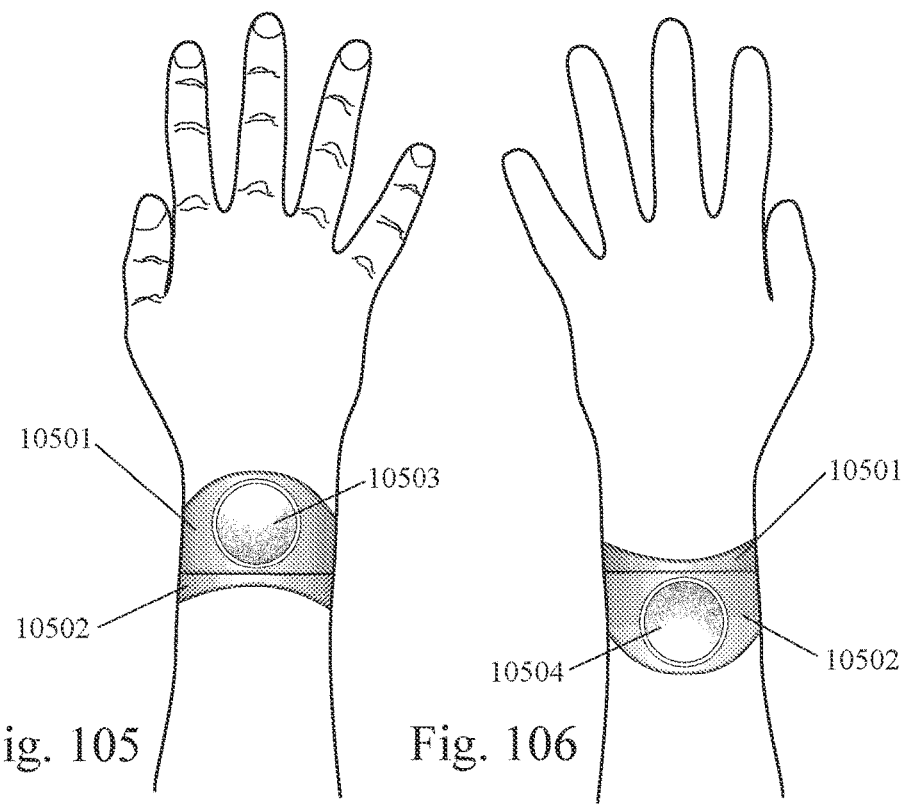
Figures 107, 108:
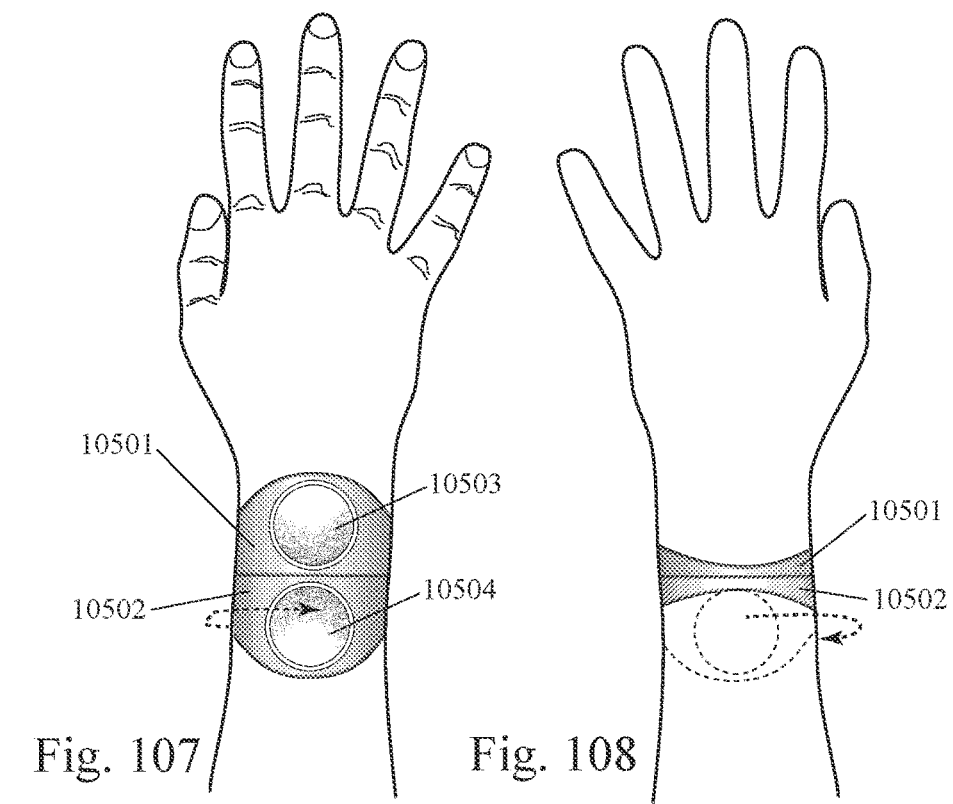

FIGS. 105 and 106 show this device at a first point in time wherein the distal attachment member and the proximal attachment member are in the first configuration. FIG. 105 shows this device from a top-down (frontal) perspective—on the top of the person's wrist and/or forearm. FIG. 106 shows this device from a bottom-up (dorsal) perspective—on the bottom of the person's wrist and/or forearm. FIGS. 107 and 108 show this device at a second point in time, after the distal attachment member and the proximal attachment member have been moved into the second configuration. This movement is symbolically represented by dotted-line arrows. FIG. 107 shows this device from a top-down (frontal) perspective—on the top of the person's wrist and/or forearm. FIG. 108 shows this device from a bottom-up (dorsal) perspective—on the bottom of the person's wrist and/or forearm.

In the first configuration, shown in FIGS. 105 and 106, the wide portion of the distal attachment member is on the top of the person's wrist and/or forearm and the wide portion of the proximal attachment member is on the bottom of the person's wrist and/or forearm. The device can be put in this first configuration to minimize its size as seen from the top when large-scale viewing (e.g. viewing both display members) is not needed. This design can help the device to be relatively unobtrusive (in this first configuration) when large-scale viewing (e.g. viewing both display members) is not needed.

In the second configuration, shown in FIGS. 107 and 108, the proximal attachment member has been rotated so that the wide portions of the distal and proximal attachment members are both on the top of the person's wrist and/or forearm, as well as both display members. The device can be put in this second configuration to maximize large-scale viewing (e.g. viewing both display members) when this is needed. The device is temporarily more obtrusive (in this second configuration) when large-scale viewing (e.g. viewing both display members) is needed. When large-scale viewing is no longer needed, then the device can be rotated back into the first (less obtrusive) configuration.

In an example, an attachment member can be a bracelet, armlet, bangle, coil, band, strap, chain, or cuff. In an example, the ends of an attachment member can be attached around a person/s wrist and/or forearm by a buckle, clasp, clip, hook, hook-and-eye material, pin, latch, button, and/or zipper. In an example, an attachment member can be slipped over a person's hand to fit around a person/s wrist and/or forearm. In an example, the distal attachment member can be attached to the proximal attachment member by a sliding track and/or bearings which enable the proximal attachment member to rotate around the wrist and/or forearm relative to the distal attachment member, or vice versa.

In an example, a display member can be a computer display screen. In an example, a display member can have a cross-sectional shape which is selected from the group consisting of: rectangular with rounded vertexes, hexagonal with rounded vertexes, square, rectangular, hexagonal, circular, elliptical, and oblong. In an example, the two display members can be centrally aligned along the same proximal-to-distal axis of the person's wrist and/or forearm. In an example, a display member can have a flat display surface. In an example, a display member can be a touch screen which responds to finger movements. In an example, a display member can display images which appear three-dimensional without the need for special eyewear using the technology disclosed in U.S. Pat. No. 7,978,407 entitled "Holovision™ 3D Imaging with Rotating Light-Emitting Members." In an example, the two display members can display two different sections of the same text content. In an example, the two display members can display two different sections of the same image content. In an example, the two display members can display text and image, respectively, from the same multi-media content.

FIGS. 109 and 110 show another example of a forearm-wearable computing device with a large display area. This example comprises: (a) a first display member 10902; (b) a second display member 10903; (c) a third display member 1904, and (d) an arcuate attachment member 10901, wherein this arcuate attachment member is configured to span at least 50% of the circumference of the person's wrist and/or forearm, wherein this arcuate attachment member holds the display members on the person's wrist and/or forearm, wherein this arcuate attachment member has a right-side portion which is attached to a display member, wherein this arcuate attachment member has a left-side portion which is attached to a display member, wherein this arcuate attachment member has a first configuration in which the left-side portion and the right-side portion are aligned along the same circumference of the person's wrist and/or forearm, wherein arcuate attachment member has a second configuration in which the left-side portion and the right-side portion are not aligned along the same circumference of the person's wrist and/or forearm, and wherein the arcuate attachment member is moved from the first configuration to the second configuration when the first display member is rotated relative to the second display member.

FIG. 109 shows this device at a first point in time wherein the arcuate attachment member is in the first configuration. FIG. 110 shows this device at a second point in time wherein the arcuate attachment member has been moved into the second configuration. In the first configuration shown in FIG. 109, the left-side and right-side portions of the arcuate attachment member are aligned along the same circumference around the person's wrist and/or forearm. Also, in this first configuration, first display member 10902 is on the outer surface of the device and visible to the person. In the second configuration shown in FIG. 110, the right-side portion of the arcuate attachment member has been flipped and moved proximally relative to the left-side portion of the arcuate attachment member. This movement is symbolically represented by dotted-line arrows. Also, in this second configuration, the second and third display members (10903 and 10904) are now on the outer surface of the device and visible by the person. In this example, the arcuate attachment member is circular in the first configuration and helical in the second configuration.

This design gives the device flexibility in the trade-off between inconspicuousness and screen size. When a small display area is sufficient, the device can be set to the first configuration with a smaller surface area and only the first display member being visible. However, when a larger display area is needed, the device can be changed to the second configuration with a larger surface area and two display members (the second and the third) being visible. In an example, two display members can be connected by a hinge or joint which enables one display member to be rotated relative to the other display member. In an example, the third display member can located on the bottom of a rotating member and the first display member can be located on the top of that rotating member, in the first configuration. In an example, if the first display member is visible from either the top or the bottom, then a third display member is not needed.

In an example, an arcuate attachment member can be a bracelet, armlet, bangle, coil, band, strap, chain, or cuff. In an example, the ends of an arcuate attachment member can be attached around a person/s wrist and/or forearm by a buckle, clasp, clip, hook, hook-and-eye material, pin, latch, button, and/or zipper. In an example, an arcuate attachment member can be slipped over a person's hand to fit around a person/s wrist and/or forearm.

In an example, a display member can be a computer display screen. In an example, a display member can have a cross-sectional shape which is selected from the group consisting of: rectangular with rounded vertexes, hexagonal with rounded vertexes, square, rectangular, hexagonal, circular, elliptical, and oblong. In an example, the two display members can be centrally aligned along the same proximal-to-distal axis of the person's wrist and/or forearm. In an example, a display member can have a flat display surface. In an example, a display member can be a touch screen which responds to finger movements. In an example, the two display members can display two different sections of the same text content. In an example, the two display members can display two different sections of the same image content. In an example, the two display members can display text and image, respectively, from the same multi-media content.

The example shown in FIGS. 111 and 112 is similar to the one shown in FIGS. 109 and 110 except that the first display member is moved from a first configuration to a second configuration by sliding instead of by rotation. FIGS. 111 and 112 show an example of a forearm-wearable computing device with a large display area comprising: (a) a first display member 11102; (b) a second display member 11103; and (c) an arcuate attachment member 11101, wherein this arcuate attachment member is configured to span at least 50% of the circumference of the person's wrist and/or forearm, wherein this arcuate attachment member holds the display members on the person's wrist and/or forearm, wherein this arcuate attachment member has a left-side portion which is attached to the second display member, wherein this arcuate attachment member has a right-side portion which is attached to the first display member, wherein this arcuate attachment member has a first configuration in which the left-side portion and the right-side portion are aligned along the same circumference of the person's wrist and/or forearm, wherein arcuate attachment member has a second configuration in which the left-side portion and the right-side portion are not aligned along the same circumference of the person's wrist and/or forearm, and wherein the arcuate attachment member is moved from the first configuration to the second configuration when the first display member is slid relative to the second display member.

FIG. 111 shows this device at a first point in time wherein the arcuate attachment member is in the first configuration. FIG. 112 shows this device at a second point in time wherein the arcuate attachment member has been moved into the second configuration. In the first configuration shown in FIG. 111, the left-side and right-side portions of the arcuate attachment member are aligned along the same circumference around the person's wrist and/or forearm. Also, in this first configuration, only first display member 11102 is visible to the person. In the second configuration shown in FIG. 112, the right-side portion of the arcuate attachment member has been slid relative to the left-side portion of the arcuate attachment member. In an example, the second display member can be attached to the first display member by inter-locking tracks which enable this sliding motion. In this second configuration, the second display member is now also visible to the person. In this example, the arcuate attachment member is circular in the first configuration and is helical in the second configuration.

FIGS. 113 and 114 show another example of a forearm-wearable computing device with a large display area. This example comprises: (a) an arcuate attachment member 11301 which is configured to span at least 50% of the circumference of the person's wrist and/or forearm, wherein a central longitudinal axis is defined as a line along the upper (ventral) surface of the person's forearm, from the elbow to the hand, which is equidistant from the lateral sides of the person's forearm; (b) a first display member 11302, wherein this first display member has a first configuration in which its centroid is a first distance from the central longitudinal axis, wherein this first display member has a second configuration in which its centroid is a second distance from the central longitudinal axis, and wherein the second distance is less than the first distance; (c) a second display member 11303; and (d) a third display member 11304, wherein this third display member has a third configuration in which its centroid is a third distance from the central longitudinal axis, wherein this third display member has a fourth configuration in which its centroid is a fourth distance from the central longitudinal axis, wherein the fourth distance is less than the third distance, and wherein the third display member is moved from the third configuration to the fourth configuration when the first display member is moved from the first configuration to the second configuration.

FIG. 113 shows this device at a first point in time when the first and third display members are in their first and third configurations, respectively. In FIG. 113, the arcuate attachment member and the three display members are all aligned around the circumference of the person's wrist and/or forearm in a minimally-obtrusive manner. However, only the second display member is located on the flat portion of the upper surface of the person's wrist and/or forearm. FIG. 114 shows this device at a second point in time after the first and third display members have been moved into their second and fourth configurations, respectively. In an example, this movement can be done manually by the person. In an example, this movement can be done automatically by an actuator which is included in the device. In FIG. 114, the arcuate attachment member is still aligned around the circumference of the person's wrist and/or forearm, but the three display members have been rotated into alignment with the central longitudinal axis to create more visible display area on the flat portion of the upper surface of the person's wrist and/or forearm. This design enables the device to transition, when needed, from a less-obtrusive configuration with less display screen area on the upper surface of the forearm to a more-intrusive configuration with more display screen area on the upper surface of the forearm.

In this example, this device has multiple display members which are oriented in a partially-circumferential manner around a person's wrist and/or forearm in one configuration and are oriented along a central longitudinal axis of the upper surface of the person's forearm in another configuration. In this example, the multiple display members are moved from one configuration to another by being rotated around a central point on an arcuate attachment member. In this example, the left and right side members of a three member sequence of display members are attached to a central display member that rotates. In an example, the display members can be connected by joints or hinges so that they are not coplanar when they are oriented circumferentially around the person's wrist and/or forearm, but are coplanar when they are rotated onto the upper surface of the person's wrist and/or forearm. In an example, these joints or hinges can be spring loaded to bias the display members against the surface of the wrist and/or forearm in either configuration. In this example, there are three display members in a sequence of display members which is rotated from a circumferential orientation to a central longitudinal orientation when greater display area is needed. In another example, a device may have two display members which are rotated from a circumferential orientation to a central longitudinal orientation when greater display area is needed.

In an example, a display member can be a computer display screen. In an example, a display member can have a cross-sectional shape which is selected from the group consisting of: rectangular with rounded vertexes, hexagonal with rounded vertexes, square, rectangular, hexagonal, circular, elliptical, and oblong. In an example, multiple display members can be centrally aligned along the same proximal-to-distal axis of the person's wrist and/or forearm. In an example, a display member can have a flat display surface. In an example, a display member can be a touch screen which responds to finger movements. In an example, a display member can display images which appear three-dimensional without the need for special eyewear using the technology disclosed in U.S. Pat. No. 7,978,407 entitled "Holovision™ 3D Imaging with Rotating Light-Emitting Members." In an example, different display members can display different sections of the same text content. In an example, different display members can display different sections of the same image content. In an example, the different display members can display text and image, respectively, from the same multi-media content.

In an example, an arcuate attachment member can be a bracelet, armlet, bangle, coil, band, strap, chain, or cuff. In an example, the lower ends of an attachment member can be attached around a person/s wrist and/or forearm by a buckle, clasp, clip, hook, hook-and-eye material, pin, latch, button, and/or zipper. In an example, an attachment member can be slipped over a person's hand to fit around a person/s wrist and/or forearm.

FIGS. 115 and 116 show another example of a forearm-wearable computing device with a large display area. This example comprises: (a) an arcuate attachment member

11501 which encircles at least 50% of the circumference of a person's wrist and/or forearm, wherein the central longitudinal axis can be defined as a line along the upper surface of the person's forearm from the person's elbow to the person's hand which is equidistant from the lateral sides of the wrist and/or forearm; (b) a left-side display member 11502 which is attached to (or an integral part of) the arcuate attachment member at a location to the left of the central longitudinal axis (when the person's hand is extended outward with the palm down), wherein this left-side member has a first configuration in which it has a first amount of overlap with the arcuate attachment member, wherein this left-side member has a second configuration in which it has a second amount of overlap with the arcuate attachment member, wherein the second amount is less than the first amount, and wherein the left-side display member transitions from the first configuration to the second configuration by being rotated relative to the arcuate attachment member; and (c) a right-side display member 11503 which is attached to (or an integral part of) the arcuate attachment member at a location to the right of the central longitudinal axis (when the person's hand is extended outward with the palm down), wherein this right-side member has a third configuration in which it has a third amount of overlap with the arcuate attachment member, wherein this right-side member has a fourth configuration in which it has a fourth amount of overlap with the arcuate attachment member, wherein the fourth amount is less than the third amount, and wherein the right-side display member transitions from the third configuration to the fourth configuration by being rotated relative to the arcuate attachment member.

FIG. 115 shows this forearm-wearable computing device at a first time when the left-side and right-side display members (11502 and 11503) are in their first and third configurations, respectively. FIG. 116 shows this forearm-wearable computing device at a second time after the left-side and right-side display members (11502 and 11503) have been rotated into their second and fourth configurations, respectively. In an example, the left-side and right-side display members can be manually rotated from one configuration to another. In an example, the left-side and right-side display members can be automatically rotated from one configuration to another by one or more actuators which are incorporated into the device. In an example, the left-side and right-side display members can connect, attach, and/or link to each other when they are in their second and fourth configurations, respectively.

In an example, the left-side and right-side display members can be longitudinally aligned with the circumference of the arcuate attachment member when the display members are in their first and third configurations, respectively. In an example, the left-side and right-side display members can be perpendicular to this circumference when they are in their second and fourth configurations, respectively. In an example, the ends of the left-side and right-side display members can be rotated distally (toward the person's hand) as they move to their second and fourth configurations, respectively. In another example, the ends of the left-side and right-side display members can be rotated proximally (toward the person's elbow) as they move to their second and fourth configurations, respectively. In an example, the left-side and right-side display members can share a common longitudinal axis in their first and third configurations and can have parallel longitudinal axes in their second and fourth configurations.

In an example, the left-side and right-side display members can be rigid, but be biased toward the surface of the person's wrist and/or forearm so that they are remain close to the surface of the person's wrist and/or forearm in either of their configurations. In an example, the left-side and right-side display members can be flexible and be biased toward the surface of the person's wrist and/or forearm so that they remain close to the surface of the person's wrist and/or forearm in either of their configurations. In an example, the left-side and right-side display members can further comprise one or more tensile hinges (or other flexible tensile connections) which bias the display members toward the surface of the person's wrist and/or forearm so that they remain close to the surface of the person's wrist and/or forearm in either of their configurations.

In an example, the arcuate attachment member can be a bracelet, armlet, bangle, coil, or band which is sufficiently inflexible or resiliently-flexible that it holds the device onto the person's wrist and/or forearm even if its ends are not connected to each other. In an example, the arcuate attachment member can be a band, strap, mesh, cuff, or chain which is flexible, stretchable, and/or elastic and which encircles the entire circumference of the person's wrist and/or forearm after being slipped over the person's hand. In an example, the arcuate attachment member can be a band, strap, mesh, cuff, or chain with ends which are connected to each other by a buckle, clasp, clip, hook, hook-and-eye material, pin, latch, button, and/or zipper to hold it onto the person's wrist and/or forearm.

In an example, a display member can be a computer display screen. In an example, a display member can have a cross-sectional shape which is selected from the group consisting of: oblong, elliptical, rectangular with rounded vertexes, and rectangular. In an example, a display member can be a touch screen which responds to finger movements. In an example, left-side and right-side display members can display different sections of the same text content. In an example, left-side and right-side display members can display two different sections of the same image content. In an example, left-side and right-side display members can display text and image, respectively, from the same multimedia content.

In an example, display members can display information with a proximal-to-distal or distal-to-proximal orientation. In an example, display members can display information with a lateral orientation. In an example, a device can automatically change the radial orientation of information on display members based on the orientation and/or movement of the device as detected by a gyroscope and/or motion sensor which is incorporated into the device. In an example, the orientation of information on display members can be automatically changed based on the orientation and/or position of the device relative to the person's eyes. In an example, the orientation and/or position of the device relative to the person's eyes can be determined based on data from one or more cameras, motion sensors, inertial sensors, and/or bend sensors which are incorporated into the device.

FIGS. 117 and 118 show another example of a forearm-wearable computing device with a large display area. This example comprises: (a) an arcuate attachment member which encircles at least 50% of the circumference of a person's wrist and/or forearm, wherein this arcuate attachment member further comprises a inner circular portion 11701 and an outer arcuate portion 11702, wherein the perimeter of the inner circular portion is within the perimeter of the outer arcuate portion, wherein the perimeters of the inner circular portion and the outer arcuate portion connect to each other at two or more locations, and wherein there are areas of open access to the surface of the person's wrist and/or forearm between the inner circular portion and the outer arcuate portion; (b) a first display member 11703 which is attached to (or an integral part of) the inner circular portion; (c) a second display member 11704 which is attached to (or an integral part of) the inner circular portion, wherein the first display member and the second display member have a first configuration in which a virtual line connecting their centroids forms a first angle with respect to the central longitudinal axis of the person's wrist and/or forearm, wherein the first display member and the second display member have a second configuration in which a virtual line connecting their centroids forms a second angle with respect to the central longitudinal axis of the person's wrist and/or forearm, wherein the absolute value of the difference between the first and second angles is at least 10 degrees, and wherein the first and second display members are moved from their first configuration to their second configuration by being rotated relative to the outer arcuate portion; and (d) a sensor 11705.

FIG. 117 shows this forearm-wearable computing device at a first time when the display members are in their first configuration. FIG. 118 shows this forearm-wearable computing device at a second time after the display members have been rotated into their second configuration. In an example, the display members can be manually rotated from one configuration to another. In an example, the display members can be automatically rotated from one configuration to another by one or more actuators which are incorporated into the device. In an example, the display members are rotated by rotation of inner circular member 11701 within outer arcuate member 11702. In an example, the display members are rotated within inner circular member 11701 which remains stationary.

In this example, a virtual line between the centroids of the first and second display members is substantially perpendicular to the central longitudinal axis in the first configuration and is substantially parallel to the central longitudinal axis in the second configuration. In an example, the two display members can be longitudinally aligned with the circumference of the person's wrist and/or forearm in the first configuration and can be perpendicular to this circumference when they are in their second configuration.

In an example, the arcuate attachment member can comprise a bracelet, armlet, bangle, coil, or band which is sufficiently inflexible or resiliently-flexible that it holds the device onto the person's wrist and/or forearm even if its ends are not connected to each other. In an example, the arcuate attachment member can comprise a band, strap, mesh, cuff, or chain which is flexible, stretchable, and/or elastic and which encircles the entire circumference of the person's wrist and/or forearm after being slipped over the person's hand. In an example, the arcuate attachment member can comprise a band, strap, mesh, cuff, or chain with ends which are connected to each other by a buckle, clasp, clip, hook, hook-and-eye material, pin, latch, button, and/or zipper to hold it onto the person's wrist and/or forearm.

In an example, a display member can be a computer display screen. In an example, a display member can have a cross-sectional shape which is selected from the group consisting of: circular, hexagonal, elliptical, oblong, and pie-slice shape. In an example, a display member can be a touch screen which responds to finger movements. In an example, different display members can display different sections of the same text content. In an example, different display members can display two different sections of the same image content. In an example, different display members can display text and image, respectively, from the same multi-media content.

In an example, display members can display information with a proximal-to-distal or distal-to-proximal orientation. In an example, display members can display information with a lateral orientation. In an example, a device can automatically change the radial orientation of information on display members based on the orientation of the inner circular portion. In an example, a device can automatically change the radial orientation of information on display members based on the orientation and/or movement of the device as detected by a gyroscope and/or motion sensor which is incorporated into the device. In an example, the orientation of information on display members can be automatically changed based on the orientation and/or position of the device relative to the person's eyes. In an example, the orientation and/or position of the device relative to the person's eyes can be determined based on data from one or more cameras, motion sensors, inertial sensors, and/or bend sensors which are incorporated into the device.

In an example, sensor 11705 can be a multi-axial accelerometer. In an example, this sensor can be a gyroscope. In an example, this sensor can be a light energy sensor. In an example, this sensor can be a spectroscopic sensor which collects data concerning the spectrum of light reflected from and/or transmitted through tissue of the person's wrist and/or forearm. In an example, this sensor can be an electromagnetic energy sensor. In an example, this sensor can measure the resistance, impedance, and/or conductivity of tissue of the person's wrist and/or forearm with respect to the transmission of electromagnetic energy. In an example, this sensor can measure electromagnetic energy emitted from muscles and/or nerves in the person's wrist and/or forearm. In an example, this sensor can be a capacitive electromagnetic energy sensor.

In an example, this sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

FIGS. 119 and 120 show another example of a forearm-wearable computing device with a large display area. This example comprises: (a) an arcuate attachment member which encircles at least 50% of the circumference of a person's wrist and/or forearm, wherein this arcuate attachment member further comprises a circular portion 11901 and a convex portion 11902, wherein the circular portion is inside the convex portion, and wherein there are open areas to the person's wrist and/or forearm between the circular portion and the convex portion; (b) a display member 11903 which is attached to (or an integral part of) the circular portion; and (c) a sensor 11904.

The upper portion of FIG. 119 shows a lateral (side surface) view of this forearm-wearable computing device on a person's wrist and/or forearm. The lower portion of FIG.

119 shows a top-down (upper surface) view of this forearm-wearable computing device on a person's wrist and/or forearm. In an example, the top-down view of this device makes the device look like an eye with the circular portion like a pupil and the convex portion like the visible portion of the rest of the eyeball. Perhaps now many people can finally get an eye watch? FIG. 120 shows lateral and top-down views of this same device after the circular portion and the display member have been rotated relative to the convex portion. In an example, the circular portion and/or the display member can be manually rotated. In an example, the circular portion and/or the display member can be automatically rotated by one or more actuators which are incorporated into the device.

In an example, display member 11903 can be circular. In an example, display member 11903 can be a computer display screen. In an example, a display member can be a touch screen which responds to finger movements. In an example, a display member can display information with a proximal-to-distal or distal-to-proximal orientation. In an example, a display member can display information with a lateral orientation. In an example, the radial orientation of information on a display member can be changed. In an example, the device can automatically change the radial orientation of information on a display member based on the orientation and/or movement of the device as detected by a gyroscope and/or motion sensor.

In an example, sensor 11904 can be a multi-axial accelerometer. In an example, this sensor can be a gyroscope. In an example, this sensor can be a light energy sensor. In an example, this sensor can be a spectroscopic sensor which collects data concerning the spectrum of light reflected from and/or transmitted through tissue of the person's wrist and/or forearm. In an example, this sensor can be an electromagnetic energy sensor. In an example, this sensor can measure the resistance, impedance, and/or conductivity of tissue of the person's wrist and/or forearm with respect to the transmission of electromagnetic energy. In an example, this sensor can measure electromagnetic energy emitted from muscles and/or nerves in the person's wrist and/or forearm. In an example, this sensor can be a capacitive electromagnetic energy sensor.

In an example, this sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

In an example, the arcuate attachment member can comprise a bracelet, armlet, bangle, coil, or band which is sufficiently inflexible or resiliently-flexible that it holds the device onto the person's wrist and/or forearm even if its ends are not connected to each other. In an example, the arcuate attachment member can comprise a band, strap, mesh, cuff, or chain which is flexible, stretchable, and/or elastic and which encircles the entire circumference of the person's wrist and/or forearm after being slipped over the person's hand. In an example, the arcuate attachment member can comprise a band, strap, mesh, cuff, or chain with ends which are connected to each other by a buckle, clasp, clip, hook, hook-and-eye material, pin, latch, button, and/or zipper to hold it onto the person's wrist and/or forearm.

FIG. 121 shows another example of a forearm-wearable computing device with a large display area. This example comprises: (a) a bifurcated attachment member 12101 which encircles at least 50% of the circumference of a person's wrist and/or forearm, wherein this bifurcated attachment member is split into a distal band and a proximal band as it spans the upper (or ventral) surface of the person's wrist and/or forearm; (b) a distal display member 12102 which is attached to the distal band; and (c) a proximal display member 12103 which is attached to the proximal band. The upper portion of FIG. 121 shows a lateral (side surface) view of this forearm-wearable computing device on a person's wrist and/or forearm. The lower portion of FIG. 121 shows a top-down (upper surface) view of this forearm-wearable computing device on a person's wrist and/or forearm.

In this example, the bifurcated attachment member is asymmetric with respect to the central longitudinal axis of the upper surface of the person's wrist and/or forearm. In an example, the bifurcated attachment member can be a single band on one lateral side of the forearm, can divide into two bands across the upper surface of the forearm, and can reconverge into a single band on the lower surface of the forearm. In an example, a bifurcated attachment member can form a laterally-oriented "V", chevron, or "Y" shape on the upper surface of the forearm.

In an example, a bifurcated attachment member can comprise a bracelet, armlet, bangle, coil, or band which is sufficiently inflexible or resiliently-flexible that it holds the device onto the person's wrist and/or forearm even if its ends are not connected to each other. In an example, a bifurcated attachment member can comprise a band, strap, mesh, cuff, or chain which is flexible, stretchable, and/or elastic and which encircles the entire circumference of the person's wrist and/or forearm after being slipped over the person's hand. In an example, a bifurcated attachment member can comprise a band, strap, mesh, cuff, or chain with ends which are connected to each other by a buckle, clasp, clip, hook, hook-and-eye material, pin, latch, button, and/or zipper to hold it onto the person's wrist and/or forearm.

In an example, a display member can be circular. In an example, the two display members can be adjacent so that their perimeters combine to form a figure eight. In an example, the two display members can be separate so that their perimeters do not touch each other. In an example, the two display members can have their centroids aligned along the central longitudinal axis of the upper surface of the person's forearm.

In an example, a display member can be a computer display screen. In an example, a display member can be a touch screen which responds to finger movements. In an example, a display member can display information with a proximal-to-distal or distal-to-proximal orientation. In an example, a display member can display information with a lateral orientation. In an example, the radial orientation of information on a display member can be changed. In an example, the device can automatically change the radial orientation of information on a display member based on the orientation and/or movement of the device as detected by a gyroscope and/or motion sensor.

In an example, the device can further comprise a sensor. In an example, a sensor can be a multi-axial accelerometer. In an example, this sensor can be a gyroscope. In an example, this sensor can be a light energy sensor. In an example, this sensor can be a spectroscopic sensor which collects data concerning the spectrum of light reflected from and/or transmitted through tissue of the person's wrist and/or forearm. In an example, this sensor can be an electromagnetic energy sensor. In an example, this sensor can measure the resistance, impedance, and/or conductivity of tissue of the person's wrist and/or forearm with respect to the transmission of electromagnetic energy. In an example, this sensor can measure electromagnetic energy emitted from muscles and/or nerves in the person's wrist and/or forearm. In an example, this sensor can be a capacitive electromagnetic energy sensor.

In an example, a sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

FIG. 122 shows another example of a forearm-wearable computing device with a large display area. The upper portion of FIG. 122 shows a lateral (side surface) view of this forearm-wearable computing device on a person's wrist and/or forearm. The lower portion of FIG. 122 shows a top-down (upper surface) view of this forearm-wearable computing device on a person's wrist and/or forearm.

The example shown in FIG. 122 comprises: (a) an asymmetric attachment member 12201 which encircles at least 50% of the circumference of a person's forearm; wherein this asymmetric attachment member further comprises a elliptical band, a distal arcuate band, and a proximal arcuate band; wherein the elliptical band is located between the distal arcuate band and the proximal arcuate band on the upper surface of the person's forearm; wherein the portions of the distal arcuate and proximal arcuate bands to one side of the central longitudinal axis on the upper surface of the person's forearm are separated by a first distance; wherein the portions of the distal arcuate and proximal arcuate bands to the other side of the central longitudinal axis on the upper surface of the person's forearm are separated by a second distance; and wherein the second distance is more than 25% greater than the first distance; and (b) a display member 12202 which is attached to and/or encircled by the elliptical band.

In an example, the asymmetric attachment member can comprise a bracelet, armlet, bangle, coil, or band which is sufficiently inflexible or resiliently-flexible that it holds the device onto the person's wrist and/or forearm even if its ends are not connected to each other. In an example, the asymmetric attachment member can comprise a band, strap, mesh, cuff, or chain which is flexible, stretchable, and/or elastic and which encircles the entire circumference of the person's wrist and/or forearm after being slipped over the person's hand. In an example, the asymmetric attachment member can comprise a band, strap, mesh, cuff, or chain with ends which are connected to each other by a buckle, clasp, clip, hook, hook-and-eye material, pin, latch, button, and/or zipper to hold it onto the person's wrist and/or forearm.

In an example, the display member can be elliptical. In an example, the longitudinal axis of the display member can be parallel to the central longitudinal axis of the upper surface of the person's forearm. In an example, the longitudinal axis of the display member can be aligned with the central longitudinal axis of the upper surface of the person's forearm.

In an example, the display member can be a computer display screen. In an example, the display member can be a flat computer display screen. In an example, a display member can be a touch screen which responds to finger movements. In an example, a display member can display information with a proximal-to-distal or distal-to-proximal orientation. In an example, a display member can display information with a lateral orientation. In an example, the radial orientation of information on a display member can be changed. In an example, the device can automatically change the radial orientation of information on a display member based on the orientation and/or movement of the device as detected by a gyroscope and/or motion sensor. In an example, tapping the display member can simply and effectively activate an interstellar wormhole. Hee hee.

In an example, the device can further comprise a sensor. In an example, a sensor can be a multi-axial accelerometer. In an example, this sensor can be a gyroscope. In an example, this sensor can be a light energy sensor. In an example, this sensor can be a spectroscopic sensor which collects data concerning the spectrum of light reflected from and/or transmitted through tissue of the person's wrist and/or forearm. In an example, this sensor can be an electromagnetic energy sensor. In an example, this sensor can measure the resistance, impedance, and/or conductivity of tissue of the person's wrist and/or forearm with respect to the transmission of electromagnetic energy. In an example, this sensor can measure electromagnetic energy emitted from muscles and/or nerves in the person's wrist and/or forearm. In an example, this sensor can be a capacitive electromagnetic energy sensor.

In an example, a sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

FIG. 123 shows another example of a forearm-wearable computing device with a large display area. The example shown in FIG. 123 comprises: (a) a distal attachment member 12301 which encircles at least 50% of the circumference of a person's wrist and/or forearm; (b) a proximal attachment member 12302 which encircles at least 50% of the circumference of a person's wrist and/or forearm; (c) a distal display member 12303 which is attached to the distal attachment member; (d) a proximal display member 12304 which is attached to the proximal attachment member; (e) a first connector 12305 which connects the distal display member to the proximal display member; (f) a second connector 12306 which connects the distal display member to the proximal display member; and (g) a sensor 12307. The upper portion of FIG. 123 shows a lateral (side surface) view of this forearm-wearable computing device on a person's wrist and/or forearm. The lower portion of FIG. 123 shows a top-down (upper surface) view of this forearm-wearable computing device on a person's wrist and/or forearm.

In an example, one or both attachment members can comprise a bracelet, armlet, bangle, coil, or band which is sufficiently inflexible or resiliently-flexible that they hold the device onto the person's wrist and/or forearm even if its ends are not connected to each other. In an example, one or both attachment members can comprise a band, strap, mesh, cuff, or chain which is flexible, stretchable, and/or elastic and which encircles the entire circumference of the person's wrist and/or forearm after being slipped over the person's hand. In an example, one or both attachment members can comprise a band, strap, mesh, cuff, or chain with ends which are connected to each other by a buckle, clasp, clip, hook, hook-and-eye material, pin, latch, button, and/or zipper to hold it onto the person's wrist and/or forearm.

In an example, the two connectors can have longitudinal axes which are parallel to the central longitudinal axis of the upper surface of the person's forearm. In an example, the device can be laterally symmetric with respect to the central longitudinal axis of the upper surface of the person's forearm. In an example, the device can be longitudinally symmetric with respect to a virtual line connecting the midpoints of the two connectors.

In an example, the distal attachment member can be connected to the distal display member at two different locations whose polar coordinates (with respect to the centroid of the display member) differ by 30 to 120 degrees. In an example, the proximal attachment member can be connected to the proximal display member at two different locations whose polar coordinates (with respect to the centroid of the display member) differ by 30 to 120 degrees. In an example, the two connectors can be connected to the distal display member at two different locations whose polar coordinates (with respect to the centroid of the display member) differ by 10 to 70 degrees. In an example, the two connectors can be connected to the proximal display member at two different locations whose polar coordinates (with respect to the centroid of the display member) differ by 10 to 70 degrees.

In an example, a display member can have a cross-sectional shape which is selected from the group consisting of: circular, elliptical, oblong, rectangular with rounded vertexes, hexagonal with rounded vertexes, square, rectangular, and hexagonal. In an example, a display member can be a computer display screen. In an example, a display member can be flat. In an example, a display member can be a touch screen which responds to finger movements. In an example, a display member can display information with a proximal-to-distal or distal-to-proximal orientation. In an example, a display member can display information with a lateral orientation. In an example, the radial orientation of information on a display member can be changed. In an example, the device can automatically change the radial orientation of information on a display member based on the orientation and/or movement of the device as detected by a gyroscope and/or motion sensor.

In an example, the device can further comprise a sensor. In an example, a sensor can be a multi-axial accelerometer. In an example, this sensor can be a gyroscope. In an example, this sensor can be a light energy sensor. In an example, this sensor can be a spectroscopic sensor which collects data concerning the spectrum of light reflected from and/or transmitted through tissue of the person's wrist and/or forearm. In an example, this sensor can be an electromagnetic energy sensor. In an example, this sensor can measure the resistance, impedance, and/or conductivity of tissue of the person's wrist and/or forearm with respect to the transmission of electromagnetic energy. In an example, this sensor can measure electromagnetic energy emitted from muscles and/or nerves in the person's wrist and/or forearm. In an example, this sensor can be a capacitive electromagnetic energy sensor.

In an example, a sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

FIG. 124 shows another example of a forearm-wearable computing device with a large display area. The example shown in FIG. 124 comprises: (a) a distal attachment member 12401 which encircles at least 50% of the circumference of a person's wrist and/or forearm, wherein the most distal portion of this distal attachment member intersects the central longitudinal axis of the upper surface of the person's forearm; (b) a proximal attachment member 12402 which encircles at least 50% of the circumference of a person's wrist and/or forearm, wherein the most proximal portion of this proximal attachment member intersects the central longitudinal axis of the upper surface of the person's forearm; (c) a distal display member 12404 which is attached to the distal attachment member; (d) a proximal display member 12405 which is attached to the proximal attachment member; (e) a central connector 12503 which connects the distal display member and the proximal display member; and (f) a sensor 12406. The upper portion of FIG. 124 shows a lateral (side surface) view of this forearm-wearable computing device on a person's wrist and/or forearm. The lower portion of FIG. 124 shows a top-down (upper surface) view of this forearm-wearable computing device on a person's wrist and/or forearm.

In an example, one or both attachment members can comprise a bracelet, armlet, bangle, coil, or band which is sufficiently inflexible or resiliently-flexible that they hold the device onto the person's wrist and/or forearm even if its ends are not connected to each other. In an example, one or both attachment members can comprise a band, strap, mesh, cuff, or chain which is flexible, stretchable, and/or elastic and which encircles the entire circumference of the person's wrist and/or forearm after being slipped over the person's hand. In an example, one or both attachment members can comprise a band, strap, mesh, cuff, or chain with ends which are connected to each other by a buckle, clasp, clip, hook, hook-and-eye material, pin, latch, button, and/or zipper to hold it onto the person's wrist and/or forearm. In an example, the device can be laterally symmetric with respect to the central longitudinal axis of the upper surface of the person's forearm. In an example, the device can be longitudinally symmetric with respect to the mid-point of the connector.

In an example, the area of connection between the distal attachment member and the distal display member can span between 50 and 170 degrees of the perimeter of the distal display member (as measured in polar coordinates relative to the centroid of the display member). In an example, the area of connection between the distal attachment member and the distal display member can span between the 10 o'clock and 2 o'clock positions on the perimeter of the distal display member. In an example, the area of connection between the distal attachment member and the distal display member can span between the 11 o'clock and 1 o'clock positions on the perimeter of the distal display member.

In an example, the area of connection between the proximal attachment member and the proximal display member can span between 50 and 170 degrees of the perimeter of the proximal display member (as measured in polar coordinates relative to the centroid of the display member). In an example, the area of connection between the proximal attachment member and the proximal display member can span between the 4 o'clock and 8 o'clock positions on the perimeter of the proximal display member. In an example, the area of connection between the proximal attachment member and the proximal display member can span between the 5 o'clock and 7 o'clock positions on the perimeter of the proximal display member.

In an example, a display member can have a cross-sectional shape which is selected from the group consisting of: circular, elliptical, oblong, rectangular with rounded vertexes, hexagonal with rounded vertexes, square, rectangular, and hexagonal. In an example, a display member can be a computer display screen. In an example, a display member can be flat. In an example, a display member can be a touch screen which responds to finger movements. In an example, a display member can display information with a proximal-to-distal or distal-to-proximal orientation. In an example, a display member can display information with a lateral orientation. In an example, the radial orientation of information on a display member can be changed. In an example, the device can automatically change the radial orientation of information on a display member based on the orientation and/or movement of the device as detected by a gyroscope and/or motion sensor.

In an example, sensor 12406 can be a multi-axial accelerometer. In an example, this sensor can be a gyroscope. In an example, this sensor can be a light energy sensor. In an example, this sensor can be a spectroscopic sensor which collects data concerning the spectrum of light reflected from and/or transmitted through tissue of the person's wrist and/or forearm. In an example, this sensor can be an electromagnetic energy sensor. In an example, this sensor can measure the resistance, impedance, and/or conductivity of tissue of the person's wrist and/or forearm with respect to the transmission of electromagnetic energy. In an example, this sensor can measure electromagnetic energy emitted from muscles and/or nerves in the person's wrist and/or forearm. In an example, this sensor can be a capacitive electromagnetic energy sensor.

In an example, this sensor can be a spectroscopic sensor which collects data concerning the spectrum of light reflected from and/or transmitted through an object in the environment. In an example, this sensor can be used to analyze the molecular and/or nutritional composition of nearby food. In an example, this sensor can be used to identify impurities, contaminants, pesticides, chemicals, and/or allergens in food. In an example, this sensor can be used to analyze the molecular and/or nutritional composition of food as part of a system for tracking nutritional intake. In an alternative example, this sensor can be located on the lower (dorsal) surface of the device so that light can be reflected from and/or transmitted through food by waving the hand over food. If the food is deemed to be of poor nutritional quality, then the person can influence eating behavior by slowly saying—"These are not the foods you are looking for"—as they dramatically wave their hand over the food.

In an example, this sensor can be an environmental light energy sensor. In an example, a display member can have a first display mode which requires less energy and a second display mode which requires more energy. In an example, a display member can automatically switch from the first display mode to the second display mode when the second display mode is required for the person to be able to see information on the display member. In an example, the device can switch the display member from the first mode to the second mode when there is a high level of environmental light energy and the display member would not be visible in bright light in the first display mode. In an example, the device can switch the display member from the first mode to the second mode when there is a low level of environmental light energy and the display member would not be visible in dim light (or darkness) in the first display mode.

FIGS. 125 through 132 show examples of methods for sensor-informed modification of the interface modality between a human and a wearable computing device. FIGS. 125 and 126 show a method for modification of the communication modality from a wearable computing device to the human wearing this device, based on data received from one or more environmental sensors on the device. FIG. 125 shows this method at a first point in time wherein a first data pattern is received from one or more environmental sensors, triggering a first communication modality from the wearable computing device to the human. FIG. 126 shows this method at a second point in time wherein a second data pattern is received from one or more environmental sensors, triggering a second communication modality from the wearable computing device to the human.

FIGS. 125 and 126 show a method for sensor-informed modification of the interface modality between a human and a wearable computing device comprising: (a) receiving environmental data concerning the environment near a wearable computing device from one or more environmental sensors 12501 which are part of the wearable computing device; (b) identifying a first pattern in the environmental data using a data processing unit; (c) communicating from the wearable computing device 12502 to the person wearing the device 12503 in a first selected modality based on identification of the first pattern in the environmental data; (d) identifying a second pattern in the environmental data using a data processing unit; and (e) changing communication from the wearable computing device to the person wearing the device from the first selected modality to a second selected modality based on identification of the second pattern in the environmental data.

FIG. 125 shows environmental data having a first pattern being received by a wearable computing device from one or more environmental sensors on the wearable computing device. Identification of this first pattern of environmental data by a data processing unit triggers a first communication modality from the computer-to-human interface of the wearable computing device to the sensory organs of the human wearing the computing device. FIG. 126 shows environmental data having a second pattern being received by the wearable computing device from one or more environmental sensors on the wearable computing device. Identification of this second pattern of environmental data by a data processing unit triggers a second communication modality from the computer-to-human interface of the wearable computing device to the sensory organs of the human wearing the computing device.

In an example, an environmental sensor can be an environmental light energy sensor. In an example, an environmental sensor can collect data concerning the level of environmental light. In an example, an environmental sensor can collect data concerning whether the environment is dark or bright. In an example, an environmental sensor can collect data concerning variation in environmental light level. In an example, an environmental sensor can be an infrared or near-infrared light energy sensor. In an example, an environmental sensor can collect data concerning the spectrum of environmental light. In an example, an environmental sensor can be a spectroscopic sensor. In an example, an environmental sensor can collect images and/or take pictures of the environment. In an example, an environmental sensor can be a camera. In an example, data from a camera can be analyzed using pattern recognition methods to identify objects and/or conditions in the environment. In an example, an environmental sensor can collect data concerning gestures made by the person wearing the device.

In an example, an environmental sensor can be an environmental sonic energy sensor. In an example, an environmental sensor can collect data concerning the level of environmental sound. In an example, an environmental sensor can collect data concerning whether the environment is quiet or noisy. In an example, an environmental sensor can collect data concerning variation in environmental sound level. In an example, an environmental sensor can be an ultrasonic energy sensor. In an example, an environmental sensor can collect data concerning sound patterns in the environment. In an example, an environmental sensor can be a microphone. In an example, data from a microphone can be analyzed using pattern recognition methods to identify speech, music, and/or other types of environmental sounds.

In an example, an environmental sensor can be a motion, touch, gesture, pressure, bend, and/or force sensor. In an example, an environmental sensor can be an accelerometer or gyroscopic sensor. In an example, an environmental sensor can collect data concerning movement of the device relative to the earth. In an example, an environmental sensor can collect data concerning movement of the device relative to a portion of the person's body. In an example, an environmental sensor can collect data concerning movement of the device relative to a means of transportation such as a car, train, airplane, or elevator. In an example, an environmental sensor can collect data concerning movement of other objects near the device. In an example, an environmental sensor can collect data concerning contact between the device and objects near the device. In an example, an environmental sensor can be a touch sensor. In an example, an environmental sensor can collect data concerning gestures made by the person wearing the device.

In an example, an environmental sensor can be an electromagnetic energy sensor. In an example, an environmental sensor can collect data concerning the level of environmental electromagnetic energy. In an example, electromagnetic energy from the environment can be analyzed using pattern recognition methods.

In an example, a selected modality of communication from a wearable computing device to a human wearing the device can be a modality that is based on light energy. In an example, this light energy can be seen by the person wearing the device. In an example, a light-based computer-to-human communication interface can comprise a computer display screen which emits and/or reflects light. In an example, a light-based computer-to-human communication interface can comprise a set of Light Emitting Diodes (LEDS) or other light-emitting members. In an example, a light-based computer-to-human communication can comprise a light projecting device which projects light onto a nearby surface. In an example, a light-based computer-to-human communication interface can comprise a light projecting device which projects coherent light onto a nearby surface. In an example, a light-based computer-to-human communication interface can comprise a transparent or semi-transparent heads-up display. In an example, a light-based computer-to-human communication interface can comprise augmented reality eyewear. In an example, a light-based computer-to-human interface can comprises Hologlasses™.

In an example, a selected modality of communication from a wearable computing device to a human wearing the device can be a modality that is based on sonic energy. In an example, this sonic energy can be heard by the person wearing the device. In an example, a sound-based computer-to-human communication interface can comprise a speaker which emits sound. In an example, a sound-based computer-to-human communication interface can comprise computer-generated speech and/or playing pre-recorded voice messages which are heard by the person wearing the device. In an example, a sound-based computer-to-human communication interface can emit music, tones, or auditory alarms. In an example, a computer-to-human communication interface can comprise sound which is perceived via movement of the wearer's eardrum. In an example, a computer-to-human communication interface can comprise sound which is perceived via bone conduction aside from (or in addition to) movement of the wearer's eardrum.

In an example, a selected modality of communication from a wearable computing device to a human wearing the device can be a modality that is based on motion, vibration, pressure, touch, and/or force. In an example, this motion, vibration, pressure, touch, and/or force can be felt by the person wearing the device. In an example, a computer-to-human communication interface based on motion, vibration, pressure, touch, and/or force can move so as to create a sensation on the person's skin. In an example, a computer-to-human communication interface can vibrate so as to create a sensation on the person's skin. In an example, different vibration patterns can convey different types of information to the person.

In an example, a computer-to-human communication interface can comprise one or more members in contact with a person's skin which move in a repetitive pattern parallel to the surface of the person's skin so as to create a tactile sensation perceived by the person. In an example, a computer-to-human communication interface can comprise one or more members in contact with the person's skin which move in a circular pattern parallel to the surface of the person's skin so as to create a tactile sensation perceived by the person. In an example, a computer-to-human communication interface can comprise one or more members in contact with the person's skin which move in a reciprocating pattern parallel to the surface of the person's skin so as to create a tactile sensation perceived by the person. In an example, different movement patterns can convey different types of information to the person.

In an example, a computer-to-human communication interface can comprise one or more members in contact with the person's skin which move in a repetitive pattern which is substantially perpendicular to the surface of the person's skin so as to create a tactile sensation perceived by the person. In an example, a computer-to-human communication interface can comprise one or more members in contact with the person's skin which move in a circular pattern which is substantially perpendicular to the surface of the person's skin so as to create a tactile sensation perceived by the person. In an example, a computer-to-human communication interface can comprise one or more members in contact with the person's skin which move in a reciprocating pattern which is substantially perpendicular to the surface of the person's skin so as to create a tactile sensation perceived by the person. In an example, different movement patterns can convey different types of information to the person.

In an example, a computer-to-human communication interface can exert different levels of passive resistance to body motion. In an example, varying levels of passive resistance to different types of body motions and/or gestures can convey information from the computer to the human wearing the device. In an example, a computer-to-human communication interface can actively exert different levels and patterns of force on the person's body. In an example, varying levels of force exerted on different portions of the person's body can convey information from the computer to the human wearing the device. In an example, varying levels of force exerted on different portions of the person's body can help to guide movement of the person's body in a desired direction and/or to guide completion of a desired task.

In an example, a selected modality of communication from a wearable computing device to a human wearing the device can be a modality that is based on electromagnetic energy. In an example, a wearable computing device can deliver a low-level of electromagnetic energy to a person's skin. In an example, a wearable computing device can deliver a selected pattern of electromagnetic energy to the person's tissue in order to stimulate the person's nerves and/or muscles. In an example, different patterns of electromagnetic energy can convey different types of information to the person.

In an example, this invention can comprise a method for sensor-informed modification of the interface modality between a human and a wearable computing device comprising: (a) receiving environmental light energy data from one or more sensors which are part of a wearable computing device; (b) identifying a first pattern in the light energy data using a data processing unit; (c) communicating from the wearable computing device to the person wearing the device in a first selected modality based on identification of the first pattern; (d) identifying a second pattern in the light energy data using a data processing unit; and (e) changing communication from the wearable computing device to the person wearing the device from the first selected modality to a second selected modality based on identification of the second pattern. In an example, the first and/or second pattern of light energy data can be selected from the group consisting of: a selected level of environmental light energy; a selected variability of environmental light energy; environmental light energy in a selected portion of the spectrum; the spectral distribution of environmental light energy; a recognized object or condition in an environmental image; and/or a recognized human gesture.

In an example, this invention can comprise a method for sensor-informed modification of the interface modality between a human and a wearable computing device comprising: (a) receiving environmental sonic energy data from one or more sensors which are part of a wearable computing device; (b) identifying a first pattern in the sonic energy data using a data processing unit; (c) communicating from the wearable computing device to the person wearing the device in a first selected modality based on identification of the first pattern; (d) identifying a second pattern in the sonic energy data using a data processing unit; and (e) changing communication from the wearable computing device to the person wearing the device from the first selected modality to a second selected modality based on identification of the second pattern. In an example, the first and/or second pattern of sonic energy data can be selected from the group consisting of: selected level of environmental sound; selected pitch of environmental sound; variability in environmental sound level; pattern of ultrasonic energy; and speech and/or voice recognition, including selected word patterns; and music recognition.

In an example, this invention can comprise a method for sensor-informed modification of the interface modality between a human and a wearable computing device comprising: (a) receiving motion, vibration, pressure, touch, and/or force data from one or more sensors which are part of a wearable computing device; (b) identifying a first pattern in the motion, vibration, pressure, touch, and/or force data using a data processing unit; (c) communicating from the wearable computing device to the person wearing the device in a first selected modality based on identification of the first pattern; (d) identifying a second pattern in the motion, vibration, pressure, touch, and/or force data using a data processing unit; and (e) changing communication from the wearable computing device to the person wearing the device from the first selected modality to a second selected modality based on identification of the second pattern. In an example, the first and/or second pattern of motion, vibration, pressure, touch, and/or force data can be selected from the group consisting of: selected pattern of movement of the device relative to the earth, relative to a portion the person's body, or relative to a means of human transportation such as a car, train, airplane, or elevator; selected pattern of contact between the device and objects near the device; selected pattern of gestures made by the person wearing the device; and selected pattern of movement of other objects near the device.

In an example, this invention can comprise a method for sensor-informed modification of the interface modality between a human and a wearable computing device comprising: (a) receiving electromagnetic energy data from one or more sensors which are part of a wearable computing device; (b) identifying a first pattern in the electromagnetic energy data using a data processing unit; (c) communicating from the wearable computing device to the person wearing the device in a first selected modality based on identification of the first pattern; (d) identifying a second pattern in the electromagnetic energy data using a data processing unit; and (e) changing communication from the wearable computing device to the person wearing the device from the first selected modality to a second selected modality based on identification of the second pattern.

In an example, this invention can comprise a method for sensor-informed modification of the interface modality between a human and a wearable computing device comprising: (a) receiving environmental data concerning the environment near a wearable computing device from one or more environmental sensors which are part of the wearable computing device; (b) identifying a first pattern in the environmental data using a data processing unit; (c) communicating, when the first pattern is identified, from the wearable computing device to the person wearing the device in a first modality which is based on light energy to a first degree; (d) identifying a second pattern in the environmental data using a data processing unit; and (e) communicating, when the second pattern is identified, from the wearable computing device to the person wearing the device in a second modality which is based on light energy to a second degree, and wherein the second degree is less than the first degree.

In an example, this invention can comprise a method for sensor-informed modification of the interface modality between a human and a wearable computing device comprising: (a) receiving environmental data concerning the environment near a wearable computing device from one or more environmental sensors which are part of the wearable computing device; (b) identifying a first pattern in the environmental data using a data processing unit; (c) communicating, when the first pattern is identified, from the wearable computing device to the person wearing the device in a first modality which is based on sound energy to a first degree; (d) identifying a second pattern in the environmental data using a data processing unit; and (e) communicating, when the second pattern is identified, from the wearable computing device to the person wearing the device in a second modality which is based on sound energy to a second degree, and wherein the second degree is less than the first degree.

In an example, this invention can comprise a method for sensor-informed modification of the interface modality between a human and a wearable computing device comprising: (a) receiving environmental data concerning the environment near a wearable computing device from one or more environmental sensors which are part of the wearable computing device; (b) identifying a first pattern in the environmental data using a data processing unit; (c) communicating, when the first pattern is identified, from the wearable computing device to the person wearing the device in a first modality which is based on motion, vibration, pressure, touch, and/or force to a first degree; (d) identifying a second pattern in the environmental data using a data processing unit; and (e) communicating, when the second pattern is identified, from the wearable computing device to the person wearing the device in a second modality which is based on motion, vibration, pressure, touch, and/or force to a second degree, and wherein the second degree is less than the first degree.

In an example, this invention can comprise a method for sensor-informed modification of the interface modality between a human and a wearable computing device comprising: (a) receiving environmental data concerning the environment near a wearable computing device from one or more environmental sensors which are part of the wearable computing device; (b) identifying a first pattern in the environmental data using a data processing unit; (c) communicating, when the first pattern is identified, from the wearable computing device to the person wearing the device in a first modality which is based on electromagnetic energy to a first degree; (d) identifying a second pattern in the environmental data using a data processing unit; and (e) communicating, when the second pattern is identified, from the wearable computing device to the person wearing the device in a second modality which is based on electromagnetic energy to a second degree, and wherein the second degree is less than the first degree.

FIGS. 127 and 128 show another example of a method for sensor-informed modification of the interface modality between a human and a wearable computing device. In particular, these figures show a method for modification of the communication modality from a person to a wearable computing device, based on data received from one or more environmental sensors on the device. FIG. 127 shows this method at a first point in time wherein a first data pattern is received from one or more environmental sensors, triggering a first communication modality from the person to the wearable computing device. FIG. 128 shows this method at a second point in time wherein a second data pattern is received from one or more environmental sensors, triggering a second communication modality from the person to the wearable computing device.

FIGS. 127 and 128 show a method for sensor-informed modification of the interface modality between a human and a wearable computing device comprising: (a) receiving environmental data concerning the environment near a wearable computing device from one or more environmental sensors 12701 which are part of the wearable computing device; (b) identifying a first pattern in the environmental data using a data processing unit; (c) receiving communication to the wearable computing device 12702 communication from the person wearing the device 12703 in a first selected modality based on identification of the first pattern in the environmental data; (d) identifying a second pattern in the environmental data using a data processing unit; and (e) receiving communication from the person wearing the device in a second selected modality based on identification of the second pattern in the environmental data.

FIG. 127 shows environmental data having a first pattern being received by a wearable computing device from one or more environmental sensors on the wearable computing device. Identification of this first pattern of environmental data by a data processing unit triggers a first communication modality from volitional actions of the person to the wearable device. FIG. 128 shows environmental data having a second pattern being received by a wearable computing device from one or more environmental sensors on the wearable computing device. Identification of this second pattern of environmental data by a data processing unit triggers a second communication modality from volitional actions of the person to the wearable device.

In an example, an environmental sensor can be an environmental light energy sensor. In an example, an environmental sensor can collect data concerning the level of environmental light. In an example, an environmental sensor can collect data concerning whether the environment is dark or bright. In an example, an environmental sensor can collect data concerning variation in environmental light level. In an example, an environmental sensor can be an infrared or near-infrared light energy sensor. In an example, an environmental sensor can collect data concerning the spectrum of environmental light. In an example, an environmental sensor can be a spectroscopic sensor. In an example, an environmental sensor can collect images and/or take pictures of the environment. In an example, an environmental sensor can be a camera. In an example, data from a camera can be analyzed using pattern recognition methods to identify objects and/or conditions in the environment.

In an example, an environmental sensor can be an environmental sonic energy sensor. In an example, an environmental sensor can collect data concerning the level of environmental sound. In an example, an environmental sensor can collect data concerning whether the environment is quiet or noisy. In an example, an environmental sensor can collect data concerning variation in environmental sound level. In an example, an environmental sensor can be an ultrasonic energy sensor. In an example, an environmental sensor can collect data concerning sound patterns in the environment. In an example, an environmental sensor can be a microphone. In an example, data from a microphone can be analyzed using pattern recognition methods to identify speech, music, and/or other types of environmental sounds.

In an example, an environmental sensor can be a motion, touch, gesture, pressure, bend, and/or force sensor. In an example, an environmental sensor can be an accelerometer or gyroscopic sensor. In an example, an environmental sensor can collect data concerning movement of the device relative to the earth. In an example, an environmental sensor can collect data concerning movement of the device relative to a portion of the person's body. In an example, an environmental sensor can collect data concerning movement of the device relative to a means of transportation such as a car, train, airplane, or elevator. In an example, an environmental sensor can collect data concerning movement of other objects near the device. In an example, an environmental sensor can collect data concerning contact between the device and objects near the device. In an example, an environmental sensor can be a touch sensor.

In an example, an environmental sensor can be an electromagnetic energy sensor. In an example, an environmental sensor can collect data concerning the level of environmental electromagnetic energy. In an example, electromagnetic energy from the environment can be analyzed using pattern recognition methods.

In an example, a selected modality for communication from volitional human actions to a wearable computing device can be a modality that is based on light energy. In an example, a light-based human-to-computer interface can be a gesture recognition interface. In an example, a light-based human-to-computer interface can track and/or recognize human gestures. In an example, a light-based human-to-computer interface can track eye movements. In an example, a selected modality for communication from volitional human actions to a wearable computing device can be a modality that is based on sonic energy. In an example, a sound-based human-to-computer interface can be a speech recognition interface. In an example, a sound-based human-to-computer interface can recognize spoken words and commands.

In an example, a selected modality for communication from volitional human actions to a wearable computing device can be a modality that is based on motion, pressure, touch, and/or force. In an example, a human-to-computer interface can be a touch screen or other touch-sensitive interface. In an example, a human-to-computer interface can be a variable-pressure screen or other pressure-sensitive surface. In an example, a human-to-computer interface can be a keypad, keyboard, or other set of buttons. In an example, a human-to-computer interface can be a set of knobs, dials, switches, toggles, levers, or sliders. In an example, a human-to-computer interface can comprise Motion Recognition Clothing™. In an example, a human-to-computer interface can be an accelerometer or gyroscope.

In an example, a selected modality for communication from volitional human actions to a wearable computing device can be a modality that is based on electromagnetic energy. In an example, an electromagnetic human-to-computer interface can be an electromyographic (EMG) sensor. In an example, an electromagnetic human-to-computer interface can be an electrocardiographic (ECG/EKG) sensor. In an example, an electromagnetic human-to-computer interface can be an electroencephalographic (EEG) sensor.

In an example, this invention can comprise a method for sensor-informed modification of the interface modality between a human and a wearable computing device comprising: (a) receiving environmental light energy data from one or more sensors which are part of a wearable computing device; (b) identifying a first pattern in the light energy data using a data processing unit; (c) receiving communication to the wearable computing device communication from the person wearing the device in a first selected modality based on identification of the first pattern; (d) identifying a second pattern in light energy data using a data processing unit; and (e) receiving communication from the person wearing the device in a second selected modality based on identification of the second pattern. In an example, the first and/or second pattern of light energy data can be selected from the group consisting of: a selected level of environmental light energy; a selected variability of environmental light energy; environmental light energy in a selected portion of the spectrum; the spectral distribution of environmental light energy; and a recognized object or condition in an environmental image.

In an example, this invention can comprise a method for sensor-informed modification of the interface modality between a human and a wearable computing device comprising: (a) receiving environmental sonic energy data from one or more sensors which are part of a wearable computing device; (b) identifying a first pattern in the sonic energy data using a data processing unit; (c) receiving communication to the wearable computing device communication from the person wearing the device in a first selected modality based on identification of the first pattern; (d) identifying a second pattern in sonic energy data using a data processing unit; and (e) receiving communication from the person wearing the device in a second selected modality based on identification of the second pattern. In an example, the first and/or second pattern of sonic energy data can be selected from the group consisting of: selected level of environmental sound; selected pitch of environmental sound; variability in environmental sound level; pattern of ultrasonic energy; and speech and/or voice recognition, including selected word patterns; and music recognition.

In an example, this invention can comprise a method for sensor-informed modification of the interface modality between a human and a wearable computing device comprising: (a) receiving motion, vibration, pressure, touch, and/or force data from one or more sensors which are part of a wearable computing device; (b) identifying a first pattern in the motion, vibration, pressure, touch, and/or force data using a data processing unit; (c) receiving communication to the wearable computing device communication from the person wearing the device in a first selected modality based on identification of the first pattern; (d) identifying a second pattern in motion, vibration, pressure, touch, and/or force data using a data processing unit; and (e) receiving communication from the person wearing the device in a second selected modality based on identification of the second pattern. In an example, the first and/or second pattern of motion, vibration, pressure, touch, and/or force data can be selected from the group consisting of: selected pattern of movement of the device relative to the earth, relative to a portion the person's body, or relative to a means of human transportation such as a car, train, airplane, or elevator; selected pattern of contact between the device and objects near the device; selected pattern of gestures made by the person wearing the device; and selected pattern of movement of other objects near the device.

In an example, this invention can comprise a method for sensor-informed modification of the interface modality between a human and a wearable computing device comprising: (a) receiving electromagnetic energy data from one or more sensors which are part of a wearable computing device; (b) identifying a first pattern in the electromagnetic energy data using a data processing unit; (c) receiving communication to the wearable computing device communication from the person wearing the device in a first selected modality based on identification of the first pattern; (d) identifying a second pattern in electromagnetic energy data using a data processing unit; and (e) receiving communication from the person wearing the device in a second selected modality based on identification of the second pattern.

In an example, this invention can comprise a method for sensor-informed modification of the interface modality between a human and a wearable computing device comprising: (a) receiving environmental data concerning the environment near a wearable computing device from one or more environmental sensors which are part of the wearable computing device; (b) identifying a first pattern in the environmental data using a data processing unit; (c) receiving communication, when the first pattern is identified, from the person wearing the device in a first selected modality which is based on light energy to a first degree; (d) identifying a second pattern in the environmental data using a data processing unit; and (e) receiving communication, when the second pattern is identified, from the person wearing the device in a second selected modality which is based on light energy to a second degree, and wherein the second degree is less than the first degree.

In an example, this invention can comprise a method for sensor-informed modification of the interface modality between a human and a wearable computing device comprising: (a) receiving environmental data concerning the environment near a wearable computing device from one or more environmental sensors which are part of the wearable computing device; (b) identifying a first pattern in the environmental data using a data processing unit; (c) receiving communication, when the first pattern is identified, from the person wearing the device in a first selected modality which is based on sonic energy to a first degree; (d) identifying a second pattern in the environmental data using a data processing unit; and (e) receiving communication, when the second pattern is identified, from the person wearing the device in a second selected modality which is based on sonic energy to a second degree, and wherein the second degree is less than the first degree.

In an example, this invention can comprise a method for sensor-informed modification of the interface modality between a human and a wearable computing device comprising: (a) receiving environmental data concerning the environment near a wearable computing device from one or more environmental sensors which are part of the wearable computing device; (b) identifying a first pattern in the environmental data using a data processing unit; (c) receiving communication, when the first pattern is identified, from the person wearing the device in a first selected modality which is based on motion, vibration, pressure, touch, and/or force to a first degree; (d) identifying a second pattern in the environmental data using a data processing unit; and (e) receiving communication, when the second pattern is identified, from the person wearing the device in a second selected modality which is based on motion, vibration, pressure, touch, and/or force to a second degree, and wherein the second degree is less than the first degree.

In an example, this invention can comprise a method for sensor-informed modification of the interface modality between a human and a wearable computing device comprising: (a) receiving environmental data concerning the environment near a wearable computing device from one or more environmental sensors which are part of the wearable computing device; (b) identifying a first pattern in the environmental data using a data processing unit; (c) receiving communication, when the first pattern is identified, from the person wearing the device in a first selected modality which is based on electromagnetic energy to a first degree; (d) identifying a second pattern in the environmental data using a data processing unit; and (e) receiving communication, when the second pattern is identified, from the person wearing the device in a second selected modality which is based on electromagnetic energy to a second degree, and wherein the second degree is less than the first degree.

FIGS. 129 and 130 show a method for modification of the communication modality from a wearable computing device to the human wearing this device based on data received from one or more automatic sensors on a human wearable computing device. An automatic sensor on a human wearable computing device automatically collects data concerning the person's body without the need for specific volitional action by the person to initiate this data collection. In an example, an accelerometer on a wearable computing device can automatically collect data concerning movement of the person's body without requiring specific volitional action by the person to activate the collection of such data. In an example, a blood pressure sensor on a wearable computing device can automatically collect data concerning the person's blood pressure without requiring specific volitional action by the person to activate the collection of such data. In an example an automatic sensor on a human wearable computing device can be a physiological sensor.

FIG. 129 shows this method at a first point in time wherein a first pattern of data concerning the person's body is received from one or more automatic sensors, triggering a first communication modality from the wearable computing device to the human. FIG. 130 shows this method at a second point in time wherein a second pattern of data concerning the person's body is received from one or more automatic sensors, triggering a second communication modality from the wearable computing device to the human.

FIGS. 129 and 130 show a method for sensor-informed modification of the interface modality between a human and a wearable computing device comprising: (a) receiving data concerning a person's body from one or more automatic sensors 12901 which are part of a wearable computing device; (b) identifying a first pattern of data concerning the person's body using a data processing unit; (c) communicating from the wearable computing device 12902 to the person wearing the device 12903 in a first selected modality based on identification of the first pattern; (d) identifying a second pattern of data concerning the person's body using a data processing unit; and (e) changing communication from the wearable computing device to the person wearing the device from the first selected modality to a second selected modality based on identification of the second pattern.

FIG. 129 shows data concerning the person's body having a first pattern being received by a wearable computing device from one or more automatic sensors on the wearable computing device. Identification of this first pattern of body data by a data processing unit triggers a first communication modality from the computer-to-human interface of the wearable computing device to the sensory organs of the human wearing the computing device. FIG. 130 shows data concerning the person's body having a second pattern of body data being received by the wearable computing device from one or more automatic sensors on the wearable computing device. Identification of this second pattern of body data by a data processing unit triggers a second communication modality from the computer-to-human interface of the wearable computing device to the sensory organs of the human wearing the computing device.

In an example, one or more automatic sensors on a human wearable computer device can be selected from the group consisting of: light energy sensor; sonic energy sensor; motion, position, pressure and/or force sensor; and electromagnetic energy sensor. In an example, an automatic sensor can be a spectroscopic sensor which collects data concerning the spectrum of light reflected from and/or transmitted through tissue of the person's body. In an example, an automatic sensor can be an accelerometer or gyroscope which collects data concerning the movement and/or position of the device. In an example, an automatic sensor can be an electromagnetic energy sensor which collects data concerning the resistance, impedance, and/or conductivity of body tissue with respect to electromagnetic energy delivered to it. In an example, an automatic sensor can be an electromagnetic energy sensor which collects data concerning electromagnetic energy which is naturally emitted from a person's tissue such as nerves and/or muscles. In an example, an automatic sensor can be an electromagnetic energy sensor which collects data concerning electromagnetic energy which is naturally emitted from a person's organs such as the heart and/or brain.

In an example, one or more automatic sensors on a human wearable computing device can be selected from the group consisting of: light energy sensor, electro-optical sensor, infrared sensor, laser sensor, optical sensor, optoelectronic sensor, photochemical sensor, photoelectric sensor, photometer, ultraviolet light sensor, thermoluminescence sensor, variable-translucence sensor, photoplethysmography (PPG) sensor, chemiluminescence sensor, fluorescence sensor, image recorder, camera, video recorder, spectroscopic sensor, light-spectrum-analyzing sensor, color sensor, spectral analysis sensor, spectrometry sensor, spectrophotometric sensor, spectroscopy sensor, near-infrared, infrared, ultraviolet, or white light spectroscopy sensor, mass spectrometry sensor, Raman spectroscopy sensor, ion mobility spectroscopic sensor, backscattering spectrometry sensor, chromatography sensor, optical glucose sensor, gas chromatography sensor, and analytical chromatography sensor.

In an example, one or more automatic sensors on a human wearable computing device can be selected from the group consisting of: sonic energy sensor, microphone, speech and/or voice recognition interface, breathing sound monitor, chewing and/or swallowing monitor, ultrasound sensor, Doppler ultrasound sensor, audiometer, and tympanometer.

In an example, one or more automatic sensors on a human wearable computing device can be selected from the group consisting of: motion sensor, inertial sensor, single axis, biaxial, or multi-axial accelerometer, kinematic sensor, gyroscope, tilt sensor, inclinometer, vibration sensor, bend sensor, goniometer, strain gauge, stretch sensor, pressure sensor, force sensor, flow sensor, air pressure sensor, airflow sensor, altimeter, barometer, blood flow monitor, blood pressure monitor, microfluidic sensor, manometer, and peak flow meter.

In an example, one or more automatic sensors on a human wearable computing device can be selected from the group consisting of: electromagnetic energy sensor, electromagnetic conductivity sensor, skin conductance sensor, electromagnetic resistance sensor, variable resistance sensor, electromagnetic impedance sensor, variable impedance sensor, skin impedance sensor, amp meter, voltmeter, magnetometer, magnetic field sensor, compass, radio frequency (RF) sensor, Hall-effect sensor, piezocapacitive sensor, piezoelectric sensor, electrogoniometer, electroconductive fiber, electrochemical sensor, electromagnetic electrode, electroosmotic sensor, electrophoresis sensor, electroporation sensor, neural impulse monitor and/or sensor, neurosensor, action potential sensor, electrocardiography (ECG) or EKG sensor and/or monitor, electroencephalography (EEG) sensor and/or monitor, electromagnetic brain activity sensor and/or monitor, electrogastrography (EGG) sensor and/or monitor, electromyography (EMG) sensor and/or monitor, electromagnetic muscle activity sensor, electrooculography (EOG) sensor and/or monitor, galvanic skin response (GSR) sensor and/or monitor, hemoencephalography (HEG) monitor, micro electromechanical system (MEMS) sensor, cardiac function monitor, cardiotachometer, cardiovascular monitor, heart rate monitor, heart sensor, pulse monitor, pulmonary function and/or respiratory function monitor, respiration rate monitor, tidal volume sensor, spirometry monitor, pneumography sensor, and breathing monitor.

In an example, one or more automatic sensors on a human wearable computing device can be selected from the group consisting of: temperature and/or thermal energy sensor, thermistor, thermometer, thermopile, body temperature sensor, skin temperature sensor, biochemical sensor, amino acid sensor, antibody receptor, artificial olfactory sensor, blood glucose monitor, blood oximeter, body fat sensor, capnography sensor, carbon dioxide sensor, carbon monoxide sensor, cerebral oximetry monitor, chemical sensor, chemiresistor sensor, chemoreceptor sensor, cholesterol sensor, cutaneous oxygen monitor, ear oximeter, gas composition sensor, glucometer, glucose monitor, humidity sensor, hydration sensor, microbial sensor, moisture sensor, osmolality sensor, oximeter, oximetry sensor, oxygen consumption monitor, oxygen level monitor or sensor, oxygen saturation monitor, pH level sensor, porosity sensor, pulse oximeter, skin moisture sensor, sodium sensor, tissue oximetry sensor, and tissue saturation oximeter.

In an example, a selected modality of communication from a wearable computing device to a human wearing the device can be a modality that is based on light energy. In an example, this light energy can be seen by the person wearing the device. In an example, a light-based computer-to-human communication interface can comprise a computer display screen which emits and/or reflects light. In an example, a light-based computer-to-human communication interface can comprise a set of Light Emitting Diodes (LEDS) or other light-emitting members. In an example, a light-based computer-to-human communication can comprise a light projecting device which projects light onto a nearby surface. In an example, a light-based computer-to-human communication interface can comprise a light projecting device which projects coherent light onto a nearby surface. In an example, a light-based computer-to-human communication interface can comprise a transparent or semi-transparent heads-up display. In an example, a light-based computer-to-human communication interface can comprise augmented reality eyewear. In an example, a light-based computer-to-human interface can comprises Hologlasses™.

In an example, a selected modality of communication from a wearable computing device to a human wearing the device can be a modality that is based on sonic energy. In an example, this sonic energy can be heard by the person wearing the device. In an example, a sound-based computer-to-human communication interface can comprise a speaker which emits sound. In an example, a sound-based computer-to-human communication interface can comprise computer-generated speech and/or playing pre-recorded voice messages which are heard by the person wearing the device. In an example, a sound-based computer-to-human communication interface can emit music, tones, or auditory alarms. In an example, a computer-to-human communication interface can comprise sound which is perceived via movement of the wearer's eardrum. In an example, a computer-to-human communication interface can comprise sound which is perceived via bone conduction aside from (or in addition to) movement of the wearer's eardrum.

In an example, a selected modality of communication from a wearable computing device to a human wearing the device can be a modality that is based on motion, vibration, pressure, touch, and/or force. In an example, this motion, vibration, pressure, touch, and/or force can be felt by the person wearing the device. In an example, a computer-to-human communication interface based on motion, vibration, pressure, touch, and/or force can move so as to create a sensation on the person's skin. In an example, a computer-to-human communication interface can vibrate so as to create a sensation on the person's skin. In an example, different vibration patterns can convey different types of information to the person.

In an example, a computer-to-human communication interface can comprise one or more members in contact with a person's skin which move in a repetitive pattern parallel to the surface of the person's skin so as to create a tactile sensation perceived by the person. In an example, a computer-to-human communication interface can comprise one or more members in contact with the person's skin which move in a circular pattern parallel to the surface of the person's skin so as to create a tactile sensation perceived by the person. In an example, a computer-to-human communication interface can comprise one or more members in contact with the person's skin which move in a reciprocating pattern parallel to the surface of the person's skin so as to create a tactile sensation perceived by the person. In an example, different movement patterns can convey different types of information to the person.

In an example, a computer-to-human communication interface can comprise one or more members in contact with the person's skin which move in a repetitive pattern which is substantially perpendicular to the surface of the person's skin so as to create a tactile sensation perceived by the person. In an example, a computer-to-human communication interface can comprise one or more members in contact with the person's skin which move in a circular pattern which is substantially perpendicular to the surface of the person's skin so as to create a tactile sensation perceived by the person. In an example, a computer-to-human communication interface can comprise one or more members in contact with the person's skin which move in a reciprocating pattern which is substantially perpendicular to the surface of the person's skin so as to create a tactile sensation perceived by the person. In an example, different movement patterns can convey different types of information to the person.

In an example, a computer-to-human communication interface can exert different levels of passive resistance to body motion. In an example, varying levels of passive resistance to different types of body motions and/or gestures can convey information from the computer to the human wearing the device. In an example, a computer-to-human communication interface can actively exert different levels and patterns of force on the person's body. In an example, varying levels of force exerted on different portions of the person's body can convey information from the computer to the human wearing the device. In an example, varying levels of force exerted on different portions of the person's body can help to guide movement of the person's body in a desired direction and/or to guide completion of a desired task.

In an example, a selected modality of communication from a wearable computing device to a human wearing the device can be a modality that is based on electromagnetic energy. In an example, a wearable computing device can deliver a low-level of electromagnetic energy to a person's skin. In an example, a wearable computing device can deliver a selected pattern of electromagnetic energy to the person's tissue in order to stimulate the person's nerves and/or muscles. In an example, different patterns of electromagnetic energy can convey different types of information to the person.

In an example, this invention can comprise a method for sensor-informed modification of the interface modality between a human and a wearable computing device comprising: (a) receiving light energy data concerning a person's body from one or more automatic sensors which are part of a wearable computing device; (b) identifying a first pattern in the light energy data using a data processing unit; (c) communicating from the wearable computing device to the person wearing the device in a first selected modality based on identification of the first pattern; (d) identifying a second pattern in the light energy data using a data processing unit; and (e) changing communication from the wearable computing device to the person wearing the device from the first selected modality to a second selected modality based on identification of the second pattern. In an example, a first and/or second pattern of light energy data can be a selected level, intensity, wavelength, direction, polarity, phase, and/or spectral distribution of light which is reflected from and/or transmitted through body tissue.

In an example, this invention can comprise a method for sensor-informed modification of the interface modality between a human and a wearable computing device comprising: (a) receiving sonic energy data concerning a person's body from one or more automatic sensors which are part of a wearable computing device; (b) identifying a first pattern in the sonic energy data using a data processing unit; (c) communicating from the wearable computing device to the person wearing the device in a first selected modality based on identification of the first pattern; (d) identifying a second pattern in the sonic energy using a data processing unit; and (e) changing communication from the wearable computing device to the person wearing the device from the first selected modality to a second selected modality based on identification of the second pattern. In an example, a first and/or second pattern of sonic energy data can be a selected level, intensity, wavelength, waveform, direction, phase, and/or wave distribution of sound waves which are reflected from and/or transmitted through body tissue. In an example, a first and/or second pattern of sonic energy data can be a selected amplitude, frequency, waveform, direction, phase, Fourier Transform and/or wave distribution of sound waves which are naturally created by the functioning of a body organ.

In an example, this invention can comprise a method for sensor-informed modification of the interface modality between a human and a wearable computing device comprising: (a) receiving motion, pressure, and/or force data concerning a person's body from one or more automatic sensors which are part of a wearable computing device; (b) identifying a first pattern in the motion, pressure, and/or force data using a data processing unit; (c) communicating from the wearable computing device to the person wearing the device in a first selected modality based on identification of the first pattern; (d) identifying a second pattern in the motion, pressure, and/or force data using a data processing unit; and (e) changing communication from the wearable computing device to the person wearing the device from the first selected modality to a second selected modality based on identification of the second pattern. In an example, a first and/or second pattern of motion, pressure, and/or force data can be a selected level, force, direction, configuration, and/or frequency of movement of one or more portions of the body. In an example, a first and/or second pattern of motion, pressure, and/or force data can be a selected pattern of contact between the person's fingers and the device.

In an example, this invention can comprise a method for sensor-informed modification of the interface modality between a human and a wearable computing device comprising: (a) receiving electromagnetic data concerning a person's body from one or more automatic sensors which are part of a wearable computing device; (b) identifying a first pattern in the electromagnetic data using a data processing unit; (c) communicating from the wearable computing device to the person wearing the device in a first selected modality based on identification of the first pattern; (d) identifying a second pattern in the electromagnetic data using a data processing unit; and (e) changing communication from the wearable computing device to the person wearing the device from the first selected modality to a second selected modality based on identification of the second pattern. In an example, a first and/or second pattern of electromagnetic data can be a selected level or pattern of resistance, impedance, and/or conductivity of body tissue with respect to electromagnetic energy delivered to it. In an example, a first and/or second pattern of electromagnetic data can be a selected level or pattern of electromagnetic energy which is naturally emitted from a person's tissue such as nerves and/or muscles. In an example, a first and/or second pattern of electromagnetic data can be a selected level or pattern of electromagnetic energy which is naturally emitted from a person's organs such as the heart and/or brain.

In an example, this invention can comprise a method for sensor-informed modification of the interface modality between a human and a wearable computing device comprising: (a) receiving data concerning a person's body from one or more automatic sensors which are part of a wearable computing device; (b) identifying a first pattern in the data using a data processing unit; (c) communicating, when the first pattern is identified, from the wearable computing device to the person wearing the device in a first modality which is based on light energy to a first degree; (d) identifying a second pattern in the data using a data processing unit; and (e) communicating, when the second pattern is identified, from the wearable computing device to the person wearing the device in a second modality which is based on light energy to a second degree, and wherein the second degree is less than the first degree.

In an example, this invention can comprise a method for sensor-informed modification of the interface modality between a human and a wearable computing device comprising: (a) receiving data concerning a person's body from one or more automatic sensors which are part of a wearable computing device; (b) identifying a first pattern in the data using a data processing unit; (c) communicating, when the first pattern is identified, from the wearable computing device to the person wearing the device in a first modality which is based on sonic energy to a first degree; (d) identifying a second pattern in the data using a data processing unit; and (e) communicating, when the second pattern is identified, from the wearable computing device to the person wearing the device in a second modality which is based on sonic energy to a second degree, and wherein the second degree is less than the first degree.

In an example, this invention can comprise a method for sensor-informed modification of the interface modality between a human and a wearable computing device comprising: (a) receiving data concerning a person's body from one or more automatic sensors which are part of a wearable computing device; (b) identifying a first pattern in the data using a data processing unit; (c) communicating, when the first pattern is identified, from the wearable computing device to the person wearing the device in a first modality which is based on motion, vibration, pressure, touch, and/or force to a first degree; (d) identifying a second pattern in the data using a data processing unit; and (e) communicating, when the second pattern is identified, from the wearable computing device to the person wearing the device in a second modality which is based on motion, vibration, pressure, touch, and/or force to a second degree, and wherein the second degree is less than the first degree.

In an example, this invention can comprise a method for sensor-informed modification of the interface modality between a human and a wearable computing device comprising: (a) receiving data concerning a person's body from one or more automatic sensors which are part of a wearable computing device; (b) identifying a first pattern in the data using a data processing unit; (c) communicating, when the first pattern is identified, from the wearable computing device to the person wearing the device in a first modality which is based on electromagnetic energy to a first degree; (d) identifying a second pattern in the data using a data processing unit; and (e) communicating, when the second pattern is identified, from the wearable computing device to the person wearing the device in a second modality which is based on electromagnetic energy to a second degree, and wherein the second degree is less than the first degree.

FIGS. 131 and 132 show a method for modification of the communication modality from a person to a wearable computing device based on data concerning the person's body received from one or more automatic sensors on the device. An automatic sensor on a human wearable computing device automatically collects data concerning a person's body without the need for specific volitional action by the person to initiate this data collection. In an example, an accelerometer on a wearable computing device can automatically collect data concerning movement of the person's body without requiring specific volitional action by the person to activate the collection of such data. In an example, a blood pressure sensor on a wearable computing device can automatically collect data concerning the person's blood pressure without requiring specific volitional action by the person to activate the collection of such data. In an example an automatic sensor on a human wearable computing device can be a physiological sensor.

FIG. 131 shows this method at a first point in time wherein a first pattern of data concerning a person's body is received from one or more automatic sensors, triggering a first communication modality from the person to the wearable computing device. FIG. 132 shows this method at a second point in time wherein a second pattern of data concerning the person's body is received from one or more automatic sensors, triggering a second communication modality from the wearable computing device.

FIGS. 131 and 132 show a method for sensor-informed modification of the interface modality between a human and a wearable computing device comprising: (a) receiving data concerning a person's body from one or more automatic sensors 13101 which are part of a wearable computing device; (b) identifying a first pattern of data concerning the person's body using a data processing unit; (c) receiving communication to the wearable computing device 13102 communication from the person wearing the device 13103 in a first selected modality based on identification of the first pattern; (d) identifying a second pattern of data concerning the person's body using a data processing unit; and (e) receiving communication from the person wearing the device in a second selected modality based on identification of the second pattern.

FIG. 131 shows data concerning the person's body having a first pattern being received by a wearable computing device from one or more automatic sensors on the wearable computing device. Identification of this first pattern of body data by a data processing unit triggers a first communication modality from volitional actions of the person to the wearable device. FIG. 132 shows data concerning the person's body having a second pattern of body data being received by the wearable computing device from one or more automatic sensors on the wearable computing device. Identification of this second pattern of body data by a data processing unit triggers a second communication modality from volitional actions of the person to the wearable device.

In an example, one or more automatic sensors on a human wearable computer device can be selected from the group consisting of: light energy sensor; sonic energy sensor; motion, position, pressure and/or force sensor; and electromagnetic energy sensor. In an example, an automatic sensor can be a spectroscopic sensor which collects data concerning the spectrum of light reflected from and/or transmitted through tissue of the person's body. In an example, an automatic sensor can be an accelerometer or gyroscope which collects data concerning the movement and/or position of the device. In an example, an automatic sensor can be an electromagnetic energy sensor which collects data concerning the resistance, impedance, and/or conductivity of body tissue with respect to electromagnetic energy delivered to it. In an example, an automatic sensor can be an electromagnetic energy sensor which collects data concerning electromagnetic energy which is naturally emitted from a person's tissue such as nerves and/or muscles. In an example, an automatic sensor can be an electromagnetic energy sensor which collects data concerning electromagnetic energy which is naturally emitted from a person's organs such as the heart and/or brain.

In an example, one or more automatic sensors on a human wearable computing device can be selected from the group consisting of: light energy sensor, electro-optical sensor, infrared sensor, laser sensor, optical sensor, optoelectronic sensor, photochemical sensor, photoelectric sensor, photometer, ultraviolet light sensor, thermoluminescence sensor, variable-translucence sensor, photoplethysmography (PPG) sensor, chemiluminescence sensor, fluorescence sensor, image recorder, camera, video recorder, spectroscopic sensor, light-spectrum-analyzing sensor, color sensor, spectral analysis sensor, spectrometry sensor, spectrophotometric sensor, spectroscopy sensor, near-infrared, infrared, ultraviolet, or white light spectroscopy sensor, mass spectrometry sensor, Raman spectroscopy sensor, ion mobility spectroscopic sensor, backscattering spectrometry sensor, chromatography sensor, optical glucose sensor, gas chromatography sensor, and analytical chromatography sensor.

In an example, one or more automatic sensors on a human wearable computing device can be selected from the group consisting of: sonic energy sensor, microphone, speech and/or voice recognition interface, breathing sound monitor, chewing and/or swallowing monitor, ultrasound sensor, Doppler ultrasound sensor, audiometer, and tympanometer.

In an example, one or more automatic sensors on a human wearable computing device can be selected from the group consisting of: motion sensor, inertial sensor, single axis, biaxial, or multi-axial accelerometer, kinematic sensor, gyroscope, tilt sensor, inclinometer, vibration sensor, bend sensor, goniometer, strain gauge, stretch sensor, pressure sensor, force sensor, flow sensor, air pressure sensor, airflow sensor, altimeter, barometer, blood flow monitor, blood pressure monitor, microfluidic sensor, manometer, and peak flow meter.

In an example, one or more automatic sensors on a human wearable computing device can be selected from the group consisting of: electromagnetic energy sensor, electromagnetic conductivity sensor, skin conductance sensor, electromagnetic resistance sensor, variable resistance sensor, electromagnetic impedance sensor, variable impedance sensor, skin impedance sensor, amp meter, voltmeter, magnetometer, magnetic field sensor, compass, radio frequency (RF) sensor, Hall-effect sensor, piezocapacitive sensor, piezoelectric sensor, electrogoniometer, electroconductive fiber, electrochemical sensor, electromagnetic electrode, electroosmotic sensor, electrophoresis sensor, electroporation sensor, neural impulse monitor and/or sensor, neurosensor, action potential sensor, electrocardiography (ECG) or EKG sensor and/or monitor, electroencephalography (EEG) sensor and/or monitor, electromagnetic brain activity sensor and/or monitor, electrogastrography (EGG) sensor and/or monitor, electromyography (EMG) sensor and/or monitor, electromagnetic muscle activity sensor, electrooculography (EOG) sensor and/or monitor, galvanic skin response (GSR) sensor and/or monitor, hemoencephalography (HEG) monitor, micro electromechanical system (MEMS) sensor, cardiac function monitor, cardiotachometer, cardiovascular monitor, heart rate monitor, heart sensor, pulse monitor, pulmonary function and/or respiratory function monitor, respiration rate monitor, tidal volume sensor, spirometry monitor, pneumography sensor, and breathing monitor.

In an example, one or more automatic sensors on a human wearable computing device can be selected from the group consisting of: temperature and/or thermal energy sensor, thermistor, thermometer, thermopile, body temperature sensor, skin temperature sensor, biochemical sensor, amino acid sensor, antibody receptor, artificial olfactory sensor, blood glucose monitor, blood oximeter, body fat sensor, capnography sensor, carbon dioxide sensor, carbon monoxide sensor, cerebral oximetry monitor, chemical sensor, chemiresistor sensor, chemoreceptor sensor, cholesterol sensor, cutaneous oxygen monitor, ear oximeter, gas composition sensor, glucometer, glucose monitor, humidity sensor, hydration sensor, microbial sensor, moisture sensor, osmolality sensor, oximeter, oximetry sensor, oxygen consumption monitor, oxygen level monitor or sensor, oxygen saturation monitor, pH level sensor, porosity sensor, pulse oximeter, skin moisture sensor, sodium sensor, tissue oximetry sensor, and tissue saturation oximeter.

In an example, a selected modality for communication from volitional human actions to a wearable computing device can be a modality that is based on light energy. In an example, a light-based human-to-computer interface can be a gesture recognition interface. In an example, a light-based human-to-computer interface can track and/or recognize human gestures. In an example, a light-based human-to-computer interface can track eye movements. In an example, a selected modality for communication from volitional human actions to a wearable computing device can be a modality that is based on sonic energy. In an example, a sound-based human-to-computer interface can be a speech recognition interface. In an example, a sound-based human-to-computer interface can recognize spoken words and commands.

In an example, a selected modality for communication from volitional human actions to a wearable computing device can be a modality that is based on motion, pressure, touch, and/or force. In an example, a human-to-computer interface can be a touch screen or other touch-sensitive interface. In an example, a human-to-computer interface can be a variable-pressure screen or other pressure-sensitive surface. In an example, a human-to-computer interface can be a keypad, keyboard, or other set of buttons. In an example, a human-to-computer interface can be a set of knobs, dials, switches, toggles, levers, or sliders. In an example, a human-to-computer interface can comprise Motion Recognition Clothing™. In an example, a human-to-computer interface can be an accelerometer or gyroscope.

In an example, a selected modality for communication from volitional human actions to a wearable computing device can be a modality that is based on electromagnetic energy. In an example, an electromagnetic human-to-computer interface can be an electromyographic (EMG) sensor. In an example, an electromagnetic human-to-computer interface can be an electrocardiographic (ECG/EKG) sensor. In an example, an electromagnetic human-to-computer interface can be an electroencephalographic (EEG) sensor.

In an example, this invention can comprise a method for sensor-informed modification of the interface modality between a human and a wearable computing device comprising: (a) receiving light energy data concerning a person's body from one or more automatic sensors which are part of a wearable computing device; (b) identifying a first pattern in the light energy data using a data processing unit; (c) receiving communication from the person to the wearable computing device in a first selected modality based on identification of the first pattern; (d) identifying a second pattern in the light energy data using a data processing unit; and (e) receiving communication from the person to the wearable computing device in a second selected modality based on identification of the second pattern. In an example, a first and/or second pattern of light energy data can be a selected level, intensity, wavelength, direction, polarity, phase, and/or spectral distribution of light which is reflected from and/or transmitted through body tissue.

In an example, this invention can comprise a method for sensor-informed modification of the interface modality between a human and a wearable computing device comprising: (a) receiving sonic energy data concerning a person's body from one or more automatic sensors which are part of a wearable computing device; (b) identifying a first pattern in the sonic energy data using a data processing unit; (c) receiving communication from the person to the wearable computing device in a first selected modality based on identification of the first pattern; (d) identifying a second pattern in the sonic energy using a data processing unit; and (e) receiving communication from the person to the wearable computing device in a second selected modality based on identification of the second pattern. In an example, a first and/or second pattern of sonic energy data can be a selected level, intensity, wavelength, waveform, direction, phase, and/or wave distribution of sound waves which are reflected from and/or transmitted through body tissue. In an example, a first and/or second pattern of sonic energy data can be a selected amplitude, frequency, waveform, direction, phase, Fourier Transform and/or wave distribution of sound waves which are naturally created by the functioning of a body organ.

In an example, this invention can comprise a method for sensor-informed modification of the interface modality between a human and a wearable computing device comprising: (a) receiving motion, pressure, and/or force data concerning a person's body from one or more automatic sensors which are part of a wearable computing device; (b) identifying a first pattern in the motion, pressure, and/or force data using a data processing unit; (c) receiving communication from the person to the wearable computing device in a first selected modality based on identification of the first pattern; (d) identifying a second pattern in the motion, pressure, and/or force data using a data processing unit; and (e) receiving communication from the person to the wearable computing device in a second selected modality based on identification of the second pattern. In an example, a first and/or second pattern of motion, pressure, and/or force data can be a selected level, force, direction, configuration, and/or frequency of movement of one or more portions of the body. In an example, a first and/or second pattern of motion, pressure, and/or force data can be a selected pattern of contact between the person's fingers and the device.

In an example, this invention can comprise a method for sensor-informed modification of the interface modality between a human and a wearable computing device comprising: (a) receiving electromagnetic data concerning a person's body from one or more automatic sensors which are part of a wearable computing device; (b) identifying a first pattern in the electromagnetic data using a data processing unit; (c) receiving communication from the person to the wearable computing device in a first selected modality based on identification of the first pattern; (d) identifying a second pattern in the electromagnetic data using a data processing unit; and (e) receiving communication from the person to the wearable computing device in a second selected modality based on identification of the second pattern. In an example, a first and/or second pattern of electromagnetic data can be a selected level or pattern of resistance, impedance, and/or conductivity of body tissue with respect to electromagnetic energy delivered to it. In an example, a first and/or second pattern of electromagnetic data can be a selected level or pattern of electromagnetic energy which is naturally emitted from a person's tissue such as nerves and/or muscles. In an example, a first and/or second pattern of electromagnetic data can be a selected level or pattern of electromagnetic energy which is naturally emitted from a person's organs such as the heart and/or brain.

In an example, this invention can comprise a method for sensor-informed modification of the interface modality between a human and a wearable computing device comprising: (a) receiving data concerning a person's body from one or more automatic sensors which are part of a wearable computing device; (b) identifying a first pattern in the data using a data processing unit; (c) receiving communication, when the first pattern is identified, from the person wearing the device in a first modality which is based on light energy to a first degree; (d) identifying a second pattern in the data using a data processing unit; and (e) receiving communication, when the second pattern is identified, from the person wearing the device in a second modality which is based on light energy to a second degree, and wherein the second degree is less than the first degree.

In an example, this invention can comprise a method for sensor-informed modification of the interface modality between a human and a wearable computing device comprising: (a) receiving data concerning a person's body from one or more automatic sensors which are part of a wearable computing device; (b) identifying a first pattern in the data using a data processing unit; (c) receiving communication, when the first pattern is identified, from the person wearing the device in a first modality which is based on sonic energy to a first degree; (d) identifying a second pattern in the data using a data processing unit; and (e) receiving communication, when the second pattern is identified, from the person wearing the device in a second modality which is based on sonic energy to a second degree, and wherein the second degree is less than the first degree.

In an example, this invention can comprise a method for sensor-informed modification of the interface modality between a human and a wearable computing device comprising: (a) receiving data concerning a person's body from one or more automatic sensors which are part of a wearable computing device; (b) identifying a first pattern in the data using a data processing unit; (c) receiving communication, when the first pattern is identified, from the person wearing the device in a first modality which is based on motion, vibration, pressure, touch, and/or force to a first degree; (d) identifying a second pattern in the data using a data processing unit; and (e) receiving communication, when the second pattern is identified, from the person wearing the device in a second modality which is based on motion, vibration, pressure, touch, and/or force to a second degree, and wherein the second degree is less than the first degree.

In an example, this invention can comprise a method for sensor-informed modification of the interface modality between a human and a wearable computing device comprising: (a) receiving data concerning a person's body from one or more automatic sensors which are part of a wearable computing device; (b) identifying a first pattern in the data using a data processing unit; (c) receiving communication, when the first pattern is identified, from the person wearing the device in a first modality which is based on electromagnetic energy to a first degree; (d) identifying a second pattern in the data using a data processing unit; and (e) receiving communication, when the second pattern is identified, from the person wearing the device in a second modality which is based on electromagnetic energy to a second degree, and wherein the second degree is less than the first degree.

FIGS. 133 through 163 show examples of a forearm-wearable computing device with a computer-to-human interface which is adjusted based on the results of data collected by an environmental and/or physiological sensor. FIG. 133 shows a forearm-wearable computing device comprising: (a) a band 13301 which is configured to be worn on a person's forearm and/or wrist; (b) an environmental light energy sensor 13302; (c) a data processing unit 13303 which analyzes data from the sensor; and (d) a computer-to-human visual display 13304, wherein the level of light energy emitted from the display is automatically adjusted based on the light energy level in the environment. The display can be selected from the group consisting of: a computer display screen, a semi-transparent display, and a projected image.

The left side of FIG. 133 shows this device at a first time when there is a first light energy level in the environment and a second level of light energy emitted from the display. The right side of FIG. 133 shows this same device at a second time after the level of light energy emitted from the display has been automatically adjusted to a fourth level based on a third light energy level in the environment. In an example, when the environment is bright then the light level from the display is increased to make the display easier to see in bright light. In an example, when the environment is dark, then the light level from the display is increased to make the display easier to see in the dark. This figure also shows a speaker 13305.

FIG. 134 shows a forearm-wearable computing device comprising: (a) a bracelet 13401 which is configured to be worn on a person's forearm and/or wrist; (b) an environmental light energy sensor 13402; (c) a data processing unit 13403 which analyzes data from the sensor; and (d) a computer-to-human visual display 13404, wherein the level of light energy emitted from the display is automatically adjusted based on the light energy level in the environment. The display can be selected from the group consisting of: a computer display screen, a semi-transparent display, and a projected image.

The left side of FIG. 134 shows this device at a first time when there is a first light energy level in the environment and a second level of light energy emitted from the display. The right side of FIG. 134 shows this same device at a second time after the level of light energy emitted from the display has been automatically adjusted to a fourth level based on a third light energy level in the environment. In an example, when the environment is bright then the light level from the display is increased to make the display easier to see in bright light. In an example, when the environment is dark, then the light level from the display is increased to make the display easier to see in the dark. This figure also shows a speaker 13405.

FIG. 135 shows a forearm-wearable computing device comprising: (a) a cuff 13501 which is configured to be worn on a person's forearm and/or wrist; (b) an environmental light energy sensor 13502; (c) a data processing unit 13503 which analyzes data from the sensor; and (d) a computer-to-human visual display 13504, wherein the level of light energy emitted from the display is automatically adjusted based on the light energy level in the environment. The display can be selected from the group consisting of: a computer display screen, a semi-transparent display, and a projected image.

The left side of FIG. 135 shows this device at a first time when there is a first light energy level in the environment and a second level of light energy emitted from the display. The right side of FIG. 135 shows this same device at a second time after the level of light energy emitted from the display has been automatically adjusted to a fourth level based on a third light energy level in the environment. In an example, when the environment is bright then the light level from the display is increased to make the display easier to see in bright light. In an example, when the environment is dark, then the light level from the display is increased to make the display easier to see in the dark. This figure also shows a speaker 13505.

FIG. 136 shows a forearm-wearable computing device comprising: (a) an attachment member 13601 which is configured to be worn on a person's forearm and/or wrist; (b) an environmental light energy sensor 13602; (c) a data processing unit 13603 which analyzes data from the sensor; and (d) a computer-to-human visual display 13604, wherein the level of light energy emitted from the display is automatically adjusted based on the light energy level in the environment. The attachment member can be selected from the group consisting of: a band, a bracelet, an armlet, a cuff, and a sleeve. The display can be selected from the group consisting of: a computer display screen, a semi-transparent display, and a projected image.

The left side of FIG. 136 shows this device at a first time when there is a first light energy level in the environment and a second level of light energy emitted from the display. The right side of FIG. 136 shows this same device at a second time after the level of light energy emitted from the display has been automatically adjusted to a fourth level based on a third light energy level in the environment. In an example, when the environment is bright then the light level from the display is increased to make the display easier to see in bright light. In an example, when the environment is dark, then the light level from the display is increased to make the display easier to see in the dark. This figure also shows a speaker 13605.

FIG. 137 shows a forearm-wearable computing device comprising: (a) an attachment member 13701 which is configured to be worn on a person's forearm and/or wrist; (b) an environmental light energy sensor 13702; (c) a data processing unit 13703 which analyzes data from the sensor; and (d) a computer-to-human visual display 13704, wherein the level of light energy emitted from the display is automatically adjusted based on the variability of light energy in the environment. The attachment member can be selected from the group consisting of: a band, a bracelet, an armlet, a cuff, and a sleeve. The display can be selected from the group consisting of: a computer display screen, a semi-transparent display, and a projected image.

The left side of FIG. 137 shows this device at a first time when there is a first variability in light energy in the environment and a first level of light energy emitted from the display. The right side of FIG. 137 shows this same device at a second time after the level of light energy emitted from the display has been automatically adjusted to a second level based on a second variability in energy in the environment. In an example, when environmental light is flickering then the light level from the display is increased to make the display easier to see in the midst of flickering light. This figure also shows a speaker 13705.

FIG. 138 shows a forearm-wearable computing device comprising: (a) an attachment member 13801 which is configured to be worn on a person's forearm and/or wrist; (b) an environmental light energy sensor 13802; (c) a data processing unit 13803 which analyzes data from the sensor; and (d) a computer-to-human visual display 13804, wherein the spectrum of light energy emitted from the display is automatically adjusted based on the spectrum of light energy in the environment. The attachment member can be selected from the group consisting of: a band, a bracelet, an armlet, a cuff, and a sleeve. The display can be selected from the group consisting of: a computer display screen, a semi-transparent display, and a projected image.

The left side of FIG. 138 shows this device at a first time when there is a first spectrum of light energy in the environment and a second spectrum of light energy emitted from the display. The right side of FIG. 138 shows this same device at a second time after the spectrum of light energy emitted from the display has been automatically adjusted to a fourth spectrum based on a third spectrum of light energy in the environment. This figure also shows a speaker 13805.

FIG. 139 shows a forearm-wearable computing device comprising: (a) an attachment member 13901 which is configured to be worn on a person's forearm and/or wrist; (b) a camera 13902; (c) a data processing unit 13903 which analyzes images from the camera in order to recognize a selected object or person; and (d) a computer-to-human visual display 13904, wherein the level of light energy emitted from the display is automatically adjusted when the selected object or person is recognized in the environment. The attachment member can be selected from the group consisting of: a band, a bracelet, an armlet, a cuff, and a sleeve. The display can be selected from the group consisting of: a computer display screen, a semi-transparent display, and a projected image.

The left side of FIG. 139 shows this device at a first time when a selected object or person is not recognized in the environment and a first level of light energy emitted from the display. The right side of FIG. 139 shows this same device at a second time after the level of light energy emitted from the display has been automatically adjusted to a second level based on recognition of the selected object or person in the environment. In an example, when a selected object or person is recognized in the environment then the level of light energy emitted from the display is automatically decreased to maintain privacy or confidentiality. In an example, when a selected object or person is recognized in the environment then the level of light energy emitted from the display is automatically decreased to avoid disturbing the setting with light emission. In an example, when a selected object or person is recognized in the environment then the level of light energy emitted from the display is automatically increased to highlight important information about the object or person. This figure also shows a speaker 13905.

FIG. 140 shows a forearm-wearable computing device comprising: (a) an attachment member 14001 which is configured to be worn on a person's forearm and/or wrist; (b) an environmental light energy sensor 14002; (c) a data processing unit 14003 which analyzes data from the sensor; and (d) a speaker 14005, wherein the level of sound energy emitted from the speaker is automatically adjusted based on the light energy level in the environment. The attachment member can be selected from the group consisting of: a band, a bracelet, an armlet, a cuff, and a sleeve.

The left side of FIG. 140 shows this device at a first time when there is a first light energy level in the environment and a first level of sound energy emitted from the speaker. The right side of FIG. 140 shows this same device at a second time after the level of sound energy emitted from the speaker has been automatically adjusted to a second sound level based on a second light energy level in the environment. In an example, when the environment is bright then the sound level from the speaker is increased because the person relies more heavily on audio communication when a computer display is hard to see in bright light. In an example, when the environment is dark then the sound level from the speaker is increased because the person relies more heavily on audio communication when a computer display is hard to see in the dark. In an example, when the environment is dark then the sound level from the speaker is decreased because the person does not wish to be disturbed when it is dark. This figure also shows a computer-to-human visual display 14004.

FIG. 141 shows a forearm-wearable computing device comprising: (a) an attachment member 14101 which is configured to be worn on a person's forearm and/or wrist; (b) a camera 14102; (c) a data processing unit 14103 which analyzes images from the camera in order to recognize a selected object or person; and (d) a speaker 14105, wherein the level of sound energy emitted from the speaker is automatically adjusted when the selected object or person is recognized in the environment. The attachment member can be selected from the group consisting of: a band, a bracelet, an armlet, a cuff, and a sleeve.

The left side of FIG. 141 shows this device at a first time when a selected object or person is not recognized in the environment and there is a first level of sound energy emitted from the speaker. The right side of FIG. 141 shows this same device at a second time after the level of sound energy emitted from the speaker has been automatically adjusted to a second sound level based on recognition of the selected object or person in the environment. In an example, when a selected object or person is recognized in the environment then the level of sound energy emitted from the speaker is automatically decreased to maintain privacy or confidentiality. In an example, when a selected object (such as a stage or movie screen) or person is recognized in the environment then the level of sound energy emitted from the speaker is automatically decreased to avoid disturbing the setting (such as a theater or conference room) with noise. In an example, when a selected object (such as a weapon) or person (such as the target of a search) is recognized in the environment then the level of sound energy emitted from the speaker is automatically increased to highlight important information (such as an alert) about the object or person. This figure also shows a computer-to-human visual display 14104.

FIG. 142 shows a forearm-wearable computing device comprising: (a) an attachment member 14201 which is configured to be worn on a person's forearm and/or wrist; (b) an environmental light energy sensor 14202; (c) a data processing unit 14203 which analyzes data from the sensor; and (d) a vibrating member 14205, wherein the level of vibration is automatically adjusted based on the light energy level in the environment. The attachment member can be selected from the group consisting of: a band, a bracelet, an armlet, a cuff, and a sleeve. In an example, the vibrating member can be an electromagnetic vibrator.

The left side of FIG. 142 shows this device at a first time when there is a first light energy level in the environment and a first level of vibration by the device. The right side of FIG. 142 shows this same device at a second time after the level of vibration by the device has been automatically adjusted to a second level based on a second light energy level in the environment. In an example, when the environment is well lit then the vibration level is decreased because the person can clearly see a visual display, but when the environment is dark then the vibration level is increased because the person cannot rely on the visual display to receive information from the device. This figure also shows a computer-to-human visual display 14204.

FIG. 143 shows a forearm-wearable computing device comprising: (a) an attachment member 14301 which is configured to be worn on a person's forearm and/or wrist; (b) a camera 14302; (c) a data processing unit 14303 which analyzes images from the camera in order to recognize a selected object or person; and (d) a vibrating member 14305, wherein the level of vibration is automatically adjusted when the selected object or person is recognized in the environment. The attachment member can be selected from the group consisting of: a band, a bracelet, an armlet, a cuff, and a sleeve. In an example, the vibrating member can be an electromagnetic vibrator.

The left side of FIG. 143 shows this device at a first time when a selected object or person is not recognized in the environment and there is a first level of vibration by the device. The right side of FIG. 143 shows this same device at a second time after the level of vibration by the device has been automatically adjusted to a second level based on recognition of the selected object or person in the environment. In an example, when a selected object or person is recognized in the environment then the vibration level is automatically increased because the person will rely more on tactile communication than visual communication or sonic communication from the device in the presence of that object or person. In an example, when a selected object (such as a weapon) or person (such as the target of a search) is recognized in the environment then the vibration level is automatically increased as a mode of alert which is not perceived by other people. This figure also shows a computer-to-human visual display 14304.

FIG. 144 shows a forearm-wearable computing device comprising: (a) an attachment member 14401 which is configured to be worn on a person's forearm and/or wrist; (b) a microphone 14402; (c) a data processing unit 14403 which analyzes data from the microphone; and (d) a computer-to-human visual display 14404, wherein the level of light energy emitted from the display is automatically adjusted based on the sound level in the environment. The attachment member can be selected from the group consisting of: a band, a bracelet, an armlet, a cuff, and a sleeve. The display can be selected from the group consisting of: a computer display screen, a semi-transparent display, and a projected image.

The left side of FIG. 144 shows this device at a first time when there is a first sound energy level in the environment and a first level of light energy emitted from the display. The right side of FIG. 144 shows this same device at a second time after the level of light energy emitted from the display has been automatically adjusted to a second light level based on a second sound energy level in the environment. In an example, when the environment is noisy then the level of light energy emitted from the display is automatically increased because audio communication is harder to hear, so the person relies more on visual communication. In an example, when the environment is quiet then the level of light energy emitted from the display is automatically increased because audio communication would disturb the setting, so the person relies more on visual communication. This figure also shows a speaker 14405.

FIG. 145 shows a forearm-wearable computing device comprising: (a) an attachment member 14501 which is configured to be worn on a person's forearm and/or wrist; (b) a microphone 14502; (c) a data processing unit 14503 which analyzes data from the microphone; and (d) a computer-to-human visual display 14504, wherein the level of light energy emitted from the display is automatically adjusted based on the amount of speech detected in the environment. The attachment member can be selected from the group consisting of: a band, a bracelet, an armlet, a cuff, and a sleeve. The display can be selected from the group consisting of: a computer display screen, a semi-transparent display, and a projected image.

The left side of FIG. 145 shows this device at a first time when there is a first amount of speech detected in the environment and a first level of light energy emitted from the display. The right side of FIG. 145 shows this same device at a second time after the level of light energy emitted from the display has been automatically adjusted to a second light level based on a second amount of speech in the environment. In an example, when there is a lot of speech and/or multiple loud conversations detected in the environment then the level of light energy emitted from the display is automatically increased because speech-based communication from the device is harder to hear, so the person relies more on visual communication. This figure also shows a speaker 14505.

FIG. 146 shows a forearm-wearable computing device comprising: (a) an attachment member 14601 which is configured to be worn on a person's forearm and/or wrist; (b) a microphone 14602; (c) a data processing unit 14603 which analyzes data from the microphone; and (d) a speaker 14605, wherein the level of sound energy emitted from the speaker is automatically adjusted based on the sound level in the environment. The attachment member can be selected from the group consisting of: a band, a bracelet, an armlet, a cuff, and a sleeve. The display can be selected from the group consisting of: a computer display screen, a semi-transparent display, and a projected image.

The left side of FIG. 146 shows this device at a first time when there is a first sound energy level in the environment and a second level of sound energy emitted from the speaker. The right side of FIG. 146 shows this same device at a second time after the level of sound energy emitted from the speaker has been automatically adjusted to a fourth sound level based on a third sound energy level in the environment. In an example, when the environment is noisy then the level of sound energy emitted from the speaker is automatically increased to make the device easier to hear. In an example, when the environment is quiet then the level of sound energy emitted from the speaker is automatically decreased in order to not disturb the quiet setting. This figure also shows a computer-to-human visual display 14604.

FIG. 147 shows a forearm-wearable computing device comprising: (a) an attachment member 14701 which is configured to be worn on a person's forearm and/or wrist; (b) a microphone 14702; (c) a data processing unit 14703 which analyzes data from the microphone; and (d) a speaker 14705, wherein the frequency of sound energy emitted from the speaker is automatically adjusted based on the frequency spectrum of sound in the environment. The attachment member can be selected from the group consisting of: a band, a bracelet, an armlet, a cuff, and a sleeve.

The left side of FIG. 147 shows this device at a first time when there is a first frequency spectrum of sound in the environment and a second frequency spectrum of sound energy emitted from the speaker. The right side of FIG. 147 shows this same device at a second time after the frequency spectrum of sound energy emitted from the speaker has been automatically adjusted to a fourth frequency spectrum based on a third frequency spectrum of sound in the environment. In an example, when sound in the environment is concentrated in a low frequency range then sound energy emitted from the speaker is in a high frequency range to make the device easier to hear over environmental sound. In an example, when sound in the environment is concentrated in a high frequency range then the sound energy emitted from the speaker is in a low frequency range to make the device easier to hear over environmental sound. In an example, when the environment is all about that bass then the device can be all about that treble. This figure also shows a computer-to-human visual display 14704.

FIG. 148 shows a forearm-wearable computing device comprising: (a) an attachment member 14801 which is configured to be worn on a person's forearm and/or wrist; (b) a microphone 14802; (c) a data processing unit 14803 which analyzes data from the microphone; and (d) a speaker 14805, wherein the amount of speech emitted from the speaker is automatically adjusted based on the amount of speech detected in the environment. The attachment member can be selected from the group consisting of: a band, a bracelet, an armlet, a cuff, and a sleeve.

The left side of FIG. 148 shows this device at a first time when there is a first amount of speech detected in the environment and a second amount of speech emitted from the speaker. The right side of FIG. 148 shows this same device at a second time after the amount of speech emitted from the speaker has been automatically adjusted to a fourth amount based on a third amount of speech in the environment. In an example, when a high amount of speech and/or multiple loud conversations are detected in the environment then the device communicates by emitting tones, beeps, music, or other non-speech sounds to be better heard above the environmental speech, but when there is a low amount of speech detected in the environment then the device communicates using speech. In an example, when a low level of speech is detected in the environment then the device communicates by emitting tones, beeps, music, or other non-speech sounds in order to insure privacy and/or confidentiality. This figure also shows a computer-to-human visual display 14804.

FIG. 149 shows a forearm-wearable computing device comprising: (a) an attachment member 14901 which is configured to be worn on a person's forearm and/or wrist; (b) a microphone 14902; (c) a data processing unit 14903 which analyzes data from the sensor; and (d) a vibrating member 14905, wherein the level of vibration is automatically adjusted based on the sound energy level in the environment. The attachment member can be selected from the group consisting of: a band, a bracelet, an armlet, a cuff, and a sleeve. In an example, the vibrating member can be an electromagnetic vibrator.

The left side of FIG. 149 shows this device at a first time when there is a first sound energy level in the environment and a first level of vibration by the device. The right side of FIG. 149 shows this same device at a second time after the level of vibration by the device has been automatically adjusted to a second level based on a second sound energy level in the environment. In an example, when the environment is quiet then the vibration level is decreased because the person can clearly hear audio communication from the device, but when the environment is noisy then the vibration level is increased because the person cannot rely on audio communication from the from the device. This figure also shows a computer-to-human visual display 14904.

FIG. 150 shows a forearm-wearable computing device comprising: (a) an attachment member 15001 which is configured to be worn on a person's forearm and/or wrist; (b) a motion sensor 15002; (c) a data processing unit 15003 which analyzes data from the motion sensor; and (d) a computer-to-human visual display 15004, wherein the level of light energy emitted from the display is automatically adjusted based on the level of device motion detected. The attachment member can be selected from the group consisting of: a band, a bracelet, an armlet, a cuff, and a sleeve. The display can be selected from the group consisting of: a computer display screen, a semi-transparent display, and a projected image.

The left side of FIG. 150 shows this device at a first time when there is a first level of device motion and a first level of light energy emitted from the display. The right side of FIG. 150 shows this same device at a second time after the level of light energy emitted from the display has been automatically adjusted to a second light level based on a second level of device motion. In an example, when the device is moving a lot then the level of light energy emitted from the display is automatically decreased to save power (because it is less likely that the person would be looking at the device). In an example, motion detected by motion sensor 15002 can be compared to motion detected by a sensor worn elsewhere on the person in order to estimate movement of the device relative to the rest of the person's body. In an example, when the device is moving a lot relative to the rest of the person's body, then the level of light energy emitted from the display is automatically decreased to save power because it is less likely that the person would be looking at the device. However, if the device is moving, but not moving a lot relative to the rest of the person's body, then the person may be traveling in a vehicle and the light energy level of the display is not decreased. This figure also shows a speaker 15005.

FIG. 151 shows a forearm-wearable computing device comprising: (a) an attachment member 15101 which is configured to be worn on a person's forearm and/or wrist; (b) a motion, position, and/or orientation sensor 15102; (c) a data processing unit 15103 which analyzes data from the motion, position, and/or orientation sensor; and (d) a computer-to-human visual display 15104, wherein the level of light energy emitted from the display is automatically adjusted based on the position and/or orientation of the device. The attachment member can be selected from the group consisting of: a band, a bracelet, an armlet, a cuff, and a sleeve. The motion, position, and/or orientation sensor can be selected from the group consisting of: an accelerometer, a gyroscope, an inclinometer, a compass, a bend sensor, and a stretch sensor. The display can be selected from the group consisting of: a computer display screen, a semi-transparent display, and a projected image.

The left side of FIG. 151 shows this device at a first time when the device has a first position or orientation and there is a first level of light energy emitted from the display. The right side of FIG. 151 shows this same device at a second time after the level of light energy emitted from the display has been automatically adjusted to a second light level based on a second position or orientation of the device. In an example, when the device is oriented away from the person's head then the level of light energy emitted from the display is automatically decreased to save power (because it is less likely that the person would be looking at the device) or to maintain confidentiality of information. In an example, the position and/or orientation of the device can be compared to the position and/or orientation of a sensor worn on the person's head (such as in eyewear) in order to estimate the position and/or orientation of the device relative to the person's head. This figure also shows a speaker 15105.

FIG. 152 shows a forearm-wearable computing device comprising: (a) an attachment member 15201 which is configured to be worn on a person's forearm and/or wrist; (b) a motion sensor 15202; (c) a data processing unit 15203 which analyzes data from the motion sensor; and (d) a speaker 15205, wherein the level of sound energy emitted from the speaker is automatically adjusted based on the level of device motion detected. The attachment member can be selected from the group consisting of: a band, a bracelet, an armlet, a cuff, and a sleeve. The motion sensor can be selected from the group consisting of: an accelerometer, a gyroscope, and an inclinometer. The display can be selected from the group consisting of: a computer display screen, a semi-transparent display, and a projected image.

The left side of FIG. 152 shows this device at a first time when there is a first level of device motion and a first level of sound energy emitted from the speaker. The right side of FIG. 152 shows this same device at a second time after the level of sound energy emitted from the speaker has been automatically adjusted to a second sound energy level based on a second level of device motion. In an example, when the device is moving a lot then the level of sound energy emitted from the display is automatically decreased to save power (because it is less likely that the person would be listening to the device). In an example, when the device is moving a lot then the level of sound energy emitted from the display is automatically increased because the person is relying more on audio communication than visual communication. This figure also shows a visual computer display 15204.

FIG. 153 shows a forearm-wearable computing device comprising: (a) an attachment member 15301 which is configured to be worn on a person's forearm and/or wrist; (b) a motion sensor 15302; (c) a data processing unit 15303 which analyzes data from the motion sensor; and (d) a vibrating member 15305, wherein the level of vibration is automatically adjusted based on the level of device motion detected. The attachment member can be selected from the group consisting of: a band, a bracelet, an armlet, a cuff, and a sleeve. The motion sensor can be selected from the group consisting of: an accelerometer, a gyroscope, and an inclinometer. In an example, the vibrating member can be an electromagnetic vibrator.

The left side of FIG. 153 shows this device at a first time when there is a first level of device motion and a first level of vibration by the device. The right side of FIG. 153 shows this same device at a second time after the level of vibration by the device has been automatically adjusted to a second vibration level based on a second level of device motion. In an example, when the device moving a lot then the vibration level is increased because it is harder for the person to sense the vibration when there is a lot of movement. This figure also shows a computer-to-human visual display 15304.

FIG. 154 shows a forearm-wearable computing device comprising: (a) an attachment member 15401 which is configured to be worn on a person's forearm and/or wrist; (b) an environmental vibration sensor 15402; (c) a data processing unit 15403 which analyzes data from the environmental vibration sensor; and (d) a vibrating member 15405, wherein the frequency of device vibration is automatically adjusted based on the frequency of environmental vibration detected. The attachment member can be selected from the group consisting of: a band, a bracelet, an armlet, a cuff, and a sleeve. In an example, the vibrating member can be an electromagnetic vibrator.

The left side of FIG. 154 shows this device at a first time when there is environmental vibration with first frequency and a second frequency of vibration by the device. The right side of FIG. 154 shows this same device at a second time after vibration frequency of the device has been automatically adjusted to a fourth vibration frequency based on a third frequency of environmental vibration. In an example, when environmental vibration is at a low frequency then the device vibrates at a high frequency so that device vibration can be more easily felt. In an example, when environmental vibration is at a high frequency than the device vibrates at a low frequency so that device vibration can be more easily felt. This figure also shows a computer-to-human visual display 15404.

FIG. 155 shows a forearm-wearable computing device comprising: (a) an attachment member 15501 which is configured to be worn on a person's forearm and/or wrist; (b) a spectroscopic sensor 15502 which collects data concerning the spectrum of light reflected from (or passing through) the person's tissue; (c) a data processing unit 15503 which analyzes data from the spectroscopic sensor; and (d) a computer-to-human visual display 15504, wherein the level of light energy emitted from the display is automatically adjusted based on the spectrum of light reflected from (or passing through) the person's tissue. The attachment member can be selected from the group consisting of: a band, a bracelet, an armlet, a cuff, and a sleeve. The display can be selected from the group consisting of: a computer display screen, a semi-transparent display, and a projected image.

The left side of FIG. 155 shows this device at a first time when there is a first spectrum of light reflected from (or passing through) the person's tissue and a first level of light energy emitted from the display. The right side of FIG. 155 shows this same device at a second time after the level of light energy emitted from the display has been automatically adjusted to a second light level based on a second spectrum of light reflected from (or passing through) the person's tissue. This figure also shows a speaker 15505.

FIG. 156 shows a forearm-wearable computing device comprising: (a) an attachment member 15601 which is configured to be worn on a person's forearm and/or wrist; (b) a spectroscopic sensor 15602 which collects data concerning the spectrum of light reflected from (or passing through) the person's tissue; (c) a data processing unit 15603 which analyzes data from the spectroscopic sensor; and (d) a speaker 15605, wherein the level of sound energy emitted from the speaker is automatically adjusted based on the spectrum of light reflected from (or passing through) the person's tissue. The attachment member can be selected from the group consisting of: a band, a bracelet, an armlet, a cuff, and a sleeve.

The left side of FIG. 156 shows this device at a first time when there is a first spectrum of light reflected from (or passing through) the person's tissue and a first level of sound energy emitted from the speaker. The right side of FIG. 156 shows this same device at a second time after the level of sound energy emitted from the display has been automatically adjusted to a second sound energy level based on a second spectrum of light reflected from (or passing through) the person's tissue. This figure also shows a visual computer display 15604.

FIG. 157 shows a forearm-wearable computing device comprising: (a) an attachment member 15701 which is configured to be worn on a person's forearm and/or wrist; (b) a spectroscopic sensor 15702 which collects data concerning the spectrum of light reflected from (or passing through) the person's tissue; (c) a data processing unit 15703 which analyzes data from the spectroscopic sensor; and (d) a vibrating member 15705, wherein the level of device vibration is automatically adjusted based on the spectrum of light reflected from (or passing through) the person's tissue. The attachment member can be selected from the group consisting of: a band, a bracelet, an armlet, a cuff, and a sleeve.

The left side of FIG. 157 shows this device at a first time when there is a first spectrum of light reflected from (or passing through) the person's tissue and a first level of device vibration. The right side of FIG. 157 shows this same device at a second time after the level of device vibration has been automatically adjusted to a second level of device vibration based on a second spectrum of light reflected from (or passing through) the person's tissue. This figure also shows a visual computer display 15704.

FIG. 158 shows a forearm-wearable computing device comprising: (a) an attachment member 15801 which is configured to be worn on a person's forearm and/or wrist; (b) an ultrasonic energy sensor 15802 which collects data concerning a pattern of ultrasonic energy reflected from (or passing through) the person's tissue; (c) a data processing unit 15803 which analyzes data from the ultrasonic energy sensor; and (d) a computer-to-human visual display 15804, wherein the level of light energy emitted from the display is automatically adjusted based on the pattern of ultrasonic energy reflected from (or passing through) the person's tissue. The attachment member can be selected from the group consisting of: a band, a bracelet, an armlet, a cuff, and a sleeve. The display can be selected from the group consisting of: a computer display screen, a semi-transparent display, and a projected image.

The left side of FIG. 158 shows this device at a first time when there is a first pattern of ultrasonic energy reflected from (or passing through) the person's tissue and a first level of light energy emitted from the display. The right side of FIG. 158 shows this same device at a second time after the level of light energy emitted from the display has been automatically adjusted to a second light level based on a second pattern of ultrasonic energy reflected from (or passing through) the person's tissue. This figure also shows a speaker 15805.

FIG. 159 shows a forearm-wearable computing device comprising: (a) an attachment member 15901 which is configured to be worn on a person's forearm and/or wrist; (b) an ultrasonic energy sensor 15902 which collects data concerning a pattern of ultrasonic energy reflected from (or passing through) the person's tissue; (c) a data processing unit 15903 which analyzes data from the ultrasonic energy sensor; and (d) a speaker 15905, wherein the level of sound energy emitted from the speaker is automatically adjusted based on the pattern of ultrasonic energy reflected from (or passing through) the person's tissue. The attachment member can be selected from the group consisting of: a band, a bracelet, an armlet, a cuff, and a sleeve.

The left side of FIG. 159 shows this device at a first time when there is a first pattern of ultrasonic energy reflected from (or passing through) the person's tissue and a first level of sound energy emitted from the speaker. The right side of FIG. 159 shows this same device at a second time after the level of sound energy emitted from the display has been automatically adjusted to a second sound energy level based on a second pattern of ultrasonic energy reflected from (or passing through) the person's tissue. This figure also shows a visual computer display 15904.

FIG. 160 shows a forearm-wearable computing device comprising: (a) an attachment member 16001 which is configured to be worn on a person's forearm and/or wrist; (b) an ultrasonic energy sensor 16002 which collects data concerning a pattern of ultrasonic energy reflected from (or passing through) the person's tissue; (c) a data processing unit 16003 which analyzes data from the ultrasonic energy sensor; and (d) a vibrating member 16005, wherein the level of device vibration is automatically adjusted based on the pattern of ultrasonic energy reflected from (or passing through) the person's tissue. The attachment member can be selected from the group consisting of: a band, a bracelet, an armlet, a cuff, and a sleeve.

The left side of FIG. 160 shows this device at a first time when there is a first pattern of ultrasonic energy reflected from (or passing through) the person's tissue and a first level of device vibration. The right side of FIG. 160 shows this same device at a second time after the level of device vibration has been automatically adjusted to a second level of device vibration based on a second pattern of ultrasonic energy reflected from (or passing through) the person's tissue. This figure also shows a visual computer display 16004.

FIG. 161 shows a forearm-wearable computing device comprising: (a) an attachment member 16101 which is configured to be worn on a person's forearm and/or wrist; (b) an electromagnetic energy sensor 16102 which collects data concerning patterns of electromagnetic energy emitted by (or transmitted through) the person's tissue; (c) a data processing unit 16103 which analyzes data from the electromagnetic energy sensor; and (d) a computer-to-human visual display 16104, wherein the level of light energy emitted from the display is automatically adjusted based on the pattern of electromagnetic energy emitted by (or transmitted through) the person's tissue. The attachment member can be selected from the group consisting of: a band, a bracelet, an armlet, a cuff, and a sleeve.

In an example, the electromagnetic energy sensed by the electromagnetic energy sensor can be naturally emitted from the person's muscles, nerves, and/or other organs. In an example, the electromagnetic energy sensor can be an electromyography (EMG) sensor. In an example, the electromagnetic energy sensed by the electromagnetic energy sensor can be externally delivered to a first location on the person's body tissue and measured at a second location on the person's body in order to measure the conductivity, resistance, and/or impedance of the body tissue. In an example, the electromagnetic energy sensor can be an impedance sensor. The display can be selected from the group consisting of: a computer display screen, a semitransparent display, and a projected image.

The left side of FIG. 161 shows this device at a first time when there is a first pattern of electromagnetic energy emitted by (or transmitted through) the person's tissue and a first level of light energy emitted from the display. The right side of FIG. 161 shows this same device at a second time after the level of light energy emitted from the display has been automatically adjusted to a second light level based on a second pattern of electromagnetic energy emitted by (or transmitted through) the person's tissue. This figure also shows a speaker 16105.

FIG. 162 shows a forearm-wearable computing device comprising: (a) an attachment member 16201 which is configured to be worn on a person's forearm and/or wrist; (b) an electromagnetic energy sensor 16202 which collects data concerning patterns of electromagnetic energy emitted by (or transmitted through) the person's tissue; (c) a data processing unit 16203 which analyzes data from the electromagnetic energy sensor; and (d) a speaker 16205, wherein the level of sound energy emitted from the speaker is automatically adjusted based on the pattern of electromagnetic energy emitted by (or transmitted through) the person's tissue. The attachment member can be selected from the group consisting of: a band, a bracelet, an armlet, a cuff, and a sleeve.

In an example, the electromagnetic energy sensed by the electromagnetic energy sensor can be naturally emitted from the person's muscles, nerves, and/or other organs. In an example, the electromagnetic energy sensor can be an electromyography (EMG) sensor. In an example, the electromagnetic energy sensed by the electromagnetic energy sensor can be externally delivered to a first location on the person's body tissue and measured at a second location on the person's body in order to measure the conductivity, resistance, and/or impedance of the body tissue. In an example, the electromagnetic energy sensor can be an impedance sensor. The display can be selected from the group consisting of: a computer display screen, a semitransparent display, and a projected image.

The left side of FIG. 162 shows this device at a first time when there is a first pattern of electromagnetic energy emitted by (or transmitted through) the person's tissue and a first level of sound energy emitted from the speaker. The right side of FIG. 162 shows this same device at a second time after the level of sound energy emitted from the display has been automatically adjusted to a second sound energy level based on a second pattern of electromagnetic energy emitted by (or transmitted through) the person's tissue. This figure also shows a visual computer display 16204.

FIG. 163 shows a forearm-wearable computing device comprising: (a) an attachment member 16301 which is configured to be worn on a person's forearm and/or wrist; (b) an electromagnetic energy sensor 16302 which collects data concerning patterns of electromagnetic energy emitted by (or transmitted through) the person's tissue; (c) a data processing unit 16303 which analyzes data from the electromagnetic energy sensor; and (d) a vibrating member 16305, wherein the level of device vibration is automatically adjusted based on the pattern of electromagnetic energy emitted by (or transmitted through) the person's tissue. The attachment member can be selected from the group consisting of: a band, a bracelet, an armlet, a cuff, and a sleeve.

In an example, the electromagnetic energy sensed by the electromagnetic energy sensor can be naturally emitted from the person's muscles, nerves, and/or other organs. In an example, the electromagnetic energy sensor can be an electromyography (EMG) sensor. In an example, the electromagnetic energy sensed by the electromagnetic energy sensor can be externally delivered to a first location on the person's body tissue and measured at a second location on the person's body in order to measure the conductivity, resistance, and/or impedance of the body tissue. In an example, the electromagnetic energy sensor can be an impedance sensor. The display can be selected from the group consisting of: a computer display screen, a semitransparent display, and a projected image.

The left side of FIG. 163 shows this device at a first time when there is a first pattern of electromagnetic energy emitted by (or transmitted through) the person's tissue and a first level of device vibration. The right side of FIG. 163 shows this same device at a second time after the level of device vibration has been automatically adjusted to a second level of device vibration based on a second pattern of electromagnetic energy emitted by (or transmitted through) the person's tissue. This figure also shows a visual computer display 16304.

In an example, this invention can be embodied in a wearable computing device for the wrist and/or forearm comprising: a bifurcating attachment member which is configured to be worn on a person's wrist and/or forearm; one or more display members which are attached to and/or part of the branches of the bifurcating attachment member; a data control unit; and one or more sensors. In an example, the bifurcating attachment member can be selected from the group consisting of: an armlet, a band, a bangle, a bracelet, a chain, a coil, a cuff, a gauntlet, a mesh, a sleeve, and a strap. In an example, the bifurcating attachment member can span the entire circumference of the person's wrist and/or forearm. In an example, the bifurcating attachment member can span at least 50% of the circumference of the person's wrist and/or forearm. In an example, the bifurcating attachment member can have ends which are connected to each other by a buckle, clasp, clip, hook, hook-and-eye material, pin, latch, button, and/or zipper. In an example, the bifurcating attachment member can be sufficiently inflexible or resiliently-flexible that it holds the device onto the person's wrist and/or forearm even if it has ends which are not connected to each other. In an example, the bifurcating attachment member can be flexible, stretchable, and/or elastic and can encircle the entire circumference of the person's wrist and/or forearm after being slipped over the person's hand.

In an example, the bifurcating attachment member can bifurcate into two branches on the lateral surfaces of the person's wrist and/or forearm. In an example, the bifurcating attachment member can be a single band, strap, mesh, cuff, or chain on the lower and/or dorsal surface of a person's wrist and/or forearm and can bifurcate to form a distal branch and a proximal branch on the upper and/or frontal surface of the person's wrist and/or forearm. In an example, the bifurcating attachment member can have an upper portion which is configured to be worn on the upper and/or frontal surface of a person's wrist and/or forearm, wherein this upper portion further comprises a distal branch which is a first distance from the person's elbow and a proximal branch which is a second distance from the person's elbow, wherein the second distance is less than the first distance, and wherein the distal and proximal branches converge along the side surfaces or the lower and/or dorsal surface of the person's wrist and/or forearm. In an example, a display member can be selected from the group consisting of: a computer display screen and/or touch screen, an image projector, and a see-through display.

In an example, this invention can be embodied in a wearable computing device for the wrist and/or forearm comprising: an attachment member which is configured to be worn on a person's wrist and/or forearm; a first display member, wherein this first display member is attached to and/or part of the attachment member at a first location, and wherein this first location is a first distance from the outer circumference of the person's arm at the elbow when the arm is fully extended; a second display member, wherein this second display member is attached to and/or part of the attachment member at a second location, wherein this second location is a second distance from the outer circumference of the person's arm at the elbow when the arm is fully extended, and wherein the second distance is less than the first distance; a data control unit; and one or more sensors.

In an example, distal can be defined as further from the circumference of the person's arm around the elbow when the arm is fully extended and proximal can be defined as closer to the circumference of the person's arm around the elbow when the arm is fully extended, the first display member can have an outer surface with a first centroid, the second display member can have an outer surface with a second centroid, and the second centroid can be more proximal than the first centroid. In an example, distal can be defined as further from the circumference of the person's arm around the elbow when the arm is fully extended and proximal can be defined as closer to the circumference of the person's arm around the elbow when the arm is fully extended, the first display member can have an outer surface with a first distal edge and a first proximal edge, the second display member can have an outer surface with a second distal edge and a second proximal edge, and the second distal edge can be more proximal than the first proximal edge.

In an example, the first display member can have a distal edge which is furthest from the outer circumference of the arm around the elbow, a centroid, and a proximal edge which is closest to the outer circumference of the arm around the elbow; the second display member can have a distal edge which is furthest from the outer circumference of the arm around the elbow, a centroid, and a proximal edge which is closest to the outer circumference of the arm around the elbow; and the proximal edge of the first display member can be further from the outer circumference of the arm around the elbow than the distal edge of the second display member. In an example, the first display member can have a distal edge which is furthest from the outer circumference of the arm around the elbow, a centroid, and a proximal edge which is closest to the outer circumference of the arm around the elbow; the second display member can have a distal edge which is furthest from the outer circumference of the arm around the elbow, a centroid, and a proximal edge which is closest to the outer circumference of the arm around the elbow; the proximal edge of the first display member can be further from the outer circumference of the arm around the elbow than the distal edge of the second display member; and the centroid of the first display member and the centroid of the second display member can both be intersected by the same distal-to-proximal axis of the attachment member.

In an example, the attachment member can be a bifurcating attachment member. In an example, the first display member and the second display member can be flexibly connected by joints, hinges, cords, fabric, or membrane. In an example, the first display member and the second display member can be part of a row-by-ring array of flexibly-connected display members, wherein the row dimension is along a distal-to-proximal axis and the ring dimension is around a circumference of the person's arm, and wherein the (row×ring) array size is at least (2×2).

In an example, the invention can be embodied in a wearable computing device for the wrist and/or forearm comprising: an attachment member which is configured to be worn on a person's wrist and/or forearm; one or more display members which are attached to and/or part of the attachment member; a data control unit; and an electromagnetic energy sensor which collects data concerning electromagnetic energy from the person's muscles and/or nerves.

FIG. 164 provides visual illustration and clarification of the definitions of distal and proximal for the purpose of this disclosure. Distal is defined as being further from the plane which contains the outer circumference of a person's arm around the elbow when the arm is fully extended and proximal is defined as being closer to the plane which contains the outer circumference of the person's arm around the elbow when the arm is fully extended. FIG. 164 shows humerus bone 16401 within a person's upper arm (wherein the humerus bone ends within the person's elbow), outer circumference 16402 of the person's arm drawn around the elbow (at the end of the humerus), and virtual plane 16403 which contains circumference 16402 and extends radially outward into space from the center of the person's elbow. FIG. 164 shows virtual plane 16403 as a finite ring for diagrammatic purposes, but it is to be understood that virtual plane 16403 extends infinitely outward into space from the center of the person's elbow. FIG. 164 shows three example distal-to-proximal vectors relative to virtual plane 16403 for diagrammatic purposes, but it is to be understood that there are an infinite number of distal-to-proximal vectors relative to virtual plane 16403.

I claim:
1. A wearable computing device for the wrist and/or forearm comprising:
   a bifurcating attachment member which is configured to be worn on a person's wrist and/or forearm, wherein the attachment member has a first portion of its circumference which splits into a distal branch and a proximal branch, wherein there is a gap in the attach- ment member between the distal branch and the proximal branch, wherein the distal branch and the proximal branch together span a first width, wherein the attachment member has a second portion of its circumference with a second width, and wherein the second width is narrower than the first width;

a first display member, wherein this first display member is attached to and/or part of the distal branch at a first location, and wherein this first location is a first distance from the plane which contains the outer circumference of the person's arm at the elbow when the arm is fully extended;

a second display member, wherein this second display member is attached to and/or part of the proximal branch at a second location, wherein this second location is a second distance from the plane which contains the outer circumference of the person's arm at the elbow when the arm is fully extended, and wherein the second distance is less than the first distance;

a data control unit; and one or more sensors.

2. The device in claim 1 wherein distal is defined as further from the plane which contains the circumference of the person's arm around the elbow when the arm is fully extended and proximal is defined as closer to from the plane which contains the circumference of the person's arm around the elbow when the arm is fully extended, wherein the first display member has an outer surface with a first centroid, wherein the second display member has an outer surface with a second centroid, and wherein the second centroid is more proximal than the first centroid.

3. The device in claim 1 wherein distal is defined as further from the plane which contains the circumference of the person's arm around the elbow when the arm is fully extended and proximal is defined as closer to from the plane which contains the circumference of the person's arm around the elbow when the arm is fully extended, wherein the first display member has an outer surface with a first distal edge and a first proximal edge, wherein the second display member has an outer surface with a second distal edge and a second proximal edge, and wherein the second distal edge is more proximal than the first proximal edge.

4. The device in claim 1 wherein the first display member has a distal edge which is furthest from the plane which contains the outer circumference of the arm around the elbow, a centroid, and a proximal edge which is closest to from the plane which contains the outer circumference of the arm around the elbow; wherein the second display member has a distal edge which is furthest from the plane which contains the outer circumference of the arm around the elbow, a centroid, and a proximal edge which is closest to from the plane which contains the outer circumference of the arm around the elbow; and wherein the proximal edge of the first display member is further from the plane which contains the outer circumference of the arm around the elbow than the distal edge of the second display member.

5. The device in claim 1 wherein the first display member has a distal edge which is furthest from the plane which contains the outer circumference of the arm around the elbow, a centroid, and a proximal edge which is closest to from the plane which contains the outer circumference of the arm around the elbow; wherein the second display member has a distal edge which is furthest from the plane which contains the outer circumference of the arm around the elbow, a centroid, and a proximal edge which is closest to from the plane which contains the outer circumference of the arm around the elbow; wherein the proximal edge of the first display member is further from the plane which contains the outer circumference of the arm around the elbow than the distal edge of the second display member; and wherein the centroid of the first display member and the centroid of the second display member are both intersected by the same distal-to-proximal axis of the attachment member.

6. The device in claim 1 wherein the attachment member is a bifurcating attachment member.

7. The device in claim 1 wherein the first display member and the second display member are flexibly connected by joints, hinges, cords, fabric, or membrane.

8. The device in claim 1 wherein the first display member and the second display member are part of a row-by-ring array of flexibly-connected display members, wherein the row dimension is along a distal-to-proximal axis and the ring dimension is around a circumference of the person's arm, and wherein the (row×ring) array size is at least (2×2).

9. A wearable computing device for the wrist and/or forearm comprising:

a bifurcating attachment member which is configured to be worn on a person's wrist and/or forearm, wherein the attachment member has a first portion of its circumference which splits into a distal branch and a proximal branch, wherein there is a gap in the attachment member between the distal branch and the proximal branch, wherein the distal branch and the proximal branch together span a first width, wherein the attachment member has a second portion of its circumference with a second width, and wherein the second width is narrower than the first width;

a first arcuate display member, wherein this first arcuate display member is attached to and/or part of the distal branch at a first location, and wherein this first location is a first distance from the plane which contains the outer circumference of the person's arm at the elbow when the arm is fully extended;

a second arcuate display member, wherein this second arcuate display member is attached to and/or part of the proximal branch at a second location, wherein this second location is a second distance from the plane which contains the outer circumference of the person's arm at the elbow when the arm is fully extended, and wherein the second distance is less than the first distance;

a data control unit; and one or more sensors.

* * * * *